US012715872B2

(12) United States Patent
Hyvonen et al.

(10) Patent No.: US 12,715,872 B2
(45) **Date of Patent: *Aug. 25, 2026**

(54) BENZO[C][2,6]NAPHTHYRIDINE DERIVATIVES, COMPOSITIONS AND THERAPEUTIC USES THEREOF

(71) Applicant: Cambridge Enterprise Limited, Cambridge (GB)

(72) Inventors: Marko Juhana Hyvonen, Cambridge (GB); Paul Brear, Cambridgeshire (GB); David Robert Spring, Cambridge (GB); Paul Glossop, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 377 days.

This patent is subject to a terminal disclaimer.

(21) Appl. No.: 18/279,732

(22) PCT Filed: Feb. 28, 2022

(86) PCT No.: PCT/GB2022/050536
§ 371 (c)(1),
(2) Date: Aug. 31, 2023

(87) PCT Pub. No.: WO2022/185041
PCT Pub. Date: Sep. 9, 2022

(65) Prior Publication Data

US 2024/0287060 A1 Aug. 29, 2024

(30) Foreign Application Priority Data

Mar. 1, 2021 (GB) ..................................... 2102895

(51) Int. Cl.
*C07D 471/06* (2006.01)
*A61K 31/4375* (2006.01)
*A61K 31/4745* (2006.01)
*C07D 471/04* (2006.01)

(52) U.S. Cl.
CPC ........ *C07D 471/04* (2013.01); *A61K 31/4745* (2013.01)

(58) Field of Classification Search
CPC ... C07D 471/06; A61K 31/4375; A61P 35/00; A61P 31/12; A61P 25/28; A61P 3/10; A61P 9/00
USPC ............................................ 546/81; 514/292
See application file for complete search history.

(56) References Cited

U.S. PATENT DOCUMENTS

| | | | |
|---|---|---|---|
| 4,346,093 A | 8/1982 | Friebe et al. |
| 5,478,830 A | 12/1995 | Higley et al. |
| 11,866,436 B2 | 1/2024 | Hyvonen et al. |
| 2023/0250097 A1 | 8/2023 | Hyvonen et al. |
| 2026/0070901 A1 | 3/2026 | Hyvonen et al. |

FOREIGN PATENT DOCUMENTS

| | | | |
|---|---|---|---|
| WO | WO-01/35947 A2 | 5/2001 |
| WO | WO-2008/028168 A2 | 3/2008 |
| WO | WO-2008/143759 A1 | 11/2008 |

(Continued)

OTHER PUBLICATIONS

Healy et al.: Pharmaceutical solvates, hydrates and amorphous forms: A special emphasis on cocrystals. Adv. Drug Deliv. Rev., vol. 117, pp. 25-46, 2017.*
International Search Report and Written Opinion for Application No. PCT/GB2022/050536 dated May 16, 2022.
Vahter Jurgen et al: "Oligo-aspartic acid 1-25 conjugates with benzo[c] [2,6]naphthyridine-8-carboxylic acid scaffold as picomolar inhibitors of CK2", Biorganic and Medicinal Chemistry, vol. 25, No. 7, pp. 2277-2284 (2017).
Hong et al., "Synthesis and biological activities of some N4-substituted 4-aminopyrazolo [3, 4-d] pyrimidines," Journal of Medicinal Chemistry 19.4 (1976): 555-558.
International Search Report and Written Opinion for International Application No. PCT/GB23/52325 dated Nov. 27, 2023.
International Search Report and Written Opinion for International Application No. PCT/GB23/52327 dated Nov. 8, 2023.

(Continued)

*Primary Examiner* — Charanjit Aulakh
(74) *Attorney, Agent, or Firm* — Foley Hoag LLP; David P. Halstead; Alexander J. Chatterley

(57) ABSTRACT

Provided are compounds of the Formula I, and salts, hydrates and solvates thereof:

I

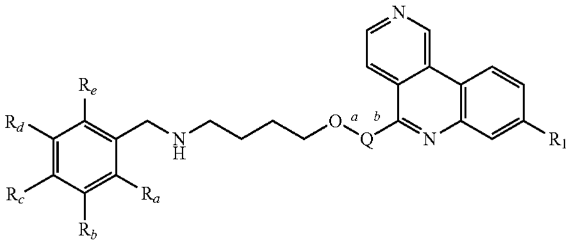

wherein $R_1$, Q, $R_a$, $R_b$, $R_c$, $R_d$ and $R_e$ are each as defined in the specification. The compounds are inhibitors of Casein Kinase 2 alpha (CK2α) and are useful for the treatment and/or prevention of diseases and conditions in which CK2α activity is implicated, such as, for example, but not limited to, the treatment and/or prevention of proliferative disorders (e.g. cancer), viral infections, inflammation, diabetes, vascular and ischemic disorders, neurodegeneration and the regulation of circadian rhythm. The present invention also relates to pharmaceutical compositions comprising the compounds defined herein, to processes for synthesising these compounds and to their use for the treatment of diseases and/or conditions in which CK2α activity is implicated.

20 Claims, No Drawings

(56) References Cited

FOREIGN PATENT DOCUMENTS

| | | | |
|---|---|---|---|
| WO | WO-2009/108912 | A1 | 9/2009 |
| WO | WO-2011/025859 | A1 | 3/2011 |
| WO | WO-2011/041785 | A1 | 4/2011 |
| WO | WO-2011/063398 | A1 | 5/2011 |
| WO | WO-2012/054493 | A1 | 4/2012 |
| WO | WO-2017/197324 | A1 | 11/2017 |
| WO | WO-2018/049068 | A1 | 3/2018 |
| WO | WO-2019/173653 | A1 | 9/2019 |
| WO | WO-2020/006315 | A1 | 1/2020 |
| WO | WO-2020/076862 | A1 | 4/2020 |
| WO | WO-2020/210404 | A1 | 10/2020 |
| WO | WO-2021/225912 | A1 | 11/2021 |
| WO | WO-2022/185041 | A1 | 9/2022 |
| WO | WO-2022/232838 | A1 | 11/2022 |
| WO | WO-2024/052690 | A1 | 3/2024 |
| WO | WO-2024/052692 | A1 | 3/2024 |
| WO | WO-2024/052693 | A1 | 3/2024 |
| WO | WO-2024/052701 | A1 | 3/2024 |
| WO | WO-2024/052702 | A1 | 3/2024 |

OTHER PUBLICATIONS

International Search Report and Written Opinion for International Application No. PCT/GB23/52328 dated Dec. 8, 2023.

International Search Report and Written Opinion for International Application No. PCT/GB23/52338 dated Nov. 27, 2023.

International Search Report and Written Opinion for International Application No. PCT/GB23/52339 dated Nov. 8, 2023.

Lindenblatt et al., "Molecular Plasticity of Crystalline CK2[alpha]' Leads to KN2, a Bivalent Inhibitor of Protein Kinase CK2 with Extraordinary Selectivity," Journal of Medicinal Chemistry 65.2 (2021): 1302-1312.

Pierre et al., "Discovery and SAR of 5-(3-Chlorophenylamino)benzo[c][2,6]naphthyridine-8-carboxylic Acid (CX-4945), the First Clinical Stage Inhibitor of Protein Kinase CK2 for the treatment of Cancer," Journal of Medicinal Chemistry 54.2 (2011): 635-654.

Rangasamy et al., "New Dual CK2/HDAC1 Inhibitors with Nanomolar Inhibitory Activity against Both Enzymes," ACS Medicinal Chemistry Letters 11.5 (2020): 713-719.

Atkinson et al., "Development of small cyclic peptides targeting the CK2α/β interface." Chemical Communications 58.30 (2022): 4791-4794.

Atkinson et al., "Downfalls of chemical probes acting at the kinase ATP-Site: CK2 as a case study." Molecules 26.7 (2021): 1977.

Brear et al., "A fragment-based approach leading to the discovery of inhibitors of CK2α with a novel mechanism of action." RSC Medicinal Chemistry 13.11 (2022): 1420-1426.

Brear et al., "Crystal structure of the Rho-associated coiled-coil kinase 2 inhibitor belumosudil bound to CK2α." Structural Biology and Crystallization Communications 78.10 (2022): 348-353.

Brear et al., "Novel non-ATP competitive small molecules targeting the CK2 α/β interface." Bioorganic & Medicinal Chemistry 26.11 (2018): 3016-3020.

Brear et al., "Proposed allosteric inhibitors bind to the ATP site of CK2α." Journal of medicinal chemistry 63.21 (2020): 12786-12798.

Brear et al., "Specific inhibition of CK2α from an anchor outside the active site." Chemical Science 7, (2016): 6839-6845.

Chen et al., "Chemically induced degradation of CK2 by proteolysis targeting chimeras based on a ubiquitin-proteasome pathway." Bioorganic chemistry 81 (2018): 536-544.

De Fusco et al., "A fragment-based approach leading to the discovery of a novel binding site and the selective CK2 inhibitor CAM4066." Bioorganic & Medicinal Chemistry 25.13 (2017): 3471-3482.

Kufareva et al., "Discovery of holoenzyme-disrupting chemicals as substrate-selective CK2 inhibitors." Scientific Reports 9.1 (2019): 15893.

Legre et al. "Chemical probes targeting the kinase CK2: A journey outside the catalytic box." Organic & Biomolecular Chemistry 19.20 (2021): 4380-4396.

Legre et al., "Efficient development of stable and highly functionalised peptides targeting the CK2a/CK2b protein-protein interaction." Chemical Science 10, (2019): 5056-5063.

Legre et al., "Second-generation CK2α inhibitors targeting the αD pocket." Chemical Science 9, (2018): 3041-3049.

Li et al., "Identification and biological evaluation of CK2 allosteric fragments through structure-based virtual screening." Molecules 25.1 (2020): 237.

Liu et al., "Structural determinants of CX-4945 derivatives as protein kinase CK2 inhibitors: A computational study." International Journal of Molecular Sciences 12.10 (2011): 7004-7021.

Wang et al., "Exploring the prominent performance of CX-4945 derivatives as protein kinase CK2 inhibitors by a combined computational study." Molecular BioSystems 10.5 (2014): 1196-1210.

U.S. Appl. No. 18/134,894, Granted.

U.S. Appl. No. 18/134,894, Issued.

Not yet assigned, Pending.

* cited by examiner

BENZO[C][2,6]NAPHTHYRIDINE DERIVATIVES, COMPOSITIONS AND THERAPEUTIC USES THEREOF

CROSS-REFERENCE TO RELATED APPLICATION

This application is a § 371 National Stage of PCT/GB2022/050536, filed Feb. 28, 2022, which claims the benefit of GB 210895.6, filed Mar. 1, 2021. The contents of PCT/GB2022/050536 are hereby incorporated by reference in their entirety.

INTRODUCTION

The present invention relates to novel therapeutic compounds. More specifically, the present invention relates to novel therapeutic compounds that inhibit Casein Kinase 2 alpha subunit (CK2α (CSNK2A1) and/or CK2α' (CSNK2A2)) and as part of the CK2 holoenzyme. The novel therapeutic compounds are therefore useful for the treatment and/or prevention of diseases and conditions in which CK2α activity is implicated, such as, for example but not limited to, the treatment and/or prevention of proliferative disorders (e.g. cancer), viral infections, inflammation, diabetes, vascular and ischemic disorders, neurodegeneration and the regulation of circadian rhythm.

The present invention also relates to pharmaceutical compositions comprising the novel therapeutic compounds defined herein, to processes for synthesising these compounds and to their use for the treatment of diseases and/or conditions in which CK2α activity is implicated.

BACKGROUND OF THE INVENTION

CK2α is a serine/threonine kinase that is a key regulator of many cellular processes and is involved in cellular proliferation and anti-apoptotic mechanisms (Battistutta & Lolli, Mol. Cell. Biochem. 2011). It mainly exists as a holoenzyme composed of two catalytic (α and/or α') and a dimer of regulatory (β) subunits, but it can also be found as the isolated subunits (Niefind et al, EMBO J 2001). Unlike most other kinases, it is constitutively active and more than 300 proteins have been identified as putative CK2α substrates, making it one of the most pleiotropic proteins in eukaryotic systems (Meggio & Pinna, FASEB 2003).

CK2α is a pro-survival kinase that operates across multiple signaling pathways to convey a proliferative and anti-apoptotic phenotype to cells. Consequently, cancer cells are often described as being addicted to CK2α activity and a high-profile genome-wide CRISPR-Cas9 screen highlighted CK2α as a top tier, high priority drug target for Colorectal Cancer (CRC) (Behan et al, Nature 2019). The target is well validated by human data that correlates poor patient survival in numerous tumor types, including CRC, with increased CK2α expression (Lin et al, PLoS ONE 2011). Additionally, data from clinical samples shows CK2α expression is upregulated in numerous tumor types (Ortega et al, PLoS ONE 2014; Di Maira et al, 2019).

The human genetics of CRC are well characterized and approximately 80% tumors are identified as being wnt pathway mutation driven (e.g. APC, β-catenin) (Zhan et al, Oncogene 2017). The wnt pathway is known to be sensitive to and amplified by CK2α activity and can be inhibited by loss of CK2α function (Gao & Wang, JBC 2006). For example, in animal models, CK2α inhibition prevents tumor growth that is driven by different mutations in the wnt pathway (Dowling et al, ACS 2016).

CK2α also contributes to the malignant phenotype in cholangiocarinoma (CCA), which is known to be a wnt-dysregulated tumor type (Zhan et al, Oncogene 2017). CK2α is over-expressed in human CCA samples and CCA tumor cell lines (Di Maira et al, Oncogenesis 2019); and disruption of CK2α activity in CCA cell models is reported to inhibit tumorigenic properties. (Zakharia et al, Translational Oncology 2019).

It is hypothesised that a CK2α inhibitor given either as a monotherapy, in combination with standard of care chemotherapy or in combination with other targeted therapies in development, such as, but not limited to, KRAS inhibitors, will inhibit CRC tumor growth by reversing aberrant mutation-driven upregulation of wnt signaling to the restore normal balance of apoptosis and proliferation.

Existing CK2α inhibitors target the highly conserved ATP binding site. This design strategy often leads to a poor selectivity profile for such inhibitors over other kinases. There is therefore a need for potent and more selective CK2α inhibitors that bind to the catalytic ATP site of CK2α (to drive potent enzyme inhibition) but also interact with other areas of CK2α, such as the αD site (to drive high levels of selectivity over other kinases).

The present invention was devised with the foregoing in mind.

SUMMARY OF THE INVENTION

In one aspect, the present invention provides a compound of Formula I as defined herein, and/or a pharmaceutically acceptable salt, hydrate or solvate thereof.

In another aspect, the present invention provides a pharmaceutical composition which comprises a compound of Formula I as defined herein, or a pharmaceutically acceptable salt, hydrate or solvate thereof, and one or more pharmaceutically acceptable excipients.

In another aspect, the present invention provides a compound of Formula I as defined herein, or a pharmaceutically acceptable salt, hydrate or solvate thereof, or a pharmaceutical composition as defined herein, for use in therapy.

In another aspect, the present invention provides a compound of Formula I as defined herein, or a pharmaceutically acceptable salt, hydrate or solvate thereof, or a pharmaceutical composition as defined herein, for use in the treatment of a disease or condition in which CK2α activity is implicated.

In another aspect, the present invention provides a compound of Formula I as defined herein, or a pharmaceutically acceptable salt, hydrate or solvate thereof, or a pharmaceutical composition as defined herein, for use in the treatment of a disease or condition associated with aberrant activity of CK2α.

In another aspect, the present invention provides a compound of Formula I as defined herein, or a pharmaceutically acceptable salt, hydrate or solvate thereof, or a pharmaceutical composition as defined herein, for use in the treatment of proliferative disorders (e.g. cancer or benign neoplasms), viral infections, an inflammatory disease or condition, diabetes, vascular and ischemic disorders, neurodegenerative disorders and/or the regulation of circadian rhythm.

In another aspect, the present invention provides a compound of Formula I as defined herein, or a pharmaceutically acceptable salt, hydrate or solvate thereof, or a pharmaceutical composition as defined herein, for use in the treatment of a cancer.

In another aspect, the present invention provides a compound of Formula I as defined herein, or a pharmaceutically acceptable salt, hydrate or solvate thereof, or a pharmaceutical composition as defined herein, for use in the treatment of a viral infection.

In another aspect, the present invention provides the use of a compound of Formula I as defined herein, or a pharmaceutically acceptable salt, hydrate or solvate thereof, in the manufacture of a medicament for use in the treatment of a disease or condition in which CK2α activity is implicated.

In another aspect, the present invention provides the use of a compound of Formula I as defined herein, or a pharmaceutically acceptable salt, hydrate or solvate thereof, in the manufacture of a medicament for use in the treatment of a disease or condition associated with aberrant activity of CK2α.

In another aspect, the present invention provides the use of a compound of Formula I as defined herein, or a pharmaceutically acceptable salt, hydrate or solvate thereof, in the manufacture of a medicament for use in the treatment of proliferative disorders (e.g. cancer or benign neoplasms), viral infections, an inflammatory disease or condition, diabetes, vascular and ischemic disorders, neurodegenerative disorders and/or the regulation of circadian rhythm.

In another aspect, the present invention the use of a compound of Formula I as defined herein, or a pharmaceutically acceptable salt, hydrate or solvate thereof, in the manufacture of a medicament for use in the treatment of a cancer.

In another aspect, the present invention provides the use of a compound of Formula I as defined herein, or a pharmaceutically acceptable salt, hydrate or solvate thereof, in the manufacture of a medicament for use in the treatment of a viral infection.

In another aspect, the present invention provides a method of treating a disease or condition in which CK2α activity is implicated, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a method of treating a disease or condition associated with aberrant activity of CK2α, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a method of treating a proliferative disorder (e.g. cancer or benign neoplasms), a viral infection, an inflammatory disease or condition, diabetes, vascular and ischemic disorders, neurodegenerative disorders and/or regulating cardiac rhythm, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a method of treating cancer, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a method of treating a viral infection, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a combination treatment comprising a compound of Formula I, or a pharmaceutically acceptable salt, hydrate or solvate thereof, as defined herein, with one or more additional therapeutic agents.

In another aspect, the present invention provides processes for preparing compounds of Formula I as defined herein, or a pharmaceutically acceptable salt, hydrate or solvate thereof, as defined herein, with one or more additional therapeutic agents.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

References to "Casein Kinase 2 alpha" or "CK2α" herein include CK2α (CSNK2A1) and/or CK2α' (CSNK2A2). Where reference is made to the compounds of the present invention defined herein inhibiting CK2α or being CK2α inhibitors, we mean that the compounds function as inhibitors of CK2α (CSNK2A1) and/or CK2α' (CSNK2A2) and the CK2 holoenzyme. In a particular embodiment, the compounds of the invention inhibit CK2α (CSNK2A1). In another embodiment, the compounds of the invention inhibit CK2α' (CSNK2A2).

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I", "compounds of the invention" and the more general term "compounds" refer to and include any and all compounds described by and/or with reference to Formula I herein. It should also be understood that these terms encompasses all stereoisomers, i.e. cis and trans isomers, as well as optical isomers, i.e. R and S enantiomers, of such compounds, in substantially pure form and/or any mixtures of the foregoing in any ratio. This understanding extends to pharmaceutical compositions and methods of treatment that employ or comprise one or more compounds of the Formula I, either by themselves or in combination with additional agents.

Unless specified otherwise, atoms are referred to herein by their chemical symbol as appearing in the IUPAC periodic table of the Elements. For example, "C" refers to a carbon atom.

The term "(m-nC)" or "(m-nC) group" used alone or as a prefix, refers to any group having m to n carbon atoms.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For Example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

An "alkylene" group is an alkyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(3-6C)cycloalkyl" means a hydrocarbon ring containing from 3 to 6 carbon atoms, for example, cyclopropyl, cyclobutyl, cyclopentyl, cyclohexyl, cycloheptyl or bicyclo [2.2.1]heptyl.

The term "halo" or "halogeno" refers to fluoro, chloro, bromo and iodo.

As used herein by themselves or in conjunction with another term or terms, "haloalkyl" and "haloalkyl group" refer to alkyl groups in which one or more hydrogen atoms are replaced by halogen atoms. Representative examples include, but are not limited to, $-CF_3$, $-CHF_2$, $-CH_2F$, $-CF_2CF_3$, $-CHFCF_3$, and $-CH_2CF_3$. Suitably, a haloalkyl group is selected from $-CHF_2$ and $-CF_3$, suitably $-CF_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Representative examples include, but are not limited to, $-OCF_3$, $-OCHF_2$, $-OCH_2F$, and $-OCF_2CF_3$. Suitably, a haloalkyoxy group is selected from $-OCHF_2$ and $-OCF_3$, suitably $-OCF_3$.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as, but not limited to, oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydrooxathiolyl, tetrahydrooxazolyl, tetrahydro-oxadiazolyl, tetrahydrodioxazolyl, tetrahydrooxathiazolyl, hexahydrotriazinyl, tetrahydrooxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as, but not limited to, tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry, by Jerry March*, 4th Edition, Wiley Interscience, pages 131-133, 1992. Examples of bridged heterocyclyl ring systems include, aza-bicyclo [2.2.1]heptane, 2-oxa-5-azabicyclo[2.2.1]heptane, aza-bicyclo[2.2.2]octane, aza-bicyclo[3.2.1]octane and quinuclidine.

By "spiro bicyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4] octane, 2-oxa-6-azaspiro[3.4]octane, 2-azaspiro[3.3]heptanes, 2-oxa-6-azaspiro[3.3]heptanes, 7-oxa-2-azaspiro[3.5] nonane, 6-oxa-2-azaspiro[3.4]octane, 2-oxa-7-azaspiro[3.5] nonane and 2-oxa-6-azaspiro[3.5]nonane.

The term "heteroaryl" or "heteroaromatic" means an aromatic mono-, bi-, or polycyclic ring incorporating one or more (for example 14, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3b]-furanyl-, 2H-furo[3,2b]-pyranyl-, 5H-pyrido[2,3-d]-ooxazinyl-, 1H-pyrazolo[4,3-d]-oxazolyl, 4H-imidazo[4,5d]thiazolyl, pyrazino[2,3d]pyridazinyl, -imidazo[2,1b]thiazolyl, -imidazo[1,2b][1,2,4]-triazinyl. “Heteroaryl” also covers partially aromatic bi- or polycyclic ring systems wherein at least one ring is an aromatic ring and one or more of the other ring(s) is a nonaromatic, saturated or partially saturated ring, provided at least one ring contains one or more heteroatoms selected from nitrogen, oxygen or -sulfur-. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl, 3,4-dihydro-2H-pyrido[3,2-b][1,4]oxazinyl and 6,8-dihydro-5H-[1,2,4]triazolo[4,3-a]pyrazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

- a benzene ring fused to a 5- or 6-membered ring containing 1, 2 or 3 ring heteroatoms;
- a pyridine ring fused to a 5- or 6-membered ring containing 1, 2 or 3 ring heteroatoms;
- a pyrimidine ring fused to a 5- or 6-membered ring containing 1 or 2 ring heteroatoms;
- a pyrrole ring fused to a 5- or 6-membered ring containing 1, 2 or 3 ring heteroatoms;
- a pyrazole ring fused to a 5- or 6-membered ring containing 1 or 2 ring heteroatoms;
- a pyrazine ring fused to a 5- or 6-membered ring containing 1 or 2 ring heteroatoms;
- an imidazole ring fused to a 5- or 6-membered ring containing 1 or 2 ring heteroatoms;
- an oxazole ring fused to a 5- or 6-membered ring containing 1 or 2 ring heteroatoms;
- an isoxazole ring fused to a 5- or 6-membered ring containing 1 or 2 ring heteroatoms;
- a thiazole ring fused to a 5- or 6-membered ring containing 1 or 2 ring heteroatoms;
- an isothiazole ring fused to a 5- or 6-membered ring containing 1 or 2 ring heteroatoms;
- a thiophene ring fused to a 5- or 6-membered ring containing 1, 2 or 3 ring heteroatoms;
- a furan ring fused to a 5- or 6-membered ring containing 1, 2 or 3 ring heteroatoms;
- a cyclohexyl ring fused to a 5- or 6-membered heteroaromatic ring containing 1, 2 or 3 ring heteroatoms; and
- a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term “aryl” means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

This specification also makes use of several composite terms to describe groups comprising more than one functionality. Such terms will be understood by a person skilled in the art. For Example heterocyclyl(m-nC)alkyl comprises (m-nC)alkyl substituted by heterocyclyl.

The term “aryl(1-2C)alkyl” means an aryl group covalently attached to a (1-2C)alkylene group, both of which are defined herein. Examples of aryl-(1-2C)alkyl groups include benzyl, phenylethyl, and the like.

“Heteroaryl(1-3C)alkyl” means a heteroaryl group covalently attached to a (1-3C)alkylene group, both of which are defined herein. Examples of heteroaryl-alkyl groups include pyridin-3-ylmethyl, 2-(benzofuran-2-yl)ethyl, and the like.

“Heterocyclyl(1-2C)alkyl” means a heterocyclyl group covalently attached to a (1-2C)alkylene group, both of which are defined herein.

“(3-6C)cycloalkyl-(1-2C)alkyl” means a (3-6C)cycloalkyl group covalently attached to a (1-2C)alkylene group, both of which are defined herein.

The term “optionally substituted” refers to either groups, structures, or molecules that are substituted and those that are not substituted. The term “wherein a/any CH, $CH_2$, $CH_3$ group or heteroatom (i.e. NH) within a $R^1$ group is optionally substituted” suitably means that (any) one of the hydrogen radicals of the $R^1$ group is substituted by a relevant stipulated group.

Where optional substituents are chosen from “one or more” groups it is to be understood that this definition includes all substituents being chosen from one of the specified groups or the substituents being chosen from two or more of the specified groups.

A wavy bond (  ) is used herein to show a point of attachment.

The phrase “compound of the invention” means those compounds which are disclosed herein, both generically and specifically.

As used herein by itself or in conjunction with another term or terms, “pharmaceutically acceptable” refers to materials that are generally chemically and/or physically compatible with other ingredients (such as, for example, with reference to a formulation), and/or are generally physiologically compatible with the recipient (such as, for example, a subject) thereof.

As used herein by themselves or in conjunction with another term or terms, “subject(s)” and “patient(s)”, suitably refer to mammals, in particular humans.

Compounds of the Invention

In a first aspect, the present invention relates to a compound, or pharmaceutically acceptable salt, hydrate or solvate thereof, having the structural formula I shown below:

I

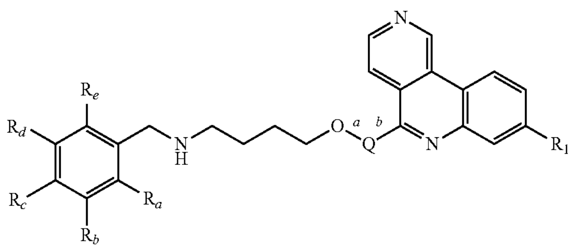

wherein:

$R_1$ is selected from —C(O)OH or —C(O)$NH_2$;

Q is selected from formula Ia or Ib:

Ia

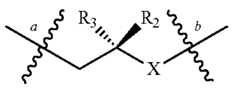

Ib

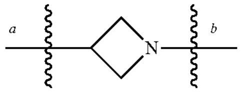

wherein:

bond a in formulae Ia and Ib corresponds with bond a in formula I and bond b in formulae Ia and Ib corresponds with bond b in formula I;

$R_2$ and $R_3$ are each independently selected from hydrogen or methyl; and

X is NH or O;

$R_a$ and $R_e$ are both independently selected from hydrogen, methyl or halo;

$R_b$ and $R_d$ are each independently selected from hydrogen, halo, cyano, (1-4C)alkyl, —$[CH_2]_{0-3}$-(1-4C)alkoxy,
—$[CH_2]_{0-3}$—C(O)$NH_2$,
—$[CH_2]_{0-3}$—C(O)NH(1-4C)alkyl,
—$[CH_2]_{0-3}$—C(O)N[(1-4C)alkyl]$_2$,
—$[CH_2]_{0-3}$—NH(1-4C)alkyl,
—$[CH_2]_{0-3}$—N[(1-4C)alkyl]$_2$,
—$[CH_2]_{0-3}$—S(O)$_q$-(1-4C)alkyl (wherein q is 0, 1 or 2),
—$[CH_2]_{0-3}$—C(O)(1-4C)alkyl,
—$[CH_2]_{0-3}$—C(O)O-(1-4C)alkyl,
—$[CH_2]_{0-3}$—N($R_f$)C(O)-(1-4C)alkyl (wherein $R_f$ is hydrogen or methyl),
—$[CH_2]_{0-3}$—S(O)$_2$NH(1-4C)alkyl,
—$[CH_2]_{0-3}$—S(O)$_2$N[(1-4C)alkyl]$_2$,
—$[CH_2]_{0-3}$—N($R_g$)$SO_2$-(1-4C)alkyl (wherein $R_g$ is hydrogen or methyl), a group of the formula:

—$Y_1$—$[CH_2]_{0-3}$—$Z_1$ wherein $Y_1$ is absent, —O—, —NH—, —NMe-, —S—, —S(O)— or —S(O)$_2$—; and $Z_1$ is (3-6C)cycloalkyl, phenyl, a 4- to 6-membered heterocyclyl or 5 or 6-membered heteroaryl;

and wherein:

any alkyl, alkoxy or any alkyl moiety within a $R_b$ and $R_d$ substituent group is optionally substituted by one or more substituents selected from halo, hydroxy, cyano, amino, —C(O)OH, —C(O)$NH_2$, (1-2C) alkoxy, or (3-4C)cycloalkoxy; and $Z_1$ is optionally substituted by one or more substituents selected from: halo, hydroxy, cyano, amino, —C(O) OH, —C(O)$NH_2$, (1-2C)alkoxy, (1-2C)alkyl, (3-4C) cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C) alkyl, —N($R_f$)C(O)-(1-2C)alkyl, —S(O)$_2$NH(1-2C) alkyl, —S(O)$_2$N[(1-2C)alkyl]$_2$, or —$NHSO_2$-(1-2C) alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl;

$R_c$ is selected from hydrogen, halo, cyano, —C(O)$NH_2$, (1-4C)alkyl,

—$[CH_2]_{0-3}$-(1-4C)alkoxy,
—$[CH_2]_{0-3}$-(3-6C)cycloalkoxy,
—$[CH_2]_{0-3}$—C(O)$NH_2$,
—$[CH_2]_{0-3}$—C(O)NH(1-4C)alkyl,
—$[CH_2]_{0-3}$—C(O)N[(1-4C)alkyl]$_2$,
—$[CH_2]_{0-3}$—NH(1-4C)alkyl,
—$[CH_2]_{0-3}$—N[(1-4C)alkyl]$_2$,
—$[CH_2]_{0-3}$—S(O)$_q$(1-4C)alkyl (wherein q is 0, 1 or 2),
—$[CH_2]_{0-3}$—C(O)(1-4C)alkyl,
—$[CH_2]_{0-3}$—C(O)O-(1-4C)alkyl,
—$[CH_2]_{0-3}$—N(Rn)C(O)-(1-4C)alkyl (wherein $R_h$ is hydrogen or methyl),
—$[CH_2]_{0-3}$—S(O)$_2$NH(1-4C)alkyl,
—$[CH_2]_{0-3}$—S(O)$_2$N[(1-4C)alkyl]$_2$,
—$[CH_2]_{0-3}$—N($R_i$)$SO_2$-(1-4C)alkyl (wherein $R_i$ is hydrogen or methyl), a group of the formula:

—$Y_2$—$[CH_2]_{0-3}$—$Z_2$ wherein $Y_2$ is absent, —O—, —NH—, —NMe-, —S—, —S(O)— or —S(O)$_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —C(O)$NH_2$, (1-2C) alkoxy, or (3-4C)cycloalkoxy; and $Z_2$ is optionally substituted by one or more substituents selected from: halo, hydroxy, cyano, amino, —C(O) OH, —C(O)$NH_2$, (1-2C)alkoxy, (1-2C)alkyl, (3-4C) cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C) alkyl, —N($R_f$)C(O)-(1-2C)alkyl, —S(O)$_2$NH(1-2C) alkyl, —S(O)$_2$N[(1-2C)alkyl]$_2$, or —$NHSO_2$-(1-2C) alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl.

Particular compounds of the invention include, for example, compounds of the formula I, or pharmaceutically acceptable salts, hydrates and/or solvates thereof, wherein, unless otherwise stated, each of $R_1$, Q, $R_a$, $R_d$, $R_c$, $R_d$ and $R_e$ each have any of the meanings defined hereinbefore or are as defined in any one of paragraphs (1) to (60) hereinafter:—

(1) $R_1$ is —C(O)OH;

(2) $R_1$ is —C(O)$NH_2$;

(3) Q is selected from formula Ia or Ib:

Ia

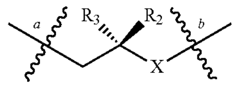

Ib

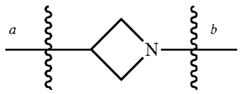

wherein:

bond a in formulae Ia and Ib corresponds with bond a in formula I and bond b in formulae Ia and Ib corresponds with bond b in formula I;

$R_2$ and $R_3$ are each independently selected from hydrogen or methyl; and

X is O;

(4) Q is selected from formula Ia or Ib:

Ia

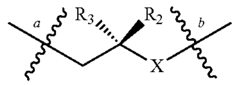

Ib

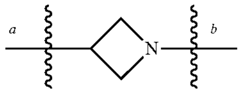

wherein:

bond a in formulae Ia and Ib corresponds with bond a in formula I and bond b in formulae Ia and Ib corresponds with bond b in formula I;

$R_2$ and $R_3$ are both hydrogen or one of $R_2$ and $R_3$ is hydrogen and the other is methyl;

X is O;

(5) Q is selected from formula Ia or Ib:

Ia

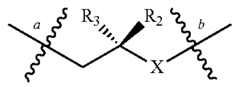

Ib

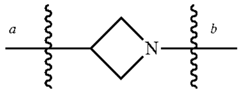

wherein:

bond a in formulae Ia and Ib corresponds with bond a in formula I and bond b in formulae Ia and Ib corresponds with bond b in formula I; $R_2$ and $R_3$ are both hydrogen;

X is O;

(6) Q is selected from formula Ia or Ib:

Ia

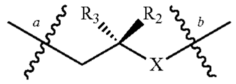

Ib

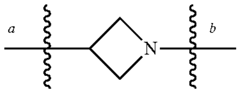

wherein:

bond a in formulae Ia and Ib corresponds with bond a in formula I and bond b in formulae Ia and Ib corresponds with bond b in formula I;

$R_2$ and $R_3$ are each independently selected from hydrogen or methyl;

X is NH;

(7) Q is selected from formula Ia or Ib:

Ia

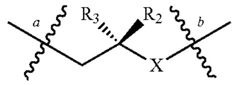

Ib

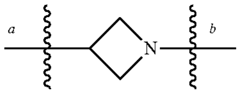

wherein:

bond a in formulae Ia and Ib corresponds with bond a in formula I and bond b in formulae Ia and Ib corresponds with bond b in formula I;

$R_2$ and $R_3$ are both hydrogen or one of $R_2$ and $R_3$ is hydrogen and the other is methyl;

X is NH; or

Q is selected from formula Ia or Ib above, wherein:

bond a in formulae Ia and Ib corresponds with bond a in formula I and bond b in formulae Ia and Ib corresponds with bond b in formula I;

$R_2$ and $R_3$ are both hydrogen;

X is NH;

(8) Q is selected from formula Ia:

Ia

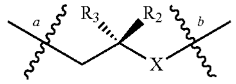

wherein:

bond a in formula Ia corresponds with bond a in formula I and bond b in formula Ia corresponds with bond b in formula I;

$R_2$ and $R_3$ are each independently selected from hydrogen or methyl; and

X is NH or O;

(9) Q is a group of formula Ia as defined in paragraph (3) above;

(10) Q is a group of formula Ia as defined in paragraph (4) above;

(11) Q is a group of formula Ia as defined in paragraph (5) above;

(12) Q is a group of formula Ia as defined in paragraph (6) above;

(13) Q is a group of formula Ia as defined in paragraph (7) above;

(14) Q is a group of formula Ib:

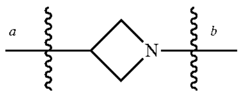

Ib wherein:

bond a in formula Ib corresponds with bond a in formula I and bond b in formula Ib corresponds with bond b in formula I;

(15) $R_a$ and $R_e$ are each independently selected from hydrogen, methyl, fluoro, chloro or bromo;

(16) $R_a$ and $R_e$ are each independently selected from hydrogen, fluoro, chloro or bromo;

(17) $R_a$ and $R_e$ are each independently selected from hydrogen, methyl, fluoro or chloro;

(18) $R_a$ and $R_e$ are each independently selected from hydrogen, fluoro or chloro;

(19) $R_a$ and $R_e$ are each independently selected from hydrogen or chloro;

(20) $R_e$ and $R_e$ are both hydrogen;

(21) one of $R_a$ and $R_e$ is hydrogen and the other is hydrogen, methyl or halo;

(22) one of $R_e$ and $R_e$ is hydrogen and the other is hydrogen, methyl, fluoro, chloro or bromo;

(23) one of $R_a$ and $R_e$ is hydrogen and the other is hydrogen, methyl, fluoro or chloro;

(24) one of $R_a$ and $R_e$ is hydrogen and the other is hydrogen or methyl;

(25) one of $R_a$ and $R_e$ is hydrogen and the other is hydrogen or fluoro;

(26) one of $R_a$ and $R_e$ is hydrogen and the other is hydrogen or chloro;

(27) $R_b$ and $R_d$ are each independently selected from hydrogen, halo, cyano, (1-4C)alkyl, $—[CH_2]_{0-2}$-(1-4C)alkoxy, $—[CH_2]_{0-2}—C(O)NH_2$, $—[CH_2]_{0-2}$—C(O)NH(1-4C)alkyl, $—[CH_2]_{0-2}$—C(O)N[(1-4C)alkyl]$_2$, $—[CH_2]_{0-2}$—NH(1-4C)alkyl, $—[CH_2]_{0-2}$—N[(1-4C)alkyl]$_2$, $—[CH_2]_{0-2}$—S(O)$_q$-(1-4C)alkyl (wherein q is 0, 1 or 2), $—[CH_2]_{0-2}$—C(O)(1-4C)alkyl, $—[CH_2]_{0-2}$—C(O)O-(1-4C)alkyl, $—[CH_2]_{0-2}$—NHC(O)-(1-4C)alkyl, $—[CH_2]_{0-2}$—S(O)$_2$NH(1-4C)alkyl, $—[CH_2]_{0-2}$—S(O)$_2$N[(1-4C)alkyl]$_2$, $—[CH_2]_{0-2}$—$NHSO_2$-(1-4C)alkyl, a group of the formula:

$—Y_1—[CH_2]_{0-2}—Z_1$ wherein $Y_1$ is absent, —O—, —NH—, —NMe-, —S—, —S(O)— or —S(O)$_2$—; and $Z_1$ is (3-6C)cycloalkyl, phenyl, a 4- to 6-membered heterocyclyl or 5 or 6-membered heteroaryl;

and wherein:

any alkyl, alkoxy or any alkyl moiety within a $R_b$ and $R_d$ substituent group is optionally substituted by one or more substituents selected from halo, hydroxy, cyano, amino, —C(O)OH, —C(O)NH$_2$, (1-2C) alkoxy, or (3-4C)cycloalkoxy; and $Z_1$ is optionally substituted by one or more substituents selected from: halo, hydroxy, cyano, amino, —C(O)OH, —C(O)NH$_2$, (1-2C)alkoxy, (1-2C)alkyl, (3-4C) cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C) alkyl, —N($R_f$)C(O)-(1-2C)alkyl, —S(O)$_2$NH(1-2C) alkyl, —S(O)$_2$N[(1-2C)alkyl]$_2$, or —$NHSO_2$-(1-2C) alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl;

(28) $R_d$ and $R_d$ are each independently selected from hydrogen, halo, cyano, (1-4C)alkyl, $—[CH_2]_{0-1}$-(1-4C)alkoxy, $—[CH_2]_{0-1}—C(O)NH_2$, $—[CH_2]_{0-1}$—C(O)NH(1-4C)alkyl, $—[CH_2]_{0-1}$—C(O)N[(1-4C)alkyl]$_2$, $—[CH_2]_{0-1}$—NH(1-4C)alkyl, $—[CH_2]_{0-1}$—N[(1-4C)alkyl]$_2$, $—[CH_2]_{0-1}$—S(O)$_g$-(1-4C)alkyl (wherein q is 0, 1 or 2), $—[CH_2]_{0-1}$—C(O)(1-4C)alkyl, $—[CH_2]_{0-1}$—C(O)O-(1-4C)alkyl, $—[CH_2]_{0-1}$—NHC(O)-(1-4C)alkyl, $—[CH_2]_{0-1}$—S(O)$_2$NH(1-4C)alkyl, $—[CH_2]_{0-1}$—S(O)$_2$N[(1-4C)alkyl]$_2$, $—[CH_2]_{0-1}$—$NHSO_2$-(1-4C)alkyl, a group of the formula:

$—Y_1—[CH_2]_{0-1}—Z_1$ wherein $Y_1$ is absent, —O—, —NH—, —NMe-, —S—, —S(O)— or —S(O)$_2$; and $Z_1$ is (3-6C)cycloalkyl, phenyl, a 4- to 6-membered heterocyclyl or 5 or 6-membered heteroaryl;

and wherein:

any alkyl, alkoxy or any alkyl moiety within a Ry and Ry substituent group is optionally substituted by one or more substituents selected from halo, hydroxy, cyano, amino, —C(O)OH, —C(O)NH$_2$, (1-2C) alkoxy, or (3-4C)cycloalkoxy; and $Z_1$ is optionally substituted by one or more substituents selected from: halo, hydroxy, cyano, amino, —C(O)OH, —C(O)NH$_2$, (1-2C)alkoxy, (1-2C)alkyl, (3-4C) cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C) alkyl, —N($R_f$)C(O)-(1-2C)alkyl, —S(O)$_2$NH(1-2C) alkyl, —S(O)$_2$N[(1-2C)alkyl]$_2$, or —$NHSO_2$-(1-2C) alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl;

(29) $R_d$ and $R_d$ are each independently selected from hydrogen, halo, cyano, (1-4C)alkyl, $—[CH_2]_{0-2}$-(1-2C)alkoxy, $—[CH_2]_{0-2}—C(O)NH_2$, $—[CH_2]_{0-2}$—C(O)NH(1-2C)alkyl, —$[CH_2]_{0-2}$—NH(1-2C)alkyl,
—$[CH_2]_{0-2}$—N[(1-2C)alkyl]$_2$,
—$[CH_2]_{0-2}$—S(O)$_q$-(1-2C)alkyl (wherein q is 0, 1 or 2),
—$[CH_2]_{0-2}$—C(O)(1-2C)alkyl,
—$[CH_2]_{0-2}$—C(O)O-(1-2C)alkyl,
—$[CH_2]_{0-2}$—NHC(O)-(1-2C)alkyl,
—$[CH_2]_{0-2}$—S(O)$_2$NH(1-2C)alkyl,
—$[CH_2]_{0-2}$—S(O)$_2$N[(1-2C)alkyl]$_2$,
—$[CH_2]_{0-2}$—NHSO$_2$-(1-2C)alkyl,
a group of the formula:

—$Y_1$—$[CH_2]_{0-2}$—$Z_1$ wherein $Y_1$ is absent, —O—, —NH—, —NMe-, —S—, —S(O)— or —S(O)$_2$—; and
$Z_1$ is (3-6C)cycloalkyl, phenyl, a 4- to 6-membered heterocyclyl or 5 or 6-membered heteroaryl;

and wherein:
any alkyl, alkoxy or any alkyl moiety within a $R_b$ and $R_d$ substituent group is optionally substituted by one or more substituents selected from halo, hydroxy, cyano, amino, —C(O)OH, —C(O)NH$_2$, (1-2C)alkoxy, or (3-4C)cycloalkoxy; and
$Z_1$ is optionally substituted by one or more substituents selected from: halo, hydroxy, cyano, amino, —C(O)OH, —C(O)NH$_2$, (1-2C)alkoxy, (1-2C)alkyl, (3-4C)cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C)alkyl, —N($R_f$)C(O)-(1-2C)alkyl, —S(O)$_2$NH(1-2C)alkyl, —S(O)$_2$N[(1-2C)alkyl]$_2$, or —NHSO$_2$-(1-2C)alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl;

(30) $R_b$ and $R_d$ are each independently selected from hydrogen, halo, cyano, (1-4C)alkyl,
—$[CH_2]_{0-1}$-(1-2C)alkoxy,
—$[CH_2]_{0-1}$—C(O)NH$_2$,
—$[CH_2]_{0-1}$—C(O)NH(1-2C)alkyl,
—$[CH_2]_{0-1}$—C(O)N[(1-2C)alkyl]$_2$,
—$[CH_2]_{0-1}$—N H(1-2C)alkyl,
—$[CH_2]_{0-1}$—N[(1-2C)alkyl]$_2$,
—$[CH_2]_{0-1}$—S(O)$_q$-(1-2C)alkyl (wherein q is 0, 1 or 2),
—$[CH_2]_{0-1}$—C(O)(1-2C)alkyl,
—$[CH_2]_{0-1}$—C(O)O-(1-2C)alkyl,
—$[CH_2]_{0-1}$—NHC(O)-(1-2C)alkyl,
—$[CH_2]_{0-1}$—S(O)$_2$NH(1-2C)alkyl,
—$[CH_2]_{0-1}$—S(O)$_2$N[(1-2C)alkyl]$_2$,
—$[CH_2]_{0-1}$—NHSO$_2$-(1-2C)alkyl,
a group of the formula:

—$Y_1$—$[CH_2]_{0-1}$—$Z_1$ wherein $Y_1$ is absent, —O—, —NH—, —NMe-, —S—, —S(O)— or —S(O)$_2$—; and
$Z_1$ is (3-6C)cycloalkyl, phenyl, a 4- to 6-membered heterocyclyl or 5 or 6-membered heteroaryl;

and wherein:
any alkyl, alkoxy or any alkyl moiety within a $R_b$ and $R_d$ substituent group is optionally substituted by one or more substituents selected from halo, hydroxy, cyano, amino, —C(O)OH, —C(O)NH$_2$, (1-2C)alkoxy, or (3-4C)cycloalkoxy; and
$Z_1$ is optionally substituted by one or more substituents selected from: halo, hydroxy, cyano, amino, —C(O)OH, —C(O)NH$_2$, (1-2C)alkoxy, (1-2C)alkyl, (3-4C)cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C)alkyl, —N($R_f$)C(O)-(1-2C)alkyl, —S(O)$_2$NH(1-2C)alkyl, —S(O)$_2$N[(1-2C)alkyl]$_2$, or —NHSO$_2$-(1-2C)alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl;

(31) $R_b$ and $R_d$ are each independently selected from hydrogen, halo, cyano, (1-4C)alkyl,
—$[CH_2]_{0-2}$-(1-4C)alkoxy,
—$[CH_2]_{0-2}$—C(O)NH$_2$,
—$[CH_2]_{0-2}$—C(O)NH(1-4C)alkyl,
—$[CH_2]_{0-2}$—C(O)N[(1-4C)alkyl]$_2$,
—$[CH_2]_{0-2}$—NH(1-4C)alkyl,
—$[CH_2]_{0-2}$—N[(1-4C)alkyl]$_2$,
—$[CH_2]_{0-2}$—S(O)$_q$-(1-4C)alkyl (wherein q is 0, 1 or 2),
—$[CH_2]_{0-2}$—C(O)(1-4C)alkyl,
—$[CH_2]_{0-2}$—C(O)O-(1-4C)alkyl,
—$[CH_2]_{0-2}$—N($R_f$)C(O)-(1-4C)alkyl,
—$[CH_2]_{0-2}$—S(O)$_2$NH(1-4C)alkyl,
—$[CH_2]_{0-2}$—S(O)$_2$N[(1-4C)alkyl]$_2$,
—$[CH_2]_{0-2}$—NHSO$_2$-(1-4C)alkyl,
a group of the formula:

—$Y_1$—$[CH_2]_{0-2}$—$Z_1$ wherein $Y_1$ is absent, —O—, —NH—, —NMe-, —S—, —S(O)— or —S(O)$_2$—; and
$Z_1$ is (3-6C)cycloalkyl, phenyl, or 5 or 6-membered heteroaryl;

and wherein:
any alkyl, alkoxy or any alkyl moiety within a $R_b$ and $R_d$ substituent group is optionally substituted by one or more substituents selected from halo, hydroxy, cyano, amino, —C(O)NH$_2$ or (1-2C)alkoxy; and
$Z_1$ is optionally substituted by one or more substituents selected from: halo, hydroxy, cyano, amino, (1-2C)alkoxy, (1-2C)alkyl, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, or —C(O)O-(1-2C)alkyl, and wherein any (1-2C)alkoxy or (1-2C)alkyl group is optionally substituted by one or more substituents selected from halo, cyano, hydroxy, or (1-2C)alkoxy;

(32) $R_b$ and $R_d$ are each independently selected from hydrogen, halo, cyano, (1-4C)alkyl,
—$[CH_2]_{0-1}$-(1-4C)alkoxy,
—$[CH_2]_{0-1}$—C(O)NH$_2$,
—$[CH_2]_{0-1}$—C(O)NH(1-4C)alkyl,
—$[CH_2]_{0-1}$—C(O)N[(1-4C)alkyl]$_2$,
—$[CH_2]_{0-1}$—NH(1-4C)alkyl,
—$[CH_2]_{0-1}$—N[(1-4C)alkyl]$_2$,
—$[CH_2]_{0-1}$—S(O)$_g$-(1-4C)alkyl (wherein q is 0, 1 or 2),
—$[CH_2]_{0-1}$—C(O)(1-4C)alkyl,
—$[CH_2]_{0-1}$—C(O)O-(1-4C)alkyl,
—$[CH_2]_{0-1}$—N($R_f$)C(O)-(1-4C)alkyl,
—$[CH_2]_{0-1}$—S(O)$_2$NH(1-4C)alkyl,
—$[CH_2]_{0-1}$—S(O)$_2$N[(1-4C)alkyl]$_2$,
—$[CH_2]_{0-1}$—NHSO$_2$-(1-4C)alkyl, a group of the formula:

$$-Y_1-[CH_2]_{0-1}-Z_1$$

wherein $Y_1$ is absent, —O—, —NH—, —NMe-, —S—, —S(O)— or —$S(O)_2$—; and $Z_1$ is (3-6C)cycloalkyl, phenyl, or 5 or 6-membered heteroaryl;

and wherein:

any alkyl, alkoxy or any alkyl moiety within a $R_d$ and $R_d$ substituent group is optionally substituted by one or more substituents selected from halo, hydroxy, cyano, amino, —$C(O)NH_2$ or (1-2C)alkoxy; and $Z_1$ is optionally substituted by one or more substituents selected from: halo, hydroxy, cyano, amino, (1-2C) alkoxy, (1-2C)alkyl, —C(O)NH(1-2C)alkyl, —C(O) N[(1-2C)alkyl]$_2$, —NH(1-2C)alkyl, —N[(1-2C)alkyl]$_2$, —$S(O)_q$-(1-2C)alkyl (wherein q is 0, 1 or 2), —C(O)(1-2C)alkyl, or —C(O)O-(1-2C)alkyl, and wherein any (1-2C)alkoxy or (1-2C)alkyl group is optionally substituted by one or more substituents selected from halo, cyano, hydroxy, or (1-2C)alkoxy;

(33) $R_d$ and $R_d$ are each independently selected from hydrogen, halo, cyano, (1-4C)alkyl, —$[CH_2]_{0-1}$-(1-4C)alkoxy,

—$[CH_2]_{0-1}$—$C(O)NH_2$,

—$[CH_2]_{0-1}$—C(O)NH(1-4C)alkyl,

—$[CH_2]_{0-1}$—C(O)N[(1-4C)alkyl]$_2$,

—$[CH_2]_{0-1}$—N H(1-4C)alkyl,

—$[CH_2]_{0-1}$—N[(1-4C)alkyl]$_2$,

—$[CH_2]_{0-1}$—$S(O)_q$-(1-4C)alkyl (wherein q is 0, 1 or 2),

—$[CH_2]_{0-1}$—C(O)(1-4C)alkyl,

—$[CH_2]_{0-1}$—C(O)O-(1-4C)alkyl, a group of the formula:

$$-Y_1-[CH_2]_{0-1}-Z_1$$

wherein $Y_1$ is absent, —O—, —NH—, —NMe-, —S—, —S(O)— or —$S(O)_2$—; and $Z_1$ is (3-6C)cycloalkyl or 5 or 6-membered heteroaryl;

and wherein:

any alkyl, alkoxy or any alkyl moiety within a $R_d$ and $R_d$ substituent group is optionally substituted by one or more substituents selected from halo, hydroxy, cyano, amino, —$C(O)NH_2$ or (1-2C)alkoxy; and $Z_1$ is optionally substituted by one or more substituents selected from: halo, hydroxy, cyano, amino, (1-2C) alkoxy, (1-2C)alkyl or (1-2C)haloalkyl;

(34) $R_b$ and $R_d$ are each independently selected from hydrogen, halo, cyano, (1-4C)alkyl, —$[CH_2]_{0-1}$-(1-4C)alkoxy,

—$[CH_2]_{0-1}$—$C(O)NH_2$, a group of the formula:

$$[CH_2]_{0-1}-Z_1$$

wherein $Z_1$ is (3-6C)cycloalkyl or a 5 or 6-membered heteroaryl;

and wherein:

any alkyl, alkoxy or any alkyl moiety within a $R_d$ and $R_d$ substituent group is optionally substituted by one or more substituents selected from halo, hydroxy, cyano, amino, —$C(O)NH_2$ or (1-2C)alkoxy; and $Z_1$ is optionally substituted by one or more substituents selected from: halo, hydroxy, cyano, amino, (1-2C) alkoxy, (1-2C)alkyl or (1-2C)haloalkyl;

(35) $R_d$ and $R_d$ are each independently selected from hydrogen, halo, cyano, (1-4C)alkyl, -(1-4C)alkoxy, —$[CH_2]_{0-1}$—$C(O)NH_2$, a group of the formula:

$$[CH_2]_{0-1}-Z_1$$

wherein $Z_1$ is (3-6C)cycloalkyl or a 5-membered heteroaryl;

and wherein:

any alkyl, alkoxy or any alkyl moiety within a $R_d$ and $R_d$ substituent group is optionally substituted by one or more substituents selected from halo, hydroxy, cyano, amino, —$C(O)NH_2$ or (1-2C)alkoxy; and $Z_1$ is optionally substituted by one or more substituents selected from: halo, hydroxy or cyano;

(36) $R_d$ and $R_d$ are each independently selected from hydrogen, halo, cyano, (1-4C)alkyl, (1-4C)alkoxy, —$[CH_2]_{0-1}$—$C(O)NH_2$, a group of the formula:

$$[CH_2]_{0-1}-Z_1$$

wherein $Z_1$ is (3-6C)cycloalkyl or a 5-membered heteroaryl;

and wherein:

any alkyl, alkoxy or any alkyl moiety within a $R_d$ and $R_d$ substituent group is optionally substituted by one or more substituents selected from halo, hydroxy, cyano, amino, —$C(O)NH_2$ or (1-2C)alkoxy; and $Z_1$ is optionally substituted by one or more cyano;

(37) $R_d$ and $R_d$ are each independently selected from hydrogen, halo, cyano, (1-4C)alkyl, halo(1-4C)alkyl, hydroxy(1-4C)alkyl, cyano(1-4C)alkyl, amino(1-4C) alkyl, (1-2C)alkoxy(1-4C)alkyl, (1-4C)alkoxy, halo(1-4C)alkoxy, hydroxy(1-4C)alkoxy, —$[CH_2]_{0-3}$—C(O) $NH_2$, a group of the formula:

$$[CH_2]_{0-1}-Z_1$$

wherein $Z_1$ is (3-6C)cycloalkyl or a 5-membered heteroaryl;

and wherein $Z_1$ is optionally substituted by one or more cyano;

(38) $R_b$ and $R_d$ are each independently selected from hydrogen, halo, (1-2C)alkyl, (1-2C)alkoxy, a group of the formula:

$$[CH_2]_{0-1}-Z_1$$

wherein $Z_1$ is (3-4C)cycloalkyl;

and wherein:

any alkyl, alkoxy or any alkyl moiety within a $R_b$ and $R_d$ substituent group is optionally substituted by one or more substituents selected from halo;

(39) $R_b$ and $R_d$ are each independently selected from hydrogen, fluoro, chloro, bromo, cyano, methyl, ethyl, methoxy, ethoxy, —$CH_2OH$, —$CH_2OCH_3$, —$CH_2NH_2$, —$CH_2CN$, —$CH_2CH_2OH$, —$CF_3$, —$OCF_3$, —O—$CH_2CH_2OH$, —O—$CH_2CF_3$, —C(O) $NH_2$, —$CH_2$—$C(O)NH_2$, —$CH(CH_3)CN$, —$C(CH_3)_2$ CN, cyclopropyl, 1-cyanocyclopropyl, cyclopropylmethyl, furanylmethyl (e.g. furan-3-ylmethyl), imidazolylmethyl (e.g. imidazo-1-ylmethyl), pyrazolylmethyl (e.g. pyrazol-4-ylmethyl), oxazolylmethyl (e.g. oxazo-4-ylmethyl);

(40) $R_b$ and $R_d$ are each independently selected from hydrogen, fluoro, chloro, bromo, methyl, —$OCF_3$, or cyclopropyl;

(41) One of $R_b$ and $R_d$ is hydrogen, halogen, (1-2C)alkyl, halo(1-2C)alkyl, (1-2C)alkoxy, halo(1-2C)alkoxy, (1-2C)alkoxy(1-2C)alkyl, (3-4C)cycloalkyl, (3-4C)cycloalkyl(1-2C)alkyl and the other is selected from any one of the options defined in paragraphs (27) to (40) above;

(42) One of $R_b$ and $R_d$ is hydrogen or halogen or —$OCF_3$ and the other is selected from hydrogen, fluoro, chloro, bromo, cyano, methyl, ethyl, methoxy, ethoxy, —$CH_2OH$, —$CH_2OCH_3$, —$CH_2NH_2$, —$CH_2CN$, —$CH_2CH_2OH$, —$CF_3$, —$OCF_3$, —O—$CH_2CH_2OH$, —O—$CH_2CF_3$, —C(O)$NH_2$, —$CH_2$—C(O)$NH_2$, —CH($CH_3$)CN, —C($CH_3$)$_2$CN, cyclopropyl, 1-cyano-cyclopropyl, cyclopropylmethyl, furanylmethyl (e.g. furan-3-ylmethyl), imidazolylmethyl (e.g. imidazo-1-ylmethyl), pyrazolylmethyl (e.g. pyrazol-4-ylmethyl), oxazolylmethyl (e.g. oxazo-4-ylmethyl);

(43) One of $R_b$ and $R_d$ is hydrogen or halogen or —$OCF_3$ and the other is selected from hydrogen, fluoro, chloro, bromo, methyl, —$OCF_3$ or cyclopropyl;

(44) $R_c$ is selected from hydrogen, halo, cyano, —C(O)$NH_2$, (1-4C)alkyl,
—$[CH_2]_{0-2}$-(1-4C)alkoxy,
—$[CH_2]_{0-2}$-(3-6C)cycloalkoxy,
—$[CH_2]_{0-2}$—C(O)$NH_2$,
—$[CH_2]_{0-2}$—C(O)NH(1-4C)alkyl,
—$[CH_2]_{0-2}$—C(O)N[(1-4C)alkyl]$_2$,
—$[CH_2]_{0-2}$—NH(1-4C)alkyl,
—$[CH_2]_{0-2}$—N[(1-4C)alkyl]$_2$,
—$[CH_2]_{0-2}$—S(O)$_q$(1-4C)alkyl (wherein q is 0, 1 or 2),
—$[CH_2]_{0-2}$—C(O)(1-4C)alkyl,
—$[CH_2]_{0-2}$—C(O)O-(1-4C)alkyl,
—$[CH_2]_{0-2}$—N(H)C(O)-(1-4C)alkyl,
—$[CH_2]_{0-2}$—S(O)$_2$NH(1-4C)alkyl,
—$[CH_2]_{0-2}$—S(O)$_2$N[(1-4C)alkyl]$_2$,
—$[CH_2]_{0-2}$—N(H)$SO_2$-(1-4C)alkyl,
a group of the formula:

$$—Y_2—[CH_2]_{0-2}—Z_2$$

wherein $Y_2$ is absent, —O—, —NH—, —NMe-, —S—, —S(O)— or —S(O)$_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —C(O)$NH_2$, (1-2C) alkoxy, or (3-4C)cycloalkoxy; and $Z_2$ is optionally substituted by one or more substituents selected from: halo, hydroxy, cyano, amino, —C(O)OH, —C(O)$NH_2$, (1-2C)alkoxy, (1-2C)alkyl, (3-4C) cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C) alkyl, —N($R_f$)C(O)-(1-2C)alkyl, —S(O)$_2$NH(1-2C) alkyl, —S(O)$_2$N[(1-2C)alkyl]$_2$, or —$NHSO_2$-(1-2C) alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl or (1-2C)alkoxy;

(45) $R_c$ is selected from hydrogen, halo, cyano, —C(O)$NH_2$, (1-4C)alkyl,
—$[CH_2]_{0-1}$-(1-4C)alkoxy,
—$[CH_2]_{0-1}$-(3-6C)cycloalkoxy,
—$[CH_2]_{0-1}$—C(O)$NH_2$,
—$[CH_2]_{0-1}$—C(O)NH(1-4C)alkyl,
—$[CH_2]_{0-1}$—C(O)N[(1-4C)alkyl]$_2$,
—$[CH_2]_{0-1}$—N H(1-4C)alkyl,
—$[CH_2]_{0-1}$—N[(1-4C)alkyl]$_2$,
—$[CH_2]_{0-1}$—S(O)$_q$-(1-4C)alkyl (wherein q is 0, 1 or 2),
—$[CH_2]_{0-1}$—C(O)(1-4C)alkyl,
—$[CH_2]_{0-1}$—C(O)O-(1-4C)alkyl,
—$[CH_2]_{0-1}$—N(H)C(O)-(1-4C)alkyl,
—$[CH_2]_{0-1}$—S(O)$_2$NH(1-4C)alkyl,
—$[CH_2]_{0-1}$—S(O)$_2$N[(1-4C)alkyl]$_2$,
—$[CH_2]_{0-1}$—N(H)$SO_2$-(1-4C)alkyl,
a group of the formula:

$$—Y_2—[CH_2]_{0-1}—Z_2$$

wherein $Y_2$ is absent, —O—, —NH—, —NMe-, —S—, —S(O)— or —S(O)$_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —C(O)$NH_2$, (1-2C) alkoxy, or (3-4C)cycloalkoxy; and $Z_2$ is optionally substituted by one or more substituents selected from: halo, hydroxy, cyano, amino, —C(O)OH, —C(O)$NH_2$, (1-2C)alkoxy, (1-2C)alkyl, (3-4C) cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C) alkyl, —N($R_f$)C(O)-(1-2C)alkyl, —S(O)$_2$NH(1-2C) alkyl, —S(O)$_2$N[(1-2C)alkyl]$_2$, or —$NHSO_2$-(1-2C) alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl or (1-2C)alkoxy;

(46) $R_c$ is selected from hydrogen, halo, cyano, —C(O)$NH_2$, (1-4C)alkyl,
—$[CH_2]_{0-2}$-(1-2C)alkoxy,
—$[CH_2]_{0-2}$-(3-6C)cycloalkoxy,
—$[CH_2]_{0-2}$—C(O)$NH_2$,
—$[CH_2]_{0-2}$—C(O)NH(1-2C)alkyl,
—$[CH_2]_{0-2}$—C(O)N[(1-2C)alkyl]$_2$,
—$[CH_2]_{0-2}$—N H(1-2C)alkyl,
—$[CH_2]_{0-2}$—N[(1-2C)alkyl]$_2$,
—$[CH_2]_{0-2}$—S(O)$_q$-(1-2C)alkyl (wherein q is 0, 1 or 2),
—$[CH_2]_{0-2}$—C(O)(1-2C)alkyl,
—$[CH_2]_{0-2}$—C(O)O-(1-2C)alkyl,
—$[CH_2]_{0-2}$—N(H)C(O)-(1-2C)alkyl,
—$[CH_2]_{0-2}$—S(O)$_2$NH(1-2C)alkyl,
—$[CH_2]_{0-2}$—S(O)$_2$N[(1-2C)alkyl]$_2$,
—$[CH_2]_{0-2}$—N(H)$SO_2$-(1-2C)alkyl,
a group of the formula:

$$—Y_2—[CH_2]_{0-2}—Z_2$$

wherein $Y_2$ is absent, —O—, —NH—, —NMe-, —S—, —S(O)— or —S(O)$_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —C(O)$NH_2$, (1-2C) alkoxy, or (3-4C)cycloalkoxy; and $Z_2$ is optionally substituted by one or more substituents selected from: halo, hydroxy, cyano, amino, —C(O)OH, —C(O)$NH_2$, (1-2C)alkoxy, (1-2C)alkyl, (3-4C)cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C)alkyl, —N($R_f$)C(O)-(1-2C)alkyl, —S(O)$_2$NH(1-2C)alkyl, —S(O)$_2$N[(1-2C)alkyl]$_2$, or —NHSO$_2$-(1-2C)alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl or (1-2C)alkoxy;

(47) $R_c$ is selected from hydrogen, halo, cyano, —C(O)$NH_2$, (1-4C)alkyl,

—[$CH_2$]$_{0-1}$-(1-2C)alkoxy,
—[$CH_2$]$_{0-1}$-(3-6C)cycloalkoxy,
—[$CH_2$]$_{0-1}$—C(O)$NH_2$,
—[$CH_2$]$_{0-1}$—C(O)NH(1-2C)alkyl,
—[$CH_2$]$_{0-1}$—C(O)N[(1-2C)alkyl]$_2$,
—[$CH_2$]$_{0-1}$—N H(1-2C)alkyl,
—[$CH_2$]$_{0-1}$—N[(1-2C)alkyl]$_2$,
—[$CH_2$]$_{0-1}$—S(O)$_q$-(1-2C)alkyl (wherein q is 0, 1 or 2),
—[$CH_2$]$_{0-1}$—C(O)(1-2C)alkyl,
—[$CH_2$]$_{0-1}$—C(O)O-(1-2C)alkyl,
—[$CH_2$]$_{0-1}$—N(H)C(O)-(1-2C)alkyl,
—[$CH_2$]$_{0-1}$—S(O)$_2$NH(1-2C)alkyl,
—[$CH_2$]$_{0-1}$—S(O)$_2$N[(1-2C)alkyl]$_2$,
—[$CH_2$]$_{0-1}$—N(H)SO$_2$-(1-2C)alkyl, a group of the formula:

—$Y_2$—[$CH_2$]$_{0-1}$—$Z_2$ wherein $Y_2$ is absent, —O—, —NH—, —NMe-, —S—, —S(O)— or —S(O)$_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —C(O)$NH_2$, (1-2C)alkoxy, or (3-4C)cycloalkoxy; and $Z_2$ is optionally substituted by one or more substituents selected from: halo, hydroxy, cyano, amino, —C(O)OH, —C(O)$NH_2$, (1-2C)alkoxy, (1-2C)alkyl, (3-4C)cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C)alkyl, —N($R_f$)C(O)-(1-2C)alkyl, —S(O)$_2$NH(1-2C)alkyl, —S(O)$_2$N[(1-2C)alkyl]$_2$, or —NHSO$_2$-(1-2C)alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl or (1-2C)alkoxy;

(48) $R_c$ is selected from hydrogen, halo, cyano, —C(O)$NH_2$, (1-4C)alkyl,

—[$CH_2$]$_{0-2}$-(1-4C)alkoxy,
—[$CH_2$]$_{0-2}$-(3-6C)cycloalkoxy,
—[$CH_2$]$_{0-2}$—C(O)$NH_2$,
—[$CH_2$]$_{0-2}$—C(O)NH(1-4C)alkyl,
—[$CH_2$]$_{0-2}$—C(O)N[(1-4C)alkyl]$_2$,
—[$CH_2$]$_{0-2}$—NH(1-4C)alkyl,
—[$CH_2$]$_{0-2}$—N [(1-4C)alkyl]2,
—[$CH_2$]$_{0-2}$—S(O)$_q$-(1-4C)alkyl (wherein q is 0, 1 or 2),
—[$CH_2$]$_{0-2}$—C(O)(1-4C)alkyl,
—[$CH_2$]$_{0-2}$—C(O)O-(1-4C)alkyl,
—[$CH_2$]$_{0-2}$—N(H)C(O)-(1-4C)alkyl,
—[$CH_2$]$_{0-2}$—S(O)$_2$NH(1-4C)alkyl,
—[$CH_2$]$_{0-2}$—S(O)$_2$N[(1-4C)alkyl]$_2$,
—[$CH_2$]$_{0-2}$—N(H)SO$_2$-(1-4C)alkyl, a group of the formula:

—$Y_2$—[$CH_2$]$_{0-2}$—$Z_2$ wherein $Y_2$ is absent, —O—, —NH—, —NMe-, —S—, —S(O)— or —S(O)$_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —C(O)$NH_2$, or (1-2C)alkoxy; and $Z_2$ is optionally substituted by one or more substituents selected from: halo, hydroxy, cyano, amino, (1-2C)alkoxy, (1-2C)alkyl, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, or —C(O)O-(1-2C)alkyl, and wherein any (1-2C)alkoxy or (1-2C)alkyl group is optionally substituted by one or more substituents selected from halo, cyano, hydroxy or (1-2C)alkoxy;

(49) $R_c$ is selected from hydrogen, halo, cyano, —C(O)$NH_2$, (1-4C)alkyl,

—[$CH_2$]$_{0-1}$-(1-4C)alkoxy,
—[$CH_2$]$_{0-1}$-(3-6C)cycloalIkoxy,
—[$CH_2$]$_{0-1}$—C(O)$NH_2$,
—[$CH_2$]$_{0-1}$—C(O)NH(1-4C)alkyl,
—[$CH_2$]$_{0-1}$—C(O)N[(1-4C)alkyl]$_2$,
—[$CH_2$]$_{0-1}$—N H(1-4C)alkyl,
—[$CH_2$]$_{0-1}$—N[(1-4C)alkyl]$_2$,
—[$CH_2$]$_{0-1}$—S(O)$_q$-(1-4C)alkyl (wherein q is 0, 1 or 2),
—[$CH_2$]$_{0-1}$—C(O)(1-4C)alkyl,
—[$CH_2$]$_{0-1}$—C(O)O-(1-4C)alkyl,
—[$CH_2$]$_{0-1}$—N(H)C(O)-(1-4C)alkyl,
—[$CH_2$]$_{0-1}$—S(O)$_2$NH(1-4C)alkyl,
—[$CH_2$]$_{0-1}$—S(O)$_2$N[(1-4C)alkyl]$_2$,
—[$CH_2$]$_{0-1}$—N(H)SO$_2$-(1-4C)alkyl, a group of the formula:

—$Y_2$—[$CH_2$]$_{0-1}$—$Z_2$ wherein $Y_2$ is absent, —O—, —NH—, —NMe-, —S—, —S(O)— or —S(O)$_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —C(O)$NH_2$, or (1-2C)alkoxy; and $Z_2$ is optionally substituted by one or more substituents selected from: halo, hydroxy, cyano, amino, (1-2C)alkoxy, (1-2C)alkyl, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, or —C(O)O-(1-2C)alkyl, and wherein any (1-2C)alkoxy or (1-2C)alkyl group is optionally substituted by one or more substituents selected from halo, cyano, hydroxy or (1-2C)alkoxy;

(50) $R_c$ is selected from hydrogen, halo, cyano, (1-4C) alkyl, (1-4C)alkoxy, a group of the formula:

$$—Y_2—[CH_2]_{0-1}—Z_2$$

wherein $Y_2$ is absent or —O—; and $Z_2$ is (3-6C)cycloalkyl or phenyl;

and wherein:

any alkyl or alkoxy substituent group is optionally substituted by one or more substituents selected from halo, hydroxy, cyano, amino, —C(O)OH, —C(O)$NH_2$, or (1-2C)alkoxy; and $Z_2$ is optionally substituted by one or more substituents selected from: halo, hydroxy, cyano, amino, (1-2C)alkoxy, (1-2C)alkyl, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, or —C(O)O-(1-2C)alkyl, and wherein any (1-2C)alkoxy or (1-2C)alkyl group is optionally substituted by one or more substituents selected from halo, cyano, hydroxy or (1-2C)alkoxy;

(51) $R_c$ is selected from hydrogen, halo, cyano, (1-4C) alkyl, (1-4C)alkoxy, a group of the formula:

$$—Y_2—[CH_2]_{0-1}—Z_2$$

wherein $Y_2$ is absent or —O—; and $Z_2$ is (3-6C)cycloalkyl or phenyl;

and wherein:

any alkyl or alkoxy substituent group is optionally substituted by one or more substituents selected from halo, hydroxy, cyano, or (1-2C)alkoxy; and $Z_2$ is optionally substituted by one or more substituents selected from: halo, hydroxy, cyano, amino, (1-2C)alkoxy, or (1-2C)alkyl, and wherein any (1-2C)alkoxy or (1-2C)alkyl group is optionally substituted by one or more substituents selected from halo, cyano, hydroxy or (1-2C)alkoxy; (52) $R_c$ is selected from hydrogen, halo, cyano, (1-4C)alkyl, (1-4C)alkoxy, a group of the formula:

$$—Y_2—[CH_2]_{0-1}—Z_2$$

wherein $Y_2$ is absent or —O—; and $Z_2$ is (3-6C)cycloalkyl or phenyl;

and wherein:

any alkyl or alkoxy substituent group is optionally substituted by one or more substituents selected from halo or cyano; and $Z_2$ is optionally substituted by one or more (1-2C)alkyl substituents, and wherein a (1-2C)alkyl group is optionally substituted by one or more hydroxy substituents;

(53) $R_c$ is selected from hydrogen, halo, cyano, (1-2C) alkyl or (1-2C)alkoxy, wherein any alkyl or alkoxy substituent group is optionally substituted by one or more halo substituents;

(54) $R_c$ is selected from hydrogen, halo or (1-2C)alkoxy, wherein an alkoxy substituent group is optionally substituted by one or more halo substituents;

(55) $R_c$ is selected from hydrogen, halo or halo(1-2C) alkoxy,

(56) $R_c$ is selected from hydrogen, halo or (1-2C)alkoxy, wherein an alkoxy substituent group is optionally substituted by one or more fluoro substituents;

(57) $R_c$ is selected from hydrogen, fluoro, chloro, bromo, cyano, methyl, ethyl, methoxy, ethoxy, —O—CH$(CH_3)_2$, —$CH_2CN$, —$CF_3$, —$OCF_3$, —O—$CH_2CF_3$, cyclopropyl, cyclopropoxy, cyclobutoxy, cyclopentoxy, phenyl or 2-hydroxymethylphenyl;

(58) $R_c$ is selected from hydrogen, fluoro, chloro, bromo, cyano, methoxy, ethoxy, —O—CH$(CH_3)_2$, —$CH_2CN$, —$CF_3$, —$OCF_3$, —O—$CH_2CF_3$, cyclopropyl, cyclopropoxy, cyclobutoxy, cyclopentoxy, phenyl or 2-hydroxymethylphenyl;

(59) $R_c$ is selected from hydrogen, fluoro, chloro or —$OCF_3$;

(60) $R_c$ is selected from hydrogen, chloro or —$OCF_3$.

Suitably, in any of the definitions of formula I set out herein, at least one of $R_a$, $R_b$, $R_c$, $R_d$ or $R_e$ is a non-hydrogen substituent. By "non-hydrogen substituent" we mean a substituent selected from any one of the options defined herein for $R_a$, $R_b$, $R_c$, $R_d$ or $R_e$ other than hydrogen. More suitably, one to four of $R_a$, $R_b$, $R_c$, $R_d$ or $R_e$ is/are a non-hydrogen substituent(s). Most suitably, one to three of $R_a$, $R_b$, $R_c$, $R_d$ or $R_e$ is/are a non-hydrogen substituent(s).

Suitably, in any of the definitions of formula I set out herein, up to four of $R_a$, $R_b$, $R_c$, $R_d$ or $R_e$ are hydrogen and the remainder are non-hydrogen substituents (i.e. selected from any one of the options set out herein for $R_a$, $R_b$, $R_c$, $R_d$ or $R_e$ other than hydrogen). More suitably, two to four of $R_a$, $R_b$, $R_c$, $R_d$ or $R_e$ are hydrogen and the remainder are non-hydrogen substituents.

In a particular group of compounds of formula I, if $R_c$ is a group of the formula —$Y_2$—$[CH_2]_{0-3}$—$Z_2$, then $R_b$ and $R_d$ cannot be a group of the formula —$Y_1$—$[CH_2]_{0-3}$—$Z_1$.

In a further group of compounds of formula I, if one or both of $R_e$ and $R_d$ is a group of the formula —$Y_1$—$[CH_2]_{0-3}$—$Z_1$ as defined herein, then $R_c$ cannot be a group of the formula —$Y_2$—$[CH_2]_{0-3}$—$Z_2$.

In a particular group of compounds of formula I:

(i) if $R_c$ is a group of the formula —$Y_2$—$[CH_2]_{0-3}$—$Z_2$ then $R_e$ and $R_d$ cannot be a group of the formula —$Y_1$—$[CH_2]_{0-3}$—$Z_1$; and/or (ii) if one or both of $R_b$ and $R_d$ is a group of the formula —$Y_1$—$[CH_2]_{0-3}$—$Z_1$ as defined herein, then $R_c$ cannot be a group of the formula —$Y_2$—$[CH_2]_{0-3}$—$Z_2$.

In another particular group of compounds of formula I:

(i) if $R_c$ is a group of the formula —$Y_2$—$[CH_2]_{0-3}$—$Z_2$ then $R_e$ and $R_d$ cannot be a group of the formula —$Y_1$—$[CH_2]_{0-3}$—$Z_1$; and (ii) if one of $R_b$ and $R_d$ is a group of the formula —$Y_1$—$[CH_2]_{0-3}$—$Z_1$ as defined herein, then the other cannot be a group of the formula —$Y_1$—$[CH_2]_{0-3}$—$Z_1$ and $R_c$ cannot be a group of the formula —$Y_2$—$[CH_2]_{0-3}$—$Z_2$.

Suitably, in any of the definitions of formula I set out herein, a heteroaryl is a 5- or 6-membered heteroaryl ring comprising one, two or three heteroatoms selected from N, O or S.

Suitably, in any of the definitions of formula I set out herein, a heterocyclyl group is a 4-, 5- or 6-membered heterocyclyl ring comprising one, two or three heteroatoms selected from N, O or S. Most suitably, a heterocyclyl group is a 4-, 5- or 6-membered ring comprising one or two heteroatoms selected from N, O or S [e.g. morpholinyl (e.g. 4-morpholinyl), piperidinyl, piperazinyl or pyrrolidinyl].

Suitably, in any of the definitions of formula I set out herein, $R_1$ is as defined in formula I above or as defined in either paragraph (1) and/or (2) above. In a particular group of compounds of the invention, $R_1$ is as defined in paragraph (1) above. In another particular group of compounds of the invention, $R_1$ is as defined in paragraph (2) above.

Suitably, in any of the definitions of formula I set out herein, Q is as defined in formula I above or is as defined in any one of paragraphs (3) to (14) above.

Suitably, in any of the definitions of formula I set out herein, $R_a$ and $R_e$ are as defined in any one of paragraphs (15) to (26) above. More suitably, $R_a$ and $R_e$ are as defined in any one of paragraphs (16), (21), (22), (23) or (26) above. Even more suitably, $R_a$ and $R_e$ are as defined in any one of paragraphs (21), (22), (23) or (26) above. Most suitably, $R_a$ and $R_e$ are as defined in paragraphs (23) or (26) above.

In a particular group of compounds of formula I, $R_a$ and $R_e$ areas defined in paragraph (16) above, and $R_1$, Q, $R_b$, $R_c$, and $R_d$ are each as defined in formula I above.

In a particular group of compounds of formula I, $R_a$ and $R_e$ are as defined in paragraph (21) above, and $R_1$, Q, $R_b$, $R_c$ and $R_d$ are each as defined in formula I above.

In a particular group of compounds of formula I, $R_a$ and $R_e$ areas defined in paragraph (22) above, and $R_1$, Q, $R_b$, $R_c$ and $R_d$ are each as defined in formula I above.

In a particular group of compounds of formula I, $R_a$ and $R_e$ are as defined in paragraph (23) above, and $R_1$, Q, $R_b$, $R_c$ and $R_d$ are each as defined in formula I above.

In a particular group of compounds of formula I, $R_a$ and $R_e$ areas defined in paragraph (26) above, and $R_1$, Q, $R_b$, $R_c$ and $R_d$ are each as defined in formula I above.

Suitably, in any of the definitions of formula I set out herein, $R_b$ and $R_d$ are as defined in any one of paragraphs (27) to (43) above. More suitably, $R_b$ and $R_d$ are as defined in any one of paragraphs (36), (37), (38), (39), (40), (41), (42) or (43) above. Even more suitably, $R_a$ and $R_e$ are as defined in any one of paragraphs (39), (40), (41), (42) or (43) above. Most suitably, $R_a$ and $R_e$ are as defined in paragraphs (38) or (43) above.

In a particular group of compounds of formula I, $R_b$ and $R_d$ are as defined in paragraph (28) above, and $R_1$, Q, $R_a$, $R_c$ and $R_e$ are each as defined in formula I above.

In a particular group of compounds of formula I, $R_b$ and $R_d$ are as defined in paragraph (30) above, and $R_1$, Q, $R_a$, $R_c$ and $R_e$ are each as defined in formula I above.

In a particular group of compounds of formula I, $R_b$ and $R_d$ areas defined in paragraph (32) above, and $R_1$, Q, $R_a$, $R_c$ and $R_e$ are each as defined in formula I above.

In a particular group of compounds of formula I, $R_b$ and $R_d$ are as defined in paragraph (34) above, and $R_1$, Q, $R_a$, $R_c$ and $R_e$ are each as defined in formula I above.

In a particular group of compounds of formula I, $R_b$ and $R_d$ areas defined in paragraph (36) above, and $R_1$, Q, $R_a$, $R_c$ and $R_e$ are each as defined in formula I above.

In a particular group of compounds of formula I, $R_b$ and $R_d$ are as defined in paragraph (37) above, and $R_1$, Q, $R_a$, $R_c$ and $R_e$ are each as defined in formula I above.

In a particular group of compounds of formula I, $R_b$ and $R_d$ areas defined in paragraph (38) above, and $R_1$, Q, $R_a$, $R_c$ and $R_e$ are each as defined in formula I above.

In a particular group of compounds of formula I, $R_b$ and $R_d$ are as defined in paragraph (39) above, and $R_1$, Q, $R_a$, $R_c$ and $R_e$ are each as defined in formula I above.

In a particular group of compounds of formula I, $R_b$ and $R_d$ areas defined in paragraph (40) above, and $R_1$, Q, $R_a$, $R_c$ and $R_e$ are each as defined in formula I above.

In a particular group of compounds of formula I, $R_b$ and $R_d$ are as defined in paragraph (41) above, and $R_1$, Q, $R_a$, $R_c$ and $R_e$ are each as defined in formula I above.

In a particular group of compounds of formula I, $R_b$ and $R_d$ areas defined in paragraph (42) above, and $R_1$, Q, $R_a$, $R_c$ and $R_e$ are each as defined in formula I above.

In a particular group of compounds of formula I, $R_b$ and $R_d$ are as defined in paragraph (43) above, and $R_1$, Q, $R_a$, $R_c$ and $R_e$ are each as defined in formula I above.

Suitably, in any of the definitions of formula I set out herein, $R_c$ is as defined in any one of paragraphs (44) to (60) above. More suitably, $R_c$ is as defined in any one of paragraphs (51), (52), (53), (54), (55), (56), (57), (58), (59) or (60) above. Even more suitably, $R_c$ is as defined in any one of paragraphs (56), (56), (57), (58), (59) or (60) above. Most suitably, $R_c$ is as defined in paragraphs (58), (59) or (60) above.

In a particular group of compounds of formula I, $R_c$ is as defined in paragraph (45) above, and $R_1$, Q, $R_a$, $R_b$, $R_d$ and $R_e$ are each as defined in formula I above.

In a particular group of compounds of formula I, $R_c$ is as defined in paragraph (47) above, and $R_1$, Q, $R_a$, $R_b$, $R_d$ and $R_e$ are each as defined in formula I above.

In a particular group of compounds of formula I, $R_c$ is as defined in paragraph (49) above, and $R_1$, Q, $R_a$, $R_b$, $R_d$ and $R_e$ are each as defined in formula I above.

In a particular group of compounds of formula I, $R_c$ is as defined in paragraph (51) above, and $R_1$, Q, $R_a$, $R_b$, $R_d$ and $R_e$ are each as defined in formula I above.

In a particular group of compounds of formula I, $R_e$ is as defined in paragraph (53) above, and $R_1$, Q, $R_a$, $R_b$, $R_d$ and $R_e$ are each as defined in formula I above.

In a particular group of compounds of formula I, $R_c$ is as defined in paragraph (55) above, and $R_1$, Q, $R_a$, $R_b$, $R_d$ and $R_e$ are each as defined in formula I above.

In a particular group of compounds of formula I, $R_c$ is as defined in paragraph (56) above, and $R_1$, Q, $R_a$, $R_b$, $R_d$ and $R_e$ are each as defined in formula I above.

In a particular group of compounds of formula I, $R_c$ is as defined in paragraph (57) above, and $R_1$, Q, $R_a$, $R_b$, $R_d$ and $R_e$ are each as defined in formula I above.

In a particular group of compounds of formula I, $R_e$ is as defined in paragraph (58) above, and $R_1$, Q, $R_a$, $R_b$, $R_d$ and $R_e$ are each as defined in formula I above.

In a particular group of compounds of formula I, $R_c$ is as defined in paragraph (59) above, and $R_1$, Q, $R_a$, $R_b$, $R_d$ and $R_e$ are each as defined in formula I above.

In a particular group of compounds of formula I, $R_c$ is as defined in paragraph (60) above, and $R_1$, Q, $R_a$, $R_b$, $R_d$ and $R_e$ are each as defined in formula I above.

In a particular group of compounds of formula I defined herein:

$R_1$ and Q are both as defined in formula I above;

$R_a$ and $R_e$ are both as defined in paragraph (23) above;

$R_b$ and $R_d$ are both as defined in paragraph (27) above; and $R_e$ is as defined in paragraph (44) above.

In a particular group of compounds of formula I defined herein:

$R_1$ and Q are both as defined in formula I above;

$R_a$ and $R_e$ are both as defined in paragraph (23) above;

$R_b$ and $R_d$ are both as defined in paragraph (28) above; and $R_e$ is as defined in paragraph (45) above.

In a particular group of compounds of formula I defined herein:

$R_1$ and Q are both as defined in formula I;

$R_a$ and $R_e$ are both as defined in paragraph (23) above;

$R_b$ and $R_d$ are both as defined in paragraph (29) above; and $R_e$ is as defined in paragraph (46) above.

In a particular group of compounds of formula I defined herein:

$R_1$ and Q are both as defined in formula I;

$R_a$ and $R_e$ are both as defined in paragraph (23) above;

$R_b$ and $R_d$ are both as defined in paragraph (30) above; and $R_e$ is as defined in paragraph (47) above.

In a particular group of compounds of formula I defined herein:

$R_1$ and Q are both as defined in formula I;

$R_a$ and $R_e$ are both as defined in paragraph (23) above;

$R_b$ and $R_d$ are both as defined in paragraph (31) above; and $R_e$ is as defined in paragraph (48) above.

In a particular group of compounds of formula I defined herein:

$R_1$ and Q are both as defined in formula I;

$R_a$ and $R_e$ are both as defined in paragraph (23) above;

$R_b$ and $R_d$ are both as defined in paragraph (32) above; and $R_e$ is as defined in paragraph (49) above.

In a particular group of compounds of formula I defined herein:

$R_1$ and Q are both as defined in formula I;

$R_a$ and $R_e$ are both as defined in paragraph (23) above;

$R_b$ and $R_d$ are both as defined in paragraph (33) above; and $R_e$ is as defined in paragraph (50) above.

In a particular group of compounds of formula I defined herein:

$R_1$ and Q are both as defined in formula I;

$R_a$ and $R_e$ are both as defined in paragraph (23) above;

$R_b$ and $R_d$ are both as defined in paragraph (34) above; and $R_e$ is as defined in paragraph (51) above.

In a particular group of compounds of formula I defined herein:

$R_1$ and Q are both as defined in formula I;

$R_a$ and $R_e$ are both as defined in paragraph (23) above;

$R_b$ and $R_d$ are both as defined in paragraph (35) above; and $R_e$ is as defined in paragraph (52) above.

In a particular group of compounds of formula I defined herein:

$R_1$ and Q are both as defined in formula I;

$R_a$ and $R_e$ are both as defined in paragraph (23) above;

$R_b$ and $R_d$ are both as defined in paragraph (36) above; and $R_e$ is as defined in paragraph (53) above.

In a particular group of compounds of formula I defined herein:

$R_1$ and Q are both as defined in formula I;

$R_d$ and $R_e$ are both as defined in paragraph (26) above;

$R_b$ and $R_d$ are both as defined in paragraph (37) above; and $R_e$ is as defined in paragraph (54) above.

In a particular group of compounds of formula I defined herein:

$R_1$ and Q are both as defined in formula I;

$R_a$ and $R_e$ are both as defined in paragraph (26) above;

$R_d$ and $R_d$ are both as defined in paragraph (38) above; and $R_e$ is as defined in paragraph (54) above.

In a particular group of compounds of formula I defined herein:

$R_1$ and Q are both as defined in formula I;

$R_a$ and $R_e$ are both as defined in paragraph (26) above;

$R_d$ and $R_d$ are both as defined in paragraph (39) above; and $R_e$ is as defined in paragraph (58) above.

In a particular group of compounds of formula I defined herein:

$R_1$ and Q are both as defined in formula I;

$R_a$ and $R_e$ are both as defined in paragraph (26) above;

$R_d$ and $R_d$ are both as defined in paragraph (41) above; and $R_e$ is as defined in paragraph (58) above.

In a particular group of compounds of formula I defined herein:

$R_1$ and Q are both as defined in formula I;

$R_a$ and $R_e$ are both as defined in paragraph (26) above;

$R_d$ and $R_d$ are both as defined in paragraph (40) above; and $R_e$ is as defined in paragraph (59) above.

In a particular group of compounds of formula I defined herein:

$R_1$ and Q are both as defined in formula I;

$R_a$ and $R_e$ are both as defined in paragraph (26) above;

$R_d$ and $R_d$ are both as defined in paragraph (43) above; and $R_e$ is as defined in paragraph (59) above.

In a particular group of compounds of formula I defined herein:

$R_1$ and Q are both as defined in formula I;

$R_a$ and $R_e$ are both as defined in paragraph (26) above;

$R_b$ and $R_d$ are both as defined in paragraph (40) above; and $R_e$ is as defined in paragraph (60) above.

In a particular group of compounds of formula I defined herein:

$R_1$ and Q are both as defined in formula I;

$R_a$ and $R_e$ are both as defined in paragraph (26) above;

$R_b$ and $R_d$ are both as defined in paragraph (43) above; and $R_e$ is as defined in paragraph (60) above.

In a particular group of compounds of the invention, the compound is a compound of formula I defined herein in which Q is as defined in paragraph (11) above, i.e. the compounds have the formula Ic shown below, or a pharmaceutically acceptable salt thereof:

(Ic)

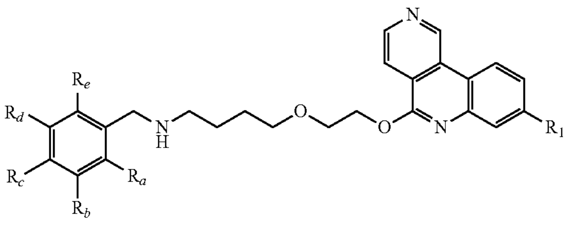

wherein $R_1$, $R_a$, $R_b$, $R_c$, $R_d$ and $R_e$ each have any one of the definitions set out herein.

In a particular group of compounds of formula Ic:

$R_1$ is selected from —C(O)OH or —C(O)$NH_2$;

$R_a$ and $R_e$ are both as defined in paragraph (23) above;

$R_b$ and $R_d$ are both as defined in paragraph (36) above; and $R_c$ is as defined in paragraph (50) above.

In a particular group of compounds of formula Ic:

$R_1$ is selected from —C(O)OH or —C(O)$NH_2$;

$R_a$ and $R_e$ are both as defined in paragraph (26) above;

$R_b$ and $R_d$ are both as defined in paragraph (38) above; and $R_c$ is as defined in paragraph (54) above.

In a particular group of compounds of formula Ic:

$R_1$ is selected from —C(O)OH or —C(O)$NH_2$;

$R_a$ and $R_e$ are both as defined in paragraph (20) above;

$R_d$ and $R_d$ are both as defined in paragraph (40) above; and $R_c$ is as defined in paragraph (58) above.

In a particular group of compounds of formula Ic:

$R_1$ is —C(O)OH;

$R_a$ and $R_e$ are both as defined in paragraph (20) above;

$R_b$ and $R_d$ are both as defined in paragraph (43) above; and $R_c$ is as defined in paragraph (60) above.

In a particular group of compounds of the invention, the compound is a compound of formula I defined herein in which Q is as defined in paragraph (11) above and $R_a$ and $R_e$ are as defined in paragraph (20) above, i.e. the compounds have the formula Id shown below, or a pharmaceutically acceptable salt thereof:

(Id)

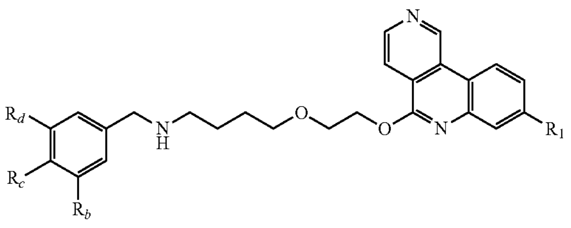

wherein $R_1$, $R_b$, $R_c$ and $R_d$ each have any one of the definitions set out hereinbefore.

In a particular group of compounds of formula Id:

$R_1$ is selected from —C(O)OH or —C(O)$NH_2$;

$R_b$ and $R_d$ are both as defined in paragraph (36) above; and $R_c$ is as defined in paragraph (50) above.

In a particular group of compounds of formula Id:

$R_1$ is selected from —C(O)OH or —C(O)$NH_2$;

$R_b$ and $R_d$ are both as defined in paragraph (38) above; and $R_c$ is as defined in paragraph (54) above.

In a particular group of compounds of formula Id:

$R_1$ is selected from —C(O)OH or —C(O)$NH_2$;

$R_b$ and $R_d$ are both as defined in paragraph (40) above; and $R_c$ is as defined in paragraph (58) above.

In a particular group of compounds of formula Id:

In a particular group of compounds of formula I, Ic or Id defined herein $R_b$ and $R_d$ are selected from hydrogen or fluoro.

In a particular group of compounds of formula I, Ic or Id defined herein $R_b$ and $R_d$ are hydrogen.

In a particular group of compounds of formula I, Ic or Id defined herein $R_b$ and $R_d$ are fluoro.

In a particular group of compounds of formula I, Ic or Id defined herein $R_c$ is —$OCF_3$.

In a particular group of compounds of formula I, Ic or Id defined herein $R_b$ and $R_d$ are selected from hydrogen or fluoro and $R_c$ is —$OCF_3$.

In a particular group of compounds of formula I, Ic or Id defined herein $R_b$ and $R_d$ are hydrogen and $R_c$ is —$OCF_3$.

In a particular group of compounds of formula I, Ic or Id defined herein $R_d$ and $R_d$ are fluoro and $R_c$ is —$OCF_3$.

Particular compounds of the present invention include any of the compounds described in the example section of the present application, or a pharmaceutically acceptable salt, hydrate or solvate thereof, and, in particular, any of the following:

5-((2-(4-(((2-chloro-[1,1'-biphenyl]-4-yl)methyl)amino)butoxy)ethyl)amino)benzo[c][2,6]naphthyridine-8-carboxamide;

5-((2-(4-((3-chloro-4-(trifluoromethoxy)benzyl)amino)butoxy)ethyl)amino)benzo[c][2,6]naphthyridine-8-carboxamide;

5-((2-(4-((3-chlorobenzyl)amino)butoxy)ethyl)amino)benzo[c][2,6]naphthyridine-8-carboxamide;

5-((2-(4-(((2-chloro-2'-(hydroxymethyl)-[1,1'-biphenyl]-4-yl)methyl)amino)butoxy)ethyl)amino)benzo[c][2,6]naphthyridine-8-carboxamide;

5-((2-(4-((3-fluoro-4-(trifluoromethoxy)benzyl)amino)butoxy)ethyl)amino)benzo[c][2,6]naphthyridine-8-carboxamide;

5-((2-(4-((3-chloro-4-(trifluoromethyl)benzyl)amino)butoxy)ethyl)amino)benzo[c][2,6]naphthyridine-8-carboxamide;

5-((2-(4-((3-chloro-4-cyclopropylbenzyl)amino)butoxy)ethyl)amino)benzo[c][2,6]naphthyridine-8-carboxamide;

5-((2-(4-((3-chloro-4-cyclobutoxybenzyl)amino)butoxy)ethyl)amino)benzo[c][2,6]naphthyridine-8-carboxamide;

5-((2-(4-((3-chloro-4-(cyclopentyloxy)benzyl)amino)butoxy)ethyl)amino)benzo[c][2,6]naphthyridine-8-carboxamide;

5-((2-(4-((3-chloro-4-cyclopropoxybenzyl)amino)butoxy)ethyl)amino)benzo[c][2,6]naphthyridine-8-carboxamide;

5-((2-(4-((3-(2-hydroxyethyl)benzyl)amino)butoxy)ethyl)amino)benzo[c][2,6]naphthyridine-8-carboxamide;

5-((2-(4-((3-chloro-4-(trifluoromethoxy)benzyl)amino)butoxy)ethyl)amino)benzo[c][2,6]naphthyridine-8-carboxylic acid;

5-(2-(4-((3-chloro-4-(trifluoromethoxy)benzyl)amino)butoxy)ethoxy)benzo[c][2,6]naphthyridine-8-carboxamide;

5-(2-(4-((3-chlorobenzyl)amino)butoxy)ethoxy)benzo[c][2,6]naphthyridine-8-carboxamide;

5-((2-(4-((3-(2-hydroxyethoxy)benzyl)amino)butoxy)ethyl)amino)benzo[c][2,6]naphthyridine-8-carboxamide;

5-((2-(4-((3-cyano-4-cyclopropylbenzyl)amino)butoxy)ethyl)amino)benzo[c][2,6]naphthyridine-8-carboxamide;

5-((2-(4-((3-chloro-5-(hydroxymethyl)benzyl)amino)butoxy)ethyl)amino)benzo[c][2,6]naphthyridine-8-carboxamide;

5-((2-(4-((3-cyano-4-(trifluoromethoxy)benzyl)amino)butoxy)ethyl)amino)benzo[c][2,6]naphthyridine-8-carboxamide;

5-((2-(4-((3-(hydroxymethyl)benzyl)amino)butoxy)ethyl)amino)benzo[c][2,6]naphthyridine-8-carboxamide;

5-((2-(4-((3-(cyanomethyl)benzyl)amino)butoxy)ethyl)amino)benzo[c][2,6]naphthyridine-8-carboxamide;

5-((2-(4-((3-cyano-4-cyclobutoxybenzyl)amino)butoxy)ethyl)amino)benzo[c][2,6]naphthyridine-8-carboxamide;

5-((2-(4-((3-(hydroxymethyl)-4-(trifluoromethoxy)benzyl)amino)butoxy)ethyl)amino)benzo[c][2,6]naphthyridine-8-carboxamide;

5-((2-(4-((4-cyclobutoxy-3-(hydroxymethyl)benzyl)amino)butoxy)ethyl)amino)benzo[c][2,6]naphthyridine-8-carboxamide;

5-((2-(4-((4-chloro-3-(2-hydroxyethoxy)benzyl)amino)butoxy)ethyl)amino)benzo[c][2,6]naphthyridine-8-carboxamide;

5-((2-(4-((3-chloro-4-cyclobutoxybenzyl)amino)butoxy)ethyl)amino)benzo[c][2,6]naphthyridine-8-carboxylic acid;

5-((2-(4-((3-(2-hydroxyethoxy)benzyl)amino)butoxy)ethyl)amino)benzo[c][2,6]naphthyridine-8-carboxylic acid;

5-((2-(4-((3-(cyanomethyl)benzyl)amino)butoxy)ethyl)amino)benzo[c][2,6]naphthyridine-8-carboxylic acid;

5-((2-(4-((3-fluoro-4-(trifluoromethoxy)benzyl)amino)butoxy)ethyl)amino)benzo[c][2,6]naphthyridine-8-carboxylic acid;

5-((2-(4-((4-cyclopropyl-3-(hydroxymethyl)benzyl)amino)butoxy)ethyl)amino)benzo[c][2,6]naphthyridine-8-carboxamide;

5-((2-(4-((3-chlorobenzyl)amino)butoxy)ethyl)amino)benzo[c][2,6]naphthyridine-8-carboxylic acid;

5-((2-(4-((3-chloro-5-(hydroxymethyl)benzyl)amino)butoxy)ethyl)amino)benzo[c][2,6]naphthyridine-8-carboxylic acid;

5-((2-(4-((3-(2-hydroxyethyl)benzyl)amino)butoxy)ethyl)amino)benzo[c][2,6]naphthyridine-8-carboxylic acid;

5-((2-(4-((3-chloro-4-cyclopropylbenzyl)amino)butoxy)ethyl)amino)benzo[c][2,6]naphthyridine-8-carboxylic acid;
5-((2-(4-((3-chloro-4-cyclopropoxybenzyl)amino)butoxy)ethyl)amino)benzo[c][2,6]naphthyridine-8-carboxylic acid;
5-((2-(4-((3-(2-hydroxyethoxy)-4-(trifluoromethoxy)benzyl)amino)butoxy)ethyl)amino)benzo[c][2,6]naphthyridine-8-carboxamide;
5-((2-(4-((4-cyclobutoxy-3-(2-hydroxyethoxy)benzyl)amino)butoxy)ethyl)amino)benzo[c][2,6]naphthyridine-8-carboxamide
5-((2-(4-((3-(hydroxymethyl)benzyl)amino)butoxy)ethyl)amino)benzo[c][2,6]naphthyridine-8-carboxylic acid;
5-((2-(4-((3-(2-hydroxyethoxy)-4-(trifluoromethyl)benzyl)amino)butoxy)ethyl)amino)benzo[c][2,6]naphthyridine-8-carboxamide;
5-((2-(4-((3-cyano-4-cyclopropylbenzyl)amino)butoxy)ethyl)amino)benzo[c][2,6]naphthyridine-8-carboxylic acid;
5-((2-(4-((3-chloro-5-(cyanomethyl)benzyl)amino)butoxy)ethyl)amino)benzo[c][2,6]naphthyridine-8-carboxamide;
5-((2-(4-((3-cyano-4-cyclobutoxybenzyl)amino)butoxy)ethyl)amino)benzo[c][2,6]naphthyridine-8-carboxylic acid;
5-((2-(4-((3-chloro-5-(cyanomethyl)benzyl)amino)butoxy)ethyl)amino)benzo[c][2,6]naphthyridine-8-carboxylic acid;
5-((2-(4-((3-(aminomethyl)-5-chlorobenzyl)amino)butoxy)ethyl)amino)benzo[c][2,6]naphthyridine-8-carboxamide;
5-(2-(4-((3-chloro-5-(cyanomethyl)benzyl)amino)butoxy)ethoxy)benzo[c][2,6]naphthyridine-8-carboxamide;
5-(2-(4-((3-chloro-4-cyclobutoxybenzyl)amino)butoxy)ethoxy)benzo[c][2,6]naphthyridine-8-carboxamide;
5-(2-(4-((3-chloro-4-(trifluoromethoxy)benzyl)amino)butoxy)ethoxy)benzo[c][2,6]naphthyridine-8-carboxylic acid;
5-((2-(4-((3-(hydroxymethyl)-5-methylbenzyl)amino)butoxy)ethyl)amino)benzo[c][2,6]naphthyridine-8-carboxamide;
5-((2-(4-((2-chloro-5-(hydroxymethyl)benzyl)amino)butoxy)ethyl)amino)benzo[c][2,6]naphthyridine-8-carboxamide;
5-((2-(4-((3-(hydroxymethyl)-5-(trifluoromethyl)benzyl)amino)butoxy)ethyl)amino)benzo[c][2,6]naphthyridine-8-carboxamide;
5-((2-(4-((4-chloro-3-(hydroxymethyl)benzyl)amino)butoxy)ethyl)amino)benzo[c][2,6]naphthyridine-8-carboxamide;
5-(2-(4-((3-fluoro-4-(trifluoromethoxy)benzyl)amino)butoxy)ethoxy)benzo[c][2,6]naphthyridine-8-carboxamide;
5-(2-(4-((3-cyano-4-cyclopropylbenzyl)amino)butoxy)ethoxy)benzo[c][2,6]naphthyridine-8-carboxamide;
5-(2-(4-((4-cyclobutoxy-3-(hydroxymethyl)benzyl)amino)butoxy)ethoxy)benzo[c][2,6]naphthyridine-8-carboxamide;
5-(2-(4-((3-chloro-5-(hydroxymethyl)benzyl)amino)butoxy)ethoxy)benzo[c][2,6]naphthyridine-8-carboxamide;
5-(3-(4-((3-chloro-4-(trifluoromethoxy)benzyl)amino)butoxy)azetidin-1-yl)benzo[c][2,6]naphthyridine-8-carboxylic acid;
5-((2-(4-((3-fluoro-5-(hydroxymethyl)benzyl)amino)butoxy)ethyl)amino)benzo[c][2,6]naphthyridine-8-carboxamide;
5-((2-(4-((3-(cyanomethyl)-5-(trifluoromethyl)benzyl)amino)butoxy)ethyl)amino)benzo[c][2,6]naphthyridine-8-carboxamide;
5-((2-(4-((3-(cyanomethyl)-5-fluorobenzyl)amino)butoxy)ethyl)amino)benzo[c][2,6]naphthyridine-8-carboxamide;
5-((2-(4-((3-(cyanomethyl)-5-methylbenzyl)amino)butoxy)ethyl)amino)benzo[c][2,6]naphthyridine-8-carboxamide;
5-((2-(4-((2-chloro-5-(cyanomethyl)benzyl)amino)butoxy)ethyl)amino)benzo[c][2,6]naphthyridine-8-carboxamide;
5-((2-(4-((4-cyano-3-cyclopropylbenzyl)amino)butoxy)ethyl)amino)benzo[c][2,6]naphthyridine-8-carboxamide;
5-((2-(4-((3-chloro-4-(cyanomethyl)benzyl)amino)butoxy)ethyl)amino)benzo[c][2,6]naphthyridine-8-carboxamide;
5-((2-(4-((3-(hydroxymethyl)-4-(2,2,2-trifluoroethoxy)benzyl)amino)butoxy)ethyl)amino)benzo[c][2,6]naphthyridine-8-carboxamide;
5-((2-(4-((3-(hydroxymethyl)-4-isopropoxybenzyl)amino)butoxy)ethyl)amino)benzo[c][2,6]naphthyridine-8-carboxamide;
5-((2-(4-((4-(cyclopentyloxy)-3-(hydroxymethyl)benzyl)amino)butoxy)ethyl)amino)benzo[c][2,6]naphthyridine-8-carboxamide;
5-((2-(4-((4-chloro-3-(cyanomethyl)benzyl)amino)butoxy)ethyl)amino)benzo[c][2,6]naphthyridine-8-carboxamide;
5-((2-(4-((2-chloro-3-(cyanomethyl)benzyl)amino)butoxy)ethyl)amino)benzo[c][2,6]naphthyridine-8-carboxamide;
5-((2-(4-((2-chloro-3-(hydroxymethyl)benzyl)amino)butoxy)ethyl)amino)benzo[c][2,6]naphthyridine-8-carboxamide;
5-((2-(4-((4-ethoxy-3-(hydroxymethyl)benzyl)amino)butoxy)ethyl)amino)benzo[c][2,6]naphthyridine-8-carboxamide;
5-((2-(4-((3-fluoro-5-(hydroxymethyl)benzyl)amino)butoxy)ethyl)amino)benzo[c][2,6]naphthyridine-8-carboxylic acid;
5-((2-(4-((3-(hydroxymethyl)-5-(trifluoromethyl)benzyl)amino)butoxy)ethyl)amino)benzo[c][2,6]naphthyridine-8-carboxylic acid;
5-((2-(4-((3-(cyanomethyl)-5-fluorobenzyl)amino)butoxy)ethyl)amino)benzo[c][2,6]naphthyridine-8-carboxylic acid;
5-((2-(4-((3-(cyanomethyl)-5-(trifluoromethyl)benzyl)amino)butoxy)ethyl)amino)benzo[c][2,6]naphthyridine-8-carboxylic acid;
5-((2-(4-((3-(cyanomethyl)-5-methylbenzyl)amino)butoxy)ethyl)amino)benzo[c][2,6]naphthyridine-8-carboxylic acid;
5-(2-(4-((3-fluoro-5-(hydroxymethyl)benzyl)amino)butoxy)ethoxy)benzo[c][2,6]naphthyridine-8-carboxylic acid;
5-(2-(4-((3-(hydroxymethyl)-5-(trifluoromethyl)benzyl)amino)butoxy)ethoxy)benzo[c][2,6]naphthyridine-8-carboxylic acid;
5-(2-(4-((3-chloro-5-(cyanomethyl)benzyl)amino)butoxy)ethoxy)benzo[c][2,6]naphthyridine-8-carboxylic acid;
5-(2-(4-((3-(cyanomethyl)-5-(trifluoromethyl)benzyl)amino)butoxy)ethoxy)benzo[c][2,6]naphthyridine-8-carboxylic acid;
5-(2-(4-((3-(cyanomethyl)-5-methylbenzyl)amino)butoxy)ethoxy)benzo[c][2,6]naphthyridine-8-carboxylic acid;
5-(3-(4-((3-(cyanomethyl)-5-fluorobenzyl)amino)butoxy)azetidin-1-yl)benzo[c][2,6]naphthyridine-8-carboxylic acid;
5-(3-(4-((3-(cyanomethyl)-5-methylbenzyl)amino)butoxy)azetidin-1-yl)benzo[c][2,6]naphthyridine-8-carboxylic acid;
5-(3-(4-((3-chloro-5-(hydroxymethyl)benzyl)amino)butoxy)azetidin-1-yl)benzo[c][2,6]naphthyridine-8-carboxylic acid;

5-(3-(4-((3-chloro-5-(hydroxymethyl)benzyl)amino)butoxy)azetidin-1-yl)benzo[c][2,6]naphthyridine-8-carboxamide;

5-(3-(4-((3-fluoro-5-(hydroxymethyl)benzyl)amino)butoxy)azetidin-1-yl)benzo[c][2,6]naphthyridine-8-carboxylic acid;

5-(3-(4-((3-fluoro-5-(hydroxymethyl)benzyl)amino)butoxy)azetidin-1-yl)benzo[c][2,6]naphthyridine-8-carboxamide;

5-(3-(4-((3-(hydroxymethyl)-5-(trifluoromethyl)benzyl)amino)butoxy)azetidin-1-yl)benzo[c][2,6]naphthyridine-8-carboxamide;

5-(3-(4-((3-fluoro-4-(trifluoromethoxy)benzyl)amino)butoxy)azetidin-1-yl)benzo[c][2,6]naphthyridine-8-carboxamide;

5-((2-(4-((3-(hydroxymethyl)-5-(trifluoromethoxy)benzyl)amino)butoxy)ethyl)amino)benzo[c][2,6]naphthyridine-8-carboxamide;

5-((2-(4-((3-(hydroxymethyl)-4-(trifluoromethyl)benzyl)amino)butoxy)ethyl)amino)benzo[c][2,6]naphthyridine-8-carboxamide;

(S)-5-((1-(4-((3-chloro-4-(trifluoromethoxy)benzyl)amino)butoxy)propan-2-yl)amino)benzo[c][2,6]naphthyridine-8-carboxylic acid;

5-((2-(4-((3-(cyanomethyl)-5-methoxybenzyl)amino)butoxy)ethyl)amino)benzo[c][2,6]naphthyridine-8-carboxamide;

(R)-5-((1-(4-((3-chloro-4-(trifluoromethoxy)benzyl)amino)butoxy)propan-2-yl)amino)benzo[c][2,6]naphthyridine-8-carboxylic acid;

5-((2-(4-((3-(cyanomethyl)-5-(trifluoromethoxy)benzyl)amino)butoxy)ethyl)amino)benzo[c][2,6]naphthyridine-8-carboxamide;

5-(2-(4-((3-chloro-5-(hydroxymethyl)benzyl)amino)butoxy)ethoxy)benzo[c][2,6]naphthyridine-8-carboxylic acid;

5-(2-(4-((3-(hydroxymethyl)-5-(trifluoromethyl)benzyl)amino)butoxy)ethoxy)benzo[c][2,6]naphthyridine-8-carboxamide;

5-(2-(4-((3-(cyanomethyl)-5-fluorobenzyl)amino)butoxy)ethoxy)benzo[c][2,6]naphthyridine-8-carboxamide;

5-(2-(4-((3-fluoro-4-(trifluoromethoxy)benzyl)amino)butoxy)ethoxy)benzo[c][2,6]naphthyridine-8-carboxylic acid;

5-(2-(4-((3-fluoro-5-(hydroxymethyl)benzyl)amino)butoxy)ethoxy)benzo[c][2,6]naphthyridine-8-carboxamide;

5-(2-(4-((3-(cyanomethyl)-5-fluorobenzyl)amino)butoxy)ethoxy)benzo[c][2,6]naphthyridine-8-carboxylic acid;

5-(2-(4-((3-(cyanomethyl)-5-methylbenzyl)amino)butoxy)ethoxy)benzo[c][2,6]naphthyridine-8-carboxamide;

5-(2-(4-((3-(cyanomethyl)-5-(trifluoromethyl)benzyl)amino)butoxy)ethoxy)benzo[c][2,6]naphthyridine-8-carboxamide;

5-(3-(4-((3-(cyanomethyl)-5-methylbenzyl)amino)butoxy)azetidin-1-yl)benzo[c][2,6]naphthyridine-8-carboxamide;

5-(3-(4-((3-(cyanomethyl)-5-fluorobenzyl)amino)butoxy)azetidin-1-yl)benzo[c][2,6]naphthyridine-8-carboxamide;

5-(3-(4-((3-(cyanomethyl)-5-(trifluoromethyl)benzyl)amino)butoxy)azetidin-1-yl)benzo[c][2,6]naphthyridine-8-carboxamide;

5-(3-(4-((3-chloro-4-(trifluoromethoxy)benzyl)amino)butoxy)azetidin-1-yl)benzo[c][2,6]naphthyridine-8-carboxamide;

5-(3-(4-((3-(hydroxymethyl)-5-(trifluoromethyl)benzyl)amino)butoxy)azetidin-1-yl)benzo[c][2,6]naphthyridine-8-carboxylic acid;

5-(3-(4-((3-fluoro-4-(trifluoromethoxy)benzyl)amino)butoxy)azetidin-1-yl)benzo[c][2,6]naphthyridine-8-carboxylic acid;

5-(3-(4-((3-chloro-5-(cyanomethyl)benzyl)amino)butoxy)azetidin-1-yl)benzo[c][2,6]naphthyridine-8-carboxylic acid;

5-(3-(4-((3-(cyanomethyl)-5-(trifluoromethyl)benzyl)amino)butoxy)azetidin-1-yl)benzo[c][2,6]naphthyridine-8-carboxylic acid;

5-(3-(4-((3-chloro-5-(cyanomethyl)benzyl)amino)butoxy)azetidin-1-yl)benzo[c][2,6]naphthyridine-8-carboxamide;

5-((2-(4-((3-chloro-5-(2-cyanopropan-2-yl)benzyl)amino)butoxy)ethyl)amino)benzo[c][2,6]naphthyridine-8-carboxamide;

5-((2-(4-((3-chloro-5-(1-cyanocyclopropyl)benzyl)amino)butoxy)ethyl)amino)benzo[c][2,6]naphthyridine-8-carboxamide;

5-(2-(4-((3-(cyanomethyl)-5-(trifluoromethoxy)benzyl)amino)butoxy)ethoxy)benzo[c][2,6]naphthyridine-8-carboxamide;

5-((2-(4-((3-(cyanomethyl)-5-(trifluoromethoxy)benzyl)amino)butoxy)ethyl)amino)benzo[c][2,6]naphthyridine-8-carboxylic acid;

5-(3-(4-((3-(cyanomethyl)-5-(trifluoromethoxy)benzyl)amino)butoxy)azetidin-1-yl)benzo[c][2,6]naphthyridine-8-carboxylic acid;

5-(3-(4-((3-(cyanomethyl)-5-(trifluoromethoxy)benzyl)amino)butoxy)azetidin-1-yl)benzo[c][2,6]naphthyridine-8-carboxamide;

5-(2-(4-((3-(cyanomethyl)-5-(trifluoromethoxy)benzyl)amino)butoxy)ethoxy)benzo[c][2,6]naphthyridine-8-carboxylic acid;

5-(2-(4-((3-bromo-4-(trifluoromethoxy)benzyl)amino)butoxy)ethoxy)benzo[c][2,6]naphthyridine-8-carboxylic acid;

5-(2-(4-((4-chloro-3-(trifluoromethoxy)benzyl)amino)butoxy)ethoxy)benzo[c][2,6]naphthyridine-8-carboxylic acid;

5-(2-(4-((3-chloro-5-(trifluoromethoxy)benzyl)amino)butoxy)ethoxy)benzo[c][2,6]naphthyridine-8-carboxylic acid;

5-(2-(4-((3-bromo-5-(trifluoromethoxy)benzyl)amino)butoxy)ethoxy)benzo[c][2,6]naphthyridine-8-carboxylic acid;

5-(2-(4-((3,5-difluoro-4-(trifluoromethoxy)benzyl)amino)butoxy)ethoxy)benzo[c][2,6]naphthyridine-8-carboxylic acid;

5-(2-(4-((3-cyclopropyl-5-(trifluoromethoxy)benzyl)amino)butoxy)ethoxy)benzo[c][2,6]naphthyridine-8-carboxylic acid;

5-(3-(4-((3-fluoro-5-(trifluoromethoxy)benzyl)amino)butoxy)azetidin-1-yl)benzo[c][2,6]naphthyridine-8-carboxylic acid;

5-(3-(4-((3,5-difluoro-4-(trifluoromethoxy)benzyl)amino)butoxy)azetidin-1-yl)benzo[c][2,6]naphthyridine-8-carboxylic acid;

5-(3-(4-((3-chloro-5-(trifluoromethoxy)benzyl)amino)butoxy)azetidin-1-yl)benzo[c][2,6]naphthyridine-8-carboxylic acid;

5-(3-(4-((3-bromo-4-(trifluoromethoxy)benzyl)amino)butoxy)azetidin-1-yl)benzo[c][2,6]naphthyridine-8-carboxylic acid;

5-(3-(4-((3-cyclopropyl-5-(trifluoromethoxy)benzyl)amino)butoxy)azetidin-1-yl)benzo[c][2,6]naphthyridine-8-carboxylic acid;

5-(2-(4-((3-chloro-5-(1-cyanocyclopropyl)benzyl)amino)butoxy)ethoxy)benzo[c][2,6]naphthyridine-8-carboxylic acid;

5-(2-(4-((3-chloro-5-(2-cyanopropan-2-yl)benzyl)amino)butoxy)ethoxy)benzo[c][2,6]naphthyridine-8-carboxylic acid;

5-(2-(4-((3-cyclopropyl-4-(trifluoromethoxy)benzyl)amino)butoxy)ethoxy)benzo[c][2,6]naphthyridine-8-carboxylic acid;

5-(2-(4-((3-methyl-4-(trifluoromethoxy)benzyl)amino)butoxy)ethoxy)benzo[c][2,6]naphthyridine-8-carboxylic acid;

5-(2-(4-((3-methoxy-4-(trifluoromethoxy)benzyl)amino)butoxy)ethoxy)benzo[c][2,6]naphthyridine-8-carboxylic acid;

5-(2-(4-((3,4-dichloro-5-(trifluoromethoxy)benzyl)amino)butoxy)ethoxy)benzo[c][2,6]naphthyridine-8-carboxylic acid;

5-((2-(4-((3-(cyanomethyl)-5-cyclopropylbenzyl)amino)butoxy)ethyl)amino)benzo[c][2,6]naphthyridine-8-carboxamide;

5-((2-(4-((3-(cyanomethyl)-5-ethoxybenzyl)amino)butoxy)ethyl)amino)benzo[c][2,6]naphthyridine-8-carboxamide;

5-((2-(4-((3-cyclopropyl-5-(hydroxymethyl)benzyl)amino)butoxy)ethyl)amino)benzo[c][2,6]naphthyridine-8-carboxamide;

(R)-5-((2-(4-((3-chloro-5-(1-cyanoethyl)benzyl)amino)butoxy)ethyl)amino)benzo[c][2,6]naphthyridine-8-carboxamide;

(S)-5-((2-(4-((3-chloro-5-(1-cyanoethyl)benzyl)amino)butoxy)ethyl)amino)benzo[c][2,6]naphthyridine-8-carboxamide;

5-((2-(4-((3-(cyanomethyl)-5-(2,2,2-trifluoroethoxy)benzyl)amino)butoxy)ethyl)amino)benzo[c][2,6]naphthyridine-8-carboxamide;

(R)-5-((1-(4-((3-chloro-4-(trifluoromethoxy)benzyl)amino)butoxy)propan-2-yl)amino)benzo[c][2,6]naphthyridine-8-carboxamide;

5-(3-(4-((3-cyclopropyl-4-(trifluoromethoxy)benzyl)amino)butoxy)azetidin-1-yl)benzo[c][2,6]naphthyridine-8-carboxylic acid;

5-(3-(4-((3-bromo-5-(trifluoromethoxy)benzyl)amino)butoxy)azetidin-1-yl)benzo[c][2,6]naphthyridine-8-carboxylic acid;

5-(3-(4-((4-chloro-3-(trifluoromethoxy)benzyl)amino)butoxy)azetidin-1-yl)benzo[c][2,6]naphthyridine-8-carboxylic acid;

5-(3-(4-((3-methyl-4-(trifluoromethoxy)benzyl)amino)butoxy)azetidin-1-yl)benzo[c][2,6]naphthyridine-8-carboxylic acid;

5-(3-(4-((3-methoxy-4-(trifluoromethoxy)benzyl)amino)butoxy)azetidin-1-yl)benzo[c][2,6]naphthyridine-8-carboxylic acid;

5-(3-(4-((3,4-dichloro-5-(trifluoromethoxy)benzyl)amino)butoxy)azetidin-1-yl)benzo[c][2,6]naphthyridine-8-carboxylic acid;

(S)-5-((1-(4-((3-chloro-4-(trifluoromethoxy)benzyl)amino)butoxy)propan-2-yl)amino)benzo[c][2,6]naphthyridine-8-carboxamide;

5-((1-(4-((3-chloro-4-(trifluoromethoxy)benzyl)amino)butoxy)-2-methylpropan-2-yl)amino)benzo[c][2,6]naphthyridine-8-carboxylic acid;

5-((2-(4-((3-(cyanomethyl)-5-ethylbenzyl)amino)butoxy)ethyl)amino)benzo[c][2,6]naphthyridine-8-carboxamide;

5-((2-(4-((3-(cyanomethyl)-5-(cyclopropylmethyl)benzyl)amino)butoxy)ethyl)amino)benzo[c][2,6]naphthyridine-8-carboxamide;

5-((1-(4-((3-chloro-4-(trifluoromethoxy)benzyl)amino)butoxy)-2-methylpropan-2-yl)amino)benzo[c][2,6]naphthyridine-8-carboxamide;

5-((2-(4-((3-(cyanomethyl)-5-(methoxymethyl)benzyl)amino)butoxy)ethyl)amino)benzo[c][2,6]naphthyridine-8-carboxamide;

(R)-5-((1-(4-((3-chloro-4-(trifluoromethoxy)benzyl)amino)butoxy)propan-2-yl)oxy)benzo[c][2,6]naphthyridine-8-carboxylic acid;

(R)-5-((1-(4-((3-chloro-4-(trifluoromethoxy)benzyl)amino)butoxy)propan-2-yl)oxy)benzo[c][2,6]naphthyridine-8-carboxamide;

5-((2-(4-((3-cyano-5-(trifluoromethoxy)benzyl)amino)butoxy)ethyl)amino)benzo[c][2,6]naphthyridine-8-carboxamide;

5-((2-(4-((3-(2-hydroxyethoxy)-5-(trifluoromethoxy)benzyl)amino)butoxy)ethyl)amino)benzo[c][2,6]naphthyridine-8-carboxamide;

5-((2-(4-((3-(oxazol-4-ylmethyl)-5-(trifluoromethoxy)benzyl)amino)butoxy)ethyl)amino)benzo[c][2,6]naphthyridine-8-carboxamide;

5-((2-(4-((3-(oxazol-5-ylmethyl)-5-(trifluoromethoxy)benzyl)amino)butoxy)ethyl)amino)benzo[c][2,6]naphthyridine-8-carboxamide;

5-(2-(4-((3-cyano-5-(trifluoromethoxy)benzyl)amino)butoxy)ethoxy)benzo[c][2,6]naphthyridine-8-carboxamide;

5-(2-(4-((3-(2-hydroxyethoxy)-5-(trifluoromethoxy)benzyl)amino)butoxy)ethoxy)benzo[c][2,6]naphthyridine-8-carboxamide;

5-(2-(4-((3-(oxazol-5-ylmethyl)-5-(trifluoromethoxy)benzyl)amino)butoxy)ethoxy)benzo[c][2,6]naphthyridine-8-carboxamide;

5-(2-(4-((3-(oxazol-4-ylmethyl)-5-(trifluoromethoxy)benzyl)amino)butoxy)ethoxy)benzo[c][2,6]naphthyridine-8-carboxamide;

5-(2-(4-((3-(2-hydroxyethyl)-5-(trifluoromethoxy)benzyl)amino)butoxy)ethoxy)benzo[c][2,6]naphthyridine-8-carboxamide;

5-((2-(4-((3-(2-hydroxyethyl)-5-(trifluoromethoxy)benzyl)amino)butoxy)ethyl)amino)benzo[c][2,6]naphthyridine-8-carboxamide;

(S)-5-((1-(4-((3-chloro-4-(trifluoromethoxy)benzyl)amino)butoxy)propan-2-yl)oxy)benzo[c][2,6]naphthyridine-8-carboxylic acid;

(S)-5-((1-(4-((3-chloro-4-(trifluoromethoxy)benzyl)amino)butoxy)propan-2-yl)oxy)benzo[c][2,6]naphthyridine-8-carboxamide;

5-((2-(4-((3-carbamoyl-5-(trifluoromethoxy)benzyl)amino)butoxy)ethyl)amino)benzo[c][2,6]naphthyridine-8-carboxamide;

5-(2-(4-((3-carbamoyl-5-(trifluoromethoxy)benzyl)amino)butoxy)ethoxy)benzo[c][2,6]naphthyridine-8-carboxamide;

5-((2-(4-((3-(2-amino-2-oxoethyl)-5-(trifluoromethoxy)benzyl)amino)butoxy)ethyl)amino)benzo[c][2,6]naphthyridine-8-carboxamide;

5-(2-(4-((3-(2-amino-2-oxoethyl)-5-(trifluoromethoxy)benzyl)amino)butoxy)ethoxy)benzo[c][2,6]naphthyridine-8-carboxamide;

5-((2-(4-((3-((1H-imidazol-1-yl)methyl)-5-(trifluoromethoxy)benzyl)amino)butoxy)ethyl)amino)benzo[c][2,6]naphthyridine-8-carboxamide;

5-((2-(4-((3-(furan-3-ylmethyl)-5-(trifluoromethoxy)benzyl)amino)butoxy)ethyl)amino)benzo[c][2,6]naphthyridine-8-carboxamide;
5-(2-(4-((3-((1H-imidazol-1-yl)methyl)-5-(trifluoromethoxy)benzyl)amino)butoxy)ethoxy)benzo[c][2,6]naphthyridine-8-carboxamide;
5-((2-(4-((3-((1H-pyrazol-4-yl)methyl)-5-(trifluoromethoxy)benzyl)amino)butoxy)ethyl)amino)benzo[c][2,6]naphthyridine-8-carboxamide;
5-(2-(4-((3-(furan-3-ylmethyl)-5-(trifluoromethoxy)benzyl)amino)butoxy)ethoxy)benzo[c][2,6]naphthyridine-8-carboxamide;
5-(2-(4-((3-((1H-pyrazol-4-yl)methyl)-5-(trifluoromethoxy)benzyl)amino)butoxy)ethoxy)benzo[c][2,6]naphthyridine-8-carboxamide;
5-((2-(4-((3,5-difluoro-4-(trifluoromethoxy)benzyl)amino)butoxy)ethyl)amino)benzo[c][2,6]naphthyridine-8-carboxylic acid;
(R)-5-((1-(4-((3,5-difluoro-4-(trifluoromethoxy)benzyl)amino)butoxy)propan-2-yl)oxy)benzo[c][2,6]naphthyridine-8-carboxylic acid;
(R)-5-((1-(4-((3-fluoro-4-(trifluoromethoxy)benzyl)amino)butoxy)propan-2-yl)oxy)benzo[c][2,6]naphthyridine-8-carboxylic acid;
(R)-5-((1-(4-((3-fluoro-4-(trifluoromethoxy)benzyl)amino)butoxy)propan-2-yl)amino)benzo[c][2,6]naphthyridine-8-carboxylic acid;
(R)-5-((1-(4-((3,5-difluoro-4-(trifluoromethoxy)benzyl)amino)butoxy)propan-2-yl)amino)benzo[c][2,6]naphthyridine-8-carboxylic acid; or
5-(2-(4-((3,5-Difluoro-4-(trifluoromethoxy)benzyl)amino)butoxy)ethoxy)benzo[c][2,6]naphthyridine-8-carboxamide.

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I and sub-formulae thereof are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as, but not limited to, sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I and sub-formulae thereof may exist in solvated as well as unsolvated forms such as, for example, hydrated forms. It is to be understood that the invention encompasses all such solvated forms that possess the biological activity described herein.

Polymorphs

It is also to be understood that certain compounds of the Formula I and sub-formulae thereof may exhibit polymorphism, and that the invention encompasses all such forms that possess the biological activity described herein.

N-Oxides

Compounds of the Formula I and sub-formulae thereof containing an amine function may also form N-oxides. A reference herein to a compound of the Formula I and sub-formulae thereof that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as, but not limited to, hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as, but not limited to, dichloromethane.

Tautomers

Compounds of the Formula I and sub-formulae thereof may exist in a number of different tautomeric forms and references to compounds of the Formula I and sub-formulae thereof include all such forms. For the avoidance of doubt, where a compound can exist in one of several tautomeric forms, and only one is specifically described or shown, all others are nevertheless embraced by Formula I and sub-formulae thereof. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

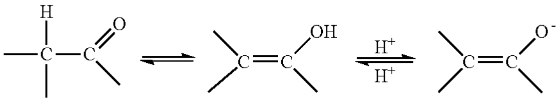

keto enol enolate

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I and sub-formulae thereof may have one or more asymmetric centres and therefore can exist in a number of stereoisomeric configurations. Consequently, such compounds can be synthesized and/or isolated as mixtures of enantiomers and/or as individual (pure) enantiomers, and, in the case of two or more asymmetric centres, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of Formula I and sub-formulae thereof may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I and sub-formulae thereof.

Accordingly, the present invention includes those compounds of the Formula I and sub-formulae thereof as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I and sub-formulae thereof may be a synthetically-produced compound or a metabolically-produced compound.

A suitable pharmaceutically acceptable pro-drug of a compound of the Formula I and sub-formulae thereof is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);

b) Design of Pro-drugs, edited by H. Bundgaard, (Elsevier, 1985);

c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, *Advanced Drug Delivery Reviews,* 8, 1-38 (1992);

e) H. Bundgaard, et al., *Journal of Pharmaceutical Sciences,* 77, 285 (1988);

f) N. Kakeya, et al., *Chem. Pharm. Bull.,* 32, 692 (1984);

g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable pro-drug of a compound of the Formula I and sub-formulae thereof that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as, but not limited to, methyl, ethyl and tert-butyl, $C_{1-6}$alkoxymethyl esters such as, but not limited to, methoxymethyl esters, $C_{1-6}$ alkanoyloxymethyl esters such as, but not limited to, pivaloyloxymethyl esters, 3-phthalidyl esters, $C_{3-8}$cycloalkylcarbonyloxy-$C_{1-6}$alkyl esters such as, but not limited to, cyclopentylcarbonyloxymethyl and 1-cyclohexylcarbonyloxyethyl esters, 2-oxo-1,3-dioxolenylmethyl esters such as, but not limited to, 5-methyl-2-oxo-1,3-dioxolen-4-ylmethyl esters and $C_{1-6}$alkoxycarbonyloxy-$C_{1-6}$alkyl esters such as, but not limited to, methoxycarbonyloxymethyl and 1-methoxycarbonyloxyethyl esters.

A suitable pharmaceutically acceptable pro-drug of a compound of the Formula I and sub-formulae thereof that possesses a hydroxy group is, for example, an in vivo cleavable ester or ether thereof. An in vivo cleavable ester or ether of a compound of the Formula I and sub-formulae thereof containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as, but not limited to, phosphate esters (including phosphoramidic cyclic esters). Further suitable pharmaceutically acceptable ester forming groups for a hydroxy group include $C_{1-10}$alkanoyl groups such as, but not limited to, acetyl, benzoyl, phenylacetyl and substituted benzoyl and phenylacetyl groups, $C_{1-10}$alkoxycarbonyl groups such as, but not limited to, ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as, but not limited to, acetoxymethyl and pivaloyloxymethyl groups.

A suitable pharmaceutically acceptable pro-drug of a compound of the Formula I and sub-formulae thereof that possesses a carboxy group is, for example, an in vivo cleavable amide thereof, for example an amide formed with an amine such as, but not limited to, ammonia, a $C_{1-4}$alkylamine such as, but not limited to, methylamine, a $(C_{1-4}alkyl)_2$amine such as, but not limited to, dimethylamine, N-ethyl-N-methylamine or diethylamine, a $C_{1-4}$ alkoxy-$C_{2-4}$alkylamine such as, but not limited to, 2-methoxyethylamine, a phenyl-$C_{1-4}$ alkylamine such as, but not limited to, benzylamine and amino acids such as, but not limited to, glycine or an ester thereof.

A suitable pharmaceutically acceptable pro-drug of a compound of the Formula I and sub-formulae thereof that possesses an amino group is, for example, an in vivo cleavable amide derivative thereof. Suitable pharmaceutically acceptable amides from an amino group include, for example an amide formed with $C_{1-10}$alkanoyl groups such as, but not limited to, an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the Formula I and sub-formulae thereof may be exerted in part by one or more metabolites that are formed within the human or animal body after administration of a compound of the Formula I and sub-formulae thereof. As stated hereinbefore, the in vivo effects of a compound of the Formula I and sub-formulae thereof may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 1.5 g of active agent (more suitably from 0.5 to 600 mg, for example from 1 to 200 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well-known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used.

For the compounds of the present invention, oral administration is particularly suitable. The compounds of the present invention may be formulated as a tablet, capsule or solution for oral administration. Suitably, the compound of the present invention is formulated in a unit dosage form (e.g. a tablet or capsule) for oral administration. Typically, unit dosage forms will contain about 0.5 mg to 1.5 g of a compound of this invention.

Synthesis

The compounds of the present invention can be prepared by any suitable technique known in the art. Particular methods for forming compounds of formula I defined herein are shown below and in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For Examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as, but not limited to, acetyl, an alkoxycarbonyl group, for example a methoxycarbonyl, ethoxycarbonyl or tbutoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as, but not limited to, an alkali metal hydroxide, for example lithium or sodium hydroxide. Alternatively an acyl group such as a tertbutoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively, an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium on carbon.

Resins may also be used as a protecting group.

The methodology employed to synthesise a compound of formula (I) will vary depending on the nature of $R_1$, Q, $R_a$, $R_b$, $R_c$, $R_d$ and $R_e$ and any substituent groups associated therewith. Suitable processes for their preparation are described further in the accompanying Examples.

Once a compound of formula (I) has been synthesised by any one of the processes defined herein, the processes may then further comprise one or more of the additional steps of:

(i) removing any residual protecting groups present; or optionally converting any COOMe groups present (e.g. in the $R_1$ position) to $CONH_2$;

(ii) converting the compound formula (I) into another compound of formula (I);

(iii) forming a pharmaceutically acceptable salt, hydrate or solvate of the compound of formula I; and/or (iv) forming a prodrug of the compound of formula I.

An Example of (ii) above is when a compound of formula (I) is synthesised and then one or more of the groups of $R_1$, Q, $R_a$, $R_b$, $R_c$, $R_d$ and $R_e$ may be further reacted to change the nature of the group and provide an alternative compound of formula (I).

The resultant compounds of formula (I) can be isolated and purified using techniques well known in the art.

According to a further aspect of the invention, there is provided a process for preparing a compound of formula (I) as hereinbefore described which comprises:

(a) preparing a compound of formula (I) by reacting a compound of formula (111) with a compound of formula (II), where, if necessary, followed by a suitable deprotection step:

Scheme 1

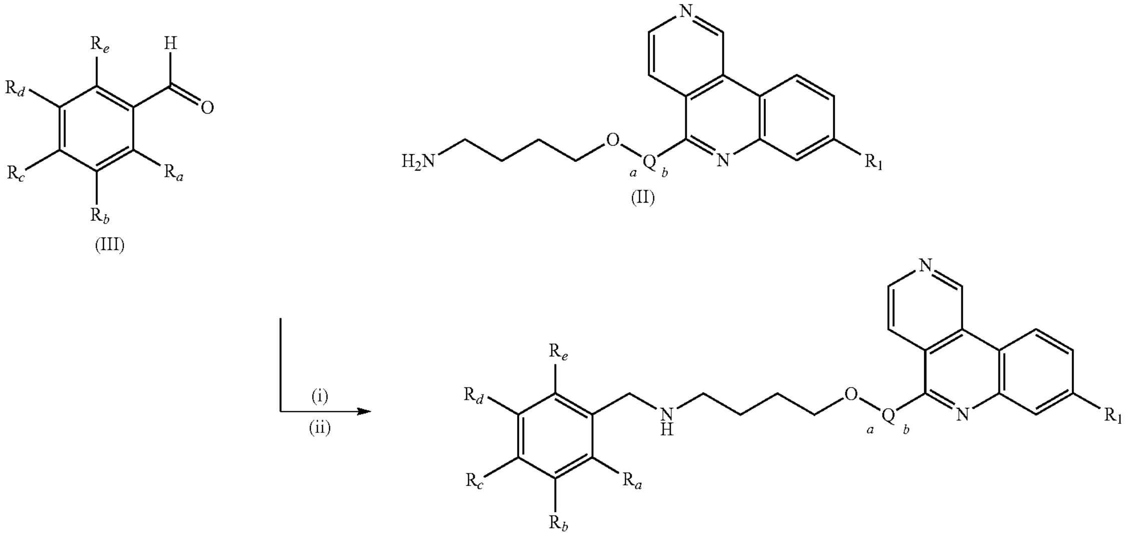

(III) (II) (I)

wherein ${}_aQ_b$ and $R_{a-e}$ are as hereinbefore described, and $R_1$ may be —$CONH_2$, —$CO_2H$ or $CO_2PG$, a protected form of —$CO_2H$, wherein PG is methyl; or (b) preparing a compound of formula (I) by reacting a compound of formula (IV) with a compound of formula (V), where, if necessary, followed by a suitable deprotection step:

Scheme 2

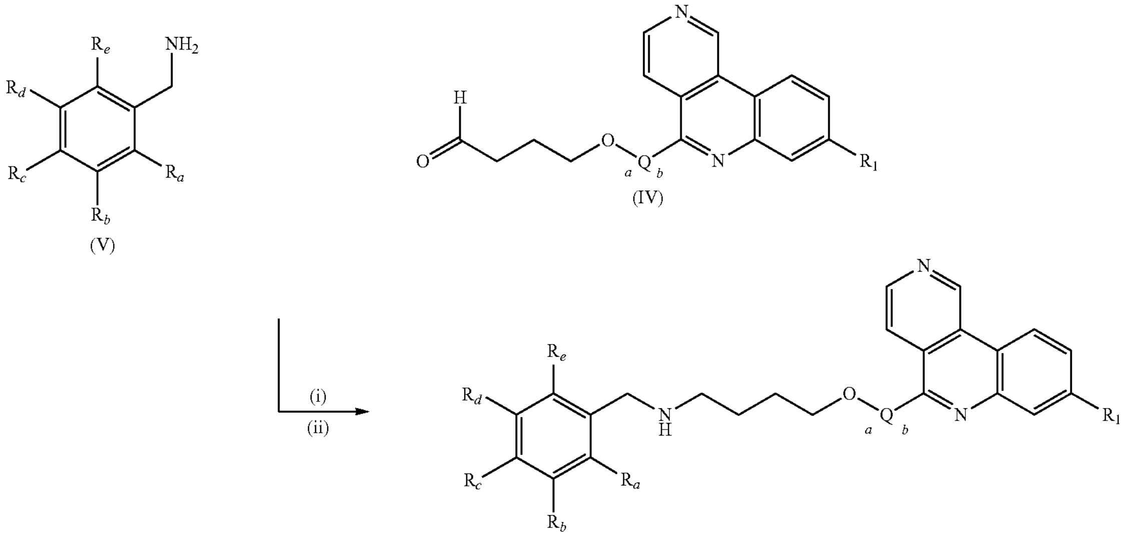

(V) (IV) (I)

wherein $_aQ_b$ and $R_{a-e}$ are as hereinbefore described, and $R_1$ may be —$CONH_2$, —$CO_2H$ or $CO_2PG$, a protected form of —$CO_2H$, wherein PG is methyl; or (c) preparing a compound of formula (I) by reacting a compound of formula (VII) with a compound of formula (VI), where, if necessary, followed by a suitable deprotection step:

Scheme 3

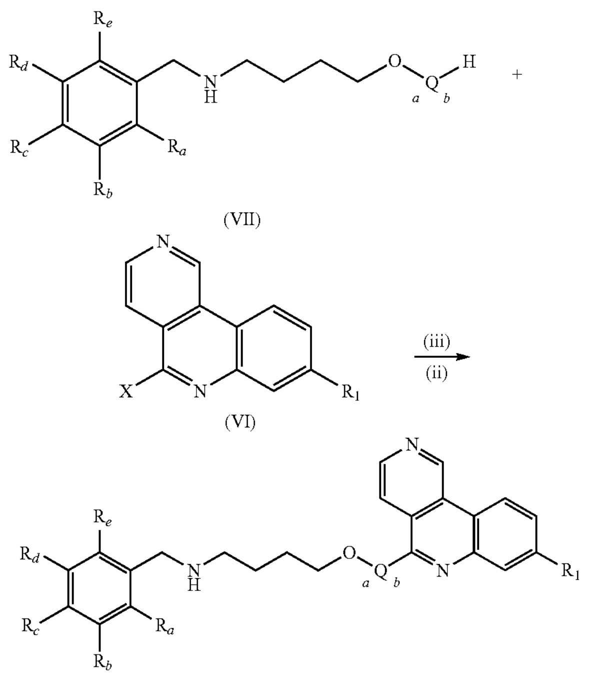

(VII)

(VI)

(I)

wherein $_aQ_b$ and $R_{a-e}$ are as hereinbefore described, and $R_1$ may be —$CONH_2$, —$CO_2H$ or $CO_2PG$ (wherein PG is methyl), a protected form of —$CO_2H$, In process (a) above:

Step (i) comprises a reductive amination step, which typically comprises formation of an imine in an alcoholic solvent, either with or without acid or base, followed by reduction with a hydride-based reagent. Preferred conditions comprise sodium triacetoxyborohydride or sodium cyanoborohydride in methanol either with or without sodium acetate or DIPEA at from 0° C. to 50° C.

When $R_1$ is —$CO_2PG$, step (ii) comprises a hydrolysis reaction with a suitable inorganic hydroxide in a mixture of water and an alcoholic solvent. Preferred conditions comprise lithium hydroxide in methanol with water at room temperature.

In process (b) above:

Step (i) and step (ii) comprise a reductive amination step followed by a suitable deprotection step if necessary, as described in process (a).

In process (c) above:

Step (iii) comprises an aromatic substitution reaction which typically comprises a base in a suitable organic solvent. Preferred conditions comprise NaH in THF at from 0° C. to 60° C.

Where a protecting group is employed, step (ii) comprises a deprotection reaction. Where PG is a Boc group, preferred conditions comprise HCl in 1,4-dioxane.

Compounds of formula (II), (III), (IV), (V), (VI) or (VII) are either commercially available, prepared according to the methods described herein, or prepared according to the literature.

Therapeutic Uses and Applications

The compounds of the present invention are potent inhibitors of Casein Kinase 2 alpha (CK2α). Data showing the CK2α inhibition for the exemplified compounds is presented in the accompanying example section.

The compounds of the present invention are designed to bind to the catalytic ATP site of CK2α (to drive potent enzyme inhibition) and the aD site (to drive high levels of selectivity over other kinases) [Brear et al, Chem Sci 2016].

Accordingly, the compounds of formula I are useful for the treatment and/or prevention of diseases and conditions in which CK2α activity is implicated, such as, for example, but not limited to, the treatment and/or prevention of proliferative disorders (e.g. cancer), viral infections, inflammation, diabetes, vascular and ischemic disorders, neurodegeneration and the regulation of circadian rhythm.

In another aspect, the present invention provides a compound of Formula I as defined herein, or a pharmaceutically acceptable salt, hydrate or solvate thereof, or a pharmaceutical composition as defined herein, for use in therapy.

In another aspect, the present invention provides a compound of Formula I as defined herein, or a pharmaceutically acceptable salt, hydrate or solvate thereof, or a pharmaceutical composition as defined herein, for use in the treatment of a disease or condition in which CK2α activity is implicated.

In another aspect, the present invention provides the use of a compound of Formula I as defined herein, or a pharmaceutically acceptable salt, hydrate or solvate thereof, in the manufacture of a medicament for use in the treatment of a disease or condition in which CK2α activity is implicated.

In another aspect, the present invention provides a method of treating a disease or condition in which CK2α activity is implicated, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a compound of Formula I as defined herein, or a pharmaceutically acceptable salt, hydrate or solvate thereof, or a pharmaceutical composition as defined herein, for use in the treatment of a disease or condition associated with aberrant activity of CK2α.

In another aspect, the present invention provides the use of a compound of Formula I as defined herein, or a pharmaceutically acceptable salt, hydrate or solvate thereof, in the manufacture of a medicament for use in the treatment of a disease or condition associated with aberrant activity of CK2α.

In another aspect, the present invention provides a method of treating a disease or condition associated with aberrant activity of CK2α, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a compound of Formula I as defined herein, or a pharmaceutically acceptable salt, hydrate or solvate thereof, or a pharmaceutical composition as defined herein, for use in the treatment of proliferative disorders (e.g. cancer or benign neoplasms), viral infections, an inflammatory disease or condition, diabetes, vascular and ischemic disorders, neurodegenerative disorders and/or the regulation of circadian rhythm.

In another aspect, the present invention provides the use of a compound of Formula I as defined herein, or a pharmaceutically acceptable salt, hydrate or solvate thereof, in the manufacture of a medicament for use in the treatment of proliferative disorders (e.g. cancer or benign neoplasms), viral infections, an inflammatory disease or condition, diabetes, vascular and ischemic disorders, neurodegenerative disorders and/or the regulation of circadian rhythm.

In another aspect, the present invention provides a method of treating a proliferative disorder (e.g. cancer or benign neoplasms), a viral infection, an inflammatory disease or condition, diabetes, vascular and ischemic disorders, neurodegenerative disorders and/or regulating cardiac rhythm, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a compound of Formula I as defined herein, or a pharmaceutically acceptable salt, hydrate or solvate thereof, or a pharmaceutical composition as defined herein, for use in the treatment of a proliferative disorder.

In another aspect, the present invention provides the use of a compound of Formula I as defined herein, or a pharmaceutically acceptable salt, hydrate or solvate thereof, in the manufacture of a medicament for use in the treatment of a proliferative disorder (e.g. cancer or a benign neoplasms).

In another aspect, the present invention provides a method of treating a proliferative disorder (e.g. cancer or benign neoplasms), said method comprising administering to a subject in need thereof an effective amount of a compound of Formula I as defined herein, or a pharmaceutically acceptable salt, hydrate or solvate thereof, or a pharmaceutical composition as defined herein.

The terms "proliferative disorder" and "proliferative condition" are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, pre-malignant and malignant cellular proliferation, including but not limited to, cancers, psoriasis, bone diseases, fibroproliferative disorders (e.g. of connective tissues), and atherosclerosis.

Any type of cell may be treated, including but not limited to, lung, colon, breast, ovarian, prostate, liver, pancreas, brain, blood and skin.

In certain aspects of the present invention, the proliferative disorder is cancer, suitably a cancer selected from lung, colon/colorectal, breast, ovarian, prostate, liver, pancreas, brain, blood, cholangiocarcinoma and skin cancer.

In a particular aspect of the invention, the proliferative disorder is colon/colorectal, cholangiocarcinoma, ovarian or prostate cancer.

In a particular aspect of the invention, the proliferative disorder is colorectal cancer.

In certain aspects of the present invention, the proliferative disorder is hematopoietic tumour, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); and myelofibrosis.

A benign neoplasm may be, for example, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas or pituitary adenomas. The benign neoplasm may be endometrial implants or a keratocystic odontogenic tumor.

In another aspect, the present invention provides a compound of Formula I as defined herein, or a pharmaceutically acceptable salt, hydrate or solvate thereof, or a pharmaceutical composition as defined herein, for use in the treatment of a cancer.

In another aspect, the present invention the use of a compound of Formula I as defined herein, or a pharmaceutically acceptable salt, hydrate or solvate thereof, in the manufacture of a medicament for use in the treatment of a cancer.

In another aspect, the present invention provides a method of treating cancer, said method comprising administering to a subject in need thereof an effective amount of a compound of Formula I as defined herein, or a pharmaceutically acceptable salt, hydrate or solvate thereof, or a pharmaceutical composition as defined herein.

The cancer may be non-metastatic or metastatic and which may be a solid tumour or a haematological ("liquid") cancer. The cancer may, for example, be selected from:

(1) Carcinoma, including for example tumours derived from stratified squamous epithelia (squamous cell carcinomas) and tumours arising within organs or glands (adenocarcinomas). Examples include breast, colon, lung, prostate, ovary, esophageal carcinoma (including, but not limited to, esophageal adenocarcinoma and squamous cell carcinoma), basal-like breast carcinoma, basal cell carcinoma (a form of skin cancer), squamous cell carcinoma (various tissues), head and neck carcinoma (including, but not limited to, squamous cell carcinomas), stomach carcinoma (including, but not limited to, stomach adenocarcinoma, gastrointestinal stromal tumor), signet ring cell carcinoma, bladder carcinoma (including transitional cell carcinoma (a malignant neoplasm of the bladder)), bronchogenic carcinoma, colorectal carcinoma (including, but not limited to, colon carcinoma and rectal carcinoma), anal carcinoma, gastric carcinoma, lung carcinoma (including but not limited to small cell carcinoma (SCLC) and non-small cell carcinoma of the lung (NSCLC), lung adenocarcinoma, squamous cell carcinoma, large cell carcinoma, bronchioloalveolar carcinoma, and mesothelioma), neuroendocrine tumors (including but not limited to carcinoids of the gastrointestinal tract, breast, and other organs), adrenocortical carcinoma, thyroid carcinoma, pancreatic carcinoma (including, but not limited to, pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumors), breast carcinoma (including, but not limited to, ductal carcinoma, lobular carcinoma, inflammatory breast cancer, clear cell carcinoma, mucinous carcinoma), ovarian carcinoma (including, but not limited to, ovarian epithelial carcinoma or surface epithelial-stromal tumor including serous tumor, endometrioid tumor and mucinous cystadenocarcinoma, sex-cord-stromal tumor), liver and bile duct carcinoma (including, but not limited to, hepatocellular carcinoma, cholangiocarcinoma and hemangioma), prostate carcinoma, adenocarcinoma, brain tumours (including, but not limited to glioma, glioblastoma and medulloblastoma), germ cell tumors, sweat gland carcinoma, sebaceous gland carcinoma, papillary carcinoma, papillary adenocarcinoma, cystadenocarcinoma, kidney carcinoma (including, but not limited to, renal cell carcinoma, clear cell carcinoma and Wilm's tumor), medullary carcinoma, ductal carcinoma in situ or bile duct carcinoma, choriocarcinoma, seminoma, embryonal carcinoma, cervical carcinoma, uterine carcinoma (including, but not limited to, endometrial adenocarcinoma, uterine papillary serous carcinoma, uterine clear-cell carcinoma, uterine sarcomas and leiomyosarcomas, mixed mullerian tumors), testicular carcinoma, osteogenic carcinoma, epithelial carcinoma, sarcomatoid carcinoma, nasopharyngeal carcinoma, laryngeal carcinoma; oral and oropharyngeal squamous carcinoma;

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and hemangioendothelioma (blood vessels); liposarcoma (adipose tissue); glioma and astrocytoma (neurogenic connective tissue found in the brain); myxosarcoma (primitive embryonic connective tissue); chordoma, endotheliosarcoma, lymphangiosarcoma, lymphangioendotheliosarcoma, synovioma, Ewing's sarcoma, mesenchymous and mixed mesodermal tumor (mixed connective tissue types) and other soft tissue sarcomas;

(3) Myeloma and multiple myeloma;

(4) Hematopoietic tumours, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); myelofibrosis.

(5) Lymphomas, including: Hodgkin and Non-Hodgkin lymphomas;

(6) Solid tumors of the nervous system including medulloblastoma, craniopharyngioma, ependymoma, pinealoma, hemangioblastoma, acoustic neuroma, oligodendroglioma, meningioma, neuroblastoma and schwannoma;

(7) Melanoma, uveal melanoma and retinoblastoma; and (8) Mixed Types, including, e.g., adenosquamous carcinoma, mixed mesodermal tumor, carcinosarcoma or teratocarcinoma.

Suitably, a compound of the invention, or a pharmaceutically acceptable salt thereof may be for use in the treatment of a cancer selected from cancer selected from lung, colon/colorectal, breast, ovarian, prostate, liver, pancreas, brain, blood, cholangiocarcinoma and skin cancer.

More suitably, the cancer is selected from colon/colorectal cancer, prostate cancer, ovarian cancer or cholangiocarcinoma.

In a particular aspect of the present invention, the cancer is colorectal cancer.

In a particular aspect of the present invention, the cancer is cholangiocarcinoma.

In another aspect of the present invention, the cancer is a hematopoietic tumour.

It is hypothesised that the compounds of the present invention will be particularly suited to the treatment of wnt pathway mutated cancers, e.g. wnt pathway mutated colorectal cancer or cholangiocarcinoma (Di Maira et al, 2019).

In addition to CK2α having a very well characterized function in wnt pathway activity, it also plays a role in other key cellular pathways known to be upregulated in cancer, such as, but not limited to, the DNA damage response (Ruzzene & Pinna, 2010; Montenarh, Transl. Cancer Res 2016). Thus, the compounds of the present invention may have a further use in the treatment of PARP insensitive tumors in prostate/ovarian cancer.

CK2α has also recently been identified as a key host protein required for viral replication (e.g. in SARS-CoV2) and as such could represent an antiviral treatment (Gordon et al. Nature 2020).

Thus, in another aspect, the present invention provides a compound of Formula I as defined herein, or a pharmaceutically acceptable salt, hydrate or solvate thereof, or a pharmaceutical composition as defined herein, for use in the treatment of a viral infection.

In another aspect, the present invention provides the use of a compound of Formula I as defined herein, or a pharmaceutically acceptable salt, hydrate or solvate thereof, in the manufacture of a medicament for use in the treatment of a viral infection.

In another aspect, the present invention provides a method of treating a viral infection, said method comprising administering to a subject in need thereof an effective amount of a compound of Formula I as defined herein, or a pharmaceutically acceptable salt, hydrate or solvate thereof, or a pharmaceutical composition as defined herein.

Suitably, the virus is a coronavirus, e.g. SARS-CoV2.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (e.g. by a patch, plaster, etc.); transmucosal (e.g. by a patch, plaster, etc.); intranasal (e.g. by nasal spray); ocular (e.g. by eye drops, eye ointment etc.); pulmonary (e.g. by inhalation or insufflation therapy, for example via an aerosol, for example by the nose or mouth); rectal (e.g. by suppository or enema); vaginal (e.g. by pessary); parental, for example by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir dosage form, for example subcutaneously or intramuscularly.

The compounds of the present invention are particularly suitable for oral administration.

Combination Therapies

The compounds of the invention and salts, solvates thereof defined hereinbefore may be applied as a sole therapy or may involve, in addition to the compound of the invention, one or more additional therapeutic agents, e.g. an anti-tumour agent.

In the context of cancer treatment, in addition to the compound of the invention therapy may involve conventional surgery or radiotherapy or chemotherapy. Such chemotherapy may include one or more of the following categories of anti-tumour agents:— other antiproliferative/antineoplastic drugs and combinations thereof, as used in medical oncology, such as, but not limited to, alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as, but not limited to, fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

cytostatic agents such as, but not limited to, antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as, but not limited to, finasteride;

anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as, but not limited to, N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (Cl 1033), erbB2 tyrosine kinase inhibitors such as, but not limited to, lapatinib); inhibitors of the hepatocyte growth factor family; inhibitors of the insulin growth factor family; inhibitors of the platelet-derived growth factor family such as, but not limited to, imatinib and/or nilotinib (AMN107); inhibitors of serine/threonine kinases (for example Ras/Raf signalling inhibitors such as, but not limited to, farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, PIt3 kinase inhibitors, CSF-1R kinase inhibitors, IGF receptor (insulin-like growth factor) kinase inhibitors; aurora kinase inhibitors (for example AZD1152, PH739358, VX-680, MLN8054, $R_{763}$, MP235, MP529, VX-528 AND AX39459) and cyclin dependent kinase inhibitors such as, but not limited to, CDK2 and/or CDK4 inhibitors;

antiangiogenic agents such as, but not limited to, those which inhibit the effects of vascular endothelial growth factor, [for example the anti-vascular endothelial cell growth factor antibody bevacizumab (Avastin™) and for example, a VEGF receptor tyrosine kinase inhibitor such as, but not limited to, vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as, but not limited to, those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

vascular damaging agents such as, but not limited to, Combretastatin A4 and compounds disclosed in International Patent Applications WO 99/02166, WO 00/40529, WO 00/41669, WO 01/92224, WO 02/04434 and WO 02/08213;

an endothelin receptor antagonist, for example zibotentan (ZD4054) or atrasentan;

antisense therapies, for example those which are directed to the targets listed above, such as, but not limited to, ISIS 2503, an anti-ras antisense;

gene therapy approaches, including for example approaches to replace aberrant genes such as, but not limited to, aberrant p53 or aberrant BRCA1 or BRCA2, GDEPT (gene-directed enzyme pro-drug therapy) approaches such as, but not limited to, those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex-vivo and in-vivo approaches to increase the immunogenicity of patient tumour cells, such as, but not limited to, transfection with cytokines such as interleukin 2, interleukin 4 or granulocyte-macrophage colony stimulating factor, approaches to decrease T-cell anergy, approaches using transfected immune cells such as, but not limited to, cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

In a further particular embodiment, the antiproliferative treatment defined hereinbefore may involve, in addition to the compound of the invention, standard chemotherapy for the cancer concerned.

In a particular embodiment, the antiproliferative treatment defined hereinbefore may involve, in addition to the compound of the invention, therapy with K-ras inhibitors and/or DNA damage repair inhibitors (e.g. PARP inhibitors).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as, but not limited to, cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination. In one embodiment, a combination refers to a combination product.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

Biological Activity

The biological assay described in the example section (Biological Assay 1) may be used to measure the pharmacological effects of the compounds of the present invention.

Although the pharmacological properties of the compounds of formula I vary with structural change, as expected, the compounds of the invention were found to be active in the assays described in Biological Assay 1. In general, the compounds of the invention demonstrate an $IC_{50}$ of 500 nM or less in the assay described in Biological Assay 1, with preferred compounds of the invention demonstrating an $IC_{50}$ of 100 nM or less and the most preferred compounds of the invention demonstrating an $IC_{50}$ of 30 nM or less.

Compounds of the invention may also show activity in Assay 3 described in the accompanying Biological Assay section.

EXAMPLES

The invention will now be illustrated, but not limited, by reference to the specific embodiments described in the following examples. Compounds are named using conventional IUPAC nomenclature, or as named by the chemical supplier.

The following synthetic procedures are provided for illustration of the methods used; for a given preparation or step the precursor used may not necessarily derive from the individual batch synthesized according to the step in the description given.

Analytical Methods (AM)

Where examples and preparations cite analytical data, the following analytical methods were used unless otherwise specified.

All LCMS spectra were obtained by using one of the below methods.

Method 1 (AM1): (5-95 A-B_1.5 min_220 & 254 nm): Instrument: Agilent 1100\G1956A; Column: Kinetex@ 5 um EVO C18 30×2.1 mm×5 μm; Run Time: 1.5 min; Solvents: A) 0.0375% TFA in water (v/v), B) 0.01875% TFA in acetonitrile (v/v). The gradient runs with 5% B; Gradient: 5-95% B with A, 0.8 min; hold at 95% B to 1.2 min; 5% B at 1.21 min and hold at 5% B to 1.5 min@1.5 mL/min, 50° C.

Method 2 (AM2): (5-95 A-B_1.5 min_220 & 254 nm): Instrument: Agilent 1200\G6110A; Column: Kinetex@ 5 um EVO C18 30×2.1 mm×5 μm; Run Time: 1.5 min; Solvents: A) 0.0375% TFA in water (v/v), B) 0.01875% TFA in acetonitrile (v/v). The gradient runs with 5% B; Gradient: 5-95% B with A, 0.8 min; hold at 95% B to 1.2 min; 5% B at 1.21 min and hold at 5% B to 1.5 min@1.5 mL/min, 50° C.

Method 3 (AM3): (5-95 A-B_1.55 min_220 & 254 nm): Instrument: SHIMADZU LCMS-2020; Column: Kinetex EVO C18 30×2.1 mm×5 μm; Run Time: 1.55 min; Solvents: A) 0.0375% TFA in water (v/v), B) 0.01875% TFA in acetonitrile (v/v). The gradient runs with 5% B; Gradient: 5-95% B with A, 0.8 min; hold at 95% B to 1.2 min; 5% B at 1.21 min and hold at 5% B to 1.55 min@1.5 mL/min, 50° C.

Method 4 (AM4): (5-95 A-B_1.5 min_220 & 254 nm): Instrument: Agilent 1200 LC/G1956A MSD; Column: Kinetex EVO C18 30×2.1 mm×5 μm; Run Time: 1.5 min; Solvents: A) 0.0375% TFA in water (v/v), B) 0.01875% TFA in acetonitrile (v/v). The gradient runs with 5% B; Gradient: 5-95% B with A, 0.8 min; hold at 95% B to 1.2 min; 5% B at 1.21 min and hold at 5% B to 1.5 min@1.5 mL/min, 50° C.

Method 5 (AM5): (0-60 A-B_1.55 min_220 & 254 nm): Instrument: SHIMADZU LCMS-2020; Column: Kinetex EVO C18 30×2.1 mm×5 μm; Run Time: 1.55 min; Solvents: A) 0.0375% TFA in water (v/v), B) 0.01875% TFA in ACN (v/v). The gradient runs with 0% B; Gradient: 0-60% B with A, 0.8 min; hold at 60% B to 1.20 min; 0% B at 1.21 min and hold at 0% B to 1.55 min@1.5 mL/min, 50° C.

Method 6 (AM6): (0-60 C-D_2.20 min_220 & 254 nm): Instrument: SHIMADZU LCMS-2020; Column: Kinetex EVO C18 30×2.1 mm×5 μm; Run Time: 2.20 min; Solvents: A) 0.025% $NH_3·H_2O$in water (vlv), B) acetonitrile. The gradient runs with 0% B; Gradient: 0-60% B with A, 1.2 min; hold at 60% B to 1.6 min; 0% B at 1.61 min and hold at 0% B to 2.2 min@1.5 mL/min, 40° C.

Method 7 (AM7): (5-95 C-D_1.5 min_R_220&254_POS): Instrument: SHIMADZU LCMS-2020; Column: Kinetex EVO C18 30×2.1 mm×5 μm; Run Time: 1.5 min; Solvents A) 0.025% $NH_3 \cdot H_2O$ in water (v/v) B) Acetonitrile. The gradient runs with 5% B. Gradient: 5-95% B with A 0.8 min, hold at 95% B to 1.2 min; 5% B at 1.21 min and hold at 5% B to 1.5 min@1.5 ml/min, 40° C.

Method 8 (AM8): (10-80 C-D_2.00 min_220 & 254 nm): Instrument: Agilent 1200\G6110A; Column: ACE Excel 5 C18 30×2.1 mm×5 μm; Run Time: 2.00 min; Solvents: A) 0.025% $NH_3 \cdot H_2O$ in water (v/v), B) Acetonitrile (v/v). The gradient runs with 10% B; Gradient: 10-80% B with A, 1.2 min; hold at 80% B to 1.6 min; 10% B at 1.61 min and hold at 10% B to 2.00 min @ 1.0 mL/min, 40° C.

Method 9 (AM9): (10-80 A-B_7 min_220 & 254 nm): Instrument: SHIMADZU LCMS-2020; Column: AB:Xtimate C18 30×2.1 mm×3 μm; Run Time: 7.0 min; Solvents: A) 0.0375% TFA in water (v/v), B) 0.01875% TFA in acetonitrile (v/v). The gradient runs with 10% B; Gradient: 10-80% B with A, 6.5 min; hold at 80% B to 7 min; 10% B at 6.5 min and hold at 10% B to 7 min@1.5 mL/min, 50° C.

$^1$H NMR spectra were acquired on a BrukerAvance III spectrometer at 400 MHz using residual undeuterated solvent as reference, and annotated using ACD Labs.

Purification Methods (PM)

Chromatography

| Purification method | Column | Eluent | Eluent Ratio |
|---|---|---|---|
| PM1 | $SiO_2$ | PE | 1 |
| PM2 | $SiO_2$ | PE:EA | 1:1 |
| PM3 | $SiO_2$ | PE:EA | 2:1 |
| PM4 | $SiO_2$ | PE:EA | 3:1 |
| PM5 | $SiO_2$ | PE:EA | 4:1 |
| PM6 | $SiO_2$ | PE:EA | 5:1 |
| PM7 | $SiO_2$ | PE:EA | 10:1 |
| PM8 | $SiO_2$ | PE:EA | 13:1 |
| PM9 | $SiO_2$ | PE:EA | 15:1 |
| PM10 | $SiO_2$ | PE:EA | 16:1 |
| PM11 | $SiO_2$ | PE:EA | 20:1 |
| PM12 | $SiO_2$ | PE:EA | 30:1 |
| PM13 | $SiO_2$ | PE:EA | 40:1 |
| PM14 | $SiO_2$ | PE:EA | 50:1 |
| PM15 | $SiO_2$ | PE:EA | 60:1 |
| PM16 | $SiO_2$ | PE:EA | 80:1 |
| PM17 | $SiO_2$ | PE:EA | 100:1 |
| PM18 | $SiO_2$ | PE:EA | 200:1 |

Reverse-Phase HPLC Conditions

| Purification Method (PM) | Column | Mobile phase | Gradient |
|---|---|---|---|
| PM19 | Phenomenex Synergi C18 150 × 25 mm × 10 μm | water (0.05% HCl)-ACN | 55%-75%, 12 min |
| PM20 | Phenomenex luna C18 250 × 50 mm × 10 μm | water (0.1% TFA)-ACN | 50%-70%, 10 min |
| PM21 | Phenomenex luna C18 250 × 50 mm × 10 μm | water (0.1% TFA)-ACN | 20%-40%, 10 min |
| PM22 | Phenomenex Synergi C18 150 × 25 mm × 10 μm | water (0.1% HCl)-ACN] | 10%-90%, 20 min |
| PM23 | Waters Xbridge 150 × 25 mm × 5 μm | water (10 mM $NH_4HCO_3$)-ACN | 11%-44%, 11 min |
| PM24 | Phenomenex luna C18 250 × 50 mm × 10 μm | water (0.1% TFA)-ACN | 15%-45%, 10 min |
| PM25 | Phenomenex luna C18 150 × 25 mm × 10 μm | water (0.075% TFA)-ACN | 12%-42%, 9 min |
| PM26 | Phenomenex luna C18 150 × 25 mm × 10 μm | water (0.075% TFA)-ACN | 5%-35%, 9 min |
| PM27 | Phenomenex Synergi C18 150 × 25 mm × 10 μm | water (0.1% TFA)-ACN | 20%-40%, 10 min |
| PM28 | Phenomenex luna C18 150 × 25 mm × 10 μm | water (0.075% TFA)-ACN | 10%-40%, 9 min |
| PM29 | Phenomenex Synergi C18 150 × 25 mm × 10 μm | water (0.1% TFA)-ACN | 22%-42%, 10 min |
| PM30 | Phenomenex Synergi C18 150 × 25 mm × 10 μm | water (0.1% TFA)-ACN | 25%-45%, 10 min |
| PM31 | Phenomenex Synergi C18 150 × 25 mm × 10 μm | water (0.1% TFA)-ACN | 15%-35%, 10 min |
| PM32 | Phenomenex Synergi C18 150 × 25 mm × 10 μm | water (0.1% TFA)-ACN | 12%-32%, 10 min |
| PM33 | Phenomenex Gemini-NX C18 75 × 30 mm × 3 μm | water (0.1% TFA)-ACN | 15%-45%, 7 min |
| PM34 | Phenomenex Gemini-NX C18 75 × 30 mm × 3 μm | water (0.1% TFA)-ACN | 12%-42%, 7 min |
| PM35 | Phenomenex luna C18 250 × 50 mm × 10 μm | water (0.1% TFA)-ACN | 15%-45%, 9 min) |
| PM36 | Phenomenex Gemini-NX C18 75 × 30 mm × 3 μm | water (0.1% TFA)-ACN | 1%-30%, 7 min |
| PM37 | Phenomenex Synergi C18 150 × 25 mm × 10 μm | water (0.1% TFA)-ACN | 18%-38%, 10 min |
| PM38 | Phenomenex Synergi C18 150 × 25 mm × 10 μm | water (0.1% TFA)-ACN | 18%-38%, 20 min |
| PM39 | Phenomenex Gemini-NX C18 75 × 30 mm × 3 μm | water (0.1% TFA)-ACN | 2%-32%, 7 min |
| PM40 | Phenomenex luna C18 150 × 25 mm × 10 μm | water (0.1% TFA)-ACN | 1%-22%, 10 min |

-continued

| Purification Method (PM) | Column | Mobile phase | Gradient |
|---|---|---|---|
| PM41 | Phenomenex Gemini-NX C18 75 × 30 mm × 3 μm | water (0.1% TFA)-ACN | 8%-38%, 7 min |
| PM42 | Phenomenex Gemini-NX C18 75 × 30 mm × 3 μm | water (0.1% TFA)-ACN | 15%-25%, 7 min |
| PM43 | Welch Xtimate C18 150 × 40 mm × 10 μm | water (0.05% ammonium hydroxide v/v)-ACN | 13%-43%, 10 min |
| PM44 | Welch Xtimate C18 150 × 40 mm × 10 μm | water (0.05% ammonium hydroxide v/v)-ACN | 5%-25%, 10 min |
| PM45 | Welch Xtimate C18 150 × 40 mm × 10 μm | water (0.05% ammonium hydroxide v/v)-ACN | 2%-32%, 10 min |
| PM46 | Phenomenex Gemini-NX C18 75 × 30 mm × 3 μm | water (0.1% TFA)-ACN | 20%-30%, 7 min |
| PM47 | Phenomenex Synergi C18 150 × 25 mm × 10 μm | water (0.1% TFA)-ACN | 10%-90%, 20 min |
| PM48 | Phenomenex luna C18 150 × 25 mm × 10 μm | water (0.1% TFA)-ACN | 12%-32%, 10 min |
| PM49 | Phenomenex Gemini-NX C18 75 × 30 mm × 3 μm | water (0.1% TFA)-ACN | 22%-32%, 7 min |
| PM50 | Phenomenex Gemini-NX C18 75 × 30 mm × 3 μm | water (0.1% TFA)-ACN | 18%-28%, 7 min |
| PM51 | Phenomenex Gemini-NX C18 75 × 30 mm × 3 μm | water (0.1% TFA)-ACN | 12%-22%, 7 min |
| PM52 | Waters Xbridge 150 × 50 mm × 10 μm | water (10 mM $NH_4HCO_3$)-ACN | 10%-40%, 10 min |
| PM53 | Waters Xbridge 150 × 25 mm × 5 μm | water (0.05% ammonium hydroxide v/v)-ACN | 6%-36%, 10 min |
| PM54 | Phenomenex Gemini-NX C18 75 × 30 mm × 3 μm | water (0.05% ammonium hydroxide v/v)-ACN | 23%-50%, 7 min |
| PM55 | Phenomenex Gemini-NX C18 75 × 30 mm × 3 μm | water (0.05% ammonium hydroxide v/v)-ACN | 5%-33%, 7 min |
| PM56 | Phenomenex Synergi C18 150 × 25 mm × 10 μm | water (0.1% TFA)-ACN | 18%-38%, 20 min |
| PM57 | Waters Xbridge 150 × 25 mm × 5 μm | water (0.05% ammonia hydroxide v/v)-ACN | 25%-55%, 10 min |
| PM58 | Phenomenex luna C18 150 × 25 mm × 10 μm | water (0.1% TFA)-ACN | 8%-28%, 10 min |
| PM59 | Phenomenex Synergi C18 150 × 25 mm × 10 μm | water (0.225% FA)-ACN | 15%-45%, 8.5 min |
| PM60 | Phenomenex Synergi C18 150 × 25 mm × 10 μm | water (0.225% FA)-ACN | 25%-55%, 8.5 min |
| PM61 | Phenomenex Synergi C18 150 × 25 mm × 10 μm | water (0.225% FA)-ACN | 28%-58%, 8.5 min |
| PM62 | Phenomenex Synergi C18 150 × 25 mm × 10 μm | water (0.225% FA)-ACN | 0%-30%, 8.5 min |
| PM63 | Phenomenex Synergi C18 150 × 25 mm × 10 μm | water (0.225% FA)-ACN | 5%-35%, 8.5 min |
| PM64 | Phenomenex Synergi C18 150 × 25 mm × 10 μm | water (0.225% FA)-ACN | 20%-50%, 8.5 min |
| PM65 | Phenomenex luna C18 150 × 25 mm × 10 μm | water (0.225% FA)-ACN | 10%-40%, 10 min |
| PM66 | Phenomenex Synergi C18 150 × 25 mm × 10 μm | water (0.225% FA)-ACN | 18%-48%, 8.5 min |
| PM67 | Phenomenex luna C18 150 × 40 mm × 15 μm | water (0.225% FA)-ACN | 14%-44%, 11 min |
| PM68 | Unisil 3-100 C18 Ultra 150 × 50 mm × 3 μm | water (0.225% FA)-ACN | 1%-30%, 10 min |
| PM69 | Phenomenex Synergi C18 150 × 25 mm × 10 μm | water (0.225% FA)-ACN | 3%-33%, 8.5 min |
| PM70 | Phenomenex luna C18 150 × 25 mm × 10 μm | water (0.225% FA)-ACN | 2%-32%, 10 min |
| PM71 | Shim-pack C18 150 × 25 mm × 10 μm | water (0.225% FA)-ACN | 8%-38%, 10 min |
| PM72 | Phenomenex luna C18 150 × 25 mm × 10 μm | water (0.225% FA)-ACN | 1%-30%, 10 min |
| PM73 | Unisil 3-100 C18 Ultra 150 × 50 mm × 3 μm | water (0.225% FA)-ACN | 1%-25%, 10 min |
| PM74 | Waters Xbridge 150 × 25 mm × 5 μm | water (0.05% ammonium hydroxide v/v)-ACN | 3%-33%, 10 min |
| PM75 | Waters Xbridge 150 × 25 mm × 5 μm | water (0.05% ammonium hydroxide v/v)-ACN | 7%-35%, 10 min |
| PM76 | Waters Xbridge 150 × 25 mm × 5 μm | water (0.05% ammonium hydroxide v/v)-ACN | 7%-37%, 10 min |
| PM77 | Welch Xtimate C18 150 × 30 mm × 5 μm | water (0.05% ammonium hydroxide v/v)-ACN | 5%-35%, 11.5 min |

-continued

| Purification Method (PM) | Column | Mobile phase | Gradient |
|---|---|---|---|
| PM78 | Waters Xbridge 150 × 25 mm × 5 μm | water (0.05% ammonium hydroxide v/v)-ACN | 7%-37%, 10 min |
| PM79 | Waters Xbridge 150 × 50 mm × 10 μm | water (0.05% ammonium hydroxide v/v)-ACN | 8%-38%, 11 min |
| PM80 | Waters Xbridge 150 × 50 mm × 10 μm | water (0.05% ammonium hydroxide v/v)-ACN | 10%-40%, 11 min |
| PM81 | Welch Xtimate C18 150 × 30 mm × 5 μm | water (0.05% ammonium hydroxide v/v)-ACN | 6%-36%, 11.5 min |
| PM82 | Phenomenex Synergi C18 150 × 25 mm × 10 μm | water (0.1% ammonium hydroxide v/v)-ACN | 10%-90%, 20 min |
| PM83 | Waters Xbridge 150 × 50 mm × 10 μm | water (0.05% ammonium hydroxide v/v)-ACN | 6%-36%, 11 min |
| PM84 | Waters Xbridge 150 × 50 mm × 10 μm | water (0.05% ammonium hydroxide v/v)-ACN | 38%-68%, 11 min |
| PM85 | Waters Xbridge 150 × 25 mm × 5 μm | water (0.05% ammonium hydroxide v/v)-ACN | 26%-55%, 9 min |
| PM86 | Waters Xbridge 150 × 25 mm × 5 μm | water (0.05% ammonium hydroxide v/v)-ACN | 27%-57%, 9 min |
| PM87 | Waters Xbridge 150 × 25 mm × 5 μm | water (10 mM $NH_4HCO_3$)-CAN | 11%-41%, 10 min |
| PM88 | Phenomenex Synergi C18 150 × 25 mm × 10 μm | water (0.225% FA)-ACN | 19%-49%, 10 min |
| PM89 | Waters Xbridge 150 × 25 mm × 5 μm | water (0.05% ammonium hydroxide v/v)-ACN | 13%-43%, 10 min |
| PM90 | Welch Ultimate XB-SiOH 250 × 50 mm × 10 μm | Heptane-EtOH (0.1% ammonium hydroxide) | 35%-75%, 10 min |
| PM91 | Phenomenex luna C18 150 ′ 25 mm ′ 10 mm | water (0.1% TFA)-ACN | 23%-53%, 11 min |
| PM92 | Welch Xtimate C18 150 × 30 mm × 5 μm | water (10 mM $NH_4HCO_3$)-ACN | 20%-50%, 11.5 min |
| PM93 | Welch Ultimate XB-CN 250 × 70 mm × 10 μm | Heptane-EtOH (0.1% ammonium hydroxide) | 40%-80%, 10 min |
| PM94 | Welch Xtimate C18 150 × 30 mm × 5 μm | water (0.05% ammonium hydroxide v/v)-ACN | 14%-44%, 11.5 min |
| PM95 | Welch Ultimate XB-SiOH 250 × 50 mm × 10 μm | 0.1% ammonium hydroxide in EtOH, Hexane-EtOH | 25%-65%, 15 min |
| PM96 | Waters Xbridge 150 × 25 mm × 5 μm | water (0.05% ammonium hydroxide v/v)-ACN | 7%-37%, 10 min |
| PM97 | Welch Ultimate XB-SiOH 250 × 50 mm × 10 μm | 0.1% ammonium hydroxide in EtOH, Hexane-EtOH | 20%-60%, 15 min |
| PM98 | Waters Xbridge 150 × 50 mm × 10 μm | water (0.05% ammonium hydroxide v/v)-ACN | 32%-62%, 11 min |
| PM99 | Waters Xbridge 150 × 50 mm × 10 μm | water (0.05% ammonium hydroxide v/v)-ACN | 30%-60%, 11 min |
| PM100 | Phenomenex Gemini-NX C18 75 × 30 mm × 3 μm | water (0.05% ammonium hydroxide v/v)-ACN | 34%-64%, 11.5 min |
| PM101 | Waters Xbridge 150 × 50 mm × 10 μm | water (0.05% ammonium hydroxide v/v)-ACN | 10%-40%, 11 min |
| PM102 | Waters Xbridge 150 × 50 mm × 10 μm | water (0.05% ammonium hydroxide v/v)-ACN | 13%-43%, 11 min |
| PM103 | Waters Xbridge 150 × 50 mm × 10 μm | water (0.05% ammonium hydroxide v/v)-ACN | 8%-38%, 11 min |
| PM104 | Waters Xbridge 150 × 50 mm × 10 μm | water (0.05% ammonium hydroxide v/v)-ACN | 17%-47%, 11 min |
| PM105 | Welch Ultimate XB-CN 250 × 70 mm × 10 μm | Hexane-EtOH | 40%-80%, 15 min |
| PM106 | Phenomenex luna C18 150 × 25 mm × 10 μm | water (0.225% FA)-ACN | 5%-35%, 10 min |
| PM107 | Phenomenex luna C18 150 × 25 mm × 10 μm | water (0.225% FA)-ACN | 3%-33%, 10 min |
| PM108 | Phenomenex Gemini-NX C18 75 × 30 mm × 3 μm | water (0.05% ammonium hydroxide v/v)-ACN | 30%-60%, 7 min |
| PM109 | Phenomenex Gemini-NX C18 75 × 30 mm × 3 μm | water (0.05% ammonium hydroxide v/v)-ACN | 8%-38%, 7 min |
| PM110 | Phenomenex Gemini-NX C18 75 × 30 mm × 3 μm | water (0.05% ammonium hydroxide v/v)-ACN | 27%-57%, 7 min |
| PM111 | Waters Xbridge 150 × 50 mm × 10 μm | water (10 mM $NH_4HCO_3$)-ACN | 16%-46%, 11 min |
| PM112 | Waters Xbridge 150 × 50 mm × 10 μm | water (10 mM $NH_4HCO_3$)-ACN | 20%-50%, 11 min |
| PM113 | Waters Xbridge 150 × 50 mm × 10 μm | water (10 mM $NH_4HCO_3$)-ACN | 22%-52%, 11 min |

-continued

| Purification Method (PM) | Column | Mobile phase | Gradient |
|---|---|---|---|
| PM114 | Phenomenex Gemini-NX C18 75 × 30 mm × 3 μm | water (0.05% ammonium hydroxide v/v)-ACN | 12%-42%, 7 min |
| PM115 | Phenomenex Gemini-NX C18 75 × 30 mm × 3 μm | water (0.05% ammonium hydroxide v/v)-ACN | 14%-44%, 7 min |
| PM116 | Phenomenex Gemini-NX C18 75 × 30 mm × 3 μm | water (0.05% ammonium hydroxide v/v)-ACN | 15%-45%, 7 min |
| PM117 | Phenomenex Gemini-NX C18 75 × 30 mm × 3 μm | water (0.05% ammonium hydroxide v/v)-ACN | 13%-43%, 7 min |
| PM118 | Waters Xbridge 150 × 25 mm × 5 μm | water (10 mM $NH_4HCO_3$)-ACN | 17%-47%, 9 min |
| PM119 | Phenomenex Synergi C18 150 × 25 mm × 10 μm | water (0.1% TFA)-ACN | 25%-55%, 10 min |
| PM120 | Phenomenex luna C18 150 × 40 mm × 15 μm | water (0.05% HCl)-ACN | 10%-40%, 10 min |
| PM121 | Shim-pack C18 150 × 25 mm × 10 μm | water (0.225% FA)-ACN | 17%-47%, 10 min |
| PM122 | Phenomenex Synergi C18 150 × 25 mm × 10 μm | water (0.1% HCl)-ACN] | 10%-90%, 20 min |
| PM123 | Phenomenex luna C18 150 × 40 mm × 15 μm | water (0.05% HCl)-ACN | 10%-40%, 10 min |
| PM124 | Welch Ultimate XB-SiOH 250 × 50 mm × 10 μm | Hexane-EtOH | 30%-70%, 15 min |
| PM125 | Waters Xbridge 150 × 50 mm × 10 μm | water (0.05% ammonium hydroxide v/v)-ACN | 18%-48%, 11 min |
| PM126 | Waters Xbridge 150 × 50 mm × 10 μm | water (0.05% ammoniam hydroxide v/v)-ACN | 25%-55%, 11 min |
| PM127 | Welch Ultimate XB-SiOH 250 × 50 mm × 10 μm | Hexane-EtOH | 35%-75%, 15 min |
| PM128 | Waters Xbridge 150 × 50 mm × 10 μm | water (0.05% ammoniam hydroxide v/v)-ACN | 23%-53%, 11 min |
| PM129 | Phenomenex Gemini-NX C18 75 × 30 mm × 3 μm | water (0.05% ammonium hydroxide v/v)-ACN | 6%-36%, 11.5 min |
| PM130 | Waters Xbridge 150 × 25 mm × 5 μm | water (0.05% ammonium hydroxide v/v)-ACN | 17%-47%, 10 min |
| PM131 | Waters Xbridge 150 × 25 mm × 5 μm | water (0.05% ammonium hydroxide v/v)-ACN | 21%-51%, 9 min |
| PM132 | Waters Xbridge 150 × 25 mm × 5 μm | water (0.05% ammonium hydroxide v/v)-ACN | 18%-48%, 9 min |
| PM133 | Phenomenex Gemini-NX C18 75 × 30 mm × 3 μm | water (0.05% ammonium hydroxide v/v)-ACN | 10%-40%, 7 min |
| PM134 | Phenomenex Gemini-NX C18 75 × 30 mm × 3 μm | water (0.05% ammonium hydroxide v/v)-ACN | 20%-50%, 7 min |
| PM135 | Phenomenex Synergi C18 150 × 25 mm × 10 μm | water (0.225% FA)-ACN | 1%-33%, 11 min |
| PM136 | Phenomenex Gemini-NX C18 75 × 30 mm × 3 μm | water (0.225% FA)-ACN | 1%-30%, 7 min |
| PM137 | Phenomenex Gemini-NX C18 75 × 30 mm × 3 μm | water (0.05% ammonium hydroxide v/v)-ACN | 24%-54%, 11.5 min |
| PM138 | Phenomenex Synergi C18 150 × 25 mm × 10 μm | water (0.225% FA)-ACN | 8%-38%, 10 min |
| PM139 | Phenomenex Gemini-NX C18 75 × 30 mm × 3 μm | water (0.05% ammonium hydroxide v/v)-ACN | 11%-41%, 11.5 min |
| PM140 | Phenomenex Gemini-NX C18 75 × 30 mm × 3 μm | water (0.05% ammonium hydroxide v/v)-ACN | 8%-38%, 11.5 min |
| PM141 | Unisil 3-100 C18 Ultra 150 × 50 mm × 3 μm | water (0.225% FA)-ACN | 20%-40%, 10 min |
| PM142 | Phenomenex luna C18 150 × 25 mm × 10 μm | water (0.225% FA)-ACN | 6%-36%, 10 min |
| PM143 | Phenomenex Luna C18 150 × 25 mm × 10 μm | water (0.225% FA)-ACN | 28%-58%, 10 min |
| PM144 | Unisil 3-100 C18 Ultra 150 × 50 mm × 3 μm | water (0.225% FA)-ACN | 25%-45%, 10 min |
| PM145 | Phenomenex luna C18 150 × 25 mm × 10 μm | water (0.225% FA)-ACN | 11%-41%, 10 min |
| PM146 | Phenomenex Synergi C18 150 × 25 mm × 10 μm | water (0.225% FA)-ACN | 1%-31%, 10 min |
| PM147 | Unisil 3-100 C18 Ultra 150 × 50 mm × 3 μm | water (0.225% FA)-ACN | 13%-33%, 10 min |
| PM148 | Phenomenex luna C18 150 × 25 mm × 10 μm | water (0.225% FA)-ACN | 13%-43%, 10 min |
| PM149 | Waters Xbridge 150 × 25 mm × 5 μm | water (10 mM $NH_4HCO_3$)-ACN | 15%-45%, 10 min |
| PM150 | Phenomenex Synergi C18 150 × 25 mm × 10 μm | water (0.1% FA)-ACN] | 10%-90%, 20 min |

-continued

| Purification Method (PM) | Colμmn | Mobile phase | Gradient |
|---|---|---|---|
| PM151 | Phenomenex Synergi C18 150 × 25 mm × 10 μm | water (0.1% ammonium hydroxide)-ACN] | 10%-90%, 20 min |
| PM152 | Phenomenex Gemini-NX C18 75 × 30 mm × 3 μm | water (0.05% ammonium hydroxide v/v)-ACN | 45%-70%, 8 min |
| PM153 | Waters Xbridge 150 × 25 mm × 5 μm | water (0.05% ammonium hydroxide v/v)-ACN | 28%-58%, 10 min |
| PM154 | Phenomenex Gemini-NX C18 75 × 30 mm × 3 μm | water (0.225% FA)-ACN | 8%-28%, 7 min |
| PM155 | Phenomenex Gemini-NX C18 75 × 30 mm × 3 μm | water (0.225% FA)-ACN | 12%-32%, 7 min |
| PM156 | Waters Xbridge 150 × 25 mm × 5 μm | water (10 mM $NH_4HCO_3$)-ACN | 39%-69%, 10 min |
| PM157 | Phenomenex Gemini-NX C18 75 × 30 mm × 3 μm | water (0.225% FA)-ACN | 9%-39%, 10 min |
| PM158 | Phenomenex Gemini-NX C18 75 × 30 mm × 3 μm | water (0.225% FA)-ACN | 15%-45%, 7 min |
| PM159 | Phenomenex Synergi C18 150 × 25 mm × 10 μm | water (0.225% FA)-ACN | 12%-42%, 10 min |
| PM160 | Phenomenex Gemini-NX C18 75 × 30 mm × 3 μm | water (0.225% FA)-ACN | 12%-42%, 7 min |
| PM161 | Phenomenex Gemini-NX C18 75 × 30 mm × 3 μm | water (0.05% ammonium hydroxide v/v)-ACN | 9%-39%, 10 min |
| PM162 | Shim-pack C18 150 × 25 mm × 10 μm | water (0.225% FA)-ACN | 22%-42%, 10 min |
| PM163 | Phenomenex Gemini-NX C18 75 × 30 mm × 3 μm | water (0.05% ammonium hydroxide v/v)-ACN | 17%-47%, 7 min |
| PM164 | Phenomenex Gemini-NX C18 75 × 30 mm × 3 μm | water (0.225% FA)-ACN | 1%-30%, 7 min |
| PM165 | Phenomenex Gemini-NX C18 75 × 30 mm × 3 μm | water (0.05% ammonium hydroxide v/v)-ACN | 18%-48%, 10 min |
| PM166 | Phenomenex Gemini-NX C18 75 × 30 mm × 3 μm | water (0.225% FA)-ACN | 12%-42%, 7 min |
| PM167 | Phenomenex Gemini-NX C18 75 × 30 mm × 3 μm | water (0.225% FA)-ACN | 0%-25%, 7 min |
| PM168 | Waters Xbridge 150 × 25 mm × 5 μm | water (0.05% ammonium hydroxide v/v)-ACN | 43%-73%, 10 mins |
| PM169 | Phenomenex Gemini-NX C18 75 × 30 mm × 3 μm | water (0.225% FA)-ACN | 8%-38%, 2 min |
| PM170 | Phenomenex Gemini-NX C18 75 × 30 mm × 3 μm | water (0.225% FA)-ACN | 18%-48%, 7 min |
| PM171 | Waters Xbridge 150 × 25 mm × 5 μm | water (10 mM $NH_4HCO_3$)-ACN | 40%-70%, 9 min |
| PM172 | Waters Xbridge 150 × 25 mm × 5 μm | water (0.05% ammonium hydroxide v/v)-ACN | 12%-42%, 10 min |
| PM173 | Phenomenex Gemini-NX C18 75 × 30 mm × 3 μm | water (0.225% FA)-ACN | 22%-52%, 7 min |
| PM174 | Phenomenex Gemini-NX C18 75 × 30 mm × 3 μm | water (0.225% FA)-ACN | 20%-50%, 7 min |
| PM175 | Phenomenex Gemini-NX C18 75 × 30 mm × 3 μm | water (0.225% FA)-ACN | 12%-42%, 2 min |
| PM176 | Phenomenex luna C18 75 × 30 mm × 3 μm | water (0.1% TFA)-ACN] | 46%-76%, 7 min |
| PM177 | Waters Xbridge 150 × 25 mm × 5 μm | water (10 mM $NH_4HCO_3$)-ACN | 22%-52%, 8 min |
| PM178 | Phenomenex Synergi C18 150 × 25 mm × 10 μm | water (0.225% FA)-ACN | 11%-41%, 10 min |
| PM179 | Waters Xbridge 150 × 25 mm × 5 μm | water (10 mM $NH_4HCO_3$)-ACN | 23%-53%, 10 min |
| PM180 | Phenomenex Gemini-NX C18 75 × 30 mm × 3 μm | water (0.225% FA)-ACN | 28%-38%, 7 min |
| PM181 | Waters Xbridge 150 × 25 mm × 5 μm | water (10 mM $NH_4HCO_3$)-ACN | 60%-90%, 8 min |
| PM182 | Waters Xbridge 150 × 25 mm × 5 μm | water (10 mM $NH_4HCO_3$)-ACN | 25%-55%, 7 min |
| PM183 | Waters Xbridge 150 × 25 mm × 5 μm | water (10 mM $NH_4HCO_3$)-ACN | 45%-75%, 7 min |
| PM184 | Waters Xbridge 150 × 25 mm × 5 μm | water (0.05% ammonium hydroxide v/v)-ACN | 13%-43%, 9 min |
| PM185 | Waters Xbridge 150 × 25 mm × 5 μm | water (10 mM $NH_4HCO_3$)-ACN | 24%-57%, 8 min |
| PM186 | Waters Xbridge 150 × 25 mm × 5 μm | water (10 mM $NH_4HCO_3$)-ACN | 32%-62%, 10 min |
| PM187 | Waters Xbridge 150 × 25 mm × 5 μm | water (10 mM $NH_4HCO_3$)-ACN | 29%-59%, 10 min |

-continued

| Purification Method (PM) | Column | Mobile phase | Gradient |
|---|---|---|---|
| PM188 | Waters Xbridge 150 × 25 mm × 5 μm | water (0.05% ammonium hydroxide v/v)-ACN | 21%-51%, 10 min |
| PM189 | Phenomenex luna C18 75 × 30 mm × 3 μm | water (0.1% TFA)-ACN] | 25%-55%, 7 min |
| PM190 | Phenomenex luna C18 150 × 40 mm × 15 μm | water (0.1% TFA)-ACN] | 25%-55%, 11 min |
| PM191 | Phenomenex luna C18 75 × 30 mm × 3 μm | water (0.1% TFA)-ACN] | 30%-60%, 7 min |
| PM192 | Waters Xbridge 150 × 25 mm × 5 μm | water (0.05% ammonium hydroxide v/v)-ACN | 10%-40%, 9 min |
| PM193 | Phenomenex Gemini-NX C18 75 × 30 mm × 3 μm | water (0.225% FA)-ACN | 25%-55%, 7 min |
| PM194 | Phenomenex luna C18 150 × 25 mm × 10 μm | water (0.1% TFA)-ACN] | 16%-46%, 11 min |

Abbreviations

Wherein the following abbreviations have been used, the following meanings apply:

ACN is acetonitrile,
AcOH is acetic acid,
$AlCl_3$ is aluminum chloride,
AM is analytical method,
aq. is aqueous,
9-BBN is 9-borabicyclo(3.3.1)nonane,
$Boc_2O$ is di-tert-butyl dicarbonate,
$Br_2$ is bromine solution,
$CBr_4$ is carbon tetrabromide,
CDI is 1,1'-carbonyldiimidazole,
$CHCl_3$-d is deuterated chloroform,
$CsCO_3$ is cesium carbonate,
CsF is cesium fluoride,
CuI is copper iodide,
DCE is dichloroethane,
DCM is dichloromethane,
DIPEA is N,N-diisopropylethylamine,
DMAP is dimethylaminopyridine,
DME is 1,2-dimethoxyethane,
DMF is N,N-dimethylformamide,
DMP is Dess-Martin periodinane,
DMS is dimethylsulfide,
DMSO is dimethyl sulfoxide,
DMSO-$d_6$ is deuterated dimethyl sulfoxide,
dppf is 1,1'-ferrocenediyl-bis(diphenylphosphine),
EA is ethyl acetate,
EDCl is N-(3-dimethylaminopropyl)-N'-ethylcarbodiimide hydrochloride,
EtOH is ethanol,
FA is formic acid,
Fmoc is 9-fluorenylmethoxycarbonyl,
h is hours,
NMR is Nuclear Magnetic Resonance
HATU is (1-[bis(dimethylamino)methylene]-1H-1,2,3-triazolo[4,5-b]pyridinium 3-oxide hexafluorophosphate
HCl is hydrochloric acid,
HOBt is 1-hydroxybenzotriazole,
$H_2O$ is water,
$H_2O_2$ is hydrogen peroxide,
HPLC is High Performance Liquid Chromatography,
KF is potassium fluoride,
$K_2CO_3$ is potassium carbonate,
$K_2SO_4$ is potassium sulphate,
LAH is lithium aluminum hydride,
LCMS is Liquid Chromatography Mass Spectrometry,
$LiOH \cdot H_2O$ is lithium hydroxide monohydrate,
mCPBA is meta-chloroperoxybenzoic acid,
Mel is methyl iodide,
MeOH is methanol,
MeOH-$d_4$ is deuterated methanol,
min is minutes
$MnO_2$ is manganese dioxide,
MS is molecular sieves,
MTBE is methyltertbutylether,
$N_2$ is nitrogen gas,
NaH is sodium hydride,
$NH_4Cl$ is ammonium chloride,
$NaHCO_3$ is sodium bicarbonate,
NaHMDS is sodium bis(trimethylsilyl)amide,
NaOH is sodium hydroxide,
NaOMe is sodium methoxide,
$Na_2SO_4$ is anhydrous sodium sulfate,
n-BuLi is n-butyllithium,
NCS is N-chlorosuccinimide,
$Pd(PPh_3)_4$ is tetrakis(triphenylphosphine)palladium(0),
$Pd(dppf)Cl_2$ is [1,1'-bis(diphenylphosphino)ferrocene]dichloropalladium(II)
$Pd(dppf)Cl_2 \cdot CHCl_2$ is [1,1'-bis(diphenylphosphino)ferrocene]dichloropalladium(II), complex with dichloromethane
PE is petroleum ether,
PM is purification method,
$POCl_3$ is phosphorous oxychloride
rt is retention time,
SEM is silylethoxymethyl,
$SOCl_2$ is thionyl chloride,
TBAC is tetrabutylammonium chloride,
TBAF is tetrabutylammonium fluoride,
TBAl is tetramethylammonium iodide,
TEA is triethylamine,
TFA is trifluoroacetic acid,
TFAA is trifluoroacetic anhydride,
THE is tetrahydrofuran,
TLC is thin layer chromatography,
TMEDA is N'-tetramethylethylenediamine
TMSCN is trimethylsilyl cyanide,
T3P is propylphosphonic anhydride, and
$TsOH \cdot H_2O$ is p-toluenesulfonic acid monohydrate.

Preparation of Intermediates

The following Preparations describe the methods used for common intermediates required for synthesis of the Examples.

Compound 1.1 may be prepared according to the method described in J. Med. Chem. 2011, 54 (2), 635-654.

Synthesis of Intermediate E tert-butyl (4-(cyanomethoxy)butyl)carbamate 1.19

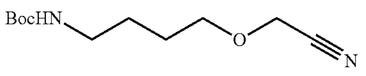 [SMILES: CC(C)(C)OC(=O)NCCCCOCC#N]

To a mixture of tert-butyl (4-hydroxybutyl)carbamate (7 g, 36.99 mmol) and 2-bromoacetonitrile (8.87 g, 73.98 mmol) in DCM (100 mL) was added silver(I) oxide (18.55 g, 80.05 mmol) and TBAl (2.94 g, 7.96 mmol) at 25° C. The mixture was stirred at 25° C. for 16 h. The mixture was filtered, the filtrate washed with aq. $NaHCO_3$ (100 mL), dried with $Na_2SO_4$, filtered and concentrated in vacuo. The crude product was purified (PM7) to afford compound 1.19 (1.0 g, 4.38 mmol, 11.8% yield) as a yellow oil.

$^1$H NMR (CDCl3, 400 MHz) δ: 4.56 (br s, 1H), 4.24 (s, 2H), 3.62-3.59 (t, 2H), 3.18-3.13 (m, 2H), 1.71-1.63 (m, 2H), 1.58-1.53 (m, 2H), 1.45 (s, 9H) ppm.

tert-butyl (4-(2-aminoethoxy)butyl)carbamate 1.20

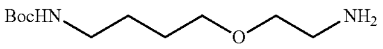

To a solution of compound 1.19 (1.0 g, 4.38 mmol) in MeOH (10 mL) was added ammonium hydroxide (2 mL, 25% wt.) and Raney nickel (100 mg, 1.17 mmol) under nitrogen protection at 25° C. The suspension was degassed under vacuum and purged with hydrogen three times. The mixture was stirred under hydrogen (45 psi) at 25° C. for 16 h. The mixture was filtered and the filtrate concentrated in vacuo to afford compound 1.20 (1 g) as a green oil, which was used directly in the next step.

Methyl 5-((2-(4-((tert-butoxycarbonyl)amino)butoxy)ethyl)amino)benzo[c][2,6]naphthyridine-8-carboxylate, 1.58

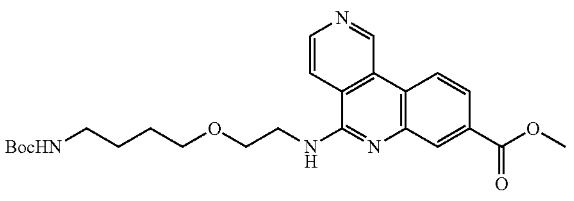 [SMILES: COC(=O)c1ccc2c(c1)nc(NCCOCCCCNC(=O)OC(C)(C)C)c1ccncc12]

To a solution of compound 1.1 (3.20 g, 11.74 mmol) in DMSO (50 mL) was added DIPEA (3.03 g, 23.48 mmol) and compound 1.20 (3 g, 12.91 mmol), sequentially at 25° C. The reaction mixture was then heated to 75° C. and stirred for 12 h. The mixture was diluted with water (100 mL) and extracted with EA (100 mL×2). The combined organic layer was washed with brine (100 mL), dried over anhydrous $Na_2SO_4$, filtered and concentrated in vacuo to afford compound 1.58 (5 g) as a brown solid.

LCMS (AM3): rt=0.841 min, (469.3 $[M+H]^+$), 63.4% purity.

5-((2-(4-((tert-butoxycarbonyl)amino)butoxy)ethyl)amino)benzo[c][2,6]naphthyridine-8-carboxylic acid, 1.59

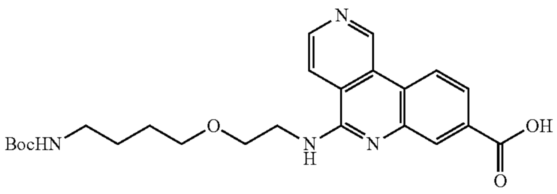 [SMILES: CC(C)(C)OC(=O)NCCCCOCCNc1nc2cc(C(=O)O)ccc2c2cnccc12]

To a solution of compound 1.58 (5 g, 10.67 mmol) in THE (15 mL), MeOH (15 mL) and water (15 mL) was added NaOH (853.65 mg, 21.34 mmol) at 20° C. The reaction mixture was then stirred at 20° C. for 4 h. The organic solvents were concentrated in vacuo and the remaining aqueous solution was acidified with aq. HCl (1 N) to pH5. The resulting precipitate was collected by filtration and dried under vacuum to afford compound 1.59 (4.5 g) as a brown solid.

LCMS (AM3): rt=0.808 min, (455.3 $[M+H]^+$), 88.98% purity.

tert-butyl (4-(2-((8-carbamoylbenzo[c][2,6]naphthyridin-5-yl)amino)ethoxy)butyl) carbamate, 1.60

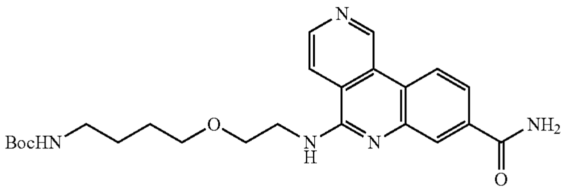 [SMILES: CC(C)(C)OC(=O)NCCCCOCCNc1nc2cc(C(N)=O)ccc2c2cnccc12]

To a stirred solution of compound 1.59 (4.5 g, 9.90 mmol) in DMF (25 mL) was added EDCI (2.85 g, 14.85 mmol), HOBt (2.01 g, 14.85 mmol), DIPEA (1.92 g, 14.85 mmol) and $NH_4Cl$ (2.12 g, 39.60 mmol), sequentially at 20° C. The reaction mixture was then stirred for 3 h at 20° C. The reaction mixture was diluted with water (100 mL) and extracted with EA (100 mL×2). The combined organic layer was washed with brine (80 mL×2), dried over anhydrous $Na_2SO_4$, filtered and concentrated in vacuo. The residue was purified (PM19) to afford compound 1.60 (3.8 g, 6.70 mmol, 67.6% yield, TFA salt) as a yellow oil.

LCMS (AM3): rt=0.758 min, (454.4 $[M+H]^+$), 59.9% purity.

5-((2-(4-aminobutoxy)ethyl)amino)benzo[c][2,6]naphthyridine-8-carboxamide, Intermediate E

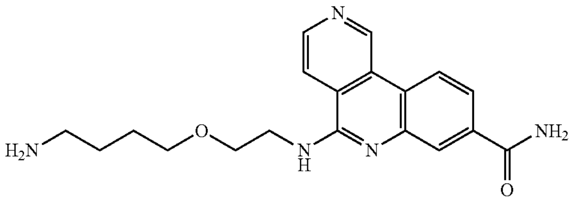 [SMILES: NCCCCOCCNc1nc2cc(C(N)=O)ccc2c2cnccc12]

To a solution of compound 1.60 (3.8 g, 8.38 mmol) in MeOH (5 mL) was added a solution of HCl in MeOH (4 M, 2.09 mL) dropwise at 0° C. The reaction mixture was then warmed to 20° C. and stirred for 2 h. The reaction mixture was concentrated in vacuo to afford Intermediate E (2.8 g, 7.18 mmol, 85.7% yield, HCl salt) as a yellow solid.

LCMS (AM3): rt=0.229 min, (354.1 [M+H]$^+$), 89.5% purity.

Synthesis of Intermediate 1.57 tert-butyl (4-(allyloxy)butyl)carbamate, 1.53

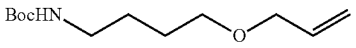 [SMILES: C=CCOCCCCNC(=O)OC(C)(C)C]

To a solution of NaOH (2.11 g, 52.84 mmol) in 1,4-dioxane (176.1 mL) was added tert-butyl N-(4-hydroxybutyl)carbamate (10 g, 52.84 mmol) and 3-bromoprop-1-ene (12.78 g, 105.68 mmol), sequentially at 20° C. The reaction mixture was heated to 70° C. and stirred for 12 h. The reaction mixture was diluted with water (100 mL) and extracted with EA (100 mL×3). The combined organic layer was washed with brine (80 mL×2), dried over anhydrous $Na_2SO_4$, filtered and concentrated in vacuo. The residue was purified (PM6) to afford compound 1.53 (5.5 g, 23.98 mmol, 45.4% yield) as a light yellow oil.

$^1$H NMR (400 MHz, $CHCl_3$-d) δ: 5.93-5.82 (m, 1H), 5.27-5.20 (m, 1H), 5.16-5.11 (m, 1H), 4.70 (br, s, 1H), 3.93-3.91 (m, 2H), 3.43-3.39 (t, 2H), 3.12-3.08 (m, 2H), 1.62-1.49 (m, 4H), 1.40 (s, 9H) ppm.

tert-butyl (4-(2-hydroxyethoxy)butyl)carbamate, 1.54

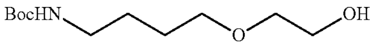 [SMILES: CC(C)(C)OC(=O)NCCCCOCCO]

$O_3$ was bubbled into a solution of compound 1.53 (5.5 g, 23.98 mmol) in DCM (50 mL) at −78° C. until the mixture turned blue, then the reaction mixture was warmed to 0° C. and $NaBH_4$ (1.77 g, 46.79 mmol) was added slowly at 0° C. The reaction mixture was warmed to 20° C. and stirred for 12 h. The reaction was quenched with water (50 mL) and extracted with DCM (80 mL×2). The combined organic layer was washed with brine (80 mL×2), dried over anhydrous $Na_2SO_4$, then filtered and concentrated in vacuo. The residue was purified (PM3) to afford compound 1.54 (2.65 g, 11.36 mmol, 47.4% yield) as a colorless oil.

$^1$H NMR (400 MHz, $CHCl_3$-d) δ: 4.78 (br s, 1H), 3.72-3.71 (m, 2H), 3.53-3.51 (t, 2H), 3.51-3.46 (t, 2H), 3.13-3.12 (m, 2H), 2.41 (br s, 1H), 1.66-1.50 (m, 4H), 1.42 (s, 9H) ppm.

5-(2-(4-((tert-butoxycarbonyl)amino)butoxy)ethoxy)benzo[c][2,6]naphthyridine-8-carboxylic acid, 1.55

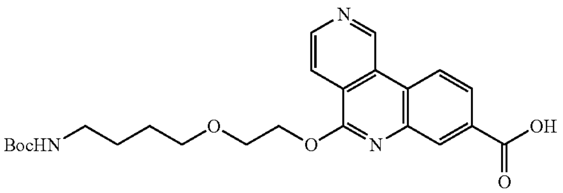 [SMILES: CC(C)(C)OC(=O)NCCCCOCCOc1nc2cc(C(=O)O)ccc2c2cnccc12]

To a mixture of compound 1.54 (427.79 mg, 1.83 mmol) in DMF (10 mL) was added NaH (110.02 mg, 2.75 mmol) in one portion followed by compound 1.1 (500 mg, 1.83 mmol), under nitrogen protection at 0° C. The mixture was then heated to 80° C. and stirred for 12 h. The mixture was diluted with water (50 mL) and extracted with EA (50 mL×2). The combined organic phases were washed with brine (50 mL), dried over $Na_2SO_4$ and concentrated in vacuo. The residue was purified (PM20) to afford compound 1.55 (300 mg, 645.44 μmol, 35.2% yield, 98.2% purity) as a light yellow solid.

LCMS (AM3): rt=0.903 min, (456.3 [M+H]$^+$), 98.2% purity.

tert-butyl (4-(2-((8-carbamoylbenzo[c][2,6]naphthyridin-5-yl)oxy)ethoxy)butyl) carbamate, 1.56

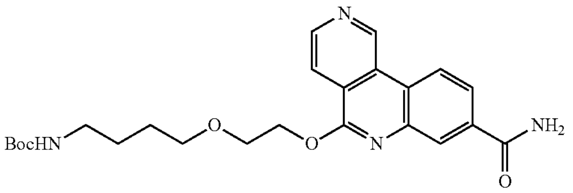 [SMILES: CC(C)(C)OC(=O)NCCCCOCCOc1nc2cc(C(N)=O)ccc2c2cnccc12]

To a mixture of compound 1.55 (300 mg, 645.44 μmol), ammonium chloride (51.79 mg, 968.16 μmol) and DIPEA (208.54 mg, 1.61 mmol) in DMF (10 mL) was added HATU (294.50 mg, 774.53 μmol) at 25° C. The resulting mixture was stirred at 25° C. for 11 h under nitrogen protection. The reaction mixture was filtered and concentrated in vacuo to give a residue which was purified (PM21) to afford compound 1.56 (250 mg, 473.03 μmol, 73.3% yield, 86.2% purity) as a light yellow solid.

LCMS (AM3): rt=0.757 min, (455.3 [M+H]$^+$), 86.2% purity.

5-(2-(4-aminobutoxy)ethoxy)benzo[c][2,6]naphthyridine-8-carboxamide, 1.57

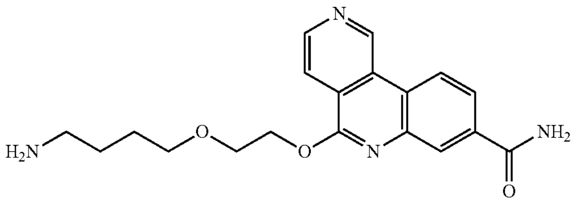 [SMILES: NCCCCOCCOc1nc2cc(C(N)=O)ccc2c2cnccc12]

To a mixture of compound 1.56 (250 mg, 473.03 μmol, 1 eq) in DCM (20 mL) was added TFA (6.16 g, 54.03 mmol, 4 mL) at 25° C. and the mixture was stirred for 0.5 h. The reaction mixture was concentrated in vacuo and purified (PM21) to afford compound 1.57 (220 mg, 432.09 μmol, 91.3% yield, 92.1% purity, TFA salt) as a light yellow solid.

LCMS (AM3): rt=0.675 min, (355.2 [M+H]$^+$), 92.1% purity.

Synthesis of Intermediate Q 5-(2-(4-Aminobutoxy)ethoxy)benzo[c][2,6]naphthyridine-8-carboxylic acid; Intermediate Q

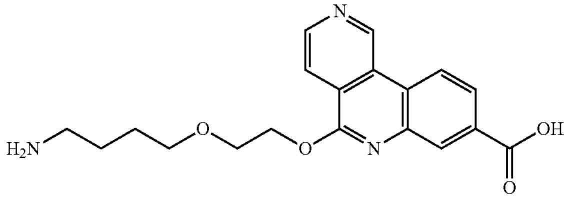 [SMILES: NCCCCOCCOc1nc2cc(C(=O)O)ccc2c2cnccc12]

To a solution of compound 1.55 (100 mg, 219.54 μmol) in DCM (5 mL) was added TFA (1 mL, 13.51 mmol). The mixture was stirred at 25° C. for 0.5 h. The mixture was concentrated in vacuo to afford Intermediate Q (100 mg, 213.03 μmol, 97% yield, TFA salt) as a brown solid, which was used without purification.

LCMS (AM3): rt=0.745 min, (356.3 [M+H]), 79.9% purity.

Synthesis of Intermediate 1.154

Methyl 5-((2-(4-aminobutoxy)ethyl)amino)benzo[c][2,6]naphthyridine-8-carboxylate 1.154

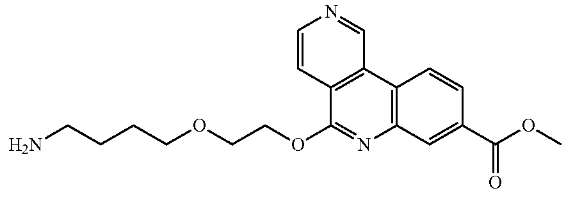 [SMILES: COC(=O)c1ccc2c(c1)nc(OCCOCCCCN)c1ccncc12]

To solution of compound 1.58 (200 mg, 426.85 μmol) in 1,4-dioxane (5 mL) was added a solution of HCl in 1,4-dioxane (4 M, 5 mL) at 20° C. The mixture was stirred at 20° C. for 1 h. The mixture was concentrated in vacuo to afford compound 1.154 (201 mg, HCl salt) as a yellow oil, which was used directly without purification.

LCMS (AM3): rt=0.673 min, (369.2 $[M+H]^+$), 99% purity.

Synthesis of Intermediate R 5-((2-(4-Aminobutoxy)ethyl)amino)benzo[c][2,6]naphthyridine-8-carboxylic acid; Intermediate R

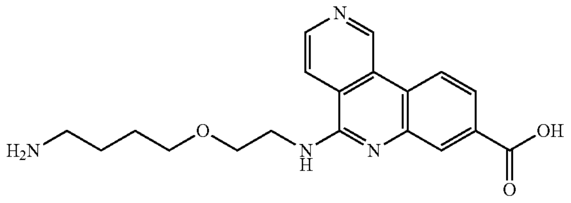 [SMILES: NCCCCOCCNc1nc2cc(C(=O)O)ccc2c2cnccc12]

Compound 1.59 (4 g, 8.80 mmol) in a solution of HCl in 1,4-dioxane (40.00 mL, 4 M) was stirred at 25° C. for 16 h. The precipitate was collected by filtration and dried under vacuum to afford Intermediate R (2.5 g, HCl salt) as a yellow solid.

LCMS (AM3): rt=0.501 min, (354.9 $[M+H]^+$), 96.1% purity.

Synthesis of Intermediate O

Benzyl 3-(4-((tert-butoxycarbonyl)amino)butoxy)azetidine-1-carboxylate 1.493

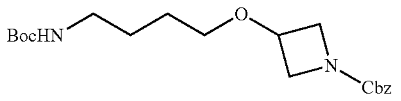 [SMILES: CC(C)(C)OC(=O)NCCCCOC1CN(C(=O)OCc2ccccc2)C1]

To a mixture of 4-((tert-butoxycarbonyl)amino)butyl 4-methylbenzenesulfonate (77.3 g, 225.08 mmol) (*Journal of Medicinal Chemistry,* 2006, 49 (14), 4183-4195), benzyl 3-hydroxyazetidine-1-carboxylate (31.09 g, 150.05 mmol), TBAl (13.86 g, 37.51 mmol) in toluene (500 mL) and water (100 mL) was added NaOH (60.02 g, 1.50 mol). The mixture was heated to 60° C. and stirred for 12 h. The mixture was diluted with water (1 L) and extracted with MTBE (200 mL×3). The combined organic layer was washed with brine (200 mL), dried over $Na_2SO_4$ and concentrated in vacuo. The residue was purified (PM2) to afford compound 1.493 (43.5 g, 76.6% yield).

$^1H$ NMR (400 MHz, $CHCl_3$-d) δ: 7.35-7.26 (m, 5H), 5.07 (s, 2H), 4.74 (br s, 1H), 4.23-4.17 (m, 1H), 4.14-4.07 (m, 2H), 3.88-3.85 (m, 2H), 3.34 (t, J=5.6 Hz, 2H), 3.12-3.08 (m, 2H), 1.61-1.48 (m, 4H), 1.41 (s, 9H) ppm.

tert-Butyl (4-(azetidin-3-yloxy)butyl)carbamate 1.494

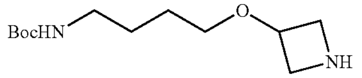 [SMILES: CC(C)(C)OC(=O)NCCCCOC1CNC1]

To a solution of compound 1.493 (43.5 g, 114.94 mmol) in MeOH (500 mL) was added 10% palladium on carbon (5 g) under nitrogen protection at 20° C. The reaction mixture was degassed three times and purged with hydrogen. The mixture was hydrogenated under one atmosphere $H_2$ at 20° C. for 12 h. The mixture was filtered and concentrated in vacuo to obtain compound 1.494 (26.37 g, 93.9% yield) as a light yellow oil, which was used without further purification.

$^1H$ NMR (400 MHz, $CHCl_3$-d) δ: 4.89 (br s, 1H), 4.26-4.19 (m, 1H), 3.67-3.65 (m, 2H), 3.55 (t, J=5.6 Hz, 2H), 3.28 (t, J=6.0 Hz, 2H), 3.10-3.00 (m, 2H), 1.55-1.45 (m, 4H), 1.37 (s, 9H) ppm.

Methyl 5-(3-(4-((tert-butoxycarbonyl)amino)butoxy)azetidin-1-yl)benzo[c][2,6]naphthyridine-8-carboxylate 1.495

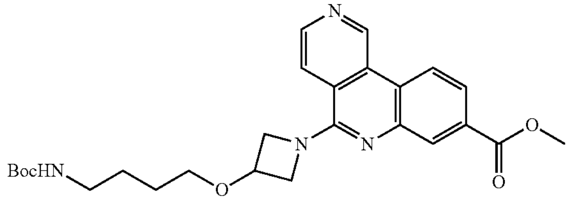 [SMILES: COC(=O)c1ccc2c(c1)nc(N1CC(OCCCCNC(=O)OC(C)(C)C)C1)c1ccncc12]

To a solution of compound 1.1 (9.5 g, 34.84 mmol) and compound 1.494 (11.07 g, 45.29 mmol) in DMSO (200 mL) was added DIPEA (22.51 g, 174.19 mmol). The mixture was heated to 80° C. and stirred for 12 h. The reaction mixture was poured into water (600 mL) and stirred for 10 min. The precipitate was collected by filtration and dried under vacuum to afford compound 1.495 (14.1 g, 27.29 mmol, 78.3% yield) as a yellow solid.

LCMS (AM3): rt=0.839 min, (481.3 $[M+H]^+$), 93.3% purity.

5-(3-(4-((tert-Butoxycarbonyl)amino)butoxy)azetidin-1-yl)benzo[c][2,6]naphthyridine-8-carboxylic acid 1.496

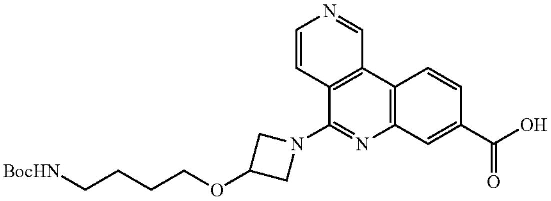 [SMILES: CC(C)(C)OC(=O)NCCCCOC1CN(c2nc3cc(C(=O)O)ccc3c3cnccc23)C1]

To a mixture of compound 1.495 (14.1 g, 29.34 mmol) in THF (100 mL), water (100 mL) and MeOH (50 mL) was added lithium hydroxide monohydrate (6.16 g, 146.71 mmol), and the reaction mixture was heated to 50° C. and stirred for 3 h. The solvent was removed under reduced pressure and acidified to pH 5 with aq. 1 M HCl. The precipitate was collected by filtration and the filter cake was washed with water and dried under vacuum to afford compound 1.496 (15.6 g) as a yellow solid.

LCMS (AM3): rt=0.813 min, (467.3 $[M+H]^+$), 98.7% purity.

5-(3-(4-Aminobutoxy)azetidin-1-yl)benzo[c][2,6]naphthyridine-8-carboxylic acid; Intermediate O

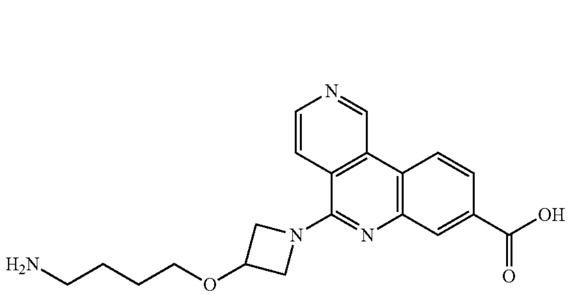 [SMILES: NCCCCOC1CN(c2nc3cc(C(=O)O)ccc3c3cnccc23)C1]

Compound 1.496 (7.6 g, 16.29 mmol) in a solution of HCl in dioxane (80.07 mL, 4 M) was stirred at 20° C. for 1 h. The mixture was concentrated in vacuo to afford Intermediate O (6.9 g, HCl salt) as a yellow solid.

LCMS (AM5): rt=0.737 min, (367.2 $[M+H]^+$), 99.3% purity.

Synthesis of Intermediate P tert-Butyl (4-((1-(8-carbamoylbenzo[c][2,6]naphthyridin-5-yl)azetidin-3-yl)oxy)butyl)carbamate 1.497

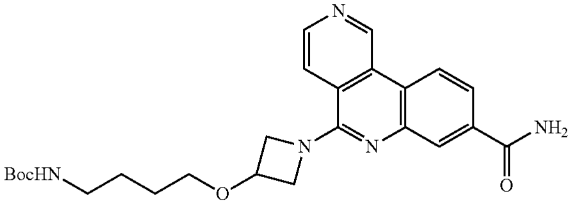 [SMILES: CC(C)(C)OC(=O)NCCCCOC1CN(c2nc3cc(C(N)=O)ccc3c3cnccc23)C1]

To a solution of compound 1.496 (8 g, 17.15 mmol), HATU (15.65 g, 20.58 mmol) and DIPEA (6.65 g, 51.44 mmol) in DMF (100 mL) was added $NH_4Cl$ (917.27 mg, 17.15 mmol). The resulting mixture was stirred at 20° C. for 12 h. The mixture was poured into water (200 mL) and extracted with EA (100 mL×2). The combined organic phase was washed with brine (100 mL), dried over $Na_2SO_4$ and concentrated in vacuo. The residue was purified (PM22) to afford compound 1.497 (6.6 g, 14.05 mmol, 81.9% yield) as a yellow solid.

LCMS (AM3): rt=0.793 min, (466.3 $[M+H]^+$), 99.2% purity.

5-(3-(4-Aminobutoxy)azetidin-1-yl)benzo[c][2,6]naphthyridine-8-carboxamide; Intermediate P

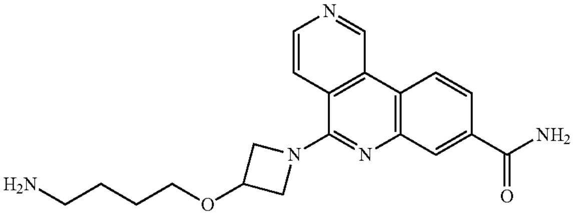 [SMILES: NCCCCOC1CN(c2nc3cc(C(N)=O)ccc3c3cnccc23)C1]

Compound 1.497 (6.6 g, 14.18 mmol) in a solution of HCl in 1,4-dioxane (35 mL, 4 M) was stirred at 20° C. for 1 h. The mixture was concentrated in vacuo to give Intermediate P (5.5 g, HCl salt) as a yellow solid.

LCMS (AM5): rt=0.690 min, (366.2 [M+H]), 92.4% purity

Synthesis of Intermediate 1.32

3-chloro-4-cyclobutoxybenzaldehyde 1.32

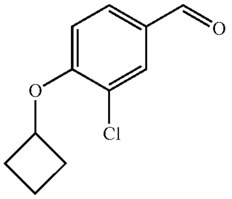 [SMILES: O=Cc1ccc(OC2CCC2)c(Cl)c1]

A mixture of bromocyclobutane (0.25 mL, 2.65 mmol), 3-chloro-4-hydroxybenzaldehyde (200 mg, 1.28 mmol) and potassium carbonate (440 mg, 3.18 mmol) in DMF (10 mL) was stirred at 80° C. for 15 h. The reaction mixture was poured into water (60 mL) and the resulting mixture was extracted with EA (20 mL×3). The combined organic phase was washed with brine (30 mL), dried over anhydrous $Na_2SO_4$, filtered and concentrated in vacuo to give the crude product which was purified (PM11) to afford compound 1.32 (134 mg, 49.8% yield) as a colorless oil.

LCMS (AM1): rt=0.969 min, (211.0 $[M+H]^+$), 66.6% purity.

Synthesis of Intermediate 1.33

3-chloro-4-(cyclopentyloxy)benzaldehyde 1.33

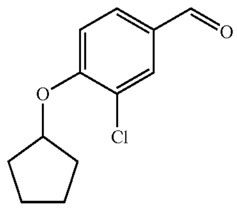 [SMILES: O=Cc1ccc(OC2CCCC2)c(Cl)c1]

A mixture of bromocyclopentane (0.274 mL, 2.56 mmol,), 3-chloro-4-hydroxy-benzaldehyde (200 mg, 1.28 mmol) and potassium carbonate (441 mg, 3.19 mmol) in DMF (10 mL) was stirred at 80° C. for 15 h. The reaction mixture was poured into water (60 mL) and the resulting mixture was extracted with EA (20 mL×3). The combined organic phase was washed with brine (30 mL), dried over anhydrous $Na_2SO_4$, filtered and concentrated in vacuo. The crude product was purified (PM11) to afford compound 1.33 (270 mg, 93.9% yield) as a colourless oil.

LCMS (AM3): rt=1.017 min, (266.0 $[M+H_2O+Na]^+$), 96.9% purity.

Synthesis of Intermediate 1.47

3-bromo-4-cyclobutoxybenzaldehyde 1.46

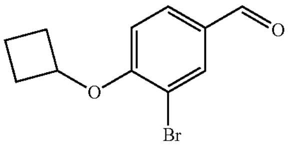 [SMILES: O=Cc1ccc(OC2CCC2)c(Br)c1]

To a mixture of 3-bromo-4-hydroxybenzaldehyde (1.0 g, 4.97 mmol) and bromocyclobutane (1.01 g, 7.46 mmol) in DMF (10 mL) was added potassium carbonate (2.06 g, 14.92 mmol) at room temperature. The resulting mixture was heated to 80° C. and stirred for 12 h. The reaction mixture was concentrated in vacuo to give a residue that was poured into water (10 mL) and extracted with EA (50 mL×3). The combined organic phases were washed with brine (50 mL), dried with anhydrous $Na_2SO_4$ and concentrated in vacuo. The crude product was purified (PM4) to afford compound 1.46 (1.0 g, 3.80 mmol, 76.4% yield, 97% purity) as a yellow solid.

LCMS (AM3): rt=0.983 min, (257.0 $[M+H]^+$), 86.62% purity.

$^1H$ NMR (400 MHz, MeOD-d4) δ: 9.79 (s, 1H), 8.07 (d, J=2.0 Hz, 1H), 7.84 (dd, J=2.0, 8.5 Hz, 1H), 7.03 (d, J=8.6 Hz, 1H), 4.93-4.85 (m, 1H), 2.61-2.48 (m, 2H), 2.29-2.14 (m, 2H), 1.99-1.65 (m, 2H) ppm.

2-cyclobutoxy-5-formylbenzonitrile 1.47

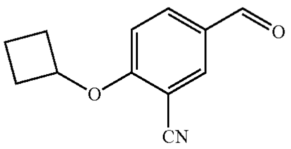 [SMILES: N#Cc1cc(C=O)ccc1OC1CCC1]

To a mixture of compound 1.46 (200 mg, 783.98 μmol) in DMF (1 mL) was added zinc cyanide (460.32 mg, 3.92 mmol) and tetrakis(triphenylphosphine)palladium (90.59 mg, 78.40 μmol), sequentially at 25° C. under nitrogen protection. The reaction mixture was then heated to 100° C. and stirred for 12 h. The mixture was concentrated in vacuo and purified (PM38) to afford compound 1.47 (80 mg, 397.57 μmol, 50.7% yield, 100% purity) as a white solid.

LCMS (AM3): rt=0.885 min, (202.0 $[M+H]^+$), 100.0% purity.

$^1H$ NMR (400 MHz, $CHCl_3$-d) δ: 9.88 (s, 1H), 8.09 (d, J=2.0 Hz, 1H), 8.03 (dd, J=2.0, 8.8 Hz, 1H), 6.95 (d, J=8.8 Hz, 1H), 4.88-4.81 (m, 1H), 2.59-2.49 (m, 2H), 2.38-2.28 (m, 2H), 2.03-1.91 (m, 1H), 1.85-1.73 (m, 1H) ppm.

Synthesis of Intermediate 1.52

2-cyclopropyl-5-formylbenzonitrile 1.52

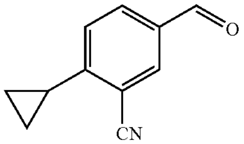

To a mixture of cyclopropylboronic acid (122.69 mg, 1.43 mmol) and 2-bromo-5-formylbenzonitrile (200 mg, 952.26 μmol) in 1,4-dioxane (1 mL) and water (0.1 mL) was added $Pd(dppf)Cl_2{\cdot}CH_2Cl_2$ (77.77 mg, 95.23 μmol) and potassium carbonate (263.22 mg, 1.90 mmol), sequentially at 25° C. under nitrogen protection. The mixture was heated to 90° C. and stirred for 12 h. The mixture was concentrated in vacuo and purified by prep-TLC ($SiO_2$, PE: EA=3:1) to afford compound 1.52 (100 mg, 566.61 μmol, 59.5% yield, 97% purity) as a white solid.

LCMS (AM3): rt=0.808 min, (172.2 $[M+H]^+$), 97.81% purity.

$^1H$ NMR (400 MHz, $CHCl_3$-d) δ: 9.96 (s, 1H), 8.09 (d, J=1.6 Hz, 1H), 7.97 (dd, J=1.6, 8.4 Hz, 1H), 7.06 (d, J=8.4 Hz, 1H), 2.40 (m, 1H), 1.31-1.30 (m, 2H), 0.95-0.93 (m, 2H) ppm.

Synthesis of Intermediate 1.90

3-Chloro-4-cyclopropoxybenzaldehyde 1.90

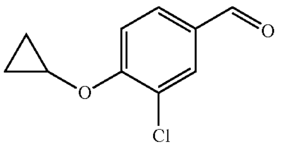 [SMILES: O=Cc1ccc(OC2CC2)c(Cl)c1]

To a solution of 3-chloro-4-fluoro-benzaldehyde (1.8 g, 11.35 mmol) in acetonitrile (20 mL) was added potassium carbonate (2.35 g, 17.03 mmol) and cyclopropanol (725.27 mg, 12.49 mmol) at 25° C. The reaction mixture was heated to 80° C. and stirred for 12 h. The reaction mixture was filtered and concentrated in vacuo. The residue was purified (PM11) to afford compound 1.90 (120 mg, 610.28 μmol, 5% yield) as a yellow oil.

$^1$H NMR (400 MHz, $CHCl_3$-d) δ: 9.87 (s, 1H), 7.90 (d, J=2.1 Hz, 1H), 7.79 (dd, J=2.0, 8.5 Hz, 1H), 7.44 (d, J=8.4 Hz, 1H), 3.94-3.87 (m, 1H), 0.92 (d, J=4.5 Hz, 4H) ppm.

Synthesis of Intermediate 1.102

3-Chloro-5-(hydroxymethyl)benzaldehyde, 1.102

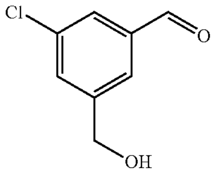 [SMILES: O=Cc1cc(Cl)cc(CO)c1]

To a mixture of (3-bromo-5-chloro-phenyl)methanol (2 g, 9.03 mmol) and TMEDA (2.10 g, 18.05 mmol, 2.72 mL) in THF (20 mL) was added n-BuLi (2.4 M, 7.53 mL) at −78° C. dropwise, then the resulting mixture was allowed to warm to −20° C. and stirred for 1 h. The reaction mixture was cooled again to −78° C. and DMF (10 mL) was added. The resulting mixture was warmed to 20° C. and stirred for another 1 h. The reaction mixture was quenched with a saturated aqueous solution of ammonium chloride (100 mL) and extracted with EA (20 mL×3). The combined organic layers were washed with brine (10 mL), dried over $Na_2SO_4$, filtered and concentrated in vacuo. The residue was purified (PM2) to afford compound 1.102 (400 mg, 2.34 mmol, 26% yield) as a yellow oil.

$^1$H NMR (400 MHz, $CHCl_3$-d) δ: 9.99 (s, 1H), 7.78 (m, 2H), 7.65 (s, 1H), 4.80 (d, J=4.6 Hz, 2H) pm.

Synthesis of Intermediate 1.134

2-(3-(Hydroxymethyl)phenyl)acetonitrile 1.133

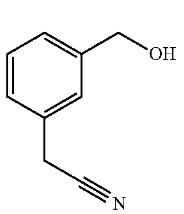 [SMILES: N#CCc1cccc(CO)c1]

To a solution of methyl 3-(cyanomethyl)benzoate (1.5 g, 8.56 mmol) in THF (15 mL) was added $LiBH_4$ (2 M, 12.84 mL, 25.69 mmol) at ambient temperature. The reaction mixture was then heated to 70° C. and stirred for 4 h. The mixture was cooled to room temperature, quenched with aq. HCl (1 N, 50 mL) and extracted with EA (20 mL×3). The combined organic phases were washed with brine (50 mL), dried over anhydrous $Na_2SO_4$ and concentrated in vacuo. The residue was purified (PM6) to afford compound 1.133 (1.0 g, 6.79 mmol, 79.3% yield) as a colorless oil.

$^1$H NMR (400 MHz, $CHCl_3$-d) δ: 7.35-7.18 (m, 4H), 4.65 (s, 2H), 3.68 (s, 2H) ppm.

2-(3-Formylphenyl)acetonitrile 1.134

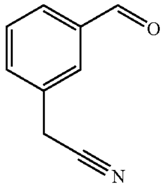 [SMILES: N#CCc1cccc(C=O)c1]

To a solution of compound 1.133 (500 mg, 3.40 mmol) in DCM (20 mL) was added manganese (IV) oxide (2.95 g, 33.97 mmol) at 30° C. The reaction mixture was stirred at 30° C. for 12 h. The reaction mixture was filtered and the filtrate was concentrated in vacuo. The residue was purified (PM6) to afford compound 1.134 (50 mg, 344.45 μmol, 10.1% yield) as a yellow oil.

$^1$H NMR (400 MHz, $CHCl_3$-d) δ: 10.05 (s, 1H), 7.89-7.87 (m, 2H), 7.67-7.57 (m, 2H), 3.86 (s, 2H) ppm.

Synthesis of Intermediate 1.136

5-Formyl-2-(trifluoromethoxy)benzonitrile 1.136

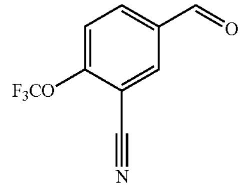 [SMILES: N#Cc1cc(C=O)ccc1OC(F)(F)F]

To a solution of 3-bromo-4-(trifluoromethoxy)benzaldehyde (500 mg, 1.86 mmol) in DMF (15 mL) was added zinc cyanide (0.82 g, 6.98 mmol) and tetrakis(triphenylphosphine) palladium (214.78 mg, 185.86 μmol) at ambient temperature. The reaction mixture was then heated to 100° C. and stirred for 12 h under nitrogen protection. The mixture was cooled to room temperature and poured into water (50 mL). The aqueous mixture was extracted with EA (20 mL×3). The combined organic phases were washed with brine (50 mL), dried over anhydrous $Na_2SO_4$ and concentrated in vacuo. The obtained residue was purified (PM12) to afford compound 1.136 (170 mg, 790.23 μmol, 42.5% yield) as a brown oil.

$^1$H NMR (400 MHz, $CHCl_3$-d) δ: 10.03 (s, 1H), 8.25 (d, J=1.4 Hz, 1H), 8.19 (dd, J=8.4, 1.4 Hz, 1H), 7.58 (dd, J=8.4, 1.8 Hz, 1H) ppm.

Synthesis of Intermediate 1.153

Methyl 5-bromo-2-(trifluoromethoxy)benzoate, 1.150

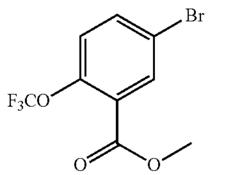 [SMILES: COC(=O)c1cc(Br)ccc1OC(F)(F)F]

To an ice-cooled solution of 5-bromo-2-(trifluoromethoxy)benzoic acid (2 g, 7.02 mmol) in MeOH (20 mL) was added $SOCl_2$ (1.67 g, 14.03 mmol) slowly. The resulting mixture was heated to 70° C. and stirred for 1 h. The mixture was concentrated in vacuo and the obtained residue was diluted with EA (100 mL). The organic phase was washed with sodium bicarbonate (50 mL) and brine (50 mL), dried over $Na_2SO_4$ and concentrated in vacuo to afford compound 1.150 (2.9 g) as a yellow oil, which was used directly without further purification.

$^1$H NMR (400 MHz, $CHCl_3$-d) δ: 8.09 (d, J=2.6 Hz, 1H), 7.68 (dd, J=2.5, 8.7 Hz, 1H), 7.22 (dd, J=1.0, 8.7 Hz, 1H), 3.95 (s, 3H) ppm.

(5-Bromo-2-(trifluoromethoxy)phenyl)methanol, 1.151

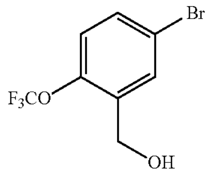 [SMILES: OCc1cc(Br)ccc1OC(F)(F)F]

To a solution of compound 1.150 (2.9 g, 9.70 mmol) in THF (20 mL) was added $LiAlH_4$ (368.07 mg, 9.70 mmol) at 0° C. under nitrogen. The mixture was warmed to 20° C. and stirred for 1 h. The mixture was cooled to 0° C. and diluted with EA (10 mL). The resulting mixture was then quenched with water (0.2 mL) followed by addition of aq. 10% NaOH (0.2 mL) and water (0.6 mL). Anhydrous $Na_2SO_4$ (5 g) was added, the resulting suspension was stirred for another 0.5 h and then filtered. The filtrate was concentrated in vacuo to afford compound 1.151 (2.23 g, 8.23 mmol, 84.8% yield) as a white solid, which was used directly without further purification.

LCMS (AM3): rt=0.801 min, (290.3 $[M+NH_4]^+$), 85.1% purity.

(2-(Trifluoromethoxy)-5-vinylphenyl)methanol, 1.152

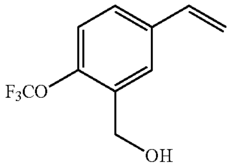

To a solution of compound 1.151 (2.23 g, 8.23 mmol) and tributyl(vinyl)stannane (2.61 g, 8.23 mmol) in toluene (50 mL) was added $Pd(PPh_3)_4$ (665.54 mg, 575.95 μmol) under nitrogen protection at ambient temperature. The mixture was heated to 95° C. and stirred for 12 h. The residue was poured into saturated aqueous KF solution (100 mL) and the resulting mixture was stirred for 15 min, then extracted with EA (50 mL×3). The combined organic phase was washed with brine (100 mL×3), dried with anhydrous $Na_2SO_4$, filtered and concentrated in vacuo. The residue was purified (PM7) to afford compound 1.152 (1.43 g, 6.55 mmol, 79.7% yield) as a yellow oil.

$^1$H NMR (400 MHz, $CHCl_3$-d) δ: 7.49 (d, J=2.2 Hz, 1H), 7.26 (dd, J=2.2, 8.4 Hz, 1H), 7.10-7.08 (dd, 1H), 6.61 (dd, J=10.9, 17.6 Hz, 1H), 5.67 (d, J=17.6 Hz, 1H), 5.21 (d, J=10.9 Hz, 1H), 4.67 (s, 2H), 2.12-2.04 (br s, 1H) ppm.

3-(Hydroxymethyl)-4-(trifluoromethoxy)benzaldehyde, 1.153

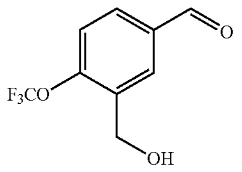 [SMILES: O=Cc1ccc(OC(F)(F)F)c(CO)c1]

Ozone was bubbled into a solution of compound 1.152 (500 mg, 2.29 mmol) in DCM (10 mL) at −70° C. until the mixture turned blue. Dimethyl sulfide (1.42 g, 22.92 mmol) was then added. The mixture was warmed up to 20° C. and stirred for 12 h. The mixture was concentrated in vacuo and purified (PM7) to afford compound 1.153 (326 mg, 1.48 mmol, 64.6% yield) as a light yellow oil.

$^1$H NMR (400 MHz, $CHCl_3$-d) δ: 9.93 (s, 1H), 8.06 (d, 1H), 7.79 (dd, J=2.1, 8.5 Hz, 1H), 7.31 (dd, J=1.8, 8.4 Hz, 1H), 4.77 (s, 2H), 2.40 (br s, 1H) ppm.

Synthesis of Intermediate 1.202

3-Chloro-4-cyclopropylbenzaldehyde 1.202

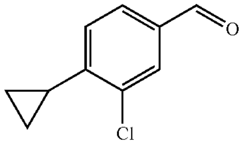

To a mixture of cyclopropylboronic acid (156 mg, 1.82 mmol) in 1,4-dioxane (8 mL) and water (2 mL) was added 4-bromo-3-chloro-benzaldehyde (200 mg, 0.911 mmol) followed by addition of $K_2CO_3$ (315 mg, 2.28 mmol) and $Pd(dppf)Cl_2$ (66 mg, 0.090 mmol) at ambient temperature. The mixture was degassed and purged with nitrogen three times, then it was heated to 80° C. and stirred for 14 h. The reaction mixture was filtered and the filtrate was concentrated in vacuo. The residue was purified (PM11) to afford compound 1.202 (130 mg, 79% yield) as a colorless oil.

$^1$H NMR (400 MHz, MeOH-$d_4$) δ: 9.89 (s, 1H), 7.87 (d, J=1.6 Hz, 1H), 7.73 (dd, J=8.0 Hz, 1.2 Hz, 1H), 7.15 (d, J=8.0 Hz, 1H), 2.35-2.29 (m, 1H), 1.18-1.12 (m, 2H), 0.84-0.80 (m, 2H) ppm.

Synthesis of Intermediate 1.345

2-Chloro-2'-(hydroxymethyl)-[1,1'-biphenyl]-4-carbaldehyde, 1.345

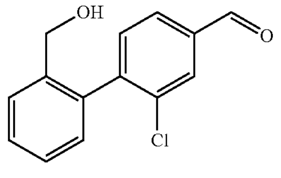 [SMILES: O=Cc1ccc(-c2ccccc2CO)c(Cl)c1]

To a mixture of (2-(hydroxymethyl)phenyl)boronic acid (250 mg, 1.65 mmol), 4-bromo-3-chlorobenzaldehyde (361 mg, 1.64 mmol) and $K_2CO_3$ (569 mg, 4.12 mmol) in 1,4-dioxane (8 mL) and water (2 mL), was added Pd(dppf) $Cl_2 \cdot CH_2Cl_2$ (67 mg, 0.082 mmol). The reaction was degassed and purged with nitrogen three times, then the reaction mixture was heated to 80° C. and stirred for 17 h. The reaction mixture was filtered and the filtrate concentrated in vacuo. The residue was purified (PM6) to afford compound 1.345 (400 mg, 98.6% yield) as a colorless oil.

$^1$H NMR (400 MHz, DMSO-$d_6$) δ: 10.05 (s, 1H), 8.07 (d, J=1.6 Hz, 1H), 7.92 (dd, J=1.6 Hz, 8.0 Hz, 1H), 7.61 (dd, J=0.8 Hz, 7.6 Hz, 1H), 7.55 (d, J=7.6 Hz, 1H), 7.47-7.44 (t, 1H), 7.38-7.34 (t, 1H), 7.14 (dd, J=1.2 Hz, 7.6 Hz, 1H), 5.12 (t, J=5.6 Hz, 1H), 4.30-4.15 (qd, 2H) ppm.

Synthesis of Intermediate 1.366

2-(3-Chloro-5-vinylphenyl)acetonitrile 1.365

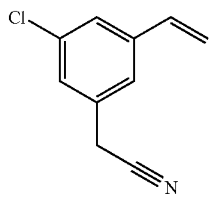

A mixture of 2-(3-bromo-5-chlorophenyl)acetonitrile (500 mg, 1.08 mmol) (US2008221127A1), tributyl(vinyl) stannane (343.94 mg, 1.08 mmol) and $Pd(PPh_3)_4$ (125 mg, 1.08 μmol) in toluene (10 mL) was stirred at 90° C. for 15 h. The mixture was poured into saturated aqueous KF solution (100 mL) and then extracted with EA (100 mL×2). The combined organic phases were washed with brine (50 mL), dried over $Na_2SO_4$ and concentrated. The residue was purified (PM14) to afford compound 1.365 (200 mg) as a yellow oil.

$^1$H NMR (400 MHz, $CHCl_3$-d) δ: 7.37 (s, 1H), 7.23 (d, J=6.0 Hz, 2H), 6.69-6.62 (dd, 1H), 5.82 (d, J=12 Hz, 1H), 5.40 (d, J=16.4 Hz, 1H), 3.74 (s, 2H) ppm.

2-(3-Chloro-5-formylphenyl)acetonitrile 1.366

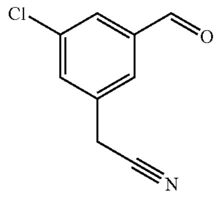 [SMILES: N#CCc1cc(Cl)cc(C=O)c1]

To a solution of compound 1.365 (200 mg, 1.13 mmol) in DCM (20 mL) was bubbled ozone for 0.5 h at −78° C.; the reaction mixture turned blue, then DMS (3.66 g, 58.91 mmol) was added slowly to the above mixture at −78° C. The reaction mixture was warmed up to 20° C. and stirred for another 12 h. The reaction mixture was concentrated in vacuo and the residue was purified (PM7) to afford compound 1.366 (150 mg, 835.18 μmol, 74.2% yield) as a white solid.

$^1$H NMR (400 MHz, $CHCl_3$-d) δ: 9.99 (s, 1H), 7.84 (t, J=1.6 Hz, 1H), 7.75 (d, J=1.6 Hz, 1H), 7.62 (t, J=1.2 Hz, 1H), 3.84 (s, 2H) ppm.

Synthesis of Intermediate 1.402

2-(5-Bromo-2-(trifluoromethoxy)phenoxy)ethanol 1.401

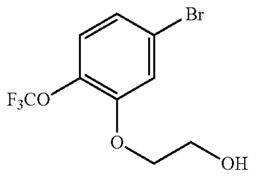 [SMILES: OCCOc1cc(Br)ccc1OC(F)(F)F]

A mixture of 5-bromo-2-(trifluoromethoxy)phenol (900 mg, 3.5 mmol), 2-bromoethanol (0.63 mL, 8.87 mmol) and $K_2CO_3$ (1.21 g, 8.73 mmol) in acetonitrile (18 mL) was heated to 80° C. and stirred for 15 h. The reaction mixture was concentrated in vacuo and the residue was purified (PM6) to afford compound 1.401 (850 mg, 80.6% yield) as a colorless oil.

$^1$H NMR (400 MHz, DMSO-$d_6$) δ: 7.48 (d, J=2.4 Hz, 1H), 7.32 (dd, J=8.8 Hz, 1.2 Hz, 1H), 7.2 (dd, J=8.8 Hz, 2.4 Hz, 1H), 4.90 (t, J=5.2 Hz, 1H), 4.12 (t, J=4.8 Hz, 2H), 3.71 (q, J=5.2 Hz, 2H) ppm.

3-(2-Hydroxyethoxy)-4-(trifluoromethoxy)benzaldehyde 1.402

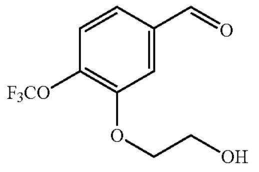 [SMILES: O=Cc1ccc(OC(F)(F)F)c(OCCO)c1]

To a mixture of compound 1.401 (650 mg, 2.16 mmol), DMF (315 mg, 4.32 mmol) and TMEDA (500 mg, 4.31 mmol) in THE (20 mL) was added n-BuLi (1.76 mL, 2.5 M in hexane) at −70° C. The reaction mixture was stirred at −70° C. for 1 h, then it was warmed up to 25° C. and stirred for another 1 h. The reaction mixture was quenched by adding water (1 mL) and extracted with EA (50 mL×2). The combined organic phase was washed with brine (30 mL), dried over $Na_2SO_4$ and concentrated in vacuo. The residue was purified (PM47) to afford compound 1.402 (48 mg, 6% yield) as a yellow oil.

LCMS (AM2): rt=0.739 min, (251.1 $[M+H]^+$), 66.6% purity.

Synthesis of Intermediate 1.406

Methyl 3-(2-hydroxyethoxy)-4-(trifluoromethyl)benzoate 1.404

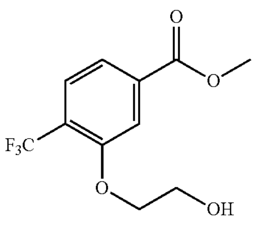 [SMILES: COC(=O)c1ccc(C(F)(F)F)c(OCCO)c1]

A mixture of methyl 3-hydroxy-4-(trifluoromethyl)benzoate (1.1 g, 5.00 mmol) (*Journal of Medicinal Chemistry,* 2005, 48 (9), 3290-3312), 2-bromoethanol (0.71 mL, 10 mmol) and $K_2CO_3$ (1.39 g, 10.03 mmol) in DMF (15 mL) was stirred at 80° C. for 16 h. The reaction mixture was filtered and the filtrate was poured into water (100 mL) and extracted with EA (50 mL×2). The combined organic phase was washed with brine (30 mL), dried over $Na_2SO_4$ and concentrated in vacuo. The residue was purified (PM47) to afford compound 1.404 (850 mg, 64.4% yield) as a brown oil.

LCMS (AM2): rt=0.779 min, (286.9 $[M+Na]^+$), 100% purity.

2-(5-(Hydroxymethyl)-2-(trifluoromethyl)phenoxy) ethanol 1.405

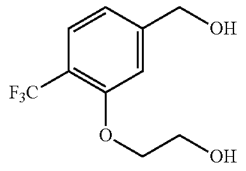 [SMILES: OCCOc1cc(CO)ccc1C(F)(F)F]

To a mixture of LAH (345 mg, 9.09 mmol) in THE (15 mL) at 0° C. was added compound 1.404 (800 mg, 3.03 mmol) in THE (5 mL). The reaction mixture was then warmed to room temperature and stirred for 2 h. The reaction was quenched by addition of water (0.4 mL) followed by 0.4 mL of aq. NaOH solution (10%) and water (1.2 mL). After stirring for 0.5 h, $Na_2SO_4$ was added and the resulting suspension was stirred for another 30 min, filtered and the filtrate was concentrated in vacuo to afford compound 1.405 (600 mg) as a brown oil, which was used directly without further purification.

$^1$H NMR (400 MHz, DMSO-$d_6$) δ: 7.54 (d, J=8.0 Hz. 1H), 7.19 (s, 1H), 7.02 (d, J=8.0 Hz, 1H), 5.41 (br, s, 1H), 4.86 (br, s, 1H), 4.55 (s, 2H), 4.10 (t, J=5.2 Hz, 2H), 3.73 (t, J=5.2 Hz, 2H) ppm.

3-(2-Hydroxyethoxy)-4-(trifluoromethyl)benzaldehyde 1.406

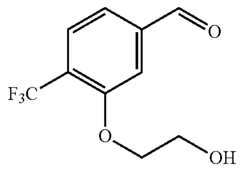 [SMILES: O=Cc1ccc(C(F)(F)F)c(OCCO)c1]

A mixture of compound 1.405 (550 mg, 2.33 mmol) and manganese (IV) oxide (2.02 g, 23.28 mmol) in DCM (20 mL) was stirred at room temperature for 20 h. The reaction mixture was filtered and the filtrate was concentrated in vacuo. The crude product was purified (PM5) to afford compound 1.406 (380 mg, 59.2% yield) as a brown oil.

$^1$H NMR (400 MHz, DMSO-$d_6$) δ: 10.08 (s, 1H), 7.86 (d, J=8.0 Hz. 1H), 7.75 (s, 1H), 7.63 (d, J=8.0 Hz, 1H), 4.90 (t, J=5.2 Hz, 1H), 4.24 (t, J=5.2 Hz, 2H), 3.76 (q, J=5.2 Hz, 2H) ppm.

Synthesis of Intermediate 1.410

3-(2-Hydroxyethoxy)-4-methoxybenzaldehyde 1.408

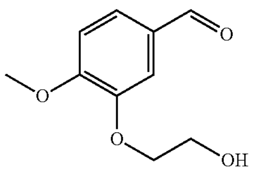

A mixture of 3-hydroxy-4-methoxy-benzaldehyde (8.8 g, 57.84 mmol), 2-bromoethanol (8 mL, 113 mmol) and $K_2CO_3$ (16 g, 116 mmol) in acetonitrile (100 mL) was stirred at 80° C. for 14 h. The reaction mixture was filtered and the filtrate was concentrated in vacuo. The residue was purified (PM3) to afford compound 1.408 (7.8 g, 66.7% yield) as a white solid.

LCMS (AM3): rt=0.778 min, (197.2 $[M+H]^+$), 97.2% purity.

4-Hydroxy-3-(2-hydroxyethoxy)benzaldehyde 1.409

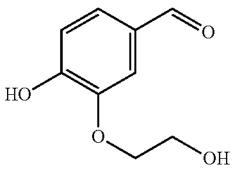 [SMILES: O=Cc1ccc(O)c(OCCO)c1]

To a solution of compound 1.408 (7.7 g, 39.25 mmol) in DCM (200 mL) was added $AlCl_3$ (26.18 g, 196.34 mmol) at room temperature. The reaction mixture was stirred at room temperature for 15 h. The reaction mixture was poured into water (300 mL) at 0° C. and extracted with a solvent mixture of DCM and MeOH (v/v=10:1, 50 mL×10). The combined organic phase was washed with brine (400 mL), dried over anhydrous $Na_2SO_4$, filtered and concentrated in vacuo. The residue was purified (PM2) to afford compound 1.409 (5.3 g, 74.1% yield) as a yellow solid.

LCMS (AM3): rt=0.699 min, (183.2 $[M+H]^+$), 97.9% purity.

4-Cyclobutoxy-3-(2-hydroxyethoxy)benzaldehyde 1.410

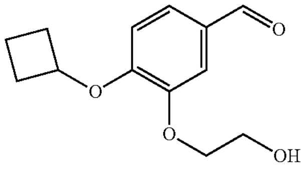 [SMILES: O=Cc1ccc(OC2CCC2)c(OCCO)c1]

A mixture of compound 1.409 (200 mg, 1.10 mmol), bromocyclobutane (296 mg, 2.19 mmol) and $K_2CO_3$ (378 mg, 2.73 mmol) in DMF (10 mL) was stirred at 100° C. for 24 h. The reaction mixture was poured into water (30 mL) and the resulting mixture was extracted with EA (10 mL×5). The combined organic phase was washed with brine (50 mL), dried over anhydrous $Na_2SO_4$, filtered and concentrated in vacuo. The residue was purified (PM4) to afford compound 1.410 (250 mg, 96.4% yield) as a light yellow oil.

LCMS (AM3): rt=0.805 min, (237.6 $[M+H]^+$), 98.5% purity.

Synthesis of Intermediate 1.412

4-Chloro-3-(2-hydroxyethoxy)benzaldehyde, 1.412

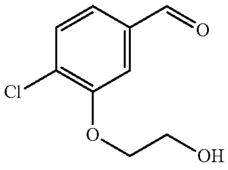 [SMILES: O=Cc1ccc(Cl)c(OCCO)c1]

A mixture of 4-chloro-3-hydroxy-benzaldehyde (200 mg, 1.28 mmol), 2-bromoethanol (0.2 mL, 2.82 mmol) and $K_2CO_3$ (440 mg, 3.18 mmol) in acetonitrile (4 mL) was stirred at 80° C. for 12 h. The reaction mixture was filtered and the filtrate was concentrated in vacuo. The residue was purified (PM6) to afford compound 1.412 (240 mg, 93.6% yield) as a colorless oil.

LCMS (AM3): rt=0.723 min, (201.1 $[M+H]^+$), 93.4% purity.

Synthesis of Intermediate 1.469

1-Bromo-3-(chloromethyl)-5-(trifluoromethyl)benzene 1.466

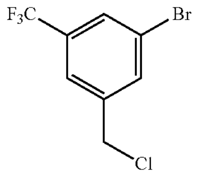 [SMILES: FC(F)(F)c1cc(Br)cc(CCl)c1]

To a solution of (3-bromo-5-(trifluoromethyl)phenyl) methanol (2 g, 7.84 mmol) in 1,4-dioxane (10 mL) was added $SOCl_2$ (1.87 g, 15.68 mmol) at 0° C. The mixture was then heated to 90° C. and stirred for 1 h. The mixture was concentrated in vacuo to give compound 1.466 (2 g, crude) as a black oil.

$^1$H NMR (400 MHz, $CHCl_3$-d) δ: 7.75 (d, J=1.0 Hz, 2H), 7.59 (s, 1H), 4.59 (s, 2H) ppm.

2-(3-Bromo-5-(trifluoromethyl)phenyl)acetonitrile 1.467

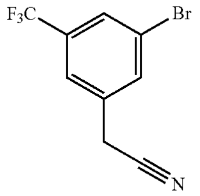 [SMILES: N#CCc1cc(Br)cc(C(F)(F)F)c1]

To a solution of trimethylsilanecarbonitrile (870.62 mg, 8.78 mmol) and compound 1.466 (2 g, 7.31 mmol) in acetonitrile (4 mL) was added TBAF (8.78 mL, 8.78 mmol, 1 M in THF). The mixture was stirred at 25° C. for 12 h. The mixture was concentrated in vacuo and the residue was purified (PM14) to give compound 1.467 (1.48 g, 5.61 mmol, 76.6% yield) as a light yellow oil.

$^1$H NMR (400 MHz, $CHCl_3$-d) δ: 7.77 (s, 1H), 7.72 (s, 1H), 7.55 (s, 1H), 3.83 (s, 2H) ppm.

2-(3-(Trifluoromethyl)-5-vinylphenyl)acetonitrile 1.468

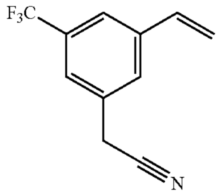

To a solution of compound 1.467 (1.38 g, 5.23 mmol) and 4,4,5,5-tetramethyl-2-vinyl-1,3,2-dioxaborolane (1.21 g, 7.84 mmol, 1.33 mL) in DME (20 mL) was added Pd(dppf) $Cl_2$ (382.42 mg, 522.64 μmol) and CsF (1.59 g, 10.45 mmol). The mixture was heated to 80° C. and stirred for 12 h under nitrogen protection. The reaction mixture was poured into water (50 mL) and stirred for 1 min. The aqueous phase was extracted with EA (30 mL×3). The combined organic phase was washed with brine (80 mL×2), dried with anhydrous $Na_2SO_4$, filtered and concentrated in vacuo. The residue was purified (PM13) to afford compound 1.468 (500 mg, 2.37 mmol, 45.3% yield) as a red oil.

$^1$H NMR (400 MHz, $CHCl_3$-d) δ: 7.63 (s, 1H), 7.56 (s, 1H), 7.47 (s, 1H), 6.75 (dd, J=17.6, 11.2 Hz, 1H), 5.88 (d, J=17.6 Hz, 1H), 5.45 (d, J=11.2 Hz, 1H), 3.83 (s, 2H) ppm.

2-(3-Formyl-5-(trifluoromethyl)phenyl)acetonitrile 1.469

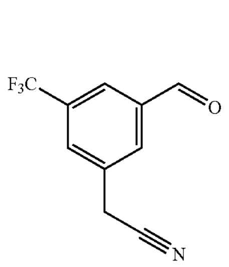 [SMILES: N#CCc1cc(C=O)cc(C(F)(F)F)c1]

Ozone was bubbled into a solution of compound 1.468 (500 mg, 2.37 mmol) in DCM (10 mL) at −70° C. until the mixture turned blue. After excess ozone was purged, DMS (1.47 g, 23.68 mmol) was added at −70° C. The mixture was then warmed to 20° C. and stirred for 12 h. The mixture was concentrated in vacuo and (PM7) to afford compound 1.469 (262 mg, 1.23 mmol, 51.9% yield) as a light yellow oil.

$^1$H NMR (400 MHz, $CHCl_3$-d) δ: 10.10 (s, 1H), 8.14 (s, 1H), 8.08 (s, 1H), 7.88 (s, 1H), 3.95 (s, 2H) ppm.

Synthesis of Intermediate 1.472

2-(3-Fluoro-5-vinylphenyl)acetonitrile 1.471

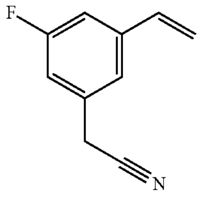

To a solution of 2-(3-bromo-5-fluorophenyl)acetonitrile (1.6 g, 7.48 mmol) and tributyl(vinyl)stannane (2.37 g, 7.48 mmol) in toluene (30 mL) was added $Pd(PPh_3)_4$ (604.68 mg, 523.28 μmol). The resulting mixture was heated to 95° C. and stirred for 12 h under nitrogen protection. The mixture was poured into saturated aqueous KF solution (100 mL) and stirred for 15 min. The aqueous phase was extracted with EA (50 mL×3). The combined organic phase was washed with brine (100 mL×3), dried with anhydrous $Na_2SO_4$, filtered and concentrated in vacuo. The residue was purified (PM14) to afford compound 1.471 (900 mg, 5.58 mmol, 74.6% yield) as a light yellow oil.

$^1$H NMR (400 MHz, $CHCl_3$-d) δ: 7.15 (s, 1H), 7.10 (d, J=8.4 Hz, 1H), 6.95 (d, J=8.4 Hz, 1H), 6.66 (dd, J=17.6, 10.8 Hz, 1H), 5.80 (d, J=17.6 Hz, 1H), 5.38 (d, J=10.8 Hz, 1H), 3.75 (s, 2H) ppm.

2-(3-Fluoro-5-formylphenyl)acetonitrile 1.472

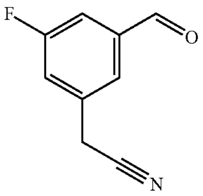

Ozone was bubbled into a solution of compound 1.471 (500 mg, 3.10 mmol) in DCM (10 mL) at −70° C. until the reaction mixture turned blue. After excess ozone was purged, DMS (1.93 g, 31.02 mmol) was added. The mixture was warm up to 20° C. and stirred for 12 h. The mixture was concentrated in vacuo and the residue was purified (PM7) to afford compound 1.472 (390 mg, 2.39 mmol, 77.1% yield) as a light yellow oil.

$^1$H NMR (400 MHz, $CHCl_3$-d) δ: 10.09 (s, 1H), 7.68 (s, 1H), 7.56 (dd, J=8.4, 1.2 Hz, 1H), 7.36 (dd, J=8.4, 1.2 Hz, 1H), 3.87 (s, 2H) ppm.

Synthesis of Intermediate 1.475

2-(3-Methyl-5-vinylphenyl)acetonitrile 1.474

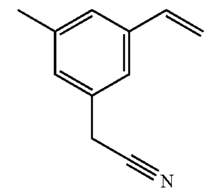

To a solution of 2-(3-bromo-5-methylphenyl)acetonitrile (1.6 g, 7.62 mmol) and tributyl(vinyl)stannane (2.42 g, 7.62 mmol) in toluene (30 mL) was added $Pd(PPh_3)_4$ (616.09 mg, 533.16 μmol). The mixture was heated to 95° C. and stirred for 12 h under nitrogen protection. The mixture was poured into saturated aqueous KF solution (100 mL) and stirred for 15 min. The aqueous phase was extracted with EA (50 mL×3). The combined organic phase was washed with brine (100 mL×3), dried with anhydrous $Na_2SO_4$, filtered and concentrated in vacuo. The residue was purified (PM14) to give compound 1.474 (820 mg, 5.22 mmol, 68.5% yield) as a yellow oil.

$^1$H NMR (400 MHz, $CHCl_3$-d) δ: 7.19 (s, 1H), 7.16 (s, 1H), 7.05 (s, 1H), 6.68 (dd, J=17.6, 10.8 Hz, 1H), 5.77 (d, J=17.6 Hz, 1H), 5.29 (d, J=10.8 Hz, 1H), 3.72 (s, 2H), 2.37 (s, 3H) ppm.

2-(3-Formyl-5-methylphenyl)acetonitrile 1.475

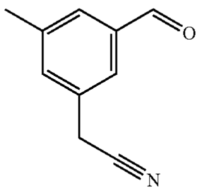

Ozone was bubbled into a solution of compound 1.474 (500 mg, 3.18 mmol) in DCM (10 mL) at −70° C. until the reaction mixture turned blue. After excess ozone was purged, DMS (1.98 g, 31.80 mmol) was added. The reaction mixture was warmed to 20° C. and stirred for 12 h. The mixture was concentrated in vacuo and purified (PM7) to give compound 1.475 (320 mg, 2.01 mmol, 63.2% yield) as a light yellow oil.

$^1$H NMR (400 MHz, $CHCl_3$-d) δ: 10.00 (s, 1H), 7.65 (d, J=8.4 Hz, 2H), 7.45 (s, 1H), 3.81 (s, 2H), 2.47 (s, 3H) ppm.

Synthesis of Intermediate 1.478

2-(2-Chloro-5-vinylphenyl)acetonitrile 1.477

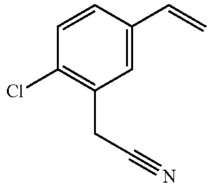

To a solution of 2-(5-bromo-2-chlorophenyl)acetonitrile (1.4 g, 6.07 mmol) and 4,4,5,5-tetramethyl-2-vinyl-1,3,2-dioxaborolane (1.40 g, 9.11 mmol) in DME (20 mL) was added Pd(dppf)$Cl_2$ (444.44 mg, 607.40 μmol) and CsF (1.85 g, 12.15 mmol). The reaction mixture was heated to 80° C. and stirred for 12 h under nitrogen protection. The mixture was poured into water (50 mL) and the aqueous phase was extracted with EA (30 mL×3). The combined organic phase was washed with brine (80 mL×2), dried with anhydrous $Na_2SO_4$, filtered and concentrated in vacuo. The residue was purified (PM17) to give compound 1.477 (600 mg, 3.38 mmol, 55.6% yield) as a light yellow oil.

$^1$H NMR (400 MHz, $CHCl_3$-d) δ: 7.43 (s, 1H), 7.25 (m, 1H), 7.24-7.21 (m, 1H), 6.59 (dd, J=17.6, 10.8, Hz, 1H), 5.70 (d, J=17.6 Hz, 1H), 5.25 (d, J=10.8 Hz, 1H), 3.74 (s, 2H) ppm.

2-(2-Chloro-5-formylphenyl)acetonitrile 1.478

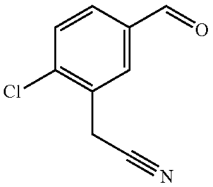 [SMILES: N#CCc1cc(C=O)ccc1Cl]

Ozone was bubbled into a solution of compound 1.477 (400 mg, 2.25 mmol) in DCM (10 mL) at −70° C. until the reaction mixture turned blue. After excess ozone was purged, DMS (1.40 g, 22.52 mmol) was added. The reaction mixture was warmed up to at 20° C. and stirred for 12 h. The mixture was concentrated in vacuo and purified (PM11) to afford compound 1.478 (200 mg, 1.11 mmol, 49.5% yield) as a light yellow solid.

$^1$H NMR (400 MHz, $CHCl_3$-d) δ: 10.03 (s, 1H), 8.05 (d, J=1.6 Hz, 1H), 7.86 (dd, J=8.4, 1.6 Hz, 1H), 7.63 (d, J=8.4 Hz, 1H), 3.93 (s, 2H) ppm.

Synthesis of Intermediate 1.483

1-Bromo-2-chloro-3-(chloromethyl)benzene 1.480

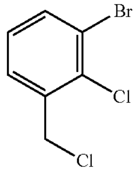

To a solution of (3-bromo-2-chlorophenyl)methanol (1 g, 4.52 mmol) in 1,4-dioxane (10 mL) was added $SOCl_2$ (1.07 g, 9.03 mmol) at 0° C. The reaction mixture was heated to 90° C. and stirred for 1 h. The mixture was concentrated in vacuo to give compound 1.480 (1 g) as a black oil.

$^1$H NMR (400 MHz, $CHCl_3$-d) δ: 7.63 (d, J=8.0 Hz, 1H), 7.45 (d, J=8.0, 1H), 7.16 (t, J=8.0 Hz, 1H), 4.74 (s, 2H) ppm.

2-(3-Bromo-2-chlorophenyl)acetonitrile 1.481

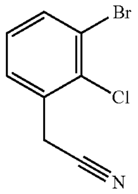 [SMILES: N#CCc1cccc(Br)c1Cl]

To a solution of trimethylsilylcyanide (516.86 mg, 5.21 mmol) and compound 1.480 (1 g, 4.17 mmol) in acetonitrile (20 mL) was added TBAF (5.22 mL, 5.22 mmol, 1 M in THF) at 25° C. The mixture was stirred at 25° C. for 12 h. The mixture was concentrated in vacuo and the residue was purified (PM14) to give compound 1.481 (837 mg, 3.63 mmol, 87.1% yield) as a white solid.

$^1$H NMR (400 MHz, $CHCl_3$-d) δ: 7.66 (d, J=8.0 Hz, 1H), 7.50 (d, J=8.0 Hz, 1H), 7.21 (t, J=8.0 Hz, 1H), 3.90 (s, 2H) ppm.

2-(2-Chloro-3-vinylphenyl)acetonitrile 1.482

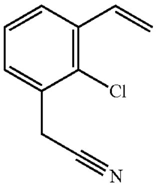

To a solution of compound 1.481 (837 mg, 3.63 mmol) and 4,4,5,5-tetramethyl-2-vinyl-1,3,2-dioxaborolane (838.93 mg, 5.45 mmol) in DME (10 mL) was added CsF (1.10 g, 7.26 mmol) and Pd(dppf)$Cl_2$ (265.71 mg, 363.14 μmol). The mixture was heated to 80° C. and stirred for 12 h under nitrogen protection. The mixture was poured into water (50 mL) and the aqueous phase was extracted with EA (30 mL×3). The combined organic phase was washed with brine (80 mL×2), dried with anhydrous $Na_2SO_4$, filtered and concentrated in vacuo. The residue was purified (PM12) to afford compound 1.482 (300 mg, 1.69 mmol, 46.5% yield) as a light yellow oil.

$^1$H NMR (400 MHz, $CHCl_3$-d) δ: 7.58 (d, J=8.0 Hz, 1H), 7.45 (d, J=8.0 Hz, 1H), 7.30 (t, J=8.0 Hz, 1H), 7.12 (dd, J=17.6, 12.0 Hz, 1H), 5.77 (d, J=17.6 Hz, 1H), 5.45 (dd, J=12.0 Hz, 1H), 3.87 (s, 2H) ppm.

2-(2-Chloro-3-formylphenyl)acetonitrile 1.483

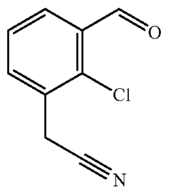 [SMILES: N#CCc1cccc(C=O)c1Cl]

Ozone was bubbled into a solution of compound 1.482 (300 mg, 1.69 mmol) in DCM (10 mL) at −70° C. until the reaction mixture turned blue. After excess ozone was purged, DMS (1.05 g, 16.89 mmol) was added. The mixture was warmed up to 20° C. and stirred for 12 h. The mixture was concentrated in vacuo and purified by (PM9) to afford compound 1.483 (297 mg, 1.65 mmol, 97.9% yield) as a white solid.

$^1$H NMR (400 MHz, $CHCl_3$-d) δ: 10.53 (s 1H), 7.96 (d, J=8.0 Hz, 1H), 7.80 (d, J=8.0 Hz, 1H), 7.49 (t, J=7.8 Hz, 1H), 3.94 (s, 2H) ppm.

Synthesis of Intermediate 1.485

(2-Chloro-3-vinylphenyl)methanol 1.484

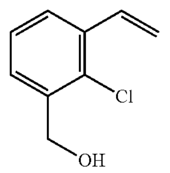

To a solution of tributyl(vinyl)stannane (1.43 g, 4.52 mmol) and (3-bromo-2-chlorophenyl)methanol (1.00 g, 4.52 mmol) in toluene (20 mL) was added $Pd(PPh_3)_4$ (365.62 mg, 316.40 μmol). The mixture was heated to 95° C. and stirred for 12 h under nitrogen protection. The reaction mixture was poured into saturated aqueous KF solution (100 mL) and stirred for 1 h. The aqueous phase was extracted with EA (50 mL×3). The combined organic phase was washed with brine (100 mL×3), dried with anhydrous $Na_2SO_4$, filtered and concentrated in vacuo. The residue was purified by (PM9) to give compound 1.484 (650 mg, 3.85 mmol, 85.3% yield) as yellow oil.

$^1$H NMR (400 MHz, $CHCl_3$-d) δ: 7.50 (dd, J=8.0, 1.6 Hz, 1H), 7.40 (dd, J=8.0, 1.6 Hz, 1H), 7.25-7.23 (m, 1H), 7.15 (dd, J=17.6, 10.0 Hz, 1H), 5.72 (d, J=17.6 Hz, 1H), 5.39 (d, J=10.0 Hz, 1H), 4.78 (s, 2H), 2.04 (br s, 1H) ppm.

2-Chloro-3-(hydroxymethyl)benzaldehyde 1.485

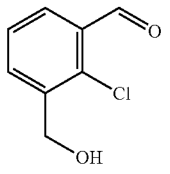 [SMILES: O=Cc1cccc(CO)c1Cl]

Ozone was bubbled into a solution of compound 1.484 (379.71 mg, 2.25 mmol) in DCM (10 mL) at −70° C. until the reaction mixture turned blue. After excess ozone was purged, DMS (1.40 g, 22.52 mmol) was added. The mixture was warmed up to 20° C. and stirred for 12 h. The mixture was concentrated in vacuo and purified by (PM9) to give compound 1.485 (230 mg, 1.35 mmol, 59.9% yield) as a light yellow solid.

$^1$H NMR (400 MHz, $CHCl_3$-d) δ: 10.53 (s, 1H), 7.87 (dd, J=7.6, 1.6 Hz, 1H), 7.79 (d, J=7.6 Hz, 1H), 7.43 (t, J=7.6 Hz, 1H), 4.88 (s, 2H), 2.22 (s, 1H) ppm.

Synthesis of Intermediate 1.488

(3-(Trifluoromethoxy)-5-vinylphenyl)methanol

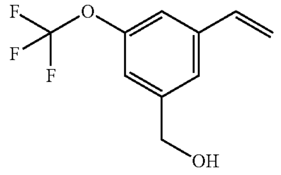

To a solution of [3-bromo-5-(trifluoromethoxy)phenyl]methanol (800 mg, 2.95 mmol) and 4,4,5,5-tetramethyl-2-vinyl-1,3,2-dioxaborolane (681.90 mg, 4.43 mmol) in DME (10 mL) was added $Pd(dppf)Cl_2$ (215.98 mg, 295.17 μmol) and CsF (896.72 mg, 5.90 mmol). The mixture was heated to 80° C. and stirred for 12 h under nitrogen protection. The mixture was poured into water (50 mL) and the aqueous phase was extracted with EA (30 mL×3). The combined organic phase was washed with brine (80 mL×2), dried with anhydrous $Na_2SO_4$, filtered and concentrated in vacuo. The residue was purified (PM12) to give compound 1.487 (600 mg) as a colorless oil.

$^1$H NMR (400 MHz, $CHCl_3$-d) δ: 7.38 (t, J=8.0 Hz, 1H), 7.33 (s, 1H), 7.25 (s, 1H), 6.69 (dd, J=17.6, 10.8 Hz, 1H), 5.80 (d, J=17.2 Hz, 1H), 5.35 (d, J=10.8 Hz, 1H), 4.73 (s, 2H) ppm.

3-(Hydroxymethyl)-5-(trifluoromethoxy)benzaldehyde 1.488

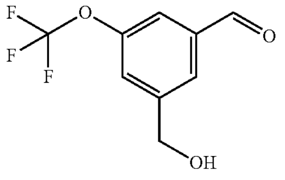 [SMILES: O=Cc1cc(CO)cc(OC(F)(F)F)c1]

Ozone was bubbled into a solution of compound 1.487 (200 mg, 916.71 μmol) in DCM (10 mL) at −70° C. until the reaction mixture turned blue. After excess ozone was purged, DMS (569.55 mg, 9.17 mmol) was added. The mixture was warmed up to 20° C. and stirred for 12 h. The mixture was concentrated in vacuo and purified (PM6) to give compound 1.488 (110 mg, 499.67 μmol, 54.5% yield) as a yellow oil.

$^1$H NMR (400 MHz, $CHCl_3$-d) δ: 10.02 (s, 1H), 7.83 (s, 1H), 7.65 (s, 1H), 7.52 (s, 1H), 4.84 (s, 2H) ppm.

Synthesis of Intermediate 1.491

2-(3-Methoxy-5-vinylphenyl)acetonitrile 1.490

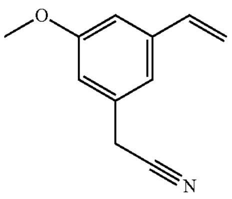

To a solution of 2-(3-bromo-5-methoxy-phenyl)acetonitrile (1.1 g, 4.87 mmol) (US2014/73629A1) and 4,4,5,5-tetramethyl-2-vinyl-1,3,2-dioxaborolane (1.12 g, 7.30 mmol) in DME (20 mL) was added Pd(dppf)$Cl_2$ (356.03 mg, 486.58 μmol) and CsF (1.48 g, 9.73 mmol). The mixture was heated to 80° C. and stirred for 12 h under nitrogen atmosphere protection. The mixture was poured into water (50 mL) and the aqueous phase was extracted with EA (30 mL×3). The combined organic phase was washed with brine (80 mL×2), dried with anhydrous $Na_2SO_4$, filtered and concentrated in vacuo. The residue was purified (PM11) to afford compound 1.490 (550 mg, 3.18 mmol, 65.3% yield) as a yellow oil.

$^1$H NMR (400 MHz, $CHCl_3$-d) δ: 6.96 (s, 1H), 6.90 (s, 1H), 6.77 (s, 1H), 6.67 (dd, J=17.2, 10.8 Hz, 1H), 5.78 (d, J=17.6 Hz, 1H), 5.32 (d, J=10.8 Hz, 1H), 3.84 (s, 3H), 3.73 (s, 2H) ppm.

2-(3-Formyl-5-methoxyphenyl)acetonitrile 1.491

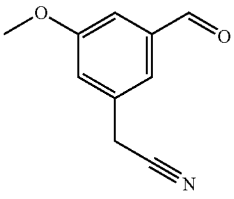

Ozone was bubbled into a solution of compound 1.490 (550 mg, 3.18 mmol) in DCM (10 mL) at −70° C. until the reaction mixture turned blue. After excess ozone was purged, DMS (1.97 g, 31.75 mmol) was added. The mixture was warmed up to 20° C. and stirred for 12 h. The mixture was concentrated in vacuo and (PM7) to afford compound 1.491 (240 mg, 1.37 mmol, 43.2% yield) as a yellow solid.

$^1$H NMR (400 MHz, $CHCl_3$-d) δ: 9.98 (s, 1H), 7.43 (s, 1H), 7.38 (s, 1H), 7.16 (s, 1H), 3.90 (s, 3H), 3.82 (s, 2H) ppm.

Synthesis of Intermediate 1.500

(3-Fluoro-5-vinylphenyl)methanol 1.499

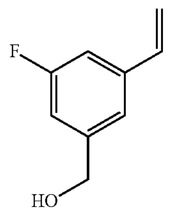

To a solution of (3-bromo-5-fluoro-phenyl)methanol (3 g, 14.63 mmol), 4,4,5,5-tetramethyl-2-vinyl-1,3,2-dioxaborolane (3.38 g, 21.95 mmol) in 1. 4-dioxane (60 mL) and water (6 mL) was added $K_2CO_3$ (4.04 g, 29.26 mmol) and Pd(dppf)$Cl_2$·$CH_2Cl_2$ (1.19 g, 1.46 mmol) under nitrogen. The resulting mixture was stirred at 90° C. for 12 h. The mixture was concentrated in vacuo and the residue was (PM7) to afford compound 1.499 (2.0 g, 13.15 mmol, 91% yield) as a yellow oil.

$^1$H NMR (400 MHz, $CHCl_3$-d) δ: 7.22 (s, 1H), 7.08 (dd, J=10.0, 1.6 Hz, 1H), 6.99 (d, J=9.6 1H), 6.72 (dd, J=17.6, 10.8 Hz, 1H), 5.82 (d, J=17.6 Hz, 1H), 5.29 (d, J=10.8 Hz, 1H), 4.60 (s, 2H) ppm.

3-Fluoro-5-(hydroxymethyl)benzaldehyde 1.500

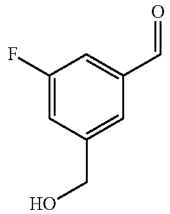

Ozone was bubbled into a solution of compound 1.499 (3.15 g, 20.70 mmol) in DCM (50 mL) at −70° C. until the reaction mixture turned blue. After excess ozone was purged, DMS (12.86 g, 207.01 mmol) was added. The mixture was warmed up to 20° C. and stirred for 12 h. The mixture was concentrated in vacuo and purified (PM6) to give compound 1.500 (2.9 g, 11.06 mmol, 53.4% yield) as a light yellow oil.

$^1$H NMR (400 MHz, $CHCl_3$-d) δ: 9.98 (s, 1H), 7.67 (s, 1H), 7.48 (dd, J=4.0, 2.4 Hz, 1H), 7.36 (d, J=4.0 Hz, 1H), 4.80 (s, 2H) ppm.

Synthesis of Intermediate 1.501

3-(Hydroxymethyl)-5-(trifluoromethyl)benzaldehyde 1.501

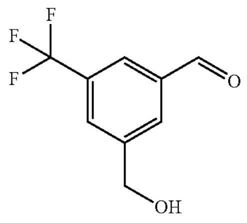 [SMILES: O=Cc1cc(CO)cc(C(F)(F)F)c1]

To a solution of (3-bromo-5-(trifluoromethyl)phenyl) methanol (10 g, 39.21 mmol) in THF (100 mL) was added n-BuLi (2.5 M, 32.94 mL) dropwise at −78° C. After being stirred for 0.5 h, DMF (3.02 mL, 39.21 mmol) was added. The resulting mixture was stirred at −78° C. for another 0.5 h. The mixture was warmed to 20° C. and quenched with water (100 mL). The mixture was extracted with EA (150 mL×3). The combined organic phase was washed with brine (100 mL), dried over anhydrous $Na_2SO_4$, filtered and concentrated in vacuo. The residue was purified (PM7) to afford compound 1.501 (3.8 g, 18.61 mmol, 47.47% yield) as a yellow oil.

$^1$H NMR (400 MHz, $CHCl_3$-d) δ: 10.08 (s, 1H), 8.06 (s, 1H), 7.92 (s, 1H), 7.65 (s, 1H), 4.89 (s, 2H), 2.49 (d, J=8.0 Hz, 1H) ppm.

Synthesis of Intermediate 1.504

1-(Chloromethyl)-3-(trifluoromethoxy)-5-vinylbenzene 1.502

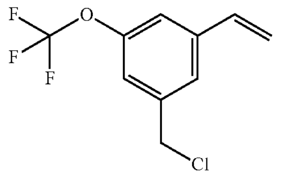

To a solution of compound 1.487 (8.3 g, 38.04 mmol) in 1,4-dioxane (100 mL) was added $SOCl_2$ (9.05 g, 76.09 mmol) at 0° C. slowly. The mixture was then heated to 90° C. and stirred for 1 h. The mixture was concentrated and diluted with EA (20 mL). The mixture was poured into aq. $NaHCO_3$ solution (150 mL) and extracted with EA (80 mL×3). The combined organic phase was washed with brine (150 mL×2), dried with anhydrous $Na_2SO_4$, filtered and concentrated in vacuo. The residue was purified (PM14) to give compound 1.502 (3.5 g, 14.79 mmol, 38.9% yield) as a yellow oil.

$^1$H NMR (400 MHz, $CHCl_3$-d) δ: 7.35 (s, 1H), 7.21 (s, 1H), 7.16 (s, 1H), 6.69 (dd, J=17.6, 11.2 Hz, 1H), 5.81 (d, J=17.6 Hz, 1H), 5.39 (d, J=11.2 Hz, 1H), 4.58 (s, 2H) ppm.

2-(3-(Trifluoromethoxy)-5-vinylphenyl)acetonitrile 1.503

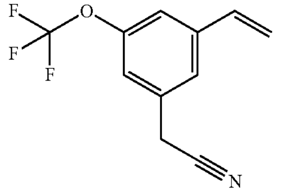 [SMILES: C=Cc1cc(CC#N)cc(OC(F)(F)F)c1]

To a solution of trimethylsilylcyanide (1.33 g, 13.41 mmol) and compound 1.502 (3.5 g, 14.79 mmol) in acetonitrile (50 mL) was added TBAF (18.54 mL, 18.54 mmol, 1 M in THF). The mixture was stirred at 25° C. for 12 h. The mixture was concentrated in vacuo and purified (PM13) to give compound 1.503 (2.6 g, 11.44 mmol, 77.4% yield) as a light yellow oil.

$^1$H NMR (400 MHz, $CHCl_3$-d) δ: 7.31 (s, 1H), 7.23 (s, 1H), 7.08 (s, 1H), 6.69 (dd, J=17.6, 10.8 Hz, 1H), 5.83 (d, J=17.6 Hz, 1H), 5.41 (d, J=10.8 Hz, 1H), 3.78 (s, 2H) ppm.

2-(3-Formyl-5-(trifluoromethoxy)phenyl)acetonitrile 1.504

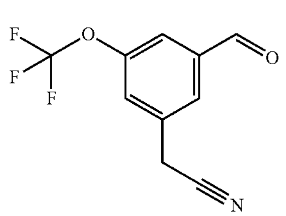 [SMILES: N#CCc1cc(C=O)cc(OC(F)(F)F)c1]

Ozone was bubbled into a solution of compound 1.503 (2.6 g, 11.44 mmol) in DCM (30 mL) at −70° C. until the reaction mixture turned blue. After excess ozone was purged, DMS (7.11 g, 114.45 mmol) was added. The mixture was warmed up to 20° C. and stirred for 12 h. The mixture was concentrated in vacuo and (PM7) to give compound 1.504 (1.9 g, 8.29 mmol, 72.5% yield) as a yellow oil.

$^1$H NMR (400 MHz, $CHCl_3$-d) δ: 10.03 (s, 1H), 7.83 (s, 1H), 7.73 (s, 1H), 7.48 (s, 1H), 3.90 (s, 2H) ppm.

Synthesis of Intermediate 1.507

1,3-Difluoro-2-(trifluoromethoxy)-5-vinylbenzene 1.506

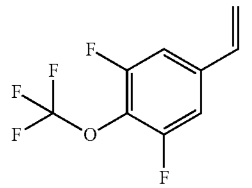

To a solution of 4,4,5,5-tetramethyl-2-vinyl-1,3,2-dioxaborolane (6.26 g, 40.62 mmol) and 5-bromo-1,3-difluoro-2-(trifluoromethoxy)benzene (7.5 g, 27.08 mmol) in DME (100 mL) was added Pd(dppf)$Cl_2$ (1.98 g, 2.71 mmol) and CsF (8.23 g, 54.15 mmol). The mixture was heated to 80° C. and stirred for 12 h under nitrogen. The mixture was poured into water (300 mL) and the aqueous phase was extracted with EA (150 mL×3). The combined organic phase was washed with brine (300 mL×2), dried with anhydrous $Na_2SO_4$, filtered and concentrated in vacuo. The residue was purified (PM14) to give compound 1.506 (3.2 g, 14.28 mmol, 52.7% yield) as a yellow oil.

$^1$H NMR (400 MHz, $CHCl_3$-d) δ: 7.05 (s, 1H), 7.03 (s, 1H), 6.61 (dd, J=17.6, 10.8 Hz, 1H), 5.78 (d, J=17.2 Hz, 1H), 5.43 (d, J=10.8 Hz, 1H) ppm.

3,5-Difluoro-4-(trifluoromethoxy)benzaldehyde 1.507

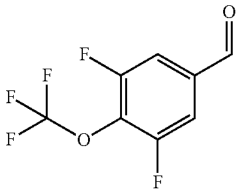 [SMILES: O=Cc1cc(F)c(OC(F)(F)F)c(F)c1]

Ozone was bubbled into a solution of compound 1.506 (3.2 g, 14.28 mmol) in DCM (40 mL) at −70° C. until the reaction mixture turned blue. After excess ozone was purged, DMS (8.87 g, 142.78 mmol) was added. The mixture was warmed up to 20° C. and stirred for 12 h. The mixture was concentrated in vacuo and purified (PM6) to give compound 1.507 (1.2 g, 5.31 mmol, 37.2% yield) as a yellow oil.

$^1$H NMR (400 MHz, $CHCl_3$-d) δ: 9.95 (s, 1H), 7.59 (s, 1H), 7.57 (s, 1H) ppm.

Synthesis of Intermediate 1.509

3-Cyclopropyl-5-(trifluoromethoxy)benzaldehyde 1.509

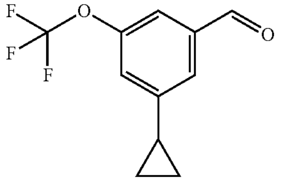 [SMILES: O=Cc1cc(OC(F)(F)F)cc(C2CC2)c1]

To a mixture of 3-bromo-5-(trifluoromethoxy)benzaldehyde (2 g, 7.43 mmol), cyclopropylboronic acid (702.47 mg, 8.18 mmol) and Pd(dppf)$Cl_2$ (271.99 mg, 371.73 μmol) in 1,4-dioxane (20 mL) and water (2 mL) was added $K_2CO_3$ (2.05 g, 14.87 mmol). The mixture was stirred at 80° C. for 12 h under nitrogen protection. The mixture was concentrated in vacuo and the residue was purified (PM14) to afford compound 1.509 (1.1 g, 4.78 mmol, 64.3% yield) as a yellow oil.

LCMS (AM3): rt=0.958 min, (231.1 $[M+H]^+$), 97.7% purity.

Synthesis of Intermediate 1.521

2-(4-Chloro-3-vinylphenyl)acetonitrile 1.520

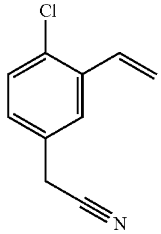

To a mixture of 2-(3-bromo-4-chlorophenyl)acetonitrile (1.2 g, 5.21 mmol) and 4,4,5,5-tetramethyl-2-vinyl-1,3,2-dioxaborolane (1.20 g, 7.81 mmol) in 1,4-dioxane (10 mL) and water (1 mL) was added Pd(dppf)$Cl_2$—$CH_2Cl_2$ (425.17 mg, 520.63 μmol) and $K_2CO_3$ (1.44 g, 10.41 mmol) under nitrogen protection. The mixture was heated to 90° C. and stirred for 12 h. The mixture was concentrated in vacuo and the residue was purified (PM6) to afford compound 1.520 (840 mg, 4.73 mmol, 90.8% yield) as a yellow oil.

$^1$H NMR (400 MHz, MeOH-$d_4$) δ: 7.61 (d, J=2.0 Hz, 1H), 7.37 (d, J=8.4 Hz, 1H), 7.23 (dd, J=8.4, 2.4 Hz, 1H), 7.07 (dd, J=17.6, 11.2 Hz 1H), 5.82 (d, J=17.6 Hz, 1H), 5.42 (d, J=11.2 Hz, 1H), 3.89 (s, 2H) ppm.

2-(4-Chloro-3-formylphenyl)acetonitrile 1.521

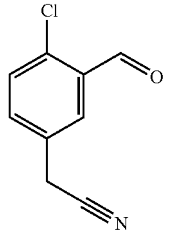 [SMILES: N#CCc1ccc(Cl)c(C=O)c1]

Ozone was bubbled into a solution of compound 1.520 (840 mg, 4.73 mmol) in DCM (20 mL) at −78° C. until the reaction mixture turned blue. After excess ozone was purged, DMS (2.94 g, 47.29 mmol) was added at −78° C. The mixture was then warmed to 25° C. and stirred for 12 h. The mixture was concentrated in vacuo and the residue was dissolved in EA (60 mL) and washed with brine (50 mL×2), dried with anhydrous $Na_2SO_4$, filtered and concentrated in vacuo. The residue was purified (PM11) to afford compound 1.521 (600 mg, 3.34 mmol, 70.6% yield) as a yellow solid.

$^1$H NMR (400 MHz, MeOH-$d_4$) δ: 10.42 (s, 1H), 7.90 (d, J=2.4 Hz, 1H), 7.64-7.56 (m, 2H), 3.99 (s, 2H) ppm.

Synthesis of Intermediate 1.524

2-(2-Chloro-4-vinylphenyl)acetonitrile 1.523

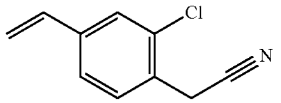

To a mixture of 2-(4-bromo-2-chloro-phenyl)acetonitrile (1.6 g, 6.94 mmol) and 4,4,5,5-tetramethyl-2-vinyl-1,3,2-dioxaborolane (1.60 g, 10.41 mmol) in 1,4-dioxane (10 mL) and water (1 mL) was added Pd(dppf)$Cl_2$—$CH_2Cl_2$ (566.89 mg, 694.18 μmol) and $K_2CO_3$ (1.92 g, 13.88 mmol) under nitrogen protection. The mixture was heated to 90° C. and stirred for 12 h. The mixture was concentrated in vacuo and the residue was purified (PM6) to afford compound 1.523 (1.1 g, 6.19 mmol, 89.2% yield) as a yellow oil.

$^1$H NMR (400 MHz, MeOH-$d_4$) δ: 7.50 (s, 1H), 7.46-7.43 (d, 1H), 7.40-7.38 (d, 1H), 6.69 (dd, J=17.6, 11.8 Hz, 1H), 5.84 (d, J=17.6 Hz, 1H), 5.33 (d, J=11.8 Hz, 1H), 3.93 (s, 2H) ppm.

2-(2-Chloro-4-formylphenyl)acetonitrile 1.524

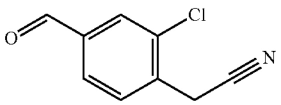 [SMILES: N#CCc1ccc(C=O)cc1Cl]

Ozone was bubbled into a solution of compound 1.523 (1.1 g, 6.19 mmol) in DCM (20 mL) at −78° C. until the reaction mixture turned blue. After excess ozone was purged, DMS (3.85 g, 61.93 mmol) was added. The mixture was warmed to 25° C. and stirred for 12 h. The mixture was concentrated in vacuo to remove the solvent. The residue was dissolved in EA (60 mL) and washed with brine (50 mL×2), dried with anhydrous $Na_2SO_4$, filtered and concentrated in vacuo. The residue was purified (PM11) to afford compound 1.524 (0.6 g, 3.34 mmol, 53.9% yield) as a pink solid.

$^1$H NMR (400 MHz, MeOH-$d_4$) δ: 9.97 (s, 1H), 8.00 (s, 1H), 7.91 (dd, J=7.6, 1.6 Hz, 1H), 7.77 (d, J=7.6 Hz, 1H), 4.10 (s, 2H) ppm.

Synthesis of Intermediate 1.526

2-Cyclopropyl-4-formylbenzonitrile 1.526

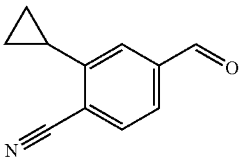 [SMILES: N#Cc1ccc(C=O)cc1C1CC1]

To a mixture of cyclopropylboronic acid (122.69 mg, 1.43 mmol) and 2-bromo-4-formyl-benzonitrile (200, mg, 952.26 μmol) in 1,4-dioxane (10 mL) and water (1 mL) was added Pd(dppf)$Cl_2$—$CH_2Cl_2$ (77.77 mg, 95.23 μmol) and $K_2CO_3$ (263.22 mg, 1.90 mmol) under nitrogen protection. The mixture was heated to 90° C. and stirred for 12 h. The mixture was concentrated in vacuo and purified (PM4) to afford compound 1.526 (100 mg, 584.13 μmol, 61.3% yield) as a yellow oil, which was used without characterization.

Synthesis of Intermediate 1.530

(5-Bromo-2-(2,2,2-trifluoroethoxy)phenyl)methanol 1.528

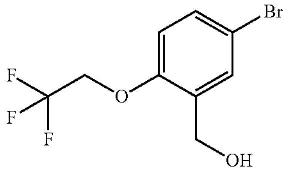 [SMILES: OCc1cc(Br)ccc1OCC(F)(F)F]

To a solution of 4-bromo-2-(hydroxymethyl)phenol (2 g, 9.85 mmol) and 2,2,2-trifluoroethyl trifluoromethanesulfonate (2.29 g, 9.85 mmol) in DMF (10 mL) was added $K_2CO_3$ (2.04 g, 14.78 mmol). The mixture was heated to 80° C. and stirred for 12 h. The reaction mixture was diluted with water (100 mL) and extracted with EA (100 mL×3). The combined organic layer was washed with brine (100 mL×2), dried over $Na_2SO_4$, filtered and concentrated in vacuo to give a residue which was purified (PM10) to afford compound 1.528 (1.83 g, 6.42 mmol, 65.2% yield) as a yellow solid.

$^1$H NMR (400 MHz, $CHCl_3$-d) δ: 7.48 (d, J=2.4 Hz, 1H), 7.32 (dd, J=8.4, 2.4 Hz, 1H), 6.65 (d, J=8.4 Hz, 1H), 4.64 (s, 2H), 4.31 (q, J=4.8 Hz, 2H), 1.87 (br s, 1H) ppm.

(2-(2,2,2-Trifluoroethoxy)-5-vinylphenyl)methanol 1.529

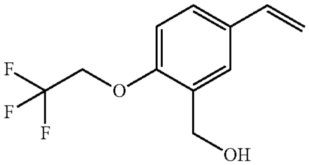 [SMILES: C=Cc1ccc(OCC(F)(F)F)c(CO)c1]

To a solution of compound 1.528 (400 mg, 1.40 mmol) in toluene (5 mL) was added tributyl(vinyl)stannane (489.45 mg, 1.54 mmol) and $Pd(PPh_3)_4$ (81.08 mg, 70.16 μmol). The reaction mixture was heated to 100° C. and stirred for 12 h under nitrogen protection. The reaction mixture was diluted with saturated aqueous KF solution (80 mL) and extracted with EA (60 mL×2). The organic layer was washed with brine (70 mL), dried over $Na_2SO_4$, filtered and concentrated in vacuo. The residue was purified (PM10) to afford compound 1.529 (580 mg) as a yellow oil, which was used directly without characterization.

3-(Hydroxymethyl)-4-(2,2,2-trifluoroethoxy)benzaldehyde 1.530

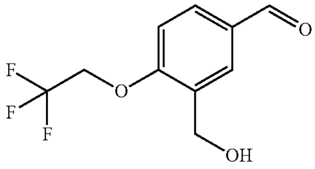 [SMILES: O=Cc1ccc(OCC(F)(F)F)c(CO)c1]

Ozone was bubbled into a solution of compound 1.529 (200 mg, 861.33 μmol) in DCM (20 mL) at −78° C. until the reaction mixture turned blue. After excess ozone was purged, DMS (535.14 mg, 8.61 mmol) was added. The mixture was warmed to 25° C. and stirred for 12 h. The mixture was concentrated in vacuo, dissolved in EA (60 mL), washed with brine (50 mL×2), dried over $Na_2SO_4$, filtered and concentrated in vacuo. The residue was purified (PM6) to afford compound 1.530 (60 mg, 256.22 μmol, 29.7% yield) as a yellow solid.

$^1$H NMR (400 MHz, MeOH-$d_4$) δ: 9.90 (s, 1H), 8.05 (s, 1H), 7.86 (dd, J=8.4, 2.0 Hz, 1H), 7.19 (d, J=8.4 Hz, 1H), 4.74-4.67 (m, 4H) ppm.

Synthesis of Intermediate 1.537

Methyl 2-bromo-5-vinylbenzoate 1.534

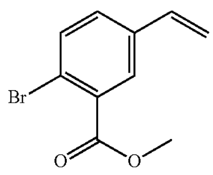

To a solution of methyl 2-bromo-5-iodobenzoate (5 g, 14.67 mmol) in toluene (80 mL) was added tributyl(vinyl) stannane (5.430 g, 17.12 mmol) and $Pd(PPh_3)_4$ (1.69 g, 1.47 mmol). The reaction mixture was heated to 90° C. and stirred for 12 h under nitrogen protection.

The reaction mixture was poured into saturated aqueous KF solution (40 mL) and extracted with EA (50 mL×3). The combined organic layer was washed with brine (80 mL×2), dried over $Na_2SO_4$, filtered and concentrated in vacuo. The residue was purified (PM1) to afford compound 1.534 (3.2 g) as a white solid.

$^1$H NMR (400 MHz, $CHCl_3$-d) δ: 7.79 (d, J=2.0 Hz, 1H), 7.59 (d, J=8.0 Hz, 1H), 7.35 (dd, J=8.0, 2.4 Hz, 1H), 6.65 (dd, J=17.2, 10.8 Hz, 1H), 5.79 (d, J=17.2 Hz, 1H), 5.34 (d, J=10.8 Hz, 1H), 3.93 (s, 3H) ppm.

(2-Bromo-5-vinylphenyl)methanol 1.535

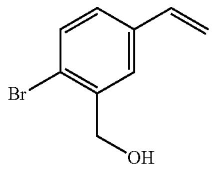

To a solution of compound 1.534 (3.2 g, 13.27 mmol) in THF (50 mL) was added $LiAlH_4$ (503.79 mg, 13.27 mmol) slowly at 0° C. The reaction mixture was warmed to 20° C. and stirred for 0.5 h. The reaction mixture was quenched with addition of EA (50 mL) under 0° C. followed by addition of water (0.5 mL), 10% NaOH aq. (0.5 mL) and water (1.0 mL). After being stirred for 0.5 h, anhydrous $Na_2SO_4$ was added. The resulting suspension was stirred for 0.5 h and filtered. The filtrate was concentrated in vacuo to afford compound 1.535 (2.5 g, 11.73 mmol, 88.4% yield) as a colorless oil.

$^1$H NMR (400 MHz, $CHCl_3$-d) δ: 7.52 (d, J=1.6 Hz, 1H), 7.49 (d, J=8.4 Hz, 1H), 7.20 (dd, J=8.0, 2.0 Hz, 1H), 6.68 (dd, J=17.2, 10.8 Hz, 1H), 5.80 (d, J=17.2 Hz, 1H), 5.30 (d, J=10.8 Hz, 1H), 4.74 (d, J=6.4 Hz, 2H), 2.06 (t, J=6.0 Hz, 1H) ppm.

4-Bromo-3-(hydroxmethyl)benzaldehyde 1.536

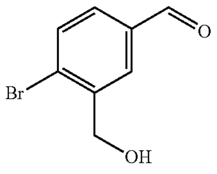 [SMILES: O=Cc1ccc(Br)c(CO)c1]

Ozone was bubble into a solution of compound 1.535 (2.5 g, 11.73 mmol) in DCM (20 mL) at −78° C. until the mixture turned blue. After excessive ozone was purged, DMS (15.6 g, 251.23 mmol) was added. The reaction mixture was warmed to 20° C. and stirred for 12.5 h. The residue was concentrated in vacuo and then diluted with water (40 mL). The mixture was extracted with DCM (50 mL×2) and the combined organic phase was washed with brine (50 mL×2), dried over $Na_2SO_4$, filtered and concentrated in vacuo. The residue was purified (PM12) to afford compound 1.536 (1.5 g, 6.98 mmol, 59.45% yield) as a light yellow oil.

$^1$H NMR (400 MHz, $CHCl_3$-d) δ: 9.99 (s, 1H), 8.03 (s, 1H), 7.70 (dd, J=8.4, 2.0 Hz, 1H), 7.65 (dd, J=8.4, 2.0 Hz, 1H), 4.81 (s, 2H), 2.47 (br s, 1H) ppm.

4-Cyclopropyl-3-(hydroxymethyl)benzaldehyde 1.537

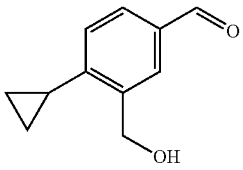 [SMILES: O=Cc1ccc(C2CC2)c(CO)c1]

A mixture of compound 1.536 (1.3 g, 6.05 mmol), cyclopropylboronic acid (571.20 mg, 6.65 mmol), $Na_2CO_3$ (1.28 g, 12.09 mmol) and $Pd(dppf)Cl_2$ (442.34 mg, 604.53 μmol) in 1,4-dioxane (20 mL) and water (2 mL) was stirred at 80° C. for 12 h under nitrogen protection. The reaction mixture was diluted with water (30 mL) and extracted with EA (50 mL×2). The combined organic layer was washed with brine (80 mL×2), dried over $Na_2SO_4$, filtered and concentrated in vacuo. The residue was purified (PM47) to afford compound 1.537 (120 mg, 681.00 μmol, 11.3% yield) as a yellow oil.

LCMS (AM3): rt=0.763 min, (177.7 $[M+H]^+$), 94.3% purity. MeOH

Synthesis of intermediate 1.589

Methyl 2-(trifluoromethyl)-5-vinylbenzoate 1.587

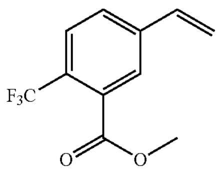 [SMILES: C=Cc1ccc(C(F)(F)F)c(C(=O)OC)c1]

To a solution of methyl 5-bromo-2-(trifluoromethyl)benzoate (730 mg, 2.58 mmol) in 1,4-dioxane (15 mL) and water (1.5 mL) was added 4,4,5,5-tetramethyl-2-vinyl-1,3,2-dioxaborolane (595.83 mg, 3.87 mmol), $K_2CO_3$ (712.92 mg, 5.16 mmol) and $Pd(dppf)Cl_2—CH_2Cl_2$ (210.62 mg, 257.91 μmol), then the reaction mixture was heated to 90° C. and stirred for 12 h under nitrogen protection. The reaction mixture was filtered and the filtrate was concentrated in vacuo. The residue was purified (PM7) to afford compound 1.587 (600 mg) as a pink oil.

$^1$H NMR (400 MHz, $CHCl_3$-d) δ: 7.79 (s, 1H), 7.70 (d, J=8.0 Hz, 1H), 7.59 (d, J=8.4 Hz, 1H), 6.75 (dd, J=17.6, 10.8 Hz, 1H), 5.90 (d, J=17.6 Hz, 1H), 5.46 (d, J=10.8 Hz, 1H), 3.94 (s, 3H) ppm.

(2-(Trifluoromethyl)-5-vinylphenyl)methanol 1.588

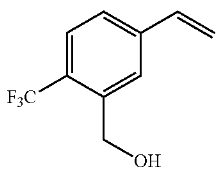

To a solution of compound 1.587 (600 mg, 2.61 mmol) in THE (10 mL) was added LAH (98.92 mg, 2.61 mmol) slowly at 0° C. The reaction mixture was stirred at 0° C. for 2 h. The reaction mixture was quenched with water (0.1 mL) slowly at 0° C., followed by addition of 10% aq. NaOH solution (0.1 mL) and subsequently water (0.3 mL). After being stirred at 0° C. for 10 min, $Na_2SO_4$ (2 g) was added. The resulting suspension was stirred for 0.5 h and then was filtered. The filtrate was concentrated in vacuo to afford compound 1.588 (450 mg, 2.23 mmol, 85.4% yield) as a colorless oil.

$^1$H NMR (400 MHz, $CHCl_3$-d) δ: 7.75 (s, 1H), 7.59 (d, J=8.0 Hz, 1H), 7.40 (d, J=8.0 Hz, 1H), 6.78 (dd, J=17.6, 10.8 Hz, 1H), 5.88 (d, J=17.6 Hz, 1H), 5.40 (d, J=10.8 Hz, 1H), 4.88 (d, J=5.4 Hz, 2H), 1.95 (br s, 1H) ppm.

3-(Hydroxymethyl)-4-(trifluoromethyl)benzaldehyde 1.589

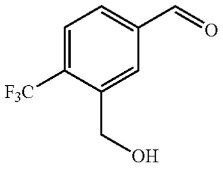 [SMILES: O=Cc1ccc(C(F)(F)F)c(CO)c1]

Ozone was bubbled into a solution of compound 1.588 (450 mg, 2.23 mmol) in DCM (10 mL) at −78° C. until the reaction mixture turned blue. After excessive ozone was purged with nitrogen, DMS (1.46 g, 23.50 mmol) was added. The reaction mixture was warmed to 20° C. and stirred for 15.5 h. The reaction mixture was concentrated in vacuo and purified (PM6) to afford compound 1.589 (380 mg, 1.86 mmol, 83.63% yield) as a colorless oil.

$^1$H NMR (400 MHz, $CHCl_3$-d) δ: 10.11 (s, 1H), 8.30 (s, 1H), 7.90 (d, J=7.6 Hz, 1H), 7.81 (d, J=8.0 Hz, 1H), 4.98 (s, 2H) ppm.

Synthesis of Intermediate 1.630

1-(3-Chloro-5-vinylphenyl)cyclopropanecarbonitrile 1.629

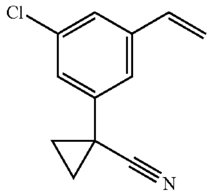

To a mixture of compound 1.365 (2 g, 11.26 mmol) in DMF (30 mL) was added NaH (990.82 mg, 24.77 mmol, 60% dispersion in oil) at 0° C. After being stirred at 0° C. for 0.5 h, 1,2-dibromoethane (2.12 g, 11.26 mmol) was added slowly. The mixture was then warmed to 25° C. and stirred for 11.5 h. The reaction mixture was quenched by addition of water (100 mL) and extracted with EA (100 mL×3). The combined organic layer was washed with brine (100 mL×2), dried over $Na_2SO_4$, filtered and concentrated in vacuo. The residue was purified (PM15) to afford compound 1.629 (1.2 g, 5.89 mmol, 52.3% yield) as a yellow oil.

$^1$H NMR (400 MHz, $CHCl_3$-d) δ: 7.48-7.35 (m, 3H), 6.80 (dd, J=17.6, 11.2 Hz, 1H), 5.95 (d, J=17.2 Hz, 1H), 5.52 (d, J=10.8 Hz, 1H), 1.94-1.90 (m, 2H), 1.60-1.55 (m, 2H) ppm.

1-(3-Chloro-5-formylphenyl)cyclopropanecarbonitrile 1.630

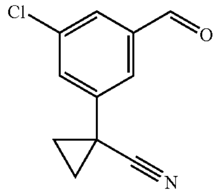 [SMILES: N#CC1(c2cc(Cl)cc(C=O)c2)CC1]

Ozone was bubbled to a solution of compound 1.629 (1.34 g, 6.58 mmol) in DCM (15 mL) at −78° C. until the mixture turned blue. After excessive ozone was purged with nitrogen, DMS (5.31 g, 85.53 mmol) was added. The mixture was warmed up to 25° C. and stirred for 12 h. The mixture was concentrated in vacuo and the residue was purified (PM14) to afford compound 1.630 (800 mg, 3.89 mmol, 59.1% yield) as a white solid.

$^1$H NMR (400 MHz, $CHCl_3$-d) δ: 9.99 (s, 1H), 7.80 (t, J=1.6 Hz, 1H), 7.66 (t, J=1.6 Hz, 1H), 7.60 (t, J=2.0 Hz, 1H), 1.89-1.86 (t, 2H), 1.54-1.51 (t, 2H) ppm.

Synthesis of Intermediate 1.632

2-(3-Chloro-5-vinylphenyl)-2-methylpropanenitrile 1.631

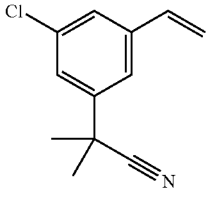

To a solution of compound 1.365 (3.85 g, 21.67 mmol) in DMF (50 mL) was added NaH (2.17 g, 54.19 mmol, 60% dispersion in oil) at 0° C. After being stirred at 0° C. for 0.5 h, MeI (6.75 mL, 108.37 mmol) was added slowly. The resulting mixture was warmed to 25° C. and stirred for 11.5 h. The reaction mixture was quenched by addition of water (150 mL) and then extracted with EA (100 mL×3). The combined organic layer was washed with brine (100 mL×2), dried over $Na_2SO_4$, filtered and concentrated in vacuo. The residue was purified (PM17) to afford compound 1.631 (4 g, 19.45 mmol, 89.7% yield) as a red oil.

$^1$H NMR (400 MHz, $CHCl_3$-d) δ: 7.38 (s, 1H), 7.32-7.20 (m, 2H), 6.60 (dd, J=17.6, 10.8 Hz, 1H), 5.73 (d, J=17.6 Hz, 1H), 5.29 (d, J=11.2 Hz, 1H), 1.19 (s, 6H) ppm.

2-(3-Chloro-5-formylphenyl)-2-methylpropanenitrile 1.632

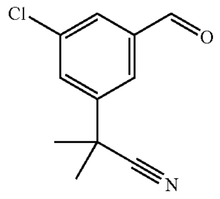

Ozone was bubbled to a solution of compound 1.631 (4 g, 19.45 mmol) in DCM (40 mL) at −78° C. until the color turned blue. After excessive ozone was purged nitrogen, DMS (15.71 g, 252.82 mmol) was added. The mixture was warmed up to 25° C. and stirred for 12 h. The mixture was concentrated in vacuo and purified (PM16) to afford compound 1.632 (750 mg, 3.61 mmol, 18.6% yield) as a yellow oil.

$^1$H NMR (400 MHz, $CHCl_3$-d) δ: 10.00 (s, 1H), 7.87 (s, 1H), 7.83 (s, 1H), 7.75 (s, 1H), 1.78 (s, 6H) ppm.

Synthesis of Intermediate 1.635

(5-Bromo-2-ethoxyphenyl)methanol 1.633

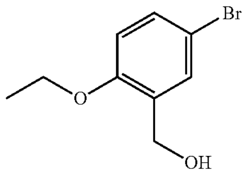

To a solution of 4-bromo-2-(hydroxymethyl)phenol (1 g, 4.93 mmol) and iodoethane (845.80 mg, 5.42 mmol) in ACN (5 mL) was added $K_2CO_3$ (1.02 g, 7.39 mmol) at 35° C. The mixture was stirred at 35° C. for 12 h. The reaction mixture was diluted with water (100 mL) and extracted with EA (100 mL×3). The combined organic layer was washed with brine (100 mL×2), dried over $Na_2SO_4$, filtered and concentrated in vacuo. The residue was purified (PM11) to afford compound 1.633 (860 mg, 3.72 mmol, 75.5% yield) as a white solid.

$^1$H NMR (400 MHz, $CHCl_3$-d) δ: 7.43 (d, J=2.4 Hz, 1H), 7.36 (dd, J=8.8, 2.4 Hz, 1H), 6.76 (d, J=8.8 Hz, 1H), 4.67 (s, 2H), 4.08 (q, J=7.2 Hz, 2H), 1.46 (t, J=7.2 Hz, 3H) ppm.

(2-Ethoxy-5-vinylphenyl)methanol 1.634

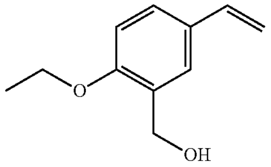

To a solution of compound 1.633 (400 mg, 1.73 mmol) in toluene (5 mL) was added tributyl(vinyl)stannane (600 mg, 1.89 mmol) and $Pd(PPh_3)_4$ (100.01 mg, 86.55 μmol). The reaction mixture was heated to 100° C. and stirred for 12 h under nitrogen protection. The reaction mixture was poured into saturated aqueous KF solution (80 mL) and extracted with EA (60 mL×2). The organic layer was washed with brine (70 mL), dried over $Na_2SO_4$, filtered and concentrated in vacuo. The residue was purified (PM10) to afford compound 1.634 (280 mg, 1.41 mmol, 81.6% yield) as a yellow oil.

$^1$H NMR (400 MHz, $CHCl_3$-d) δ: 7.43 (d, J=2.4 Hz, 1H), 7.29 (dd, J=8.1, 2.4 Hz 1H), 6.74 (d, J=8.8 Hz, 1H), 6.67 (dd, J=17.6, 10.8 Hz, 1H), 5.63 (d, J=17.6 Hz, 1H), 5.14 (d, J=10.8 Hz, 1H), 4.66 (d, J=6.4 Hz, 2H), 4.08-4.05 (m, 2H), 1.45-1.44 (m, 3H) ppm.

4-Ethoxy-3-(hydroxymethyl)benzaldehyde 1.635

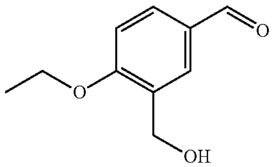

Ozone was bubbled into a solution of compound 1.634 (280 mg, 1.57 mmol) in DCM (30 mL) at −78° C. until the mixture turned blue. After excessive ozone was purged with nitrogen, DMS (1.27 g, 20.42 mmol) was added. The mixture was warmed up to 25° C. and stirred for 12 h. The mixture was concentrated in vacuo and the residue was purified (PM8) afford compound 1.635 (170 mg, 943.40 μmol, 60.1% yield) as a yellow oil.

$^1$H NMR (400 MHz, $CHCl_3$-d) δ: 9.90 (s, 1H), 7.88 (d, J=2.0 Hz, 1H), 7.82 (dd, J=8.4, 2.0 Hz, 1H), 6.98 (d, J=8.4 Hz, 1H), 4.76 (s, 2H), 4.19 (q, J=7.2 Hz, 2H), 1.49 (t, J=6.8 Hz, 3H) ppm.

Synthesis of Intermediate 1.661

4-Chloro-3-(hydroxymethyl)benzaldehyde 1.661

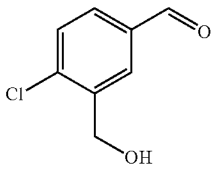 [SMILES: O=Cc1ccc(Cl)c(CO)c1]

To a solution of (5-bromo-2-chloro-phenyl)methanol (1 g, 4.52 mmol) in THF (10 mL) was added n-BuLi (3.79 mL, 2.5 M) at −78° C. After being stirred for 0.5 h, DMF (330.03 mg, 4.52 mmol) was added at −78° C. The resulting mixture was stirred at −78° C. for an additional 0.5 h. The reaction mixture was quenched with water (50 mL) and extracted with EA (100 mL×3). The combined organic layer was washed with brine (100 mL×2), dried over $Na_2SO_4$, filtered and concentrated in vacuo. The residue was purified (PM7) to afford compound 1.661 (450 mg, 2.64 mmol, 58.4% yield) as a white solid.

LCMS (AM3): rt=0.474 min, (171.1 $[M+H]^+$), 75.7% purity.

Synthesis of Intermediate 1.668

(5-Bromo-2-isopropoxyphenyl)methanol 1.666

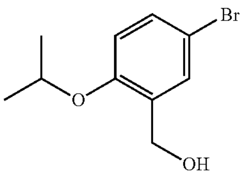

To a solution of 4-bromo-2-(hydroxymethyl)phenol (1 g, 4.93 mmol) and 2-iodopropane (921.87 mg, 5.42 mmol) in ACN (10 mL) was added $K_2CO_3$ (1.02 g, 7.39 mmol) at 35° C. The mixture was stirred at 35° C. for 12 h. The reaction mixture was diluted with water (100 mL) and extracted with EA (100 mL×3). The combined organic layer was washed with brine (100 mL×2), dried over $Na_2SO_4$, filtered and concentrated in vacuo. The residue was purified (PM10) to afford compound 1.666 (900 mg, 3.67 mmol, 74.5% yield) as a yellow oil.

$^1$H NMR (400 MHz, $CHCl_3$-d) δ: 7.43 (d, J=2.4 Hz, 1H), 7.35 (dd, J=8.8, 2.4 Hz, 1H), 6.77 (d, J=8.8 Hz, 1H), 4.64 (s, 2H), 4.58 (quint, J=6.0 Hz, 1H), 1.95 (br s, 1H), 1.37 (d, J=6.0 Hz, 6H) ppm.

(2-Isopropoxy-5-vinylphenyl)methanol 1.667

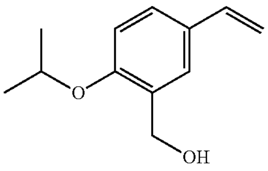

To a solution of compound 1.666 (400 mg, 1.73 mmol) in toluene (5 mL) was added tributyl(vinyl)stannane (569.22 mg, 1.80 mmol) and $Pd(PPh_3)_4$ (94.29 mg, 81.60 μmol). The reaction mixture was heated to 100° C. and stirred for 12 h under a nitrogen atmosphere. The reaction mixture was poured into saturated aqueous KF solution (80 mL) and then extracted with EA (60 mL×2). The organic layer was washed with brine (70 mL), dried over $Na_2SO_4$, filtered and concentrated in vacuo. The residue was purified (PM11) to afford compound 1.667 (200 mg, 1.04 mmol, 63.7% yield) as a yellow oil.

$^1$H NMR (400 MHz, $CHCl_3$-d) δ: 7.42 (d, J=2.4 Hz, 1H), 7.35 (d, J=2.0 Hz, 1H), 6.85 (d, J=8.8 Hz, 1H), 6.66 (dd, J=17.6, 10.8 Hz, 1H), 5.63 (d, J=17.6 Hz, 1H), 5.14 (d, J=10.8 Hz, 1H), 4.67 (s, 2H), 4.59-4.55 (m, 1H), 1.36 (d, J=6.0 Hz, 6H) ppm.

3-(Hydroxymethyl)-4-isopropoxybenzaldehyde 1.668

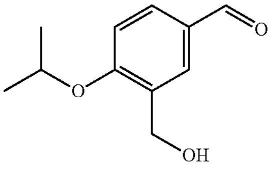

Ozone was bubbled to a solution of compound 1.667 (190 mg, 988.28 μmol) in DCM (30 mL) at −78° C. until the mixture turned blue. After excessive ozone was purged with nitrogen, DMS (614.02 mg, 9.88 mmol) was added. The mixture was warmed up to 25° C. and stirred for 12 h. The mixture was concentrated in vacuo and the residue was purified (PM6) to afford compound 1.668 (20 mg, 102.97 μmol, 10.4% yield) as a yellow oil.

$^1$H NMR (400 MHz, MeOH-$d_4$) δ: 9.83 (s, 1H), 7.98 (d, J=2.0 Hz, 1H), 7.81 (dd, J=8.4, 2.0 Hz, 1H), 7.12 (d, J=8.4 Hz, 1H), 4.83-4.78 (m, 1H), 4.65 (s, 2H), 1.38 (d, J=6.0 Hz, 6H) ppm.

Synthesis of Intermediate 1.671

(5-Bromo-2-(cyclopentyloxy)phenyl)methanol 1.669

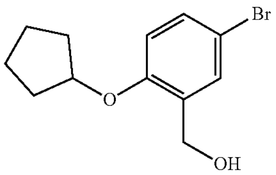 [SMILES: OCc1cc(Br)ccc1OC1CCCC1]

To a solution of 4-bromo-2-(hydroxymethyl)phenol (1 g, 4.93 mmol) and bromocyclopentane (808.18 mg, 5.42 mmol) in DMF (10 mL) was added $K_2CO_3$ (1.02 g, 7.39 mmol). The mixture was heated to 80° C. and stirred for 12 h. The reaction mixture was diluted with water (100 mL) and extracted with EA (100 mL×3). The combined organic layer was washed with brine (100 mL×2), dried over $Na_2SO_4$, filtered and concentrated in vacuo. The residue was purified (PM10) to afford compound 1.669 (700 mg, 2.58 mmol, 52.4% yield) as a yellow oil $^1$H NMR (400 MHz, $CHCl_3$-d) δ: 7.40 (d, J=2.4 Hz, 1H), 7.33 (dd, J=8.8, 2.8 Hz, 1H), 6.75 (d, J=8.8 Hz, 1H), 4.82-4.78 (m, 1H), 4.61 (s, 2H), 1.97-1.74 (m, 6H), 1.72-1.58 (m, 2H) ppm.

(2-(Cyclopentyloxy)-5-vinylphenyl)methanol 1.670

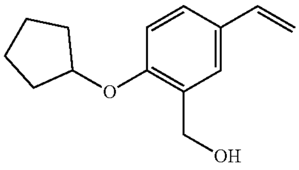 [SMILES: C=Cc1ccc(OC2CCCC2)c(CO)c1]

To a solution of compound 1.669 (400 mg, 1.48 mmol) in toluene (5 mL) was added tributyl(vinyl)stannane (514.56 mg, 1.62 mmol) and $Pd(PPh_3)_4$ (85.23 mg, 73.76 μmol). The reaction mixture was heated to 100° C. and stirred for 12 h under a nitrogen atmosphere. The reaction mixture was poured into saturated aqueous KF solution (80 mL) and extracted with EA (60 mL×2). The organic layer was washed with brine (70 mL), dried over $Na_2SO_4$, filtered and concentrated in vacuo. The residue was purified (PM10) to afford compound 1.670 (300 mg, 1.37 mmol, 93.2% yield) as a yellow oil.

$^1$H NMR (400 MHz, $CHCl_3$-d) δ: 7.47 (d, J=2.0 Hz, 1H), 7.32 (dd, J=8.4, 2.0 Hz, 1H), 6.80 (d, J=8.4 Hz, 1H), 6.68 (dd, J=17.6, 10.8 Hz, 1H), 5.69 (d, J=17.6 Hz, 1H), 5.21 (d,

J=10.8 Hz, 1H), 4.75-4.72 (m, 2H), 4.45-4.43 (m, 1H), 1.68-1.52 (m, 4H), 1.42-1.25 (m, 4H) ppm.

4-(Cyclopentyloxy)-3-(hydroxymethyl)benzaldehyde 1.671

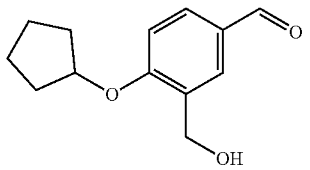 [SMILES: O=Cc1ccc(OC2CCCC2)c(CO)c1]

Ozone was bubbled into a solution of compound 1.670 (300 mg, 1.37 mmol) in DCM (30 mL) at −78° C. until the mixture turned blue. After excessive ozone was purged with nitrogen, DMS (1.28 g, 20.61 mmol) was added. The mixture was warmed up to 25° C. and stirred for 12 h. The mixture was concentrated in vacuo and purified (PM6) to afford compound 1.671 (50 mg, 227.00 μmol, 16.5% yield) as a yellow oil.

$^1$H NMR (400 MHz, $CHCl_3$-d) δ: 9.85 (s, 1H), 7.98 (d, J=1.6 Hz, 1H), 7.82 (dd, J=8.4, 2.0 Hz, 1H), 7.11 (d, J=8.4 Hz, 1H), 5.01-4.98 (m, 1H), 4.64 (s, 2H), 1.90-1.81 (m, 4H), 1.75-1.65 (m, 4H) ppm.

Synthesis of Intermediate 1.675

3-Bromo-5-(trifluoromethoxy)benzamide 1.673

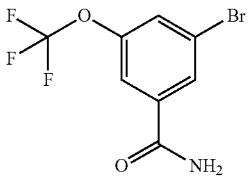 [SMILES: NC(=O)c1cc(Br)cc(OC(F)(F)F)c1]

To a solution of 3-bromo-5-(trifluoromethoxy)benzoic acid (2 g, 7.02 mmol) in DMF (20 mL) was added DIPEA (1.81 g, 14.03 mmol) and HATU (4.00 g, 10.53 mmol) at 20° C. After being stirred at 20° C. for 0.1 h, $NH_4Cl$ (1.50 g, 28.07 mmol) was added. The reaction mixture was stirred at 20° C. for 12 h. The reaction mixture was poured into water (100 mL) and extracted with EA (50 mL×2). The combined organic phase was washed with brine (100 mL), dried over $Na_2SO_4$ and concentrated in vacuo. The residue was purified (PM47) to afford compound 1.673 (980 mg, 3.27 mmol, 46.6% yield) as a yellow solid.

LCMS (AM3): rt=0.867 min, (284.0 $[M+H]^+$), 91.5% purity.

3-(Trifluoromethoxy)-5-vinylbenzamide 1.674

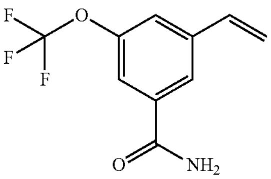 [SMILES: C=Cc1cc(OC(F)(F)F)cc(C(N)=O)c1]

To a mixture of compound 1.673 (980 mg, 3.45 mmol) in 1,4-dioxane (10 mL) and water (1 mL) was added $K_2CO_3$ (953.72 mg, 6.90 mmol), 4,4,5,5-tetramethyl-2-vinyl-1,3,2-dioxaborolane (797.10 mg, 5.18 mmol) and Pd(dppf)$Cl_2$ (252.46 mg, 345.03 μmol) sequentially. The reaction mixture was then heated to 80° C. and stirred for 12 h under a nitrogen atmosphere. The reaction mixture was filtered and concentrated in vacuo and the crude product was purified (PM4) to afford compound 1.674 (700 mg, 2.62 mmol, 75.8% yield) as a white solid.

LCMS (AM3): rt=0.870 min, (232.1 $[M+H]^+$), 87.6% purity.

3-Formyl-5-(trifluoromethoxy)benzamide 1.675

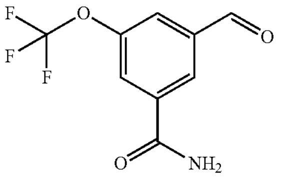 [SMILES: NC(=O)c1cc(C=O)cc(OC(F)(F)F)c1]

A solution of compound 1.674 (0.7 g, 2.62 mmol) in DCM (10 mL) was cooled to −78° C. and bubbled with ozone until the colour of the mixture turned blue. The excess ozone was purged with nitrogen and then DMS (2.170 g, 34.92 mmol) was added slowly. The reaction mixture was warmed to 20° C. and stirred for another 12.5 h. The reaction mixture was concentrated in vacuo to give the crude product that was purified (PM150) to afford compound 1.675 (260 mg, 1.12 mmol, 36.8% yield) as a white solid.

LCMS (AM3): rt=0.731 min, (234.1 $[M+H]^+$), 97.5% purity.

Synthesis of Intermediate 1.704

Methyl 3,4-dichloro-5-(trifluoromethoxy)benzoate 1.702

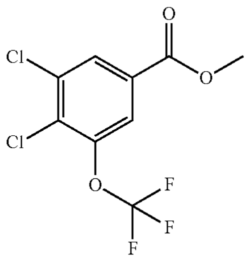 [SMILES: COC(=O)c1cc(Cl)c(Cl)c(OC(F)(F)F)c1]

To a mixture of 3,4-dichloro-5-(trifluoromethoxy)benzoic acid (500 mg, 1.82 mmol) in MeOH (30 mL) was added $SOCl_2$ (1.08 g, 9.09 mmol) slowly at 0° C. The mixture was then heated to 60° C. and stirred for 0.5 h. The mixture was poured into saturated aqueous $NaHCO_3$ solution (50 mL) and extracted with EA (50 mL×3). The combined organic phase was washed with brine (50 mL), dried with anhydrous $Na_2SO_4$, filtered and concentrated in vacuo to afford compound 1.702 (500 mg, 1.73 mmol, 95.2% yield) as a yellow oil.

$^1$H NMR (400 MHz, MeOH-$d_4$) δ: 8.15 (d, J=2.0 Hz, 1H), 7.93 (d, J=2.0 Hz, 1H), 3.95 (s, 3H) ppm.

(3,4-Dichloro-5-(trifluoromethoxy)phenyl)methanol 1.703

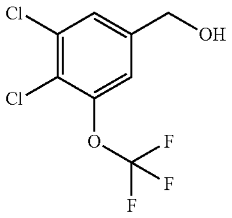 [SMILES: OCc1cc(Cl)c(Cl)c(OC(F)(F)F)c1]

To a solution of compound 1.702 (500 mg, 1.73 mmol) in THF (20 mL) was added $LiAlH_4$ (78.78 mg, 2.08 mmol) slowly at 0° C. The mixture was then warmed to 25° C. and stirred for 0.5 h. The mixture was cooled to 0° C. and diluted with EA (10 mL) and stirred for 2 min. The mixture was quenched by addition of water (0.2 mL), aq. 10% NaOH solution (0.2 mL) and water (0.6 mL). After stirring for 0.5 h, anhydrous $Na_2SO_4$ (3 g) was added and stirred for another 0.5 h. The resulting suspension was filtered and the filtrate was concentrated in vacuo. The residue was purified (PM2) to afford compound 1.703 (400 mg, 1.48 mmol, 83% yield) as a yellow oil $^1H$ NMR (400 MHz, MeOH-$d_4$) δ: 7.55 (d, J=1.6 Hz, 1H), 7.40 (d, J=1.6 Hz, 1H), 4.61 (s, 2H) ppm.

3,4-Dichloro-5-(trifluoromethoxy)benzaldehyde 1.704

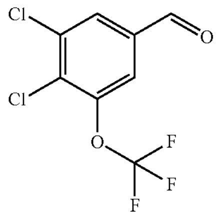 [SMILES: O=Cc1cc(Cl)c(Cl)c(OC(F)(F)F)c1]

To a solution of compound 1.703 (400 mg, 1.53 mmol) in DCM (100 mL) was added $MnO_2$ (1.33 g, 15.32 mmol) at 25° C. The mixture was stirred at 25° C. for 2 h. The mixture was filtered and concentrated in vacuo. The residue was purified (PM7) to afford compound 1.704 (140 mg, 540.52 μmol, 35.3% yield) as a yellow oil.

$^1H$ NMR (400 MHz, MeOH-$d_4$) δ: 9.96 (s, 1H), 8.12 (d, J=1.2 Hz, 1H), 7.92 (d, J=1.2 Hz, 1H) ppm.

Synthesis of Intermediate 1.707

2-Methoxy-1-(trifluoromethoxy)-4-vinylbenzene 1.706

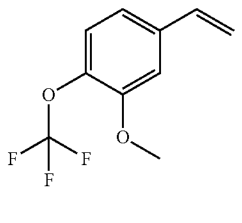

To a mixture of 4,4,5,5-tetramethyl-2-vinyl-1,3,2-dioxaborolane (596.66 mg, 3.87 mmol) and 4-bromo-2-methoxy-1-(trifluoromethoxy)benzene (0.7 g, 2.58 mmol) in 1,4-dioxane (10 mL) and $H_2O$ (1 mL) was added $K_2CO_3$ (713.90 mg, 5.17 mmol) and Pd(dppf)$Cl_2$—$CH_2Cl_2$ (105.46 mg, 129.14 μmol). The mixture was heated to 90° C. and stirred for 12 h under a nitrogen atmosphere. The mixture was filtered and concentrated in vacuo and the residue was purified (PM14) to afford compound 1.706 (0.28 g, 1.28 mmol, 49.7% yield) as a colorless oil.

$^1H$ NMR (400 MHz, MeOH-$d_4$) δ: 7.19-7.14 (m, 2H), 7.03 (dd, J=2.0, 8.4 Hz, 1H), 6.73 (dd, J=17.6, 10.8 Hz, 1H), 5.81 (d, J=17.6 Hz, 1H), 5.29 (d, J=0.8, 11.2 Hz, 1H), 3.89 (s, 3H) ppm.

3-Methoxy-4-(trifluoromethoxy)benzaldehyde 1.707

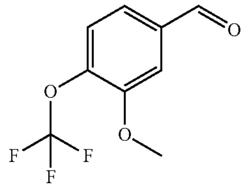

Ozone was bubbled into a solution of compound 1.706 (0.28 g, 1.28 mmol) in DCM (20 mL) cooled to −78° C. until the colour of mixture turned blue. After excess ozone was purged by nitrogen, DMS (797.37 mg, 12.83 mmol) was added and the mixture was stirred at 25° C. for 12 h. The mixture was concentrated in vacuo and the residue was purified by column chromatography (PM14) to afford compound 1.707 (0.22 g, 999.34 μmol, 77.9% yield) as a colourless oil.

$^1H$ NMR (400 MHz, MeOH-$d_4$) δ: 9.96 (s, 1H), 7.66 (d, J=2.0 Hz, 1H), 7.57 (dd, J=8.1, 2.0 Hz, 1H), 7.47 (dd, J=8.4, 1.2 Hz, 1H), 3.96 (s, 3H) ppm.

Synthesis of Intermediate 1.709

3-Methyl-4-(trifluoromethoxy)benzaldehyde 1.709

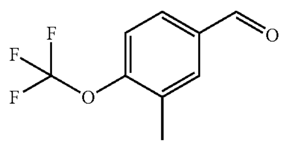

A mixture of 3-bromo-4-(trifluoromethoxy)benzaldehyde (750 mg, 2.79 mmol), $Pd(PPh_3)_4$ (322.16 mg, 278.79 μmol), 2,4,6-trimethyl-1,3,5,2,4,6-trioxatriborinane (1.40 g, 5.58 mmol) and $K_2CO_3$ (1.16 g, 8.36 mmol) in 1,4-dioxane (7 mL) was stirred at 100° C. for 12 h under nitrogen atmosphere. The residue was poured into water (20 mL) and extracted with EA (10 mL×3). The combined organic phase was washed with brine (30 mL×2), dried with anhydrous $Na_2SO_4$, filtered and concentrated in vacuo. The residue was purified by silica gel chromatography (PM1) to afford compound 1.709 (400 mg, 1.96 mmol, 70.3% yield) as a yellow oil.

$^1H$ NMR (400 MHz, $CHCl_3$-d) δ: 9.99 (s, 1H), 7.81 (d, J=1.2 Hz, 1H), 7.76 (dd, J=8.4, 1.2 Hz, 1H), 7.37 (dd, J=8.4, 1.2 Hz, 1H), 2.40 (s, 3H) ppm.

Synthesis of Intermediate 1.710

3-Cyclopropyl-4-(trifluoromethoxy)benzaldehyde 1.710

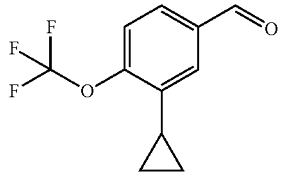 [SMILES: O=Cc1ccc(OC(F)(F)F)c(C2CC2)c1]

A mixture of 3-bromo-4-(trifluoromethoxy)benzaldehyde (500 mg, 1.86 mmol), cyclopropylboronic acid (239.48 mg, 2.79 mmol), $Pd(dppf)Cl_2 \cdot CH_2Cl_2$ (151.78 mg, 185.86 μmol) and $K_2CO_3$ (513.76 mg, 3.72 mmol) in 1,4-dioxane (10 mL) and $H_2O$ (1 mL) was stirred at 90° C. for 12 h under a nitrogen atmosphere. The mixture was concentrated in vacuo and the residue was purified by prep-TLC ($SiO_2$, PE/EA=3/1) to afford compound 1.710 (350 mg, 1.52 mmol, 81.8% yield) as a yellow oil.

$^1H$ NMR (400 MHz, DMSO-$d_6$) δ: 9.94 (s, 1H), 7.79 (dd, J=8.4, 2.0 Hz, 1H), 7.58 (d, J=2.0 Hz, 1H), 7.44 (dd, J=8.4, 1.6 Hz, 1H), 2.22-2.15 (m, 1H), 1.13-1.07 (m, 2H), 0.83-0.78 (m, 2H) ppm.

Synthesis of Intermediate 1.712

3-(4,4,5,5-Tetramethyl-1,3,2-dioxaborolan-2-yl)-5-(trifluoromethoxy)benzaldehyde 1.711

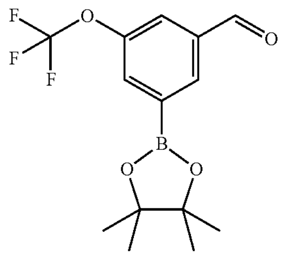 [SMILES: CC1(C)OB(c2cc(C=O)cc(OC(F)(F)F)c2)OC1(C)C]

A mixture of 3-bromo-5-(trifluoromethoxy)benzaldehyde (5 g, 18.59 mmol), KOAc (3.65 g, 37.19 mmol), $Pin_2B_2$ (5.65 g, 22.25 mmol) and $Pd(dppf)Cl_2$ (700 mg, 0.96 mmol) in 1,4-dioxane (100 mL) was degassed and purged with nitrogen three times. The reaction mixture was then heated to 80° C. and stirred for 16 h under a nitrogen atmosphere. The reaction mixture was concentrated in vacuo and the residue was purified (PM7) to afford compound 1.711 (6.1 g) as a yellow oil.

$^1H$ NMR (400 MHz, $CHCl_3$-d) δ: 10.05 (s, 1H), 8.23 (s, 1H), 7.88 (d, J=1.2 Hz, 1H), 7.82-7.81 (m, 1H), 1.38 (s, 12H) ppm.

3-(Oxazol-4-ylmethyl)-5-(trifluoromethoxy)benzaldehyde 1.712

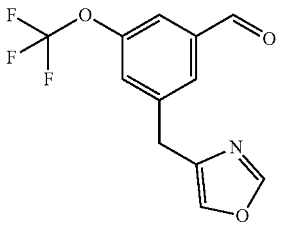 [SMILES: O=Cc1cc(Cc2cocn2)cc(OC(F)(F)F)c1]

A mixture of compound 1.711 (1.83 g, 5.79 mmol), 4-(chloromethyl)oxazole (680 mg, 5.79 mmol), $K_2CO_3$ (2.04 g, 14.76 mmol) and $Pd(dppf)Cl_2$ (212 mg, 0.29 mol) in 1,4-dioxane (16 mL) and $H_2O$ (4 mL) was degassed and purged with nitrogen three times. The reaction mixture was then heated to 80° C. and stirred for 2 h under a nitrogen atmosphere. The reaction mixture was concentrated in vacuo and the residue was purified (PM7) to afford compound 1.712 (170 mg, 10.8% yield) as a yellow oil.

$^1H$ NMR (400 MHz, $CHCl_3$-d) δ: 9.98 (s, 1H), 7.88 (s, 1H), 7.73 (s, 1H), 7.61 (s, 1H), 7.49 (s, 1H), 7.41 (s, 1H), 4.01 (s, 2H) ppm.

Synthesis of Intermediate 1.713

3-(Oxazol-5-ylmethyl)-5-(trifluoromethoxy)benzaldehyde 1.713

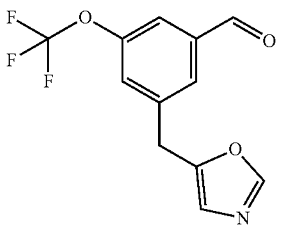 [SMILES: O=Cc1cc(Cc2cnco2)cc(OC(F)(F)F)c1]

A mixture of compound 1.711 (2.03 g, 6.41 mmol), 5-(chloromethyl)oxazole (750 mg, 6.38 mmol), $K_2CO_3$ (2.25 g, 16.28 mmol) and $Pd(dppf)Cl_2$ (240 mg, 0.33 mmol) in 1,4-dioxane (16 mL) and $H_2O$ (4 mL) was degassed and purged with nitrogen three times. The reaction mixture was then heated to 80° C. and stirred for 2 h under a nitrogen atmosphere. The reaction mixture was concentrated in vacuo and the residue was purified (PM7) to afford compound 1.713 (650 mg 37.6% yield) as a yellow oil.

$^1H$ NMR (400 MHz, $CHCl_3$-d) δ: 9.99 (s, 1H), 7.84 (s, 1H), 7.70 (s, 1H), 7.64 (s, 1H), 7.35 (s, 1H), 6.89 (s, 1H), 4.13 (s, 2H) ppm.

Synthesis of Intermediate 1.714

3-Formyl-5-(trifluoromethoxy)benzonitrile 1.714

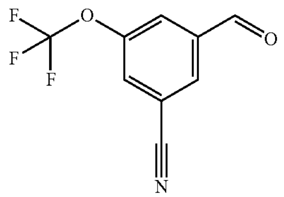 [SMILES: N#Cc1cc(C=O)cc(OC(F)(F)F)c1]

A mixture of 3-bromo-5-(trifluoromethoxy)benzaldehyde (700 mg, 2.60 mmol), $Zn(CN)_2$ (910 mg, 7.75 mmol) and $Pd(PPh_3)_4$ (300 mg, 0.26 mmol) in DMF (10 mL) was degassed and purged with nitrogen three times. The reaction mixture was heated to 90° C. and stirred for 1.5 h under nitrogen atmosphere. The reaction mixture was filtered and the filtrate was diluted with water (40 mL). The resultant mixture was extracted with EA (20 mL×3) and the combined organic phase was washed with brine (60 mL), dried over $Na_2SO_4$, filtered and concentrated in vacuo. The residue was purified (PM12) to afford compound 1.714 (0.23 g, 41.1% yield) as a white solid.

$^1$H NMR (400 MHz, $CHCl_3$-d) 6:10.05 (s, 1H), 8.12 (s, 1H), 7.98 (s, 1H), 7.76 (s, 1H) ppm.

Synthesis of Intermediate 1.718

2-(3-Bromo-5-(trifluoromethoxy)phenoxy)ethanol 1.716

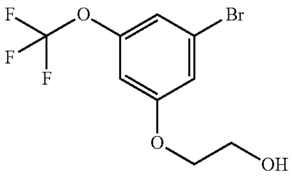 [SMILES: OCCOc1cc(Br)cc(OC(F)(F)F)c1]

A mixture of 3-bromo-5-(trifluoromethoxy)phenol (930 mg, 3.62 mmol), 2-bromoethanol (500 mg, 4.00 mmol) and $K_2CO_3$ (1.00 g, 7.24 mmol) in DMF (10 mL) was stirred at 100° C. for 16 h. The reaction mixture was diluted with water (40 mL) and the resulting mixture was extracted with EA (10 mL×3). The combined organic phase was washed with brine (30 mL), dried over $Na_2SO_4$, filtered and concentrated in vacuo. The residue was purified (PM7) to afford compound 1.716 (1.1 g) as a colourless oil.

$^1$H NMR (400 MHz, $CHCl_3$-d) δ: 7.03-7.02 (m, 2H), 6.74 (s, 1H), 4.08 (t, J=4.8 Hz, 2H), 3.97 (t, J=4.8 Hz, 2H) ppm.

2-(3-(Trifluoromethoxy)-5-vinylphenoxy)ethanol 1.717

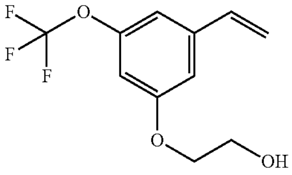 [SMILES: C=Cc1cc(OCCO)cc(OC(F)(F)F)c1]

A mixture of compound 1.716 (1.1 g, 3.65 mmol), 4,4,5,5-tetramethyl-2-vinyl-1,3,2-dioxaborolane (1.1 g, 7.14 mmol), $K_2CO_3$ (1.01 g, 7.31 mmol) and $Pd(dppf)Cl_2$ (134 mg, 0.18 mmol) in 1,4-dioxane (10 mL) and $H_2O$ (2 mL) was degassed and purged with nitrogen three times. The reaction mixture was heated to 80° C. and stirred under $N_2$ for 16 h. The reaction mixture was concentrated in vacuo and the residue was purified (PM4) to afford compound 1.717 (630 mg, 69.5% yield) as a brown oil.

$^1$H NMR (400 MHz, $CHCl_3$-d) δ: 6.89 (d, J=2.0 Hz, 2H), 6.69-6.61 (m, 2H), 5.77 (d, J=17.2 Hz, 1H), 5.34 (d, J=10.8 Hz, 1H), 4.10 (t, J=4.8 Hz, 2H), 3.98 (t, J=4.8 Hz, 2H) ppm.

3-(2-Hydroxyethoxy)-5-(trifluoromethoxy)benzaldehyde 1.718

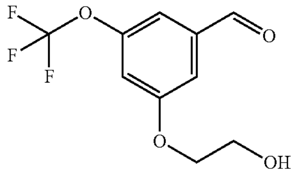 [SMILES: O=Cc1cc(OCCO)cc(OC(F)(F)F)c1]

Ozone was bubbled through a solution of compound 1.717 (630 mg, 2.54 mmol) in DCM (10 mL) at −70° C. until the colour of the solution turned blue. The excess ozone was purged with nitrogen and then DMS (1.58 g, 25.38 mmol) was added. The mixture was warmed to room temperature and stirred for 14 h. The reaction mixture was concentrated in vacuo and the residue was purified (PM6) to afford compound 1.718 (400 mg, 63.0% yield) as a colourless oil.

$^1$H NMR (400 MHz, $CHCl_3$-d) δ: 9.95 (s, 1H), 7.36 (d, J=2.4 Hz, 1H), 7.34 (d, J=0.8 Hz, 1H), 7.06 (d, J=1.2 Hz, 1H), 4.17 (t, J=4.4 Hz, 2H), 4.02 (t, J=4.4 Hz, 2H) ppm.

Synthesis of Intermediate 1.723

Methyl 3-allyl-5-(trifluoromethoxy)benzoate 1.720

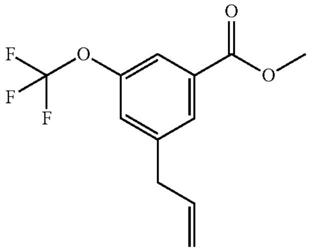 [SMILES: C=CCc1cc(OC(F)(F)F)cc(C(=O)OC)c1]

A mixture of methyl 3-bromo-5-(trifluoromethoxy)benzoate (5 g, 16.72 mmol), 2-allyl-4,4,5,5-tetramethyl-1,3,2-dioxaborolane (4.21 g, 25.08 mmol), $K_2CO_3$ (4.62 g, 33.44 mmol) and $Pd(dppf)Cl_2$ (612 mg, 0.84 mmol) in 1,4-dioxane (40 mL) and $H_2O$ (10 mL) was degassed and purged with nitrogen three times. The reaction mixture was heated to 80° C. and stirred for 16 h. The reaction mixture was concentrated in vacuo and the residue was purified (PM17) to afford compound 1.720 (3.95 g, 90.8% yield) as a colourless oil.

$^1$H NMR (400 MHz, $CHCl_3$-d) δ: 7.83 (s, 1H), 7.74 (s, 1H), 7.24 (s, 1H), 6.00-5.90 (m, 1H), 5.17-5.10 (m, 2H), 3.94 (s, 3H), 3.46 (d, J=5.6 Hz, 2H) ppm.

Methyl 3-(2-hydroxyethyl)-5-(trifluoromethoxy)benzoate 1.721

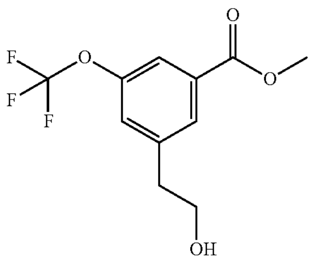 [SMILES: COC(=O)c1cc(CCO)cc(OC(F)(F)F)c1]

Ozone was bubbled through a solution of compound 1.720 (3.95 g, 15.18 mmol) in DCM (40 mL) at −70° C. until the colour of the reaction solution turned blue. After excess ozone was purged with nitrogen, $NaBH_4$ (2 g, 52.87 mmol) was added and the reaction mixture was warmed to 25° C. and stirred for 16 h. The reaction mixture was quenched with saturated aqueous $NH_4Cl$ solution (40 mL) and then extracted with DCM (40 mL×3). The combined organic phase was washed with brine (120 mL), dried over $Na_2SO_4$, filtered and concentrated in vacuo. The residue was purified (PM7) to afford compound 1.721 (1.7 g, 42.4% yield) as a yellow oil.

$^1H$ NMR (400 MHz, $CHCl_3$-d) δ: 7.86 (s, 1H), 7.75 (s, 1H), 7.30 (s, 1H), 3.95-3.89 (m, 5H), 2.93 (t, J=6.4 Hz, 2H), 1.75 (br s, 1H) ppm.

2-(3-(Hydroxymethyl)-5-(trifluoromethoxy)phenyl) ethanol 1.722

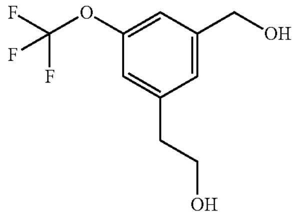 [SMILES: OCCc1cc(CO)cc(OC(F)(F)F)c1]

To a solution of compound 1.721 (0.8 g, 3.03 mmol) in THE (10 mL) was added LAH (0.2 g, 5.27 mmol) at 0° C. The reaction mixture was stirred at 0° C. for 1 h. The reaction mixture was quenched with aq. HCl (1 N, 30 mL) and the resulting mixture was extracted with EA (20 mL×3). The combined organic phase was washed with brine (60 mL), dried over $Na_2SO_4$, filtered and concentrated in vacuo to afford compound 1.722 (0.67 g, 93.7% yield) as a yellow oil, which was used directly without further purification.

$^1H$ NMR (400 MHz, $CHCl_3$-d) δ: 7.16 (s, 1H), 7.08 (s, 1H), 7.00 (s, 1H), 4.65 (s, 2H), 3.84 (t, J=6.4 Hz, 2H), 2.86 (t, J=6.4 Hz, 2H), 2.45-2.05 (br s, 2H) ppm.

3-(2-Hydroxyethyl)-5-(trifluoromethoxy)benzaldehyde 1.723

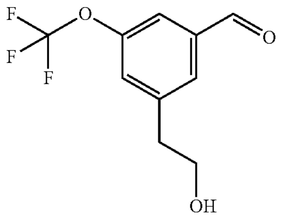 [SMILES: O=Cc1cc(CCO)cc(OC(F)(F)F)c1]

A mixture of compound 1.722 (0.67 g, 2.84 mmol) and $MnO_2$ (2.47 g, 28.37 mmol) in DCM (20 mL) was stirred at 25° C. for 16 h. The reaction mixture was concentrated in vacuo and the residue was purified (PM2) to afford compound 1.723 (520 mg, 78.3% yield) as a yellow oil.

$^1H$ NMR (400 MHz, $CHCl_3$-d) δ: 9.99 (s, 1H), 7.72 (s, 1H), 7.60 (s, 1H), 7.38 (s, 1H), 3.97-3.92 (m, 2H), 2.98 (t, J=6.4 Hz, 2H) ppm.

Synthesis of Intermediate 1.741

Ethyl 3-bromo-5-ethoxybenzoate 1.736

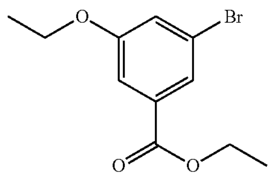

To a solution of 3-bromo-5-hydroxy-benzoic acid (2.8 g, 12.90 mmol) in ACN (50 mL) was added $K_2CO_3$ (8.92 g, 64.51 mmol) and iodoethane (5.03 g, 32.26 mmol) at ambient temperature. The resulting mixture was heated to 80° C. and stirred for 12 h. The mixture was filtered and concentrated in vacuo to afford compound 1.736 (3.4 g, 12.45 mmol, 96.5% yield) as a light-yellow oil.

$^1H$ NMR (400 MHz, $CHCl_3$-d) δ: 7.74 (t, J=1.6 Hz, 1H), 7.48 (t, J=1.6 Hz, 1H), 7.22 (t, J=2.0 Hz, 1H), 4.37 (q, J=7.2 Hz, 2H), 4.06 (q, J=7.2 Hz, 2H), 1.44-1.40 (t, 3H), 1.40-1.36 (t, 3H) ppm.

Ethyl 3-ethoxy-5-vinylbenzoate 1.737

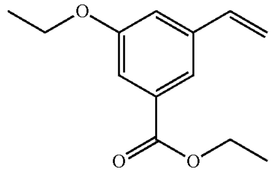 [SMILES: C=Cc1cc(OCC)cc(C(=O)OCC)c1]

To a solution of compound 1.736 (3.6 g, 13.18 mmol) in DME (50 mL) was added CsF (4.00 g, 26.36 mmol), 4,4,5,5-tetramethyl-2-vinyl-1,3,2-dioxaborolane (3.05 g, 19.77 mmol) and Pd(dppf)$Cl_2$ (964.45 mg, 1.32 mmol). The mixture was heated to 80° C. and stirred for 12 h under a nitrogen atmosphere. The mixture was concentrated in vacuo and the residue was purified (PM17) to afford compound 1.737 (2.4 g, 10.90 mmol, 82.7% yield) as a light-yellow oil.

$^1$H NMR (400 MHz, $CHCl_3$-d) δ: 7.68 (t, J=1.2 Hz, 1H), 7.45 (t, J=1.2 Hz, 1H), 7.13 (t, J=2.0 Hz, 1H), 6.71 (dd, J=17.6, 10.8 Hz, 1H), 5.81 (d, J=16.8 Hz, 1H), 5.31 (d, J=11.2 Hz, 1H), 4.38 (q, J=7.2 Hz, 2H), 4.09 (q, J=7.2 Hz, 2H), 1.45-1.41 (t, 3H), 1.41-1.37 (t, 3H) ppm.

(3-Ethoxy-5-vinylphenyl)methanol 1.738

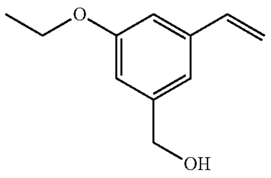

To a solution of compound 1.737 (2.4 g, 10.90 mmol) in THF (30 mL) was added LAH (620.33 mg, 16.34 mmol) at 0° C. The mixture was warmed to 25° C. and stirred for 1 h. The reaction was quenched by addition of aq. HCl (1 M) to pH=3 at 0° C. The mixture was diluted with water (50 mL) and extracted with EA (50 mL×3). The combined organic phase was washed with brine (50 mL), dried with $Na_2SO_4$, filtered and concentrated in vacuo to afford compound 1.738 (2.2 g) as a light-yellow oil, which was used directly.

$^1$H NMR (400 MHz, $CHCl_3$-d) δ: 6.99 (s, 1H), 6.88 (s, 1H), 6.83 (s, 1H), 6.68 (dd, J=17.6, 10.8 Hz, 1H), 5.75 (d, J=17.6 Hz, 1H), 5.26 (d, J=10.8 Hz, 1H), 4.66 (s, 2H), 4.06 (q, J=7.2 Hz, 2H), 1.42 (t, J=7.2 Hz, 3H) ppm.

1-(Chloromethyl)-3-ethoxy-5-vinylbenzene 1.739

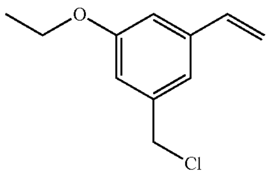

To a solution of compound 1.738 (2.2 g, 12.34 mmol) in 1,4-dioxane (30 mL) was added $SOCl_2$ (3 g, 25.22 mmol) and the resulting mixture was stirred at 60° C. for 12 h. The mixture was concentrated in vacuo and the residue was diluted with EA (30 mL) and washed with saturated aq. $NaHCO_3$ solution (10 mL). The organic layer was separated, dried over $Na_2SO_4$ and concentrated in vacuo to give compound 1.739 (2.2 g, 90.5% yield) as a brown oil, which was used directly without further purification. 2-(3-Ethoxy-5-vinylphenyl)acetonitrile 1.740

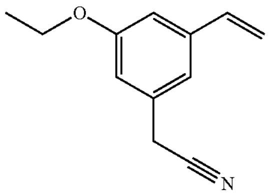

To a solution of compound 1.739 (2.2 g, 11.19 mmol) in ACN (20 mL) was added TMSCN (4.44 g, 44.74 mmol) and TBAF (16.78 mL, 2 M in THF). The resulting mixture was heated to 80° C. and stirred for 1 h. The mixture was concentrated in vacuo and the residue was purified (PM11) to afford compound 1.740 (1.4 g, 66.8% yield) as a yellow oil.

$^1$H NMR (400 MHz, $CHCl_3$-d) δ: 6.92 (s, 1H), 6.90 (s, 1H), 6.76 (s, 1H), 6.67 (dd, J=17.6, 10.8 Hz, 1H), 5.77 (d, J=17.6 Hz, 1H), 5.30 (d, J=11.2 Hz, 1H), 4.06 (q, J=7.2 Hz, 2H), 3.71 (s, 2H), 1.43 (t, J=7.2 Hz, 3H) ppm.

2-(3-Ethoxy-5-formylphenyl)acetonitrile 1.741

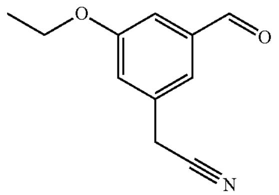

Ozone was bubbled through a solution of compound 1.740 (1.4 g, 7.48 mmol) in DCM (20 mL) at −78° C. until the colour of the reaction mixture turned blue. After excess ozone was purged with nitrogen, DMS (8.46 g, 136.16 mmol) was added. The mixture was warmed to 20° C. and stirred for 3 h. The reaction mixture was concentrated in vacuo and the residue was purified (PM11) to afford compound 1.741 (635 mg, 3.36 mmol, 44.9% yield) as a white solid.

$^1$H NMR (400 MHz, $CHCl_3$-d) δ: 9.97 (s, 1H), 7.41 (s, 1H), 7.35 (s, 1H), 7.15 (s, 1H), 4.12 (q, J=6.8 Hz, 2H), 3.81 (s, 2H), 1.46 (t, J=6.8 Hz, 3H) ppm.

Synthesis of Intermediate 1.744

Methyl 3-cyclopropyl-5-vinylbenzoate 1.742

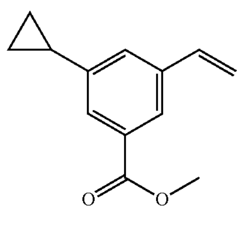

To a mixture of compound 1.683 (4.4 g, 18.25 mmol) and cyclopropylboronic acid (1.72 g, 20.08 mmol) in 1,4-dioxane (44 mL) and $H_2O$ (4.4 mL) was added $K_2CO_3$ (5.04 g, 36.50 mmol) and Pd(dppf)$Cl_2$ (667.72 mg, 912.56 μmol). The mixture was heated to 80° C. and stirred for 12 h under a nitrogen atmosphere. The mixture was concentrated in vacuo and the residue was purified (PM14, $R_f$=0.43) to afford compound 1.742 (1.45 g, 7.17 mmol, 39.3% yield) as a yellow oil, which was used directly.

(3-Cyclopropyl-5-vinylphenyl)methanol 1.743

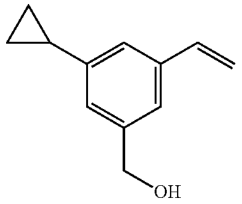

To a solution of LAH (251.47 mg, 6.63 mmol) in THF (20 mL) was added compound 1.742 (1.34 g, 6.63 mmol) at 0° C. The mixture was stirred at 0° C. for 2 h. The reaction was quenched by addition of HCl (1 M) to pH=3 at 0° C. The mixture was diluted with water (50 mL) and extracted with EA (50 mL×3). The combined organic phase was washed with brine (50 mL), dried with $Na_2SO_4$, filtered and concentrated in vacuo to afford compound 1.743 (1.2 g) as a yellow oil.

$^1$H NMR (400 MHz, $CHCl_3$-d) δ: 7.22 (s, 1H), 7.07 (s, 1H), 7.01 (s, 1H), 6.71 (dd, J=17.6, 10.8 Hz, 1H), 5.76 (d, J=17.6 Hz, 1H), 5.26 (d, J=10.8 Hz, 1H), 4.68 (d, J=3.6 Hz, 2H), 1.96-1.89 (m, 1H), 1.01-0.96 (m, 2H), 0.76-0.72 (m, 2H) ppm.

3-Cyclopropyl-5-(hydroxymethyl)benzaldehyde 1.744

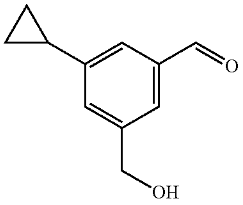 [SMILES: O=Cc1cc(CO)cc(C2CC2)c1]

Ozone was bubbled through a solution of compound 1.743 (300 mg, 1.72 mmol) in DCM (8 mL) at −78° C. until the colour of the reaction mixture turned blue. After excess ozone was purged with nitrogen, DMS (1.39 g, 22.38 mmol) was added. The mixture was warmed to 25° C. and stirred for 12 h. The mixture was concentrated in vacuo and the residue was purified (PM11) to afford compound 1.744 (200 mg, 1.14 mmol, 65.9% yield) as a colourless oil.

$^1$H NMR (400 MHz, $CHCl_3$-d) δ: 9.97 (s, 1H), 7.65 (s, 1H), 7.49 (s, 1H), 7.37 (s, 1H), 4.75 (s, 2H), 2.02-1.95 (m, 1H), 1.07-1.02 (m, 2H), 0.79-0.75 (m, 2H) ppm.

Synthesis of Intermediate 1.747

1-(Chloromethyl)-3-cyclopropyl-5-vinylbenzene 1.745

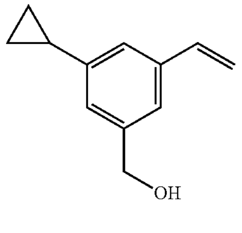

To a solution of compound 1.743 (900 mg, 5.17 mmol) in 1,4-dioxane (10 mL) was added $SOCl_2$ (1.84 g, 15.50 mmol) at 0° C. The mixture was heated to 70° C. and stirred for 2 h. The reaction mixture was quenched by addition of saturated aq. $NaHCO_3$ solution (10 mL) and extracted with EA (100 mL×3). The combined organic layer was washed with brine (100 mL×2), dried over $Na_2SO_4$, filtered and concentrated in vacuo to afford compound 1.745 (940 mg) as a yellow oil and taken on directly to the next step.

2-(3-Cyclopropyl-5-vinylphenyl)acetonitrile 1.746

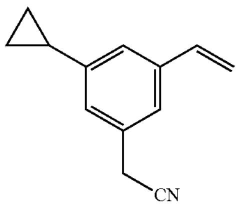

A solution of compound 1.745 (940 mg, 4.88 mmol), TMSCN (677.56 mg, 6.83 mmol) and TBAF (6.34 mL, 1 M in THF) in ACN (80 mL) was stirred at 25° C. for 12 h. The mixture was concentrated in vacuo and the residue was purified (PM16) to afford compound 1.746 (760 mg, 4.15 mmol, 85% yield) as a yellow oil.

$^1$H NMR (400 MHz, $CHCl_3$-d) δ: 7.06 (s, 1H), 6.99 (s, 1H), 6.84 (s, 1H), 6.57 (dd, J=17.6, 11.2 Hz, 1H), 5.68 (d, J=17.6 Hz, 1H), 5.21 (d, J=11.2 Hz, 1H), 3.63 (s, 2H), 1.86-1.78 (m, 1H), 0.94-0.89 (m, 2H), 0.66-0.62 (m, 2H) ppm.

2-(3-Cyclopropyl-5-formylphenyl)acetonitrile 1.747

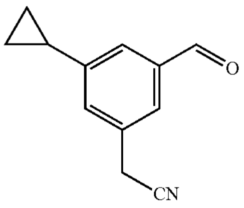 [SMILES: N#CCc1cc(C=O)cc(C2CC2)c1]

Ozone was bubbled through a solution of compound 1.746 (760 mg, 4.15 mmol) in DCM (8 mL) at −78° C. until the colour of the mixture turned blue. After excess ozone was purged with nitrogen, DMS (3.35 g, 53.92 mmol) was added, The mixture was warmed to 25° C. and stirred for 12 h. The mixture was concentrated in vacuo to give a residue that was purified (PM7) to afford compound 1.747 (380 mg, 2.05 mmol, 49.5% yield) as a yellow oil.

$^1$H NMR (400 MHz, $CHCl_3$-d) δ: 9.91 (s, 1H), 7.53 (s, 1H), 7.45 (s, 1H), 7.27 (s, 1H), 3.73 (s, 2H), 1.96-1.89 (m, 1H), 1.04-0.98 (m, 2H), 0.73-0.69 (m, 2H) ppm.

Synthesis of Intermediate 1.754

Methyl 3-bromo-5-(2,2,2-trifluoroethoxy)benzoate 1.749

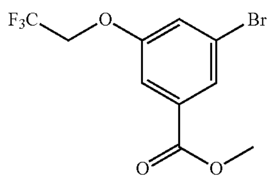 [SMILES: COC(=O)c1cc(Br)cc(OCC(F)(F)F)c1]

To a solution of methyl 3-bromo-5-hydroxybenzoate (4.1 g, 17.75 mmol) and 2,2,2-trifluoroethyl trifluoromethanesulfonate (4.12 g, 17.75 mmol) in DMF (40 mL) was added $K_2CO_3$ (3.68 g, 26.62 mmol). The mixture was heated to 80° C. and stirred for 12 h. The reaction mixture was diluted with water (100 mL) and extracted with EA (100 mL×3). The combined organic layer was washed with brine (200 mL×3), dried over $Na_2SO_4$, filtered and concentrated in vacuo to afford compound 1.749 (5.75 g) as a yellow solid.

$^1$H NMR (400 MHz, DMSO-$d_6$) δ: 7.74 (d, J=1.6 Hz, 1H), 7.65 (t, J=1.6 Hz, 1H), 7.56 (t, J=1.6 Hz, 1H), 4.92 (q, J=8.8 Hz, 2H), 3.87 (s, 3H) ppm.

Methyl 3-(2,2,2-trifluoroethoxy)-5-vinylbenzoate 1.750

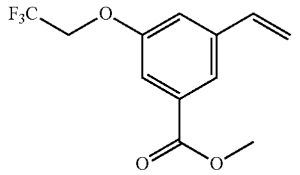 [SMILES: C=Cc1cc(OCC(F)(F)F)cc(C(=O)OC)c1]

To a solution of compound 1.749 (5.75 g, 18.37 mmol) and 4,4,5,5-tetramethyl-2-vinyl-1,3,2-dioxaborolane (4.53 g, 29.39 mmol, 4.98 mL) in DME (60 mL) was added Pd(dppf)$Cl_2$ (1.34 g, 1.84 mmol) and CsF (5.86 g, 38.57 mmol). The mixture was heated to 80° C. for 12 h under a nitrogen atmosphere. The reaction mixture was diluted with water (100 mL) and extracted with EA (100 mL×3). The combined organic layer was washed with brine (100 mL×2), dried over $Na_2SO_4$, filtered and concentrated in vacuo. The residue was purified (PM18) to afford compound 1.750 (3 g, 11.53 mmol, 62.8% yield) as a yellow oil.

$^1$H NMR (400 MHz, $CHCl_3$-d) δ: 7.81 (s, 1H), 7.49 (t, J=1.6 Hz, 1H), 7.22 (t, J=2.0 Hz, 1H), 6.72 (dd, J=17.6, 10.8 Hz, 1H), 5.86 (d, J=17.6 Hz, 1H), 5.38 (d, J=10.8 Hz, 1H), 4.43 (q, J=8.0 Hz, 2H), 3.95 (s, 3H) ppm.

(3-(2,2,2-Trifluoroethoxy)-5-vinylphenyl)methanol 1.751

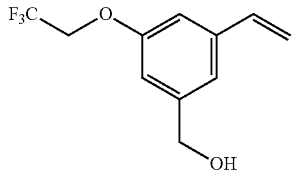 [SMILES: C=Cc1cc(CO)cc(OCC(F)(F)F)c1]

To a solution of LAH (481.34 mg, 12.68 mmol) in THF (40 mL) at 0° C. was added compound 1.750 (3.3 g, 12.68 mmol). The mixture was stirred at 0° C. for 2 h. The reaction was quenched by addition of aq. HCl (1 M) to pH=3 at 0° C. The mixture was diluted with water (100 mL) and extracted with EA (100 mL×3). The combined organic phase was washed with brine (100 mL), dried with $Na_2SO_4$, filtered and concentrated in vacuo. The residue was purified (PM7) to afford compound 1.751 (2.4 g, 10.34 mmol, 81.5% yield) as a yellow oil.

$^1$H NMR (400 MHz, $CHCl_3$-d) δ: 7.09 (s, 1H), 6.92 (s, 1H), 6.88 (s, 1H), 6.68 (dd, J=17.6, 10.8 Hz, 1H), 5.77 (d, J=17.6 Hz, 1H), 5.30 (d, J=10.8 Hz, 1H), 4.69 (s, 2H), 4.42-4.35 (m, 2H) ppm.

1-(Chloromethyl)-3-(2,2,2-trifluoroethoxy)-5-vinylbenzene 1.752

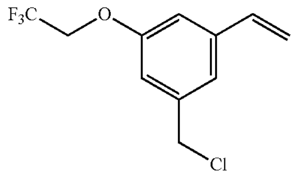 [SMILES: C=Cc1cc(CCl)cc(OCC(F)(F)F)c1]

To a solution of compound 1.751 (2.4 g, 10.34 mmol) in 1,4-dioxane (30 mL) was added $SOCl_2$ (3.69 g, 31.01 mmol, 2.25 mL) slowly at 0° C. The mixture was then heated to 70° C. and stirred for 2 h. The reaction mixture was quenched by slow addition of saturated aq. $NaHCO_3$ solution (10 mL), then diluted with water (100 mL) and extracted with EA (100 mL×3). The combined organic layer was washed with brine (100 mL×2), dried over $Na_2SO_4$, filtered and concentrated in vacuo to afford compound 1.752 (2.62 g) as a yellow oil, which was used directly without further purification.

2-(3-(2,2,2-Trifluoroethoxy)-5-vinylphenyl)acetonitrile 1.753

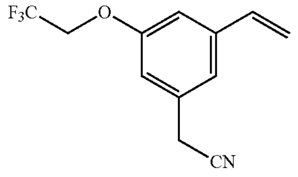 [SMILES: C=Cc1cc(CC#N)cc(OCC(F)(F)F)c1]

A mixture of compound 1.752 (2.62 g, 10.45 mmol), TMSCN (1.45 g, 14.63 mmol) and TBAF (13.59 mL, 1 M in THF) in ACN (80 mL) was stirred at 25° C. for 12 h. The mixture was concentrated in vacuo and purified (PM16) to afford compound 1.753 (1.5 g, 6.22 mmol, 59.5% yield) as a yellow oil.

$^1$H NMR (400 MHz, $CHCl_3$-d) δ: 7.06 (s, 1H), 6.95 (s, 1H), 6.83 (s, 1H), 6.67 (dd, J=17.6, 10.8 Hz, 1H), 5.78 (d, J=17.6 Hz, 1H), 5.35 (d, J=10.8 Hz, 1H), 4.38 (q, J=8.0 Hz, 2H), 3.74 (s, 2H) ppm.

2-(3-Formyl-5-(2,2,2-trifluoroethoxy)phenyl)acetonitrile 1.754

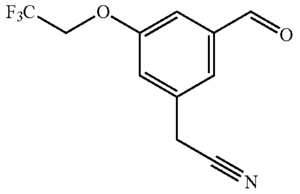 [SMILES: N#CCc1cc(C=O)cc(OCC(F)(F)F)c1]

Ozone was bubbled through a solution of compound 1.753 (1.5 g, 6.22 mmol) in DCM (15 mL) at −78° C. until the colour of mixture turned blue. After excess ozone was purged with nitrogen, DMS (5.02 g, 80.84 mmol) was added. The mixture was warmed to 25° C. and stirred for 12 h. The mixture was concentrated in vacuo and the residue was purified (PM7) to afford compound 1.754 (1 g, 4.11 mmol, 66.1% yield) as a yellow oil.

$^1$H NMR (400 MHz, $CHCl_3$-d) δ: 10.01 (s, 1H), 7.56 (s, 1H), 7.42 (d, J=1.2 Hz, 1H), 7.27 (t, J=1.6 Hz, 1H), 4.47 (q, J=8.0 Hz, 2H), 3.86 (s, 2H) ppm.

Synthesis of Intermediate 1.803

3-Bromo-5-(methoxymethyl)benzoic acid 1.797

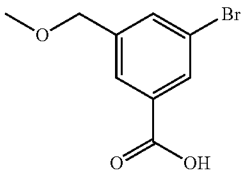

To a mixture of methyl 3-bromo-5-(bromomethyl)benzoate (900 mg, 2.92 mmol) in MeOH (10 mL) was added NaOMe (1.58 g, 29.22 mmol). The mixture was heated to 65° C. and stirred for 4 h. The mixture was cooled to 25° C. and concentrated in vacuo. The residue was diluted with water (2 mL) and adjusted to pH=5 with aq. HCl (1 M). The mixture was extracted with EA (20 mL×2) and the combined organic phase was washed with brine (20 mL), dried with anhydrous $Na_2SO_4$, filtered and concentrated in vacuo to afford compound 1.797 (700 mg) as a light yellow solid.

$^1$H NMR (400 MHz, MeOH-$d_4$) δ: 8.05 (s, 1H), 7.94 (s, 1H), 7.73 (s, 1H), 4.50 (s, 2H), 3.41 (s, 3H) ppm.

3-(Methoxymethyl)-5-vinylbenzoic acid 1.798

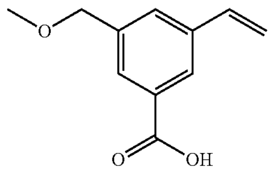

A mixture of compound 1.797 (0.7 g, 2.86 mmol), CsF (867.75 mg, 5.71 mmol), 4,4,5,5-tetramethyl-2-vinyl-1,3,2-dioxaborolane (659.87 mg, 4.28 mmol) and Pd(dppf)$Cl_2$·$CH_2Cl_2$ (116.63 mg, 142.82 μmol) in DME (10 mL) was stirred at 90° C. for 12 h under a nitrogen atmosphere. The mixture was filtered and concentrated and the residue was purified (PM7) to afford compound 1.798 (400 mg, 2.08 mmol, 72.8% yield) as a yellow oil.

$^1$H NMR (400 MHz, MeOH-$d_4$) δ: 8.00 (s, 1H), 7.89 (s, 1H), 7.64 (s, 1H), 6.80 (dd, J=17.6, 10.8 Hz, 1H), 5.87 (d, J=17.6 Hz, 1H), 5.33 (d, J=11.2 Hz, 1H), 4.51 (s, 2H), 3.41 (s, 3H) ppm.

Methyl 3-(methoxymethyl)-5-vinylbenzoate 1.799

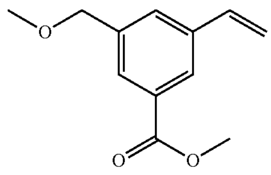

To a mixture of compound 1.798 (400 mg, 2.08 mmol) in MeOH (30 mL) was added $SOCl_2$ (1.24 g, 10.41 mmol) at 0° C. and then the mixture was heated to 60° C. and stirred for 0.5 h. The mixture was cooled to 25° C. and poured into sat. aqueous $NaHCO_3$ solution (50 mL). The aqueous phase was extracted with EA (50 mL×3) and the combined organic phase was washed with brine (50 mL), dried with anhydrous $Na_2SO_4$, filtered and concentrated in vacuo. The residue was purified (PM7) to afford compound 1.799 (380 mg, 1.84 mmol, 88.5% yield) as a yellow oil.

$^1$H NMR (400 MHz, MeOH-$d_4$) δ: 7.98 (s, 1H), 7.87 (s, 1H), 7.64 (s, 1H), 6.79 (dd, J=17.6, 11.2 Hz, 1H), 5.87 (d, J=17.6 Hz, 1H), 5.33 (d, J=11.2 Hz, 1H), 4.50 (s, 2H), 3.91 (s, 3H), 3.40 (s, 3H) ppm.

(3-(Methoxymethyl)-5-vinyl phenyl)methanol 1.800

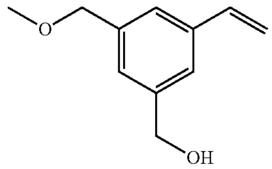

To a mixture of compound 1.799 (380 mg, 1.84 mmol) in THF (20 mL) was added LAH (83.91 mg, 2.21 mmol) in one portion under nitrogen protection at 0° C. The mixture was warmed to 25° C. and stirred for 0.5 h. The mixture was cooled to 0° C. and diluted with EA (10 mL). The mixture was quenched by addition of water (0.2 mL) followed by aqueous NaOH solution (10% wt, 0.2 mL) and water (0.6 mL). After stirring for 0.5 h, $Na_2SO_4$ (1 g) was added and stirring continued for 0.5 h. The resulting suspension was filtered and concentrated in vacuo. The residue was purified (PM2) to afford compound 1.800 (260 mg, 1.46 mmol, 79.2% yield) as a yellow oil.

$^1$H NMR (400 MHz, MeOH-$d_4$) δ: 7.36 (s, 1H), 7.31 (s, 1H), 7.23 (s, 1H), 6.75 (dd, J=17.6, 10.8 Hz, 1H), 5.80 (d, J=17.6 Hz, 1H), 5.24 (d, J=10.8 Hz, 1H), 4.60 (s, 2H), 4.46 (s, 2H), 3.38 (s, 3H) ppm.

1-(Chloromethyl)-3-(methoxymethyl)-5-vinylbenzene 1.801

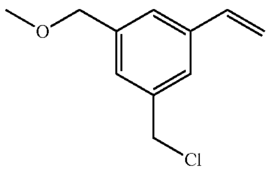

To a mixture of compound 1.800 (250 mg, 1.40 mmol) in 1,4-dioxane (20 mL) was added $SOCl_2$ (333.76 mg, 2.81 mmol) at 0° C. The mixture was then heated to 90° C. and stirred for 1 h. The mixture was concentrated in vacuo to afford compound 1.801 (250 mg), which was used without purification. $^1$H NMR (400 MHz, MeOH-$d_4$) δ: 7.41 (s, 1H), 7.36 (s, 1H), 7.29 (s, 1H), 6.74 (dd, J=17.6, 10.8 Hz, 1H), 5.82 (d, J=17.6 Hz, 1H), 5.27 (d, J=10.8 Hz, 1H), 4.64 (s, 2H), 4.46 (s, 2H), 3.39 (s, 3H) ppm.

2-(3-(Methoxymethyl)-5-vinylphenyl)acetonitrile 1.802

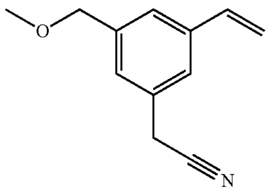

A mixture of compound 1.801 (250 mg, 1.27 mmol), TMSCN (189.16 mg, 1.91 mmol) and TBAF (2.54 mL, 1 M in THF) in ACN (50 mL) was stirred at 25° C. for 12 h. The mixture was concentrated in vacuo and the residue was purified (PM6) to afford compound 1.802 (100 mg, 534.08 μmol, 42.0% yield) as a yellow oil.

$^1$H NMR (400 MHz, MeOH-$d_4$): 7.37-7.35 (m, 2H), 7.24 (s, 1H), 6.74 (dd, J=17.6, 11.2 Hz, 1H), 5.83 (d, J=17.6 Hz, 1H), 5.29 (d, J=11.2 Hz, 1H), 4.46 (s, 2H), 3.89 (s, 2H), 3.39 (s, 3H) ppm.

2-(3-Formyl-5-(methoxymethyl)phenyl)acetonitrile 1.803

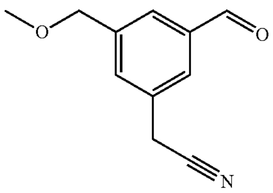

Ozone was bubbled into a solution of compound 1.802 (100 mg, 534.08 μmol) in DCM (20 mL) at −78° C. until the colour of reaction turned blue. After excessive ozone was purged with nitrogen, DMS (331.83 mg, 5.34 mmol) was added. The mixture was warmed to 20° C. and stirred for 12 h. The reaction mixture was concentrated in vacuo and the residue was purified (PM11) to afford compound 1.803 (80 mg, 422.81 μmol, 79.2% yield) as a colorless oil.

$^1$H NMR (400 MHz, MeOH-$d_4$) δ: 9.98 (s, 1H), 7.82-7.81 (m, 2H), 7.64 (s, 1H), 4.54 (s, 2H), 4.01 (s, 2H), 3.42 (s, 3H) ppm.

Synthesis of Intermediate 1.825

3-(Chloromethyl)-5-(trifluoromethoxy)benzaldehyde 1.824

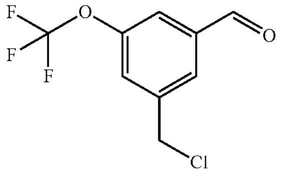 [SMILES: O=Cc1cc(CCl)cc(OC(F)(F)F)c1]

Ozone was bubbled to a solution of compound 1.502 (100 mg, 422.62 μmol) at −78° C. in DCM (5 mL) until the colour of the reaction turned blue. After excessive ozone was purged with nitrogen, DMS (0.44 g, 7.08 mmol) was added. The mixture was warmed to 20° C. and stirred for 12 h. The reaction mixture was concentrated in vacuo and the residue purified (PM7) to afford compound 1.824 (60 mg, 251.48 μmol, 59.5% yield) as a colorless oil.

$^1$H NMR (400 MHz, $CHCl_3$-d) δ: 10.02 (s, 1H), 7.86 (s, 1H), 7.69 (s, 1H), 7.53 (s, 1H), 4.65 (s, 2H) ppm.

3-((1H-imidazol-1-yl)methyl)-5-(trifluoromethoxy) benzaldehyde 1.825

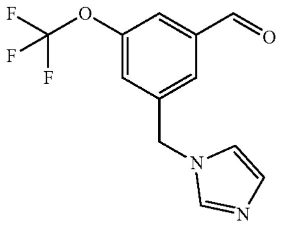 [SMILES: O=Cc1cc(Cn2ccnc2)cc(OC(F)(F)F)c1]

To a solution of compound 1.824 (500 mg, 2.10 mmol) in ACN (5 mL) was added imidazole (713.33 mg, 10.48 mmol). The reaction mixture was then heated to 60° C. and stirred for 12 h. The mixture was concentrated and the crude product was purified (PM151) to afford compound 1.825 (450 mg, 1.67 mmol, 79.5% yield) as a white solid.

LCMS (AM3): rt=0.830 min, (271.0 [M+H]$^+$), 100% purity.

Synthesis of Intermediate 1.826

3-(Furan-3-ylmethyl)-5-(trifluoromethoxy)benzaldehyde 1.826

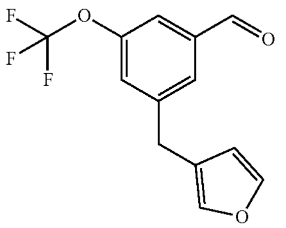 [SMILES: O=Cc1cc(Cc2ccoc2)cc(OC(F)(F)F)c1]

To a solution of compound 1.824 (500 mg, 2.10 mmol) in 1,4-dioxane (1.5 mL), $H_2O$ (0.15 mL) was added $K_2CO_3$ (579.28 mg, 4.19 mmol), furan-3-yl boronic acid (447.29 mg, 2.31 mmol) and Pd(dppf)$Cl_2$ (153.34 mg, 209.56 μmol). The reaction mixture was heated to 70° C. and stirred for 12 h under a nitrogen atmosphere The reaction mixture was filtered and the filtrate was concentrated in vacuo. The residue was purified (PM150) to afford compound 1.826 (360 mg, 1.24 mmol, 59.3% yield) as a yellow oil.

LCMS (AM3): rt=1.001 min, (271.2 $[M+H]^+$), 94.4% purity.

Synthesis of Intermediate 1.834

2-Chloro-5-(hydroxymethyl)benzaldehyde 1.834

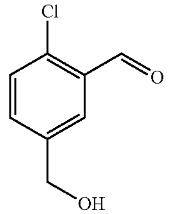 [SMILES: O=Cc1cc(CO)ccc1Cl]

To a solution of (3-bromo-4-chloro-phenyl)methanol (1 g, 4.52 mmol) in THF (10 mL) was added n-BuLi (3.79 mL, 2.5 M) at −78° C. under a nitrogen atmosphere. After stirring for 0.5 h, DMF (330.01 mg, 4.52 mmol) was added and the mixture was stirred at −78° C. for 0.5 h. The reaction mixture was diluted with water (200 mL) and extracted with EA (100 mL×3). The combined organic layer was washed with brine (100 mL×2), dried over $Na_2SO_4$, filtered and concentrated in vacuo. The crude product was purified by reverse-phase HPLC (AM46) to afford compound 1.834 (200 mg, 1.17 mmol, 25.9% yield) as a white solid.

LCMS (AM3): rt=0.570 min, (171.0 $[M+H]^+$), 39.0% purity

Synthesis of Intermediate 1.64

(5-bromo-2-cyclobutoxyphenyl)methanol, 1.62

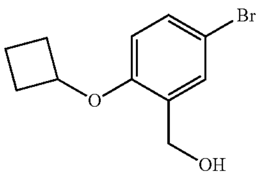 [SMILES: OCc1cc(Br)ccc1OC1CCC1]

To a mixture of 4-bromo-2-(hydroxymethyl)phenol (2.0 g, 9.95 mmol) and bromocyclobutane (2.66 g, 19.70 mmol) in DMF (10 mL) was added potassium carbonate (3.4 g, 24.63 mmol) under nitrogen protection at ambient temperature. The mixture was then heated to 80° C. and stirred for 12 h. The reaction mixture was poured into water (100 mL) and the aqueous phase was extracted with EA (50 mL×2). The combined organic phases were washed with brine (50 mL), dried over anhydrous $Na_2SO_4$ and concentrated in vacuo. The residue was purified (PM4) to afford compound 1.62 (1.6 g, 6.22 mmol, 63.2% yield) as a white solid.

$^1$H NMR (400 MHz, MeOD) δ: 7.49 (d, J=2.8 Hz, 1H), 7.28 (dd, J=2.8, 8.8 Hz, 1H), 6.67 (d, J=8.8 Hz, 1H), 4.71-4.62 (m, 1H), 4.59 (s, 2H), 2.52-2.39 (m, 2H), 2.18-2.05 (m, 2H), 1.83-1.67 (m, 2H) ppm.

(2-cyclobutoxy-5-vinylphenyl)methanol, 1.63

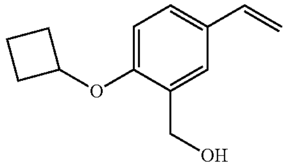

To a mixture of tributyl(vinyl)stannane (1.85 g, 5.83 mmol) and compound 1.62 (1.5 g, 5.83 mmol) in toluene (50 mL) was added tetrakis(triphenylphosphine) palladium (337.06 mg, 291.69 μmol) under nitrogen protection at ambient temperature. The mixture was then heated to 100° C. and stirred for 12 h. The mixture was cooled to room temperature and then poured into saturated aqueous KF solution (20 mL). The mixture was stirred for 30 min and then extracted with EA (50 mL×4). The combined organic phases were washed with brine (50 mL), dried with anhydrous $Na_2SO_4$, filtered and concentrated in vacuo. The residue was purified (PM11) to afford compound 1.63 (600 mg, 2.94 mmol, 50.4% yield) as a colorless oil.

$^1$H NMR (400 MHz, MeOH-$d_4$) δ: 7.48 (d, J=2.4 Hz, 1H), 7.23 (dd, J=2.4, 8.4 Hz, 1H), 6.71-6.62 (m, 2H), 5.62 (dd, J=1.2, 17.6 Hz, 1H), 5.07 (dd, J=1.2, 10.8 Hz, 1H), 4.71-4.64 (m, 1H), 4.62 (s, 2H), 2.50-2.38 (m, 2H), 2.21-2.07 (m, 2H), 1.86-1.68 (m, 2H) ppm.

4-cyclobutoxy-3-(hydroxymethyl)benzaldehyde, 1.64

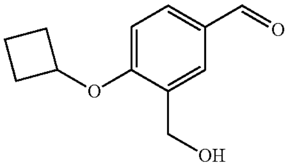 [SMILES: O=Cc1ccc(OC2CCC2)c(CO)c1]

Ozone was bubbled into a solution of compound 1.63 (600 mg, 2.94 mmol) in DCM (30 mL) at −78° C. until the reaction mixture turned blue, then the reaction mixture was warmed to 0° C. and DMS (1.82 g, 29.37 mmol) was added. The reaction mixture was warmed to 25° C. and stirred for 12 h. The reaction mixture was poured into water (50 mL) and the aqueous solution was extracted with EA (50 mL×2). The combined organic phase was washed with brine (50 mL), dried over anhydrous $Na_2SO_4$ and concentrated in vacuo. The residue was purified (PM11) to afford compound 1.64 (250 mg, 1.21 mmol, 41.3% yield) as a yellow oil.

$^{1}H$ NMR (400 MHz, MeOH-$d_4$) b: 9.83 (s, 1H), 7.98 (d, J=2.4 Hz, 1H), 7.79 (dd, J=2.4, 8.4 Hz, 1H), 6.95 (d, J=8.4 Hz, 1H), 4.74-4.68 (m, 1H), 4.67 (s, 2H), 2.54-2.46 (m, 2H), 2.22-2.10 (m, 2H), 1.92-1.70 (m, 2H) ppm.

Synthesis of Intermediate 1.155

Methyl 5-((2-(4-((3-chloro-4-(trifluoromethoxy) benzyl)amino)butoxy)ethyl)amino)benzo [c][2,6] naphthyridine-8-carboxylate, 1.155

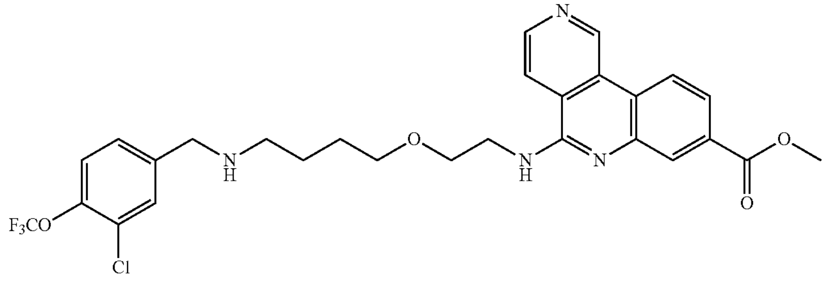 [SMILES: COC(=O)c1ccc2c(c1)nc(NCCOCCCCNCc1ccc(OC(F)(F)F)c(Cl)c1)c1ccncc12]

To a mixture of compound 1.154 (180 mg, 444.57 μmol) and sodium acetate (109.41 mg, 1.33 mmol) in MeOH (15 mL) was added 3-chloro-4-(trifluoromethoxy)benzaldehyde (90 mg, 400.78 μmol) at 20° C. The mixture was stirred at 20° C. for 2 h, then sodium triacetoxyborohydride (450.00 mg, 2.12 mmol) was added. The mixture was stirred at 20° C. for 12 h. The mixture was filtered and the filtrate was concentrated in vacuo. The residue was purified (PM33) to afford compound 1.155 (103 mg, 178.51 μmol, 36.5% yield) as a yellow oil.

LCMS (AM3): rt=0.812 min, (577.1 $[M+H]^+$), 29% purity.

Synthesis of Intermediate 1.573

5-((2-(4-((3-Chloro-5-cyanobenzyl)amino)butoxy) ethyl)amino)benzo[c][2,6]naphthyridine-8-carboxamide 1.573

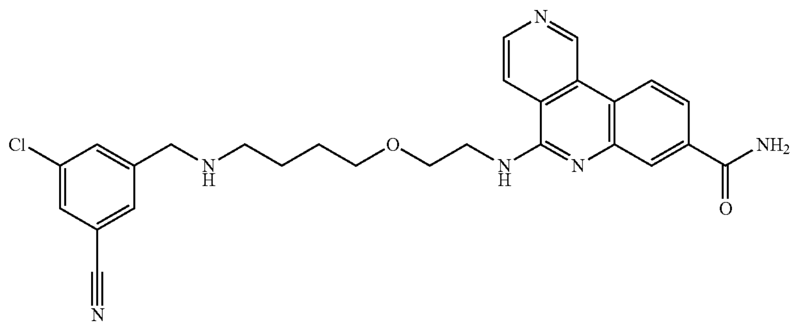 [SMILES: N#Cc1cc(Cl)cc(CNCCCCOCCNc2nc3cc(C(N)=O)ccc3c3cnccc23)c1]

A mixture of Intermediate E (80 mg, 205.19 μmol), sodium acetate (67.33 mg, 820.76 μmol) and 3-chloro-5-formylbenzonitrile (33.97 mg, 205.19 μmol) in MeOH (3 mL) was stirred at 20° C. for 12.5 h, then sodium triacetoxyborohydride (130.47 mg, 615.57 μmol) was added. The reaction mixture was stirred at 20° C. for another 3 h. The reaction mixture was filtered and the filtrate was concentrated in vacuo. The residue was purified (PM57) to afford compound 1.573 (60 mg, 119.29 μmol, 58.1% yield) as a white solid.

LCMS (AM7): rt=0.865 min, (503.1 $[M+H]^+$), 66.1% purity.

Synthesis of Intermediate 1.399 tert-Butyl 3-(4-(((benzyloxy)carbonyl)amino)butoxy)azetidine-1-carboxylate 1.395

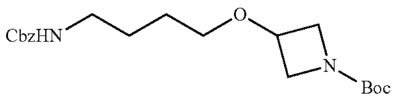 [SMILES: CC(C)(C)OC(=O)N1CC(OCCCCNC(=O)OCc2ccccc2)C1]

A mixture of benzyl N-(4-bromobutyl)carbamate (3.30 g, 11.55 mmol), tert-butyl 3-hydroxyazetidine-1-carboxylate (1 g, 5.77 mmol), NaOH (2.31 g, 57.73 mmol) and TBAl (0.11 g, 298 mmol) in $H_2O$ (5 mL) was stirred at room temperature for 20 h. The reaction mixture was diluted with water (50 mL) and extracted with MTBE (20 mL×2). The combined organic phase was washed with brine (40 mL), dried over anhydrous $Na_2SO_4$, filtered and concentrated in vacuo. The residue was purified (PM47) to afford compound 1.395 (1.1 g, 50.3% yield) as light yellow oil.

$^1$H NMR (400 MHz, $CHCl_3$-d) δ: 7.37-7.28 (m, 5H), 5.10 (s, 2H), 4.86 (br s, 1H), 4.20-4.14 (m, 1H), 4.07-4.03 (m, 2H), 3.82-3.78 (m, 2H), 3.41-3.30 (m, 2H), 3.26-3.17 (m, 2H), 1.65-1.55 (m, 4H), 1.44 (s, 9H) ppm.

Benzyl (4-(azetidin-3-yloxy)butyl)carbamate 1.396

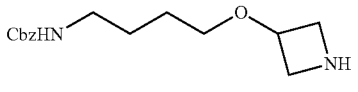

A mixture of compound 1.395 (1.1 g, 2.91 mmol) and TFA (135.06 mmol, 10 mL) in DCM (10 mL) was stirred at room temperature for 1 h. The reaction mixture was concentrated in vacuo to afford compound 1.396 (1.5 g, TFA salt) as a brown oil, which was used directly without further purification.

LCMS (AM3): rt=0.334 min, (279.2 $[M+H]^+$), 71% purity.

Methyl 5-(3-(4-(((benzyloxy)carbonyl)amino)butoxy)azetidin-1-yl)benzo[c][2,6]naphthyridine-8-carboxylate 1.397

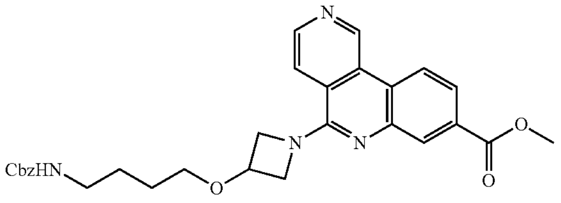 [SMILES: COC(=O)c1ccc2c(c1)nc(N1CC(OCCCCNC(=O)OCc3ccccc3)C1)c1ccncc12]

A mixture of compound 1.396 (0.4 g, 1.44 mmol), compound 1.1 (0.3 g, 1.10 mmol) and DIPEA (0.8 mL, 4.59 mmol) in DMSO (8 mL) was stirred at 90° C. for 16 h, a brown solid precipitated. The precipitate was collected by filtration and purified (PM47) to afford compound 1.397 (0.4 g, 70.7% yield) as a brown solid.

LCMS (AM3): rt=0.875 min, (515.3 $[M+H]^+$), 100% purity.

Methyl 5-(3-(4-aminobutoxy)azetidin-1-yl)benzo[c][2,6]naphthyridine-8-carboxylate 1.398

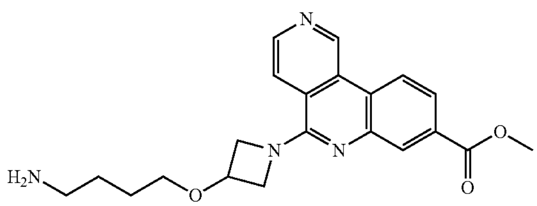 [SMILES: COC(=O)c1ccc2c(c1)nc(N1CC(OCCCCN)C1)c1ccncc12]

A mixture of compound 1.397 (0.4 g, 0.777 mmol), palladium on carbon (0.05 g, 10% wt Pd/C) and ammonium hydroxide (0.5 mL, 3.25 mmol, 25%) in MeOH (20 mL) was hydrogenated under $H_2$ atmosphere (1 atm) at room temperature for 16 h. The reaction mixture was heated to 40° C. and stirred for 5 h. The catalyst was removed by filtration and the filtrate was concentrated in vacuo to afford compound 1.398 (0.29 g, 98.1% yield) as a yellow solid, which was used directly without further purification LCMS (AM3): rt=0.690 min, (381.2 $[M+H]^+$), 94.2% purity.

Methyl 5-(3-(4-((3-chloro-4-(trifluoromethoxy)benzyl)amino)butoxy)azetidin-1-yl)benzo[c][2,6]naphthyridine-8-carboxylate 1.399

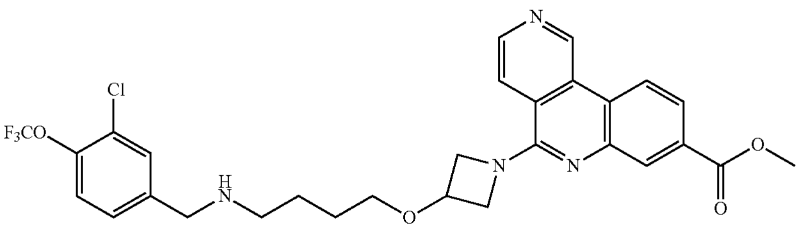 [SMILES: COC(=O)c1ccc2c(c1)nc(N1CC(OCCCCNCc3ccc(OC(F)(F)F)c(Cl)c3)C1)c1ccncc12]

A mixture of 3-chloro-4-(trifluoromethoxy)benzaldehyde (0.17 g, 0.757 mmol) and compound 1.398 (0.29 g, 0.762 mmol) in MeOH (10 mL) was stirred at room temperature for 16 h, then sodium triacetoxyborohydride (0.7 g, 3.30 mmol) was added. The reaction mixture was then stirred for 1 h. The reaction mixture was concentrated in vacuo and the residue was purified (PM67) to afford compound 1.399 (0.17 g, 38.1% yield) as a yellow solid.

LCMS (AM3): rt=0.815 min, (589.2 $[M+H]^+$), 100% purity.

Synthesis of Intermediate 1.625

Tert-butyl N-[(1S)-2-[4-(benzyloxycarbonylamino)butoxy]-1-methyl-ethyl]carbamate 1.621

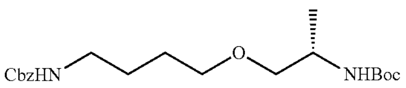 [SMILES: C[C@@H](COCCCCNC(=O)OCc1ccccc1)NC(=O)OC(C)(C)C]

A mixture of tert-butyl N-[(1S)-2-hydroxy-1-methyl-ethyl]carbamate (2 g, 11.41 mmol), benzyl (4-bromobutyl) carbamate (6.6 g, 23.06 mmol), NaOH (4.57 g, 114.14 mmol) and TBAI (0.21 g, 0.569 mmol) in $H_2O$ (11 mL) was stirred at room temperature for 18 h. The reaction mixture was added to water (80 mL) and the resulting mixture was extracted with EA (20 mL×3). The combined organic phase was washed with brine (40 mL), dried over anhydrous $Na_2SO_4$, filtered and concentrated in vacuo. The residue was purified (PM47) to afford compound 1.621 (0.93 g, 1.83 mmol, 16.1% yield) as a colorless oil.

LCMS (AM3): rt=0.968 min, (403.2 $[M+Na]^+$), 75.3% purity.

(S)-Benzyl (4-(2-aminopropoxy)butyl)carbamate 1.622

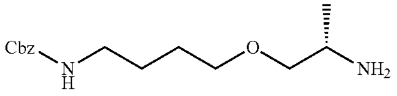 [SMILES: C[C@H](N)COCCCCNC(=O)OCc1ccccc1]

A mixture of compound 1.621 (820 mg, 2.16 mmol) in a solution of HCl in 1,4-dioxane (20 mL, 4 M) was stirred at room temperature for 1 h. The reaction mixture was concentrated in vacuo and the residue was purified (PM123) to afford compound 1.622 (460 mg, 1.64 mmol, 76.1% yield, HCl salt) as a colorless oil.

LCMS (AM3): rt=0.658 min, (281.1 $[M+H]^+$), 100% purity.

(S)-Methyl 5-((1-(4-(((benzyloxy)carbonyl)amino)butoxy)propan-2-yl)amino)benzo[c]naphthyridine-8-carboxylate 1.623

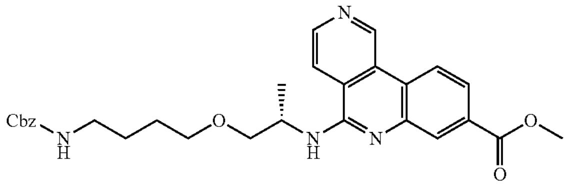 [SMILES: COC(=O)c1ccc2c(c1)nc(N[C@@H](C)COCCCCNC(=O)OCc1ccccc1)c1ccncc12]

A mixture of compound 1.622 (440 mg, 1.57 mmol, HCl salt), compound 1.1 (480.36 mg, 1.73 mmol) and DIPEA (608.50 mg, 4.71 mmol) in DMSO (10 mL) was stirred at 80° C. for 12 h. The reaction mixture was filtered and the filtrate was purified (PM122) to afford compound 1.623 (400 mg, 723.26 μmol, 46.1% yield) as a yellow gum.

LCMS (AM3): rt=0.849 min, (517.4 $[M+H]^+$), 98.9% purity.

(S)-Methyl 5-((1-(4-aminobutoxy)propan-2-yl)amino)benzo[c][2,6]naphthyridine-8-carboxylate 1.624

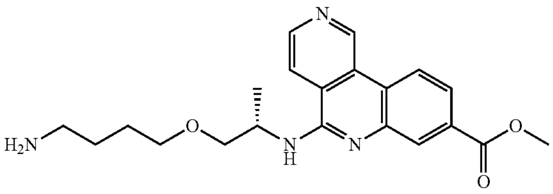 [SMILES: COC(=O)c1ccc2c(c1)nc(N[C@@H](C)COCCCCN)c1ccncc12]

To a mixture of compound 1.623 (400 mg, 723.26 μmol, HCl salt) and aq. ammonium hydroxide solution (1.00 mL, 25%) in MeOH (10 mL) was added 10% palladium on charcoal catalyst (0.2 g) under nitrogen protection. The resulting suspension was hydrogenated under one atmosphere $H_2$ at room temperature for 1 h. The catalyst was removed by filtration and the filtrate was concentrated in vacuo to afford compound 1.624 (170 mg, 61.5% yield) as a yellow solid, which was used directly without further purification.

LCMS (AM3): rt=0.599 min, (383.3 [M+H]$^+$), 88.7% purity.

(S)-Methyl 5-((1-(4-((3-chloro-4-(trifluoromethoxy)benzyl)amino)butoxy)propan-2-yl)amino)benzo[c][2,6]naphthyridine-8-carboxylate 1.625

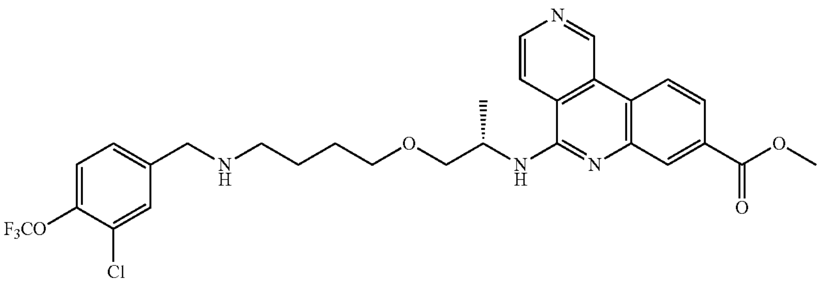 [SMILES: COC(=O)c1ccc2c(c1)nc(N[C@@H](C)COCCCCNCc1ccc(OC(F)(F)F)c(Cl)c1)c1ccncc12]

A mixture of 3-chloro-4-(trifluoromethoxy)benzaldehyde (60 mg, 267.18 μmol), compound 1.624 (120 mg, 241.70 μmol, TFA salt) and DIPEA (93.72 mg, 725.11 μmol) in MeOH (4 mL) was stirred at room temperature for 12 h, then sodium cyanoborohydride (45 mg, 716.08 μmol) was added. The reaction mixture was then stirred at room temperature for another 1 h. The reaction mixture was filtered and the filtrate was concentrated in vacuo. The residue was purified (PM91) to afford compound 1.625 (50 mg, 29.3% yield, TFA salt) as a yellow solid.

LCMS (AM3): rt=0.852 min, (591.2 [M+H]$^+$), 98.5% purity.

Synthesis of Intermediate 1.609

Tert-butyl N-[(1R)-2-[4-(benzyloxycarbonylamino)butoxy]-1-methyl-ethyl]carbamate 1.605

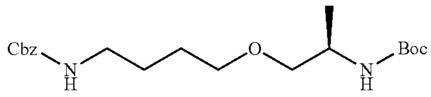 [SMILES: C[C@H](COCCCCNC(=O)OCc1ccccc1)NC(=O)OC(C)(C)C]

A mixture of tert-butyl N-[(1R)-2-hydroxy-1-methyl-ethyl]carbamate (2 g, 11.41 mmol), benzyl (4-bromobutyl) carbamate (6.6 g, 23.06 mmol) (Journal of the American Chemical Society, 2004, 126 (14), 4543-4549), NaOH (4.57 g, 114.14 mmol) and TBAl (0.21 g, 0.569 mmol) in $H_2O$ (11 mL) was stirred at room temperature for 16 h. The reaction mixture was diluted with water (80 mL) and the resulting mixture was extracted with EA (20 mL×3). The combined organic phase was washed with brine (40 mL), dried over anhydrous $Na_2SO_4$, filtered and concentrated in vacuo. The residue was purified (PM47) to afford compound 1.605 (0.86 g) as a colorless oil.

LCMS (AM3): rt=0.977 min, (281.2 [M-tBu$CO_2$+2H]$^+$), 49.7% purity.

(R)-benzyl (4-(2-aminopropoxy)butyl)carbamate 1.606

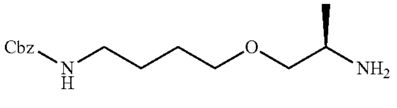 [SMILES: C[C@@H](N)COCCCCNC(=O)OCc1ccccc1]

A mixture of compound 1.605 (0.86 g, 2.26 mmol) in a solution of HCl in 1,4-dioxane (10 mL, 4 M) was stirred at room temperature for 1 h. The reaction mixture was concentrated in vacuo and the residue was purified (PM120) to afford compound 1.606 (0.41 g, 57.3% yield, HCl salt) as a colorless oil LCMS (AM3): rt=0.719 min, (281.2 [M+H]$^+$), 100% purity.

(R)-methyl 5-((1-(4-(((benzyloxy)carbonyl)amino)butoxy)propan-2-yl)amino)benzo[c]naphthyridine-8-carboxylate 1.607

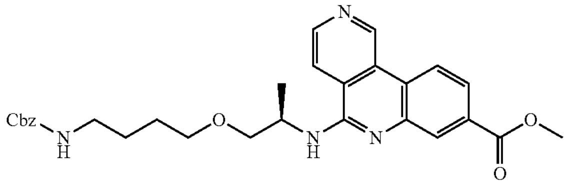 [SMILES: COC(=O)c1ccc2c(c1)nc(N[C@H](C)COCCCCNC(=O)OCc1ccccc1)c1ccncc12]

A mixture of compound 1.606 (0.41 g, 1.29 mmol, HCl salt), compound 1.1 (0.36 g, 1.32 mmol) and DIPEA (4.02 mmol, 0.7 mL) in DMSO (4 mL) was stirred at 90° C. for 18 h. The reaction mixture was filtered and the filtrate was concentrated in vacuo and purified (PM22) to afford compound 1.607 (0.5 g, 67.8% yield, HCl salt) as a yellow solid.

LCMS (AM3): rt=0.878 min, (517.3 [M+H]$^+$), 97.2% purity.

(R)-methyl 5-((1-(4-aminobutoxy)propan-2-yl)amino)benzo[c][2,6]naphthyridine-8-carboxylate 1.608

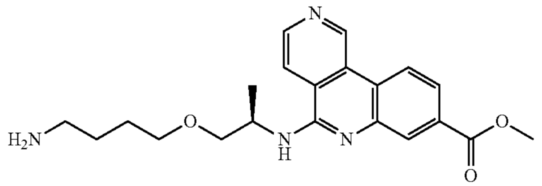 [SMILES: COC(=O)c1ccc2c(c1)nc(N[C@H](C)COCCCCN)c1ccncc12]

A mixture of compound 1.607 (0.5 g, 0.904 mmol, HCl salt), 10% palladium on carbon catalyst (0.1 g) and aqueous ammonia hydroxide solution (1.39 mL, 25%) in MeOH (20 mL) was hydrogenated under one atmosphere $H_2$ pressure at room temperature for 2 h. The catalyst was removed by filtration and the filtrate was concentrated in vacuo to afford compound 1.608 (0.34 g, 98.3% yield) as a yellow solid, which was used directly without purification.

LCMS (AM3): rt=0.703 min, (383.3 $[M+H]^+$), 90.9% purity.

(R)-methyl 5-((1-(4-((3-chloro-4-(trifluoromethoxy)benzyl)amino)butoxy)propan-2-yl)amino)benzo[c][2,6]naphthyridine-8-carboxylate 1.609

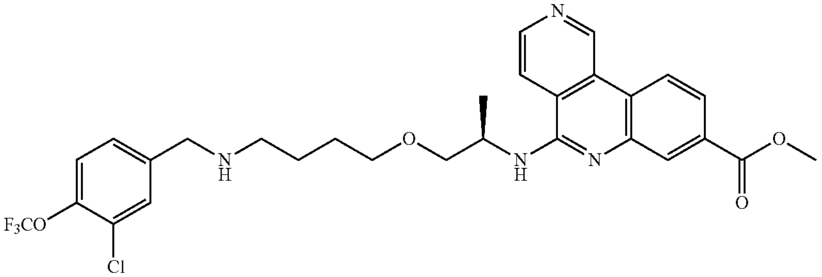 [SMILES: COC(=O)c1ccc2c(c1)nc(N[C@H](C)COCCCCNCc1ccc(OC(F)(F)F)c(Cl)c1)c1ccncc12]

A mixture of 3-chloro-4-(trifluoromethoxy)benzaldehyde (0.2 g, 0.891 mmol) and compound 1.608 (0.34 g, 0.889 mmol) in MeOH (4 mL) was stirred at room temperature for 1 h, then sodium cyanoborohydride (0.22 g, 3.50 mmol) was added. The reaction mixture was then stirred at room temperature for additional 1 h. The reaction mixture was filtered and the filtrate was concentrated in vacuo. The residue was (PM119) to afford compound 1.609 (0.15 g, 17.89% yield, TFA salt) as a yellow solid.

LCMS (AM3): rt=0.838 min, (591.2 $[M+H]^+$), 98.9% purity.

Synthesis of Intermediates 1.837 and 1.838

Intermediates 1.837 and 1.838 have been assigned the following stereochemical nomenclature but could be defined as either enantiomer as definitive stereochemistry has not been fully elucidated by analytical techniques.

(R)-2-(3-chloro-5-vinylphenyl)propanenitrile 1.835 and (S)-2-(3-chloro-5-vinylphenyl)propanenitrile 1.836

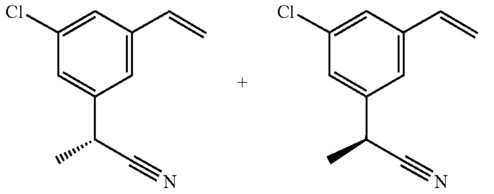

To a solution of compound 1.365 (1.15 g, 6.47 mmol) in THF (15 mL) was added NaHMDS (6.47 mL, 1 M) at −78° C. After stirring for 1 h, MeI (918.93 mg, 6.47 mmol) was added slowly and the mixture was stirred at −78° C. for 2 h. The mixture was concentrated in vacuo to give a residue that was purified (PM47) to afford 430 mg of racemic product, which was separated by SFC (column: DAICEL CHIRALCEL OD 250 mm×30 mm×10 μm; mobile phase: [0.1% ammonium hydroxide-IPA]; B %: 15%-15%, 2.4 min; 35 min) to afford compound 1.835 (160 mg, 826.48 μmol, Peak 1) and compound 1.836 (130 mg, 671.51 μmol, Peak 2) as yellow oils.

$^1$H NMR (400 MHz, $CHCl_3$-d) δ: 7.37 (t, J=1.6 Hz, 1H), 7.26 (d, J=1.2 Hz, 1H), 7.23 (t, J=1.2 Hz, 1H), 6.66 (dd, J=17.2, 10.8 Hz 1H), 5.81 (d, J=17.2 Hz, 1H), 5.38 (d, J=10.8 Hz, 1H), 3.91-3.86 (q, 1H), 1.66 (d, J=7.2 Hz, 3H) ppm.

(R)-2-(3-chloro-5-formylphenyl)propanenitrile 1.837

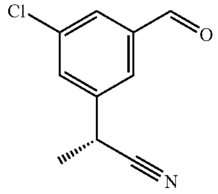

Ozone was bubbled into a solution of compound 1.835 (160 mg, 834.83 μmol) in DCM (10 mL) at −78° C. until the colour of the reaction mixture turned blue. After excessive ozone was purged with nitrogen, DMS (674.28 mg, 10.85 mmol) was added. The mixture was warmed to 25° C. and stirred for 12 h. The mixture was concentrated in vacuo and the residue was purified (PM7) to afford compound 1.837 (70 mg, 361.52 umol, 43.3% yield) as a yellow oil.

$^1$H NMR (400 MHz, $CHCl_3$-d) δ: 10.00 (s, 1H), 7.84 (t, J=1.6 Hz, 1H), 7.78 (d, J=1.2 Hz, 1H), 7.65 (t, J=1.6 Hz, 1H), 4.00 (q, J=7.2 Hz, 1H), 1.71 (d, J=7.2 Hz, 3H) ppm.

(S)-2-(3-chloro-5-formylphenyl)propanenitrile 1.838

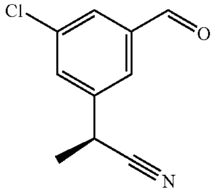

Ozone was bubbled into a solution of compound 1.836 (130 mg, 678.30 μmol) in DCM (15 mL) at −78° C. until the colour of the reaction mixture turned blue. After excessive ozone was purged with nitrogen, DMS (547.85 mg, 8.82 mmol) was added. The mixture was warmed to 25° C. and stirred for 12 h. The mixture was concentrated in vacuo and the residue was purified (PM7) to afford compound 1.838 (80 mg, 361.52 μmol, 43.3% yield) as a yellow oil.

$^1$H NMR (400 MHz, $CHCl_3$-d) δ: 10.00 (s, 1H), 7.84 (t, J=1.6 Hz, 1H), 7.78 (s, 1H), 7.64 (t, J=1.6 Hz, 1H), 4.00 (q, J=7.2 Hz, 1H), 1.71 (d, J=7.6 Hz, 3H) ppm.

Synthesis of Intermediate 1.734

Tert-butyl N-[2-[4-(benzyloxycarbonylamino)butoxy]-1,1-dimethyl-ethyl]carbamate 1.730

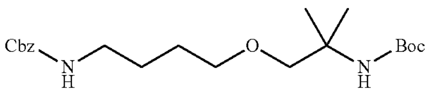 [SMILES: CC(C)(COCCCCNC(=O)OCc1ccccc1)NC(=O)OC(C)(C)C]

A mixture of benzyl (4-bromobutyl)carbamate (12 g, 41.93 mmol), tert-butyl (1-hydroxy-2-methylpropan-2-yl) carbamate (4 g, 21.14 mmol), NaOH (8.45 g, 211.36 mmol) and TBAl (0.4 g, 1.08 mmol) in $H_2O$ (20 mL) was stirred at room temperature for 14 h. Water (100 mL) was added and the resulting mixture was extracted with MTBE (30 mL×3). The combined organic phase was washed with brine (90 mL), dried over $Na_2SO_4$, filtered and concentrated in vacuo. The residue was purified (PM22) to afford compound 1.730 (0.73 g, 8.2% yield) as a colourless oil.

LCMS (AM3): rt=1.027 min, (417.4 [M+Na]$^+$), 94.3% purity.

Benzyl (4-(2-amino-2-methylpropoxy)butyl)carbamate 1.731

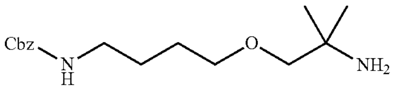 [SMILES: CC(C)(N)COCCCCNC(=O)OCc1ccccc1]

A mixture of compound 1.730 (730 mg, 1.85 mmol) and TFA (5 mL, 67.53 mmol) in DCM (5 mL) was stirred at room temperature for 0.5 h. The reaction mixture was concentrated in vacuo and the residue was purified (PM47) to afford compound 1.731 (0.69 g, 91.3% yield, TFA salt) as colourless oil.

LCMS (AM3): rt=0.660 min, (295.3 [M+H]$^+$), 98.9% purity.

Methyl 5-((1-(4-(((benzyloxy)carbonyl)amino)butoxy)-2-methylpropan-2-yl)amino)benzo[c][2,6]naphthyridine-8-carboxylate 1.732

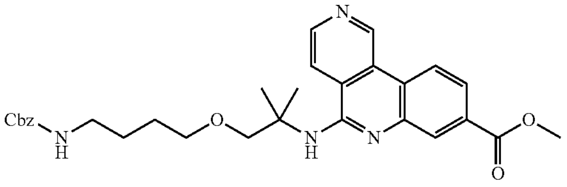 [SMILES: COC(=O)c1ccc2c(c1)nc(NC(C)(C)COCCCCNC(=O)OCc1ccccc1)c1ccncc12]

A mixture of compound 1.731 (690 mg, 1.69 mmol, TFA salt), compound 1.1 (550 mg, 2.02 mmol) and DIPEA (1 mL, 5.74 mmol) in DMSO (9 mL) was stirred at 120° C. for 20 h. The reaction mixture was filtered and the filtrate was purified (PM22) to afford compound 1.732 (250 mg, 20.9% yield) as a yellow solid.

LCMS (AM3): rt=0.915 min, (531.5 [M+H]$^+$), 75.8% purity.

Methyl 5-((1-(4-aminobutoxy)-2-methylpropan-2-yl)amino)benzo[c][2,6]naphthyridine-8-carboxylate 1.733

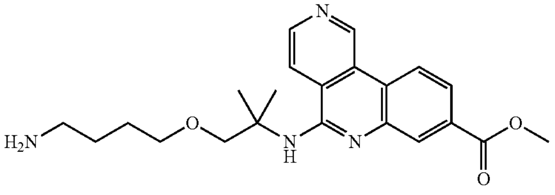 [SMILES: COC(=O)c1ccc2c(c1)nc(NC(C)(C)COCCCCN)c1ccncc12]

A mixture of compound 1.732 (250 mg, 0.47 mmol), 10% palladium on carbon (0.1 g) and aq. ammonium hydroxide solution (0.3 mL, 1.95 mmol, 25% wt.) in MeOH (10 mL) was hydrogenated under 1 atmosphere $H_2$ at room temperature for 16 h. The catalyst was removed by filtration and the filtrate was concentrated in vacuo. The residue was purified (PM47) to afford compound 1.733 (90 mg, 34.1% yield, TFA salt) as a yellow oil.

LCMS (AM3): rt=0.726 min, (397.0 $[M+H]^+$), 91.2% purity.

Methyl 5-((1-(4-((3-chloro-4-(trifluoromethoxy) benzyl)amino)butoxy)-2-methylpropan-2-yl)amino) benzo[c][2,6]naphthyridine-8-carboxylate 1.734

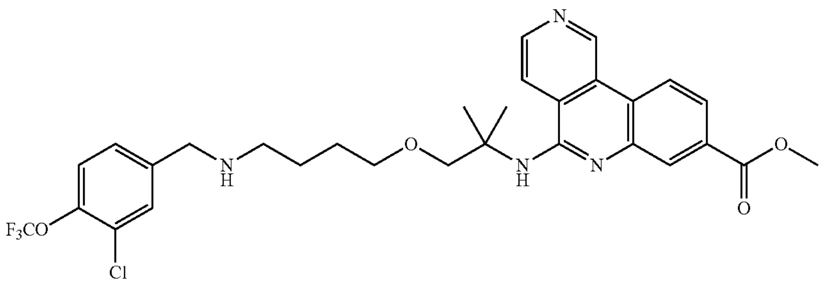 [SMILES: COC(=O)c1ccc2c(c1)nc(NC(C)(C)COCCCCNCc1ccc(OC(F)(F)F)c(Cl)c1)c1ccncc12]

A mixture of 3-chloro-4-(trifluoromethoxy)benzaldehyde (44 mg, 0.20 mmol), compound 1.733 (90 mg, 0.18 mmol, TFA salt) and DIPEA (0.1 mL, 0.54 mmol) in MeOH (2 mL) was stirred at room temperature for 15 h, then sodium triacetoxyborohydride (112 mg, 0.53 mmol) was added. The reaction mixture was then stirred at room temperature for 1 h. The reaction mixture was concentrated in vacuo and the residue was purified (PM144) to afford compound 1.734 (25 mg, 21.9% yield, FA salt) as a white solid.

LCMS (AM3): rt=0.871 min, (605.4 $[M+H]^+$), 94.6% purity.

Synthesis of Intermediate 1.689

Methyl 3-bromo-5-vinylbenzoate 1.683

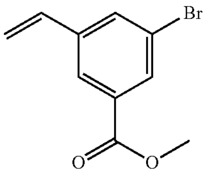

To a solution of methyl 3-bromo-5-iodo-benzoate (25.7 g, 75.38 mmol) and 4,4,5,5-tetramethyl-2-vinyl-1,3,2-dioxaborolane (11.73 g, 76.13 mmol) in DME (300 mL) was added Pd(dppf)$Cl_2$ (5.52 g, 7.54 mmol) and CsF (22.90 g, 150.76 mmol). The mixture was heated to 80° C. and stirred for 12 h under a nitrogen atmosphere. The mixture was poured into water (300 mL) and extracted with EA (200 mL×2). The combined organic phase was washed with brine (300 mL×3), dried with anhydrous $Na_2SO_4$, filtered and concentrated in vacuo. The residue was purified (PM1) to afford compound 1.683 (13.5 g, 56.00 mmol, 74.3% yield) as a light yellow oil.

$^1$H NMR (400 MHz, $CHCl_3$-d) δ: 8.05 (s, 1H), 8.00 (s, 1H), 7.72 (s, 1H), 6.66 (dd, J=17.6, 10.8 Hz, 1H), 5.84 (d, J=17.6 Hz, 1H), 5.39 (d, J=10.8 Hz, 1H), 3.94 (s, 3H) ppm.

Methyl 3-bromo-5-ethylbenzoate 1.684

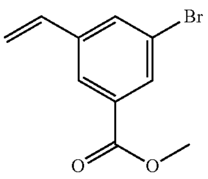

To a solution of compound 1.683 (2.5 g, 10.37 mmol) in MeOH (50 mL) was added $PtO_2$ (588.70 mg, 2.59 mmol) under a nitrogen atmosphere. The suspension was degassed under vacuum and purged with hydrogen three times. The mixture was stirred under 15 psi pressure of $H_2$ at 25° C. for 0.5 h. The catalyst was removed by filtration and the filtrate was concentrated to afford compound 1.684 (2.3 g) as a yellow oil, which was used directly without purification.

LCMS (AM3): rt=0.982 min, (243.0 $[M+H]^+$), 86.4% purity.

Methyl 3-ethyl-5-vinylbenzoate 1.685

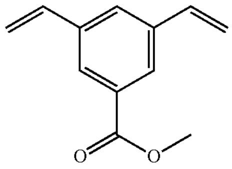

To a solution of compound 1.684 (2.3 g, 9.46 mmol) and 4,4,5,5-tetramethyl-2-vinyl-1,3,2-dioxaborolane (2.19 g, 14.19 mmol) in DME (50 mL) was added Pd(dppf)$Cl_2$ (692.29 mg, 946.12 μmol) and CsF (2.87 g, 18.92 mmol). The mixture was heated to 80° C. and stirred for 12 h under a nitrogen atmosphere. The mixture was poured into water (100 mL) and extracted with EA (80 mL×3). The combined organic phase was washed with brine (100 mL×3), dried with anhydrous $Na_2SO_4$, filtered and concentrated in vacuo. The residue was purified (PM1) to afford compound 1.685 (1.4 g, 7.36 mmol, 77.8% yield) as a yellow oil.

$^1$H NMR (400 MHz, $CHCl_3$-d) δ: 7.92 (s, 1H), 7.78 (s, 1H), 7.43 (s, 1H), 6.75 (dd, J=17.6, 10.8 Hz, 1H), 5.83 (d, J=17.6 Hz, 1H), 5.31 (d, J=10.8 Hz, 1H), 3.93 (s, 3H), 2.70 (q, J=5.2 Hz, 2H), 1.27 (t, J=5.2 Hz, 3H) ppm.

(3-Ethyl-5-vinylphenyl)methanol 1.686

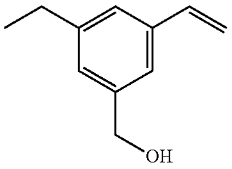

To a solution of compound 1.685 (1.4 g, 7.36 mmol) in THF (20 mL) was added LAH (430 mg, 11.33 mmol) slowly at 0° C. The reaction mixture was stirred at 0° C. for 0.5 h. The reaction mixture was cooled to 0° C. and then diluted with $H_2O$ (0.45 mL), 10% aq. NaOH solution (0.45 mL) and $H_2O$ (1.35 mL). After stirring for 0.5 h, $Na_2SO_4$ (3 g) was added. The mixture was stirred at 20° C. for another 0.5 h and then filtered and the filter cake was washed with EA (50 mL×3). The filtrate was concentrated in vacuo to afford compound 1.686 (1.1 g, 6.78 mmol, 92.1% yield) as a yellow oil.

$^1$H NMR (400 MHz, $CHCl_3$-d) δ: 7.29 (s, 1H), 7.22 (s, 1H), 7.15 (s, 1H), 6.76 (dd, J=17.6, 10.8 Hz, 1H), 5.81 (d, J=17.6 Hz, 1H), 5.29 (d, J=10.8 Hz, 1H), 4.72 (s, 2H), 2.74-2.67 (q, 2H), 1.32-1.27 (t, 3H) ppm.

1-(Chloromethyl)-3-ethyl-5-vinylbenzene 1.687

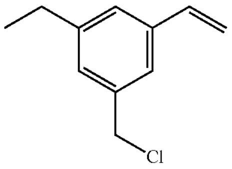

To a solution of compound 1.686 (1 g, 6.16 mmol) in 1,4-dioxane (15 mL) was added $SOCl_2$ (1.64 g, 13.78 mmol) at 0° C. slowly. The reaction mixture was then heated to 90° C. and stirred for 2 h. The reaction mixture was diluted with iced water (80 mL) slowly at 0° C. and then extracted with EA (50 mL×2). The organic layer was washed with brine (80 mL), dried over $Na_2SO_4$, filtered and concentrated in vacuo to afford compound 1.687 (1.1 g, 6.09 mmol, 98.8% yield) as a yellow oil, which was used directly in next step.

2-(3-Ethyl-5-vinylphenyl)acetonitrile 1.688

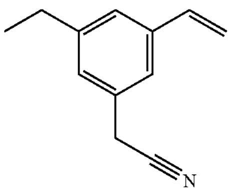

To a solution of compound 1.687 (1 g, 5.53 mmol) in ACN (20 mL) was added TMSCN (1.10 g, 11.07 mmol) and TBAF (11.07 mL, 1 M) at 20° C. The reaction mixture was stirred at 20° C. for 12 h. The reaction mixture was concentrated in vacuo and the crude product was purified (PM7) to afford compound 1.688 (900 mg, 5.26 mmol, 94.9% yield) as a yellow oil.

$^1$H NMR (400 MHz, $CHCl_3$-d) δ: 7.20-7.18 (m, 2H), 7.05 (s, 1H), 6.69 (dd, J=17.6, 10.8 Hz, 1H), 5.77 (d, J=17.6 Hz, 1H), 5.28 (d, J=10.8 Hz, 1H), 3.72 (s, 2H), 2.68-2.62 (q, 2H), 1.26-1.23 (t, 3H) ppm.

2-(3-Ethyl-5-formylphenyl)acetonitrile 1.689

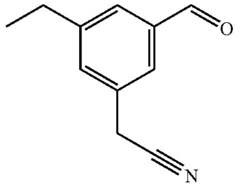

To a solution of compound 1.688 (0.9 g, 5.26 mmol) in DCM (15 mL) cooled to −78° C. was bubbled ozone until the colour of mixture turned blue. DMS (4.90 g, 78.84 mmol) was added slowly. The reaction mixture was warmed up to 20° C. and stirred for 12 h. The reaction mixture was concentrated in vacuo and the crude product was purified (PM7) to afford compound 1.689 (750 mg, 4.33 mmol, 82.38% yield) as a yellow oil.

$^1$H NMR (400 MHz, $CHCl_3$-d) δ: 10.01 (s, 1H), 7.69 (s, 1H), 7.66 (s, 1H), 7.45 (s, 1H), 3.82 (s, 2H), 2.76 (q, J=7.6 Hz, 2H), 1.29 (t, J=7.6 Hz, 3H) ppm.

Synthesis of Intermediate 1.697

Methyl 3-bromo-5-(cyclopropyl(hydroxy)methyl)benzoate 1.691

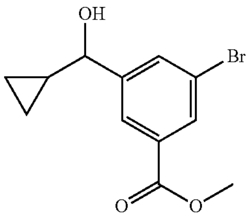 [SMILES: COC(=O)c1cc(Br)cc(C(O)C2CC2)c1]

To a solution of methyl 3-bromo-5-formyl-benzoate (1.5 g, 6.17 mmol) in THF (70 mL) was added cyclopropylmagnesium bromide (18.51 mL, 0.5 M) slowly at 0° C. The mixture was stirred at 0° C. for 0.5 h. The mixture was poured into saturated aq. $NH_4Cl$ solution (100 mL) and extracted with EA (50 mL×2). The combined organic phase was washed with brine (50 mL), dried over $Na_2SO_4$ and concentrated in vacuo. The residue was purified (PM12) to afford compound 1.691 (570 mg, 2.00 mmol, 32.4% yield) as a red oil.

$^1$H NMR (400 MHz, $CHCl_3$-d) δ: 8.09 (s, 1H), 8.02 (s, 1H), 7.81 (s, 1H), 4.04 (d, J=8.1 Hz, 1H), 3.95 (s, 3H), 2.12 (br s, 1H), 1.23-1.13 (m, 1H), 0.71-0.55 (m, 2H), 0.55-0.33 (m, 2H) ppm.

Methyl 3-bromo-5-(cyclopropylmethyl)benzoate 1.692

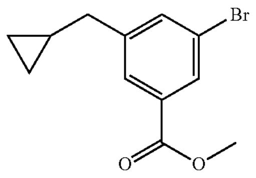

To a mixture of TFA (1.73 g, 15.13 mmol) and $Et_3SiH$ (815.60 mg, 7.01 mmol) was added compound 1.691 (1 g, 3.51 mmol) at 20° C. The reaction mixture was stirred at 20° C. for 2 h. The reaction mixture was concentrated in vacuo and the crude product was purified (PM1) to afford compound 1.692 (700 mg, 2.60 mmol, 74.2% yield) as a colorless oil.

$^1$H NMR (400 MHz, $CHCl_3$-d) δ: 8.00 (s, 1H), 7.85 (s, 1H), 7.60 (s, 1H), 3.92 (s, 3H), 2.56 (d, J=6.8 Hz, 2H), 1.02-0.92 (m, 1H), 0.58-0.54 (m, 2H), 0.24-0.19 (m, 2H) ppm.

Methyl 3-(cyclopropylmethyl)-5-vinylbenzoate 1.693

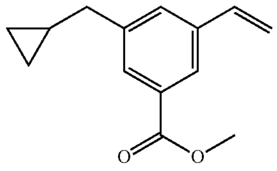 [SMILES: C=Cc1cc(CC2CC2)cc(C(=O)OC)c1]

To a solution of compound 1.692 (600 mg, 2.23 mmol) in 1,4-dioxane (6 mL) and water (0.6 mL) was added $K_2CO_3$ (616.23 mg, 4.46 mmol), 4,4,5,5-tetramethyl-2-vinyl-1,3,2-dioxaborolane (686.71 mg, 4.46 mmol) and Pd(dppf)$Cl_2$ (163.12 mg, 222.94 μmol). The reaction mixture was then heated to 80° C. and stirred for 12 h. The reaction mixture was concentrated in vacuo and the crude product was purified (PM13) to afford compound 1.693 (330 mg, 1.53 mmol, 68.4% yield) as a colorless oil.

$^1$H NMR (400 MHz, $CHCl_3$-d) δ: 7.93 (s, 1H), 7.82 (s, 1H), 7.47 (s, 1H), 6.74 (dd, J=17.6, 10.8 Hz, 1H), 5.82 (d, J=17.6 Hz, 1H), 5.31 (d, J=10.8 Hz, 1H), 3.92 (s, 3H), 2.58 (d, J=6.8 Hz, 2H), 1.05-0.96 (m, 1H), 0.57-0.53 (m, 2H), 0.24-0.20 (m, 2H) ppm.

(3-(Cyclopropylmethyl)-5-vinylphenyl)methanol 1.694

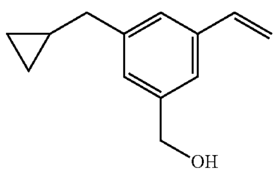

To a solution of compound 1.693 (330 mg, 1.53 mmol) in THF (5 mL) was added LAH (57.91 mg, 1.53 mmol) slowly at 0° C. The reaction mixture was stirred at 0° C. for 2 h. The reaction mixture was quenched with water (0.1 mL) followed by addition of 10% aq. NaOH solution (0.1 mL) and water (0.3 mL). After being stirred for 0.5 h, $Na_2SO_4$ (3 g) was added and stirred at 20° C. for 0.5 h. The mixture was filtered and concentrated in vacuo to give compound 1.694 (300 mg) as a colorless oil.

$^1$H NMR (400 MHz, $CHCl_3$-d) δ: 7.27 (s, 1H), 7.23 (s, 1H), 7.17 (s, 1H), 6.72 (dd, J=17.6, 11.2 Hz 1H), 5.76 (d, J=17.6 Hz, 1H), 5.25 (d, J=11.2, 1H), 4.69 (s, 2H), 2.55 (d, J=6.8 Hz, 2H), 1.64 (br s, 1H), 1.04-0.96 (m, 1H), 0.56-0.51 (m, 2H), 0.23-0.19 (m, 2H) ppm.

1-(Chloromethyl)-3-(cyclopropylmethyl)-5-vinylbenzene 1.695

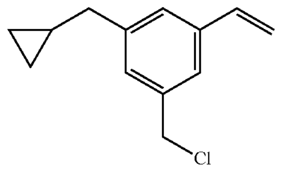

To a solution of compound 1.694 (300 mg, 1.59 mmol) in 1,4-dioxane (5 mL) was added $SOCl_2$ (492.00 mg, 4.14 mmol) slowly at 0° C. The reaction mixture was then heated to 80° C. and stirred for 2 h. The mixture was diluted with $H_2O$ (10 mL) and then extracted with EA (50 mL×2). The organic layer was washed with brine (20 mL), dried over $Na_2SO_4$, filtered and concentrated in vacuo to give compound 1.695 (300 mg, 1.45 mmol, 91.1% yield) as a yellow oil, which was used directly.

2-(3-(Cyclopropylmethyl)-5-vinylphenyl)acetonitrile 1.696

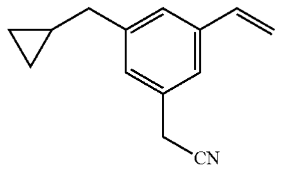

To a solution of compound 1.695 (300 mg, 1.45 mmol) in ACN (20 mL) was added TMSCN (287.96 mg, 2.90 mmol) and TBAF (2.90 mL, 1 M in THF) at 20° C. The reaction mixture was stirred at 20° C. for 12 h. The reaction mixture was concentrated in vacuo and the crude product was purified (PM7) to afford compound 1.696 (300 mg) as a yellow oil.

$^1$H NMR (400 MHz, $CHCl_3$-d) δ: 7.27 (s, 1H), 7.20 (s, 1H), 7.12 (s, 1H), 6.70 (dd, J=17.2, 10.8 Hz, 1H), 5.77 (d, J=17.2 Hz, 1H), 5.29 (d, J=10.8 Hz, 1H), 3.72 (s, 2H), 2.55 (d, J=6.8 Hz, 2H), 1.04-0.95 (m, 1H), 0.55-0.50 (m, 2H), 0.23-0.19 (m, 2H) ppm.

2(3-(Cyclopropylmethyl)-5-formylphenyl)acetonitrile 1.697

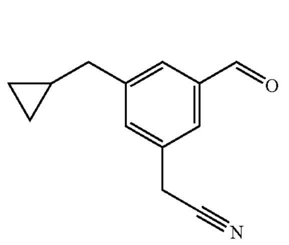 [SMILES: N#CCc1cc(C=O)cc(CC2CC2)c1]

To a solution of compound 1.696 (300 mg, 1.52 mmol) in DCM (8 mL) cooled to −78° C. was bubbled ozone until the color of mixture turned blue. After excess ozone was purge with nitrogen, DMS (2.31 g, 37.18 mmol) was added. The mixture was warmed up to 20° C. and stirred for 12 h. The reaction mixture was concentrated in vacuo and the crude product was purified (PM11) to afford compound 1.697 (230 mg, 1.15 mmol, 75.9% yield) as a yellow oil.

$^1$H NMR (400 MHz, $CHCl_3$-d) δ: 10.02 (s, 1H), 7.76 (s, 1H), 7.70 (s, 1H), 7.52 (s, 1H), 3.83 (s, 2H), 2.64 (d, J=6.8 Hz, 2H), 1.06-0.96 (m, 1H), 0.62-0.57 (q, 2H), 0.26-0.23 (q, 2H) ppm.

Synthesis of Intermediate 1.782

4-((3-Chloro-4-(trifluoromethoxy)benzyl)amino)butan-1-ol 1.157

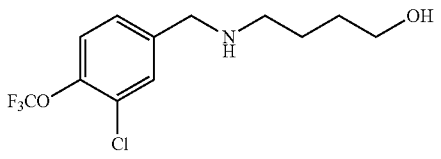 [SMILES: OCCCCNCc1ccc(OC(F)(F)F)c(Cl)c1]

A solution of 3-chloro-4-(trifluoromethoxy)benzaldehyde (1 g, 4.45 mmol) and 4-aminobutan-1-ol (1.19 g, 13.36 mmol) in MeOH (10 mL) was stirred at 20° C. for 12 h, then sodium cyanoborohydride (1.12 g, 17.81 mmol) was added. The resulting mixture was stirred at 20° C. for 1 h. The mixture was concentrated in vacuo and purified (PM150) to give compound 1.157 (1.2 g, FA salt) as a white solid.

LCMS (AM3): rt=0.911 min, (298.1 $[M+H]^+$), 96.6% purity.

tert-Butyl 3-chloro-4-(trifluoromethoxy)benzyl(4-hydroxybutyl)carbamate 1.158

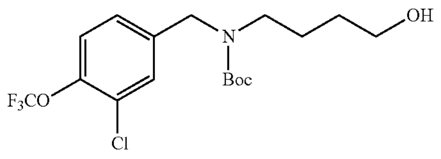 [SMILES: CC(C)(C)OC(=O)N(CCCCO)Cc1ccc(OC(F)(F)F)c(Cl)c1]

To a solution of compound 1.157 (1.2 g, 3.49 mmol) in THE (10 mL) and water (10 mL) was added $NaHCO_3$ (439.92 mg, 5.24 mmol) and $Boc_2O$ (914.32 mg, 4.19 mmol) at 20° C. The mixture was stirred at 20° C. for 12 h. The reaction mixture was diluted water (50 mL) and extracted with ethyl acetate (30 mL×3). The combined organic phase was washed with brine (90 mL×3), dried with $Na_2SO_4$, filtered and concentrated in vacuo. The residue was purified (PM6) to afford compound 1.158 (890 mg, 2.21 mmol, 63.2% yield) as a light yellow oil.

LCMS (AM3): rt=1.049 min, (420.1 $[M+Na]^+$), 73.2% purity.

Tert-butyl (4-bromobutyl)(3-chloro-4-(trifluoromethoxy)benzyl)carbamate 1.778

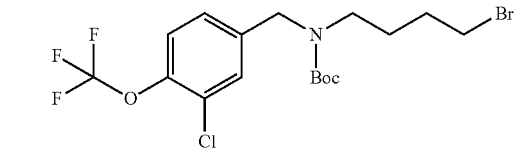 [SMILES: CC(C)(C)OC(=O)N(CCCCBr)Cc1ccc(OC(F)(F)F)c(Cl)c1]

To a solution of compound 1.158 (3.1 g, 7.79 mmol) and $CBr_4$ (3.10 g, 9.35 mmol) in DCM (40 mL) was added $PPh_3$ (2.45 g, 9.35 mmol) at 0° C. The reaction mixture was warmed to room temperature and stirred for 1 h. The reaction mixture was concentrated in vacuo and the residue was purified (PM7) to afford compound 1.778 (2 g, 55.7% yield) as a colorless oil, which was used directly.

Tert-butyl 3-chloro-4-(trifluoromethoxy)benzyl(4-((2R)-2-((tetrahydro-2H-pyran-2-yl)oxy)propoxy)butyl)carbamate 1.779

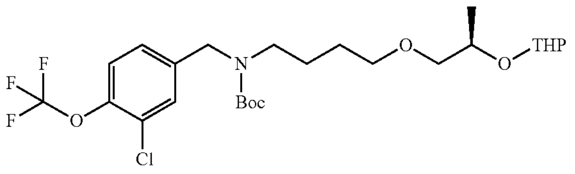

A mixture of compound 1.778 (2 g, 4.34 mmol), (2R)-2-((tetrahydro-2H-pyran-2-yl)oxy)propan-1-ol (Tetrahedron Letters, 2003, 44 (32), 6149-6151), (0.7 g, 4.37 mmol), NaOH (1.74 g, 43.41 mmol) and TBAI (160 mg, 0.43 mmol) in $H_2O$ (4 mL) was stirred at 25° C. for 14 h. The reaction mixture was diluted with water (40 mL) and the resulting mixture was extracted with MTBE (20 mL×2). The combined organic phase was washed with brine (20 mL), dried over $Na_2SO_4$, filtered and concentrated in vacuo. The residue was purified (PM47) to afford compound 1.779 (700 mg, 20.9% yield) as a brown oil.

LCMS (AM3): rt=1.071 min, (456.2 $[M-THP+2H]^+$), 69.8% purity.

(R)-tert-butyl 3-chloro-4-(trifluoromethoxy)benzyl (4-(2-hydroxypropoxy)butyl)carbamate 1.780

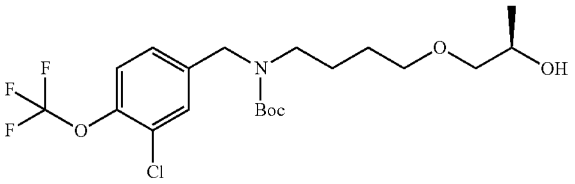 [SMILES: C[C@@H](O)COCCCCN(Cc1ccc(OC(F)(F)F)c(Cl)c1)C(=O)OC(C)(C)C]

A mixture of compound 1.779 (0.7 g, 1.30 mmol) and $TsOH{\cdot}H_2O$ (50 mg, 0.26 mmol) in MeOH (15 mL) was stirred at room temperature for 1 h. $K_2CO_3$ (1 g) was added and the mixture was stirred for 10 min. The mixture was then filtered and the filtrate was concentrated in vacuo to give a residue that was purified (PM6) to afford compound 1.780 (0.5 g, 84.6% yield) as a light yellow oil.

LCMS (AM3): rt=1.065 min, (478.1 $[M+Na]^+$), 43.3% purity.

(R)-methyl 5-((1-(4-((tert-butoxycarbonyl)(3-chloro-4-(trifluoromethoxy)benzyl)amino)butoxy)propan-2-yl)oxy)benzo[c][2,6]naphthyridine-8-carboxylate 1.781

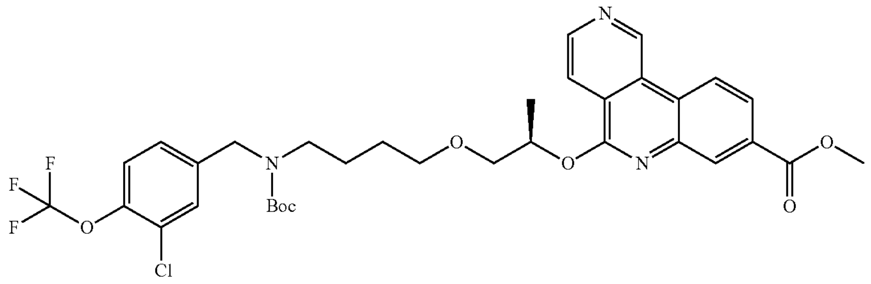 [SMILES: COC(=O)c1ccc2c(c1)nc(O[C@H](C)COCCCCN(Cc1ccc(OC(F)(F)F)c(Cl)c1)C(=O)OC(C)(C)C)c1ccncc12]

To a solution of compound 1.780 (500 mg, 1.10 mmol) in THF (10 mL) was added NaH (60 mg, 1.50 mmol, 60% dispersion in oil) at 0° C. The reaction mixture was stirred at 0° C. for 0.5 h, then compound 1.1 (450 mg, 1.65 mmol) was added. The reaction mixture was then heated to 60° C. and stirred for 20 h. The reaction mixture was filtered and the filtrate was concentrated in vacuo to give a residue that was purified (PM47) to afford compound 1.781 (100 mg, 12.5% yield) as a colorless oil.

LCMS (AM3): rt=1.247 min, (692.3 [M+H]), 96.8% purity.

(R)-5-((1-(4-((tert-butoxycarbonyl)(3-chloro-4-(trifluoromethoxy)benzyl)amino)butoxy)propan-2-yl)oxy)benzo[c][2,6]naphthyridine-8-carboxylic acid 1.782

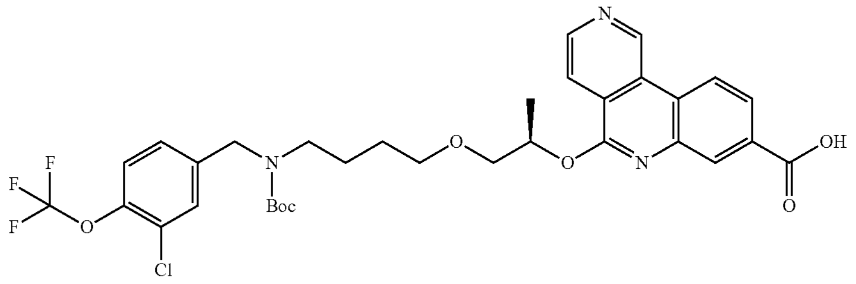 [SMILES: C[C@H](COCCCCN(Cc1ccc(OC(F)(F)F)c(Cl)c1)C(=O)OC(C)(C)C)Oc1nc2cc(C(=O)O)ccc2c2cnccc12]

A mixture of compound 1.781 (100 mg, 0.14 mmol) and lithium hydroxide monohydrate (50 mg, 1.19 mmol) in THE (8 mL) and $H_2O$ (2 mL) was stirred at room temperature for 4 h. The reaction mixture was concentrated in vacuo and the residue was purified (PM150) to afford compound 1.782 (67 mg, 68.4% yield) as a white solid.

LCMS (AM3): rt=1.153 min, (678.2 $[M+H]^+$), 100% purity.

Synthesis of Intermediate 1.729

Tert-butyl (4-((2R)-2-((tetrahydro-2H-pyran-2-yl) oxy)propoxy)butyl)carbamate 1.725

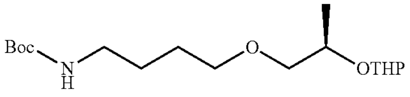

A mixture of tert-butyl (4-bromobutyl)carbamate (29.27 g, 116.10 mmol), (2R)-2-((tetrahydro-2H-pyran-2-yl)oxy) propan-1-ol (Tetrahedron Letters, 2003, 44 (32), 6149-6151), (9.3 g, 58.05 mmol), NaOH (23.22 g, 580.49 mmol) and TBAI (2.14 g, 5.79 mmol) in $H_2O$ (58 mL) was stirred at room temperature for 12 h. The reaction mixture was poured into water (200 mL) and the resulting mixture was extracted with MTBE (100 mL×3). The combined organic phase was washed with brine (200 mL), dried over $Na_2SO_4$, filtered and concentrated in vacuo. The residue was purified (PM6) to afford compound 1.725 (6.5 g) as a colourless oil.

$^1$H NMR (400 MHz, $CHCl_3$-d) 5:4.78-4.67 (m, 1H), 4.01-3.77 (m, 2H), 3.57-3.33 (m, 5H), 3.17-3.07 (m, 2H), 1.86-1.73 (m, 2H), 1.63-1.52 (m, 8H), 1.43 (s, 9H), 1.22-1.10 (m, 3H) ppm.

(R)-Tert-butyl (4-(2-hydroxypropoxy)butyl)carbamate 1.726

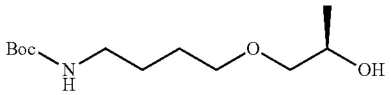 [SMILES: C[C@@H](O)COCCCCNC(=O)OC(C)(C)C]

A mixture of compound 1.725 (5.6 g, 16.90 mmol) and TsOH·$H_2O$ (321 mg, 1.69 mmol) in MeOH (50 mL) was stirred at room temperature for 1 h. $K_2CO_3$ (1 g) was added and the resulting mixture was concentrated in vacuo. The residue was purified (PM3) to afford compound 1.726 (1.1 g) as a yellow oil.

$^1$H NMR (400 MHz, $CHCl_3$-d) δ: 4.80-4.60 (br s, 1H), 3.99-3.87 (m, 1H), 3.67-3.45 (m, 2H), 3.43-3.40 (m, 1H), 3.24-3.20 (m, 1H), 3.13 (t, J=6.4 Hz, 2H), 1.65-1.52 (m, 4H), 1.44 (s, 9H), 1.14 (d, J=6.4 Hz, 3H) ppm.

(R)-5-((1-(4-((Tert-butoxycarbonyl)amino)butoxy) propan-2-yl)oxy)benzo[c][2,6]naphthyridine-8-carboxylic acid 1.727

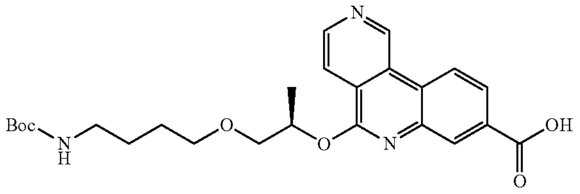 [SMILES: C[C@H](COCCCCNC(=O)OC(C)(C)C)Oc1nc2cc(C(=O)O)ccc2c2cnccc12]

To a solution of compound 1.726 (1.1 g, 4.45 mmol) in THF (20 mL) was added NaH (0.22 g, 5.50 mmol, 60% dispersion in oil) at 0° C. After stirring at 0° C. for 0.5 h, compound 1.1 (1.46 g, 5.34 mmol) was added. The reaction mixture was then warmed to room temperature and stirred for 16 h. The reaction mixture was quenched by water (1 mL) and concentrated in vacuo and the residue was purified (PM47) to afford compound 1.727 (0.66 g) as a brown solid.

LCMS (AM3): rt=0.931 min, (470.4 $[M+H]^+$), 68.6% purity.

(R)-Tert-butyl (4-(2-((8-carbamoylbenzo[c][2,6] naphthyridin-5-yl)oxy)propoxy)butyl)carbamate 1.728

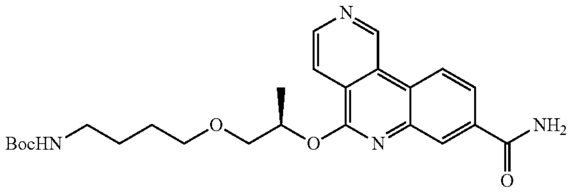 [SMILES: C[C@H](COCCCCNC(=O)OC(C)(C)C)Oc1nc2cc(C(N)=O)ccc2c2cnccc12]

To a mixture of compound 1.727 (0.66 g, 1.41 mmol), DIPEA (1.22 mL, 7.03 mmol), EDCI (540 mg, 2.82 mmol) and HOBt (380 mg, 2.81 mmol) in DMF (7 mL) was added $NH_4Cl$ (300 mg, 5.61 mmol) at ambient temperature. The reaction mixture was heated to 70° C. and stirred for 15 h. The reaction mixture was filtered and the filtrate was purified (PM150) to afford compound 1.728 (0.26 g, 39.1% yield) as a brown solid.

LCMS (AM3): rt=0.906 min, (469.2 $[M+H]^+$), 98.9% purity.

(R)-5-((1-(4-Aminobutoxy)propan-2-yl)oxy)benzo [c][2,6]naphthyridine-8-carboxamide 1.729

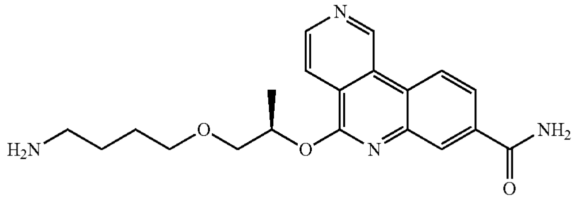 [SMILES: C[C@H](COCCCCN)Oc1nc2cc(C(N)=O)ccc2c2cnccc12]

A mixture of compound 1.728 (260 mg, 0.55 mmol) in a solution of HCl in 1,4-dioxane (10 mL, 2 M) was stirred at room temperature for 1 h. The reaction mixture was concentrated in vacuo to afford compound 1.729 (0.25 g, HCl salt) as a brown solid, which was used directly without further purification.

LCMS (AM3): rt=0.723 min, (369.4 $[M+H]^+$), 93.3% purity.

Synthesis of Intermediate 1.681

Tert-butyl (4-((2S)-2-((tetrahydro-2H-pyran-2-yl)oxy)propoxy)butyl)carbamate 1.677

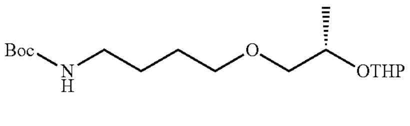

To a solution of NaOH (13.23 g, 330.81 mmol) in $H_2O$ (33.08 mL) was added (2S)-2-((tetrahydro-2H-pyran-2-yl)oxy)propan-1-ol (5.3 g, 33.08 mmol) (Journal of the American Chemical Society, 1984, 106, (17) 4916-4922), tert-butyl (4-bromobutyl)carbamate (20 g, 79.32 mmol) and TBAl (610.96 mg, 1.65 mmol) at 20° C. The reaction mixture was stirred at 20° C. for 12 h. The reaction mixture was diluted with $H_2O$ (100 mL) and then extracted with MTBE (100 mL×2). The combined organic layer was washed with brine (150 mL), dried over $Na_2SO_4$, filtered and concentrated in vacuo to give the crude product, which was purified (PM7) to afford compound 1.677 (3 g, 9.05 mmol, 27.4% yield) as a colorless oil, which was used directly.

(S)-Tert-butyl (4-(2-hydroxypropoxy)butyl)carbamate 1.678

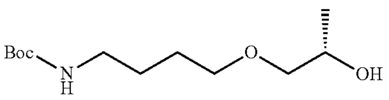 [SMILES: C[C@H](O)COCCCCNC(=O)OC(C)(C)C]

To a solution of compound 1.677 (3 g, 9.05 mmol) in MeOH (25 mL) was added TsOH·$H_2O$ (200 mg, 1.16 mmol) at 20° C. The reaction mixture was stirred at 20° C. for 1 h. The reaction mixture was concentrated in vacuo to give the crude product which was purified (PM4) to afford compound 1.678 (940 mg, 3.80 mmol, 42% yield) as a colorless oil.

$^1H$ NMR (400 MHz, $CHCl_3$-d) δ: 4.71 (br s, 1H), 4.00-3.92 (m, 1H), 3.54-3.44 (m, 2H), 3.42-3.39 (m, 1H), 3.24-3.19 (t, 1H), 3.15-3.05 (m, 2H), 1.96 (br s, 1H), 1.65-1.51 (m, 4H), 1.44 (s, 9H), 1.14 (d, J=6.4 Hz, 3H) ppm.

(S)-Methyl 5-((1-(4-((tert-butoxycarbonyl)amino)butoxy)propan-2-yl)oxy)benzo[c][2,6]naphthyridine-8-carboxylate 1.679

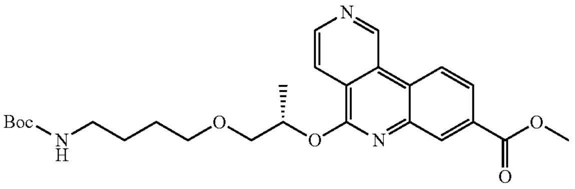 [SMILES: COC(=O)c1ccc2c(c1)nc(O[C@@H](C)COCCCCNC(=O)OC(C)(C)C)c1ccncc12]

To a solution of compound 1.678 (820 mg, 3.32 mmol) in THE (20 mL) was added NaH (198.92 mg, 4.97 mmol, 60% dispersion in oil) at 20° C. After being stirred at 20° C. for 0.5 h, compound 1.1 (904.07 mg, 3.32 mmol) was added. The reaction mixture was stirred at 20° C. for another 2 h. The reaction mixture was diluted with $H_2O$ (80 mL) and then extracted with EA (60 mL×2). The organic layer was washed with brine (80 mL), dried over $Na_2SO_4$, filtered and concentrated in vacuo to give the crude product, which was purified (PM47) to afford compound 1.679 (460 mg, 951.29 μmol, 28.7% yield) as a brown solid.

LCMS (AM3): rt=1.029 min, (484.2 [M+H]P), 94.8% purity.

(S)-Methyl 5-((1-(4-aminobutoxy)propan-2-yl)oxy)benzo[c][2,6]naphthyridine-8-carboxylate 1.680

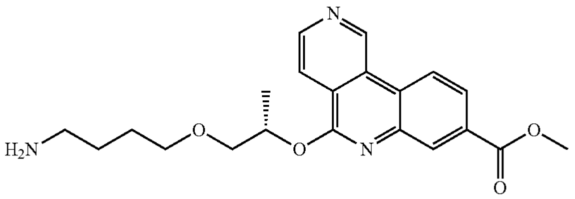 [SMILES: COC(=O)c1ccc2c(c1)nc(O[C@@H](C)COCCCCN)c1ccncc12]

To a solution of compound 1.679 (220 mg, 454.96 μmol) in 1,4-dioxane (1 mL) was added a solution of HCl in 1,4-dioxane (11.0 mL, 4 M). The reaction mixture was stirred at 20° C. for 0.5 h. The reaction mixture was concentrated in vacuo to give the crude product, which was purified (PM150) to afford compound 1.680 (240 mg, FA salt) as a yellow solid.

LCMS (AM5): rt=0.987 min, (384.2 $[M+H]^+$), 69.9% purity.

(S)-Methyl 5-((1-(4-((3-chloro-4-(trifluoromethoxy)benzyl)amino)butoxy)propan-2-yl)oxy)benzo[c][2,6]naphthyridine-8-carboxylate 1.681

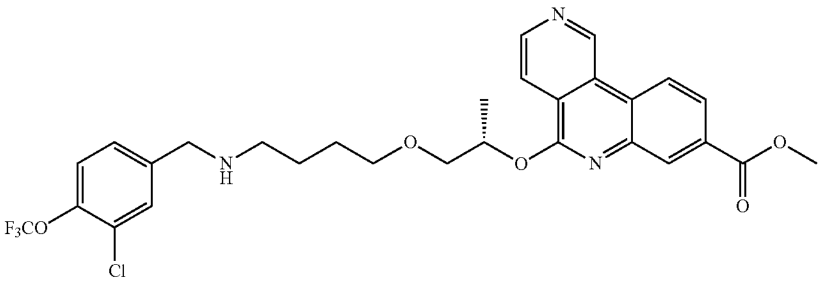 [SMILES: COC(=O)c1ccc2c(c1)nc(O[C@@H](C)COCCCCNCc1ccc(OC(F)(F)F)c(Cl)c1)c1ccncc12]

A mixture of compound 1.680 (240 mg, 481.95 μmol), sodium acetate (118.61 mg, 1.45 mmol) and 3-chloro-4-(trifluoromethoxy)benzaldehyde (108.23 mg, 481.95 μmol) in MeOH (3 mL) was stirred at 20° C. for 12 h, then sodium triacetoxyborohydride (306.44 mg, 1.45 mmol) was added. The reaction mixture was stirred at 20° C. for another 3.5 h. The crude product was purified (PM143) to afford compound 1.681 (200 mg, 337.84 μmol, 70.1% yield) as a white solid.

LCMS (AM3): rt=0.907 min, (592.2 $[M+H]^+$), 99.2% purity.

Synthesis of Intermediate 1.828

Tert-butyl 4-(3-formyl-5-(trifluoromethoxy)benzyl)-1H-pyrazole-1-carboxylate 1.827

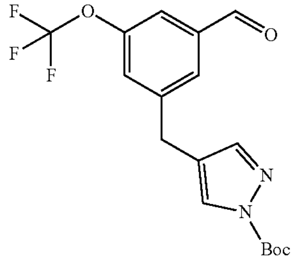 [SMILES: CC(C)(C)OC(=O)n1cc(Cc2cc(C=O)cc(OC(F)(F)F)c2)cn1]

To a mixture of compound 1.824 (500 mg, 2.10 mmol) in 1,4-dioxane (5 mL) and $H_2O$ (0.5 mL) was added $K_2CO_3$ (579.28 mg, 4.19 mmol), tert-butyl 4-(4,4,5,5-tetramethyl-1,3,2-dioxaborolan-2-yl)-1H-pyrazole-1-carboxylate (678.08 mg, 2.31 mmol) and Pd(dppf)$Cl_2$ (153.34 mg, 209.56 μmol). The reaction mixture was then heated to 70° C. and stirred for 12 h under a nitrogen atmosphere. The reaction mixture was filtered and the filtrate was concentrated in vacuo. The crude product was purified (PM150) to afford compound 1.827 (400 mg, 1.02 mmol, 48.8% yield) as a yellow oil.

LCMS (AM3): rt=0.975 min, (392.9 $[M+Na]^+$), 97.1% purity.

Tert-butyl 4-(3-(((4-(2-((8-carbamoylbenzo[c][2,6]naphthyridin-5-yl)amino)ethoxy)butyl)amino)methyl)-5-(trifluoromethoxy)benzyl)-1H-pyrazole-1-carboxylate 1.828

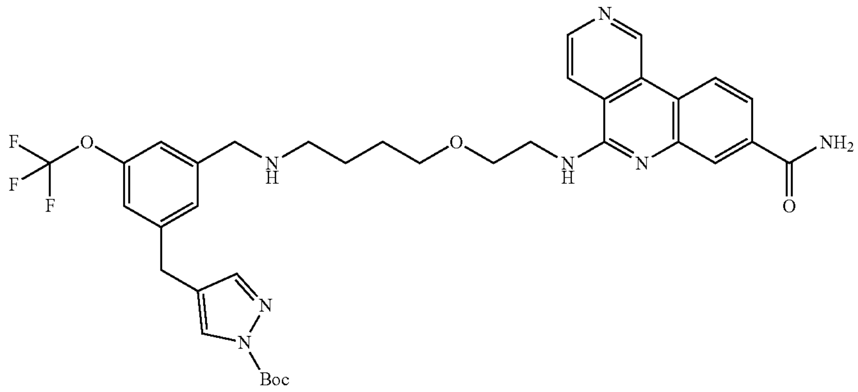 [SMILES: CC(C)(C)OC(=O)n1cc(Cc2cc(CNCCCCOCCNc3nc4cc(C(N)=O)ccc4c4cnccc34)cc(OC(F)(F)F)c2)cn1]

A mixture of Intermediate E (210.56 mg, 540.07 μmol, HCl salt), DIPEA (209.40 mg, 1.62 mmol) and compound 1.827 (200 mg, 540.07 μmol) in MeOH (3 mL) was stirred at 20° C. for 12 h, then sodium cyanoborohydride (101.81 mg, 1.62 mmol) was added. The reaction mixture was stirred at 20° C. for 3 h. The reaction mixture was filtered and the filtrate was concentrated in vacuo and purified (PM168) to afford compound 1.828 (100 mg, 129.45 μmol, 23.9% yield) as a white solid.

LCMS (AM3): rt=0.809 min, (708.3 [M+H]), 86.0% purity.

Synthesis of Intermediate 1.829

Tert-butyl 4-(3-(((4-(2-((8-carbamoylbenzo[c][2,6]naphthyridin-5-yl)oxy)ethoxy)butyl)amino)methyl)-5-(trifluoromethoxy)benzyl)-1H-pyrazole-1-carboxylate 1.829

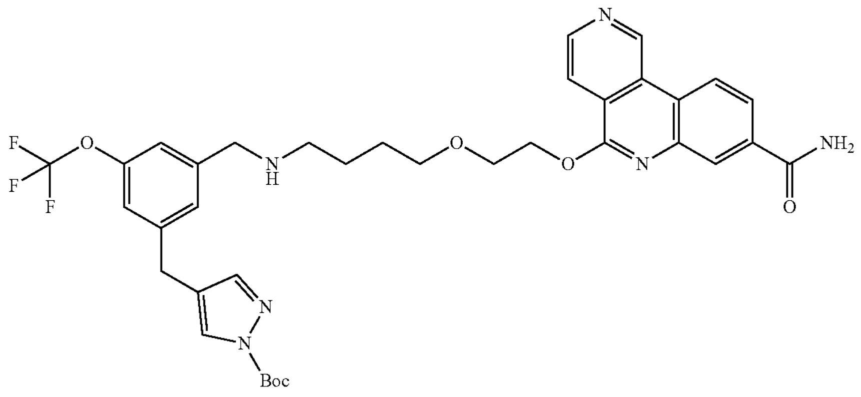 [SMILES: CC(C)(C)OC(=O)n1cc(Cc2cc(CNCCCCOCCOc3nc4cc(C(N)=O)ccc4c4cnccc34)cc(OC(F)(F)F)c2)cn1]

A mixture of compound 1.57 (216.26 mg, 540.07 μmol, FA salt), DIPEA (209.40 mg, 1.62 mmol) and compound 1.827 (200 mg, 540.07 μmol) in MeOH (3 mL) was stirred at 20° C. for 3 h, then sodium cyanoborohydride (101.82 mg, 1.62 mmol) was added. The reaction mixture was stirred at 20° C. for 0.5 h. The reaction mixture was filtered and the filtrate was purified (PM171) to afford compound 1.829 (150 mg, 211.65 μmol, 39.2% yield) as a white solid.

LCMS (AM3): rt=0.873 min, (709.3 $[M+H]^+$), 78.5% purity.

Synthesis of Intermediate 1.832 (R)-5-((1-(4-aminobutoxy)propan-2-yl)oxy)benzo[c][2,6]naphthyridine-8-carboxylic acid 1.832

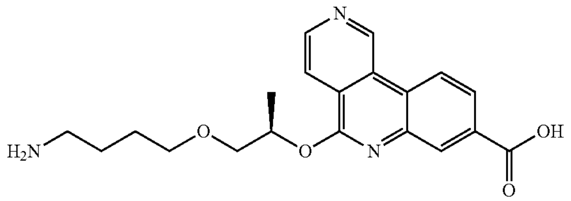 [SMILES: C[C@H](COCCCCN)Oc1nc2cc(C(=O)O)ccc2c2cnccc12]

A mixture of compound 1.727 (880 mg, 1.87 mmol) and TFA (10 mL, 135.06 mmol) in DCM (20 mL) was stirred at room temperature for 0.5 h. The reaction mixture was concentrated in vacuo to afford compound 1.832 (680 mg, 83.8% yield, TFA salt) as a white solid, which was used directly without further purification.

LCMS (AM3): rt=0.773 min, (370.4 [M+H]), 96.0% purity.

Synthesis of Intermediate 1.831

(R)-methyl 5-((1-(4-((3-fluoro-4-(trifluoromethoxy)benzyl)amino)butoxy)propan-2-yl)amino)benzo[c][2,6]naphthyridine-8-carboxylate 1.831

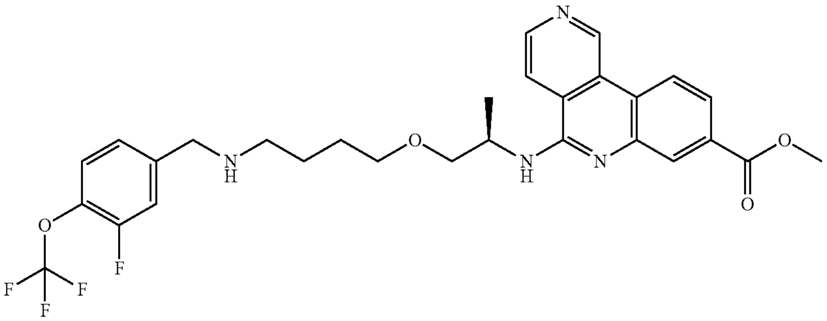 [SMILES: COC(=O)c1ccc2c(c1)nc(N[C@H](C)COCCCCNCc1ccc(OC(F)(F)F)c(F)c1)c1ccncc12]

A mixture of 3-fluoro-4-(trifluoromethoxy)benzaldehyde (75 mg, 0.36 mmol), compound 1.608 (170 mg, 0.35 mmol, HCl salt) and DIPEA (1.44 mmol, 0.25 mL) in MeOH (10 mL) was stirred at room temperature for 16 h, then sodium triacetoxyborohydride (306 mg, 1.44 mmol) was added. The reaction mixture was stirred at room temperature for 0.5 h. The reaction mixture was filtered and the filtrate was purified (PM158) to afford compound 1.831 (130 mg, 55.6% yield, FA salt) as a yellow solid.

LCMS (AM3): rt=0.832 min, (575.2 $[M+H]^+$), 95.7% purity.

Synthesis of Intermediate 1.830

(R)-methyl 5-((1-(4-((3,5-difluoro-4-(trifluoromethoxy)benzyl)amino)butoxy)propan-2-yl)amino)benzo[c][2,6]naphthyridine-8-carboxylate 1.830

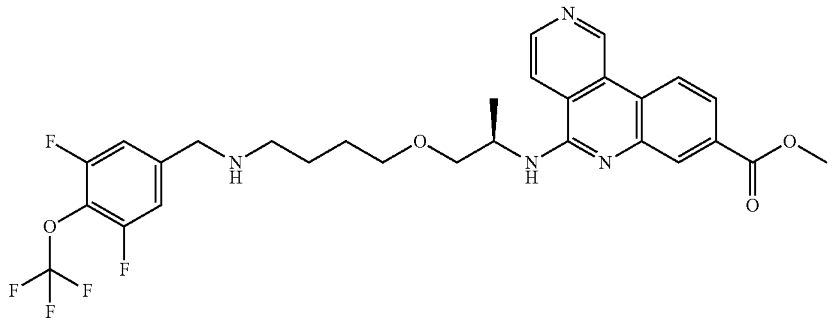 [SMILES: COC(=O)c1ccc2c(c1)nc(N[C@H](C)COCCCCNCc1cc(F)c(OC(F)(F)F)c(F)c1)c1ccncc12]

A mixture of compound 1.608 (140 mg, 284.65 μmol, HCl salt), DIPEA (147.15 mg, 1.14 mmol) and compound 1.507 (90.10 mg, 398.51 μmol) in MeOH (3 mL) was stirred at 40° C. for 12 h, then sodium triacetoxyborohydride (241.31 mg, 1.14 mmol) was added. The reaction mixture was stirred at 40° C. for 3 h. The reaction mixture was filtered and concentrated in vacuo. The crude product was purified (PM170) to afford compound 1.830 (100 mg, 156.60 μmol, 55.0% yield, FA salt) as a yellow solid.

LCMS (AM3): rt=0.827 min, (593.2 $[M+H]^+$), 95.6% purity.

Synthesis of Intermediate 1.840

5-(2-(4-((Tert-butoxycarbonyl)(3,5-difluoro-4-(trifluoromethoxy)benzyl)amino)butoxy)ethoxy)benzo[c][2,6]naphthyridine-8-carboxylic acid 1.839

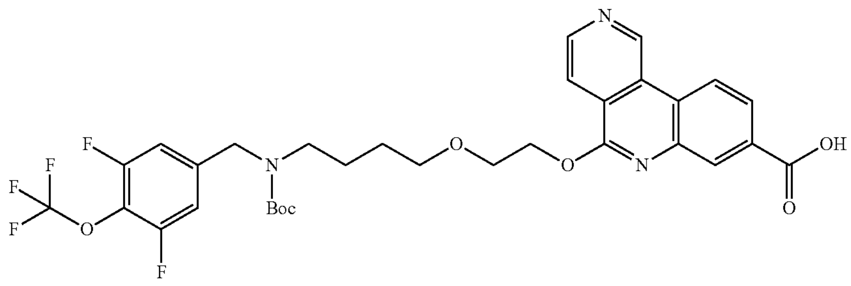 [SMILES: CC(C)(C)OC(=O)N(CCCCOCCOc1nc2cc(C(=O)O)ccc2c2cnccc12)Cc1cc(F)c(OC(F)(F)F)c(F)c1]

To a solution of Example 116 (3 g, 4.91 mmol, FA salt) in EtOH (30 mL) was added DIPEA (1.86 g, 14.35 mmol) and $Boc_2O$ (1.43 g, 6.53 mmol) at 20° C. The reaction mixture was stirred at 20° C. for 12 h. The reaction mixture was concentrated in vacuo to give the residue. The residue was purified (PM150) to afford compound 1.839 (2.6 g, 3.01 mmol, 61.42% yield) as white solid.

LCMS (AM3): rt=1.076 min, (666.1 $[M+H]^+$), 77.1% purity.

Tert-butyl (4-(2-((8-carbamoylbenzo[c][2,6]naphthyridin-5-yl)oxy)ethoxy)butyl)(3,5-difluoro-4-(trifluoromethoxy)benzyl)carbamate 1.840

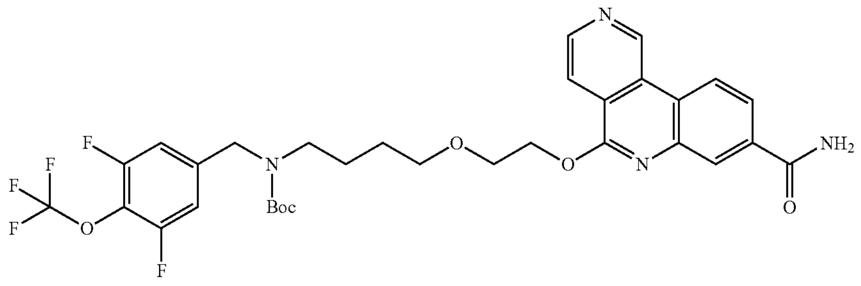 [SMILES: CC(C)(C)OC(=O)N(CCCCOCCOc1nc2cc(C(N)=O)ccc2c2cnccc12)Cc1cc(F)c(OC(F)(F)F)c(F)c1]

To a mixture of compound 1.839 (500 mg, 744.56 μmol), $NH_4Cl$ (398.28 mg, 7.45 mmol) and HATU (339.73 mg, 893.47 μmol) in DMF (5 mL) was added DIPEA (192.45 mg, 1.49 mmol) at 25° C. The resulting mixture was stirred at 25° C. for 1 h. The reaction mixture was concentrated in vacuo to give the residue. The residue was purified (PM150) to afford compound 1.840 (420 mg, 619.3 μmol, 83.2% yield) as white solid.

LCMS (AM3): rt=1.027 min, (665.2 $[M+H]^+$), 98.9% purity.

EXAMPLE COMPOUNDS

The Examples are prepared according to the methods below using the Preparations hereinbefore. Wherein additional materials have been prepared, preparations are included for each Example. Alternatively, wherein commercially available materials are used, only the final steps are included, and no intermediate reference number is necessary.

Example 1

5-((2-(4-((4-cyclobutoxy-3-(hydroxymethyl)benzyl)amino)butoxy)ethyl)amino)benzo[c][2,6]naphthyridine-8-carboxamide

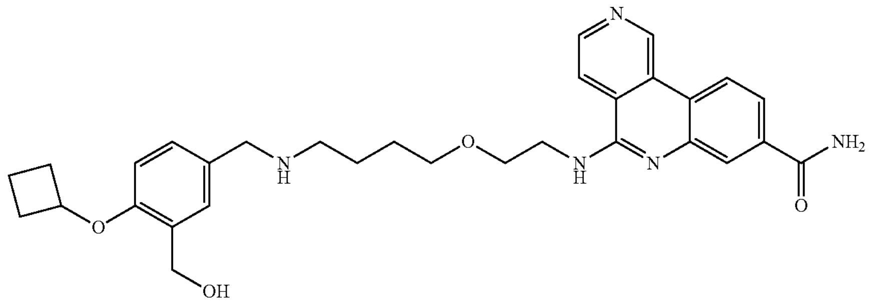 [SMILES: NC(=O)c1ccc2c(c1)nc(NCCOCCCCNCc1ccc(OC3CCC3)c(CO)c1)c1ccncc12]

A mixture of compound 1.64 (40 mg, 193.95 μmol), Intermediate E (75.62 mg, 193.95 μmol, HCl salt) and DIPEA (50.13 mg, 387.90 μmol) in MeOH (1 mL) was stirred at 25° C. for 1 h, then sodium triacetoxyborohydride (205.53 mg, 969.76 μmol) was added. The reaction mixture was stirred at 25° C. for 11 h. The reaction mixture was concentrated in vacuo to give a residue which was purified (PM23) to afford Example 1 (26.71 mg, 49.13 μmol, 25.3% yield, 100% purity) as an off-white solid.

LCMS (AM3): rt=0.726 min, (544.2 $[M+H]^+$), 100% purity.

$^1H$ NMR (400 MHz, MeOH-$d_4$) δ: 9.90 (s, 1H), 8.75 (d, J=5.6 Hz, 1H), 8.58 (d, J=8.4 Hz, 1H), 8.20 (d, J=2.0 Hz, 1H), 8.11 (d, J=5.6 Hz, 1H), 7.82 (dd, J=2.0, 8.4 Hz, 1H), 7.27 (d, J=2.4 Hz, 1H), 7.06 (dd, J=2.4, 8.4 Hz, 1H), 6.66 (d, J=8.4 Hz, 1H), 4.62 (t, J=7.2 Hz, 1H), 4.59 (s, 2H), 3.90-3.87 (t, 2H), 3.80-3.77 (t, 2H), 3.61 (s, 2H), 3.55-3.51 (m, 2H), 2.60-2.53 (m, 2H), 2.47-2.36 (m, 2H), 2.09 (tt, J=2.4, 9.6 Hz, 2H), 1.87-1.60 (m, 2H), 1.60-1.56 (m, 4H) ppm.

The following examples in Table 1 were made with non-critical changes or substitutions to the exemplified procedure in Example 1, that would be understood by one skilled in the art using intermediate E and compounds of formula (III)

TABLE 1

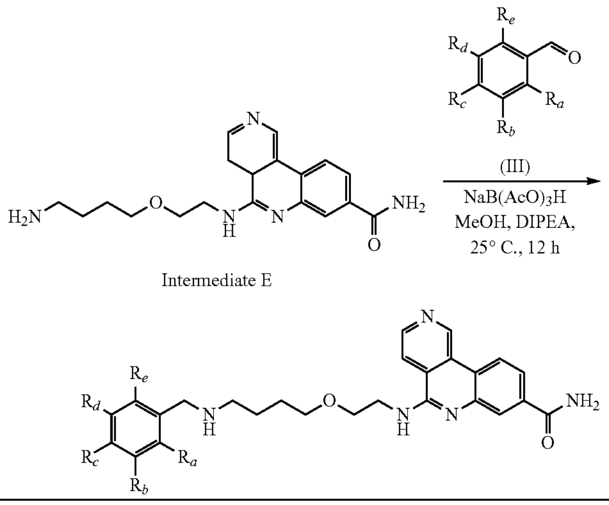

| Example No. | Chemical IUPAC name | Compound (III) | Analytical |
|---|---|---|---|
| Example 3 | 5-((2-(4-((3-chloro-4-(trifluoromethoxy) benzyl)amino) butoxy)ethyl)amino) benzo[c][2,6] naphthyridine-8-carboxamide | 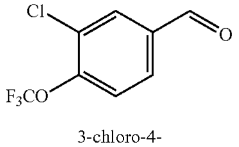 3-chloro-4-(trifluoromethoxy) benzaldehyde | $^1H$ NMR (400 MHZ, MeOH-$d_4$) δ 10.06 (s, 1H), 8.96 (d, J = 5.7 Hz, 1H), 8.75 (d, J = 8.6 Hz, 1H), 8.39 (d, 1H), 8.36-8.35 (d, 1H), 8.00 (dd, J = 1.7, 8.4 Hz, 1H), 7.73 (s, 1H), 7.51 (s, 2H), 4.18 (s, 2H), 4.05 (t, J = 5.1 Hz, 2H), 3.90-3.88 (t, 2H), 3.61 (t, J = 6.1 Hz, 2H), 3.09-3.05 (t, 2H), 1.85-1.75 (quintet, 2H), 1.73-1.62 (quintet, 2H) ppm. LCMS (AM3): rt = 0.739 min, (562.0 $[M + H]^+$), 100% purity. Purification Method 25 |
| Example 4 | 5-((2-(4-((3-chlorobenzyl) amino)butoxy)ethyl) amino)benzo[c][2,6] naphthyridine-8-carboxamide | 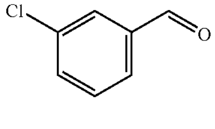 3-chlorobenzaldehyde | $^1H$ NMR (400 MHZ, MeOH-$d_4$) δ: 10.04 (s, 1H), 8.92 (d, J = 5.6 Hz, 1H), 8.73 (d, J = 8.6 Hz, 1H), 8.34 (d, J = 1.7 Hz, 1H), 8.29 (d, J = 5.6 Hz, 1H), 7.96 (dd, J = 1.7, 8.3 Hz, 1H), 7.50 (s, 1H), 7.46-7.34 (m, 3H), 4.13 (s, 2H), 4.03-4.01 (t, 2H), 3.88-3.86 (m, 2H), 3.62 (t, J = 6.0 Hz, 2H), 3.07-3.03 (m, 2H), 1.83-1.75 (quintet, 2H), 1.71-1.63 (m, 2H) ppm. LCMS (AM3): rt = 0.683 min, (478.0 $[M + H]^+$), 100% purity. Purification Method 26 |
| Example 6 | 5-((2-(4-(((2-chloro-2'-(hydroxymethyl)-[1,1'-biphenyl]-4-yl)methyl)amino) butoxy)ethyl)amino) benzo[c][2,6] naphthyridine-8-carboxamide | 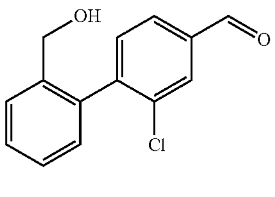 [SMILES: O=Cc1ccc(-c2ccccc2CO)c(Cl)c1] 2-Chloro-2'-(hydroxymethyl)-[1,1'-biphenyl]-4-carbaldehyde | $^1H$ NMR (400 MHZ, MeOH-$d_4$) δ: 10.06 (s, 1H), 8.96 (d, J = 5.6 Hz, 1H), 8.76 (d, J = 8.8 Hz, 1H), 8.39 (s, 1H), 8.35 (d, J = 5.6 Hz, 1H), 8.00 (dd, J = 1.6, 8.4 Hz, 1H), 7.63 (s, 1H), 7.61-7.58 (d, 1H), 7.44-7.39 (t, 2H), 7.38-7.30 (m, 2H), 7.08 (d, J = 7.4 Hz, 1H), 4.41 (d, J = 13.2 Hz, 1H), 4.27 (d, J = 13.2 Hz, 1H), 4.19 (s, 2H), 4.06 (t, J = 5.2 Hz, 2H), 3.90 (t, J = 5.2 Hz, 2H), 3.63 (t, J = 6.0 Hz, 2H), 3.09 (t, J = 8.0 Hz, 2H), 1.87-1.79 (quin, 2H), 1.73-1.66 (quin, 2H) ppm. |

TABLE 1-continued

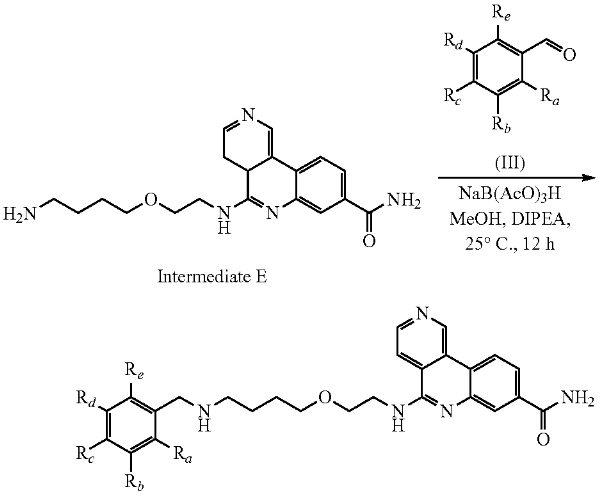

| Example No. | Chemical IUPAC name | Compound (III) | Analytical |
|---|---|---|---|
| | | 1.345 | LCMS (AM3): rt = 0.719 min, (584.0 $[M + H]^+$), 99.5% purity Purification Method 28 |
| Example 7 | 5-((2-(4-((3-fluoro-4-(trifluoromethoxy) benzyl)amino) butoxy)ethyl)amino) benzo[c][2,6] naphthyridine-8-carboxamide | 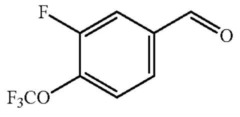 [SMILES: O=Cc1ccc(OC(F)(F)F)c(F)c1] 3-fluoro-4-(trifluoromethoxy) benzaldehyde | $^1$H NMR (400 MHz, MeOH-$d_4$) δ: 10.07 (s, 1H), 8.95 (d, J = 5.5 Hz, 1H), 8.77 (d, J = 8.4 Hz, 1H), 8.37 (d, J = 1.6 Hz, 1H), 8.34-8.32 (d, 1H), 8.00 (dd, J = 1.7, 8.5 Hz, 1H), 7.55-7.47 (m, 2H), 7.38-7.36 (m, 1H), 4.19 (s, 2H), 4.06-4.03 (t, 2H), 3.90-3.87 (t, 2H), 3.62 (t, J = 6.1 Hz, 2H), 3.09-3.05 (dd, 2H), 1.85-1.77 (m, 2H), 1.70-1.64 (quintet, 2H) ppm. LCMS (AM3): rt = 0.746 min, (546.4 $[M + H]^+$), 100% purity. Purification Method 27 |
| Example 8 | 5-((2-(4-((3-chloro-4-(trifluoromethyl) benzyl)amino) butoxy)ethyl)amino) benzo[c][2,6] naphthyridine-8-carboxamide | 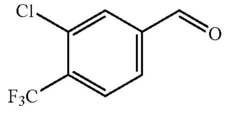 3-chloro-4-(trifluoromethyl) benzaldehyde | $^1$H NMR (400 MHZ, MeOH-$d_4$) δ: 10.08 (s, 1H), 8.97 (d, J = 5.7 Hz, 1H), 8.77 (d, J = 8.6 Hz, 1H), 8.38-8.37 (d, 1H), 8.35 (d, J = 5.5 Hz, 1H), 8.01 (dd, J = 1.8, 8.5 Hz, 1H), 7.85 (d, J = 8.2 Hz, 1H), 7.76 (s, 1H), 7.58 (d, J = 8.1 Hz, 1H), 4.24 (s, 2H), 4.07-4.05 (t, 2H), 3.90-3.88 (t, 2H), 3.64-3.61 (t, 2H), 3.10-3.06 (dd, 2H), 1.87-1.79 (m, 2H), 1.71-1.63 (m, 2H) ppm. LCMS (AM3): rt = 0.755 min, (546.4 $[M + H]^+$), 100% purity. Purification Method 27 |
| Example 9 | 5-((2-(4-((3-chloro-4-cyclopropylbenzyl) amino)butoxy) ethyl)amino)benzo [c][2,6]naphthyridine-8-carboxamide | 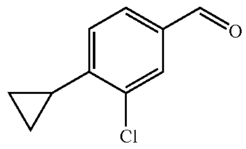 3-Chloro-4-cyclopropylbenzaldehyde 1.202 | $^1$H NMR (400 MHZ, MeOH-$d_4$) δ: 10.06 (s, 1H), 8.95 (d, J = 5.8 Hz, 1H), 8.76 (d, J = 8.5 Hz, 1H), 8.37 (d, J = 1.8 Hz, 1H), 8.33 (d, J = 5.8 Hz, 1H), 8.00 (dd, J = 1.6, 8.4 Hz, 1H), 7.47 (d, J = 2.0 Hz, 1H), 7.26 (dd, J = 1.9, 7.9 Hz, 1H), 7.03 (d, J = 8.0 Hz, 1H), 4.07 (s, 2H), 4.04 (t, J = 5.3 Hz, 2H), 3.90-3.86 (t, 2H), 3.61 (t, J = 6.0 Hz, 2H), 3.05-2.99 (m, 2H), 2.23-2.15 (m, 1H), 1.84-1.74 (m, 2H), 1.72-1.62 (m, 2H), 1.08-1.01 (m, 2H), 0.71-0.66 (m, 2H) ppm. LCMS (AM3): rt = 0.727 min, (518.1 $[M + H]^+$), 100% purity. Purification Method 29 |

TABLE 1-continued

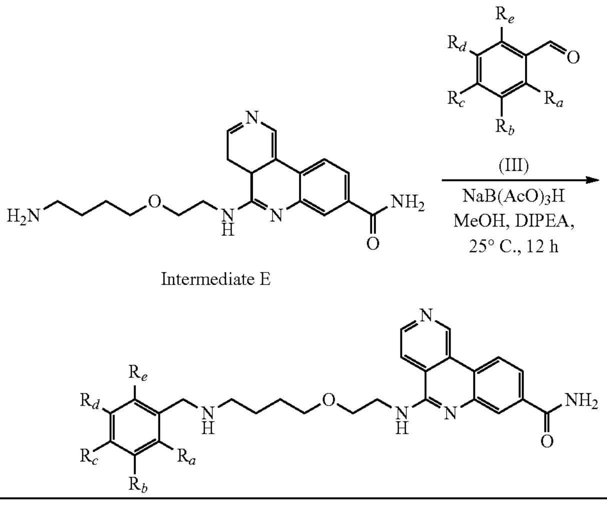

| Example No. | Chemical IUPAC name | Compound (III) | Analytical |
|---|---|---|---|
| Example 10 | 5-((2-(4-((3-chloro-4-cyclobutoxybenzyl)amino)butoxy)ethyl)amino)benzo[c][2,6]naphthyridine-8-carboxamide | 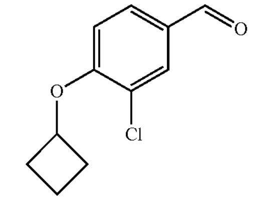 [SMILES: O=Cc1ccc(OC2CCC2)c(Cl)c1] 3-chloro-4-cyclobutoxybenzaldehyde 1.32 | $^1$H NMR (400 MHZ, MeOH-$d_4$) δ: 10.06 (s, 1H), 8.96 (d, J = 5.8 Hz, 1H), 8.76 (d, J = 8.5 Hz, 1H), 8.40-8.30 (m, 2H), 8.00 (dd, J = 1.6, 8.4 Hz, 1H), 7.47 (d, J = 2.3 Hz, 1H), 7.28 (dd, J = 2.0, 8.4 Hz, 1H), 6.92 (d, J = 8.4 Hz, 1H), 4.73 (m, J = 7.0 Hz, 1H), 4.05-4.03 (m, 4H), 3.88 (t, J = 5.2 Hz, 2H), 3.61 (t, J = 6.0 Hz, 2H), 3.02-2.98 (m, 2H), 2.53-2.43 (m, 2H), 2.23-2.09 (m, 2H), 1.94-1.62 (m, 6H) ppm. LCMS (AM3): rt = 0.737 min, (548.1 [M + H]$^+$), 100% purity. Purification Method 27 |
| Example 11 | 5-((2-(4-((3-chloro-4-(cyclopentyloxy)benzyl)amino)butoxy)ethyl)amino)benzo[c][2,6]naphthyridine-8-carboxamide | 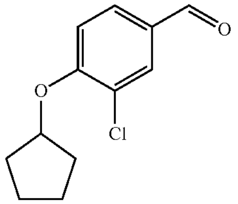 [SMILES: O=Cc1ccc(OC2CCCC2)c(Cl)c1] 3-chloro-4-(cyclopentyloxy)benzaldehyde 1.33 | $^1$H NMR (400 MHZ, MeOH-$d_4$) δ: 10.06 (s, 1H), 8.95 (d, J = 5.6 Hz, 1H), 8.76 (d, J = 8.6 Hz, 1H), 8.37 (d, J = 1.6 Hz, 1H), 8.32 (d, J = 5.6 Hz, 1H), 8.00 (dd, J = 1.6, 8.4 Hz, 1H), 7.46 (d, J = 2.2 Hz, 1H), 7.30 (dd, J = 2.2, 8.4 Hz, 1H), 7.08 (d, J = 8.6 Hz, 1H), 4.90-4.89 (m, 1H), 4.04-4.04 (m, 4H), 3.89-3.86 (t, 2H), 3.62 (t, J = 6.0 Hz, 2H), 3.03-2.99 (t, 2H), 1.97-1.90 (m, 2H), 1.86-1.73 (m, 6H), 1.70-1.62 (m, 4H) ppm. LCMS (AM3): rt = 0.779 min, (562.1 [M + H]$^+$), 100% purity Purification Method 30 |
| Example 12 | 5-((2-(4-((3-chloro-4-cyclopropoxybenzyl)amino)butoxy)ethyl)amino)benzo[c][2,6]naphthyridine-8-carboxamide | 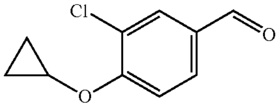 [SMILES: O=Cc1ccc(OC2CC2)c(Cl)c1] 3-Chloro-4-cyclopropoxybenzaldehyde 1.90 | $^1$H NMR (400 MHZ, MeOH-$d_4$) δ: 10.06 (s, 1H), 8.95 (d, J = 5.6 Hz, 1H), 8.76 (d, J = 8.6 Hz, 1H), 8.37-8.36 (d, 1H), 8.33-8.31 (d, 1H), 7.99 (dd, J = 1.7, 8.3 Hz, 1H), 7.46 (d, J = 2.2 Hz, 1H), 7.43-7.41 (m, 1H), 7.36-7.35 (m, 1H), 4.05-4.03 (m, 4H), 3.91-3.84 (m, 3H), 3.62 (t, J = 6.0 Hz, 2H), 3.05-2.98 (m, 2H), 1.84-1.74 (m, 2H), 1.74-1.64 (m, 2H), 0.89-0.81 (m, 2H), 0.75-0.70 (m, 2H) ppm. LCMS (AM3): rt = 0.737 min, (534.1 [M + H]$^+$), 100% purity Purification Method 37 |
| Example 23 | 5-((2-(4-((3-(hydroxymethyl)-4-(trifluoromethoxy)benzyl)amino)butoxy)ethyl)amino)benzo[c][2,6]naphthyridine-8-carboxamide | 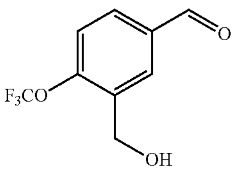 [SMILES: O=Cc1ccc(OC(F)(F)F)c(CO)c1] | $^1$H NMR (400 MHZ, MeOH-$d_4$) δ: 10.02 (s, 1H), 8.95 (d, J = 5.6 Hz, 1H), 8.72 (d, J = 8.6 Hz, 1H), 8.39-8.35 (m, 2H), 8.00 (dd, J = 1.6, 8.4 Hz, 1H), 7.74 (d, J = 2.1 Hz, 1H), 7.50-7.44 (m, 1H), 7.37-7.33 (m, 1H), 4.70 (s, 2H), 4.18 (s, 2H), 4.06 (t, J = 5.0 Hz, 2H), 3.89 (t, J = 5.1 Hz, 2H), 3.61 (t, J = 6.0 Hz, 2H), 3.08-3.03 (t, 2H), 1.87-1.77 (m, 2H), 1.71-1.61 (m, 2H) ppm. |

TABLE 1-continued

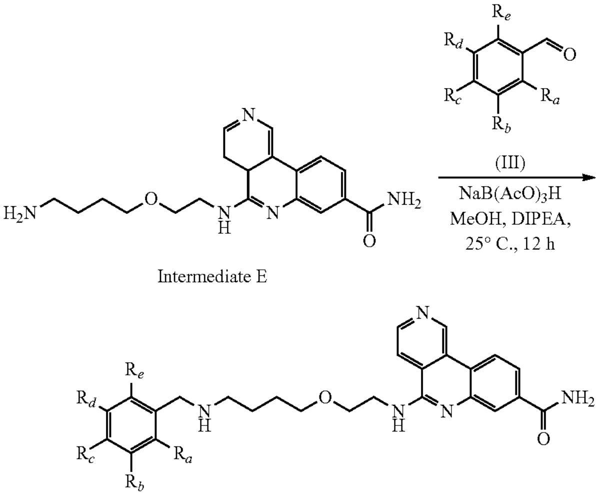

| Example No. | Chemical IUPAC name | Compound (III) | Analytical |
|---|---|---|---|
| | | 3-(Hydroxymethyl)-4-(trifluoromethoxy) benzaldehyde, 1.153 | LCMS (AM3): rt = 0.712 min, (558.2 [M + H]$^+$), 99.3% purity Purification Method 41 |
| Example 35 | 5-((2-(4-((3-(2-hydroxyethoxy)-4-(trifluoromethoxy) benzyl)amino) butoxy)ethyl)amino) benzo[c][2,6] naphthyridine-8-carboxamide | 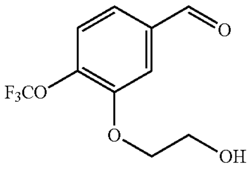 [SMILES: O=Cc1ccc(OC(F)(F)F)c(OCCO)c1] 3-(2-Hydroxyethoxy)-4-(trifluoromethoxy) benzaldehyde 1.402 | $^1$H NMR (400 MHZ, MeOH-d$_4$) δ: 10.05 (br s, 1H), 8.98 (d, J = 3.6 Hz, 1H), 8.74 (d, J = 8.4 Hz, 1H), 8.41-8.40 (m, 2H), 8.01 (dd, J = 8.4 Hz, 1.6 Hz, 1H), 7.34-7.30 (m, 2H), 7.08 (dd, J = 8.0 Hz, 2.4 Hz, 1H), 4.18-4.14 (t, 4H), 4.07 (t, J = 4.8 Hz, 2H), 3.93-3.86 (m, 4H), 3.60 (t, J = 4.8 Hz, 2H), 3.05 (t, J = 8.0 Hz, 2H), 1.85-1.76 (quin, 2H), 1.71-1.62 (quin, 2H) ppm. LCMS (AM3): rt = 0.708 min, (588.2 [M + H]$^+$), 100% purity. Purification Method 50 |
| Example 36 | 5-((2-(4-((4-cyclobutoxy-3-(2-hydroxyethoxy) benzyl)amino) butoxy)ethyl)amino) benzo[c][2,6] naphthyridine-8-carboxamide | 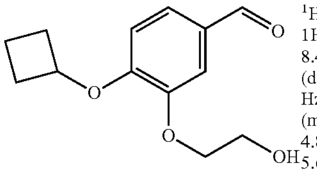 4-Cyclobutoxy-3-(2-hydroxyethoxy)benzaldehyde 1.410 | $^1$H NMR (400 MHZ, MeOH-d$_4$) δ: 9.92 (s, 1H), 8.77 (d, J = 5.6 Hz, 1H), 8.60 (d, J = 8.4 Hz, 1H), 8.21 (d, J = 2.0 Hz, 1H), 8.14 (d, J = 5.6 Hz. 1H), 7.83 (dd, J = 8.4 Hz, 2.0 Hz, 1H), 6.91 (d, J = 1.6 Hz, 1H), 6.75-6.68 (m, 2H), 4.66-4.58 (quin, 1H), 4.04 (t, J = 4.8 Hz, 2H), 3.91-3.84 (m, 4H), 3.79 (t, J = 5.6 Hz, 2H), 3.60-3.53 (m, 4H), 2.55 (t, J = 6.8 Hz, 2H), 2.44-2.36 (m, 2H), 2.18-2.07 (m, 2H), 1.85-1.76 (m, 1H), 1.72-1.55 (m, 5H) ppm. LCMS (AM3): rt = 0.708 min, (574.3 [M + H]$^+$), 96.9 % purity. Purification Method 51 |
| Example 56 | 5-((2-(4-((3-(cyanomethyl)-5-(trifluoromethyl) benzyl)amino) butoxy)ethyl)amino) benzo[c][2,6] naphthyridine-8-carboxamide | 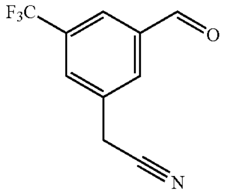 [SMILES: N#CCc1cc(C=O)cc(C(F)(F)F)c1] 2-(3-Formyl-5-(trifluoromethyl) phenyl)acetonitrile 1.469 | $^1$H NMR (400 MHZ, DMSO-d$_6$) δ: 10.06 (s, 1H), 8.85 (d, J = 5.6 Hz, 1H), 8.69 (d, J = 8.8 Hz, 1H), 8.27 (d, J = 5.6 Hz, 1H), 8.22 (s, 1H), 8.17 (br s, 1H), 8.14 (d, J = 2.0 Hz, 1H), 7.98 (t, J = 5.2 Hz, 1H), 7.80 (dd, J = 8.4, 1.8 Hz, 1H), 7.65 (s, 1H), 7.61 (s, 1H), 7.57 (s, 1H), 7.42 (br s, 1H), 4.15 (s, 2H), 3.80-3.77 (m, 2H), 3.76 (s, 2H), 3.77 (t, J = 6.4 Hz, 2H), 3.46 (t, J = 6.4 Hz, 2H), 2.52-2.51 (m, 2H), 1.58-1.44 (m, 4H) ppm. LCMS (AM3): rt = 0.714 min, (551.3 [M + H]$^+$), 99.4% purity Purification Method 68 |

TABLE 1-continued

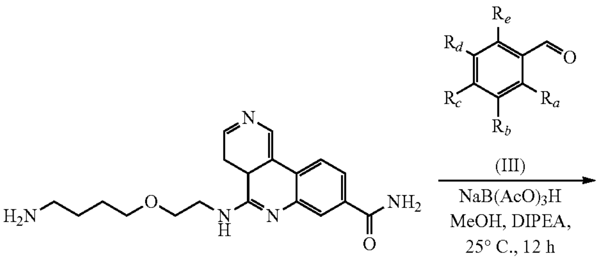

Intermediate E

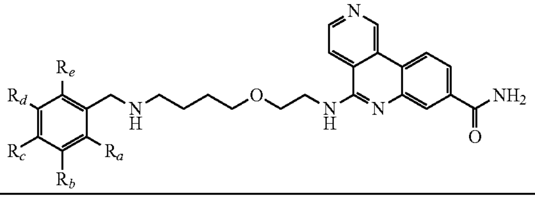

| Example No. | Chemical IUPAC name | Compound (III) | Analytical |
|---|---|---|---|
| Example 57 | 5-((2-(4-((3-(cyanomethyl)-5-fluorobenzyl)amino) butoxy)ethyl)amino) benzo[c][2,6] naphthyridine-8-carboxamide | 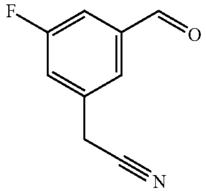 2-(3-Fluoro-5-formylphenyl) acetonitrile 1.472 | $^1$H NMR (400 MHZ, MeOH-$d_4$) δ: 9.89 (s, 1H), 8.76 (d, J = 6.0 Hz, 1H), 8.57 (d, J = 8.4 Hz, 1H), 8.48 (br s, 1H), 8.18 (d, J = 1.6 Hz, 1H), 8.10 (d, J = 5.6 Hz, 1H), 7.80 (dd, J = 8.4, 1.8 Hz, 1H), 7.25 (s, 1H), 7.17 (d, J = 9.2 Hz, 2H), 4.09 (s, 2H), 3.95 (s, 2H), 3.90 (t, J = 5.6 Hz, 2H), 3.81 (t, J = 5.6 Hz, 2H), 3.62 (t, J = 6.0 Hz, 2H), 3.03 (t, J = 6.0 Hz, 2H), 1.84-1.76 (quin, 2H), 1.72-1.66 (quin, 2H) ppm. LCMS (AM3): rt = 0.672min, (501.3 [M + H]$^+$), 100% purity Purification Method 68 |
| Example 58 | 5-((2-(4-((3-(cyanomethyl)-5-methylbenzyl) amino)butoxy)ethyl) amino)benzo[c][2,6] naphthyridine-8-carboxamide | 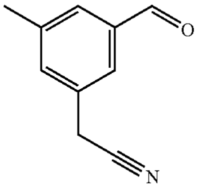 2-(3-Formyl-5-methylphenyl) acetonitrile 1.475 | $^1$H NMR (400 MHZ, MeOH-$d_4$) δ: 9.91 (s, 1H), 8.77 (d, J = 5.6 Hz, 1H), 8.59 (d, J = 8.4 Hz, 1H), 8.52 (br s, 1H), 8.19 (d, J = 1.6 Hz, 1H), 8.11 (d, J = 5.6 Hz, 1H), 7.81 (dd, J = 8.4, 1.6, Hz, 1H), 7.21-7.16 (m, 3H), 4.01 (s, 2H), 3.90 (t, J = 5.6 Hz, 2H), 3.86 (s, 2H), 3.81 (t, J = 5.6 Hz, 2H), 3.62 (t, J = 5.8 Hz, 2H), 3.02 (t, J = 7.2 Hz, 2H), 2.34 (s, 3H), 1.84-1.75 (quin, 2H), 1.72-1.65 (quin, 2H) ppm LCMS (AM3): rt = 0.705 min, (497.3 [M + H]$^+$), 100% purity. Purification Method 68 |
| Example 59 | 5-((2-(4-((2-chloro-5-(cyanomethyl) benzyl)amino) butoxy)ethyl)amino) benzo[c][2,6] naphthyridine-8-carboxamide | 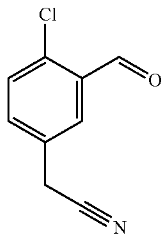 [SMILES: N#CCc1ccc(Cl)c(C=O)c1] 2-(4-Chloro-3-formylphenyl) acetonitrile 1.521 | $^1$H NMR (400 MHZ, MeOH-$d_4$, broad peaks) δ: 9.72 (s, 1H), 8.67 (d, J = 5.2 Hz, 1H), 8.48 (s, 1H), 8.39 (d, J = 8.4 Hz, 1H), 8.07-7.99 (m, 2H), 7.71 (d, J = 8.4 Hz, 1H), 7.49 (s, 1H), 7.42 (d, J = 8.0 Hz, 1H), 7.34 (d, J = 8.4 Hz, 1H), 4.18 (s, 2H), 3.89 (s, 2H), 3.84-3.80 (m, 4H), 3.61 (t, J = 5.6 Hz, 2H), 3.09 (t, J = 7.6 Hz, 2H), 1.92-1.81 (m, 2H), 1.73-1.67 (m, 2H) ppm LCMS (AM3): rt = 0.719 min, (517.3 [M + H]$^+$), 98.6% purity. Purification Method 69 |
| Example 60 | 5-((2-(4-((4-cyano-3-cyclopropylbenzyl) amino)butoxy) ethyl)amino)benzo[c] [2,6]naphthyridine-8-carboxamide | 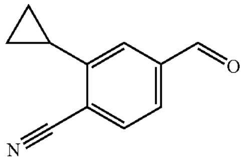 [SMILES: N#Cc1ccc(C=O)cc1C1CC1] | $^1$H NMR (400 MHZ, MeOH-$d_4$) δ: 9.91 (s, 1H), 8.77 (d, J = 5.6 Hz, 1H), 8.59 (d, J = 8.4 Hz, 1H), 8.47 (s, 1H), 8.18 (d, J = 1.6 Hz, 1H), 8.11 (d, J = 5.6 Hz, 1H), 7.81 (dd, J = 8.4, 2.0 Hz, 1H), 7.64 (d, J = 8.0 Hz, 1H), 7.30 (dd, J = 8.0, 1.2 Hz, 1H), 7.10 (s, 1H), 4.07 (s, 2H), 3.90 (t, J = 5.6 Hz, 2H), 3.83 (t, J = 5.6 Hz, 2H), 3.62 (t, J = 6.0 Hz, 2H), 3.01 (t, J = 7.2 Hz, 2H), 2.26-2.19 |

TABLE 1-continued

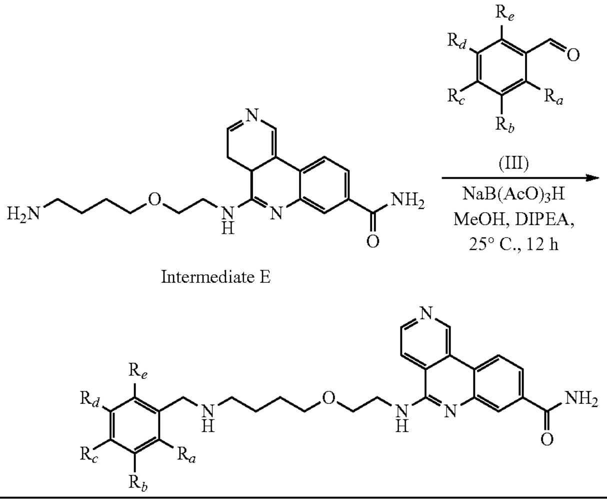

Intermediate E

| Example No. | Chemical IUPAC name | Compound (III) | Analytical |
|---|---|---|---|
| | | 2-Cyclopropyl-4-formylbenzonitrile 1.526 | (m, 1H), 1.83-1.76 (quin, 2H), 1.72-1.65 (quin, 2H), 1.17-1.13 (m, 2H), 0.84-0.80 (m, 2H) ppm<br>LCMS (AM3): rt = 0.709 min, (509.3 $[M + H]^+$), 98.4% purity<br>Purification Method 63 |
| Example 61 | 5-((2-(4-((3-chloro-4-(cyanomethyl) benzyl)amino) butoxy)ethyl)amino) benzo[c][2,6] naphthyridine-8-carboxamide | 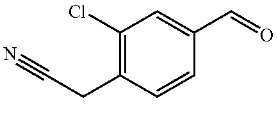 [SMILES: N#CCc1ccc(C=O)cc1Cl]<br>2-(2-Chloro-4-formylphenyl)acetonitrile 1.524 | $^1H$ NMR (400 MHZ, MeOH-$d_4$) δ: 9.86 (s, 1H), 8.74 (d, J = 5.6 Hz, 1H), 8.53 (d, J = 8.4 Hz, 1H), 8.45 (br s, 1H), 8.15 (d, J = 2.0 Hz, 1H), 8.10 (d, J = 5.6 Hz, 1H), 7.78 (dd, J = 8.4, 2.0 Hz, 1H), 7.55-7.53 (m, 2H), 7.38 (d, J = 7.8 Hz, 1H), 4.08 (s, 2H), 3.95 (s, 2H), 3.87 (t, J = 4.8 Hz, 2H), 3.82 (t, J = 5.2 Hz, 2H), 3.61 (t, J = 6.0 Hz, 2H), 3.04 (t, J = 7.2 Hz, 2H), 1.84-1.77 (quin, 2H), 1.72-1.63 (quin, 2H) ppm<br>LCMS (AM3): rt = 0.721 min, (517.3 $[M + H]^+$), 100% purity<br>Purification Method 69 |
| Example 62 | 5-((2-(4-((3-(hydroxymethyl)-4-(2,2,2-trifluoroethoxy) benzyl)amino) butoxy)ethyl)amino) benzo[c][2,6] naphthyridine-8-carboxamide | 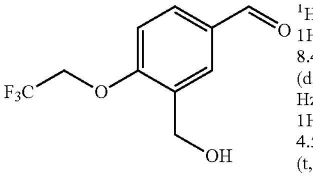<br>3-(Hydroxymethyl)-4-(2,2,2-trifluoroethoxy)benzaldehyde 1.530 | $^1H$ NMR (400 MHZ, MeOH-$d_4$) δ: 9.92 (s, 1H), 8.77 (d, J = 5.6 Hz, 1H), 8.60 (d, J = 8.4 Hz, 1H), 8.54 (s, 1H), 8.20 (s, 1H), 8.12 (d, J = 5.6 Hz, 1H), 7.82 (dd, J = 8.4, 1.6 Hz, 1H), 7.51 (s, 1H), 7.28 (d, J = 8.4 Hz, 1H), 7.01 (d, J = 8.4 Hz, 1H), 4.66 (s, 2H), 4.54 (q, J = 8.4 Hz, 2H), 4.00 (s, 2H), 3.90 (t, J = 5.6 Hz, 2H), 3.81 (t, J = 5.6 Hz, 2H), 3.61 (t, J = 6.0 Hz, 2H), 2.98 (t, J = 7.6 Hz, 2H), 1.82-1.74 (quin, 2H), 1.71-1.64 (quin, 2H) ppm<br>LCMS (AM3): rt = 0.723 min, (572.4 [M + H]+), 100% purity<br>Purification AM70 |
| Example 63 | 5-((2-(4-((3-(hydroxymethyl)-4-isopropoxybenzyl) amino)butoxy)ethyl) amino)benzo[c][2,6] naphthyridine-8-carboxamide | 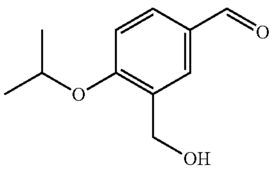<br>3-(Hydroxymethyl)-4-isopropoxybenzaldehyde 1.668 | $^1H$ NMR (400 MHZ, MeOH-$d_4$) δ: 9.90 (s, 1H), 8.76 (d, J = 5.6 Hz, 1H), 8.57 (d, J = 8.4 Hz, 1H), 8.42 (br s, 1H), 8.19 (d, J = 1.6 Hz, 1H), 8.11 (d, J = 6.0 Hz, 1H), 7.81 (dd, J = 8.4, 1.6 Hz, 1H), 7.43 (d, J = 2.0 Hz, 1H), 7.23 (dd, J = 8.4, 2.4 Hz, 1H), 6.92 (d, J = 8.4 Hz, 1H), 4.60-4.56 (m, 3H), 4.01 (s, 2H), 3.89 (t, J = 5.2 Hz, 2H), 3.81 (t, J = 5.2 Hz, 2H), 3.61 (t, J = 6.0 Hz, 2H), 3.01 (t, J = 7.6 Hz, 2H), 1.82-1.76 (m, 2H), 1.72-1.67 (m, 2H), 1.29 (d, J = 6.0 Hz, 6H) ppm<br>LCMS (AM3): rt = 0.734 min, (532.3 $[M + H]^+$), 100% purity<br>Purification AM70 |

TABLE 1-continued

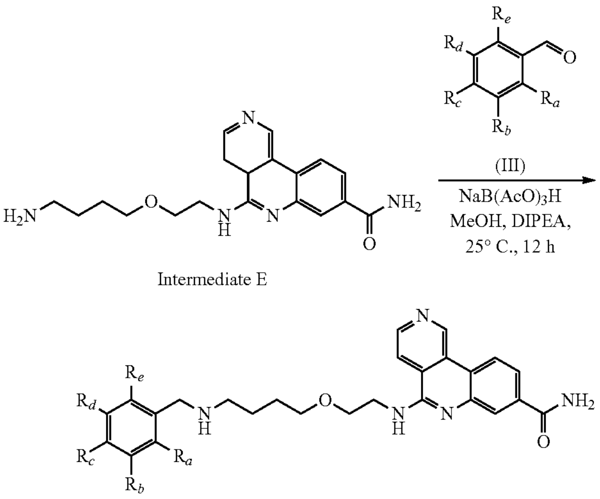

Intermediate E

| Example No. | Chemical IUPAC name | Compound (III) | Analytical |
|---|---|---|---|
| Example 64 | 5-((2-(4-((4-(cyclopentyloxy)-3-(hydroxymethyl) benzyl)amino) butoxy)ethyl)amino) benzo[c][2,6] naphthyridine-8-carboxamide | 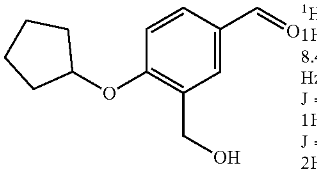 (Cyclopentyloxy)-3-(hydroxymethyl) benzaldehyde 1.671 | $^{1}$H NMR (400 MHZ, MeOH-$d_4$) δ: 9.90 (s, 1H), 8.77 (d, J = 5.6 Hz, 1H), 8.58 (d, J = 8.4 Hz, 1H), 8.52 (br s, 1H), 8.19 (d, J = 2.0 Hz, 1H), 8.12 (d, J = 5.6 Hz, 1H), 7.81 (dd, J = 8.0, 1.6 Hz, 1H), 7.42 (d, J = 1.6 Hz, 1H), 7.22 (dd, J = 8.0, 1.6 Hz, 1H), 6.88 (d, J = 8.8 Hz, 1H), 4.80-4.76 (m, 1H), 4.58 (s, 2H), 4.01 (s, 2H), 3.89 (t, J = 6.4 Hz, 2H), 3.81 (t, J = 6.4 Hz, 2H), 3.61 (t, J = 6.0 Hz, 2H), 3.01 (t, J = 7.6 Hz, 2H), 1.92-1.85 (m, 2H), 1.83-1.55 (m, 10H) ppm LCMS (AM3): rt = 0.563 min, (558.3 [M + H]$^{+}$), 100% purity. Purification AM71 |
| Example 65 | 5-((2-(4-((4-chloro-3-(cyanomethyl) benzyl)amino) butoxy)ethyl)amino) benzo[c][2,6] naphthyridine-8-carboxamide | 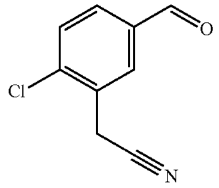 [SMILES: N#CCc1cc(C=O)ccc1Cl] 2-(2-Chloro-5-formylphenyl) acetonitrile 1.478 | $^{1}$H NMR (400 MHZ, MeOH-$d_4$) δ: 10.05 (s, 1H), 8.97 (d, J = 5.6 Hz, 1H), 8.76 (d, J = 8.4 Hz, 1H), 8.40 (d, J = 1.2 Hz, 1H), 8.38 (d, J = 5.6 Hz, 1H), 8.01 (dd, J = 8.4, 1.6 Hz, 1H), 7.64 (d, J = 1.6 Hz, 1H), 7.55 (d, J = 8.0 Hz, 1H), 7.48-7.45 (m, 1H), 4.17 (s, 2H), 4.07 (t, J = 4.8 Hz, 2H), 4.01 (s, 2H), 3.90 (t, J = 5.2 Hz, 2H), 3.61 (t, J = 6.0 Hz, 2H), 3.05 (t, J = 8.0 Hz, 2H), 1.84-1.77 (quin, 2H), 1.70-1.62 (quin, 2H) ppm LCMS (AM3): rt = 0.721min, (517.3 [M + H]$^{+}$), 98.5% purity Purification Method 50 |
| Example 66 | 5-((2-(4-((2-chloro-3-(cyanomethyl) benzyl)amino) butoxy)ethyl)amino) benzo[c][2,6] naphthyridine-8-carboxamide | 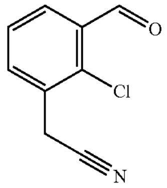 [SMILES: N#CCc1cccc(C=O)c1Cl] 2-(2-Chloro-3-formylphenyl) acetonitrile 1.483 | $^{1}$H NMR (400 MHZ, MeOH-$d_4$) δ: 9.84 (s, 1H), 8.73 (d, J = 6.0 Hz, 1H), 8.53-8.45 (m, 2H), 8.15 (d, J = 1.6 Hz, 1H), 8.08 (d, J = 5.6 Hz, 1H), 7.77 (dd, J = 8.4, 1.6 Hz, 1H), 7.55 (d, J = 7.6 Hz, 1H), 7.48 (d, J = 6.8 Hz, 1H), 7.37 (t, J = 8.0 Hz, 1H), 4.20 (s, 2H), 3.97 (s, 2H), 3.89 (t, J = 6.8 Hz, 2H), 3.82 (t, J = 5.2 Hz, 2H), 3.63 (t, J = 5.8 Hz, 2H), 3.08 (t, J = 8.0 Hz, 2H), 1.88-1.79 (quin, 2H), 1.74-1.66 (quin, 2H) ppm LCMS (AM3): rt = 0.701 min, (517.2 [M + H]$^{+}$), 100% purity Purification AM72 |
| Example 68 | 5-((2-(4-((4-ethoxy-3-(hydroxymethyl) benzyl)amino) butoxy)ethyl)amino) benzo[c][2,6] naphthyridine-8-carboxamide | 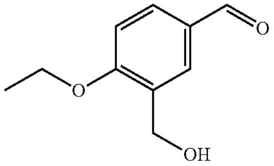 | $^{1}$H NMR (400 MHZ, DMSO-$d_6$) δ: 10.07 (s, 1H), 8.86 (d, J = 5.6 Hz, 1H), 8.71 (d, J = 8.4 Hz, 1H), 8.34 (s, 1H), 8.29 (d, J = 5.6 Hz, 1H), 8.19 (br s, 1H), 8.15 (d, J = 1.6 Hz, 1H), 8.02 ( t, J = 5.2 Hz, 1H), 7.82 (dd, J = 8.4, 1.6 Hz, 1H), 7.43-7.40 (m, 2H), 7.18-7.15 (m, 1H), 6.86 (d, J = 8.4 Hz, 1H), 4.48 (s, 2H), 3.99 (q, J = 7.2 Hz, 2H), 3.80-3.77 (m, 4H), 3.70 (t, J = 5.6 Hz, 2H), 3.46 (t, J = |

TABLE 1-continued

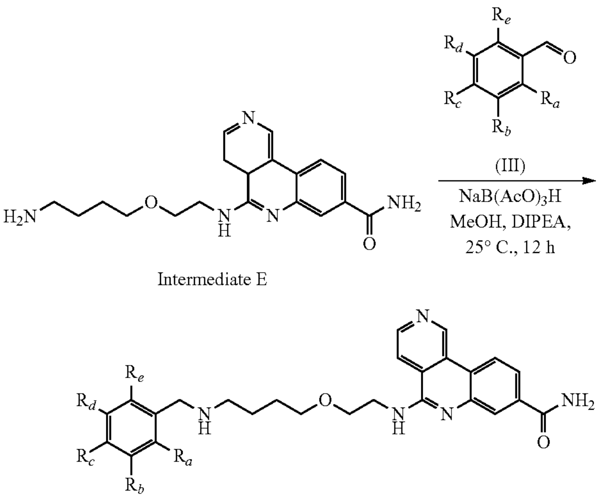

| Example No. | Chemical IUPAC name | Compound (III) | Analytical |
|---|---|---|---|
| | | 4-Ethoxy-3-(hydroxymethyl) benzaldehyde 1.635 | 5.6 Hz, 2H), 2.68-2.62 (m, 2H), 1.60-1.50 (m, 4H), 1.30 (t, J = 6.8 Hz, 3H) ppm LCMS (AM3): rt = 0.710 min, (518.3 $[M + H]^+$), 100% purity Purification Method 68 |
| Example 85 | 5-((2-(4-((3-(hydroxymethyl)-4-(trifluoromethyl) benzyl)amino) butoxy)ethyl)a benzo[c][2,6] naphthyridine-8-carboxamide | 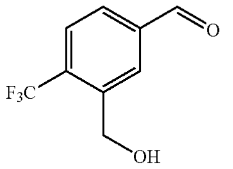 [SMILES: O=Cc1ccc(C(F)(F)F)c(CO)c1] 3-(Hydroxymethyl)-4-(trifluoromethyl) benzaldehyde 1.589 | $^1H$ NMR (400 MHZ, MeOH-$d_4$) δ: 9.89 (s, 1H), 8.78 (d, J = 5.6 Hz, 1H), 8.58 (d, J = 8.4 Hz, 1H), 8.47 (br s, 1H), 8.18 (d, J = 1.6 Hz, 1H), 8.10 (d, J = 5.6 Hz, 1H), 7.87 (s, 1H), 7.80 (dd, J = 8.4, 2.0, Hz, 1H), 7.69 (d, J = 8.0 Hz, 1H), 7.46 (d, J = 8.0 Hz, 1H), 4.80 (s, 2H), 4.17 (s, 2H), 3.90 (t, J = 5.6 Hz, 2H), 3.81 (t, J = 5.6 Hz, 2H), 3.62 (t, J = 6.0 Hz, 2H), 3.06 (t, J = 7.6 Hz, 2H), 1.86-1.78 (quin, 2H), 1.73-1.66 (quin, 2H) ppm LCMS (AM3): rt = 0.707 min, (542.2 $[M + H]^+$), 98.8% purity Purification Method 92 then 72 |
| Example 153 | 5-((2-(4-((3-(cyanomethyl)-5-(methoxymethyl) benzyl)amino) butoxy)ethyl)amino) benzo[c][2,6] naphthyridine-8-carboxamide | 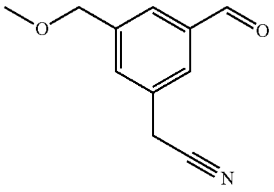 2-(3-Formyl-5-(methoxymethyl) phenyl)acetonitrile 1.803 | $^1H$ NMR (400 MHZ, MeOH-$d_4$) δ: 9.86 (s, 1H), 8.74 (d, J = 5.6 Hz, 1H), 8.54 (d, J = 8.4 Hz, 1H), 8.17 (d, J = 2.0 Hz, 1H), 8.09 (d, J = 5.6 Hz, 1H), 7.80 (dd, J = 8.4, 2.0 Hz, 1H), 7.20-7.17 (m, 3H), 4.41 (s, 2H), 3.88 (t, J = 5.6 Hz, 2H), 3.85 (s, 2H), 3.79 (t, J = 5.6 Hz, 2H), 3.64 (s, 2H), 3.55 (t, J = 6.0 Hz, 2H), 3.36 (s, 3H), 2.55 (t, J = 6.8 Hz, 2H), 1.61-1.57 (m, 4H) ppm LCMS (AM3): rt = 0.689 min, (527.1 $[M + H]^+$), 98.4% purity Purification Method 149 |
| Example 156 | 5-((2-(4-((3-cyano-5-(trifluoromethoxy) benzyl)amino) butoxy)ethyl)amino) benzo[c][2,6] naphthyridine-8-carboxamide | 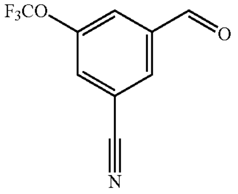 [SMILES: N#Cc1cc(C=O)cc(OC(F)(F)F)c1] 3-Formyl-5-(trifluoromethoxy) benzonitrile 1.714 | $^1H$ NMR (400 MHZ, MeOH-$d_4$) δ: 9.87 (s, 1H), 8.74 (d, J = 5.6 Hz, 1H), 8.55 (d, J = 8.4 Hz, 1H), 8.17 (d, J = 1.6 Hz, 1H), 8.09 (d, J = 5.6 Hz, 1H), 7.80 (dd, J = 8.4 Hz, 1.6 Hz, 1H), 7.65 (s, 1H), 7.55 (s, 2H), 3.89 (t, J = 5.6 Hz, 2H), 3.80 (t, J = 5.6 Hz, 2H), 3.73 (s, 2H), 3.57 (t, J = 6.0 Hz, 2H), 2.54 (t, J = 6.8 Hz, 2H), 1.65-1.55 (m, 4H) ppm LCMS (AM3): rt = 0.748 min, (553.2 $[M + H]^+$), 99.2% purity Purification Method 153 |

TABLE 1-continued

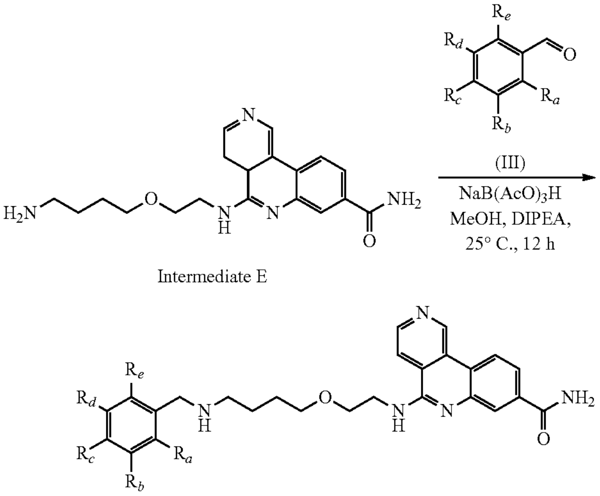

| Example No. | Chemical IUPAC name | Compound (III) | Analytical |
|---|---|---|---|
| Example 157 | 5-((2-(4-((3-(2-hydroxyethoxy)-5-(trifluoromethoxy)benzyl)amino)butoxy)ethyl)amino)benzo[c][2,6]naphthyridine-8-carboxamide | 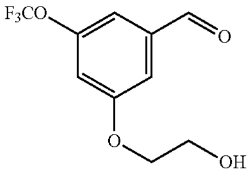 [SMILES: O=Cc1cc(OCCO)cc(OC(F)(F)F)c1] 3-(2-Hydroxyethoxy)-5-(trifluoromethoxy)benzaldehyde 1.718 | $^{1}H$ NMR (400 MHZ, MeOH-$d_4$) δ: 9.94 (s, 1H), 8.78 (d, J = 5.6 Hz, 1H), 8.61 (d, J = 8.4 Hz, 1H), 8.47 (s, 1H), 8.21 (d, J = 1.6 Hz, 1H), 8.13 (dd, J = 5.6 Hz, 0.8 Hz, 1H), 7.82 (dd, J = 8.4 Hz, 2.0 Hz, 1H), 7.01 (d, J = 2.0 Hz, 1H), 6.94 (s, 1H), 6.91 (s, 1H), 4.08-4.06 (m, 4H), 3.92 (t, J = 5.6 Hz, 2H), 3.87 (J = 5.6 Hz, 2H), 3.82 (t, J = 5.6 Hz, 2H), 3.62 (t, J = 6.0 Hz, 2H), 3.03 (t, J = 6.8 Hz, 2H), 1.84-1.76 (quin, 2H), 1.72-1.66 (quin, 2H) ppm LCMS (AM3): rt = 0.729 min, (588.3 [M + H]$^+$), 99.4% purity Purification Method 154 |
| Example 158 | 5-((2-(4-((3-(oxazol-4-ylmethyl)-5-(trifluoromethoxy)benzyl)amino)butoxy)ethyl)amino)benzo[c][2,6]naphthyridine-8-carboxamide | 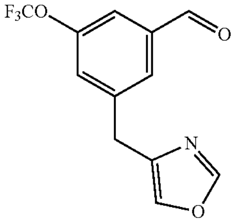 [SMILES: O=Cc1cc(Cc2cocn2)cc(OC(F)(F)F)c1] 3-(Oxazol-4-ylmethyl)-5-(trifluoromethoxy)benzaldehyde 1.712 | $^{1}H$ NMR (400 MHZ, MeOH-$d_4$) δ: 9.92 (s, 1H), 8.77 (d, J = 5.6 Hz, 1H), 8.58 (d, J = 8.4 Hz, 1H), 8.46 (s, 1H), 8.20 (d, J = 1.6 Hz, 1H), 8.16 (s, 1H), 8.12 (d, J = 5.6 Hz, 1H), 7.81 (dd, J = 8.4 Hz, 2.0 Hz, 1H), 7.77 (s, 1H), 7.33 (s, 1H), 7.24 (d, J = 6.4 Hz, 2H), 4.09 (s, 2H), 3.94 (s, 2H), 3.92 (t, J = 5.6 Hz, 2H), 3.83 (t, J = 5.6 Hz, 2H), 3.62 (t, J = 6.0 Hz, 2H), 3.04 (t, J = 7.6 Hz, 2H), 1.84-1.76 (quin, 2H), 1.74-1.66 (quin, 2H) ppm LCMS (AM3): rt = 0.765 min, (609.2 [M + H]$^+$), 100% purity. Purification Method 155 |
| Example 159 | 5-((2-(4-((3-(oxazol-5-ylmethyl)-5-(trifluoromethoxy)benzyl)amino)butoxy)ethyl)amino)benzo[c][2,6]naphthyridine-8-carboxamide | 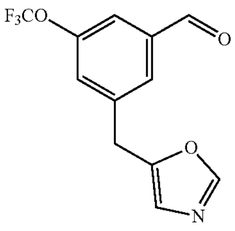 [SMILES: O=Cc1cc(Cc2cnco2)cc(OC(F)(F)F)c1] | $^{1}H$ NMR (400 MHZ, MeOH-$d_4$) δ: 9.93 (s, 1H), 8.78 (d, J = 5.6 Hz, 1H), 8.62 (d, J = 8.4 Hz, 1H), 8.48 (s, 1H), 8.22 (d, J = 1.6 Hz, 1H), 8.13-8.10 (m, 2H), 7.82 (dd, J = 8.4 Hz, 2.0 Hz, 1H), 7.31-7.25 (m, 3H), 6.93 (s, 1H), 4.13 (s, 2H), 4.08 (s, 2H), 3.92 (t, J = 5.6 Hz, 2H), 3.81 (t, J = 5.6 Hz, 2H), 3.62 (t, J = 6.0 Hz, 2H), 3.02 (t, J = 7.2 Hz, 2H), 1.82-1.75 (m, 2H), 1.71-1.64 (m, 2H) ppm LCMS (AM3): rt = 0.755 min, (609.2 |

TABLE 1-continued

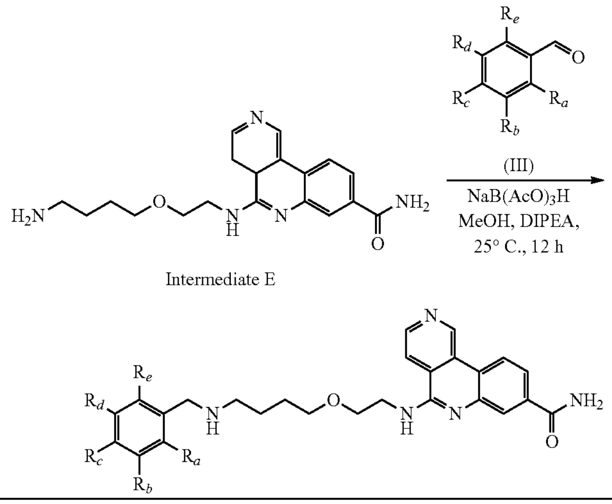

Intermediate E

| Example No. | Chemical IUPAC name | Compound (III) | Analytical |
|---|---|---|---|
| | | 3-(Oxazol-5-ylmethyl)-5-(trifluoromethoxy)benzaldehyde 1.713 | [M + H]$^+$), 100% purity Purification Method 155 |
| Example 165 | 5-((2-(4-((3-(2-hydroxyethyl)-5-(trifluoromethoxy) benzyl)amino) butoxy)ethyl)amino) benzo[c][2,6] naphthyridine-8-carboxamide | 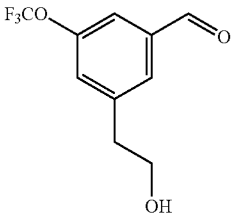 [SMILES: O=Cc1cc(CCO)cc(OC(F)(F)F)c1] 3-(2-Hydroxyethyl)-5-(trifluoromethoxy)benzaldehyde 1.723 | $^1$H NMR (400 MHZ, MeOH-$d_4$) δ: 9.92 (s, 1H), 8.77 (d, J = 5.6 Hz, 1H), 8.59 (d, J = 8.4 Hz, 1H), 8.46 (br s, 1H), 8.20 (d, J = 2.0 Hz, 1H), 8.12 (d, J = 4.4 Hz, 1H), 7.81 (dd, J = 8.4 Hz, 2.0 Hz, 1H), 7.29 (s, 1H), 7.23 (s, 2H), 4.10 (s, 2H), 3.91 (t, J = 5.6 Hz, 2H), 3.83-3.80 (t, 2H), 3.80-3.77 (t, 2H), 3.62 (t, J = 6.0 Hz, 2H), 3.05 (t, J = 7.6 Hz, 2H), 2.86 (t, J = 6.4 Hz, 2H), 1.84-1.76 (quin, 2H), 1.72-1.66 (quin, 2H) ppm LCMS (AM3): rt = 0.732 min, (572.2 [M + H]$^+$), 100% purity Purification Method 160 |

Example 2

5-((2-(4-(((2-Chloro-[1,1'-biphenyl]-4-yl)methyl) amino)butoxy)ethyl)amino)benzo[c][2,6]naphthyridine-8-carboxamide

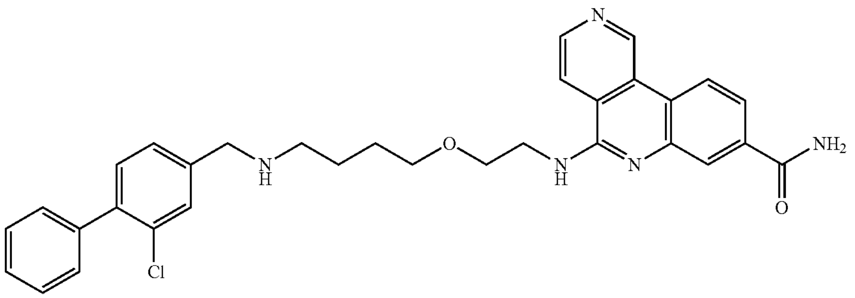 [SMILES: NC(=O)c1ccc2c(c1)nc(NCCOCCCCNCc1ccc(-c3ccccc3)c(Cl)c1)c1ccncc12]

A mixture of Intermediate E (150 mg, 0.385 mmol, HCl salt), DIPEA (44.52 mg, 0.344 mmol) and 3-chloro-4-phenylbenzaldehyde (83 mg, 0.383 mmol) in MeOH (4 mL) was stirred at 25° C. for 12 h, then sodium cyanoborohydride (75 mg, 1.19 mmol) was added. The mixture was stirred at 25° C. for 3 h. The mixture was concentrated in vacuo and purified (PM24) to afford Example 2 (63.38 mg, 0.0949 mmol, 24.7% yield, TFA salt) as a yellow solid.

LCMS (AM3): rt=0.786 min, (554.1 [M+H]$^+$), 100% purity.

$^1$H NMR (400 MHz, MeOD) δ: 10.07 (s, 1H), 8.98 (d, J=5.6 Hz, 1H), 8.77 (d, J=8.8 Hz, 1H), 8.43-8.37 (m, 2H), 8.03 (dd, J=8.4, 1.6 Hz, 1H), 7.63 (d, J=1.6 Hz, 1H), 7.46-7.35 (m, 7H), 4.19 (s, 2H), 4.07 (t, J=5.2 Hz, 2H), 3.92-3.87 (t, 2H), 3.63 (t, J=6.0 Hz, 2H), 3.12-3.05 (m, 2H), 1.88-1.77 (m, 2H), 1.75-1.64 (m, 2H) ppm The following examples in Table 2 were made with non-critical changes or substitutions to the exemplified procedure in Example 2, that would be understood by one skilled in the art using intermediate E and compounds of formula (III).

TABLE 2

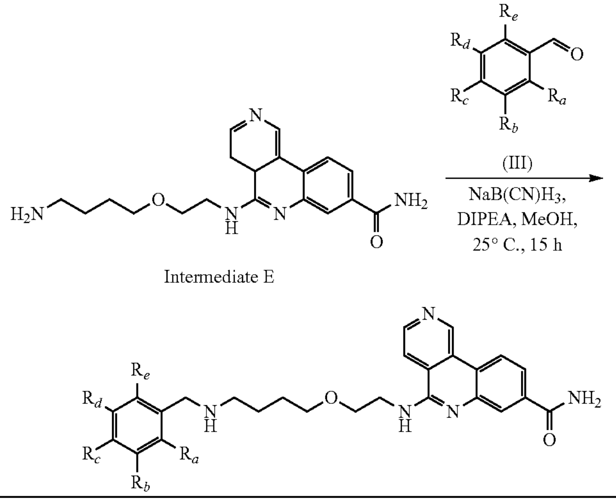

| Example No. | Chemical IUPAC name | Compound (III) | Analytical |
|---|---|---|---|
| Example 5 | 5-((2-(4-((3-cyano-4-(trifluoromethoxy)benzyl)amino)butoxy)ethyl)amino)benzo[c][2,6]naphthyridine-8-carboxamide | 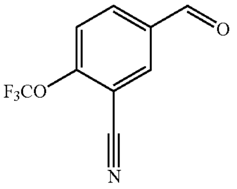 [SMILES: N#Cc1cc(C=O)ccc1OC(F)(F)F] 5-Formyl-2-(trifluoromethoxy)benzonitrile 1.136 | $^1$H NMR (400 MHZ, MeOH-$d_4$) δ: 10.06 (s, 1H), 8.94 (d, J = 4.6 Hz, 1H), 8.76 (d, J = 8.8 Hz, 1H), 8.35 (s, 1H), 8.31-8.29 (d, 1H), 7.99 (d, J = 2.2 Hz, 2H), 7.90 (d, J = 8.8 Hz, 1H), 7.65 (d, J = 8.6 Hz, 1H), 4.25 (s, 2H), 4.04 (t, J = 4.8 Hz, 2H), 3.90-3.87 (t, 2H), 3.63 (t, J = 6.0 Hz, 2H), 3.11-3.07 (dd, 2H), 1.85-1.78 (quintet, 2H), 1.72-1.63 (quintet, 2H) ppm. LCMS (AM3): rt = 0.715 min, (553.1 [M + H]$^+$), 98.1% purity. Purification Method 27 |
| Example 13 | 5-((2-(4-((3-chloro-5-(hydroxymethyl)benzyl)amino)butoxy)ethyl)amino)benzo[c][2,6]naphthyridine-8-carboxamide | 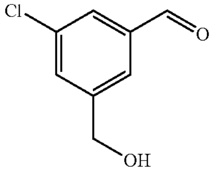 [SMILES: O=Cc1cc(Cl)cc(CO)c1] 3-Chloro-5-(hydroxymethyl)benzaldehyde | $^1$H NMR (400 MHZ, MeOH-$d_4$) δ: 10.06 (s, 1H), 8.97 (d, J = 5.4 Hz, 1H), 8.76 (d, J = 8.3 Hz, 1H), 8.43-8.35 (m, 2H), 8.02 (dd, J = 1.5, 8.6 Hz, 1H), 7.43 (m, 1H), 7.37 (d, J = 9.3 Hz, 2H), 4.62 (s, 2H), 4.13 (s, 2H), 4.07 (t, J = 5.0 Hz, 2H), 3.89 (t, J = 5.1 Hz, 2H), 3.61 (t, J = 6.0 Hz, 2H), 3.06-3.02 (m, 2H), 1.85-1.75 (m, 2H), 1.70-1.60 (m, 2H) ppm. LCMS (AM3): rt = 0.663 min, (508.0 [M + H]$^+$), 100% purity. Purification Method 31 |
| Example 14 | 5-((2-(4-((3-(2-hydroxyethyl)benzyl)amino)butoxy)ethyl)amino)benzo[c][2,6]naphthyridine-8-carboxamide | 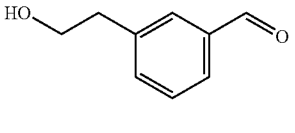 [SMILES: O=Cc1cccc(CCO)c1] 3-(2-hydroxyethyl)benzaldehyde | $^1$H NMR (400 MHZ, MeOH-$d_4$) δ:10.07 (br s, 1H), 8.98 (s, 1H), 8.75 (d, J = 8.5 Hz, 1H), 8.41 (s, 1H), 8.41-8.39 (d, 1H), 8.02 (dd, J = 1.8, 8.5 Hz, 1H), 7.37-7.26 (m, 4H), 4.12 (s, 2H) 4.12-4.06 (t, 2H), 3.89 (t, J = 5.2 Hz, 2H), 3.77 (t, J = 6.8 Hz, 2H), 3.60 (t, J = 6.0 Hz, 2H), 3.02 (m, J = 6.0 Hz, 2H), 2.84 (t, J = 6.8 Hz, 2H), 1.85-1.74 (m, 2H), 1.69-1.61 (m, 2H) ppm. LCMS (AM3): rt = 0.648 min, (488.1 [M + H]$^+$), 99.2% purity Purification Method 32 |

TABLE 2-continued

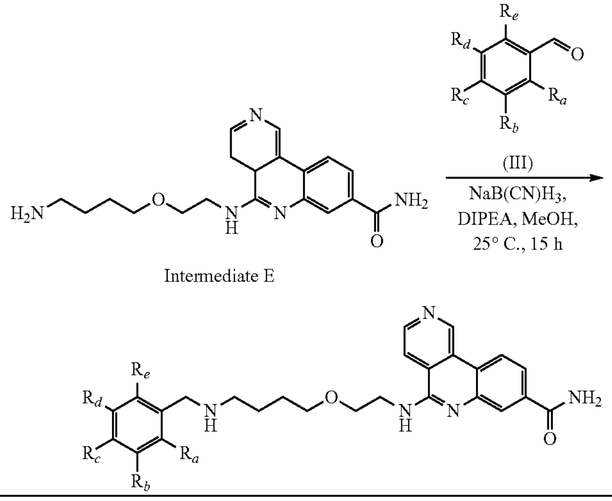

Intermediate E

| Example No. | Chemical IUPAC name | Compound (III) | Analytical |
|---|---|---|---|
| Example 18 | 5-((2-(4-((3-cyano-4-cyclopropylbenzyl)amino)butoxy)ethyl)amino)benzo[c][2,6]naphthyridine-8-carboxamide | 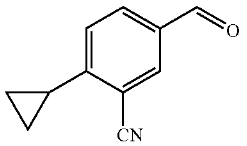 2-cyclopropyl-5-formylbenzonitrile 1.52 | $^1$H NMR (400 MHZ, MeOH-$d_4$) δ: 10.08 (s, 1H), 8.99 (d, J = 5.1 Hz, 1H), 8.78 (d, J = 8.6 Hz, 1H), 8.41 (s, 1H), 8.41-8.39 (d, 1H), 8.04 (dd, J = 1.3, 8.4 Hz, 1H), 7.75 (d, J = 1.7 Hz, 1H), 7.64-7.61 (dd, 1H), 7.11 (d, J = 8.3 Hz, 1H), 4.15 (s, 2H), 4.08 (t, J = 5.0 Hz, 2H), 3.91-3.88 (t, 2H), 3.61 (t, J = 6.1 Hz, 2H), 3.06-3.02 (t, 2H), 2.30-2.21 (septet, 1H), 1.85-1.75 (quintet, 2H), 1.69-1.61 (quintet, 2H), 1.20-1.15 (m, 2H), 0.88-0.82 (m, 2H) ppm. LCMS (AM3): rt = 0.703 min, (509.1 [M + H]$^+$), 97.4% purity. Purification Method 37 |
| Example 19 | 5-((2-(4-((3-(2-hydroxyethoxy)benzyl)amino)butoxy)ethyl)amino)benzo[c][2,6]naphthyridine-8-carboxamide | 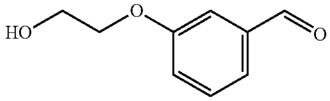 [SMILES: O=Cc1cccc(OCCO)c1] 3-(2-hydroxyethoxy)benzaldehyde | $^1$H NMR (400 MHZ, MeOH-$d_4$) δ: 10.04 (br s, 1H), 8.97 (br s, 1H), 8.73 (d, J = 8.6 Hz, 1H), 8.41 (br s, 2H), 8.01 (d, J = 8.1 Hz, 1H), 7.32 (t, J = 7.6 Hz, 1H), 7.05-6.94 (m, 3H), 4.10-4.05 (m, 6H), 3.90-3.85 (m, 4H), 3.60 (t, J = 5.5 Hz, 2H), 3.01 (t, J = 7.5 Hz, 2H), 1.85-1.72 (m, 2H), 1.70-1.58 (m, 2H) ppm. LCMS (AM3): rt = 0.647 min, (504.1 [M + H]$^+$), 100% purity Purification Method 31 |
| Example 20 | 5-((2-(4-((3-cyano-4-cyclobutoxybenzyl)amino)butoxy)ethyl)amino)benzo[c][2,6]naphthyridine-8-carboxamide | 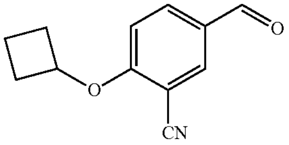 [SMILES: N#Cc1cc(C=O)ccc1OC1CCC1] 2-cyclobutoxy-5-formylbenzonitrile 1.47 | $^1$H NMR (400 MHZ, MeOH-$d_4$) δ: 10.06 (s, 1H), 8.95 (d, J = 5.6 Hz, 1H), 8.76 (d, J = 8.4 Hz, 1H), 8.36 (d, J = 1.6 Hz, 1H), 8.32 (d, J = 5.6 Hz, 1H), 7.99 (dd, J = 1.7, 8.5 Hz, 1H), 7.70 (d, J = 2.2 Hz, 1H), 7.64 (dd, J = 2.3, 8.7 Hz, 1H), 7.05 (d, J = 8.8 Hz, 1H), 4.84-4.79 (m, 1H), 4.10 (s, 2H), 4.04 (t, J = 5.2 Hz, 2H), 3.87 (t, J = 5.2 Hz, 2H), 3.62 (t, J = 6.0 Hz, 2H), 3.02 (t, J = 8.0 Hz, 2H), 2.55-2.47 (m, 2H), 2.24-2.14 (quin, 2H), 1.95-1.74 (m, 4H), 1.72-1.64 (m, 2H) ppm. LCMS (AM3): rt = 0.740 min, (539.4 [M + H]$^+$), 98.6% purity Purification Method 21 |
| Example 21 | 5-((2-(4-((3-(cyanomethyl)benzyl)amino)butoxy)ethyl)amino)benzo[c][2,6]naphthyridine-8-carboxamide | 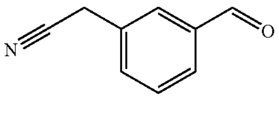 [SMILES: N#CCc1cccc(C=O)c1] 2-(3-Formylphenyl)acetonitrile | $^1$H NMR (400 MHZ, MeOH-$d_4$) δ: 10.08 (s, 1H), 8.97 (d, J = 5.8 Hz, 1H), 8.78 (d, J = 8.5 Hz, 1H), 8.39 (d, J = 1.6 Hz, 1H), 8.35 (d, J = 5.6 Hz, 1H), 8.02 (dd, J = 1.7, 8.5 Hz, 1H), 7.50-7.40 (m, 4H), 4.15 (s, 2H), 4.06 (t, J = 5.1 Hz, 2H), 3.95 (s, 2H), 3.86 (t, J = 5.1 Hz, 2H), 3.62 (t, J = 6.0 Hz, 2H), 3.04 (t, J = 8.0 Hz, 2H), 1.84-1.76 (m, 2H), 1.70-1.62 (m, 2H) ppm. LCMS (AM3): rt = 0.677 min, (483.4 [M + H]$^+$), 98.7% purity. Purification Method 39 |

TABLE 2-continued

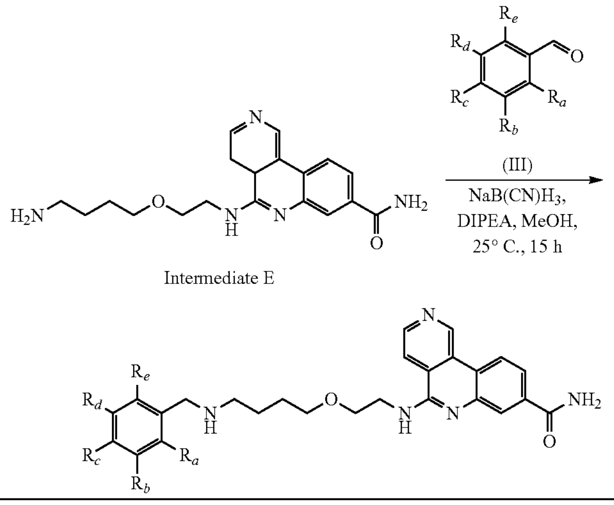

| Example No. | Chemical IUPAC name | Compound (III) | Analytical |
| --- | --- | --- | --- |
| Example 22 | 5-((2-(4-((3-(hydroxymethyl)benzyl)amino)butoxy)ethyl)amino)benzo[c][2,6]naphthyridine-8-carboxamide | 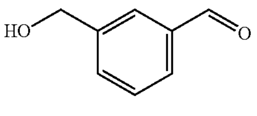 3-(hydroxymethyl)benzaldehyde | $^1$H NMR (400 MHZ, MeOH-d$_4$) δ: 10.05 (s, 1H), 8.97 (d, J = 5.6 Hz, 1H), 8.75 (d, J = 8.6 Hz, 1H), 8.42 (s, 1H), 8.40-8.38 (d, 1H), 8.02 (dd, J = 1.2, 8.8 Hz, 1H), 7.44-7.31 (m, 4H), 4.63 (s, 2H), 4.12 (s, 2H), 4.07 (t, J = 5.2 Hz, 2H), 3.89 (t, J = 4.8 Hz, 2H), 3.61 (t, J = 6.0 Hz, 2H), 3.02 (t, J = 8.0 Hz, 2H), 1.83-1.73 (quin, 2H), 1.69-1.60 (quin, 2H) ppm. LCMS (AM3): rt = 0.548 min, (474.3 [M+H]$^+$), 97.5% purity. Purification Method 40 |
| Example 24 | 5-((2-(4-((4-chloro-3-(2-hydroxyethoxy)benzyl)amino)butoxy)ethyl)amino)benzo[c][2,6]naphthyridine-8-carboxamide | 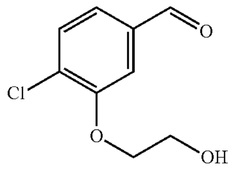 [SMILES: O=Cc1ccc(Cl)c(OCCO)c1] 4-Chloro-3-(2-hydroxyethoxy)benzaldehyde, 1.412 | $^1$H NMR (400 MHZ, MeOH-d$_4$) δ: 10.10 (s, 1H), 9.00 (d, J = 5.6 Hz, 1H), 8.80 (d, J = 8.8 Hz, 1H), 8.42-8.38 (m, 2H), 8.04 (dd, J = 8.4 Hz, 1.6 Hz, 1H), 7.42 (d, J = 8.0 Hz. 1H), 7.20 (d, J = 2.0 Hz, 1H), 7.00 (dd, J = 8.0 Hz, 1.6 Hz, 1H), 4.16-4.12 (m, 4H), 4.08 (t, J = 4.8 Hz, 2H), 3.94-3.88 (m, 4H), 3.61 (t, J = 6.0 Hz, 2H), 3.03 (t, J = 8.0 Hz, 2H), 1.84-1.76 (m, 2H), 1.70-1.63 (m, 2H) ppm. LCMS (AM3): rt = 0.660 min, (538.2 [M + H]$^+$), 100% purity. Purification Method 42 |
| Example 29 | 5-((2-(4-((4-cyclopropyl-3-(hydroxymethyl)benzyl)amino)butoxy)ethyl)amino)benzo[c][2,6]naphthyridine-8-carboxamide | 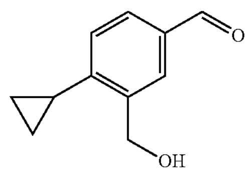 [SMILES: O=Cc1ccc(C2CC2)c(CO)c1] 4-Cyclopropyl-3-(hydroxymethyl)benzaldehyde 1.537 | $^1$H NMR (400 MHZ, MeOH-d$_4$) δ:10.05 (s, 1H), 8.93 (d, J = 5.6 Hz, 1H), 8.75 (d, J = 8.8 Hz, 1H), 8.35 (d, J = 1.6 Hz, 1H), 8.30 (d, J = 5.6 Hz, 1H), 7.98 (dd, J = 8.4, 1.6 Hz, 1H), 7.46 (d, J = 1.6 Hz, 1H), 7.22 (dd, J = 8.0, 2.0 Hz, 1H), 7.03 (d, J= 8.0 Hz, 1H), 4.84 (s, 2H), 4.07 (s, 2H), 4.01 (t, J = 4.8 Hz, 2H), 3.87 (t, J = 5.2 Hz, 2H), 3.61 (t, J = 6.0 Hz, 2H), 3.00 (t, J = 7.2 Hz, 2H), 2.00-1.94 (m, 1H), 1.80-1.72 (quin, 2H), 1.70-1.64 (quin, 2H), 0.98-0.94 (m, 2H), 0.65-0.61 (m, 2H) ppm. LCMS (AM3): rt = 0.731 min, (514.5 [M + H]$^+$), 100% purity. Purification Method 42 |
| Example 38 | 5-((2-(4-((3-(2-hydroxyethoxy)-4-(trifluoromethyl)benzyl)amino)butoxy)ethyl)amino)benzo[c][2,6]naphthyridine-8-carboxamide | 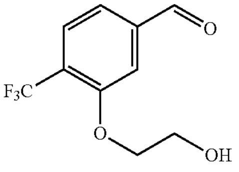 | $^1$H NMR (400 MHZ, MeOH-d$_4$) δ: 10.03 (s, 1H), 8.97 (d, J = 5.6 Hz, 1H), 8.73 (d, J = 8.4 Hz, 1H), 8.41-8.39 (m, 2H), 8.01 (dd, J = 8.4 Hz, 1.6 Hz, 1H), 7.62 (d, J = 8.0 Hz, 1H), 7.34 (s, 1H), 7.13 (d, J = 8.0 Hz. 1H), 4.21-4.17 (m, 4H), 4.07 (t, J = 5.2 Hz, 2H), 3.92-3.86 (m, 4H), 3.61 (t, J = 6.0 Hz, 2H), 3.07 (t, J = 8.0 Hz, 2H), 1.86-1.78 (quin, 2H), 1.71-1.63 (quin, 2H) ppm. |

TABLE 2-continued

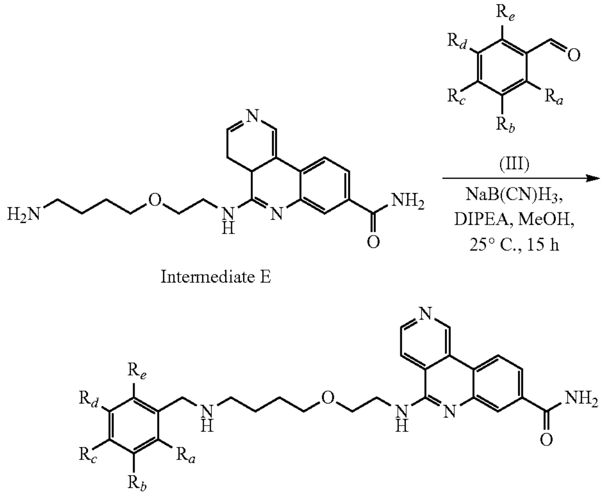

| Example No. | Chemical IUPAC name | Compound (III) | Analytical |
|---|---|---|---|
| | | 3-(2-Hydroxyethoxy)-4-(trifluoromethyl)benzaldehyde 1.406 | LCMS (AM3): rt = 0.736 min, (572.3 [M + H]$^+$), 100 % purity.<br>Purification Method 50 |
| Example 168 | 5-((2-(4-((3-carbamoyl-5-(trifluoromethoxy)benzyl)amino)butoxy)ethyl)amino)benzo[c][2,6]naphthyridine-8-carboxamide | 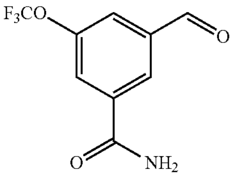 [SMILES: NC(=O)c1cc(C=O)cc(OC(F)(F)F)c1]<br>3-Formyl-5-(trifluoromethoxy)benzamide 1.675 | $^1$H NMR (400 MHZ, MeOH-d$_4$) δ: 9.92 (s, 1H), 8.76 (d, J = 6.0 Hz, 1H), 8.60 (d, J = 8.4 Hz, 1H), 8.20 (d, J = 1.6 Hz, 1H), 8.13 (d, J = 5.6 Hz, 1H), 7.82 (dd, J = 8.4, 1.6 Hz, 1H), 7.79 (s, 1H), 7.66 (s, 1H), 7.43 (s, 1H), 3.88 (t, J = 5.6 Hz, 2H), 3.80 (t, J = 5.6 Hz, 2H), 3.74 (s, 2H), 3.56 (t, J = 5.6 Hz, 2H), 2.56 (t, J = 7.2 Hz, 2H), 1.64-1.56 (m, 4H) ppm<br>LCMS (AM7): rt = 0.844 min, (571.2 [M + H]$^+$), 100%<br>Purification Method 117 |
| Example 172 | 5-((2-(4-((3-((1H-imidazol-1-yl)methyl)-5-(trifluoromethoxy)benzyl)amino)butoxy)ethyl)amino)benzo[c][2,6]naphthyridine-8-carboxamide | 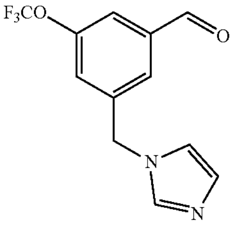 [SMILES: O=Cc1cc(Cn2ccnc2)cc(OC(F)(F)F)c1]<br>3-((1H-imidazol-1-yl)methyl)-5-(trifluoromethoxy)benzaldehyde 1.825 | $^1$H NMR (400 MHZ, MeOH-d$_4$) δ: 9.93 (s, 1H), 8.77 (d, J = 5.6 Hz, 1H), 8.61 (d, J = 8.8 Hz, 1H), 8.30 (s, 2H), 8.20 (d, J = 2.0 Hz, 1H), 8.13 (d, J = 6.0 Hz, 1H), 7.84-7.81 (m, 2H), 7.36 (s, 1H), 7.28 (s, 1H), 7.26 (s, 1H), 7.16 (s, 1H), 7.05 (s, 1H), 5.31 (s, 2H), 4.12 (s, 2H), 3.91 (t, J = 5.6 Hz, 2H), 3.81 (t, J = 5.6 Hz, 2H), 3.62 (t, J = 6.0 Hz, 2H), 3.04 (t, J = 7.6 Hz, 2H), 1.83-1.75 (quin, 2H), 1.72-1.64 (m, 2H) ppm<br>LCMS (AM3): rt = 0.661 min, (608.2 [M + H]$^+$), 96.9% purity<br>Purification Method 167 |
| Example 173 | 5-((2-(4-((3-(furan-3-ylmethyl)-5-(trifluoromethoxy)benzyl)amino)butoxy)ethyl)amino)benzo[c][2,6]naphthyridine-8-carboxamide | 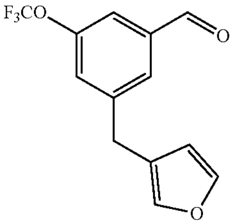 [SMILES: O=Cc1cc(Cc2ccoc2)cc(OC(F)(F)F)c1]<br>3-(Furan-3-ylmethyl)-5-(trifluoromethoxy)benzaldehyde 1.826 | $^1$H NMR (400 MHZ, MeOH-d$_4$) δ: 9.92 (s, 1H), 8.78 (d, J = 6.0 Hz, 1H), 8.60 (d, J = 8.8 Hz, 1H), 8.52 (s, 1H), 8.20 (d, J = 2.0 Hz, 1H), 8.13 (d, J = 5.6 Hz, 1H), 7.83 (dd, J = 8.4, 2.0 Hz, 1H), 7.43 (t, J = 1.6 Hz, 1H), 7.35 (s, 1H), 7.30 (s, 1H), 7.24 (s, 1H), 7.20 (s, 1H), 6.26 (s, 1H), 4.09 (s, 2H), 3.92 (t, J = 5.6 Hz, 2H), 3.84-3.81 (m, 4H), 3.63 (t, J = 6.0 Hz, 2H), 3.04 (t, J = 7.6 Hz, 2H), 1.84-1.77 (quin, 2H), 1.74-1.67 (quin, 2H) ppm<br>LCMS (AM3): rt = 0.786 min, (608.1 [M + H]$^+$), 97.5% purity<br>Purification Method 175 |

Example 15

5-((2-(4-((3-Chloro-4-(trifluoromethoxy)benzyl)amino)butoxy)ethyl)amino)benzo[c][2,6]naphthyridine-8-carboxylic acid

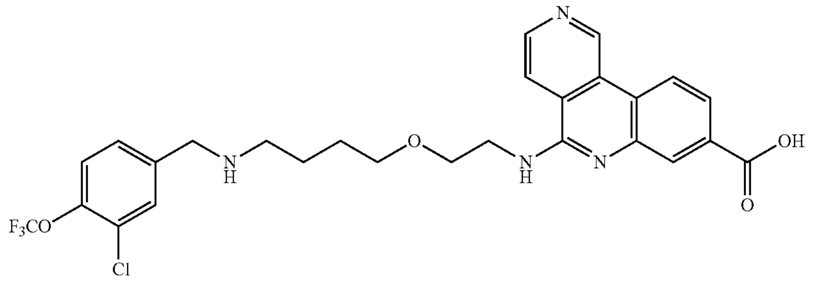 [SMILES: O=C(O)c1ccc2c(c1)nc(NCCOCCCCNCc1ccc(OC(F)(F)F)c(Cl)c1)c1ccncc12]

To a mixture of compound 1.155 (50 mg, 86.66 μmol) in THF (3 mL), MeOH (3 mL) and water (3 mL) was added $LiOH \cdot H_2O$ (18.18 mg, 433.28 μmol) at 20° C. The resulting mixture was stirred at 20° C. for 4 h. The mixture was acidified with aq. HCl (1 N) to pH4. The resulting mixture was concentrated in vacuo and purified (PM34) to afford Example 15 (26.77 mg, 39.54 μmol, 45.6% yield, TFA salt) as a yellow solid.

LCMS (AM3): rt=0.781 min, (563.1 $[M+H]^+$), 100% purity.

$^1H$ NMR (400 MHz, MeOH-$d_4$) δ: 10.07 (s, 1H), 8.95 (d, J=5.6 Hz, 1H), 8.77 (d, J=8.5 Hz, 1H), 8.50 (d, J=1.5 Hz, 1H), 8.33 (d, J=5.8 Hz, 1H), 8.13 (dd, J=1.6, 8.5 Hz, 1H), 7.71 (d, J=1.8 Hz, 1H), 7.50-7.49 (m, 2H), 4.16 (s, 2H), 4.03 (t, J=5.3 Hz, 2H), 3.88 (t, J=5.3 Hz, 2H), 3.64-3.61 (t, 2H), 3.07-3.04 (m, 2H), 1.83-1.75 (m, 2H), 1.75-1.65 (m, 2H) ppm.

Example 16

5-(2-(4-((3-chloro-4-(trifluoromethoxy)benzyl)amino)butoxy)ethoxy)benzo[c][2,6]naphthyridine-8-carboxamide

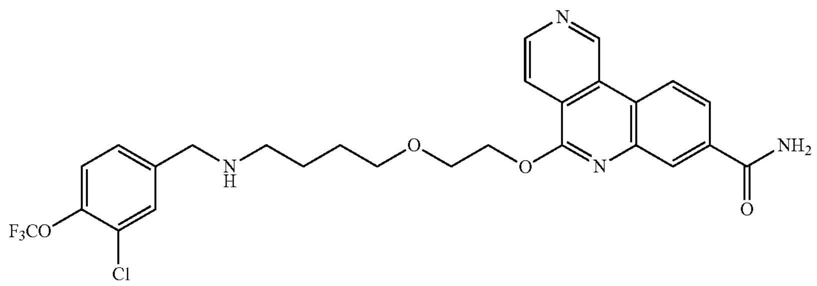 [SMILES: NC(=O)c1ccc2c(c1)nc(OCCOCCCCNCc1ccc(OC(F)(F)F)c(Cl)c1)c1ccncc12]

A mixture of 3-chloro-4-(trifluoromethoxy)benzaldehyde (33.08 mg, 147.30 μmol), compound 1.57 (75 mg, 147.30 μmol, TFA salt) and sodium acetate (24.17 mg, 294.60 μmol) in methanol (1 mL) was stirred at 25° C. for 1 h, then sodium cyanoborohydride (92.56 mg, 1.47 mmol) was added. The reaction mixture was stirred at 25° C. for 11 h. The reaction mixture was concentrated in vacuo to give a residue which was purified (PM35) to afford Example 16 (40.09 mg, 58.63 μmol, 39.8% yield, 99.08% purity, TFA salt) as a yellow solid.

LCMS (AM3): rt=0.819 min, (563.2 $[M+H]^+$), 99.08% purity.

$^1$H NMR (400 MHz, MeOH-$d_4$) δ: 10.06 (s, 1H), 8.88 (d, J=5.6 Hz, 1H), 8.81 (m, 1H), 8.42 (d, J=2.0 Hz, 1H), 8.26 (dd, J=0.8, 5.6 Hz, 1H), 8.08 (dd, J=2.0, 8.4 Hz, 1H), 7.69 (d, J=2.0 Hz, 1H), 7.53-7.45 (m, 2H), 4.87-4.83 (m, 2H), 4.17 (s, 2H), 4.01-3.99 (m, 2H), 3.69 (t, J=6.0 Hz, 2H), 3.14-3.06 (m, 2H), 1.89-1.80 (m, 2H), 1.78-1.69 (m, 2H) ppm.

Example 17

5-(2-(4-((3-chlorobenzyl)amino)butoxy)ethoxy) benzo[c][2,6]naphthyridine-8-carboxamide

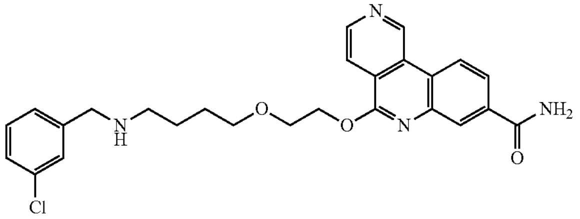 [SMILES: NC(=O)c1ccc2c(c1)nc(OCCOCCCCNCc1cccc(Cl)c1)c1ccncc12]

A mixture of 3-chlorobenzaldehyde (20.71 mg, 147.30 μmol, 16.70 μL), compound 1.57 (75 mg, 147.30 μmol, TFA salt) and sodium acetate (24.17 mg, 294.60 μmol) in methanol (1 mL) was stirred at 25° C. for 1 h, and then sodium cyanoborohydride (92.56 mg, 1.47 mmol) was added. The mixture was stirred at 25° C. for 11 h. The reaction mixture was concentrated in vacuo to give a residue which was purified (PM37) to afford Example 17 (41.86 mg, 70.59 μmol, 47.9% yield, 100% purity, TFA salt) as a yellow gum.

LCMS (AM3): rt=0.663 min, (479.2 $[M+H]^+$), 100% purity.

$^1$H NMR (400 MHz, MeOD) δ: 9.98 (s, 1H), 8.85 (d, J=5.6 Hz, 1H), 8.68 (d, J=8.8 Hz, 1H), 8.33 (d, J=2.0 Hz, 1H), 8.21 (d, J=5.6 Hz, 1H), 8.03 (dd, J=2.0, 8.4 Hz, 1H), 7.49 (d, J=0.8 Hz, 1H), 7.44-7.33 (m, 3H), 4.85-4.80 (m, 2H), 4.16 (s, 2H), 4.01-3.99 (m, 2H), 3.70 (t, J=6.0 Hz, 2H), 3.12-3.08 (m, 2H), 1.92-1.81 (m, 2H), 1.79-1.73 (m, 2H) ppm.

Example 25

5-((2-(4-((3-Chloro-4-cyclobutoxybenzyl)amino) butoxy)ethyl)amino)benzo[c][2,6]naphthyridine-8-carboxylic acid

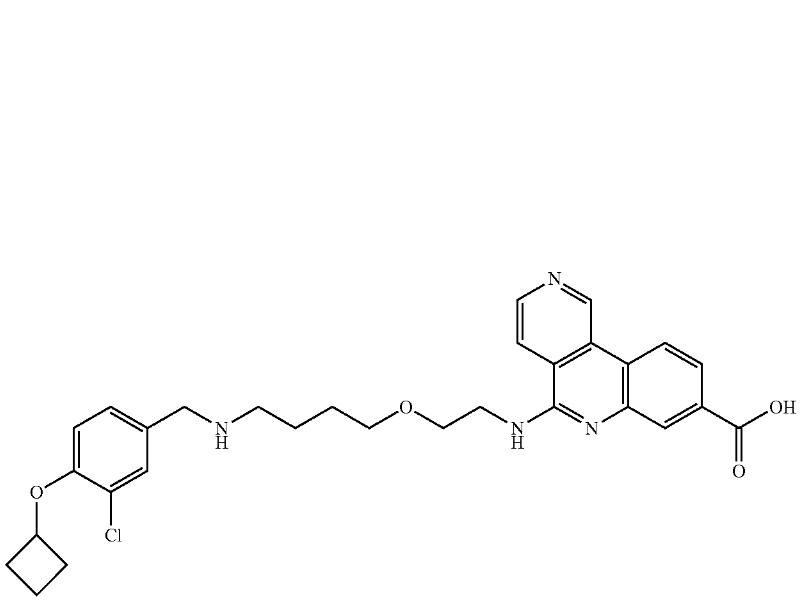 [SMILES: O=C(O)c1ccc2c(c1)nc(NCCOCCCCNCc1ccc(OC3CCC3)c(Cl)c1)c1ccncc12]

A mixture of Intermediate R (70 mg, 179.09 μmol), compound 1.32 (37.73 mg, 179.09 μmol) and sodium acetate (58.77 mg, 716.36 μmol) in MeOH (3 mL) was stirred at 20° C. for 12.5 h before sodium triacetoxyborohydride (113.87 mg, 537.27 μmol) was added. The reaction mixture was stirred at 20° C. for another 3 h. The reaction mixture was filtered and the filtrate was concentrated in vacuo. The residue was purified (PM43) to afford Example 25 (25.42 mg, 46.30 μmol, 25.9% yield) as a yellow gum.

LCMS (AM3): rt=0.790 min, (549.3 $[M+H]^+$), 100% purity.

$^1$H NMR (400 MHz, DMSO-$d_6$) δ: 10.04 (s, 1H), 8.84 (d, J=5.6 Hz, 1H), 8.66 (d, J=8.4 Hz, 1H), 8.26 (d, J=5.6 Hz, 1H), 8.13 (d, J=1.6 Hz, 1H), 7.98 (t, J=5.4 Hz, 1H), 7.83 (dd, J=8.4, 1.6 Hz, 1H), 7.39 (s, 1H), 7.18 (d, J=8.4 Hz, 1H), 6.86 (d, J=8.4 Hz, 1H), 4.72-4.64 (quin, 1H), 3.78-3.74 (m, 2H), 3.67 (t, J=5.8 Hz, 2H), 3.63 (s, 2H), 3.46 (t, J=5.6 Hz, 2H), 2.53-2.51 (m, 2H), 2.43-2.35 (m, 2H), 2.08-1.98 (quin, 2H), 1.83-1.74 (q, 1H), 1.66-1.54 (quin, 1H), 1.57-1.47 (m, 4H) ppm.

The folowing examples in Table 3 were made with non-critical changes or substitutions to the exemplified procedure in Example 25, that would be understood by one skilled in the art using intermediate R and compounds of formula (III).

TABLE 3

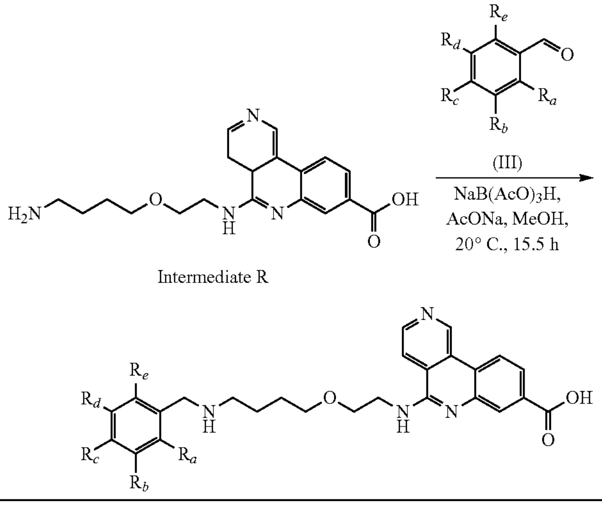

Intermediate R

| Example No. | Chemical IUPAC name | Compound (III) | Analytical |
|---|---|---|---|
| Example 26 | 5-((2-(4-((3-(2-hydroxyethoxy) benzyl)amino) butoxy)ethyl) amino)benzo[c] [2,6] naphthyridine-8-carboxylic acid | 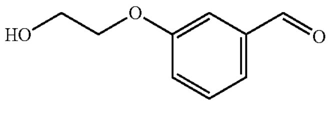 3-(2-hydroxyethoxy)benzaldehyde | $^1$H NMR (400 MHz, DMSO-$d_6$) δ: 9.99 (s, 1H), 8.78 (d, J = 5.6 Hz, 1H), 8.58 (d, J = 8.4 Hz, 1H), 8.25 (d, J = 5.6 Hz, 1H), 8.15 (d, J = 1.2 Hz, 1H), 7.97-7.92 (m, 1H), 7.85 (dd, J = 8.4, 1.2 Hz, 1H), 7.21 (t, J = 7.8 Hz, 1H), 7.07 (s, 1H), 6.96 (d, J = 7.2 Hz, 1H), 6.83 (dd, J = 8.4, 2.0 Hz, 1H), 3.94 (t, J = 4.8 Hz, 2H), 3.88 (s, 2H), 3.74-3.70 (m, 2H), 3.68-3.65 (m, 4H), 3.43 (t, J = 6.0 Hz, 2H), 2.69 (t, J = 7.2 Hz, 2H), 1.66-1.57 (m, 2H), 1.55-1.48 (m, 2H) ppm.<br>LCMS (AM3): rt = 0.689 min, (505.4 $[M + H]^+$), 98.4% purity.<br>Purification Method 44 |
| Example 27 | 5-((2-(4-((3-(cyanomethyl) benzyl)amino) butoxy)ethyl) amino)benzo[c] [2,6] naphthyridine-8-carboxylic acid | 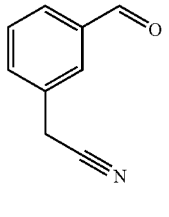 2-(3-Formylphenyl)acetonitrile 1.134 | $^1$H NMR (400 MHZ, DMSO-$d_6$) δ:10.03 (s, 1H), 8.83 (d, J = 5.6 Hz, 1H), 8.65 (d, J = 8.4 Hz, 1H), 8.26 (d, J = 5.6 Hz, 1H), 8.14 (d, J = 1.2 Hz, 1H), 7.98 (t, J = 5.2 Hz, 1H), 7.83 (dd, J = 8.4, 1.6 Hz, 1H), 7.34-7.29 (m, 3H), 7.24-7.19 (m, 1H), 4.01 (s, 2H), 3.77-3.74 (m, 4H), 3.68 (t, J = 5.6Hz, 2H), 3.45 (t, J = 5.6Hz, 2H), 2.60-2.53 (m, 2H), 1.57-1.51 (m, 4H) ppm.<br>LCMS (AM3): rt = 0.694 min, (484.4 $[M + H]^+$), 95.5% purity.<br>Purification Method 45 |
| Example 28 | 5-((2-(4-((3-fluoro-4-(trifluoromethoxy) benzyl)amino) butoxy)ethyl) amino)benzo[c] [2,6] naphthyridine-8- | 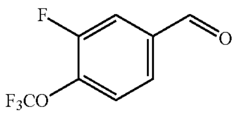 3-fluoro-4-(trifluoromethoxy) benzaldehyde | $^1$H NMR (400 MHZ, DMSO-$d_6$) δ: 10.10 (s, 1H), 8.92 (d, J = 5.6 Hz, 1H), 8.84 (br s, 2H), 8.77 (d, J = 8.4 Hz, 1H), 8.34 (d, J = 5.2 Hz, 1H), 8.22 (br s, 1H), 7.86 (d, J = 8.4 Hz, 1H), 7.69-7.61 (m, 2H), 7.41 (d, J = 8.4 Hz, 1H), 4.16 (t, J = 5.4 Hz, 2H), 3.84 (t, J = 5.2 Hz, 2H), 3.73 (t, J = 5.6 Hz, 2H), 3.49 (t, J = 6.0 Hz, 2H), 2.97-2.90 (m, 2H), 1.70-1.52 (m, 4H) ppm. |

TABLE 3-continued

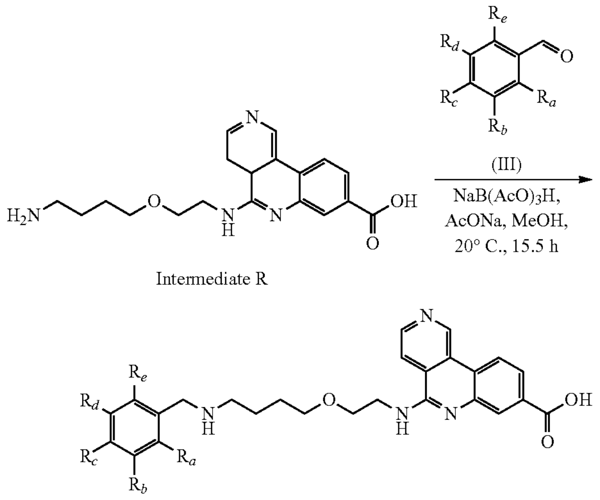

| Example No. | Chemical IUPAC name | Compound (III) | Analytical |
|---|---|---|---|
| | carboxylic acid | | LCMS (AM3): rt = 0.791 min, (547.3 $[M+H]^+$), 100% purity. Purification Method 46 |
| Example 30 | 5-((2-(4-((3-chlorobenzyl) amino)butoxy) ethyl)amino) benzo[c][2,6] naphthyridine-8-carboxylic acid | 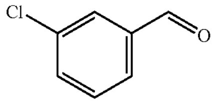 3-chlorobenzaldehyde | $^1$H NMR (400 MHZ, DMSO-$d_6$) δ: 10.11 (s, 1H), 8.93 (d, J = 6.0 Hz, 1H), 8.85-8.77 (m, 3H), 8.36 (d, J = 5.6 Hz, 1H), 8.25 (br s, 1H), 7.88 (dd, J = 1.6, 8.4 Hz 1H), 7.57 (s, 1H), 7.52-7.39 (m, 3H), 4.10 (t, J = 6.0 Hz, 2H), 3.82 (t, J = 5.2 Hz, 2H), 3.73 (t, J = 5.2 Hz, 2H), 3.49 (t, J = 6.0 Hz, 2H), 2.95-2.88 (m, 2H), 1.69-1.62 (m, 2H), 1.60-1.54 (m, 2H) ppm. LCMS (AM3): rt = 0.759 min, (479.4 $[M+H]^+$), 100% purity. Purification Method 48 |
| Example 32 | 5-((2-(4-((3-(2-hydroxyethyl) benzyl)amino) butoxy)ethyl) amino)benzo[c] [2,6] naphthyridine-8-carboxylic acid | 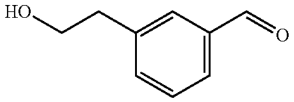 [SMILES: O=Cc1cccc(CCO)c1] 3-(2-hydroxyethyl)benzaldehyde | $^1$H NMR (400 MHZ, DMSO-$d_6$) δ: 10.18 (br s, 1H), 9.10-8.86 (br m, 4H), 8.78 (d, J = 8.4 Hz, 1H), 8.43 (br s, 1H), 8.31 (s, 1H), 7.90 (dd, J = 8.4, 1.2 Hz, 1H), 7.33-7.19 (m, 4H), 4.04 (t, J = 5.6 Hz, 2H), 3.90-3.83 (m, 2H), 3.74 (t, J = 5.6 Hz, 2H), 3.60 (t, J = 6.8 Hz, 2H), 3.48 (t, J = 6.0 Hz, 2H), 2.95-2.86 (m, 2H), 2.72 (t, J = 6.8 Hz, 2H), 1.70-1.60 (m, 2H), 1.60-1.50 (m, 2H) ppm. LCMS (AM3): rt = 0.704 min, (489.5 $[M+H]^+$), 97.7% purity. Purification Method 48 |
| Example 31 | 5-((2-(4-((3-chloro-5-(hydroxymethyl) benzyl)amino) butoxy)ethyl) amino)benzo[c] [2,6] naphthyridine-8-carboxylic acid | 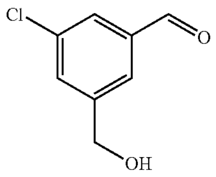 [SMILES: O=Cc1cc(Cl)cc(CO)c1] 3-Chloro-5-(hydroxymethyl) benzaldehyde 1.102 | $^1$H NMR (400 MHZ, DMSO-$d_6$) δ: 10.10 (s, 1H), 8.94 (d, J = 5.4 Hz, 1H), 8.88-8.77 (m, 3H), 8.37 (d, J = 5.6 Hz, 1H), 8.27 (br s, 1H), 7.89 (dd, J = 8.4, 1.2 Hz, 1H), 7.41 (d, J = 8.0 Hz, 2H), 7.36 (s, 1H), 4.52 (s, 2H), 4.09 (t, J = 5.6 Hz, 2H), 3.85 (t, J = 5.2 Hz, 2H), 3.74 (t, J = 5.6 Hz, 2H), 3.49 (t, J = 6.0 Hz, 2H), 2.95-2.89 (m, 2H), 1.70-1.52 (m, 4H), ppm. LCMS (AM3): rt = 0.718 min, (509.4 $[M+H]^+$), 98.3% purity. Purification Method 48 |

Example 33

5-((2-(4-((3-Chloro-4-cyclopropylbenzyl)amino) butoxy)ethyl)amino)benzo[c][2,6]naphthyridine-8-carboxylic acid

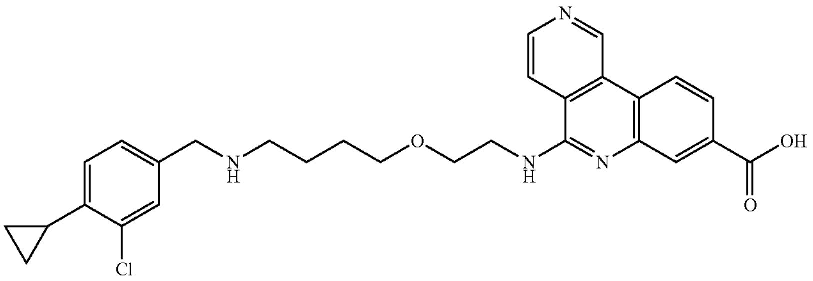 [SMILES: O=C(O)c1ccc2c(c1)nc(NCCOCCCCNCc1ccc(C3CC3)c(Cl)c1)c1ccncc12]

A mixture of Intermediate R (70 mg, 179.09 μmol), compound 1.202 (32.35 mg, 179.09 μmol) and DIPEA (46.29 mg, 358.18 μmol) in MeOH (3 mL) was stirred at 20° C. for 12 h, then sodium cyanoborohydride (33.76 mg, 537.27 μmol) was added. The reaction mixture was stirred at 20° C. for another 3 h. The reaction concentrated mixture was filtered and in vacuo. The residue was purified (PM24) to afford Example 33 45.05 mg, 71.16 μmol, 39.7% yield, TFA salt) as a yellow oil.

LCMS (AM3): rt=0.759 min, (519.4 $[M+H]^+$), 96.8% purity.

$^1H$ NMR (400 MHz, DMSO-$d_6$) δ: 10.10 (s, 1H), 8.93 (d, J=5.6 Hz, 1H), 8.79-8.73 (m, 3H), 8.36 (d, J=5.6 Hz, 1H), 8.26 (s, 1H), 7.88 (dd, J=8.4, 1.2 Hz, 1H), 7.53 (d, J=1.6 Hz, 1H), 7.30 (dd, J=8.0, 1.6 Hz, 1H), 7.05 (d, J=8.0 Hz, 1H), 4.05 (t, J=5.6 Hz 2H), 3.83 (t, J=4.8 Hz, 2H), 3.73 (t, J=5.6 Hz, 2H), 3.48 (t, J=6.0 Hz, 2H), 2.93-2.86 (m, 2H), 2.16-2.10 (m, 1H), 1.68-1.54 (m, 4H), 1.04-0.98 (m, 2H), 0.71-0.66 (m, 2H) ppm.

The following examples in Table 4 were made with non-critical changes or substitutions to the exemplified procedure in Example 33, that would be understood by one skilled in the art using intermediate R and compounds of formula (III).

TABLE 4

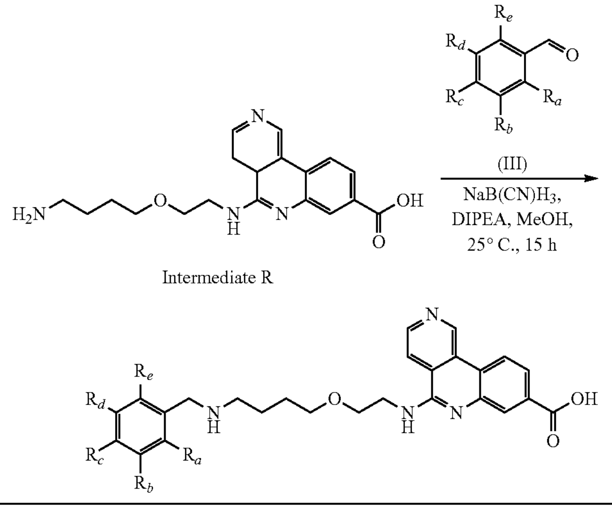

Intermediate R

| Example No. | Chemical IUPAC name | Compound (III) | Analytical |
|---|---|---|---|
| Example 34 | 5-((2-(4-((3-chloro-4-cyclopropoxybenzyl) amino)butoxy)ethyl) amino)benzo[c][2,6] naphthyridine-8-carboxylic acid | 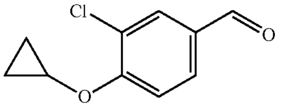 3-Chloro-4-cyclopropoxybenzaldehyde 1.90 | $^1H$ NMR (400 MHZ, DMSO-$d_6$) δ: 10.10 (s, 1H), 8.92 (d, J = 5.6 Hz, 1H), 8.77 (d, J = 8.8 Hz, 1H), 8.64 (br s, 2H), 8.32 (d, J = 5.6 Hz, 1H), 8.21 (s, 1H), 7.86 (dd, J = 8.0, 1.2 Hz, 1H), 7.54 (d, J = 2.0 Hz, 1H), 7.46-7.37 (m, 2H), 4.03 (t, J = 5.6 Hz, 2H), 3.98-3.93 (m, 1H), 3.82 (t, J = 4.8 Hz, 2H), 3.72 (t, J = 5.6 Hz, 2H), 3.50-3.47 (m, 2H), 2.95-2.85 (br m, 2H), 1.68-1.53 (m, 4H), 0.85-0.80 (q, 2H), 0.70-0.66 (m, 2H) ppm. |

TABLE 4-continued

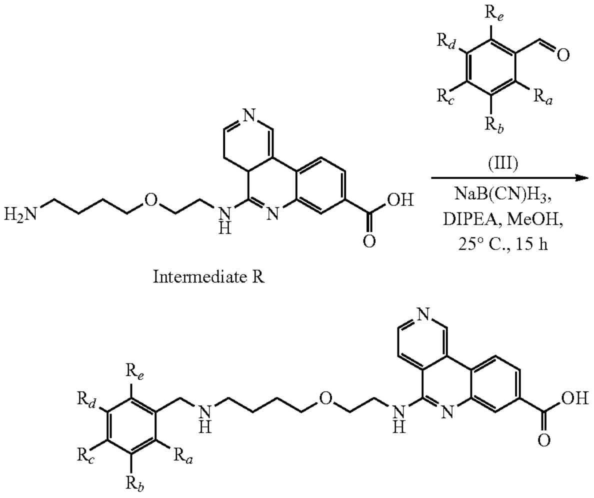

| Example No. | Chemical IUPAC name | Compound (III) | Analytical |
|---|---|---|---|
| | | | LCMS (AM3): rt = 0.754 min, (535.4 [M + H]$^+$), 96.8% purity.<br>Purification Method 49 |
| Example 37 | 5-((2-(4-((3-(hydroxymethyl) benzyl)amino) butoxy)ethyl) amino)benzo[c][2,6] naphthyridine-8-carboxylic acid | 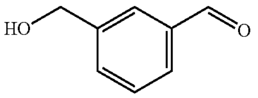<br>3-(hydroxymethyl) benzaldehyde | $^1$H NMR (400 MHZ, DMSO-$d_6$) δ: 10.12 (br s, 1H), 8.94 (br s, 1H), 8.77 (d, J = 8.4 Hz, 1H), 8.73-8.67 (br m, 2H), 8.34 (d, J = 5.2 Hz, 1H), 8.22 (br s, 1H), 7.87 (dd, J =8.4, 1.2 Hz, 1H), 7.41-7.26 (m, 4H), 4.52 (s, 2H), 4.07 (t, J = 6.0 Hz, 2H), 3.81 (t, J = 5.6 Hz, 2H), 3.73 (t, J = 5.6 Hz, 2H), 3.50 (t, J = 6.4 Hz, 2H), 2.95-2.88 (m, 2H), 1.68-1.53 (m, 4H) ppm.<br>LCMS (AM3): rt = 0.684 min, (475.2 [M + H]$^+$), 100% purity.<br>Purification Method 52 |
| Example 39 | 5-((2-(4-((3-cyano-4-cyclopropylbenzyl) amino)butoxy)ethyl) amino)benzo[c][2,6] naphthyridine-8-carboxylic acid | 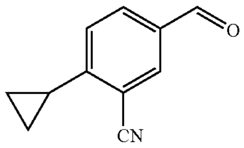 [SMILES: N#Cc1cc(C=O)ccc1C1CC1]<br>2-cyclopropyl-5-formylbenzonitrile 1.52 | $^1$H NMR (400 MHZ, DMSO-$d_6$) δ: 10.03 (s, 1H), 8.84 (d, J = 5.6 Hz, 1H), 8.66 (d, J = 8.8 Hz, 1H), 8.26 (d, J = 5.6 Hz, 1H), 8.13 (d, J = 1.2 Hz, 1H), 7.97 (t, J = 5.2 Hz, 1H), 7.83 (dd, J = 8.4, 1.6 Hz, 1H), 7.66 (d, J = 1.6 Hz, 1H), 7.50 (dd, J = 8.4, 1.6 Hz, 1H), 6.99 (d, J = 8.0 Hz, 1H), 3.76 (t, J = 5.2 Hz, 2H), 3.69-3.65 (m, 4H), 3.45 (t, J = 6.0 Hz, 2H), 2.48-2.45 (m, 2H), 2.15-2.08 (m, 1H), 1.56-1.44 (m, 4H), 1.09-1.04 (m, 2H), 0.78-0.74 (m, 2H) ppm.<br>LCMS (AM3): rt = 0.719 min, (510.2 [M + H]$^+$), 95.6% purity.<br>Purification Method 53 |
| Example 41 | 5-((2-(4-((3-cyano-4-cyclobutoxybenzyl) amino)butoxy)ethyl) amino)benzo[c][2,6] naphthyridine-8-carboxylic acid | 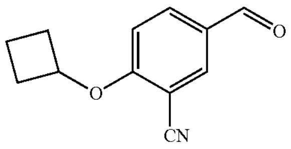 [SMILES: N#Cc1cc(C=O)ccc1OC1CCC1]<br>2-cyclobutoxy-5-formylbenzonitrile 1.47 | $^1$H NMR (400 MHZ, DMSO-$d_6$) δ: 10.04 (s, 1H), 8.85 (d, J = 5.4 Hz, 1H), 8.68 (d, J = 8.4 Hz, 1H), 8.26 (d, J = 5.6 Hz, 1H), 8.13 (d, J = 1.6 Hz, 1H), 7.99 (t, J = 5.2 Hz, 1H), 7.82 (dd, J = 8.4, 1.6 Hz, 1H), 7.64 (d, J = 2.0 Hz, 1H), 7.55 (dd, J = 8.8, 2.0 Hz, 1H), 6.97 (d, J = 8.8 Hz, 1H), 4.82-4.74 (quin, 1H), 3.76 (t, J = 5.6 Hz, 2H), 3.67 (t, J = 5.6 Hz, 2H), 3.65 (s, 2H), 3.46 (t, J = 6.0 Hz, 4H), 2.45-2.40 (m, 2H), 2.10-2.00 (m, 2H), 1.83-1.75 (m, 1H), 1.68-1.58 (m, 1H), 1.54-1.47 (m, 4H) ppm.<br>LCMS (AM3): rt = 0.780 min, (540.6 [M + H]$^+$), 99.0% purity.<br>Purification Method 55 |

TABLE 4-continued

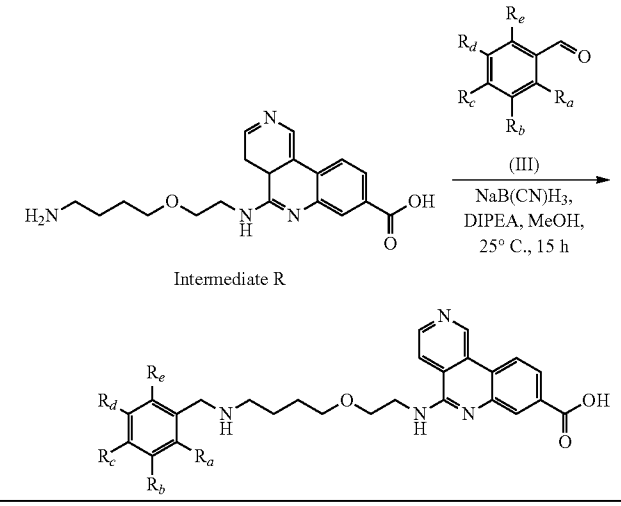

| Example No. | Chemical IUPAC name | Compound (III) | Analytical |
|---|---|---|---|
| Example 42 | 5-((2-(4-((3-chloro-5-(cyanomethyl)benzyl)amino)butoxy)ethyl)amino)benzo[c][2,6]naphthyridine-8-carboxylic acid | 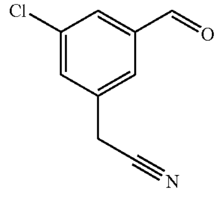 [SMILES: N#CCc1cc(Cl)cc(C=O)c1] 2-(3-Chloro-5-formylphenyl)acetonitrile 1.366 | $^1$H NMR (400 MHz, MeOH-$d_4$) δ: 10.08 (s, 1H), 8.97 (d, J = 5.6 Hz, 1H), 8.77 (d, J = 8.8 Hz, 1H), 8.52 (d, J = 1.6 Hz, 1H), 8.39 (d, J = 5.6 Hz, 1H), 8.15 (dd, J = 8.4, 1.6 Hz, 1H), 7.48 (s, 2H), 7.40 (s, 1H), 4.14 (s, 2H), 4.06 (t, J = 5.2 Hz, 2H), 3.96 (s, 2H), 3.89 (t, J = 5.2 Hz, 2H), 3.61 (t, J = 6.0 Hz, 2H), 3.05 (t, J = 7.6 Hz 2H), 1.83-1.74 (quin, 2H), 1.71-1.64 (quin, 2H) ppm. LCMS (AM3): rt = 0.728 min, (518.4 [M + H]$^+$), 100% purity. Purification Method 175 |

Example 40

5-((2-(4-((3-Chloro-5-(cyanomethyl)benzyl)amino)butoxy)ethyl)amino)benzo[c][2,6]naphthyridine-8-carboxamide

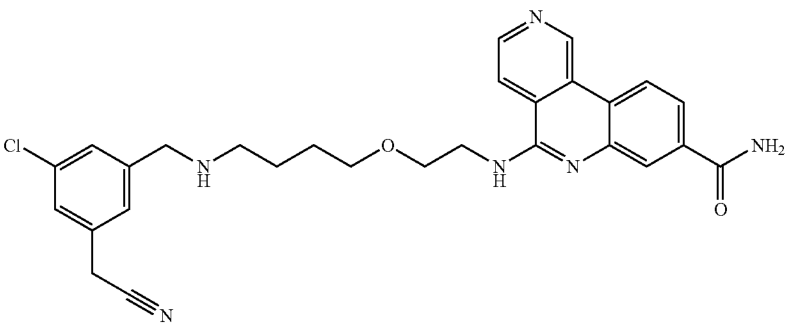 [SMILES: N#CCc1cc(Cl)cc(CNCCCCOCCNc2nc3cc(C(N)=O)ccc3c3cnccc23)c1]

A mixture of Intermediate E (80 mg, 205.19 μmol), compound 1.366 (36.85 mg, 205.19 μmol) and sodium acetate (67.33 mg, 820.77 μmol) in MeOH (3 mL) was stirred at 20° C. for 12 h, then sodium cyanoborohydride (38.68 mg, 615.58 μmol) was added. The mixture was stirred at 20° C. for another 0.5 h, The reaction mixture was concentrated in vacuo and purified (PM54) to afford Example 40 (31.75 mg, 61.19 μmol, 29.8% yield) as a yellow oil.

LCMS (AM7): rt=0.853 min, (517.2 [M+H]$^+$), 99.5% purity.

$^1$H NMR (400 MHz, DMSO-$d_6$) δ: 10.05 (s, 1H), 8.85 (d, J=5.2 Hz, 1H), 8.69 (d, J=8.8 Hz, 1H), 8.27 (d, J=5.6 Hz, 1H), 8.18 (br s, 1H), 8.14 (d, J=1.2 Hz, 1H), 7.98 (t, J=5.2 Hz, 1H), 7.81 (dd, J=8.4, 1.2 Hz, 1H), 7.42 (br s, 1H), 7.30 (s, 1H), 7.23 (d, J=4.4 Hz, 2H), 4.02 (s, 2H), 3.78 (t, J=5.6 Hz, 2H), 3.68 (t, J=6.0 Hz, 2H), 3.61 (s, 2H), 3.44 (t, J=6.4 Hz, 2H), 2.42 (t, J=6.8 Hz, 2H), 1.57-1.50 (m, 2H), 1.50-1.40 (m, 2H) ppm.

The following examples in Table 5 were made with non-critical changes or substitutions to the exemplified procedure in Example 40, that would be understood by one skilled in the art using intermediate E and compounds of formula (III).

TABLE 5

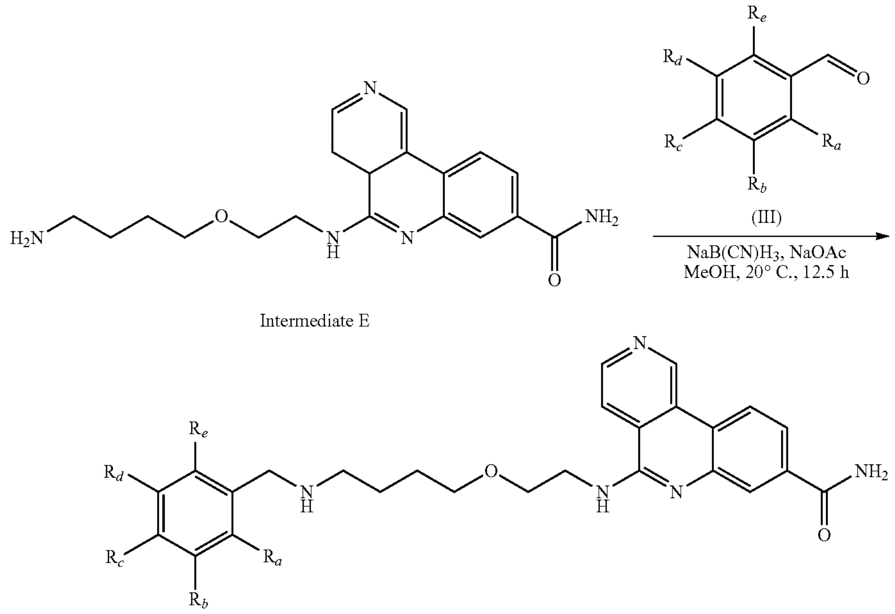

Intermediate E

| Example No. | Chemical IUPAC name | Compound (III) | Analytical |
|---|---|---|---|
| Example 47 | 5-((2-(4-((3-(hydroxymethyl)-5-methylbenzyl)amino) butoxy)ethyl)amino) benzo[c][2,6 Inaphthyridine-8-carboxamide | 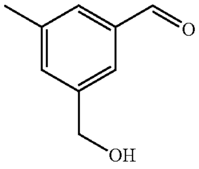 3-(hydroxymethyl)-5-methylbenzaldehyde | $^1$H NMR (400 MHz, MeOH-$d_4$) δ: 9.93 (s, 1H), 8.79 (d, J = 5.6 Hz, 1H), 8.61 (d, J = 8.4 Hz, 1H), 8.52 (br s, 1H), 8.22 (d, J = 1.6 Hz, 1H), 8.14 (d, J = 6.0 Hz, 1H), 7.83 (dd, J = 8.4, 1.6 Hz, 1H), 7.22 (s, 1H), 7.18 (s, 1H), 7.11 (s, 1H), 4.59 (s, 2H), 4.03 (s, 2H), 3.93 (t, J = 6.0 Hz, 2H), 3.83 (t, J = 6.0 Hz, 2H), 3.64 (t, J = 6.0 Hz, 2H), 3.04 (t, J = 7.6 Hz, 2H), 2.35 (s, 3H), 1.85-1.75 (quin, 2H), 1.74-1.66 (quin, 2H) ppm. LCMS (AM3): rt = 0.701 min, (488.3 $[M + H]^+$), 100% purity. Purification Method 62 |
| Example 48 | 5-((2-(4-((3-(hydroxymethyl)-5-(trifluoromethyl) benzyl)amino) butoxy)ethyl)amino) benzo[c][2,6] naphthyridine-8-carboxamide | 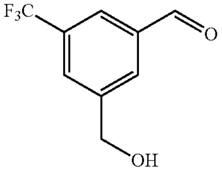 [SMILES: O=Cc1cc(CO)cc(C(F)(F)F)c1] 3-(Hydroxymethyl)-5-(trifluoromethyl)benzaldehyde 1.501 | $^1$H NMR (400 MHz, DMSO-$d_6$) δ: 10.07 (s, 1H), 8.86 (d, J = 5.6 Hz, 1H), 8.70 (d, J = 8.4 Hz, 1H), 8.28 (d, J = 5.6 Hz, 1H), 8.24 (s, 1H), 8.18 (br s, 1H), 8.14 (d, J = 2.0 Hz, 1H), 7.99 (t, J = 5.6 Hz, 1H), 7.81 (dd, J = 8.4, 2.0 Hz, 1H), 7.55 (s, 2H), 7.53 (s, 1H), 7.43 (br s, 1H), 4.57 (s, 2H), 3.80-3.78 (m, 4H), 3.72 (t, J = 4.8 Hz, 2H), 3.46 (t, J = 4.8 Hz, 2H), 2.55-2.53 (m, 2H), 1.60-1.45 (m, 4H) ppm LCMS (AM3): rt = 0.727 min, (542.2 $[M + H]^+$), 100% purity. Purification Method 63 |
| Example 49 | 5-((2-(4-((4-chloro-3-(hydroxymethyl) benzyl)amino) butoxy)ethyl)amino) benzo[c][2,6] naphthyridine-8-carboxamide | 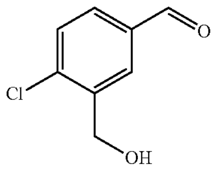 [SMILES: O=Cc1ccc(Cl)c(CO)c1] 4-Chloro-3-(hydroxymethyl) benzaldehyde 1.661 | $^1$H NMR (400 MHz, MeOH-$d_4$) δ: 9.85 (s, 1H), 8.74 (d, J = 5.6 Hz, 1H), 8.53 (d, J = 8.4 Hz, 1H), 8.48 (br s, 1H), 8.16 (d, J = 1.6 Hz, 1H), 8.08 (d, J = 5.6 Hz, 1H), 7.80 (dd, J = 8.4, 1.6 Hz, 1H), 7.64 (s, 1H), 7.39 (d, J = 8.0 Hz, 1H), 7.30 (dd, J = 10.0 Hz, 2.4 Hz, 1H), 4.70 (s, 2H), 4.11 (s, 2H), 3.89 (t, J = 5.6 Hz, 2H), 3.82 (t, J = 5.6 Hz, 2H), 3.63 (t, J = 5.6 Hz, 2H), 3.06 (t, J = 7.6 Hz, 2H), 1.87-1.79 (m, 2H), 1.74-1.66 (m, 2H) ppm. LCMS (AM3): rt = 0.717 min, (508.2 $[M + H]^+$), 96.2% purity Purification Method 62 |

TABLE 5-continued

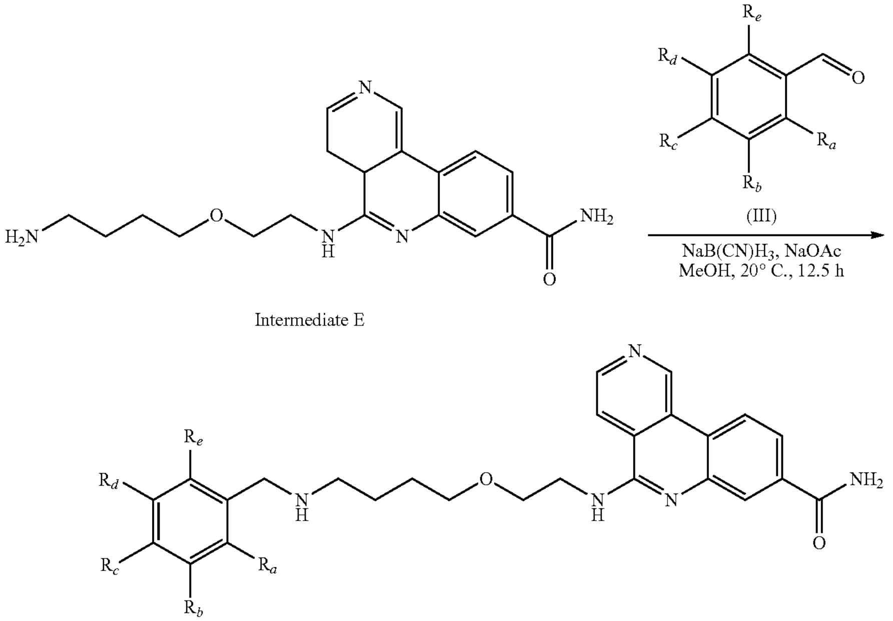

| Example No. | Chemical IUPAC name | Compound (III) | Analytical |
|---|---|---|---|
| Example 55 | 5-((2-(4-((3-fluoro-5-(hydroxymethyl) benzyl)amino) butoxy)ethyl)amino) benzo[c][2,6] naphthyridine-8-carboxamide | 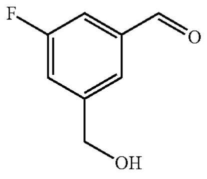 3-Fluoro-5-(hydroxymethyl) benzaldehyde 1.500 | $^1$H NMR (400 MHz, MeOH-$d_4$) δ: 9.92 (s, 1H), 8.78 (d, J = 5.6 Hz, 1H), 8.60 (d, J = 8.4 Hz, 1H), 8.20 (d, J = 1.6 Hz, 1H), 8.14 (d, J = 5.6 Hz, 1H), 7.83 (dd, J = 8.4, 2.0 Hz, 1H), 7.16 (s, 1H), 7.09 (d, J = 9.2 Hz, 1H), 7.02 (d, J = 9.2 Hz, 1H), 4.60 (s, 2H), 3.94 (s, 2H), 3.91 (t, J = 5.6 Hz, 2H), 3.81 (t, J = 5.6 Hz, 2H), 3.61 (t, J = 6.0 Hz, 2H), 2.88 (t, J = 7.6 Hz, 2H), 1.77-1.63 (m, 4H) ppm. LCMS (AM3): rt = 0.672 min, (492.3 $[M + H]^+$), 100% purity Purification Method 62 |
| Example 67 | 5-((2-(4-((2-chloro-3-(hydroxymethyl) benzyl)amino) butoxy)ethyl)amino) benzo[c][2,6] naphthyridine-8-carboxamide | 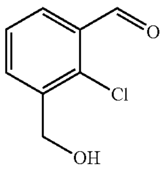 [SMILES: O=Cc1cccc(CO)c1Cl] 2-Chloro-3-(hydroxymethyl) benzaldehyde 1.485 | $^1$H NMR (400 MHz, MeOH-$d_4$) δ: 9.92 (s, 1H), 8.77 (d, J = 5.6 Hz, 1H), 8.60 (d, J = 8.4 Hz, 1H), 8.48 (br s, 1H), 8.21 (s, 1H), 8.13 (d, J = 5.6 Hz, 1H), 7.82 (dd, J = 8.4, 2.0 Hz, 1H), 7.62 (t, J = 4.8 Hz, 1H), 7.37 (d, J = 4.8 Hz, 2H), 4.67 (s, 2H), 4.19 (s, 2H), 3.92 (t, J = 5.6 Hz, 2H), 3.83 (t, J = 6.0 Hz, 2H), 3.64 (t, J = 5.6 Hz, 2H), 3.07 (t, J = 7.6 Hz, 2H), 1.86-1.78 (quin, 2H), 1.74-1.66 (quin, 2H) ppm LCMS (AM3): rt = 0.679 min, (508.2 $[M + H]^+$), 99.3% purity Purification Method 73 |
| Example 84 | 5-((2-(4-((3-(hydroxymethyl)-5-(trifluoromethoxy) benzyl)amino) butoxy)ethyl)amino) benzo[c][2,6] naphthyridine-8-carboxamide | 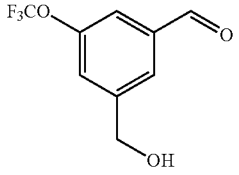 [SMILES: O=Cc1cc(CO)cc(OC(F)(F)F)c1] 3-(Hydroxymethyl)-5-(trifluoromethoxy)benzaldehyde 1.488 | $^1$H NMR (400 MHz, MeOH-$d_4$) δ: 9.93 (s, 1H), 8.78 (d, J = 5.6 Hz, 1H), 8.61 (d, J = 8.4 Hz, 1H), 8.21 (d, J = 1.6 Hz, 1H), 8.14 (d, J = 5.6 Hz, 1H), 7.83 (dd, J = 8.4, 2.0 Hz, 1H), 7.24 (br s, 1H), 7.16 (br s, 1H), 7.12 (br s, 1H), 4.61 (s, 2H), 3.91 (t, J = 5.8 Hz, 2H), 3.80 (t, J = 5.6 Hz, 2H), 3.69 (s, 2H), 3.56 (t, J = 5.8 Hz, 2H), 2.56 (t, J = 6.8 Hz, 2H), 1.62-1.58 (m, 4H) ppm LCMS (AM3): rt 0.705min, (558.3 $[M + H]^+$), 100% purity Purification Method 93 |

TABLE 5-continued

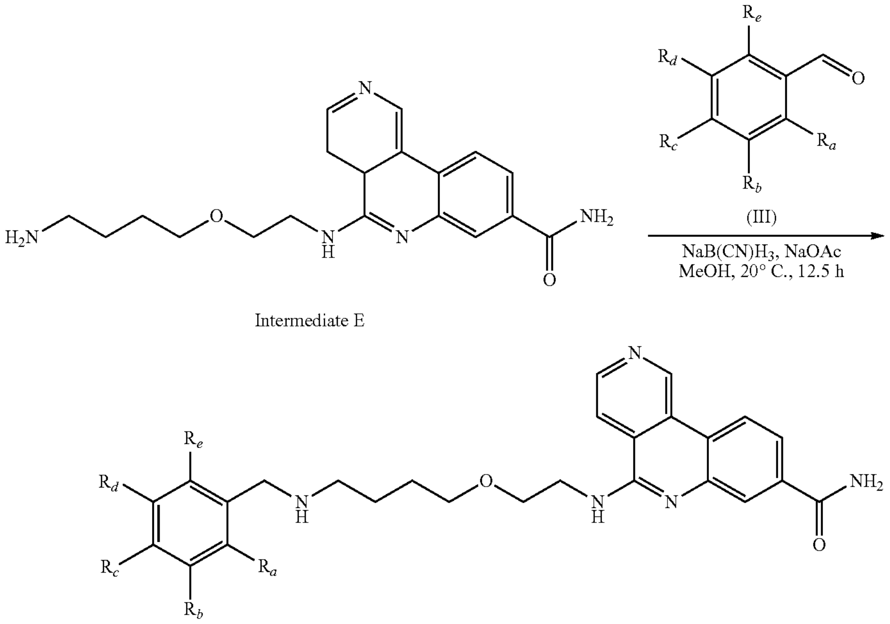

| Example No. | Chemical IUPAC name | Compound (III) | Analytical |
|---|---|---|---|
| Example 87 | 5-((2-(4-((3-(cyanomethyl)-5-methoxybenzyl)amino)butoxy)ethyl)amino)benzo[c][2,6]naphthyridine-8-carboxamide | 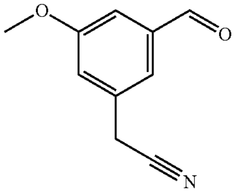 2-(3-Formyl-5-methoxyphenyl)acetonitrile 1.491 | $^1$H NMR (400 MHz, MeOH-$d_4$) δ: 9.91 (s, 1H), 8.76 (d, J = 5.6 Hz, 1H), 8.60 (d, J = 8.4 Hz, 1H), 8.20 (d, J = 1.6 Hz, 1H), 8.13 (d, J = 5.6, 1H), 7.82 (dd, J = 8.0, 1.6 Hz, 1H), 6.83-6.81 (d, 2H), 6.79 (d, J = 1.6 Hz, 1H), 3.90 (t, J = 5.6 Hz, 2H), 3.82-3.78 (m, 4H), 3.77 (s, 3H), 3.65 (s, 2H), 3.57 (t, J = 5.6 Hz, 2H), 2.60 (t, J = 6.8 Hz, 2H), 1.64-1.61 (m, 4H) ppm LCMS (AM3): rt = 0.710 min, (513.3 [M + H]$^+$), 100% purity Purification Method 90 |
| Example 89 | 5-((2-(4-((3-(cyanomethyl)-5-(trifluoromethoxy)benzyl)amino)butoxy)ethyl)amino)benzo[c][2,6]naphthyridine-8-carboxamide | 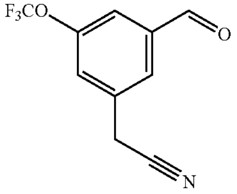 [SMILES: N#CCc1cc(C=O)cc(OC(F)(F)F)c1] 2-(3-Formyl-5-(trifluoromethoxy)phenyl)acetonitrile 1.504 | $^1$H NMR (400 MHz, MeOH-$d_4$) δ: 9.91 (s, 1H), 8.77 (d, J = 5.6 Hz, 1H), 8.59 (d, J = 8.8 Hz, 1H), 8.46 (br s, 1H), 8.19 (d, J = 2.0 Hz, 1H), 8.12 (d, J = 5.6 Hz, 1H), 7.82 (dd, J = 8.4, 2.0 Hz, 1H), 7.45 (s, 1H), 7.37-7.36 (m, 2H), 4.12 (s, 2H), 4.00 (s, 2H), 3.91 (t, J = 5.6 Hz, 2H), 3.82 (t, J = 5.6 Hz, 2H), 3.62 (t, J = 6.0 Hz, 2H), 3.04 (t, J = 7.6 Hz, 2H), 1.84-1.76 (m, 2H), 1.72-1.66 (m, 2H) ppm LCMS (AM3): rt = 0.713 min, (567.3 [M + H]$^+$), 99.5% purity Purification Method 88 |
| Example 105 | 5-((2-(4-((3-chloro-5-(2-cyanopropan-2-yl)benzyl)amino)butoxy)ethyl)amino)benzo[c][2,6]naphthyridine-8-carboxamide | 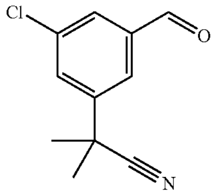 2-(3-Chloro-5-vinylphenyl)-2-methylpropanenitrile 1.632 | $^1$H NMR (400 MHz, MeOH-$d_4$) δ: 9.96 (s, 1H), 8.81 (d, J = 5.6 Hz, 1H), 8.64 (d, J = 8.4 Hz, 1H), 8.44 (br s, 1H), 8.23 (d, J = 1.6 Hz, 1H), 8.15 (d, J = 4.8 Hz, 1H), 7.84 (dd, J = 8.4, 2.0 Hz, 1H), 7.62 (m, 1H), 7.57 (m, 1H), 7.47 (m, 1H), 4.13 (s, 2H), 3.94 (t, J = 5.6 Hz, 2H), 3.84 (t, J = 5.6 Hz, 2H), 3.65 (t, J = 6.0 Hz, 2H), 3.07 (t, J = 7.2 Hz, 2H), 1.85-1.78 (m, 2H), 1.74 (s, 6H), 1.75-1.68 (m, 2H) ppm LCMS (AM3): rt = 0.742 min, (545.2 [M + H]$^+$), 98.6% purity Purification Method 106 |

TABLE 5-continued

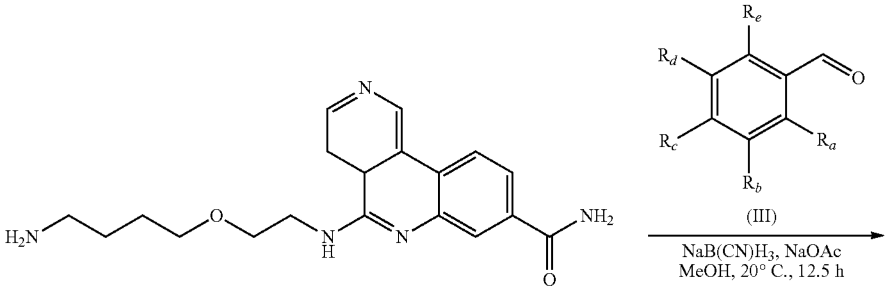

Intermediate E

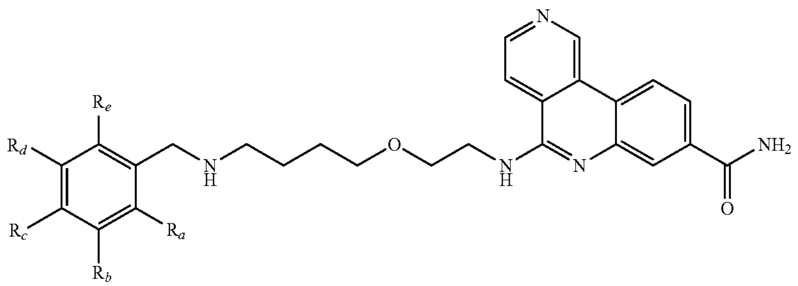

| Example No. | Chemical IUPAC name | Compound (III) | Analytical |
|---|---|---|---|
| Example 106 | 5-((2-(4-((3-chloro-5-(1-cyanocyclopropyl) benzyl)amino) butoxy)ethyl)amino) benzo[c][2,6] naphthyridine-8-carboxamide | 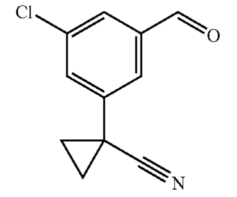 [SMILES: N#CC1(c2cc(Cl)cc(C=O)c2)CC1] 1-(3-Chloro-5-formylphenyl) cyclopropanecarbonitrile 1.630 | $^{1}$H NMR (400 MHz, MeOH-$d_4$) δ: 9.95 (s, 1H), 8.80 (d, J = 5.6 Hz, 1H), 8.62 (d, J = 8.4 Hz, 1H), 8.48 (br s, 1H), 8.22 (d, J = 2.0 Hz, 1H), 8.14 (d, J = 5.6 Hz, 1H), 7.84 (dd, J = 8.4, 2.0 Hz, 1H), 7.40-7.37 (m, 3H), 4.08 (s, 2H), 3.94 (t, J = 5.6 Hz, 2H), 3.84 (t, J = 5.6 Hz, 2H), 3.65 (t, J = 6.0 Hz, 2H), 3.05 (t, J = 7.2 Hz, 2H), 1.86-1.78 (m, 4H), 1.75-1.68 (m, 2H), 1.55-1.52 (m, 2H) ppm LCMS (AM3): rt = 0.730 min, (543.3 $[M + H]^+$), 99.7% purity Purification Method 107 |
| Example 123 | 5-((2-(4-((2-chloro-5-(hydroxymethyl) benzyl)amino) butoxy)ethyl) amino)benzo[c] [2,6]naphthyridine-8-carboxamide | 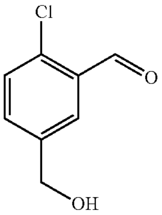 [SMILES: O=Cc1cc(CO)ccc1Cl] 2-Chloro-5-(hydroxymethyl) benzaldehyde 1.834 | $^{1}$H NMR (400 MHz, DMSO-$d_6$) δ: 10.07 (s, 1H), 8.87 (d, J = 5.6 Hz, 1H), 8.71 (d, J = 8.4 Hz, 1H), 8.28 (d, J = 5.6 Hz, 1H), 8.20 (s, 1H), 8.18 (br s, 1H), 8.15 (d, J = 2.0 Hz, 1H), 8.02-7.97 (t, 1H), 7.81 (dd, J = 8.4, 2.0 Hz, 1H), 7.44-7.41 (m, 2H), 7.33 (d, J = 8.4 Hz, 1H), 7.17 (dd, J = 8.4, 2.0 Hz, 1H), 4.47 (s, 2H), 3.79 (t, J = 5.2 Hz, 2H), 3.74 (s, 2H), 3.71 (t, J = 5.6 Hz, 2H), 3.47 (t, J = 6.0 Hz, 2H), 2.56-2.54 (m, 2H), 1.61-1.46 (m, 4H) ppm. LCMS (AM3): rt = 0.701 min, (508.2 $[M + H]^+$), 99.8% purity Purification Method 62 |
| Example 135 | 5-((2-(4-((3-(cyanomethyl)-5-cyclopropylbenzyl) amino)butoxy) ethyl)amino)benzo[c] [2,6]naphthyridine-8-carboxamide | 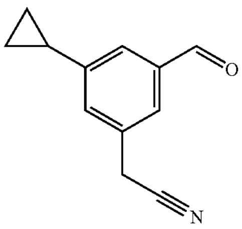 [SMILES: N#CCc1cc(C=O)cc(C2CC2)c1] 2-(3-Cyclopropyl-5-formylphenyl)acetonitrile 1.747 | $^{1}$H NMR (400 MHz, MeOH-$d_4$) δ: 9.94 (s, 1H), 8.79 (d, J = 5.6 Hz, 1H), 8.62 (d, J = 8.4 Hz, 1H), 8.23 (d, J = 5.6 Hz, 1H), 8.15 (d, J = 5.2 Hz, 1H), 7.85 (dd, J = 8.8, 1.6 Hz, 1H), 7.03 (s, 1H), 6.96 (s, 2H), 3.93 (t, J = 5.6 Hz, 2H), 3.84-3.81 (m, 4H), 3.64 (s, 2H), 3.58 (t, J = 5.2 Hz, 2H), 2.59 (t, J = 6.8 Hz, 2H), 1.92-1.85 (m, 1H), 1.64-1.60 (m, 4H), 0.99-0.94 (m, 2H), 0.71-0.67 (m, 2H) ppm LCMS (AM3): rt = 0.762 min, (523.5 $[M + H]^+$), 98.5% purity Purification Method 134 |

TABLE 5-continued

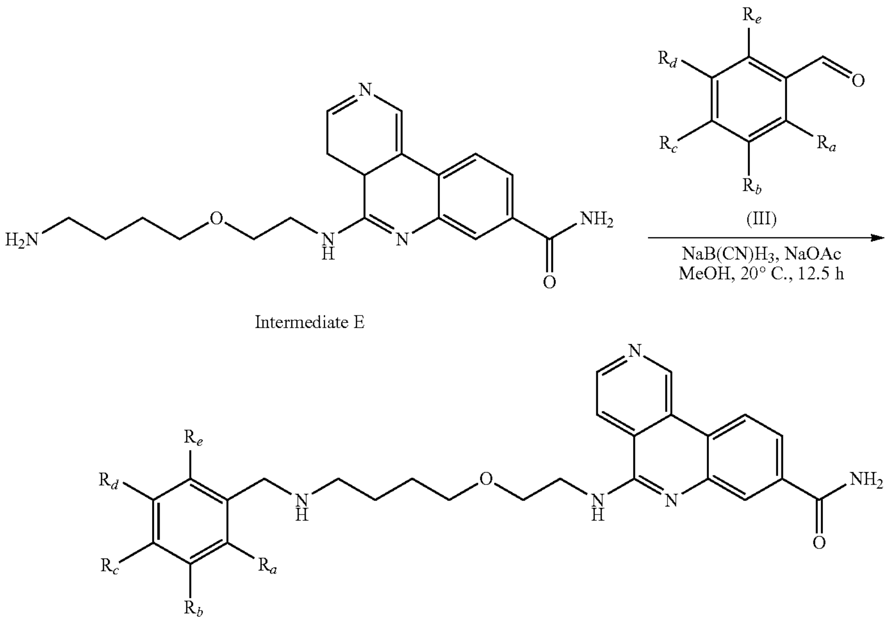

Intermediate E

| Example No. | Chemical IUPAC name | Compound (III) | Analytical |
|---|---|---|---|
| Example 136 | 5-((2-(4-((3-(cyanomethyl)-5-ethoxybenzyl)amino)butoxy)ethyl)amino)benzo[c][2,6]naphthyridine-8-carboxamide | 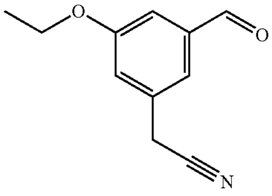 2-(3-Ethoxy-5-formylphenyl)acetonitrile 1.741 | $^1$H NMR (400 MHz, MeOH-$d_4$) δ: 9.96 (s, 1H), 8.80 (d, J = 5.6 Hz, 1H), 8.64 (d, J = 8.4 Hz, 1H), 8.50 (br s, 1H), 8.22 (d, J = 1.6 Hz, 1H), 8.15 (d, J = 5.6 Hz, 1H), 7.86 (dd, J =8.4, 1.6 Hz, 1H), 6.93 (d, J = 6.4 Hz, 2H), 6.91 (s, 1H), 4.07-4.02 (m, 4H), 3.94 (t, J = 5.6 Hz, 2H), 3.89 (s, 2H), 3.84 (t, J = 5.6 Hz, 2H), 3.65 (t, J = 6.0 Hz, 2H), 3.06 (t, J = 7.2 Hz, 2H), 1.86-1.78 (m, 2H), 1.75-1.68 (m, 2H), 1.39 (t, J = 7.2 Hz, 3H) ppm LCMS (AM3): rt = 0.708 min, (527.3 [M + H]$^+$), 100% purity Purification Method 135 |
| Example 137 | 5-((2-(4-((3-cyclopropyl-5-(hydroxymethyl)benzyl)amino)butoxy)ethyl)amino)benzo[c][2,6]naphthyridine-8-carboxamide | 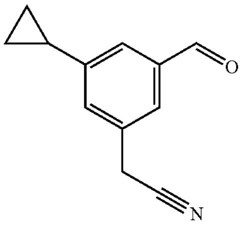 [SMILES: N#CCc1cc(C=O)cc(C2CC2)c1] 3-Cyclopropyl-5-(hydroxymethyl)benzaldehyde 1.744 | $^1$H NMR (400 MHz, MeOH-$d_4$) δ: 9.96 (d, J = 4.4 Hz, 1H), 8.81-8.79 (m, 1H), 8.66-8.61 (m, 1H), 8.52 (br s, 1H), 8.23 (s, 1H), 8.15 (d, J = 6.0 Hz, 1H), 7.86-7.84 (m, 1H), 7.15 (s, 1H), 7.11 (s, 1H), 7.02 (s, 1H), 4.59 (s, 2H), 4.02 (s, 2H), 3.94 (t, J = 5.6 Hz, 2H), 3.84 (t, J = 5.6 Hz, 2H), 3.64 (t, J = 6.0 Hz, 2H), 3.03 (t, J = 7.6 Hz, 2H), 1.96-1.89 (m, 1H), 1.84-1.77 (m, 2H), 1.73-1.67 (m, 2H), 1.01-0.96 (m, 2H), 0.73-0.68 (m, 2H) ppm LCMS (AM3): rt = 0.726 min, (514.5 [M + H]$^+$), 100% purity. Purification Method 68 |
| Example 140 | 5-((2-(4-((3-(cyanomethyl)-5-(2,2,2-trifluoroethoxy)benzyl)amino)butoxy)ethyl)amino)benzo[c][2,6]naphthyridine-8-carboxamide | 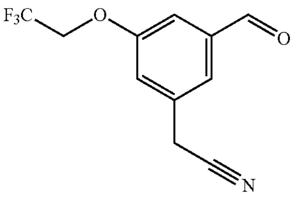 [SMILES: N#CCc1cc(C=O)cc(OCC(F)(F)F)c1] 2-(3-Formyl-5-(2,2,2-trifluoroethoxy)phenyl)acetonitrile 1.754 | $^1$H NMR (400 MHz, MeOH-$d_4$) δ: 9.94 (s, 1H), 8.79 (d, J = 5.6 Hz, 1H), 8.63 (d, J = 8.4 Hz, 1H), 8.23 (d, J = 2.0 Hz, 1H), 8.16 (d, J = 5.2 Hz, 1H), 7.85 (dd, J = 8.4, 2.0 Hz, 1H), 6.97 (s, 1H), 6.93 (s, 1H), 6.90 (s, 1H), 4.54 (q, J = 8.4 Hz, 2H), 3.93 (t, J = 5.2 Hz, 2H), 3.87-3.81 (m, 4H), 3.66 (s, 2H), 3.59 (t, J = 5.6 Hz, 2H), 2.58 (t, J = 6.8 Hz, 2H), 1.65-1.61 (m, 4H) ppm LCMS (AM3): rt = 0.737 min, (581.3 [M + H]$^+$), 100% Purification Method 137 |

Example 43

5-((2-(4-((3-(Aminomethyl)-5-chlorobenzyl)amino) butoxy)ethyl)amino)benzo[c][2,6]naphthyridine-8-carboxamide

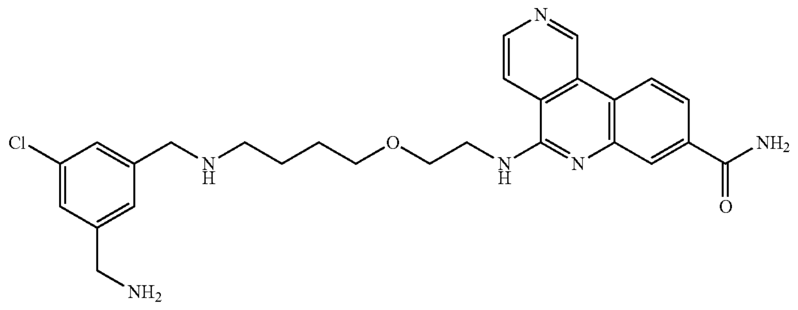 [SMILES: NCc1cc(Cl)cc(CNCCCCOCCNc2nc3cc(C(N)=O)ccc3c3cnccc23)c1]

To a mixture of compound 1.573 (60 mg, 119.29 μmol) and ammonium hydroxide (3.64 g, 25.97 mmol, 25% purity) in MeOH (10 mL) was added Raney-Ni (60.00 mg) under nitrogen protection. The reaction mixture was then hydrogenated under one atmosphere $H_2$ pressure at 20° C. for 8 h. The catalyst was removed by filtration and the filtrate was concentrated in vacuo. The residue was purified (PM58) to afford Example 43 (28.80 mg, 46.37 μmol, 38.9% yield, TFA salt) as a yellow gum.

LCMS (AM7): rt=0.916 min, (507.2 $[M+H]^+$), 98.4% purity.

$^1H$ NMR (400 MHz, MeOH-$d_4$) δ: 10.02 (br s, 1H), 8.95 (br s, 1H), 8.72 (d, J=8.4 Hz, 1H), 8.41-8.38 (m, 2H), 8.00 (dd, J=8.4, 1.6 Hz, 1H), 7.58 (s, 2H), 7.51 (s, 1H), 4.18 (s, 2H), 4.15 (s, 2H), 4.07 (t, J=5.2 Hz, 2H), 3.88 (t, J=5.2 Hz, 2H), 3.60 (t, J=6.0 Hz, 2H), 3.06 (t, J=7.6 Hz, 2H), 1.87-1.76 (quin, 2H), 1.72-1.63 (m, 2H) ppm.

Example 44

5-(2-(4-((3-Chloro-5-(cyanomethyl)benzyl)amino) butoxy)ethoxy)benzo[c][2,6]naphthyridine-8-carboxamide

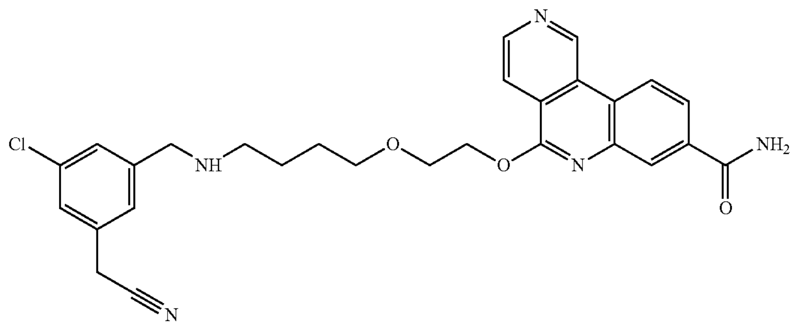 [SMILES: N#CCc1cc(Cl)cc(CNCCCCOCCOc2nc3cc(C(N)=O)ccc3c3cnccc23)c1]

A mixture of compound 1.57 (100 mg, 213.48 μmol), compound 1.366 (38.34 mg, 213.48 μmol) and DIPEA (55.18 mg, 426.96 μmol) in MeOH (10 mL) was stirred at 25° C. for 1 h, then sodium triacetoxyborohydride (226.23 mg, 1.07 mmol) was added. The mixture was stirred at 25° C. for another 11 h. The mixture was concentrated in vacuo and the residue was purified (PM59) to afford Example 44 (43.54 mg, 84.05 μmol, 39.4% yield) as a brown solid.

LCMS (AM3): rt=0.787 min, (518.2 $[M+H]^+$), 100% purity.

$^1$H NMR (400 MHz, MeOH-$d_4$) δ: 9.90 (s, 1H), 8.80 (d, J=5.2 Hz, 1H), 8.64 (d, J=8.4 Hz, 1H), 8.29 (d, J=2.0 Hz, 1H), 8.11 (d, J=5.4 Hz, 1H), 7.99 (dd, J=8.4, 2.0 Hz, 1H), 7.44 (s, 1H), 7.40 (1H, s), 7.37 (s, 1H), 4.77 (t, J=4.8 Hz, 2H), 4.12 (s, 2H), 3.98 (t, J=4.8 Hz, 2H), 3.92 (s, 2H), 3.68 (t, J=6.0 Hz, 2H), 3.07 (t, J=6.0 Hz, 2H), 1.86-1.80 (quin, 2H), 1.76-1.67 (quin, 2H) ppm.

The following examples in Table 6 were made with non-critical changes or substitutions to the exemplified procedure in Example 44, that would be understood by one skilled in the art using intermediate 1.57 and compounds of formula (III).

TABLE 6

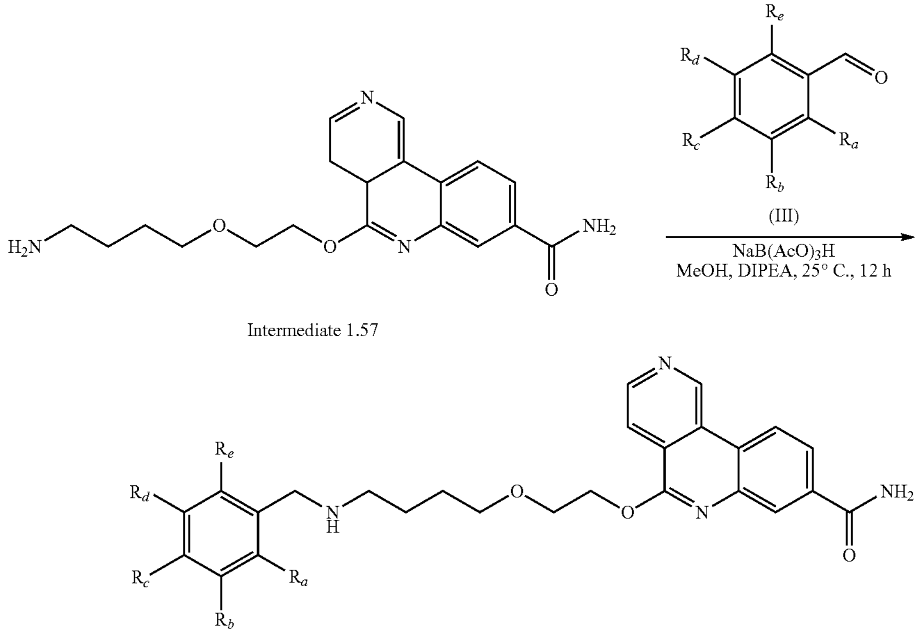

| Example No. | Chemical IUPAC name | Compound (III) | Analytical |
|---|---|---|---|
| Example 45 | 5-(2-(4-((3-chloro-4-cyclobutoxybenzyl)amino)butoxy)ethoxy)benzo[c][2,6]naphthyridine-8-carboxamide | 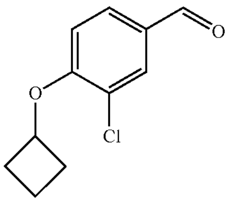 [SMILES: O=Cc1ccc(OC2CCC2)c(Cl)c1] 3-chloro-4-cyclobutoxybenzaldehyde 1.32 | $^1$H NMR (400 MHz, MeOH-$d_4$) δ: 9.95 (s, 1H), 8.82 ( d, J = 5.6 Hz, 1H), 8.69 (d, J = 8.4 Hz, 1H), 8.34 (d, J = 1.6 Hz, 1H), 8.15 (d, J = 5.2 Hz, 1H), 8.02 (dd, J = 8.4, 1.6 Hz, 1H), 7.43 (s, 1H), 7.24 ( d, J = 8.4 Hz, 1H), 6.86 (d, J = 8.4 Hz, 1H), 4.79 (t, J = 4.8 Hz, 2H), 4.71-4.64 (quin, 1H), 4.03 (s, 2H), 3.98 (t, J = 4.8 Hz, 2H), 3.67 (t, J = 5.6 Hz, 2H), 3.04 (t, J = 5.6 Hz, 2H), 2.47-2.40 (m, 2H), 2.16-2.06 (m, 2H), 1.89-1.66 (m, 6H) ppm. LCMS (AM3): rt = 0.842 min, (549.2 $[M + H]^+$), 99.2% purity. Purification Method 60 |
| Example 50 | 5-(2-(4-((3-fluoro-4-(trifluoromethoxy)benzyl)amino)butoxy)ethoxy)benzo[c][2,6]naphthyridine-8-carboxamide | 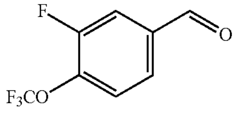 3-fluoro-4-(trifluoromethoxy)benzaldehyde | $^1$H NMR (400 MHz, MeOH-$d_4$) δ: 9.96 (s, 1H), 8.83 (d, J = 5.2 Hz, 1H), 8.70 (d, J = 8.4 Hz, 1H), 8.34 (d, J = 1.6 Hz, 1H), 8.16 (d, J = 5.2 Hz, 1H), 8.03 (dd, J = 8.4, 1.6 Hz, 1H), 7.51-7.46 (m, 2H), 7.36 ( d, J = 8.4 Hz, 1H), 4.81 (t, J = 4.8 Hz, 2H), 4.19 (s, 2H), 4.00 (t, J = 4.4 Hz, 2H), 3.70 (t, J = 5.6 Hz, 2H), 3.11 (t, J = 7.2 Hz, 2H), 1.90-1.82 (m, 2H), 1.78-1.71 (m, 2H) ppm. LCMS (AM3): rt = 0.818 min, (547.2 $[M + H]^+$), 99.5% purity. Purification Method 64 |

TABLE 6-continued

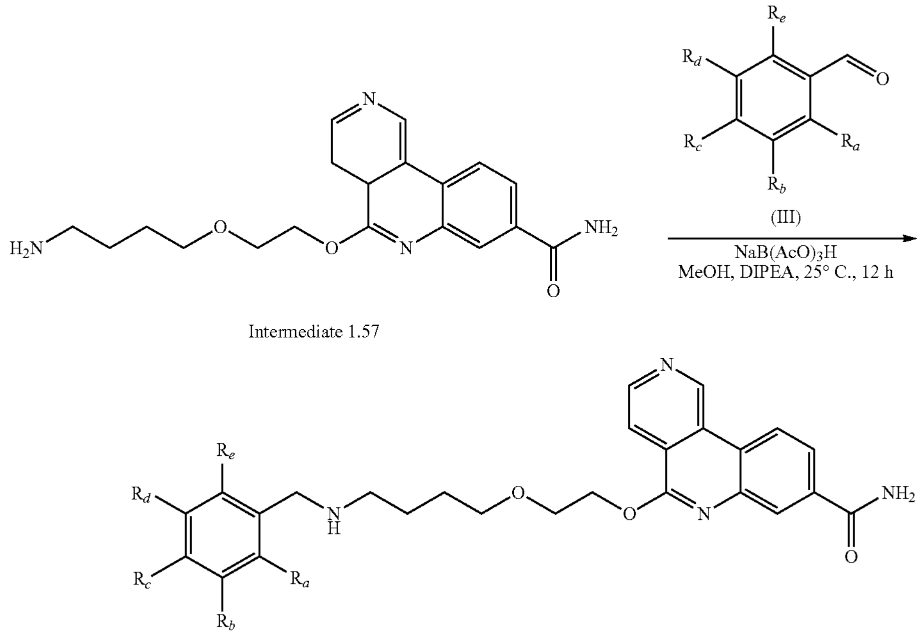

Intermediate 1.57

| Example No. | Chemical IUPAC name | Compound (III) | Analytical |
|---|---|---|---|
| Example 51 | 5-(2-(4-((3-cyano-4-cyclopropylbenzyl)amino)butoxy)ethoxy)benzo[c][2,6]naphthyridine-8-carboxamide | 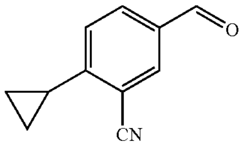 [SMILES: N#Cc1cc(C=O)ccc1C1CC1] 2-cyclopropyl-5-formylbenzonitrile 1.52 | $^1$H NMR (400 MHz, MeOH-$d_4$) δ: 9.89 (s, 1H), 8.80 (d, J = 5.6 Hz, 1H), 8.63 (d, J = 8.4 Hz, 1H), 8.50 (br s, 1H), 8.28 (d, J = 1.6 Hz, 1H), 8.10 (d, J = 5.2 Hz, 1H), 7.99 (dd, J = 8.4, 2.0 Hz, 1H), 7.71 (d, J = 1.2 Hz, 1H), 7.59 (d, J = 8.4 Hz, 1H), 7.05 (d, J = 8.4 Hz, 1H), 4.77 (t, J = 4.8 Hz, 2H), 4.13 (s, 2H), 3.99 (t, J = 4.8 Hz, 2H), 3.69 (t, J = 6.0 Hz, 2H), 3.08 (t, J = 7.2 Hz, 2H), 2.24-2.17 (m, 1H), 1.89-1.80 (quin, 2H), 1.78-1.70 (quin, 2H) 1.18-1.12 (m, 2H), 0.83-0.77 (m, 2H) ppm. LCMS (AM3): rt = 0.793 min, (510.3 [M + H]$^+$), 100% purity. Purification Method 65 |
| Example 52 | 5-(2-(4-((4-cyclobutoxy-3-(hydroxymethyl)benzyl)amino)butoxy)ethoxy)benzo[c][2,6]naphthyridine-8-carboxamide | 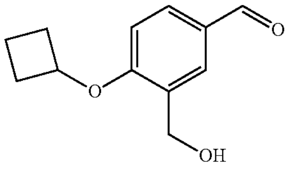 [SMILES: O=Cc1ccc(OC2CCC2)c(CO)c1] (4-cyclobutoxy-3-(hydroxymethyl)benzaldehyde) 1.64 | $^1$H NMR (400 MHz, MeOH-$d_4$) δ: 9.90 (s, 1H), 8.80 ( d, J = 5.2 Hz, 1H), 8.64 (d, J = 8.4 Hz, 1H), 8.47 (br s, 1H), 8.30 (d, J = 1.6 Hz, 1H), 8.11 (d, J = 5.6 Hz, 1H), 7.99 (d, J = 7.2 Hz, 1H), 7.43 (s, 1H), 7.21 (d, J = 8.0 Hz, 1H), 6.73 (d, J = 8.4 Hz, 1H), 4.76 (d, J = 8.4 Hz, 2H), 4.69-4.62 (m, 1H), 4.60 (s, 2H), 4.04 (s, 2H), 3.97 (t, J = 4.4 Hz, 2H), 3.67 (t, J = 5.6 Hz, 2H), 3.04 (t, J = 7.2 Hz, 2H), 2.46-2.38 (m, 2H), 2.13-2.04 (m, 2H), 1.86-1.65 (m, 6H) ppm. LCMS (AM3): rt = 0.800 min, (545.3 [M + H]$^+$), 99.0% purity Purification Method 66 |
| Example 53 | 5-(2-(4-((3-chloro-5-(hydroxymethyl)benzyl)amino)butoxy)ethoxy)benzo[c][2,6]naphthyridine-8-carboxamide | 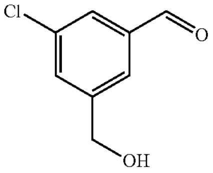 [SMILES: O=Cc1cc(Cl)cc(CO)c1] 3-Chloro-5-(hydroxymethyl)benzaldehyde 1.102 | $^1$H NMR (400 MHz, MeOH-$d_4$) c: 9.69 (s, 1H), 8.69 (d, J = 5.2 Hz, 1H), 8.49 (br s, 1H), 8.42 (d, J = 8.4 Hz, 1H), 8.13 (s, 1H), 7.94-7.86 (m, 2H), 7.36-7.30 (m, 3H), 4.66 (t, J = 4.8 Hz, 2H), 4.58 (s, 2H), 4.12 (s, 2H), 3.94 (t, J = 4.8 Hz, 2H), 3.67 (t, J = 5.6 Hz, 2H), 3.08 (t, J = 5.6 Hz, 2H), 1.91-1.80 (m, 2H), 1.77-1.69 (m, 2H) ppm. LCMS (AM3): rt = 0.769 min, (509.2 [M + H]$^+$), 100% purity Purification Method 59 |

TABLE 6-continued

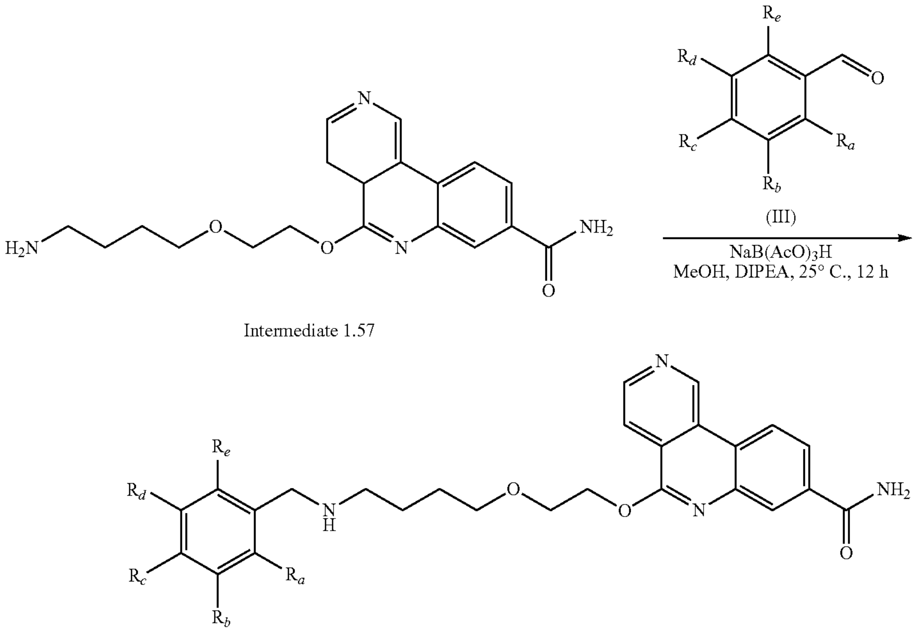

Intermediate 1.57

| Example No. | Chemical IUPAC name | Compound (III) | Analytical |
|---|---|---|---|
| Example 91 | 5-(2-(4-((3-(hydroxymethyl)-5-(trifluoromethyl)benzyl)amino)butoxy)ethoxy)benzo[c][2,6]naphthyridine-8-carboxamide | 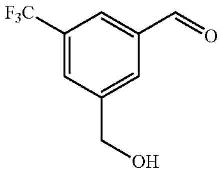 3-(Hydroxymethyl)-5-(trifluoromethyl)benzaldehyde 1.501 | $^1$H NMR (400 MHz, DMSO-$d_6$) δ: 10.18 (s, 1H), 8.93-8.88 (m, 2H), 8.37 (d, J = 1.6 Hz, 1H), 8.28 (br s, 1H), 8.10-8.05 (m, 2H), 7.55 (br s, 1H), 7.50-7.48 (m, 3H), 5.37 (br s, 1H), 4.73 (t, J = 4.4 Hz, 2H), 4.54 (s, 2H), 3.88 (t, J = 4.4 Hz, 2H), 3.68 (s, 2H), 3.53 (t, J = 6.4 Hz, 2H), 2.45 (t, J = 6.8 Hz, 2H), 1.60-1.53 (quin, 2H), 1.50-1.43 (quin, 2H) ppm LCMS (AM7): rt = 0.916 min, (543.3 [M + H]$^+$), 100% purity Purification Method 86 |
| Example 92 | 5-(2-(4-((3-(cyanomethyl)-5-fluorobenzyl)amino)butoxy)ethoxy)benzo[c][2,6]naphthyridine-8-carboxamide | 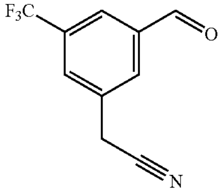 [SMILES: N#CCc1cc(C=O)cc(C(F)(F)F)c1] 2-(3-Fluoro-5-formylphenyl)acetonitrile 1.472 | $^1$H NMR (400 MHz, DMSO-$d_6$) δ: 10.15 (s, 1H), 8.90 (d, J = 5.2 Hz, 1H), 8.86 (d, J = 8.4 Hz, 1H), 8.36 (d, J = 1.6 Hz, 1H), 8.28 (br s, 1H), 8.07-8.05 (m, 2H), 7.55 (br s, 1H), 7.12 (s, 1H), 7.06 (d, J = 9.6 Hz, 1H), 6.99 ( d, J = 9.6 Hz, 1H), 4.72 (t, J = 4.8 Hz, 2H), 4.01 (s, 2H), 3.88 (t, J = 4.8 Hz, 2H), 3.61 (s, 2H), 3.52 (t, J = 6.4 Hz, 2H), 2.43 (t, J = 6.8 Hz, 2H), 1.59-1.50 (quin, 2H), 1.48-1.41 (quin, 2H) ppm LCMS (AM7): rt = 0.896 min, (502.3 [M + H]$^+$), 100% purity Purification Method 85 |
| Example 94 | 5-(2-(4-((3-fluoro-5-(hydroxymethyl)benzyl)amino)butoxy)ethoxy)benzo[c][2,6]naphthyridine-8-carboxamide | 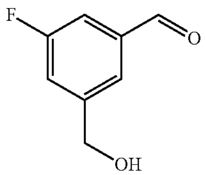 [SMILES: O=Cc1cc(F)cc(CO)c1] 3-Fluoro-5-(hydroxymethyl)benzaldehyde 1.500 | $^1$H NMR (400 MHz, MeOH-$d_4$) δ: 9.70 (br s, 1H), 8.69 (br s, 1H), 8.42 (d, J = 8.4 Hz, 1H), 8.13 (s, 1H), 7.96-7.92 (d, 1H), 7.89-7.85 (d, 1H), 7.07 (s, 1H), 6.95 (t, J = 9.2 Hz, 2H), 4.68 (t, J = 4.8 Hz, 2H), 4.55 (s, 2H), 3.92 (t, J = 4.8 Hz, 2H), 3.78 (br s, 2H), 3.62 (t, J = 5.2 Hz, 2H), 2.75-2.64 (m, 2H), 1.68-1.62 (m, 4H) ppm LCMS (AM7): rt = 0.885 min, (493.3 [M + H]$^+$), 98.9% purity Purification Method 95 |

TABLE 6-continued

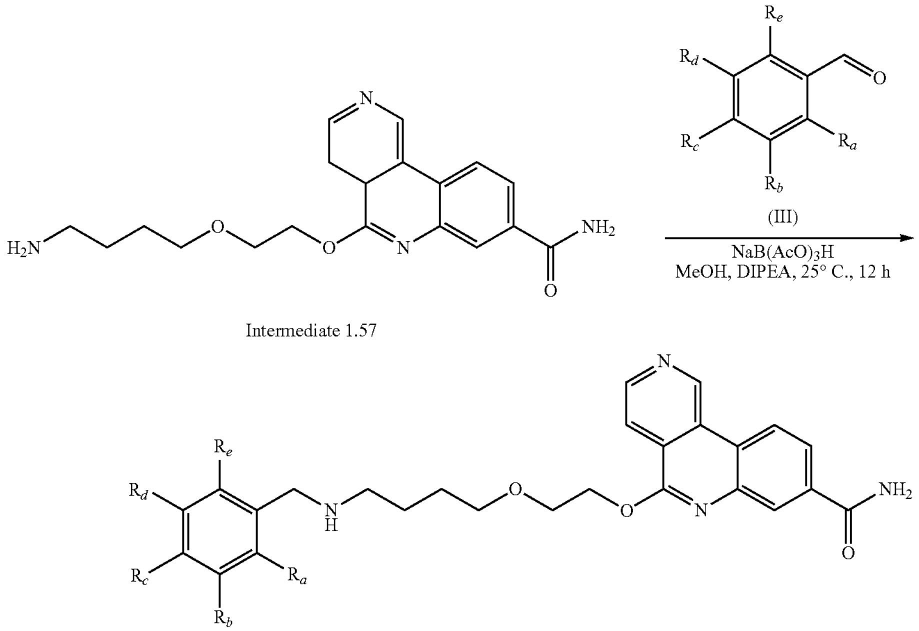

Intermediate 1.57

| Example No. | Chemical IUPAC name | Compound (III) | Analytical |
|---|---|---|---|
| Example 96 | 5-(2-(4-((3-(cyanomethyl)-5-methylbenzyl)amino)butoxy)ethoxy)benzo[c][2,6]naphthyridine-8-carboxamide | 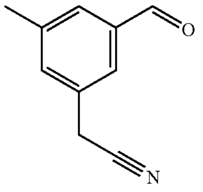 2-(3-Formyl-5-methylphenyl)acetonitrile 1.475 | $^1$H NMR (400 MHz, MeOH-$d_4$) δ: 9.80 (s, 1H), 8.74 (d, J = 5.2 Hz, 1H), 8.53 (d, J = 8.4 Hz, 1H), 8.22 (d, J = 1.6 Hz, 1H), 8.04 (d, J = 5.2 Hz, 1H), 7.93 (dd, J = 8.4, 1.6 Hz, 1H), 7.04-7.00 (m, 3H), 4.72 (t, J = 4.8 Hz, 2H), 3.94 (t, J = 4.8 Hz, 2H), 3.77 (s, 2H), 3.65-3.61 (m, 4H), 2.65-2.56 (m, 2H), 2.26 (s, 3H), 1.67-1.59 (m, 4H) ppm LCMS (AM7): rt = 0.966 min, (498.3 [M + H]$^+$), 100% purity Purification Method 97 |
| Example 97 | 5-(2-(4-((3-(cyanomethyl)-5-(trifluoromethyl)benzyl)amino)butoxy)ethoxy)benzo[c][2,6]naphthyridine-8-carboxamide | 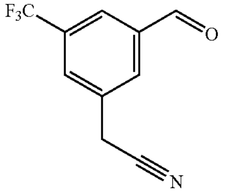 [SMILES: N#CCc1cc(C=O)cc(C(F)(F)F)c1] 2-(3-Formyl-5-(trifluoromethyl)phenyl)acetonitrile 1.469 | $^1$H NMR (400 MHz, DMSO-$d_6$) δ: 10.19 (s, 1H), 8.93-8.87 (m, 2H), 8.38 (d, J = 1.6 Hz, 1H), 8.28 (br s, 1H), 8.10-8.06 (m, 2H), 7.63-7.55 (m, 4H), 4.75-4.71 (t, 2H), 4.14 (s, 2H), 3.89 (t, J = 4.8 Hz, 2H), 3.74 (s, 2H), 3.52 (t, J = 6.0 Hz, 2H), 2.50-2.49 (m, 2H), 1.60-1.52 (m, 2H), 1.52-1.44 (m, 2H) ppm LCMS (AM7): rt = 0.932 min, (552.3 [M + H]$^+$), 98.4% purity Purification Method 98 |
| Example 107 | 5-(2-(4-((3-(cyanomethyl)-5-(trifluoromethoxy)benzyl)amino)butoxy)ethoxy)benzo[c][2,6]naphthyridine-8-carboxamide | 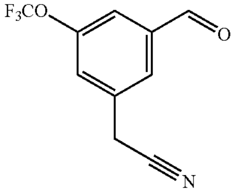 2-(3-Formyl-5-(trifluoromethoxy)phenyl)acetonitrile 1.504 | $^1$H NMR (400 MHz, DMSO-$d_6$) 0:10.19 (s, 1H), 8.93-8.87 (m, 2H), 8.38 (s, 1H), 8.28 (br s, 1H), 8.10-8.04 (m, 2H), 7.55 (br s, 1H), 7.31-7.17 (m, 3H), 4.73 (t, J = 4.4 Hz, 2H), 4.08 (s, 2H), 3.88 (t, J = 4.0 Hz, 2H), 3.67 (s, 2H), 3.53 (t, J = 6.4 Hz, 2H), 2.45 (t, J = 6.4 Hz, 2H), 1.59-1.52 (m, 2H), 1.50-1.42 (m, 2H) ppm LCMS (AM7): rt = 0.942 min, (568.3 [M + H]$^+$), 99.5% purity Purification Method 108 |

TABLE 6-continued

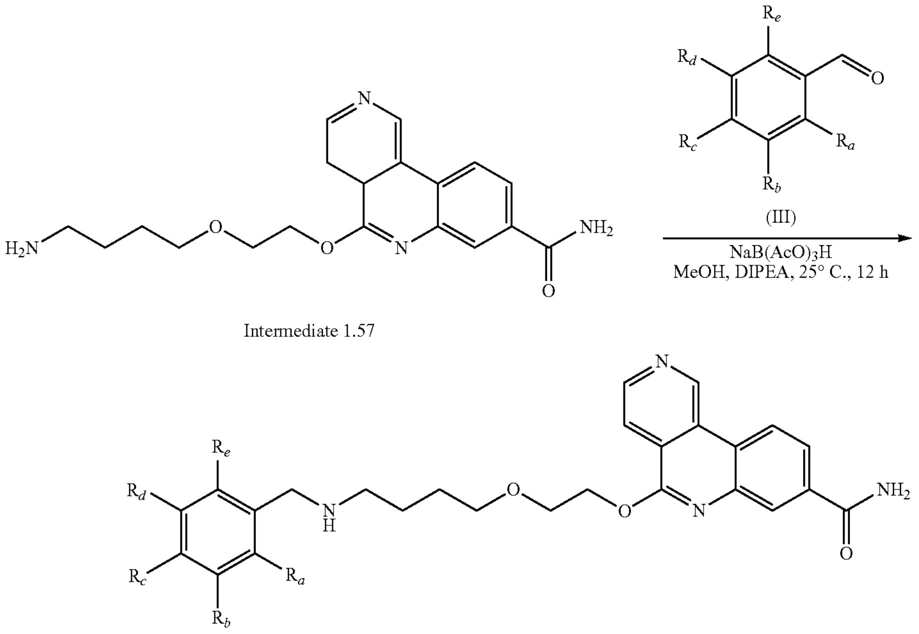

Intermediate 1.57

| Example No. | Chemical IUPAC name | Compound (III) | Analytical |
|---|---|---|---|
| Example 160 | 5-(2-(4-((3-cyano-5-(trifluoromethoxy)benzyl)amino)butoxy)ethoxy)benzo[c][2,6]naphthyridine-8-carboxamide | 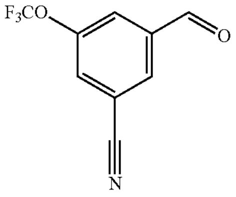 [SMILES: N#Cc1cc(C=O)cc(OC(F)(F)F)c1] 3-Formyl-5-(trifluoromethoxy)benzonitrile 1.714 | $^1$H NMR (400 MHz, MeOH-d$_4$) δ: 9.99 (s, 1H), 8.84 (d, J = 5.6 Hz, 1H), 8.74 (d, J = 8.4 Hz, 1H), 8.38 (d, J = 1.6 Hz, 1H), 8.21 (d, J = 5.6 Hz, 1H), 8.05 (dd, J = 8.4, 2.0 Hz, 1H), 7.65 (s, 1H), 7.56-7.53 (m, 2H), 4.83-4.80 (m, 2H), 3.98 (t, J = 4.8 Hz, 2H), 3.75 (s, 2H), 3.64 (t, J = 5.6 Hz, 2H), 2.57 (t, J = 6.8 Hz, 2H), 1.70-1.57 (m, 4H) ppm LCMS (AM3): rt = 0.802 min, (554.2 [M + H]$^+$), 99.1% purity Purification Method 156 |
| Example 161 | 5-(2-(4-((3-(2-hydroxyethoxy)-5-(trifluoromethoxy)benzyl)amino)butoxy)ethoxy)benzo[c][2,6]naphthyridine-8-carboxamide | 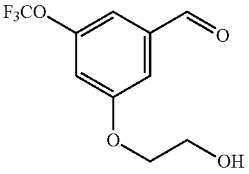 [SMILES: O=Cc1cc(OCCO)cc(OC(F)(F)F)c1] 3-(2-Hydroxyethoxy)-5-(trifluoromethoxy)benzaldehyde 1.718 | $^1$H NMR (400 MHz, MeOH-d$_4$) δ: 10.02 (s, 1H), 8.85 (d, J = 5.6 Hz, 1H), 8.76 (d, J = 8.4 Hz, 1H), 8.49 (s, 1H), 8.38 (d, J = 2.0 Hz, 1H), 8.20 (d, J = 5.6 Hz, 1H), 8.05 (dd, J = 8.4 Hz, 2.0 Hz, 1H), 7.01 (d, J = 1.6 Hz, 1H), 6.94 (s, 1H), 6.88 (s, 1H), 4.84-4.82 (m, 2H), 4.08-4.05 (m, 4H), 4.00 (t, J = 4.8 Hz, 2H), 3.85 (t, J = 4.8 Hz, 2H), 3.68 (t, J = 6.0 Hz, 2H), 3.04 (t, J = 7.2 Hz, 2H), 1.86-1.78 (m, 2H), 1.75-1.68 (m, 2H) ppm LCMS (AM3): rt = 0.793 min, (589.2 [M + H]$^+$), 100% purity Purification Method 157 |
| Example 162 | 5-(2-(4-((3-(oxazol-5-ylmethyl)-5-(trifluoromethoxy)benzyl)amino)butoxy)ethoxy)benzo[c][2,6]naphthyridine-8-carboxamide | 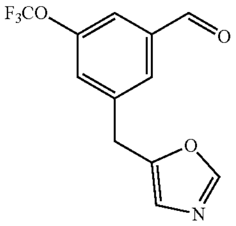 3-(Oxazol-5-ylmethyl)-5-(trifluoromethoxy)benzaldehyde 1.713 | $^1$H NMR (400 MHz, MeOH-d$_4$) δ: 10.04 (s, 1H), 8.86 (d, J = 5.6 Hz, 1H), 8.79 (d, J = 8.4 Hz, 1H), 8.47 (br s, 1H), 8.40 (d, J = 2.0 Hz, 1H), 8.22 (d, J = 5.2 Hz, 1H), 8.10 (s, 1H), 8.07 (dd, J = 8.4 Hz, 2.0 Hz, 1H), 7.31 (s, 1H), 7.28 (s, 1H), 7.23 (s, 1H), 6.93 (s, 1H), 4.84-4.81 (m, 2H), 4.12 (s, 2H), 4.10 (s, 2H), 4.00 (t, J = 4.8 Hz, 2H), 3.67 (t, J = 5.6 Hz, 2H), 3.02 (t, J = 7.6 Hz, 2H), 1.84-1.76 (quin, 2H), 1.74-1.67 (quin, 2H) ppm LCMS (AM3): rt = 0.812 min, (610.2 [M + H]$^+$), 99.4% purity Purification Method 158 |

TABLE 6-continued

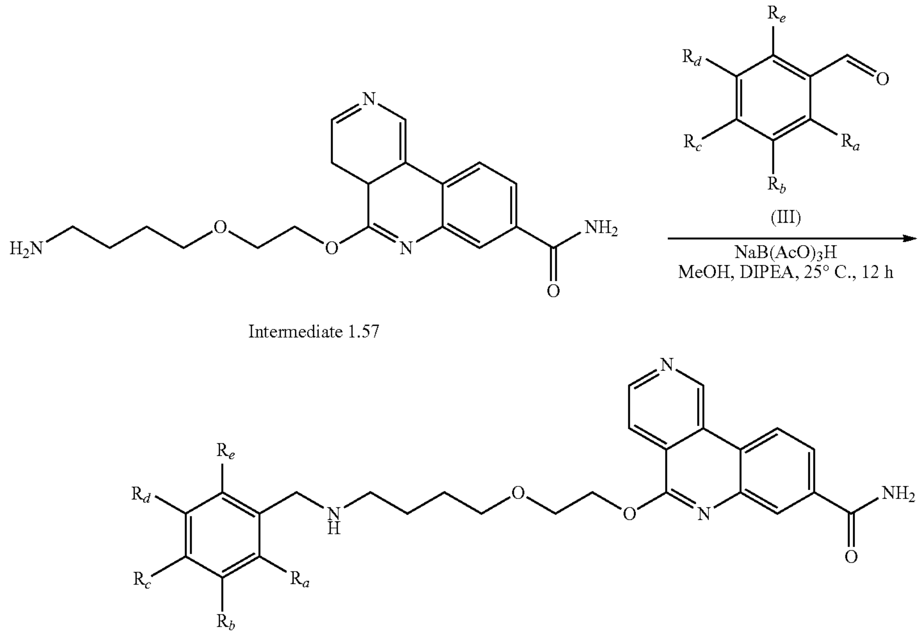

| Example No. | Chemical IUPAC name | Compound (III) | Analytical |
|---|---|---|---|
| Example 163 | 5-(2-(4-((3-(oxazol-4-ylmethyl)-5-(trifluoromethoxy)benzyl)amino)butoxy)ethoxy)benzo[c][2,6]naphthyridine-8-carboxamide | 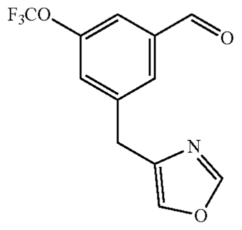 3-(Oxazol-4-ylmethyl)-5-(trifluoromethoxy)benzaldehyde 1.712 | $^1$H NMR (400 MHz, MeOH-$d_4$) 8:10.01 (s, 1H), 8.84 (d, J = 5.6 Hz, 1H), 8.75 (d, J = 8.4 Hz, 1H), 8.50 (s, 1H), 8.38 (d, J = 2.0 Hz, 1H), 8.20 (d, J 5.6 Hz, 1H), 8.15 (s, 1H), 8.04 (dd, J = 8.4 Hz, 2.0 Hz, 1H), 7.77 (s, 1H), 7.31 (s, 1H), 7.24-7.18 (m, 2H), 4.82 (t, J =4.8 Hz, 2H), 4.10 (s, 2H), 3.97 (t, J = 4.4 Hz, 2H), 3.93 (s, 2H), 3.67 (t, J = 6.0 Hz, 2H), 3.03 (t, J = 7.2 Hz, 2H), 1.85-1.77 (quin, 2H), 1.74-1.68 (quin, 2H) ppm<br>LCMS (AM3): rt = 0.818 min, (610.2 [M + H]$^+$), 100% purity<br>Purification Method 159 |
| Example 164 | 5-(2-(4-((3-(2-hydroxyethyl)-5-(trifluoromethoxy)benzyl)amino)butoxy)ethoxy)benzo[c][2,6]naphthyridine-8-carboxamide | 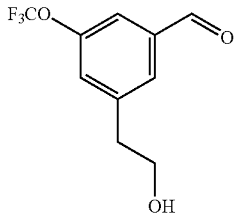 [SMILES: O=Cc1cc(CCO)cc(OC(F)(F)F)c1] 3-(2-Hydroxyethyl)-5-(trifluoromethoxy)benzaldehyde 1.723 | $^1$H NMR (400 MHz, MeOH-$d_4$) δ: 9.99 (s, 1H), 8.84 (d, J = 5.6 Hz, 1H), 8.74 (d, J = 8.4 Hz, 1H), 8.49 (s, 1H), 8.36 (d, J = 2.0 Hz, 1H), 8.19 (d, J = 5.6 Hz, 1H), 8.04 (dd, J = 8.4 Hz, 2.0 Hz, 1H), 7.30 (s, 1H), 7.22 (s, 2H), 4.83-4.80 (t, 2H), 4.12 (s, 2H), 3.99 (t, J = 5.2 Hz, 2H), 3.78 (t, J = 6.4 Hz, 2H), 3.68 (t, J = 6.0 Hz, 2H), 3.06 (t, J = 7.2 Hz, 2H), 2.85 (t, J = 6.4 Hz, 2H), 1.86-1.78 (quin, 2H), 1.75-1.68 (quin, 2H) ppm<br>LCMS (AM3): rt = 0.794 min, (573.3 [M + H]$^+$), 100% purity<br>Purification Method 160 |

Example 46

5-(2-(4-((3-Chloro-4-(trifluoromethoxy)benzyl)amino)butoxy)ethoxy)benzo[c][2,6]naphthyridine-8-carboxylic acid

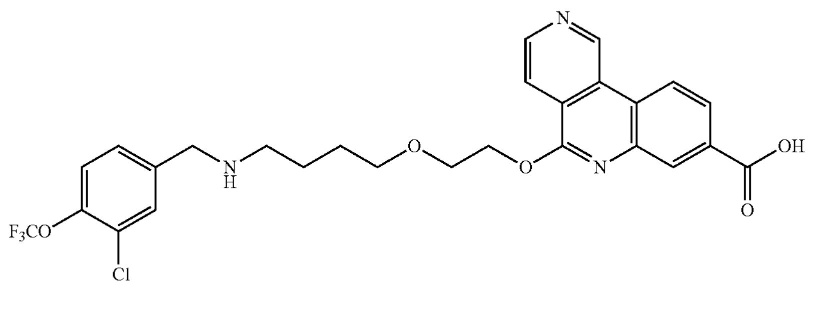 [SMILES: O=C(O)c1ccc2c(c1)nc(OCCOCCCCNCc1ccc(OC(F)(F)F)c(Cl)c1)c1ccncc12]

A mixture of Intermediate Q (100 mg, 213.03 μmol), 3-chloro-4-(trifluoromethoxy)benzaldehyde (47.84 mg, 213.03 μmol) and DIPEA (55.06 mg, 426.07 μmol) in MeOH (10 mL) was stirred at 25° C. for 1 h, then sodium triacetoxyborohydride (225.75 mg, 1.07 mmol) was added. The mixture was stirred at 25° C. for another 11 h. The mixture was concentrated in vacuo and the residue was purified (PM61) to afford Example 46 (29.02 mg, 51.46 μmol, 24.2% yield) as a brown solid.

LCMS (AM3): rt=0.857 min, (564.2 $[M+H]^+$), 100% purity.

$^1H$ NMR (400 MHz, MeOH-$d_4$) δ: 9.88 (s, 1H), 8.76 (d, J=5.6 Hz, 1H), 8.57 (d, J=8.4 Hz, 1H), 8.37 (s, 1H), 8.11-8.05 (m, 2H), 7.71 (d, J=1.6 Hz, 1H), 7.51-7.45 (m, 2H), 4.76 (t, J=4.8 Hz, 2H), 4.16 (s, 2H), 3.95 (t, J=4.8 Hz, 2H), 3.68 (t, J=6.0 Hz, 2H), 3.08 (t, J=7.8 Hz, 2H), 1.89-1.81 (quin, 2H), 1.74-1.67 (quin, 2H) ppm.

The following examples in Table 7 were made with non-critical changes or substitutions to the exemplified procedure in Example 46, that would be understood by one skilled in the art using intermediate Q and compounds of formula (III).

TABLE 7

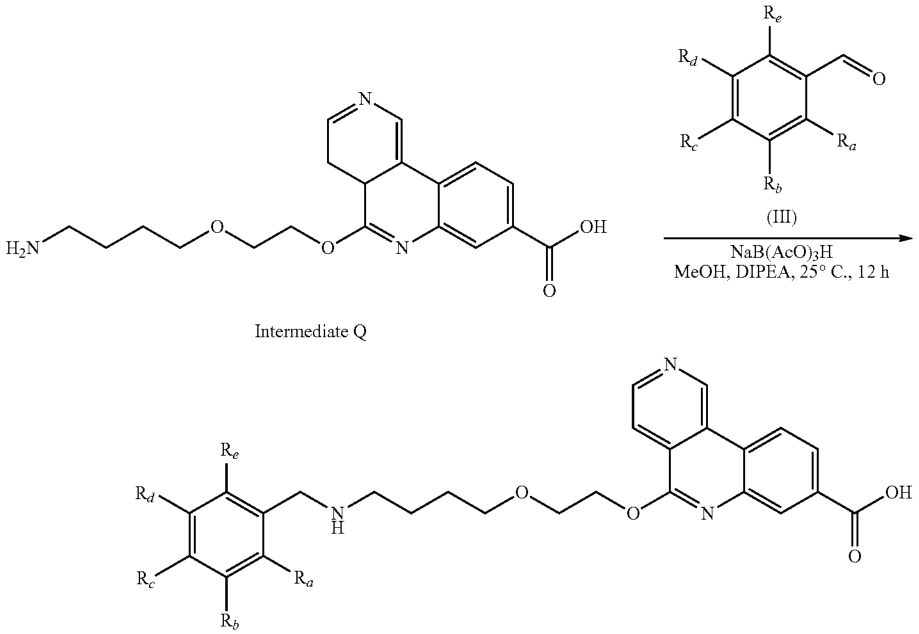

Intermediate Q

| Example No. | Chemical IUPAC name | Compound (III) | Analytical |
|---|---|---|---|
| Example 74 | 5-(2-(4-((3-fluoro-5-(hydroxymethyl) benzyl)amino) butoxy)ethoxy) benzo[c][2,6] naphthyridine-8-carboxylic acid | 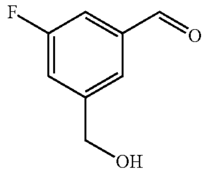 [SMILES: O=Cc1cc(F)cc(CO)c1] 3-Fluoro-5-(hydroxymethyl) benzaldehyde 1.500 | H NMR (400 MHz, MeOH-$d_4$) δ: 9.69 (br s, 1H), 8.66 (d, J = 5.2 Hz, 1H), 8.39 (d, J = 8.4 Hz, 1H), 8.29 (d, J = 1.6 Hz, 1H), 8.03 (dd, J = 8.4, 2.0 Hz, 1H), 7.87 (d, J = 5.2 Hz, 1H), 7.27 (s, 1H), 7.15-7.11 (m, 2H), 4.65 (t, J = 4.8 Hz, 2H), 4.61 (s, 2H), 4.13 (s, 2H), 3.90 (t, J = 4.8 Hz, 2H), 3.66 (t, J = 6.0 Hz, 2H), 3.05 (t, J = 7.8, 2H), 1.91-1.82 (quin, 2H), 1.75-1.68 (quin, 2H) ppm<br>LCMS (AM7): rt = 0.698 min, (494.3 $[M + H]^+$), 100% purity<br>Purification Method 78 |
| Example 75 | 5-(2-(4-((3-(hydroxymethyl)-5-(trifluoromethyl) benzyl)amino) butoxy)ethoxy) benzo[c][2,6] naphthyridine-8-carboxylic acid | 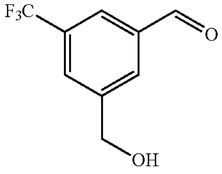 [SMILES: O=Cc1cc(CO)cc(C(F)(F)F)c1] 3-(Hydroxymethyl)-5-(trifluoromethyl) benzaldehyde 1.501 | $^1$H NMR (400 MHz, MeOH-$d_4$) δ: 9.73 (s, 1H), 8.66 (d, J = 5.6 Hz, 1H), 8.41 (d, J = 8.8 Hz, 1H), 8.33 (d, J = 1.6 Hz, 1H), 8.04 (dd, J = 8.4, 1.6 Hz, 1H), 7.91 (d, J = 5.2 Hz, 1H), 7.72-7.68 (m, 3H), 4.71-4.66 (m, 4H), 4.21 (s, 2H), 3.91 (t, J = 4.8 Hz, 2H), 3.67 (t, J =6.0 Hz, 2H), 3.07 (t, J = 7.8 Hz, 2H), 1.91-1.84 (quin, 2H), 1.76-1.69 (quin, 2H) ppm<br>LCMS (AM7): rt = 0.708 min, (544.3 $[M + H]^+$), 100% purity<br>Purification Method 79 |
| Example 76 | 5-(2-(4-((3-chloro-5-(cyanomethyl) benzyl)amino) butoxy)ethoxy) benzo [c][2,6] naphthyridine-8-carboxylic acid | 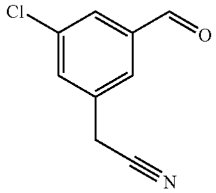 [SMILES: N#CCc1cc(Cl)cc(C=O)c1] 2-(3-Chloro-5-formylphenyl) acetonitrile 1.366 | $^1$H NMR (400 MHz, DMSO-$d_6$) δ: 10.05 (s, 1H), 8.87 (d, J = 5.2 Hz, 1H), 8.73 (d, J = 8.4 Hz, 1H), 8.30 (s, 1H), 8.06-7.98 (m, 2H), 7.43 (s, 1H), 7.32-7.26 (m, 2H), 4.69-4.63 (m, 2H), 4.03 (s, 2H), 3.88-3.80 (m, 4H), 3.57-3.47 (m, 2H), 2.65-2.58 (m, 2H), 1.59-1.51 (m, 4H) ppm<br>LCMS (AM7): rt = 0.704 min, (519.2 $[M + H]^+$), 100% purity<br>Purification Method 79 |

TABLE 7-continued

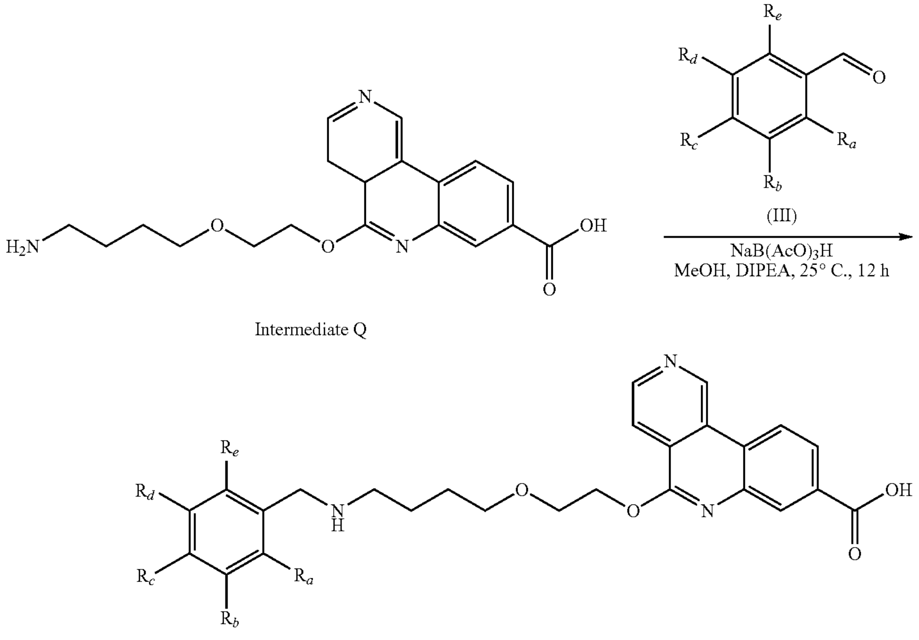

| Example No. | Chemical IUPAC name | Compound (III) | Analytical |
|---|---|---|---|
| Example 77 | 5-(2-(4-((3-(cyanomethyl)-5-(trifluoromethyl)benzyl)amino)butoxy)ethoxy)benzo[c][2,6]naphthyridine-8-carboxylic acid | 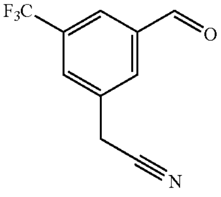 [SMILES: N#CCc1cc(C=O)cc(C(F)(F)F)c1] 2-(3-Formyl-5-(trifluoromethyl)phenyl)acetonitrile 1.469 | $^1$H NMR (400 MHz, DMSO-d$_6$) δ: 10.12 (s, 1H), 8.89 (d, J = 5.2 Hz, 1H), 8.81 (d, J = 8.4 Hz, 1H), 8.32 (d, J = 1.6 Hz, 1H), 8.08-8.04 (m, 2H), 7.68-7.62 (m, 2H), 7.57 (s, 1H), 4.71 (t, J = 4.8 Hz, 2H), 4.14 (s, 2H), 3.87 (t, J = 4.8 Hz, 2H), 3.82 (s, 2H), 3.53 (t, J = 6.0 Hz, 2H), 2.56 (t, J = 6.4 Hz, 2H), 1.61-1.49 (m, 4H) ppm LCMS (AM7): rt = 0.720 min, (553.3 [M + H]$^+$), 100% purity Purification Method 80 |
| Example 78 | 5-(2-(4-((3-(cyanomethyl)-5-methylbenzyl)amino)butoxy)ethoxy)benzo[c][2,6]naphthyridine-8-carboxylic acid | 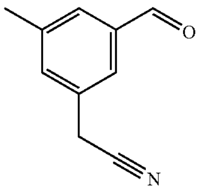 2-(3-Formyl-5-methylphenyl)acetonitrile 1.475 | $^1$H NMR (400 MHz, MeOH-d$_4$) δ: 9.63 (s, 1H), 8.59 (d, J = 5.6 Hz, 1H), 8.36-8.32 (d, 1H), 8.26 (s, 1H), 8.01 (d, J = 8.4 Hz, 1H), 7.81 (d, J = 5.2 Hz, 1H), 7.20-7.10 (m, 3H), 4.60 (t, J = 4.8 Hz, 2H), 4.03 (s, 2H), 3.87 (t, J = 4.8 Hz, 2H), 3.81 (s, 2H), 3.63 (t, J =6.0 Hz, 2H), 3.01 (t, J = 7.2 Hz, 2H), 2.27 (s, 3H), 1.88-1.80 (m, 2H), 1.70-1.62 (m, 2H) ppm LCMS (AM7): rt = 0.709 min, (499.3 [M + H]$^+$), 100% purity Purification Method 79 |
| Example 90 | 5-(2-(4-((3-chloro-5-(hydroxymethyl)benzyl)amino)butoxy)ethoxy)benzo[c][2,6]naphthyridine-8-carboxylic acid | 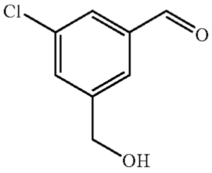 [SMILES: O=Cc1cc(Cl)cc(CO)c1] 3-Chloro-5-(hydroxymethyl)benzaldehyde 1.102 | $^1$H NMR (400 MHz, MeOH-d$_4$) δ: 9.82 (s, 1H), 8.72 (d, J = 5.6 Hz, 1H), 8.52 (d, J = 8.4 Hz, 1H), 8.35 (d, J = 1.6 Hz, 1H), 8.09-8.05 (d, 1H), 8.04-8.00 (d, 1H), 7.34-7.31 (m, 2H), 7.26-7.24 (m, 1H), 4.73 (t, J = 4.8 Hz, 2H), 4.57 (s, 2H), 4.00 (s, 2H), 3.92 (t, J = 4.8 Hz, 2H), 3.65 (t, J = 6.0 Hz, 2H), 2.95 (t, J = 7.8 Hz, 2H), 1.85-1.78 (quin, 2H), 1.72-1.64 (quin, 2H) ppm LCMS (AM3): rt = 0.699 min, (510.2 [M + H]$^+$), 97.7% purity Purification Method 87 |

TABLE 7-continued

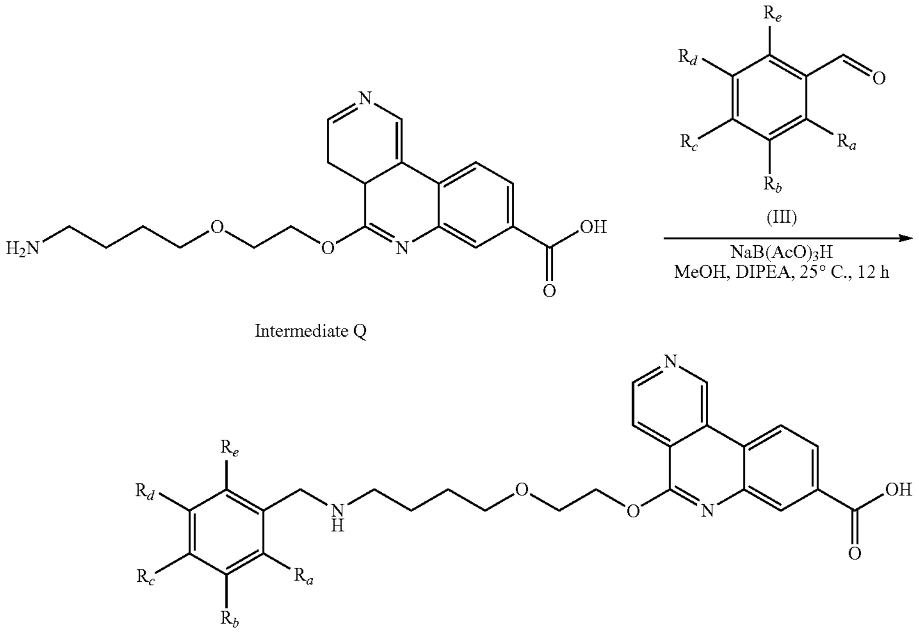

| Example No. | Chemical IUPAC name | Compound (III) | Analytical |
|---|---|---|---|
| Example 93 | 5-(2-(4-((3-fluoro-4-(trifluoromethoxy) benzyl)amino) butoxy)ethoxy) benzo[c][2,6] naphthyridine-8-carboxylic acid | 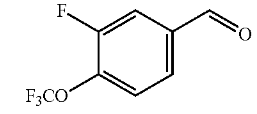 [SMILES: O=Cc1ccc(OC(F)(F)F)c(F)c1] 3-fluoro-4-(trifluoromethoxy) benzaldehyde | $^1$H NMR (400 MHz, MeOH-$d_4$) δ: 9.69 (s, 1H), 8.65 (d, J = 5.6 Hz, 1H), 8.39 (d, J = 8.4 Hz, 1H), 8.28 (d, J = 1.2 Hz, 1H), 8.02 (dd, J = 8.4, 1.6 Hz, 1H), 7.87 (d, J = 5.6 Hz, 1H), 7.52 (dd, J = 10.8, 2.0 Hz, 1H), 7.46-7.37 (m, 2H), 4.64 (t, J = 4.8 Hz, 2H), 4.16 (s, 2H), 3.89 (t, J = 4.8 Hz, 2H), 3.66 (t, J = 6.0 Hz, 2H), 3.05 (t, J = 7.8 Hz, 2H), 1.90-1.83 (quin, 2H), 1.74-1.67 (quin, 2H) ppm<br>LCMS (AM7): rt = 0.753 min, (548.3 [M + H]$^+$), 98.3% purity<br>Purification Method 94 |
| Example 95 | 5-(2-(4-((3-(cyanomethyl)-5-fluorobenzyl)amino) butoxy)ethoxy) benzo[c][2,6] naphthyridine-8-carboxylic acid | 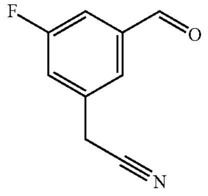 [SMILES: N#CCc1cc(F)cc(C=O)c1] 2-(3-Fluoro-5-formylphenyl) acetonitrile 1.472 | $^1$H NMR (400 MHz, MeOH-$d_4$) δ: 9.82 (s, 1H), 8.75 (d, J = 5.6 Hz, 1H), 8.52 (d, J = 8.4 Hz, 1H), 8.35 (s, 1H), 8.08 (d, J = 8.4 Hz, 1H), 8.01 (d, J = 5.2 Hz, 1H), 7.29 (s, 1H), 7.22-7.14 (m, 2H), 4.74 (t, J = 4.8 Hz, 2H), 4.14 (s, 2H), 3.95-3.91 (m, 4H), 3.68 (t, J =6.0 Hz, 2H), 3.07 (t, J = 7.8 Hz, 2H), 1.89-1.82 (quin, 2H), 1.74-1.67 (quin, 2H) ppm<br>LCMS (AM3): rt = 0.593 min, (503.2 [M + H]$^+$), 98.0% purity<br>Purification Method 96 |
| Example 111 | 5-(2-(4-((3-(cyanomethyl)-5-(trifluoromethoxy)benzyl)amino) butoxy)ethoxy) benzo[c][2,6] naphthyridine-8-carboxylic acid | 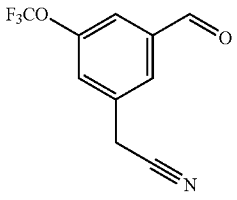 [SMILES: N#CCc1cc(C=O)cc(OC(F)(F)F)c1] 2-(3-Formyl-5-(trifluoromethoxy) phenyl)acetonitrile 1.504 | $^1$H NMR (400 MHz, DMSO-$d_6$) δ: 10.11 (s, 1H), 8.89 (d, J = 5.2 Hz, 1H), 8.82 (d, J = 8.4 Hz, 1H), 8.32 (s, 1H), 8.08-8.02 (m, 2H), 7.38-7.33 (m, 2H), 7.21 (s, 1H), 4.70 (t, J = 4.4 Hz, 2H), 4.09 (s, 2H), 3.87 (t, J = 4.0 Hz, 2H), 3.79 (s, 2H), 3.53 (t, J = 6.0 Hz, 2H), 2.56 (t, J = 6.0 Hz, 2H), 1.62-1.48 (m, 4H) ppm<br>LCMS (AM7): rt = 0.751 min, (569.3 [M + H]$^+$), 100% purity<br>Purification Method 111 |

TABLE 7-continued

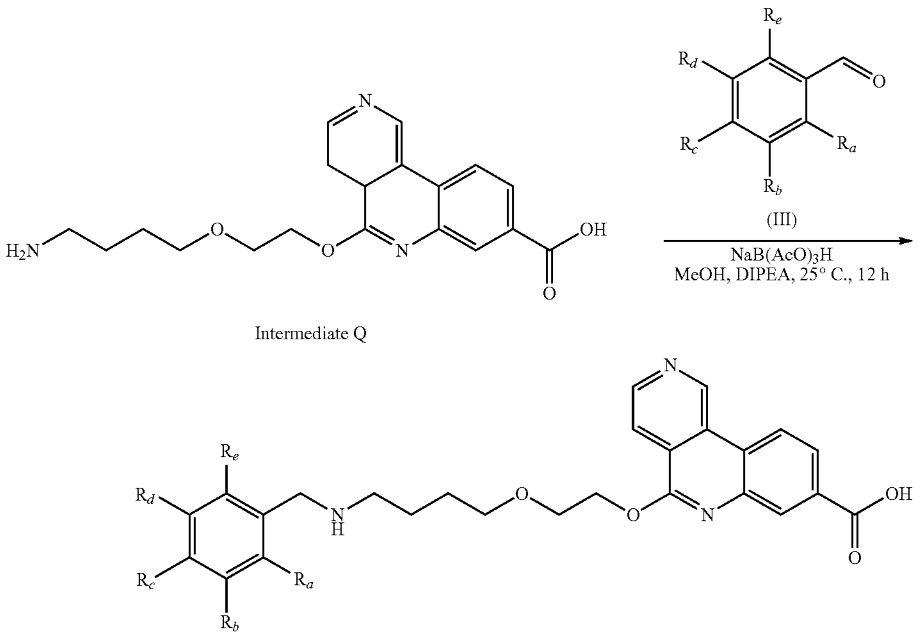

Intermediate Q

| Example No. | Chemical IUPAC name | Compound (III) | Analytical |
|---|---|---|---|
| Example 112 | 5-(2-(4-((3-bromo-4-(trifluoromethoxy)benzyl)amino)butoxy)ethoxy)benzo[c][2,6]naphthyridine-8-carboxylic acid | 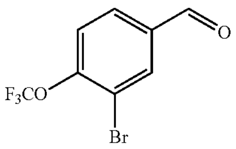 [SMILES: O=Cc1ccc(OC(F)(F)F)c(Br)c1] 3-bromo-4-(trifluoromethoxy)benzaldehyde | $^1$H NMR (400 MHz, MeOH-d$_4$) δ: 9.77 (s, 1H), 8.69 (d, J = 5.6 Hz, 1H), 8.45 (d, J = 8.4 Hz, 1H), 8.32 (d, J = 1.6 Hz, 1H), 8.05 (dd, J = 8.4, 1.6 Hz, 1H), 7.95 (d, J = 4.2 Hz, 1H), 7.87 (d, J = 2.0 Hz, 1H), 7.55 (dd, J = 8.4, 2.0 Hz, 1H), 7.43 (dd, J = 8.4, 1.6 Hz, 1H), 4.70 (t, J = 4.8 Hz, 2H), 4.12 (s, 2H), 3.92 (t, J = 4.8 Hz, 2H), 3.67 (t, J = 6.0 Hz, 2H), 3.04 (t, J = 7.8 Hz, 2H), 1.89-1.81 (quin, 2H), 1.74-1.67 (quin, 2H) ppm<br>LCMS (AM7): rt = 0.777 min, (608.1 [M + H]$^+$), 100% purity<br>Purification Method 112 |
| Example 113 | 5-(2-(4-((4-chloro-3-(trifluoromethoxy)benzyl)amino)butoxy)ethoxy)benzo[c][2,6]naphthyridine-8-carboxylic acid | 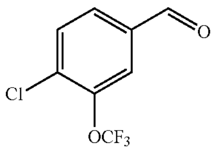 [SMILES: O=Cc1ccc(Cl)c(OC(F)(F)F)c1] 4-chloro-3-(trifluoromethoxy)benzaldehyde | $^1$H NMR (400 MHz, MeOH-d$_4$) δ: 9.75 (s, 1H), 8.69 (d, J = 5.6 Hz, 1H), 8.45 (d, J = 8.4 Hz, 1H), 8.31 (d, J = 1.6 Hz, 1H), 8.04 (dd, J = 8.4, 1.6 Hz, 1H), 7.92 (d, J = 5.2 Hz, 1H), 7.60-7.58 (m, 2H), 7.47 (dd, J = 8.4, 2.0 Hz, 1H), 4.68 (t, J = 4.8 Hz, 2H), 4.15 (s, 2H), 3.91 (t, J = 4.8 Hz, 2H), 3.66 (t, J = 6.0 Hz, 2H), 3.04 (t, J = 7.8 Hz, 2H), 1.89-1.82 (quin, 2H), 1.74-1.67 (quin, 2H) ppm<br>LCMS (AM7): rt = 0.768 min, (564.2 [M + H]$^+$), 100% purity<br>Purification Method 112 |
| Example 114 | 5-(2-(4-((3-chloro-5-(trifluoromethoxy)benzyl)amino)butoxy)ethoxy)benzo[c][2,6]naphthyridine-8-carboxylic acid | 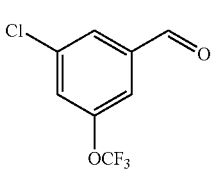 [SMILES: O=Cc1cc(Cl)cc(OC(F)(F)F)c1] 3-chloro-5-(trifluoromethoxy)benzaldehyde | $^1$H NMR (400 MHz, MeOH-d$_4$) δ: 9.79 (s, 1H), 8.71 (d, J = 5.2 Hz, 1H), 8.47 (d, J = 8.4 Hz, 1H), 8.34 (s, 1H), 8.06 (d, J = 8.4 Hz, 1H), 7.98 (d, J = 4.4 Hz, 1H), 7.54 (s, 1H), 7.40-7.33 (m, 2H), 4.70 (t, J = 4.8 Hz, 2H), 4.14 (s, 2H), 3.92 (t, J = 4.4 Hz, 2H), 3.67 (t, J = 5.6 Hz, 2H), 3.03 (t, J = 7.8 Hz, 2H), 1.88-1.81 (m, 2H), 1.74-1.66 (m, 2H) ppm<br>LCMS (AM7): rt = 0.767 min, (564.2 [M + H]$^+$), 100% purity<br>Purification Method 113 |

TABLE 7-continued

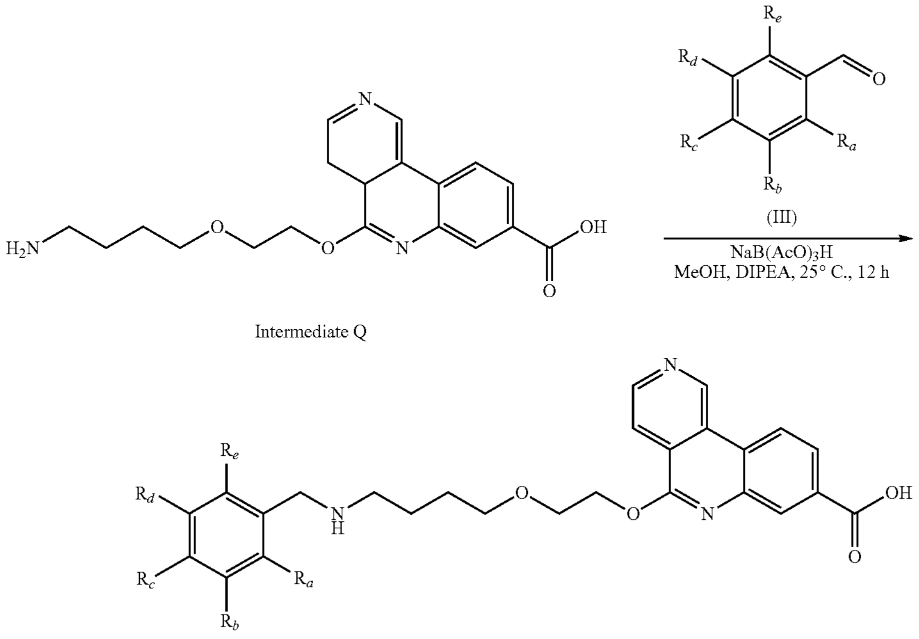

Intermediate Q

| Example No. | Chemical IUPAC name | Compound (III) | Analytical |
|---|---|---|---|
| Example 115 | 5-(2-(4-((3-bromo-5-(trifluoromethoxy)benzyl)amino)butoxy)ethoxy)benzo[c][2,6]naphthyridine-8-carboxylic acid | 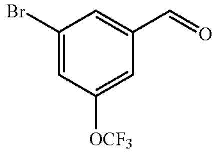 3-bromo-5-(trifluoromethoxy)benzaldehyde | $^{1}$H NMR (400 MHz, MeOH-d$_4$) δ: 9.76 (s, 1H), 8.68 (d, J = 5.6 Hz, 1H), 8.44 (d, J = 8.4 Hz, 1H), 8.32 (d, J = 1.2 Hz, 1H), 8.05 (dd, J = 8.4, 2.0 Hz, 1H), 7.93 (d, J = 5.2 Hz, 1H), 7.70 (s, 1H), 7.51 (s, 1H), 7.46 (s, 1H), 4.68 (t, J = 4.8 Hz, 2H), 4.17 (s, 2H), 3.92 (t, J = 4.8 Hz, 2H), 3.67 (t, J = 6.0 Hz, 2H), 3.07 (t, J = 7.2 Hz, 2H), 1.90-1.82 (quin, 2H), 1.74-1.67 (quin, 2H) ppm LCMS (AM7): rt = 0.781 min, (610.2 [M + H]$^+$), 100% purity Purification Method 113 |
| Example 117 | 5-(2-(4-((3-cyclopropyl-5-(trifluoromethoxy)benzyl)amino)butoxy)ethoxy)benzo[c][2,6]naphthyridine-8-carboxylic acid | 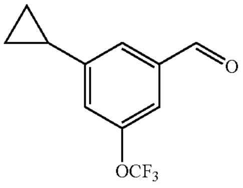 [SMILES: O=Cc1cc(OC(F)(F)F)cc(C2CC2)c1] 3-Cyclopropyl-5-(trifluoromethoxy)benzaldehyde 1.509 | $^{1}$H NMR (400 MHz, MeOH-d$_4$) δ: 9.82 (s, 1H), 8.71 (d, J = 5.2 Hz, 1H), 8.50 (d, J = 8.4 Hz, 1H), 8.36 (d, J = 1.6 Hz, 1H), 8.08 (dd, J = 8.4, 1.6 Hz, 1H), 8.00 (d, J = 5.2 Hz, 1H), 7.16 (s, 2H), 6.98 (s, 1H), 4.73 (t, J = 4.8 Hz, 2H), 4.09 (s, 2H), 3.93 (t, J = 4.8 Hz, 2H), 3.67 (t, J = 6.0 Hz, 2H), 3.03 (t, J = 7.2 Hz, 2H), 1.96-1.91 (m, 1H), 1.89-1.81 (quin, 2H), 1.74-1.66 (quin, 2H), 1.04-0.98 (m, 2H), 0.74-0.69 (m, 2H) ppm LCMS (AM7): rt = 0.785 min, (570.3 [M + H]$^+$), 98.4% purity Purification Method 113 |
| Example 129 | 5-(2-(4-((3-chloro-5-(1-cyanocyclopropyl)benzyl)amino)butoxy)ethoxy)benzo[c][2,6]naphthyridine-8-carboxylic acid | 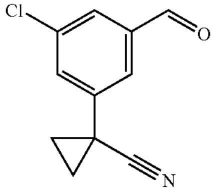 [SMILES: N#CC1(c2cc(Cl)cc(C=O)c2)CC1] 1-(3-Chloro-5-formylphenyl)cyclopropanecarbonitrile 1.630 | $^{1}$H NMR (400 MHz, MeOH-d$_4$) δ: 9.91 (s, 1H), 8.76 (d, J = 5.6 Hz, 1H), 8.58 (d, J = 8.4 Hz, 1H), 8.40 (s, 1H), 8.12-8.09 (m, 2H), 7.36-7.30 (m, 3H), 4.79 (t, J = 4.8 Hz, 2H), 3.97-3.95 (t, 4H), 3.67 (t, J = 6.0 Hz, 2H), 2.89 (t, J = 7.6 Hz, 2H), 1.81-1.65 (m, 6H), 1.51-1.48 (m, 2H) ppm LCMS (AM7): rt = 0.736 min, (545.3 [M + H]$^+$), 100% purity Purification Method 129 |

TABLE 7-continued

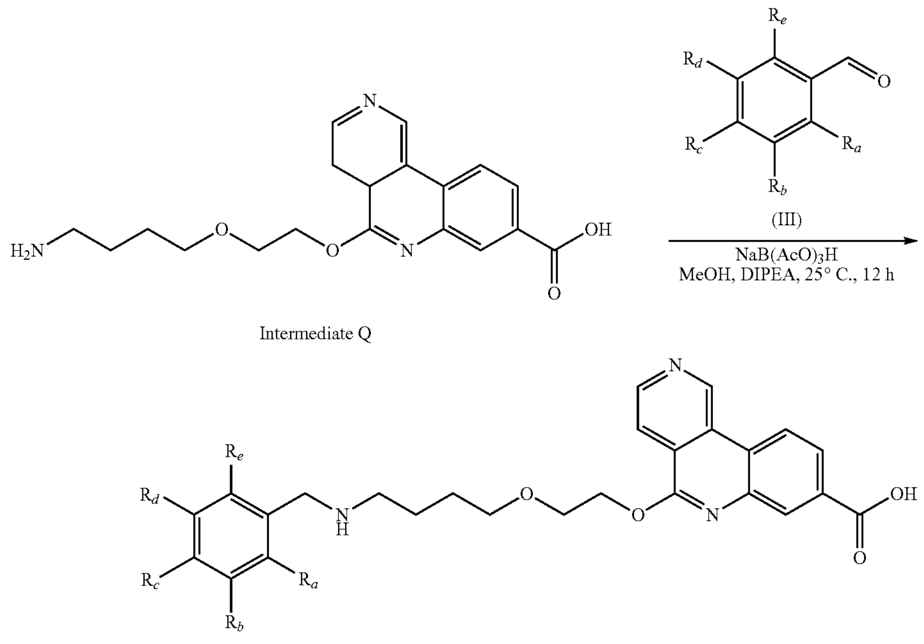

Intermediate Q

| Example No. | Chemical IUPAC name | Compound (III) | Analytical |
|---|---|---|---|
| Example 130 | 5-(2-(4-((3-chloro-5-(2-cyanopropan-2-yl)benzyl)amino)butoxy)ethoxy)benzo[c][2,6]naphthyridine-8-carboxylic acid | 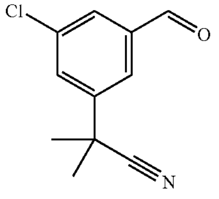 2-(3-Chloro-5-vinylphenyl)-2-methylpropanenitrile 1.632 | $^1$H NMR (400 MHz, MeOH-d$_4$) δ: 9.78 (s, 1H), 8.70 (d, J = 5.6 Hz, 1H), 8.46 (d, J = 8.4 Hz, 1H), 8.34 (s, 1H), 8.06 (dd, J = 8.4, 1.6 Hz, 1H), 7.97 (d, J = 5.2 Hz, 1H), 7.59 (s, 1H), 7.55 (t, J = 2.0 Hz, 1H), 7.48 (d, J = 1.2 Hz, 1H), 4.70 (t, J = 4.8 Hz, 2H), 4.12 (s, 2H), 3.92 (t, J = 4.8 Hz, 2H), 3.67 (t, J = 6.0 Hz, 2H), 3.03 (t, J = 7.6 Hz, 2H), 1.89-1.81 (quin, 2H), 1.74-1.71 (m, 2H), 1.70 (s, 6H) ppm<br>LCMS (AM7): rt = 0.745 min, (547.3 [M + H]$^+$), 100% purity<br>Purification Method 130 |
| Example 131 | 5-(2-(4-((3-cyclopropyl-4-(trifluoromethoxy)benzyl)amino)butoxy)ethoxy)benzo[c][2,6]naphthyridine-8-carboxylic acid | 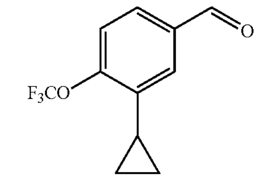 [SMILES: O=Cc1ccc(OC(F)(F)F)c(C2CC2)c1] 3-Cyclopropyl-4-(trifluoromethoxy)benzaldehyde 1.710 | $^1$H NMR (400 MHz, MeOH-d$_4$) δ: 9.82 (s, 1H), 8.71 (d, J = 5.6 Hz, 1H), 8.50 (d, J = 8.4 Hz, 1H), 8.36 (s, 1H), 8.08 (d, J = 8.4 Hz, 1H), 8.01 (d, J = 5.6 Hz, 1H), 7.31-7.24 (m, 2H), 7.12 (s, 1H), 4.73 (t, J = 4.8 Hz, 2H), 4.08 (s, 2H), 3.92 (t, J = 4.8 Hz, 2H), 3.67 (t, J = 6.0 Hz, 2H), 3.03 (t, J = 7.6 Hz, 2H), 2.13-2.06 (m, 1H), 1.87-1.80 (quin, 2H), 1.72-1.65 (quin, 2H), 1.03-0.98 (m, 2H), 0.75-0.71 (m, 2H) ppm.<br>LCMS (AM7): rt = 0.777 min, (570.3 [M + H]$^+$), 100% purity<br>Purification Method 131 |
| Example 132 | 5-(2-(4-((3-methyl-4-(trifluoromethoxy)benzyl)amino)butoxy)ethoxy)benzo[c][2,6]naphthyridine-8-carboxylic acid | 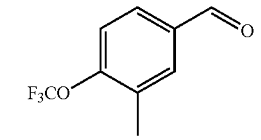 3-Methyl-4-(trifluoromethoxy)benzaldehyde 1.709 | $^1$H NMR (400 MHz, MeOH-d$_4$) δ: 9.73 (s, 1H), 8.66 (d, J = 5.6 Hz, 1H), 8.41 (d, J = 8.4 Hz, 1H), 8.30 (br s, 1H), 8.03 (d, J = 8.4 Hz, 1H), 7.90 (d, J = 5.6 Hz, 1H), 7.42 (d, J = 2.0 Hz, 1H), 7.36 (dd, J = 8.4, 2.0 Hz, 1H), 7.24 (dd, J = 8.4, 1.2 Hz, 1H), 4.66 (t, J = 4.8 Hz, 2H), 4.09 (s, 2H), 3.89 (t, J = 4.8 Hz, 2H), 3.65 (t, J = 6.0 Hz, 2H), 3.04 (t, J = 7.6 Hz, 2H), 2.27 (s, 3H), 1.89-1.81 (quin, 2H), 1.73-1.64 (quin, 2H) ppm<br>LCMS (AM7): rt = 0.763 min, (544.3 [M + H]$^+$), 100 % purity<br>Purification Method 132 |

TABLE 7-continued

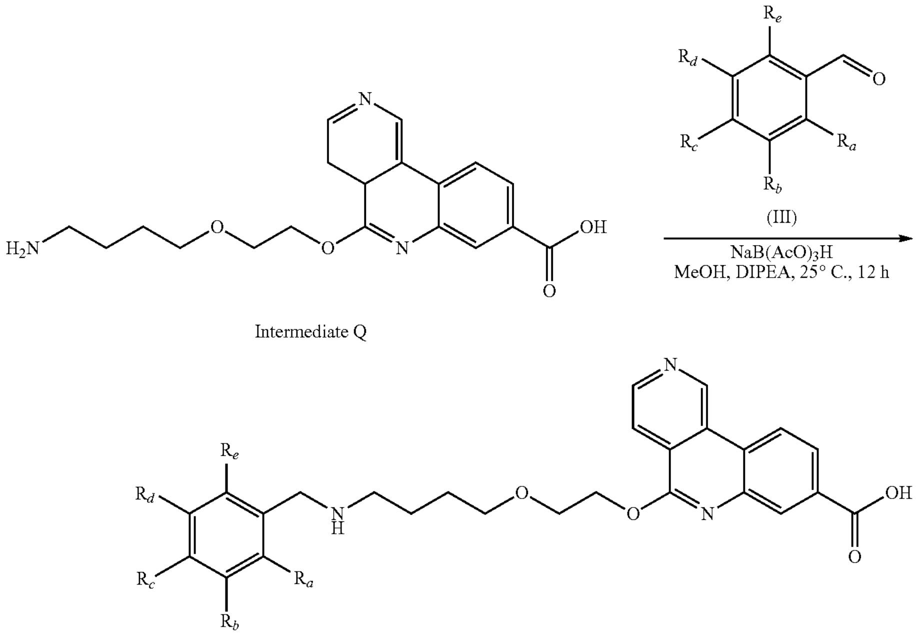

| Example No. | Chemical IUPAC name | Compound (III) | Analytical |
| --- | --- | --- | --- |
| Example 133 | 5-(2-(4-((3-methoxy-4-(trifluoromethoxy) benzyl)amino) butoxy)ethoxy) benzo[c][2,6] naphthyridine-8-carboxylic acid | 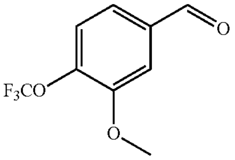 3-Methoxy-4-(trifluoromethoxy) benzaldehyde 1.707 | $^1$H NMR (400 MHz, MeOH-d$_4$) δ: 9.73 (s, 1H), 8.67 (d, J = 5.6 Hz, 1H), 8.41 (d, J = 8.4 Hz, 1H), 8.31 (d, J = 1.6 Hz, 1H), 8.04 (dd, J = 8.4, 1.6 Hz, 1H), 7.91 (d, J = 5.6 Hz, 1H), 7.30 (d, J = 2.0 Hz, 1H), 7.24 (dd, J = 8.4, 1.2 Hz, 1H), 7.03 (dd, J = 8.4, 2.0 Hz, 1H), 4.67 (t, J = 4.8 Hz, 2H), 4.08 (s, 2H), 3.90 (t, J = 4.8 Hz, 2H), 3.86 (s, 3H), 3.66 (t, J = 6.0 Hz, 2H), 3.01 (t, J = 7.6 Hz, 2H), 1.88-1.81 (m, 2H), 1.74-1.67 (m, 2H) ppm LCMS (AM3): rt = 0.829 min, (560.1 [M + H]$^+$), 100% purity. Purification Method 133 |
| Example 134 | 5-(2-(4-((3,4-dichloro-5-(trifluoromethoxy) benzyl)amino) butoxy)ethoxy) benzo[c][2,6] naphthyridine-8-carboxylic acid | 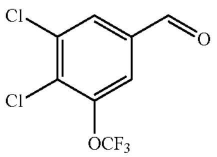 [SMILES: O=Cc1cc(Cl)c(Cl)c(OC(F)(F)F)c1] 3,4-Dichloro-5-(trifluoromethoxy) benzaldehyde 1.704 | $^1$H NMR (400 MHz, MeOH-d$_4$) δ: 9.91 (s, 1H), 8.76 (d, J = 5.6 Hz, 1H), 8.58 (d, J = 8.4 Hz, 1H), 8.41 (s, 1H), 8.13-8.10 (m, 2H), 7.59 (d, J = 2.0 Hz, 1H), 7.46 (s, 1H), 4.78 (t, J = 4.8 Hz, 2H), 3.95 (t, J = 4.8 Hz, 2H), 3.89 (s, 2H), 3.65 (t, J = 6.0 Hz, 2H), 2.78 (t, J = 7.2 Hz, 2H), 1.76-1.63 (m, 4H) ppm LCMS (AM7): rt = 0.770 min, (598.2 [M + H]$^+$), 99.1% purity Purification Method 133 |

Example 116
5-(2-(4-((3,5-difluoro-4-(trifluoromethoxy)benzyl) amino)butoxy)ethoxy)benzo[c][2,6]naphthyridine-8-carboxylic acid
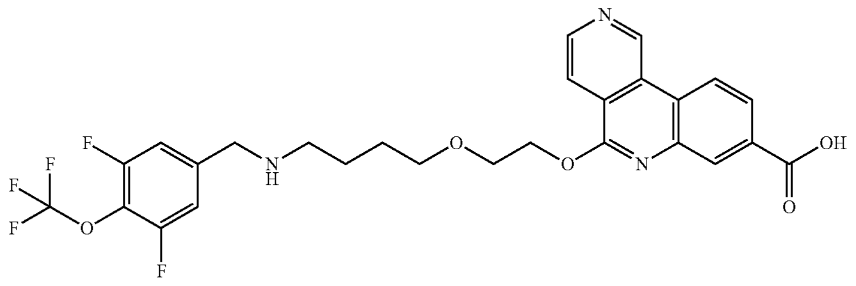 [SMILES: O=C(O)c1ccc2c(c1)nc(OCCOCCCCNCc1cc(F)c(OC(F)(F)F)c(F)c1)c1ccncc12]

A mixture of Intermediate Q (300 mg, 514.20 μmol), compound 1.507 (116.26 mg, 514.20 μmol) and DIPEA (199.36 mg, 1.54 mmol) in MeOH (5 mL) was stirred at 25° C. for 1 h, then sodium triacetoxyborohydride (544.90 mg, 2.57 mmol) was added. The mixture was stirred at 25° C. for another 11 h. The mixture was concentrated in vacuo and the residue was purified (PM113) to afford Example 116 (99.09 mg, 175.23 μmol, 34.1% yield) as a yellow solid.

LCMS (Method 7): rt=0.769 min, (566.3 $[M+H]^+$), 100% purity.

$^1$H NMR (400 MHz, MeOH-$d_4$) δ: 9.69 (s, 1H), 8.65 (d, J=5.6 Hz, 1H), 8.37 (d, J=8.4 Hz, 1H), 8.27 (d, J=1.6 Hz, 1H), 8.01 (dd, J=8.4, 1.6 Hz, 1H), 7.87 (d, J=5.2 Hz, 1H), 7.38 (d, J=8.4 Hz, 2H), 4.64 (t, J=4.8 Hz, 2H), 4.16 (s, 2H), 3.90 (t, J=4.8 Hz, 2H), 3.68 (t, J=6.0 Hz, 2H), 3.04 (t, J=7.6 Hz, 2H), 1.91-1.84 (quin, 2H), 1.76-1.69 (quin, 2H) ppm.

Example 54

5-(3-(4-((3-Chloro-4-(trifluoromethoxy)benzyl)amino)butoxy)azetidin-1-yl)benzo[c][2,6]naphthyridine-8-carboxylic acid

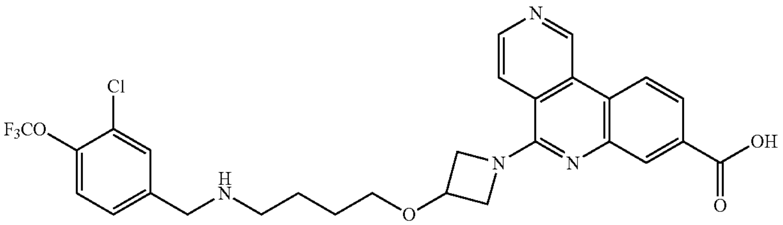 [SMILES: O=C(O)c1ccc2c(c1)nc(N1CC(OCCCCNCc3ccc(OC(F)(F)F)c(Cl)c3)C1)c1ccncc12]

A mixture of compound 1.399 (0.17 g, 0.289 mmol) and lithium hydroxide monohydrate (0.1 g, 2.38 mmol) in THF (4 mL) and water (2 mL) was stirred at room temperature for 2 h. The mixture was neutralized with formic acid (0.5 mL) and concentrated in vacuo. The residue was purified (PM65) to afford Example 54 (124.42 mg, 75.0% yield) as a yellow solid.

LCMS (AM3): rt=0.788 min, (575.2 $[M+H]^+$), 100% purity.

$^1$H NMR (400 MHz, DMSO-$d_6$) δ: 10.12 (s, 1H), 8.83 (d, J=5.6 Hz, 1H), 8.77 (d, J=8.8 Hz, 1H), 8.23-8.21 (m, 1H), 7.96 (d, J=5.2 Hz, 1H), 7.91-7.89 (d, 1H), 7.67 (s, 1H), 7.52-7.42 (q, 2H), 4.73-4.69 (t, 2H), 4.49-4.43 (m, 1H), 4.33-4.29 (m, 2H), 3.78 (s, 2H), 3.45 (t, J=6.4 Hz, 2H), 2.58-2.55 (m, 2H), 1.62-1.50 (m, 4H) ppm.

Example 69

5-((2-(4-((3-Fluoro-5-(hydroxymethyl)benzyl)amino)butoxy)ethyl)amino)benzo[c][2,6]naphthyridine-8-carboxylic acid

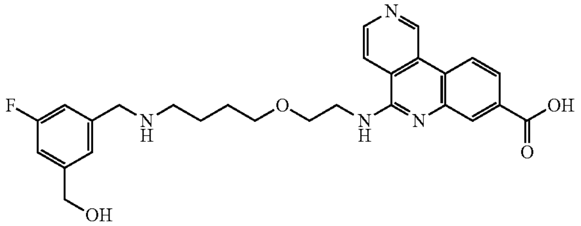 [SMILES: O=C(O)c1ccc2c(c1)nc(NCCOCCCCNCc1cc(F)cc(CO)c1)c1ccncc12]

A mixture of Intermediate R (300 mg, 646.85 μmol), compound 1.500 (99.70 mg, 646.85 μmol) and DIPEA (250.80 mg, 1.94 mmol) in MeOH (3 mL) was stirred at 25° C. for 1 h, then sodium triacetoxyborohydride (411.28 mg, 1.94 mmol) was added. The mixture was stirred at 25° C. for another 11 h. The mixture was filtered and concentrated in vacuo. The residue was purified (PM74) to afford Example 69 (74.49 mg, 151.24 μmol, 23.4% yield) as a yellow solid.

LCMS (AM7): rt=0.673 min, (493.2 $[M+H]^+$), 100% purity.

$^1H$ NMR (400 MHz, MeOH-$d_4$) δ: 9.66 (s, 1H), 8.56 (d, J=5.6 Hz, 1H), 8.31 (d, J=8.8 Hz, 1H), 8.16 (d, J=1.6 Hz, 1H), 7.86-7.82 (t, 2H), 7.22 (s, 1H), 7.08 (d, J=9.2 Hz, 2H), 4.58 (s, 2H), 4.05 (s, 2H), 3.78-3.67 (m, 4H), 3.56 (t, J=6.0 Hz, 2H), 2.98 (t, J=8.0 Hz, 2H), 1.84-1.76 (quin, 2H), 1.68-1.58 (quin, 2H) ppm.

The following examples in Table 8 were made with non-critical changes or substitutions to the exemplified procedure in Example 69, that would be understood by one skilled in the art using intermediate R and compounds of formula (III).

TABLE 8

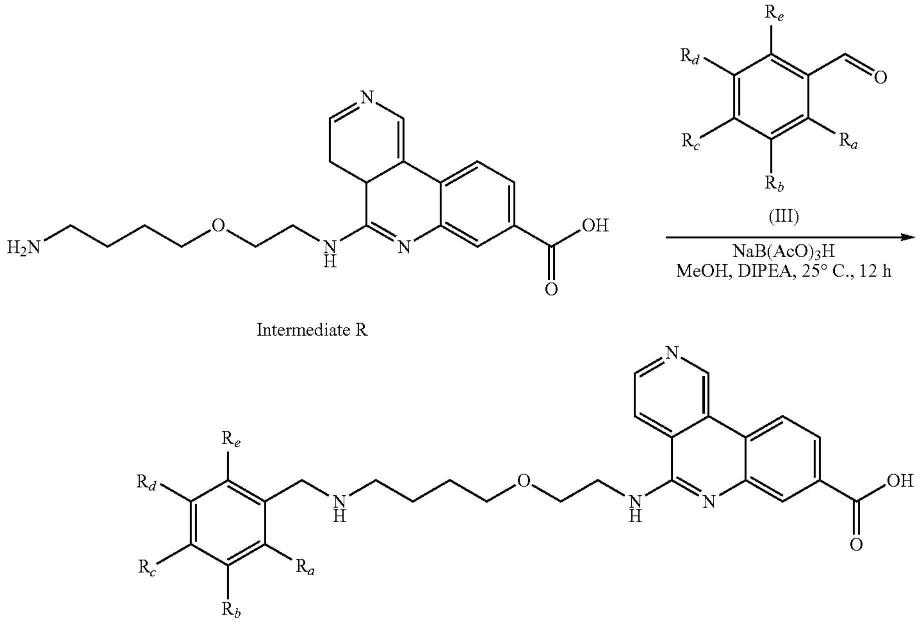

Intermediate R (III)

| Example No. | Chemical IUPAC name | Compound (III) | Analytical |
|---|---|---|---|
| Example 70 | 5-((2-(4-((3-(hydroxymethyl)-5-(trifluoromethyl) benzyl)amino) butoxy)ethyl) amino)benzo[c][2,6] naphthyridine-8-carboxylic acid | 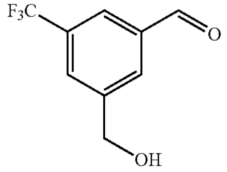 [SMILES: O=Cc1cc(CO)cc(C(F)(F)F)c1] 3-(Hydroxymethyl)-5-(trifluoromethyl)benzaldehyde 1.501 | $^1H$ NMR (400 MHz, MeOH-$d_4$) δ: 9.63 (s, 1H), 8.54 (d, J = 5.6 Hz, 1H), 8.28 (d, J = 8.4 Hz, 1H), 8.15 (s, 1H), 7.84-7.81 (m, 2H), 7.70-7.63 (m, 3H), 4.66 (s, 2H), 4.15 (s, 2H), 3.74-3.67 (m, 4H), 3.56 (t, J = 6.0 Hz, 2H), 3.01 (t, J = 7.8 Hz, 2H), 1.86-1.78 (m, 2H), 1.70-1.60 (m, 2H) ppm<br>LCMS (AM7): rt = 0.684 min, (543.3 $[M + H]^+$), 100% purity.<br>Purification Method 75 |
| Example 71 | 5-((2-(4-((3-(cyanomethyl)-5-fluorobenzyl)amino) butoxy)ethyl)amino) benzo[c][2,6] naphthyridine-8-carboxylic acid | 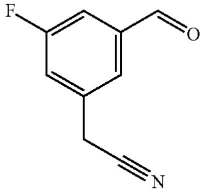 [SMILES: N#CCc1cc(F)cc(C=O)c1] 2-(3-Fluoro-5-formylphenyl)acetonitrile 1.472 | $^1H$ NMR (400 MHz, MeOH-$d_4$) δ: 9.66 (s, 1H), 8.56 (d, J = 5.6 Hz, 1H), 8.31 (d, J = 8.8 Hz, 1H), 8.15 (d, J = 1.6 Hz, 1H), 7.86-7.81 (m, 2H), 7.27 (s, 1H), 7.20-7.16 (d, 1H), 7.10-7.06 (d, 1H), 4.06 (s, 2H), 3.89 (s, 2H), 3.78-3.68 ( m, 4H), 3.57 (t, J = 6.0 Hz, 2H), 2.99 (t, J = 7.8 Hz, 2H), 1.87-1.77 (quin, 2H), 1.70-1.61 (quin, 2H) ppm<br>LCMS (AM7): rt = 0.675 min, (502.2 $[M + H]^+$), 100% purity<br>Purification Method 74 |
| Example 72 | 5-((2-(4-((3-(cyanomethyl)-5-(trifluoromethyl) benzyl)amino) butoxy)ethyl) amino)benzo[c][2,6] naphthyridine-8-carboxylic acid | 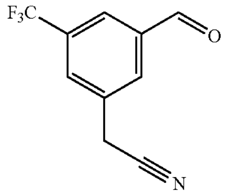 [SMILES: N#CCc1cc(C=O)cc(C(F)(F)F)c1] | $^1H$ NMR (400 MHz, MeOH-$d_4$) δ: 9.72 (br s, 1H), 8.61 (d, J = 5.4 Hz, 1H), 8.35 (d, J = 8.4 Hz, 1H), 8.18 (s, 1H), 7.93-7.87 (m, 2H), 7.76-7.65 (m, 3H), 4.13 (s, 2H), 4.02 (s, 2H), 3.81-3.71 (m, 4H), 3.60 (t, J = 6.0 Hz, 2H), 3.00 (t, J = 7.2 Hz, 2H), 1.85-1.78 (m, 2H), 1.72-1.63 (m, 2H) ppm<br>LCMS (AM7): rt = 0.710 min, (552.3 $[M + H]^+$), 100% purity<br>Purification Method 76 |

TABLE 8-continued

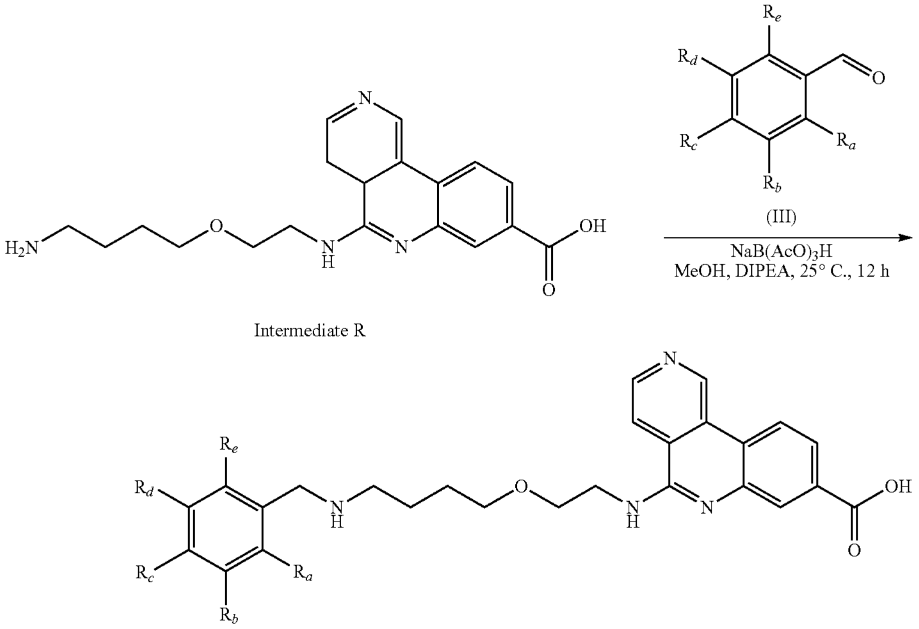

| Example No. | Chemical IUPAC name | Compound (III) | Analytical |
|---|---|---|---|
| | | 2-(3-Formyl-5-(trifluoromethyl) phenyl)acetonitrile 1.469 | |
| Example 73 | 5-((2-(4-((3-(cyanomethyl)-5-methylbenzyl) amino)butoxy) ethyl)amino) benzo[c][2,6] naphthyridine-8-carboxylic acid | 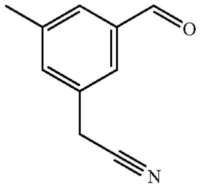 2-(3-Formyl-5-methylphenyl)acetonitrile 1.475 | $^1$H NMR (400 MHz, MeOH-$d_4$) δ: 9.71 (s, 1H), 8.59 (d, J = 5.6 Hz, 1H), 8.35 (d, J = 8.4 Hz, 1H), 8.19 (d, J = 1.6 Hz, 1H), 7.92-7.89 (d, 1H), 7.86-7.85 (d, 1H), 7.17-7.12 (m, 3H), 3.97 (s, 2H), 3.81-3.76 (m, 4H), 3.73 (t, J = 5.2 Hz, 2H), 3.60 (t, J = 5.6 Hz, 2H), 2.96 (t, J = 7.6 Hz, 2H), 2.28 (s, 3H), 1.84-1.77 (quin, 2H), 1.68-1.62 (quin, 2H) ppm LCMS (AM7): rt = 0.693 min, (498.3 [M + H]$^+$), 99.7% purity Purification Method 77 |
| Example 108 | 5-((2-(4-((3-(cyanomethyl)-5-(trifluoromethoxy) benzyl)amino) butoxy)ethyl) amino)benzo[c][2,6] naphthyridine-8-carboxylic acid | 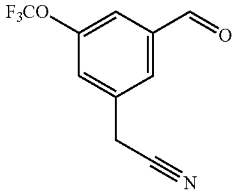 [SMILES: N#CCc1cc(C=O)cc(OC(F)(F)F)c1] 2-(3-Formyl-5-(trifluoromethoxy) phenyl)acetonitrile 1.504 | $^1$H NMR (400 MHz, DMSO-$d_6$) δ: 10.04 (s, 1H), 8.85 (d, J = 5.2 Hz, 1H), 8.68 (d, J = 8.4 Hz, 1H), 8.26 (d, J = 5.6 Hz, 1H), 8.14 (s, 1H), 8.02-7.98 (m, 1H), 7.82 (d, J = 8.0 Hz, 1H), 7.34-7.28 (m, 2H), 7.20 (s, 1H), 4.09 (s, 2H), 3.80-3.77 (m, 2H), 3.72-3.67 (m, 6H), 2.50-2.49 (m, 2H), 1.58-1.42 (m, 4H) ppm LCMS (AM7): rt = 0.734 min, (568.3 [M + H]$^+$), 99.2% purity Purification Method 101 |
| Example 178 | 5-((2-(4-((3,5-difluoro-4-(trifluoromethoxy) benzyl)amino) butoxy)ethyl) amino)benzo[c][2,6] naphthyridine-8-carboxylic acid | 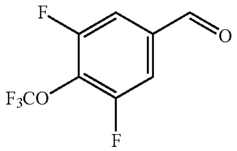 [SMILES: O=Cc1cc(F)c(OC(F)(F)F)c(F)c1] 3,5-Difluoro-4-(trifluoromethoxy) benzaldehyde 1.507 | $^1$H NMR (400 MHz, DMSO-$d_6$) δ: 10.05 (s, 1H), 8.86 (d, J = 5.6 Hz, 1H), 8.70 (d, J = 8.5 Hz, 1H), 8.27 (d, J = 5.6 Hz, 1H), 8.14 (d, J = 1.2 Hz, 1H), 8.01 (t, J = 5.6 Hz, 1H), 7.82 (dd, J = 8.4, 1.6 Hz, 1H), 7.32 (s, 1H), 7.29 (s, 1H), 3.77 (t, J = 5.2 Hz, 2H), 3.69 (t, J = 5.2 Hz, 2H), 3.67 (s, 2H), 3.45 (t, J = 5.6 Hz, 2H), 2.45 (t, J = 6.8 Hz, 2H), 1.57-1.51 (m, 2H), 1.49-1.42 (m, 2H) ppm LCMS (AM7): rt = 0.760 min, (565.2 [M + H]$^+$), 96.9% purity Purification Method 172 |

Example 79

5-(3-(4-((3-(Cyanomethyl)-5-fluorobenzyl)amino)butoxy)azetidin-1-yl)benzo[c][2,6]naphthyridine-8-carboxylic acid

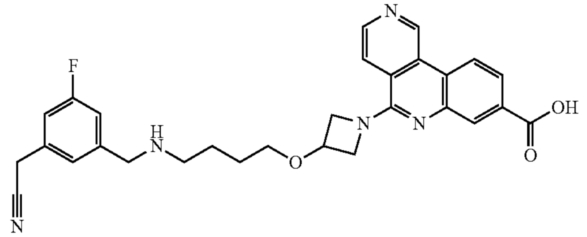 [SMILES: N#CCc1cc(F)cc(CNCCCCOC2CN(c3nc4cc(C(=O)O)ccc4c4cnccc34)C2)c1]

To a solution of compound 1.472 (121.49 mg, 744.65 μmol) and Intermediate O (300 mg, 744.65 μmol) in MeOH (10 mL) was added DIPEA (309.89 mg, 2.40 mmol) at 20° C. The mixture was stirred at 20° C. for 12 h before sodium triacetoxyborohydride (631.28 mg, 2.98 mmol) was added. The reaction mixture was stirred at 20° C. for another 1 h. The mixture was concentrated and purified (PM81) to afford Example 79 (84.42 mg, 164.38 μmol, 22% yield) as an off-white solid.

LCMS (AM3): rt=0.724 min, (514.3 $[M+H]^+$), 100% purity.

$^1H$ NMR (400 MHz, DMSO-$d_6$) δ: 10.11 (s, 1H), 8.82 (d, J=5.6 Hz, 1H), 8.76 (d, J=8.4 Hz, 1H), 8.20 (d, J=1.6 Hz, 1H), 7.94 (d, J=5.6 Hz, 1H), 7.89 (dd, J=8.4, 1.6 Hz, 1H), 7.19 (s, 1H), 7.16 (d, J=10 Hz, 1H), 7.04 (d, J=9.2 Hz, 1H), 4.72-4.68 (m, 2H), 4.48-4.43 (m, 1H), 4.32-4.28 (i, 2H), 4.04 (s, 2H), 3.75 (s, 2H), 3.44 (t, J=6.4 Hz, 2H), 2.56-2.52 (m, 2H), 1.63-1.51 (m, 4H) ppm.

The following examples in Table 9 were made with non-critical changes or substitutions to the exemplified procedure in Example 79, that would be understood by one skilled in the art using intermediate 0 and compounds of formula (III).

TABLE 9

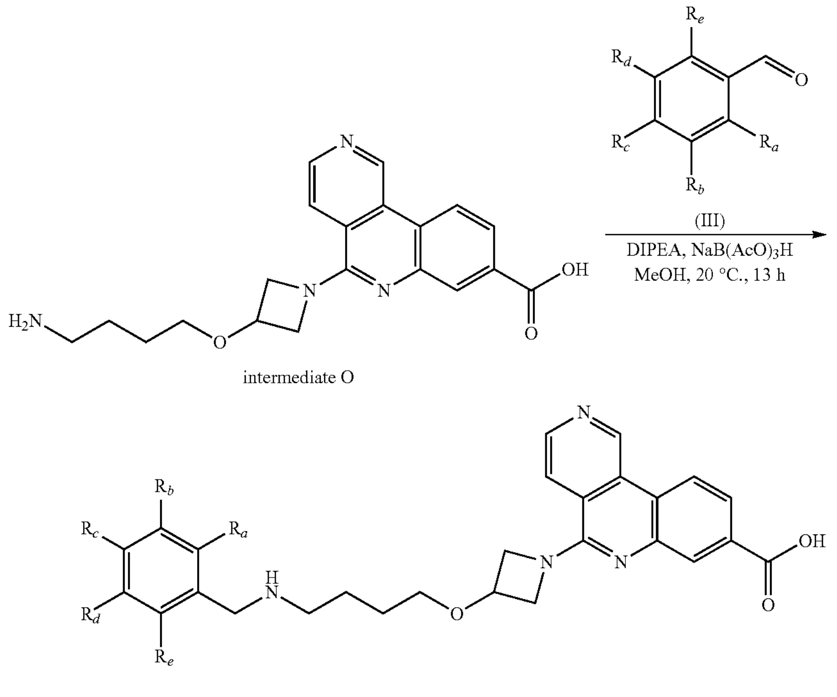

intermediate O

| Example No. | Chemical IUPAC name | Compound (III) | Analytical |
|---|---|---|---|
| Example 80 | 5-(3-(4-((3-(cyanomethyl)-5-methylbenzyl)amino)butoxy)azetidin-1-yl)benzo[c][2,6]naphthyridine-8-carboxylic acid | 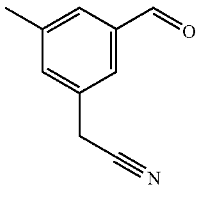 2-(3-Formyl-5-methylphenyl)acetonitrile 1.475 | $^1H$ NMR (400 MHz, DMSO-$d_6$) δ: 10.08 (s, 1H), 8.78 (d, J = 5.6 Hz, 1H), 8.68 (d, J = 8.8 Hz, 1H), 8.18 (s, 1H), 7.93 (d, J = 5.2 Hz, 1H), 7.90 (d, J = 8.4 Hz, 1H), 7.10 (s, 2H), 6.99 (s, 1H), 4.68 (t, J = 7.6 Hz, 2H), 4.48-4.42 (m, 1H), 4.29-4.24 (m, 2H), 3.95 (s, 2H), 3.67 (s, 2H), 3.45-3.42 (m, 2H), 2.54-2.52 (m, 2H), 2.27 (s, 3H), 1.62-1.49 (m, 4H) ppm LCMS (AM3): rt = 0.737 min, (510.3 $[M + H]^+$), 100% purity Purification Method 78 |

TABLE 9-continued

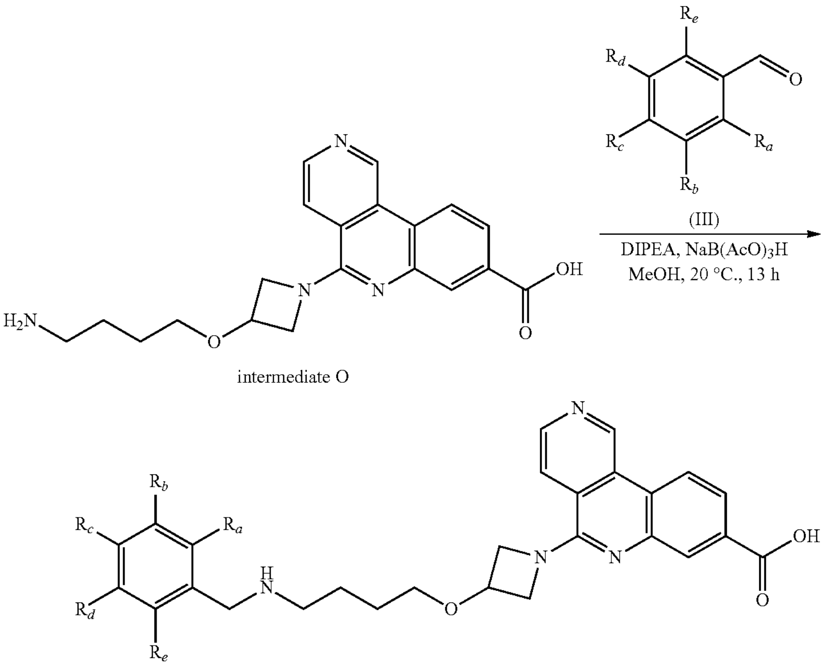

intermediate O

| Example No. | Chemical IUPAC name | Compound (III) | Analytical |
|---|---|---|---|
| Example 81 | 5-(3-(4-((3-chloro-5-(hydroxymethyl) benzyl)amino)butoxy)azetidin-1-yl)benzo[c][2,6] naphthyridine-8-carboxylic acid | 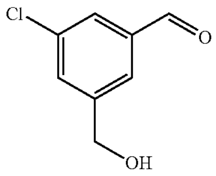 3-Chloro-5-(hydroxymethyl) benzaldehyde 1.102 | $^1$H NMR (400 MHz, DMSO-d$_6$) δ: 10.05 (s, 1H), 8.78 (d, J = 5.2 Hz, 1H), 8.69 (d, J = 8.8 Hz, 1H), 8.19 (d, J = 1.6 Hz, 1H), 7.90-7.88 (m, 2H), 7.33 (s, 1H), 7.28 (s, 1H), 7.23 (s, 1H), 4.67-4.63 (m, 2H), 4.47 (s, 2H), 4.45-4.40 (m, 1H), 4.29-4.25 (m, 2H), 3.81 (s, 2H), 3.43 (t, J = 5.6 Hz, 2H), 2.62 (t, J = 6.2 Hz, 2H), 1.61-1.55 (m, 4H) ppm<br>LCMS (AM3): rt = 0.713 min, (521.2 [M + H]$^+$), 98.9% purity<br>Purification Method 82 |
| Example 82 | 5-(3-(4-((3-fluoro-5-(hydroxymethyl) benzyl)amino)butoxy)azetidin-1-yl)benzo[c][2,6] naphthyridine-8-carboxylic acid | 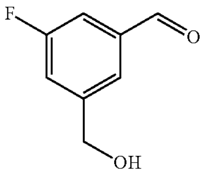 [SMILES: O=Cc1cc(F)cc(CO)c1] 3-Fluoro-5-(hydroxymethyl) benzaldehyde 1.500 | $^1$H NMR (400 MHz, DMSO-d$_6$) δ: 10.06 (s, 1H), 8.78 (d, J = 5.6 Hz, 1H), 8.70 (d, J = 8.8 Hz, 1H), 8.19 (d, J = 1.2 Hz, 1H), 7.90 (s, 1H), 7.89-7.87 (m, 1H), 7.15 (s, 1H), 7.08 (d, J = 9.6 Hz, 1H), 6.98 (d, J = 9.6 Hz, 1H), 4.68-4.64 (t, 2H), 4.48 (s, 2H), 4.45-4.41 (m, 1H), 4.29-4.26 (m, 2H), 3.80 (s, 2H), 3.44 (t, J = 6.0 Hz, 2H), 2.60 (t, J = 6.4 Hz, 2H), 1.62-1.50 (m, 4H) ppm<br>LCMS (AM3): rt = 0.705 min, (505.2 [M + H]$^+$), 100% purity<br>Purification Method 83 |
| Example 100 | 5-(3-(4-((3-(hydroxymethyl)-5-(trifluoromethyl) benzyl)amino)butoxy)azetidin-1-yl)benzo[c][2,6] naphthyridine-8-carboxylic acid | 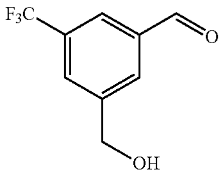 [SMILES: O=Cc1cc(CO)cc(C(F)(F)F)c1] 3-(Hydroxymethyl)-5-(trifluoromethyl) benzaldehyde 1.501 | $^1$H NMR (400 MHz, DMSO-d$_6$) δ: 10.07 (s, 1H), 8.78 (d, J = 5.6 Hz, 1H), 8.70 (d, J = 8.4 Hz, 1H), 8.19 (d, J = 1.6 Hz, 1H), 7.91-7.87 (m, 2H), 7.60 (s, 2H), 7.52 (s, 1H), 4.68-4.64 (m, 2H), 4.56 (s, 2H), 4.46-4.41 (m, 1H), 4.29-4.26 (m, 2H), 3.85 (s, 2H), 3.44 (t, J = 6.0 Hz, 2H), 2.60 (t, J = 6.4 Hz, 2H), 1.65-1.50 (m, 4H) ppm<br>LCMS (AM3): rt = 0.748 min, (555.3 [M + H]$^+$), 99.2% purity<br>Purification Method 101 |

TABLE 9-continued

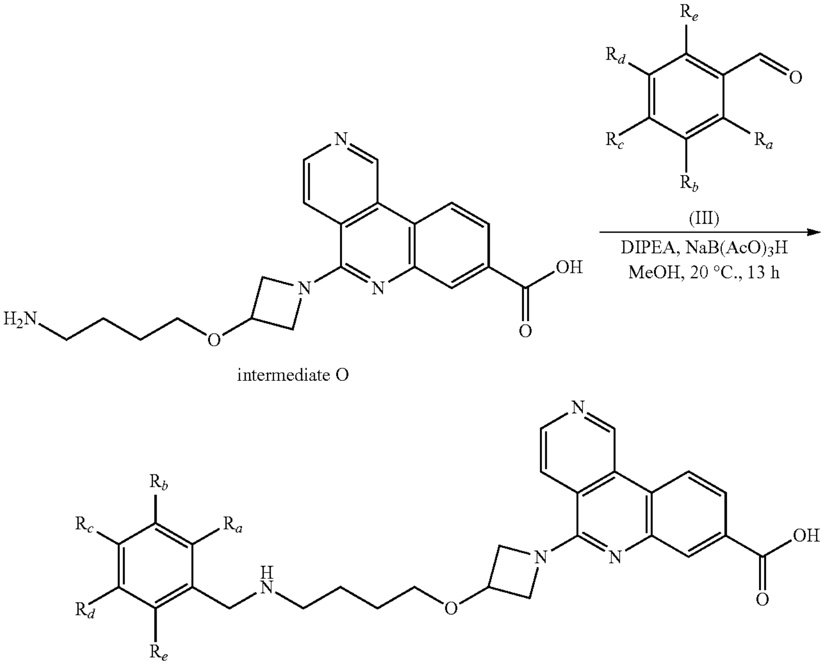

intermediate O

| Example No. | Chemical IUPAC name | Compound (III) | Analytical |
|---|---|---|---|
| Example 101 | 5-(3-(4-((3-fluoro-4-(trifluoromethoxy)benzyl)amino)butoxy)azetidin-1-yl)benzo[c][2,6]naphthyridine-8-carboxylic acid | 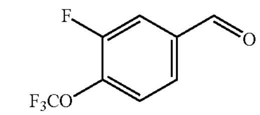 [SMILES: O=Cc1ccc(OC(F)(F)F)c(F)c1] 3-fluoro-4-(trifluoromethoxy)benzaldehyde | $^1$H NMR (400 MHz, DMSO-$d_6$) δ: 10.10 (s, 1H), 8.81 (d, J = 5.6 Hz, 1H), 8.74 (d, J = 8.8 Hz, 1H), 8.20 (d, J = 1.6 Hz, 1H), 7.94 (d, J = 5.6 Hz, 1H), 7.89 (dd, J = 8.4, 1.6 Hz, 1H), 7.47-7.43 (m, 2H), 7.28 (d, J = 8.0 Hz, 1H), 4.71-4.67 (m, 2H), 4.48-4.42 (m, 1H), 4.31-4.28 (m, 2H), 3.73 (s, 2H), 3.44 (t, J = 6.4 Hz, 2H), 2.53-2.52 (m, 2H), 1.63-1.47 (m, 4H) ppm<br>LCMS (AM3): rt = 0.784 min, (559.3 [M + H]$^+$), 100% purity<br>Purification Method 102 |
| Example 102 | 5-(3-(4-((3-chloro-5-(cyanomethyl)benzyl)amino)butoxy)azetidin-1-yl)benzo[c][2,6]naphthyridine-8-carboxylic acid | 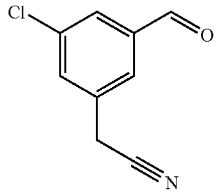 [SMILES: N#CCc1cc(Cl)cc(C=O)c1] 2-(3-Chloro-5-formylphenyl)acetonitrile 1.366 | $^1$H NMR (400 MHz, DMSO-$d_6$) δ: 10.09 (s, 1H), 8.80 (d, J = 5.6 Hz, 1H), 8.73 (d, J = 8.4 Hz, 1H), 8.20 (d, J = 1.6 Hz, 1H), 7.93 (d, J = 5.6 Hz, 1H), 7.89 (dd, J = 8.4, 1.6 Hz, 1H), 7.40 (s, 1H), 7.31 (s, 1H), 7.27 (s, 1H), 4.70-4.66 (m, 2H), 4.46-4.42 (m, 1H), 4.31-4.27 (m, 2H), 4.04 (s, 2H), 3.76 (s, 2H), 3.44 (t, J = 6.0 Hz, 2H), 2.55 (t, J = 6.8 Hz, 2H), 1.64-1.49 (m, 4H) ppm<br>LCMS (AM3): rt = 0.728 min, (530.1 [M + H]$^+$), 95.9% purity<br>Purification Method 103 |
| Example 103 | 5-(3-(4-((3-(cyanomethyl)-5-(trifluoromethyl)benzyl)amino)butoxy)azetidin-1-yl)benzo[c][2,6]naphthyridine-8-carboxylic acid | 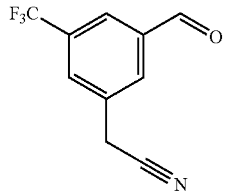 [SMILES: N#CCc1cc(C=O)cc(C(F)(F)F)c1] 2-(3-Formyl-5-(trifluoromethyl)phenyl)acetonitrile 1.469 | $^1$H NMR (400 MHz, DMSO-$d_6$) δ: 10.10 (s, 1H), 8.81 (d, J = 5.6 Hz, 1H), 8.76 (d, J = 8.4 Hz, 1H), 8.20 (d, J = 1.6 Hz, 1H), 7.94 (d, J = 5.2 Hz, 1H), 7.89 (dd, J = 8.4, 1.6 Hz, 1H), 7.70 (s, 1H), 7.66 (s, 1H), 7.58 (s, 1H), 4.71-4.67 (m, 2H), 4.47-4.43 (m, 1H), 4.31-4.28 (m, 2H), 4.15 (s, 2H), 3.84 (s, 2H), 3.44 (t, J = 6.0 Hz, 2H), 2.57 (t, J = 6.4 Hz, 2H), 1.64-1.50 (m, 4H) ppm<br>LCMS (AM3): rt = 0.751 min, (564.2 [M + H]$^+$), 99.7% purity<br>Purification Method 104 |

TABLE 9-continued

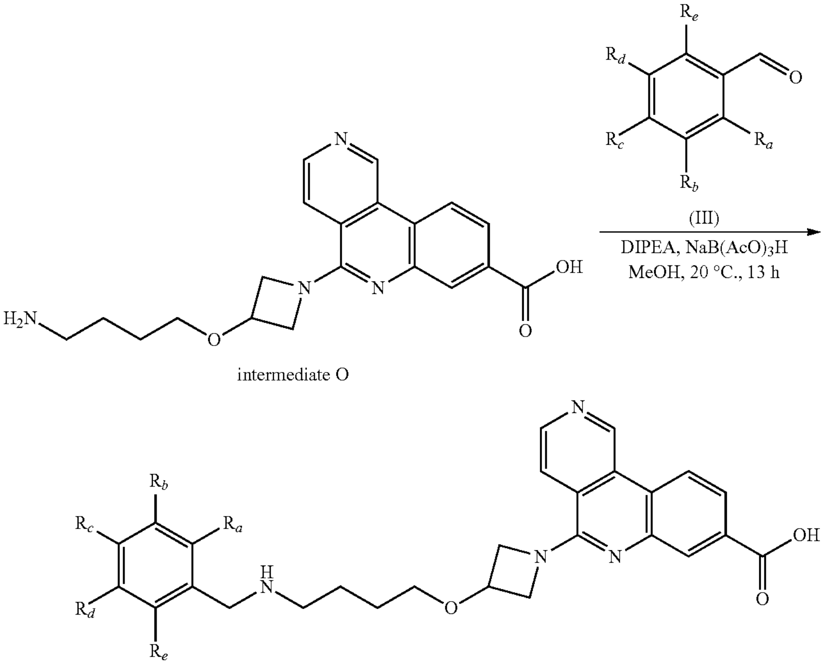

| Example No. | Chemical IUPAC name | Compound (III) | Analytical |
|---|---|---|---|
| Example 109 | 5-(3-(4-((3-(cyanomethyl)-5-(trifluoromethoxy)benzyl)amino)butoxy)azetidin-1-yl)benzo[c][2,6]naphthyridine-8-carboxylic acid | 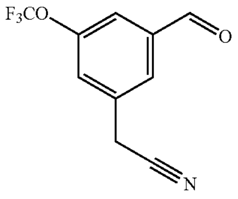 [SMILES: N#CCc1cc(C=O)cc(OC(F)(F)F)c1] 2-(3-Formyl-5-(trifluoromethoxy)phenyl)acetonitrile 1.504 | $^1$H NMR (400 MHz, DMSO-$d_6$) δ: 10.09 (s, 1H), 8.81 (d, J = 5.2 Hz, 1H), 8.74 (d, J = 8.8 Hz, 1H), 8.19 (d, J = 1.6 Hz, 1H), 7.93 (d, J = 5.6 Hz, 1H), 7.89 (dd, J = 8.4, 1.6 Hz, 1H), 7.39 (s, 1H), 7.34 (s, 1H), 7.21 (s, 1H), 4.71-4.67 (m, 2H), 4.47-4.42 (m, 1H), 4.31-4.27 (m, 2H), 4.10 (s, 2H), 3.79 (s, 2H), 3.44-3.43 (m, 2H), 2.55 (t, J = 6.8 Hz, 2H), 1.64-1.49 (m, 4H) ppm<br>LCMS (AM3): rt = 0.758 min, (580.5 $[M + H]^+$), 97.8% purity<br>Purification Method 109 |
| Example 118 | 5-(3-(4-((3-fluoro-5-(trifluoromethoxy)benzyl)amino)butoxy)azetidin-1-yl)benzo[c][2,6]naphthyridine-8-carboxylic acid | 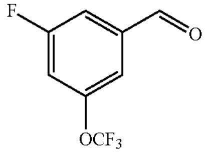 3-fluoro-5-(trifluoromethoxy)benzaldehyde | $^1$H NMR (400 MHz, DMSO-$d_6$) δ: 10.11 (s, 1H), 8.82 (d, J = 5.6 Hz, 1H), 8.77 (d, J = 8.4 Hz, 1H), 8.20 (d, J = 1.6 Hz, 1H), 7.95 (d, J = 5.2 Hz, 1H), 7.89 (dd, J = 8.4, 2.0 Hz, 1H), 7.26 (d, J = 8.8 Hz, 1H), 7.23 (s, 1H), 7.18 (d, J = 8.8 Hz, 1H), 4.72-4.68 (m, 2H), 4.47-4.43 (m, 1H), 4.31-4.28 (m, 2H), 3.77 (s, 2H), 3.44 (t, J = 6.4 Hz, 2H), 2.53-2.52 (m, 2H), 1.63-1.47 (m, 4H) ppm<br>LCMS (AM3): rt = 0.762 min, (559.3 $[M + H]^+$), 96.1% purity<br>Purification Method 114 |
| Example 119 | 5-(3-(4-((3,5-difluoro-4-(trifluoromethoxy)benzyl)amino)butoxy)azetidin-1-yl)benzo[c][2,6]naphthyridine-8-carboxylic acid | 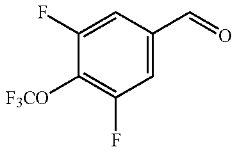 [SMILES: O=Cc1cc(F)c(OC(F)(F)F)c(F)c1] 3,5-Difluoro-4-(trifluoromethoxy)benzaldehyde 1.507 | $^1$H NMR (400 MHz, DMSO-$d_6$) δ: 10.11 (s, 1H), 8.82 (d, J = 5.6 Hz, 1H), 8.77 (d, J = 8.4 Hz, 1H), 8.20 (d, J = 1.6 Hz, 1H), 7.95 (d, J = 5.2 Hz, 1H), 7.89 (dd, J = 8.4, 2.0 Hz, 1H), 7.36 (d, J = 9.2 Hz, 2H), 4.72-4.68 (m, 2H), 4.47-4.43 (m, 1H), 4.32-4.29 (m, 2H), 3.74 (s, 2H), 3.44 (t, J = 6.4 Hz, 2H), 2.54-2.52 (m, 2H), 1.64-1.49 (m, 4H) ppm<br>LCMS (AM3): rt = 0.777 min, (577.4 $[M + H]^+$), 98.3% purity<br>Purification Method 115 |

TABLE 9-continued

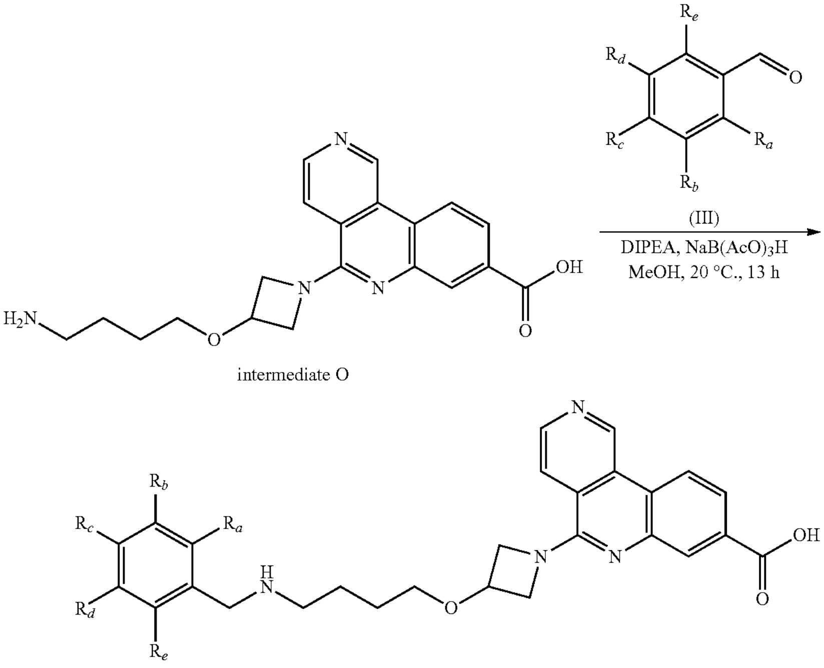

intermediate O

| Example No. | Chemical IUPAC name | Compound (III) | Analytical |
|---|---|---|---|
| Example 120 | 5-(3-(4-((3-chloro-5-(trifluoromethoxy)benzyl)amino)butoxy)azetidin-1-yl)benzo[c][2,6]naphthyridine-8-carboxylic acid | 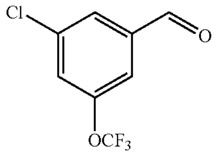 3-chloro-5-(trifluoromethoxy)benzaldehyde | $^1$H NMR (400 MHz, DMSO-$d_6$) δ: 10.11 (s, 1H), 8.82 (d, J = 5.6 Hz, 1H), 8.77 (d, J = 8.4 Hz, 1H), 8.20 (s, 1H), 7.95 (d, J = 5.6 Hz, 1H), 7.89 (dd, J = 8.4, 1.6 Hz, 1H), 7.48 (s, 1H), 7.36 (d, J = 4.4 Hz, 2H), 4.72-4.68 (m, 2H), 4.47-4.44 (m, 1H), 4.31-4.28 (m, 2H), 3.77 (s, 2H), 3.44 (t, J = 5.6 Hz, 2H), 2.53-2.52 (m, 2H), 1.62-1.48 (m, 4H) ppm<br>LCMS (AM3): rt = 0.774 min, (575.4 [M + H]$^+$), 100% purity<br>Purification Method 116 |
| Example 121 | 5-(3-(4-((3-bromo-4-(trifluoromethoxy)benzyl)amino)butoxy)azetidin-1-yl)benzo[c][2,6]naphthyridine-8-carboxylic acid | 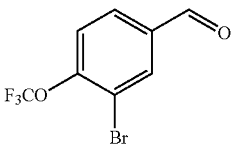 [SMILES: O=Cc1ccc(OC(F)(F)F)c(Br)c1] 3-bromo-4-(trifluoromethoxy)benzaldehyde | $^1$H NMR (400 MHz, DMSO-$d_6$) δ: 10.11 (s, 1H), 8.82 (d, J = 5.6 Hz, 1H), 8.76 (d, J = 8.8 Hz, 1H), 8.20 (d, J = 1.6 Hz, 1H), 7.95 (d, J = 5.6 Hz, 1H), 7.89 (dd, J = 8.4, 2.0 Hz, 1H), 7.78 (s, 1H), 7.46 (s, 2H), 4.72-4.68 (m, 2H), 4.47-4.44 (m, 1H), 4.32-4.28 (m, 2H), 3.74 (s, 2H), 3.45-3.43 (m, 2H), 2.55-2.53 (m, 2H), 1.63-1.48 (m, 4H) ppm<br>LCMS (AM3): rt = 0.785 min, (621.1 [M + H]$^+$), 99.7% purity.<br>Purification Method 117 |
| Example 122 | 5-(3-(4-((3-cyclopropyl-5-(trifluoromethoxy)benzyl)amino)butoxy)azetidin-1-yl)benzo[c][2,6]naphthyridine-8-carboxylic acid | 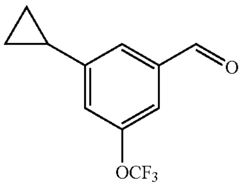 3-Cyclopropyl-5-(trifluoromethoxy)benzaldehyde 1.509 | $^1$H NMR (400 MHz, MeOH-$d_4$) δ: 9.56 (s, 1H), 8.63 (d, J = 5.6 Hz, 1H), 8.36 (d, J = 8.0 Hz, 1H), 8.18 (d, J = 5.6 Hz, 1H), 8.02 (s, 1H), 7.88 (dd, J = 8.0, 1.2 Hz, 1H), 7.07 (br s, 2H), 6.97 (br s, 1H), 4.24-4.18 (m, 3H), 3.89 (s, 2H), 3.85-3.61 (m, 4H), 2.86 (t, J = 7.6 Hz, 2H), 1.99-1.82 (m, 1H), 1.74-1.61 (m, 4H), 1.06-1.01 (m, 2H), 0.75-0.71 (m, 2H) ppm<br>LCMS (AM3): rt = 0.764 min, (581.4 [M + H]$^+$), 100% purity<br>Purification Method 118 |

TABLE 9-continued

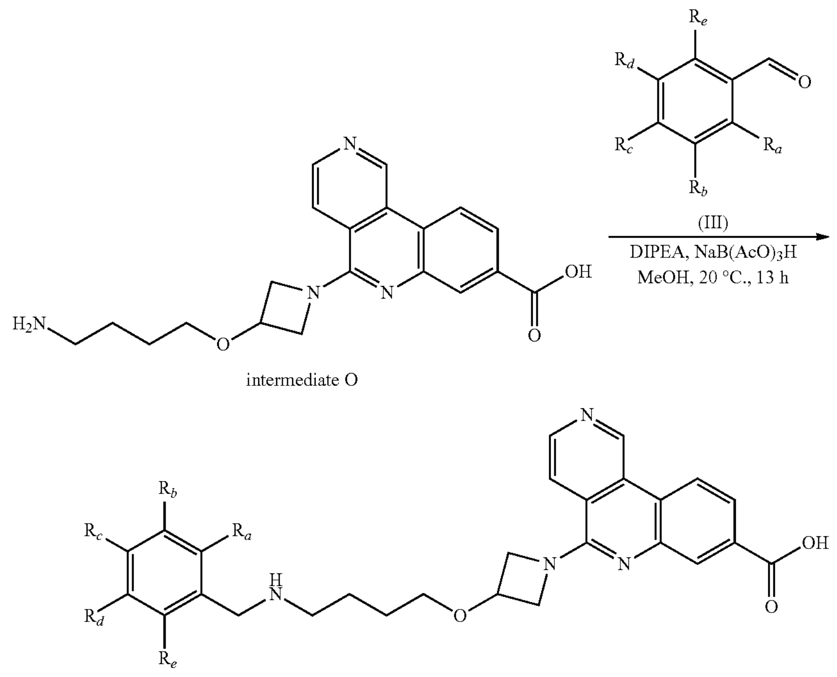

intermediate O

| Example No. | Chemical IUPAC name | Compound (III) | Analytical |
| --- | --- | --- | --- |
| Example 142 | 5-(3-(4-((3-cyclopropyl-4-(trifluoromethoxy) benzyl)amino) butoxy)azetidin-1-yl)benzo[c][2,6] naphthyridine-8-carboxylic acid | 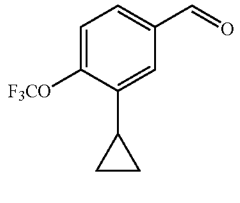 [SMILES: O=Cc1ccc(OC(F)(F)F)c(C2CC2)c1] 3-Cyclopropyl-4-(trifluoromethoxy)benzaldehyde 1.710 | $^{1}$H NMR (400 MHz, DMSO-$d_6$) δ: 10.07 (s, 1H), 8.79 (d, J = 5.6 Hz, 1H), 8.72 (d, J = 8.8 Hz, 1H), 8.19 (d, J = 1.6 Hz, 1H), 7.91-7.88 (m, 2H), 7.23 (s, 2H), 7.03 (s, 1H), 4.69-4.65 (m, 2H), 4.46-4.41 (m, 1H), 4.28-4.24 (m, 2H), 3.74 (s, 2H), 3.45-3.42 (m, 2H), 2.57 (t, J = 6.8 Hz, 2H), 2.06-1.99 (m, 1H), 1.61-1.52 (m, 4H), 0.99-0.95 (m, 2H), 0.72-0.68 (m, 2H) ppm<br>LCMS (AM3): rt = 0.802 min, (581.4 [M + H]$^+$), 100% purity<br>Purification Method 133 |
| Example 143 | 5-(3-(4-((3-bromo-5-(trifluoromethoxy) benzyl)amino) butoxy)azetidin-1-yl)benzo[c][2,6] naphthyridine-8-carboxylic acid | 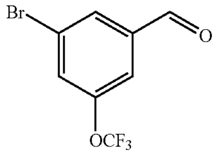 3-bromo-5-(trifluoromethoxy) benzaldehyde | $^{1}$H NMR (400 MHz, DMSO-$d_6$) δ: 10.11 (s, 1H), 8.82 (d, J = 5.6 Hz, 1H), 8.76 (d, J = 8.4 Hz, 1H), 8.20 (d, J = 1.2 Hz, 1H), 7.94 (d, J = 5.6 Hz, 1H), 7.88 (dd, J = 8.4, 1.6 Hz, 1H), 7.61 (s, 1H), 7.44 (s, 1H), 7.38 (s, 1H), 4.72-4.68 (m, 2H), 4.48-4.43 (m, 1H), 4.31-4.28 (m, 2H), 3.75 (s, 2H), 3.50-3.43 (m, 2H), 2.50-2.49 (m, 2H), 1.62-1.46 (m, 4H) ppm<br>LCMS (AM3): rt = 0.781 min, (619.4 [M + H]$^+$), 97.0% purity<br>Purification Method 133 |
| Example 144 | 5-(3-(4-((4-chloro-3-(trifluoromethoxy) benzyl)amino) butoxy)azetidin-1-yl)benzo[c][2,6] naphthyridine-8-carboxylic acid | 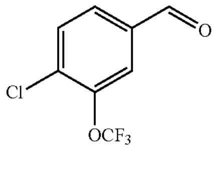 4-chloro-3-(trifluoromethoxy) benzaldehyde | $^{1}$H NMR (400 MHz, DMSO-$d_6$) δ: 10.07 (s, 1H), 8.78 (d, J = 5.6 Hz, 1H), 8.71 (d, J = 8.4 Hz, 1H), 8.19 (d, J = 1.2 Hz, 1H), 7.91-7.88 (m, 2H), 7.60 (d, J = 8.4 Hz, 1H), 7.56 (s, 1H), 7.41 (dd, J = 8.4, 2.0 Hz, 1H), 4.68-4.64 (m, 2H), 4.46-4.41 (m, 1H), 4.29-4.26 (m, 2H), 3.79 (s, 2H), 3.43 (t, J = 5.2 Hz, 2H), 2.55 (t, J = 6.8 Hz, 2H), 1.62-1.49 (m, 4H) ppm<br>LCMS (AM3): rt = 0.781 min, (575.2 [M + H]$^+$), 96.4% purity.<br>Purification Method 114 |

TABLE 9-continued

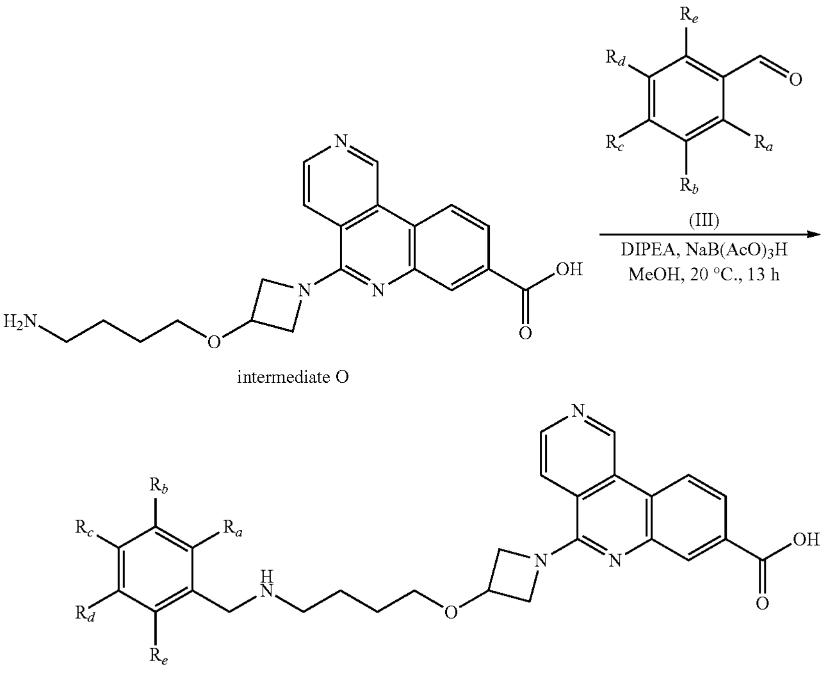

intermediate O

| Example No. | Chemical IUPAC name | Compound (III) | Analytical |
|---|---|---|---|
| Example 145 | 5-(3-(4-((3-methyl-4-(trifluoromethoxy)benzyl)amino)butoxy)azetidin-1-yl)benzo[c][2,6]naphthyridine-8-carboxylic acid | 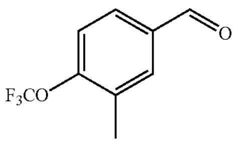 3-Methyl-4-(trifluoromethoxy)benzaldehyde 1.709 | $^1$H NMR (400 MHz, DMSO-$d_6$) δ: 10.09 (s, 1H), 8.81 (d, J = 5.6 Hz, 1H), 8.74 (d, J = 8.4 Hz, 1H), 8.19 (d, J = 1.6 Hz, 1H), 7.93 (d, J = 5.6 Hz, 1H), 7.89 (dd, J = 8.8, 1.6 Hz, 1H), 7.36 (s, 1H), 7.29 (d, J = 8.0 Hz, 1H), 7.24 (d, J = 8.4 Hz, 1H), 4.71-4.67 (m, 2H), 4.46-4.42 (m, 1H), 4.31-4.27 (m, 2H), 3.75 (s, 2H), 2.59 (t, J = 6.4 Hz, 4H), 2.24 (s, 3H), 1.61-1.52 (m, 4H) ppm LCMS (AM3): rt = 0.799 min, (555.3 [M + H]$^+$), 94.2% purity Purification Method 139 |
| Example 146 | 5-(3-(4-((3-methoxy-4-(trifluoromethoxy)benzyl)amino)butoxy)azetidin-1-yl)benzo[c][2,6]naphthyridine-8-carboxylic acid | 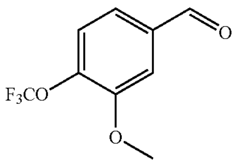 3-Methoxy-4-(trifluoromethoxy)benzaldehyde 1.707 | $^1$H NMR: (400 MHz, DMSO-$d_6$) δ: 10.08 (s, 1H), 8.80 (d, J = 5.6 Hz, 1H), 8.73 (d, J = 8.4 Hz, 1H), 8.19 (d, J = 1.2 Hz, 1H), 7.92 (d, J = 5.6 Hz, 1H), 7.89 (dd, J = 8.4, 1.2 Hz, 1H), 7.26 (dd, J = 4.4, 3.2 Hz, 2H), 6.99 (d, J = 8.4 Hz, 1H), 4.70-4.66 (m, 2H), 4.47-4.42 (m, 1H), 4.30-4.25 (m, 2H), 3.83 (s, 3H), 3.79 (s, 2H), 2.60 (t, J = 6.4 Hz, 2H), 2.53-2.52 (m, 2H), 1.63-1.52 (m, 4H) ppm LCMS (AM3): rt = 0.783 min, (571.3 [M + H]$^+$), 98.5% purity Purification Method 140 |
| Example 147 | 5-(3-(4-((3,4-dichloro-5-(trifluoromethoxy)benzyl)amino)butoxy)azetidin-1-yl)benzo[c][2,6]naphthyridine-8-carboxylic acid | 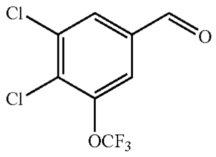 [SMILES: O=Cc1cc(Cl)c(Cl)c(OC(F)(F)F)c1] 3,4-Dichloro-5-(trifluoromethoxy)benzaldehyde 1.704 | $^1$H NMR (400 MHz, DMSO-$d_6$) δ: 10.12 (s, 1H), 8.83 (d, J = 5.6 Hz, 1H), 8.78 (d, J = 8.4 Hz, 1H), 8.21 (d, J = 1.6 Hz, 1H), 7.96 (d, J = 6.0 Hz, 1H), 7.88 (dd, J = 8.0, 1.6 Hz, 1H), 7.72 (d, J = 1.6 Hz, 1H), 7.57 (s, 1H), 4.73-4.69 (m, 2H), 4.48-4.43 (m, 1H), 4.32-4.28 (m, 2H), 3.80 (s, 2H), 2.55-2.50 (m, 4H), 1.62-1.48 (m, 4H) ppm LCMS (AM3): rt = 0.827 min, (609.1 [M + H]$^+$), 100% purity. Purification Method 141 |

Example 83

5-(3-(4-((3-Fluoro-4-(trifluoromethoxy)benzyl)amino)butoxy)azetidin-1-yl)benzo[c][2,6]naphthyridine-8-carboxamide

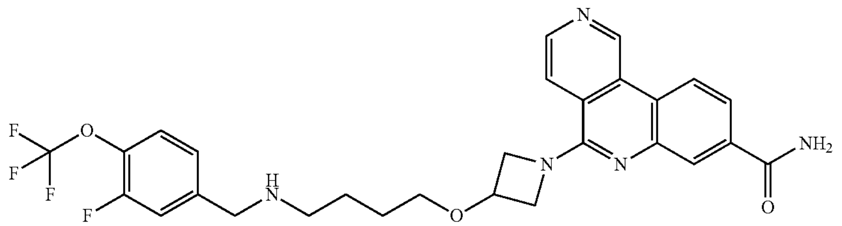 [SMILES: NC(=O)c1ccc2c(c1)nc(N1CC(OCCCCNCc3ccc(OC(F)(F)F)c(F)c3)C1)c1ccncc12]

To a solution of Intermediate P (300 mg, 820.96 μmol) and 3-fluoro-4-(trifluoromethoxy)benzaldehyde (170.85 mg, 820.96 μmol) in MeOH (10 mL) was added DIPEA (341.64 mg, 2.64 mmol). The mixture was stirred at 20° C. for 12 h before sodium triacetoxyborohydride (695.97 mg, 3.28 mmol) was added. The mixture was stirred at 20° C. for another 1 h. LCMS (AM3) indicated the reaction was complete. The mixture was concentrated in vacuo and the residue was purified (PM84) to afford Example 83 (64.07 mg, 114.46 μmol, 13.9% yield) as yellow solid.

LCMS (AM3): rt=0.747 min, (558.3 $[M+H]^+$), 99.6% purity.

$^1H$ NMR (400 MHz, MeOH-$d_4$) δ: 9.97 (s, 1H), 8.76 (d, J=5.6 Hz, 1H), 8.64 (d, J=8.8 Hz, 1H), 8.24 (s, 1H), 7.99 (d, J=5.6 Hz, 1H), 7.87 (dd, J=8.4, 1.6, Hz, 1H), 7.36-7.31 (m, 2H), 7.21 (d, J=8.8 Hz, 1H), 4.78-4.74 (m, 2H), 4.54-4.49 (m, 1H), 4.40-4.37 (m, 2H), 3.77 (s, 2H), 3.54 (t, J=5.8 Hz, 2H), 2.63 (t, J=7.0 Hz, 2H), 1.68-1.62 (m, 4H) ppm.

The following examples in Table 10 were made with non-critical changes or substitutions to the exemplified procedure in Example 83, that would be understood by one skilled in the art using intermediate P and compounds of formula (111).

TABLE 10

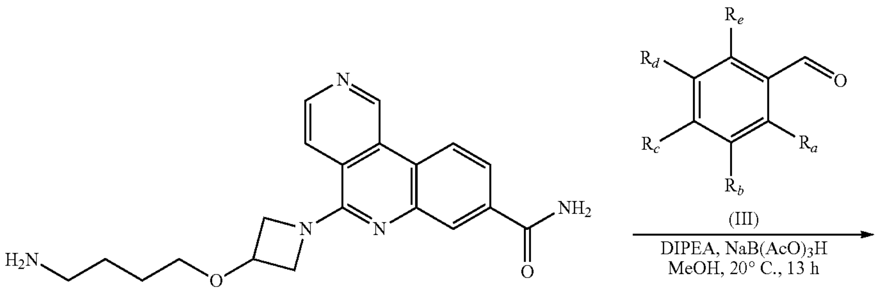

Intermediate P

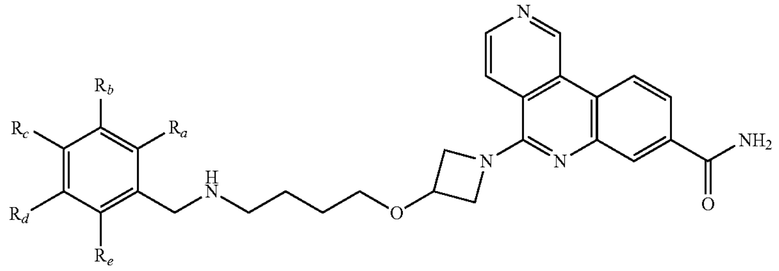

| Example No. | Chemical IUPAC name | Compound (III) | Analytical |
|---|---|---|---|
| Example 98 | 5-(3-(4-((3-(cyanomethyl)-5-(trifluoromethyl) benzyl)amino) butoxy)azetidin-1-yl)benzo[c][2,6] naphthyridine-8-carboxamide | 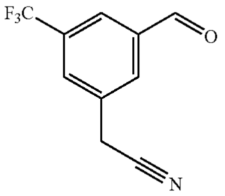 [SMILES: N#CCc1cc(C=O)cc(C(F)(F)F)c1] 2-(3-Formyl-5-(trifluoromethyl) phenyl)acetonitrile 1.469 | $^1$H NMR (400 MHz, DMSO-d$_6$) δ: 10.13 (s, 1H), 8.82 (d, J = 5.6 Hz, 1H), 8.77 (d, J = 8.4 Hz, 1H), 8.22 (d, J = 2.0 Hz, 1H), 8.20 (s, 1H), 7.96 (d, J = 5.6 Hz, 1H), 7.88 (dd, J = 8.4, 1.8 Hz, 1H), 7.66 (s, 1H), 7.63 (s, 1H), 7.56 (s, 1H), 7.46 (s, 1H), 4.73-4.69 (m, 2H), 4.48-4.44 (m, 1H), 4.32-4.29 (m, 2H), 4.15 (s, 2H), 3.78 (s, 2H), 3.44 (t, J = 6.4 Hz, 2H), 2.53-2.52 (m, 2H), 1.64-1.47 (m, 4H) ppm<br>LCMS (AM3): rt = 0.729 min, (563.3 [M + H]$^+$), 100% purity<br>Purification Method 99 |
| Example 99 | 5-(3-(4-((3-chloro-4-(trifluoromethoxy) benzyl)amino) butoxy)azetidin-1-yl)benzo[c][2,6] naphthyridine-8-carboxamide | 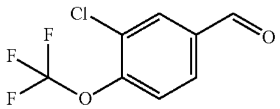 [SMILES: O=Cc1ccc(OC(F)(F)F)c(Cl)c1] 3-chloro-4-(trifluoromethoxy) benzaldehyde | $^1$H NMR (400 MHz, MeOH-d$_4$) δ: 9.96 (s, 1H), 8.75 (d, J = 5.6 Hz, 1H), 8.63 (d, J = 8.8 Hz, 1H), 8.24 (d, J = 1.6 Hz, 1H), 7.98 (d, J = 5.6 Hz, 1H), 7.87 (dd, J = 8.4, 1.6 Hz, 1H), 7.56 (s, 1H), 7.35 (s, 2H), 4.77-4.73 (m, 2H), 4.54-4.48 (m, 1H), 4.40-4.37 (m, 2H), 3.76 (s, 2H), 3.53 (t, J = 5.6 Hz, 2H), 2.62 ( t, J = 6.8 Hz, 2H), 1.68-1.62 (m, 4H) ppm<br>LCMS (AM3): rt = 0.765 min, (574.1 [M + H]$^+$), 96.2% purity<br>Purification Method 100 |
| Example 104 | 5-(3-(4-((3-chloro-5-(cyanomethyl) benzyl)amino) butoxy)azetidin-1-yl)benzo[c][2,6] naphthyridine-8-carboxamide | 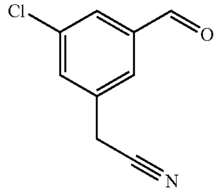 2-(3-Chloro-5-formylphenyl)acetonitrile 1.366 | $^1$H NMR (400 MHz, DMSO-d$_6$) δ: 10.13 (s, 1H), 8.82 (d, J = 5.6 Hz, 1H), 8.77 (d, J = 8.4 Hz, 1H), 8.22 (d, J = 1.6 Hz, 1H), 8.20 (s, 1H), 7.96 (d, J = 5.6 Hz, 1H), 7.88 (dd, J = 8.4, 1.6 Hz, 1H), 7.46 (s, 1H), 7.36 (s, 1H), 7.28 (s, 1H), 7.25 (s,1H), 4.73-4.69 (m, 2H), 4.48-4.44 (m, 1H), 4.32-4.29 (m, 2H), 4.04 (s, 2H), 3.68 (s, 2H), 3.44 (t, J = 6.4 Hz, 2H), 2.52-2.46 (m, 2H), 1.63-1.56 (quin, 2H), 1.53-1.45 (quin, 2H) ppm<br>LCMS (AM3): rt = 0.730 min, (529.4 [M + H]$^+$), 100% purity<br>Purification Method 105 |

TABLE 10-continued

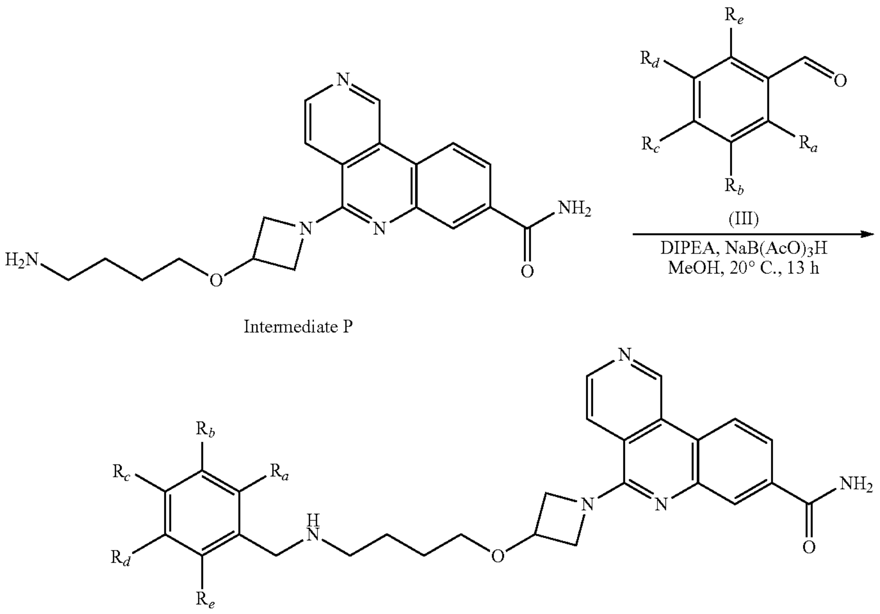

| Example No. | Chemical IUPAC name | Compound (III) | Analytical |
|---|---|---|---|
| Example 110 | 5-(3-(4-((3-(cyanomethyl)-5-(trifluoromethoxy)benzyl)amino) butoxy)azetidin-1-yl)benzo[c][2,6] naphthyridine-8-carboxamide | 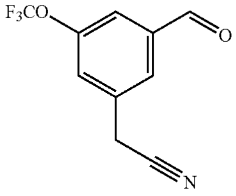 [SMILES: N#CCc1cc(C=O)cc(OC(F)(F)F)c1] 2-(3-Formyl-5-(trifluoromethoxy) phenyl)acetonitrile 1.504 | $^1H$ NMR (400 MHz, DMSO-$d_6$) δ: 10.13 (s, 1H), 8.81 (d, J = 5.6 Hz, 1H), 8.77 (d, J = 8.4 Hz, 1H), 8.22 (d, J = 1.6 Hz, 1H), 8.20 (s, 1H), 7.96 (d, J = 5.6 Hz, 1H), 7.88 (dd, J = 8.4, 2.0 Hz, 1H), 7.46 (s, 1H), 7.36 (s, 1H), 7.29 (s, 1H), 7.18 (s, 1H), 4.73-4.69 (m, 2H), 4.48-4.44 (m, 1H), 4.32-4.29 (m, 2H), 4.10 (s, 2H), 3.73 (s, 2H), 3.44 (t, J = 6.4 Hz, 2H), 2.54-2.52 (m, 2H), 1.63-1.56 (quin, 2H), 1.53-1.46 (quin, 2H) ppm<br>LCMS (AM3): rt = 0.744 min, (579.3 $[M + H]^+$), 98.1% purity<br>Purification Method 110 |
| Example 124 | 5-(3-(4-((3-chloro-5-(hydroxymethyl) benzyl)amino) butoxy)azetidin-1-yl)benzo[c][2,6] naphthyridine-8-carboxamide | 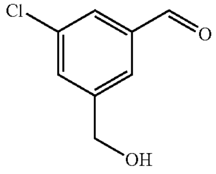 3-Chloro-5-(hydroxymethyl) benzaldehyde 1.102 | $^1H$ NMR (400 MHz, MeOH-$d_4$) δ: 9.87 (s, 1H), 8.71 (d, J = 5.2 Hz, 1H), 8.54 (d, J = 8.8 Hz, 1H), 8.17 (d, J = 1.6 Hz, 1H), 7.89 (d, J = 5.6 Hz, 1H), 7.83 (dd, J = 8.4, 2.0 Hz, 1H), 7.29 (s, 1H), 7.28 (s, 1H), 7.26 (s, 1H), 4.72-4.68 (m, 2H), 4.57 (s, 2H), 4.52-4.46 (m, 1H), 4.35-4.31 (m, 2H), 3.87 (s, 2H), 3.53 (t, J = 5.6 Hz, 2H), 2.77 (t, J = 6.8 Hz, 2H), 1.74-1.67 (m, 4H) ppm<br>LCMS (AM3): rt = 0.692 min, (520.2 $[M + H]^+$), 98.6% purity<br>Purification Method 124 |
| Example 125 | 5-(3-(4-((3-fluoro-5-(hydroxymethyl) benzyl)amino) butoxy)azetidin-1-yl)benzo[c][2,6] naphthyridine-8-carboxamide | 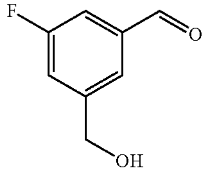 [SMILES: O=Cc1cc(F)cc(CO)c1] 3-Fluoro-5-(hydroxymethyl) benzaldehyde 1.500 | $^1H$ NMR (400 MHz, MeOH-$d_4$) δ: 9.87 (s, 1H), 8.71 (d, J = 5.6 Hz, 1H), 8.55 (d, J = 8.4 Hz, 1H), 8.18 (d, J = 1.6 Hz, 1H), 7.90 (d, J = 5.6 Hz, 1H), 7.83 (dd, J = 8.4, 1.6 Hz, 1H), 7.12 (s, 1H), 7.00-6.96 (m, 2H), 4.72-4.68 (m, 2H), 4.58 (s, 2H), 4.52-4.46 (m, 1H), 4.36-4.32 (m, 2H), 3.79 (s, 2H), 3.53 (t, J = 5.6 Hz, 2H), 2.67 (t, J = 7.2 Hz, 2H), 1.69-1.66 (m, 4H) ppm<br>LCMS (AM3): rt = 0.655 min, (504.3 $[M + H]^+$), 98.5% purity<br>Purification Method 125 |

TABLE 10-continued

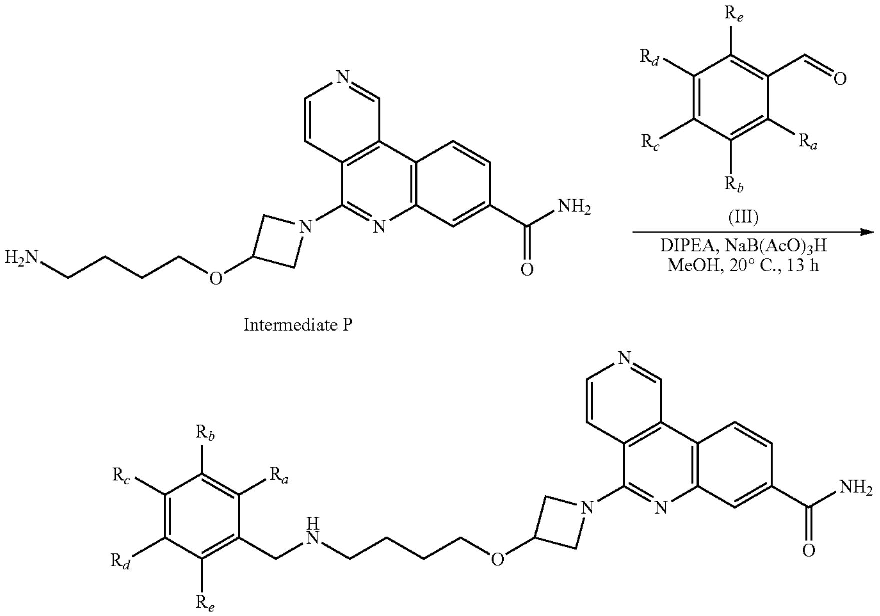

Intermediate P

| Example No. | Chemical IUPAC name | Compound (III) | Analytical |
|---|---|---|---|
| Example 126 | 5-(3-(4-((3-(hydroxymethyl)-5-(trifluoromethyl)benzyl)amino)butoxy)azetidin-1-yl)benzo[c][2,6]naphthyridine-8-carboxamide | 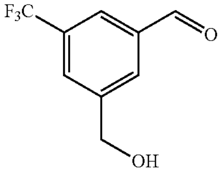 [SMILES: O=Cc1cc(CO)cc(C(F)(F)F)c1] 3-(Hydroxymethyl)-5-(trifluoromethyl)benzaldehyde 1.501 | $^1$H NMR (400 MHz, MeOH-d$_4$) δ: 9.98 (s, 1H), 8.76 (d, J = 5.6 Hz, 1H), 8.65 (d, J = 8.4 Hz, 1H), 8.25 (d, J = 1.6 Hz, 1H), 8.00 (d, J = 5.6 Hz, 1H), 7.88 (dd, J = 8.4, 2.0 Hz, 1H), 7.58-7.55 (m, 3H), 4.78-4.74 (m, 2H), 4.67 (s, 2H), 4.54-4.49 (m, 1H), 4.40-4.36 (m, 2H), 3.83 (s, 2H), 3.53 (t, J = 5.6 Hz, 2H), 2.64 (t, J = 6.8 Hz, 2H), 1.69-1.65 (m, 4H) ppm<br>LCMS (AM3): rt = 0.715 min, (554.3 [M + H]$^+$), 96.7% purity<br>Purification Method 126 |
| Example 127 | 5-(3-(4-((3-(cyanomethyl)-5-methylbenzyl)amino)butoxy)azetidin-1-yl)benzo[c][2,6]naphthyridine-8-carboxamide | 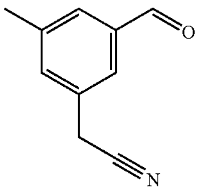 2-(3-Formyl-5-methylphenyl)acetonitrile 1.475 | $^1$H NMR (400 MHz, MeOH-d$_4$) δ: 9.93 (s, 1H), 8.75 (d, J = 5.6 Hz, 1H), 8.61 (d, J = 8.8 Hz, 1H), 8.21 (d, J = 1.6 Hz, 1H), 7.94 (d, J = 5.6 Hz, 1H), 7.86 (dd, J = 8.4, 1.6 Hz, 1H), 7.17 (s, 2H), 7.12 (s, 1H), 4.75-4.71 (m, 2H), 4.54-4.48 (m, 1H), 4.36-4.33 (m, 2H), 3.93 (s, 2H), 3.84 (s, 2H), 3.55 (t, J = 5.6 Hz, 2H), 2.86 (t, J = 7.6 Hz, 2H), 2.32 (s, 3H), 1.80-1.68 (m, 4H) ppm<br>LCMS (AM3): rt = 0.660 min, (509.2 [M + H]$^+$), 100% purity<br>Purification Method 127 |
| Example 128 | 5-(3-(4-((3-(cyanomethyl)-5-fluorobenzyl)amino)butoxy)azetidin-1-yl)benzo[c][2,6]naphthyridine-8-carboxamide | 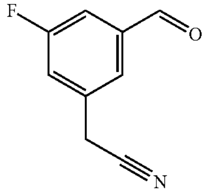 [SMILES: N#CCc1cc(F)cc(C=O)c1] 2-(3-Fluoro-5-formylphenyl)acetonitrile 1.472 | $^1$H NMR (400 MHz, DMSO-d$_6$) δ: 10.13 (s, 1H), 8.82 (d, J = 5.6 Hz, 1H), 8.77 (d, J = 8.4 Hz, 1H), 8.22-8.20 (m, 2H), 7.96 (d, J = 5.6 Hz, 1H), 7.88 (dd, J = 8.4, 2.0 Hz, 1H), 7.46 (s, 1H), 7.18-7.12 (m, 2H), 7.02 (d, J = 9.2 Hz, 1H), 4.73-4.69 (m, 2H), 4.48-4.44 (m, 1H), 4.32-4.29 (m, 2H), 4.04 (s, 2H), 3.70 (s, 2H), 3.44 (t, J = 6.4 Hz, 2H), 2.53-2.51 (m, 2H), 1.62-1.56 (m, 2H), 1.55-1.47 (m, 2H) ppm<br>LCMS (AM3): rt = 0.687 min, (513.3 [M + H]$^+$), 97.2% purity<br>Purification Method 128 |

(S)-5-((1-(4-((3-Chloro-4-(trifluoromethoxy)benzyl)amino)butoxy)propan-2-yl)amino)benzo[c][2,6]naphthyridine-8-carboxylic acid

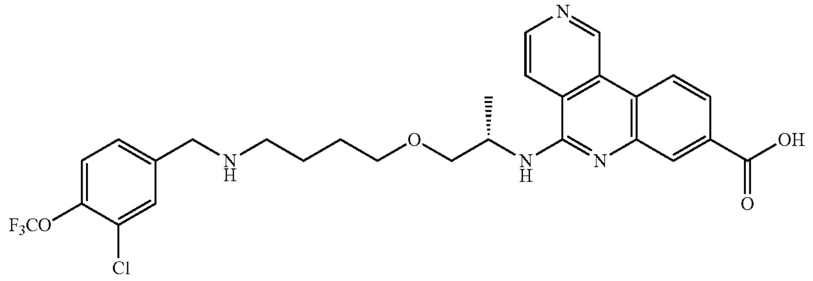 [SMILES: C[C@@H](COCCCCNCc1ccc(OC(F)(F)F)c(Cl)c1)Nc1nc2cc(C(=O)O)ccc2c2cnccc12]

A mixture of compound 1.625 (40 mg, 67.68 μmol) and lithium hydroxide monohydrate (8.52 mg, 203.04 μmol) in MeOH (0.5 mL), THF (1 mL) and $H_2O$ (1 mL) was stirred at 15° C. for 12 h. The mixture was concentrated in vacuo and the residue was purified (PM121) to afford Example 86 (16.58 mg, 42.2% yield, FA salt) as a yellow solid.

LCMS (AM3): rt=0.688 min, (577.1 $[M+H]^+$), 99.25% purity.

$^1$H NMR (400 MHz, MeOH-$d_4$) δ: 9.93 (s, 1H), 8.77 (d, J=5.6 Hz, 1H), 8.55 (d, J=8.4 Hz, 1H), 8.48 (br s, 1H), 8.28 (d, J=1.2 Hz, 1H), 8.21 (d, J=5.6 Hz, 1H), 7.95 (dd, J=8.4, 2.0 Hz, 1H), 7.67 (s, 1H), 7.48 (s, 2H), 4.91-4.89 (m, 1H), 4.07 (s, 2H), 3.82-3.76 (m, 2H), 3.64-3.59 (m, 1H), 3.55-3.51 (m, 1H), 3.02 (t, J=7.2 Hz, 2H), 1.86-1.78 (m, 2H), 1.71-1.63 (m, 2H), 1.40 (d, J=6.8 Hz, 3H) ppm.

Example 88

(R)-5-((1-(4-((3-chloro-4-(trifluoromethoxy)benzyl)amino)butoxy)propan-2-yl)amino)benzo[c][2,6]naphthyridine-8-carboxylic acid

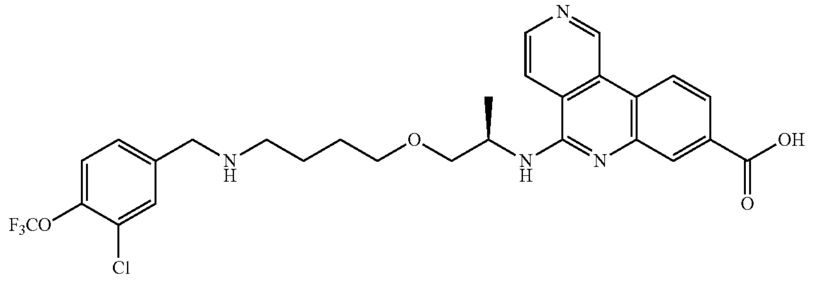 [SMILES: C[C@H](COCCCCNCc1ccc(OC(F)(F)F)c(Cl)c1)Nc1nc2cc(C(=O)O)ccc2c2cnccc12]

A mixture of compound 1.609 (0.15 g, 0.161 mmol) and lithium monohydrate (0.07 g, 1.67 mmol) in THF (3 mL) and $H_2O$ (1.5 mL) was stirred at 35° C. for 20 h. The mixture was neutralized with TFA to pH 6 and the resulting mixture was then concentrated in vacuo. The residue was purified (PM194) and then basified with aqueous NaOH solution (1 N) to pH 8. The mixture was concentrated and re-purified (PM89) afford Example 88 (35.73 mg, 61.92 μmol, 38.6% yield) as a yellow solid.

LCMS (AM3): rt=0.800 min, (577.2 $[M+H]^+$), 99.1% purity.

$^1$H NMR (400 MHz, MeOH-$d_4$) δ: 9.84 (s, 1H), 8.69 (d, J=5.6 Hz, 1H), 8.44 (d, J=8.4 Hz, 1H), 8.22 (d, J=1.6 Hz, 1H), 8.12 (d, J=6.0 Hz, 1H), 7.89 (dd, J=8.4 Hz, 1.6 Hz, 1H), 7.63 (d, J=2.0 Hz, 1H), 7.46-7.38 (m, 2H), 4.83-4.76 (m, 1H), 3.99 (s, 2H), 3.74-3.66 (m, 2H), 3.58-3.53 (m, 1H), 3.50-3.46 (m, 1H), 2.96-2.89 (m, 2H), 1.81-1.74 (m, 2H), 1.67-1.59 (m, 2H), 1.35 (d, J=6.8 Hz, 3H) ppm.

Examples 138 and 139 have been assigned the following stereochemical nomenclature but could be defined as either enantiomer as definitive stereochemistry has not been fully elucidated by analytical techniques.

Example 138

(R)-5-((2-(4-((3-chloro-5-(1-cyanoethyl)benzyl)amino)butoxy)ethyl)amino)benzo[c][2,6]naphthyridine-8-carboxamide

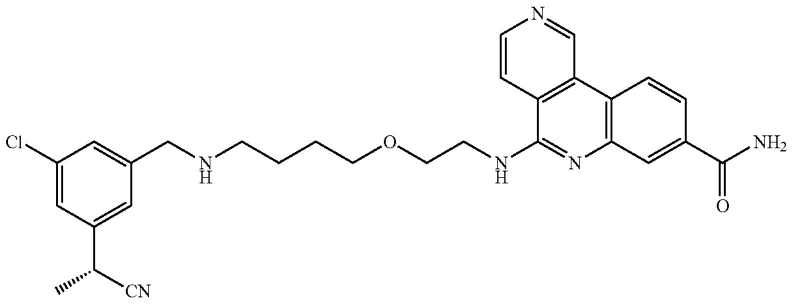 [SMILES: C[C@@H](C#N)c1cc(Cl)cc(CNCCCCOCCNc2nc3cc(C(N)=O)ccc3c3cnccc23)c1]

A mixture of Intermediate E (108.42 mg, 278.09 μmol), NaOAc (68.43 mg, 834.27 μmol) and compound 1.837 (70 mg, 361.52 μmol) in MeOH (3 mL) was stirred at 25° C. for 12 h, then sodium cyanoborohydride (174.75 mg, 2.78 mmol) was added. The mixture was stirred at 25° C. for 2 h. The mixture was filtered and the filtrate was concentrated in vacuo. The crude product was purified (PM136) to afford Example 138 (57.40 mg, 99.47 μmol, 35.8% yield, FA salt, 55% ee) as a yellow gum.

LCMS (AM3): rt=0.755 min, (531.4 $[M+H]^+$), 96.9% purity.

$^1H$ NMR (400 MHz, MeOH-$d_4$) δ: 9.91 (s, 1H), 8.77 (d, J=5.6 Hz, 1H), 8.59 (d, J=8.8 Hz, 1H), 8.43 (br s, 1H), 8.19 (d, J=1.6 Hz, 1H), 8.11 (d, J=5.6 Hz, 1H), 7.81 (dd, J=8.4, 2.0 Hz, 1H), 7.48 (d, J=1.6 Hz, 1H), 7.44 (s, 1H), 7.43 (s, 1H), 4.17 (q, J=7.6 Hz, 1H), 4.10 (s, 2H), 3.91 (t, J=5.6 Hz, 2H), 3.83 (t, J=5.6 Hz, 2H), 3.62 (t, J=6.0 Hz, 2H), 3.05 (t, J=7.6 Hz, 2H), 1.84-1.77 (m, 2H), 1.75-1.66 (m, 2H), 1.60 (d, J=7.2 Hz, 3H) ppm.

Example 139

(S)-5-((2-(4-((3-chloro-5-(1-cyanoethyl)benzyl)amino)butoxy)ethyl)amino)benzo[c][2,6]naphthyridine-8-carboxamide

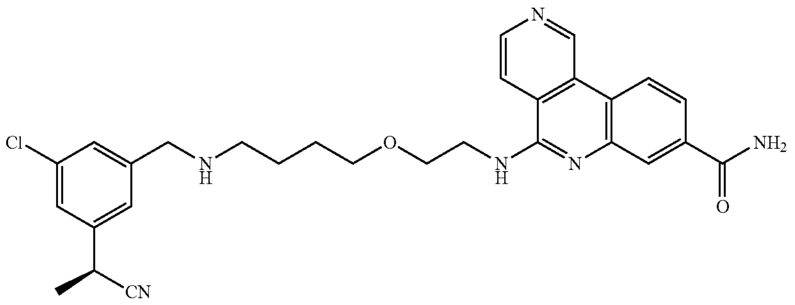 [SMILES: C[C@H](C#N)c1cc(Cl)cc(CNCCCCOCCNc2nc3cc(C(N)=O)ccc3c3cnccc23)c1]

A mixture of Intermediate E (123.91 mg, 317.82 μmol), NaOAc (78.21 mg, 953.45 μmol) and compound 1.838 (80 mg, 413.16 μmol) in MeOH (3 mL) was stirred at 25° C. for 12 h, then sodium cyanoborohydride (199.72 mg, 3.18 mmol) was added. The mixture was stirred at 25° C. for 2 h. The mixture was filtered and the filtrate was concentrated in vacuo. The crude product was purified (PM136) to afford Example 139 (57.27 mg, 99.24 μmol, 31.2% yield, FA salt, 69% ee) as a yellow solid.

LCMS (AM3): rt=0.749 min, (531.4 $[M+H]^+$), 97.7% purity.

$^1H$ NMR (400 MHz, MeOH-$d_4$) δ: 9.91 (s, 1H), 8.77 (d, J=5.6 Hz, 1H), 8.59 (d, J=8.4 Hz, 1H), 8.41 (br s, 1H), 8.19 (d, J=1.6 Hz, 1H), 8.12 (d, J=5.6 Hz, 1H), 7.81 (dd, J=8.4, 2.0 Hz, 1H), 7.48 (d, J=1.6 Hz, 1H), 7.45 (d, J=1.6 Hz, 1H), 7.43 (s, 1H), 4.17 (q, J=7.2 Hz, 1H), 4.10 (s, 2H), 3.91 (t, J=5.6 Hz, 2H), 3.82 (t, J=5.6 Hz, 2H), 3.63 (t, J=6.0 Hz, 2H), 3.06 (t, J=7.6 Hz, 2H), 1.85-1.77 (m, 2H), 1.73-1.66 (m, 2H), 1.60 (d, J=7.2 Hz, 3H) ppm.

Example 141

(R)-5-((1-(4-((3-chloro-4-(trifluoromethoxy)benzyl)amino)butoxy)propan-2-yl)amino)benzo[c][2,6]naphthyridine-8-carboxamide

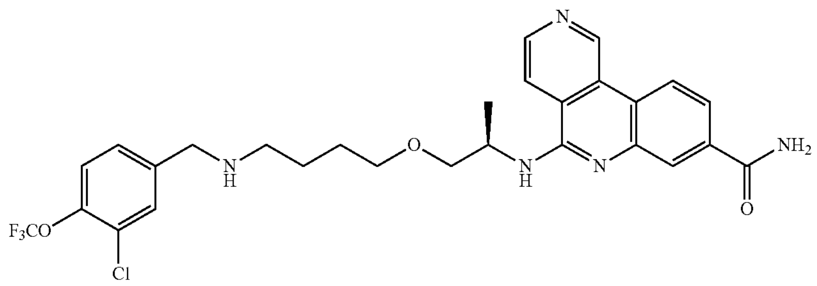 [SMILES: C[C@H](COCCCCNCc1ccc(OC(F)(F)F)c(Cl)c1)Nc1nc2cc(C(N)=O)ccc2c2cnccc12]

Compound 1.609 (90 mg, 152.28 μmol) in a solution of $NH_3$ in MeOH (10 mL, 7 M) was stirred at 90° C. in a 30 mL sealed tube for 12 h. The reaction mixture was concentrated in vacuo and the crude product was purified (PM138) to afford Example 141 (34.29 mg, 55.13 μmol, 36.2% yield, FA salt) as a yellow solid.

LCMS (AM3): rt=0.762 min, (576.3 $[M+H]^+$), 100% purity.

$^1H$ NMR (400 MHz, MeOH-$d_4$) δ: 9.92 (br s, 1H), 8.78 (d, J=5.2 Hz, 1H), 8.60 (d, J=8.4 Hz, 1H), 8.45 (br s, 1H), 8.21 (d, J=5.6 Hz, 1H), 8.19 (d, J=1.6 Hz, 1H), 7.81 (dd, J=8.4, 1.6 Hz, 1H), 7.64 (d, J=1.6 Hz, 1H), 7.47-7.40 (m, 2H), 4.85-4.83 (m, 1H), 4.07 (s, 2H), 3.77-3.73 (m, 1H), 3.70-3.53 (m, 3H), 3.02 (t, J=7.6, 2H), 1.82-1.73 (quin, 2H), 1.72-1.63 (quin, 2H), 1.38 (d, J=6.8 Hz, 3H) ppm.

Example 148

(S)-5-((1-(4-((3-Chloro-4-(trifluoromethoxy)benzyl)amino)butoxy)propan-2-yl)amino)benzo[c][2,6]naphthyridine-8-carboxamide

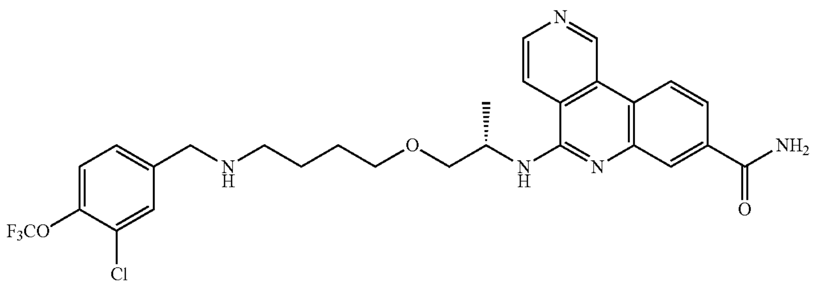 [SMILES: C[C@@H](COCCCCNCc1ccc(OC(F)(F)F)c(Cl)c1)Nc1nc2cc(C(N)=O)ccc2c2cnccc12]

Compound 1.625 (300 mg, 0.47 mmol, FA salt) in a solution of $NH_3$ in MeOH (10 mL, 7 M) was stirred in a sealed tube at 100° C. for 16 h. The reaction mixture was concentrated in vacuo and the residue was purified (PM142) to afford Example 148 (34.24 mg, 11.4% yield, FA salt) as a yellow gum.

LCMS (AM3): rt=0.798 min, (576.2 $[M+H]^+$), 100% purity.

$^1$H NMR (400 MHz, MeOH-$d_4$) δ: 9.88 (s, 1H), 8.76 (d, J=5.6 Hz, 1H), 8.55 (d, J=8.4 Hz, 1H), 8.47 (br s, 1H), 8.19-8.16 (m, 2H), 7.79 (dd, J=8.4 Hz, 1.6 Hz, 1H), 7.65 (s, 1H), 7.47-7.43 (m, 2H), 4.85-4.80 (m, 1H), 4.08 (s, 2H), 3.77-3.73 (m, 1H), 3.68-3.54 (m, 3H), 3.03 (t, J=7.6 Hz, 2H), 1.83-1.76 (quin, 2H), 1.73-1.67 (quin, 2H), 1.38 (d, J=6.8 Hz, 3H) ppm.

Example 149

5-((1-(4-((3-Chloro-4-(trifluoromethoxy)benzyl)amino)butoxy)-2-methylpropan-2-yl)amino)benzo[c][2,6]naphthyridine-8-carboxylic acid

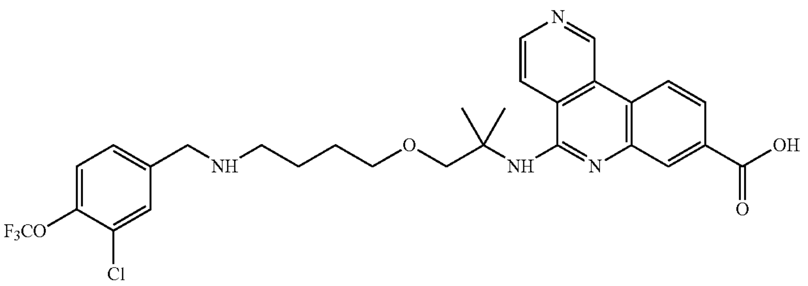 [SMILES: CC(C)(COCCCCNCc1ccc(OC(F)(F)F)c(Cl)c1)Nc1nc2cc(C(=O)O)ccc2c2cnccc12]

A mixture of compound 1.734 (25 mg, 0.04 mmol, FA salt) and $LiOH \cdot H_2O$ (17 mg, 0.41 mmol) in THF (2 mL) and $H_2O$ (0.5 mL) was stirred at room temperature for 15 h. The reaction mixture was concentrated in vacuo and the residue was purified (PM145) to afford Example 149 (14.67 mg, 64.6% yield) as a white solid.

LCMS (AM3): rt=0.824 min, (591.2 $[M+H]^+$), 100% purity.

$^1$H NMR (400 MHz, MeOH-$d_4$) δ: 9.86 (s, 1H), 8.72 (d, J=6.0 Hz, 1H), 8.47 (d, J=8.4 Hz, 1H), 8.26 (s, 1H), 8.08 (d, J=5.6 Hz, 1H), 7.89 (d, J=8.4 Hz, 1H), 7.64 (s, 1H), 7.48-7.46 (m, 1H), 7.44-7.41 (m, 1H), 4.01 (s, 2H), 3.97 (s, 2H), 3.54 (t, J=5.6 Hz, 2H), 2.89 (t, J=6.8 Hz, 2H), 1.72-1.60 (m, 4H), 1.60 (s, 6H) ppm.

Example 150

5-((2-(4-((3-(Cyanomethyl)-5-ethylbenzyl)amino)butoxy)ethyl)amino)benzo[c][2,6]naphthyridine-8-carboxamide

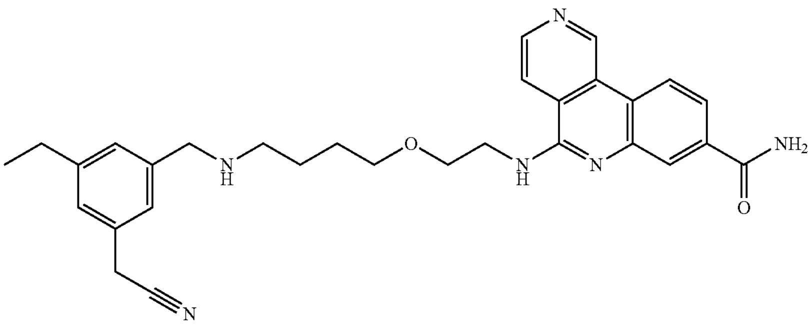 [SMILES: CCc1cc(CC#N)cc(CNCCCCOCCNc2nc3cc(C(N)=O)ccc3c3cnccc23)c1]

A mixture of Intermediate E (100 mg, 256.49 μmol, HCl salt), sodium acetate (63.12 mg, 769.47 μmol) and compound 1.689 (44.43 mg, 256.49 μmol) in MeOH (3 mL) was stirred at 20° C. for 12 h, then sodium triacetoxyborohydride (163.08 mg, 769.47 μmol) was added. The reaction mixture was stirred at 20° C. for another 3 h. The reaction mixture was filtered and concentrated and the crude product was purified (PM146) to afford Example 150 (36.44 mg, 71.36 μmol, 27.8% yield) as a yellow gum.

LCMS (AM3): rt=0.666 min, (511.2 $[M+H]^+$), 96.6% purity.

$^1$H NMR (400 MHz, DMSO-$d_6$) δ: 10.06 (s, 1H), 8.85 (d, J=5.6 Hz, 1H), 8.71 (d, J=8.4 Hz, 1H), 8.28 (d, J=5.6 Hz, 2H), 8.18 (br s, 1H), 8.14 (d, J=2.0 Hz, 1H), 8.00 (t, J=5.2 Hz, 1H), 7.81 (dd, J=8.4, 1.8 Hz, 1H), 7.42 (br s, 1H), 7.14 (br s, 2H), 7.08 (s, 1H), 3.97 (s, 2H), 3.79 (t, J=5.6 Hz, 2H), 3.75 (s, 2H), 3.70 (t, J=5.6 Hz, 2H), 3.46 (t, J=5.6 Hz, 2H), 2.63-2.58 (m, 2H), 2.57-2.55 (m, 2H), 1.57-1.51 (br m, 4H), 1.15 (t, J=7.6 Hz, 3H) ppm.

Example 151

5-((2-(4-((3-(Cyanomethyl)-5-(cyclopropylmethyl)benzyl)amino)butoxy)ethyl)amino)benzo[c][2,6]naphthyridine-8-carboxamide

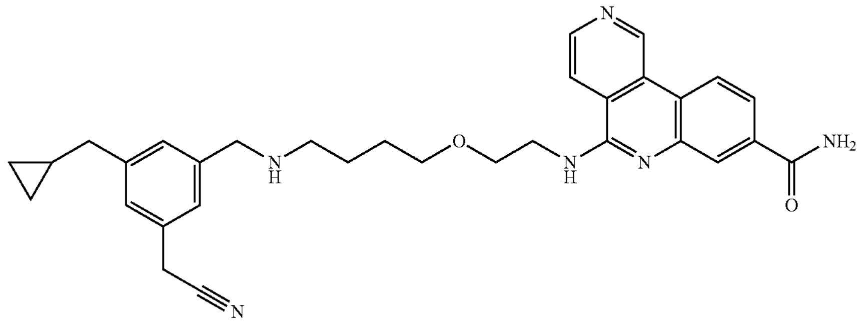 [SMILES: N#CCc1cc(CNCCCCOCCNc2nc3cc(C(N)=O)ccc3c3cnccc23)cc(CC2CC2)c1]

A mixture of Intermediate E (100 mg, 256.49 μmol, HCl salt), sodium acetate (63.12 mg, 769.47 μmol) and compound 1.697 (51.11 mg, 256.49 μmol) was stirred at 20° C. for 5 h, then sodium triacetoxyborohydride (163.08 mg, 769.47 μmol) was added. The reaction mixture was stirred at 20° C. for another 0.4 h. The reaction mixture was filtered and concentrated in vacuo to give the crude product that was purified (PM147) to afford Example 151 (54.59 mg, 93.69 μmol, 36.5% yield, FA salt) as a yellow oil.

LCMS (AM3): rt=0.748 min, (537.1 $[M+H]^+$), 98.9% purity.

$^1$H NMR (400 MHz, DMSO-$d_6$) δ: 10.06 (s, 1H), 8.85 (d, J=5.6 Hz, 1H), 8.70 (d, J=8.4 Hz, 1H), 8.28-8.26 (m, 2H), 8.19 (br s, 1H), 8.14 (d, J=1.6 Hz, 1H), 8.00 (t, J=4.8 Hz, 1H), 7.82 (dd, J=8.4, 1.6 Hz, 1H), 7.43 (br s, 1H), 7.16 (d, J=8.4 Hz, 2H), 7.09 (s, 1H), 3.99 (s, 2H), 3.78 (t, J=5.2 Hz, 2H), 3.75 (s, 2H), 3.70 (t, J=5.2 Hz, 2H), 3.46 (t, J=5.2 Hz, 2H), 2.60 (t, J=6.4 Hz, 2H), 2.50-2.46 (m, 2H), 1.55-1.50 (m, 4H), 0.96-0.88 (m, 1H), 0.47-0.42 (q, 2H), 0.18-0.14 (q, 2H) ppm.

Example 152

5-((1-(4-((3-Chloro-4-(trifluoromethoxy)benzyl)amino)butoxy)-2-methylpropan-2-yl)amino)benzo[c][2,6]naphthyridine-8-carboxamide

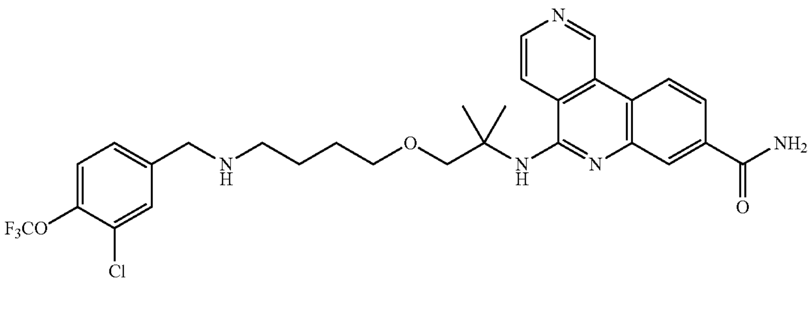 [SMILES: CC(C)(COCCCCNCc1ccc(OC(F)(F)F)c(Cl)c1)Nc1nc2cc(C(N)=O)ccc2c2cnccc12]

Compound 1.734 (10 mg, 0.017 mmol, FA salt) in a solution of $NH_3$ in MeOH (10 mL, 7 M) was stirred in a sealed tube at 90° C. for 16 h. The reaction mixture was concentrated in vacuo and the residue was purified (PM148) to afford Example 152 (4.12 mg, 39.2% yield, FA salt) as an off-white solid.

LCMS (AM3): rt=0.804 min, (590.2 $[M+H]^+$), 100% purity.

$^1$H NMR (400 MHz, MeOH-$d_4$) δ: 9.92 (s, 1H), 8.76 (d, J=6.0 Hz, 1H), 8.61 (d, J=8.4 Hz, 1H), 8.52 (br s, 1H), 8.22 (d, J=1.6 Hz, 1H), 8.14 (d, J=5.6 Hz, 1H), 7.84 (dd, J=8.4 Hz, 2.0 Hz, 1H), 7.55 (d, J=1.6 Hz, 1H), 7.43-7.40 (m, 1H), 7.35-7.32 (m, 1H), 3.99 (s, 2H), 3.79 (s, 2H), 3.52 (t, J=5.6 Hz, 2H), 2.68 (t, J=6.8 Hz, 2H), 1.63 (s, 6H), 1.60-1.55 (m, 4H) ppm.

Example 154

(R)-5-((1-(4-((3-chloro-4-(trifluoromethoxy)benzyl) amino)butoxy)propan-2-yl)oxy)benzo[c][2,6]naphthyridine-8-carboxylic acid

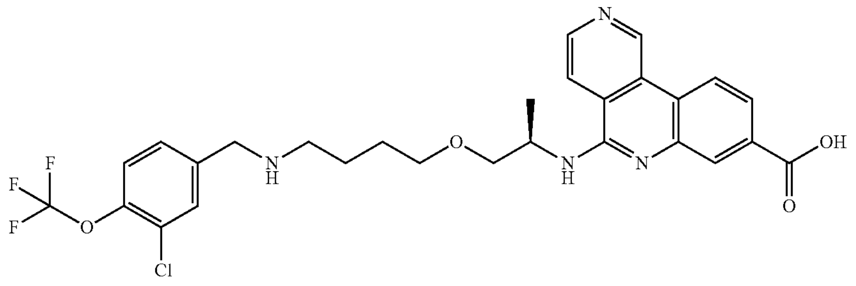 [SMILES: C[C@H](COCCCCNCc1ccc(OC(F)(F)F)c(Cl)c1)Nc1nc2cc(C(=O)O)ccc2c2cnccc12]

A mixture of compound 1.782 (67 mg, 0.1 mmol) in a solution of HCl in 1,4-dioxane (10 mL, 2 M) was stirred at room temperature for 3 h. The reaction mixture was concentrated in vacuo and the residue was purified by (PM151) to afford Example 154 (21.5 mg, 37.7% yield) as a white solid.

LCMS (AM3): rt=0.883 min, (578.2 $[M+H]^+$), 100% purity.

$^1$H NMR (400 MHz, MeOH-$d_4$) δ: 9.96 (s, 1H), 8.79 (d, J=5.6 Hz, 1H), 8.63 (d, J=8.4 Hz, 1H), 8.39 (d, J=1.6 Hz, 1H), 8.16 (d, J=5.6 Hz, 1H), 8.11 (dd, J=8.4, 1.6 Hz, 1H), 7.65 (s, 1H), 7.47-7.42 (m, 2H), 5.96-5.88 (m, 1H), 4.02 (s, 2H), 3.87-3.83 (m, 1H), 3.76-3.67 (m, 2H), 3.61-3.55 (m, 1H), 2.94 (t, J=7.6 Hz, 2H), 1.79-1.72 (m, 2H), 1.69-1.53 (m, 2H), 1.48 (d, J=6.4 Hz, 3H) ppm.

Example 155

(R)-5-((1-(4-((3-Chloro-4-(trifluoromethoxy)benzyl) amino)butoxy)propan-2-yl)oxy)benzo[c][2,6]naphthyridine-8-carboxamide

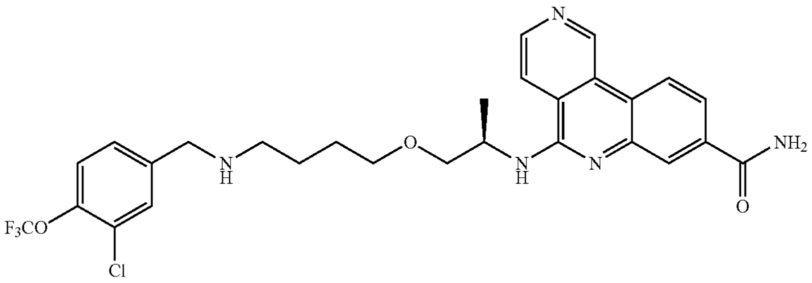 [SMILES: C[C@H](COCCCCNCc1ccc(OC(F)(F)F)c(Cl)c1)Nc1nc2cc(C(N)=O)ccc2c2cnccc12]

A mixture of 3-chloro-4-(trifluoromethoxy)benzaldehyde (140 mg, 0.62 mmol), compound 1.729 (250 mg, 0.62 mmol, HCl salt) and DIPEA (0.5 mL, 2.87 mmol) in MeOH (10 mL) was stirred at room temperature for 16 h, then sodium triacetoxyborohydride (522 mg, 2.46 mmol) was added. The reaction mixture was stirred at room temperature for 1 h. The reaction mixture was concentrated in vacuo and the residue was purified (PM152) to afford Example 155 (36.72 mg, 10.2% yield) as a white solid.

LCMS (AM3): rt=0.846 min, (577.2 $[M+H]^+$), 98.9% purity.

$^1$H NMR (400 MHz, MeOH-$d_4$) δ: 9.94 (s, 1H), 8.81 (d, J=5.6 Hz, 1H), 8.68 (d, J=8.4 Hz, 1H), 8.33 (d, J=1.6 Hz, 1H), 8.16 (d, J=5.6 Hz, 1H), 8.00 (dd, J=8.4 Hz, 2.0 Hz, 1H), 7.45 (d, J=2.0 Hz, 1H), 7.31-7.22 (m, 2H), 5.88-5.81 (m, 1H), 3.86-3.82 (m, 1H), 3.77-3.73 (m, 1H), 3.66-3.54 (m, 4H), 2.53 (t, J=7.2 Hz, 2H), 1.62-1.54 (m, 4H), 1.50 (d, J=6.4 Hz, 3H) ppm.

Example 166

(S)-5-((1-(4-((3-Chloro-4-(trifluoromethoxy)benzyl)amino)butoxy)propan-2-yl)oxy)benzo[c][2,6]naphthyridine-8-carboxylic acid

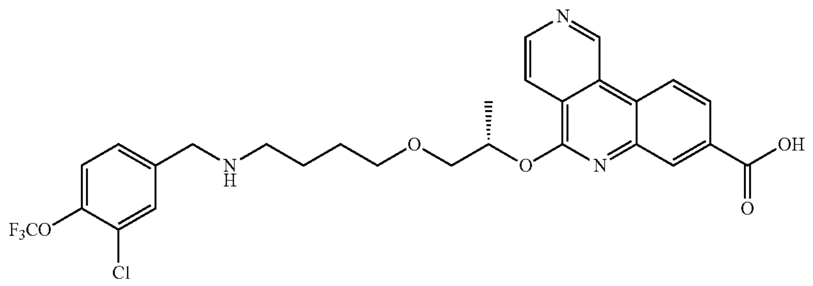 [SMILES: C[C@@H](COCCCCNCc1ccc(OC(F)(F)F)c(Cl)c1)Oc1nc2cc(C(=O)O)ccc2c2cnccc12]

To a solution of compound 1.681 (50 mg, 84.46 μmol) in $H_2O$ (1 mL) and THF (1 mL) was added $LiOH{\cdot}H_2O$ (14.18 mg, 337.84 μmol) at 20° C. The reaction mixture was stirred at 20° C. for 2 h. The reaction mixture was neutralized with formic acid and concentrated in vacuo. The crude product was purified (PM161) to afford Example 166 (19.83 mg, 34.31 μmol, 40.6% yield) as a yellow gum.

LCMS (AM3): rt=0.851 min, (578.0 $[M+H]^+$), 95.4% purity.

$^1$H NMR (400 MHz, MeOH-$d_4$) δ: 9.94 (s, 1H), 8.78 (d, J=5.6 Hz, 1H), 8.61 (d, J=8.4 Hz, 1H), 8.39 (d, J=1.2 Hz, 1H), 8.14 (d, J=5.6 Hz, 1H), 8.10 (dd, J=8.4, 1.6 Hz, 1H), 7.63 (s, 1H), 7.43 (s, 2H), 5.93-5.85 (m, 1H), 3.99 (s, 2H), 3.86-3.80 (m, 1H), 3.75-3.67 (m, 2H), 3.60-3.55 (m, 1H), 2.90 (t, J=7.6 Hz, 2H), 1.78-1.70 (quin, 2H), 1.68-1.52 (m, 2H), 1.47 (d, J=6.4 Hz, 3H) ppm.

Example 167

(S)-5-((1-(4-((3-Chloro-4-(trifluoromethoxy)benzyl)amino)butoxy)propan-2-yl)oxy)benzo[c][2,6]naphthyridine-8-carboxamide

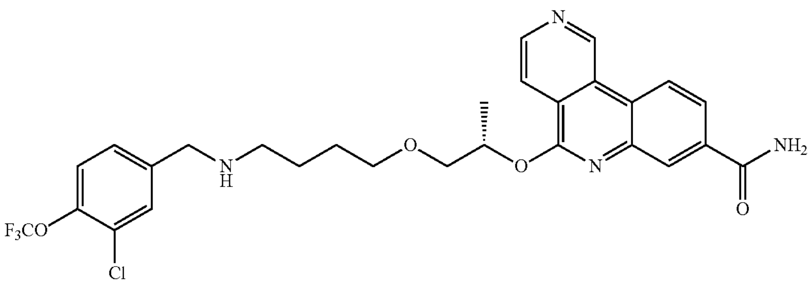 [SMILES: C[C@@H](COCCCCNCc1ccc(OC(F)(F)F)c(Cl)c1)Oc1nc2cc(C(N)=O)ccc2c2cnccc12]

Compound 1.681 (100 mg, 168.92 μmol) in a solution of $NH_3$ in MeOH (10 mL, 7 M) was stirred in a 30 mL sealed tube at 80° C. for 12 h. The reaction mixture was concentrated in vacuo and the crude product was purified (PM162) to afford Example 167 (28.11 mg, 45.12 μmol, 26.7% yield, FA salt) as a yellow solid.

LCMS (AM3): rt=0.826 min, (577.0 $[M+H]^+$), 100% purity.

$^1H$ NMR (400 MHz, MeOH-$d_4$) δ:10.03 (s, 1H), 8.86 (d, J=5.6 Hz, 1H), 8.77 (d, J=8.4 Hz, 1H), 8.48 (br s, 1H), 8.39 (d, J=2.0 Hz, 1H), 8.22 (d, J=5.2 Hz, 1H), 8.05 (dd, J=8.4, 1.6 Hz, 1H), 7.63 (d, J=1.6 Hz, 1H), 7.47-7.40 (m, 2H), 5.95-5.86 (m, 1H), 4.04 (s, 2H), 3.89-3.84 (m, 1H), 3.81-3.74 (m, 1H), 3.71-3.66 (m, 1H), 3.63-3.58 (m, 1H), 2.96 (t, J=7.6 Hz, 2H), 1.78-1.70 (m, 2H), 1.70-1.61 (m, 2H), 1.51 (d, J=6.4 Hz, 3H) ppm.

Example 169

5-(2-(4-((3-Carbamoyl-5-(trifluoromethoxy)benzyl)amino)butoxy)ethoxy)benzo[c][2,6]naphthyridine-8-carboxamide

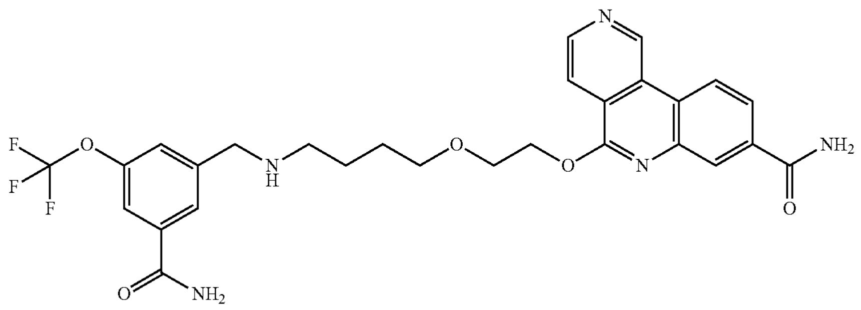 [SMILES: NC(=O)c1cc(CNCCCCOCCOc2nc3cc(C(N)=O)ccc3c3cnccc23)cc(OC(F)(F)F)c1]

A mixture of compound 1.57 (223.28 mg, 557.60 μmol, FA salt), DIPEA (216.20 mg, 1.67 mmol) and compound 1.675 (130 mg, 557.60 μmol) in MeOH (3 mL) was stirred at 20° C. for 12 h, then sodium cyanoborohydride (105.12 mg, 1.67 mmol) was added. The reaction mixture was stirred at 20° C. for 0.5 h. The reaction mixture was filtered and concentrated to give the crude product that was purified (PM163) to afford Example 169 (123.81 mg, 216.62 μmol, 38.9% yield) as a white solid.

LCMS (AM3): rt=0.872 min, (572.2 $[M+H]^+$), 100% purity.

$^1H$ NMR (400 MHz, MeOH-$d_4$) δ: 9.93 (s, 1H), 8.81 (d, J=5.6 Hz, 1H), 8.67 (d, J=8.4 Hz, 1H), 8.32 (d, J=1.6 Hz, 1H), 8.15 (dd, J=5.6, 0.8 Hz, 1H), 8.00 (dd, J=8.4, 1.6 Hz, 1H), 7.79 (s, 1H), 7.63 (br s, 1H), 7.41 (br s, 1H), 4.78 (t, J=4.4 Hz, 2H), 3.96 (t, J=4.8 Hz, 2H), 3.76 (s, 2H), 3.63 (t, J=5.6 Hz, 2H), 2.59 (t, J=7.2 Hz, 2H), 1.68-1.58 (m, 4H) ppm.

The following examples in Table 11 were made with non-critical changes or substitutions to the exemplified procedure in Example 169, that would be understood by one skilled in the art using intermediate 1.57 and compounds of formula (III).

TABLE 11

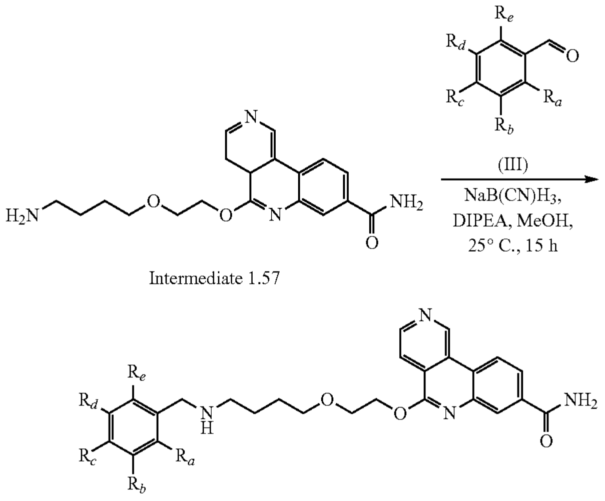

| Example No. | Chemical IUPAC name | Compound (III) | Analytical |
|---|---|---|---|
| Example 174 | 5-(2-(4-((3-((1H-imidazol-1-yl)methyl)-5-(trifluoromethoxy) benzyl)amino) butoxy)ethoxy) benzo[c][2,6] naphthyridine-8-carboxamide | 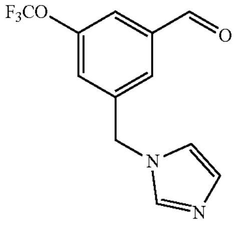 [SMILES: O=Cc1cc(Cn2ccnc2)cc(OC(F)(F)F)c1] 3-((1H-imidazol-1-yl)methyl)-5-(trifluoromethoxy) benzaidehyde 1.825 | $^1$H NMR (400 MHZ, MeOH-$d_4$) δ: 9.79 (s, 1H), 8.73 (d, J = 5.6 Hz, 1H), 8.53 (d, J = 8.8 Hz, 1H), 8.21 (d, J = 1.6 Hz, 1H), 8.04 (d, J = 5.6 Hz, 1H), 7.92 (dd, J = 8.4, 1.6 Hz, 1H), 7.76 (s, 1H), 7.16 (d, J = 5.6 Hz, 2H), 7.11 (t, J = 1.6 Hz, 1H), 6.98 (s, 2H), 5.22 (s, 2H), 4.71 (t, J = 4.8 Hz, 2H), 3.94 (t, J = 4.8 Hz, 2H), 3.67 (s, 2H), 3.62 (t, J = 6.0 Hz, 2H), 2.55 (t, J = 6.8 Hz, 2H), 1.65-1.57 (m, 4H) ppm<br>LCMS (AM7): rt = 0.980 min, (609.3 [M+H]$^+$), 99.6% purity<br>Purification Method 153 |
| Example 176 | 5-(2-(4-((3-(furan-3-ylmethyl)-5-(trifluoromethoxy) benzyl)amino) butoxy)ethoxy) benzo[c][2,6] naphthyridine-8-carboxamide | 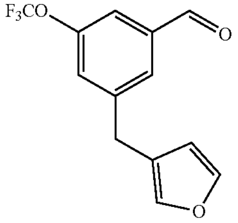 [SMILES: O=Cc1cc(Cc2ccoc2)cc(OC(F)(F)F)c1] 3-(Furan-3-ylmethyl)-5-(trifluoromethoxy) benzaldehyde 1.826 | $^1$H NMR (400 MHZ, MeOH-$d_4$) δ: 9.92 (s, 1H), 8.80 (d, J = 5.6 Hz, 1H), 8.65 (d, J = 8.8 Hz, 1H), 8.43 (s, 1H), 8.32 (d, J = 1.6 Hz, 1H), 8.12 (dd, J = 5.2, 0.4 Hz, 1H), 8.00 (dd, J = 8.8, 1.6 Hz, 1H), 7.41 (t, J = 1.6 Hz, 1H), 7.33 (s, 1H), 7.30 (s, 1H), 7.24 (s, 1H), 7.17 (s, 1H), 6.24 (d, J = 0.8 Hz, 1H), 4.78-4.76 (m, 2H), 4.13 (s, 2H), 3.98 (t, J = 4.8 Hz, 2H), 3.81 (s, 2H), 3.67 (t, J = 6.0 Hz, 2H), 3.06 (t, J = 7.6 Hz, 2H), 1.88-1.79 (m, 2H), 1.75-1.66 (m, 2H) ppm<br>LCMS (AM3): rt = 0.859 min, (609.3 [M+H] +), 99.3% purity<br>Purification Method 170 |

Example 170

5-((2-(4-((3-(2-Amino-2-oxoethyl)-5-(trifluoromethoxy)benzyl)amino)butoxy)ethyl)amino)benzo[c][2,6]naphthyridine-8-carboxamide

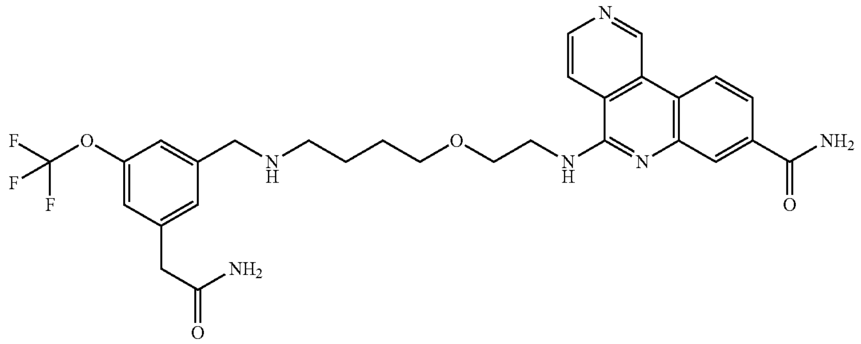 [SMILES: NC(=O)Cc1cc(CNCCCCOCCNc2nc3cc(C(N)=O)ccc3c3cnccc23)cc(OC(F)(F)F)c1]

To a mixture of Example 89 (160 mg, 282.40 μmol) and $K_2CO_3$ (19.51 mg, 141.20 μmol) in MeOH (1 mL) was added $H_2O_2$ (0.108 g, 1.11 mmol, 35% wt.) slowly at 20° C. The reaction mixture was stirred at 20° C. for 2 h. The reaction was quenched with sat. aq. $Na_2SO_3$ solution (0.5 mL), then the mixture was filtered and the filtrate was purified (PM164); and then re-purified (PM117) to afford Example 170 (34.19 mg, 58.49 μmol, 20.7% yield) as a white solid.

LCMS (AM7): rt=0.855 min, (585.3 $[M+H]^+$), 96.9% purity.

$^1H$ NMR (400 MHz, MeOH-$d_4$) δ: 9.89 (d, J=8.0 Hz, 1H), 8.76-8.74 (m, 1H), 8.57 (t, J=7.6 Hz, 1H), 8.20-8.18 (m, 1H), 8.11 (t, J=5.6 Hz, 1H), 7.83-7.80 (m, 1H), 7.22 (s, 1H), 7.13 (s, 2H), 3.91-3.87 (m, 2H), 3.88 (t, J=5.6 Hz, 2H), 3.70 (s, 2H), 3.56 (t, J=5.6 Hz, 2H), 3.53 (s, 2H), 2.59 (t, J=6.8 Hz, 2H), 1.63-1.57 (m, 4H) ppm.

Example 171

5-(2-(4-((3-(2-Amino-2-oxoethyl)-5-(trifluoromethoxy)benzyl)amino)butoxy)ethoxy)benzo[c][2,6]naphthyridine-8-carboxamide

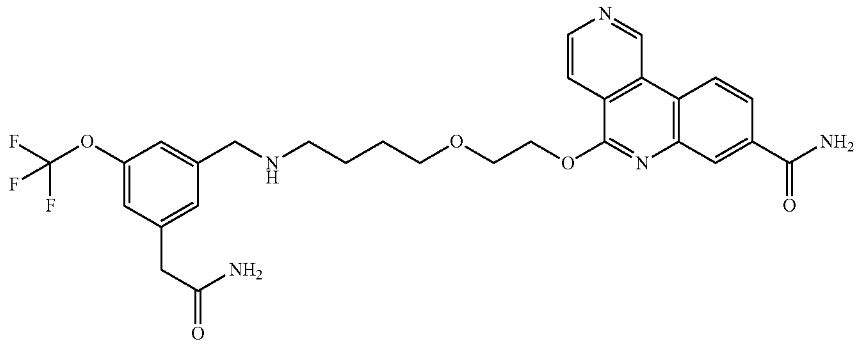 [SMILES: NC(=O)Cc1cc(CNCCCCOCCOc2nc3cc(C(N)=O)ccc3c3cnccc23)cc(OC(F)(F)F)c1]

To a mixture of Example 107 (130 mg, 229.05 μmol) and $K_2CO_3$ (15.83 mg, 114.53 μmol) in MeOH (2 mL) was added $H_2O_2$ (0.050 g, 440.99 μmol, 30% wt.) slowly at 20° C. The reaction mixture was stirred at 20° C. for 2 h. The reaction was quenched with sat. aq. $Na_2SO_3$ solution (1 mL) slowly and then the mixture was concentrated in vacuo. The crude product was purified (PM165) and re-purified (PM166) to afford Example 171 (16.06 mg, 25.21 μmol, 11.0% yield, FA salt) as an off-white gum.

LCMS (AM3): rt=0.758 min, (586.1 $[M+H]^+$), 99.1% purity.

$^1$H NMR (400 MHz, MeOH-$d_4$) δ: 10.05 (s, 1H), 8.87 (d, J=5.2 Hz, 1H), 8.80 (d, J=8.4 Hz, 1H), 8.49 (s, 1H), 8.43 (d, J=1.6 Hz, 1H), 8.24 (dd, J=5.6, 0.8 Hz, 1H), 8.07 (dd, J=8.8, 1.6 Hz, 1H), 7.34 (s, 1H), 7.27 (s, 2H), 4.85-4.84 (m, 2H), 4.10 (s, 2H), 4.00 (t, J=4.8 Hz, 2H), 3.68 (t, J=6.0 Hz, 2H), 3.58 (s, 2H), 3.04 (t, J=7.6 Hz, 2H), 1.86-1.77 (m, 2H), 1.76-1.67 (m, 2H) ppm.

Example 175

5-((2-(4-((3-((1H-pyrazol-4-yl)methyl)-5-(trifluoromethoxy)benzyl)amino)butoxy)ethyl)amino)benzo[c][2,6]naphthyridine-8-carboxamide

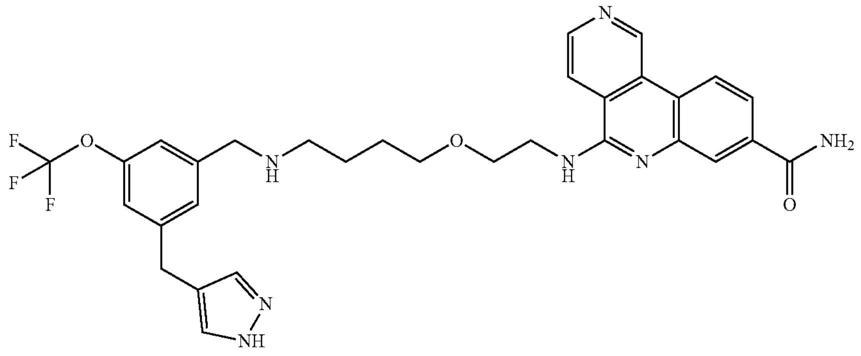 [SMILES: NC(=O)c1ccc2c(c1)nc(NCCOCCCCNCc1cc(Cc3cn[nH]c3)cc(OC(F)(F)F)c1)c1ccncc12]

To a solution of compound 1.828 (100 mg, 141.29 μmol) in DCM (2 mL) was added TFA (1.54 g, 13.51 mmol) at 20° C. The reaction mixture was stirred at 20° C. for 0.5 h. The mixture was concentrated in vacuo and purified (PM169) to afford Example 175 (73.97 mg, 113.16 μmol, 80.1% yield, FA salt) as a yellow solid.

LCMS (AM3): rt=0.748 min, (608.1 $[M+H]^+$), 98.9% purity.

$^1$H NMR (400 MHz, MeOH-$d_4$) δ: 9.92 (s, 1H), 8.77 (d, J=6.0 Hz, 1H), 8.59 (d, J=8.4 Hz, 1H), 8.35 (br s, 1H), 8.20 (d, J=2.0 Hz, 1H), 8.12 (d, J=5.6 Hz, 1H), 7.82 (dd, J=8.4, 1.6 Hz, 1H), 7.44 (s, 2H), 7.27 (s, 1H), 7.20 (d, J=2.4 Hz, 2H), 4.09 (s, 2H), 3.93-3.90 (m, 4H), 3.81 (t, J=5.2 Hz, 2H), 3.61 (t, J=6.0 Hz, 2H), 3.04 (t, J=7.8 Hz, 2H), 1.85-1.76 (m, 2H), 1.73-1.64 (m, 2H) ppm.

Example 177

5-(2-(4-((3-((1H-pyrazol-4-yl)methyl)-5-(trifluoromethoxy)benzyl)amino)butoxy)ethoxy)benzo[c][2,6]naphthyridine-8-carboxamide

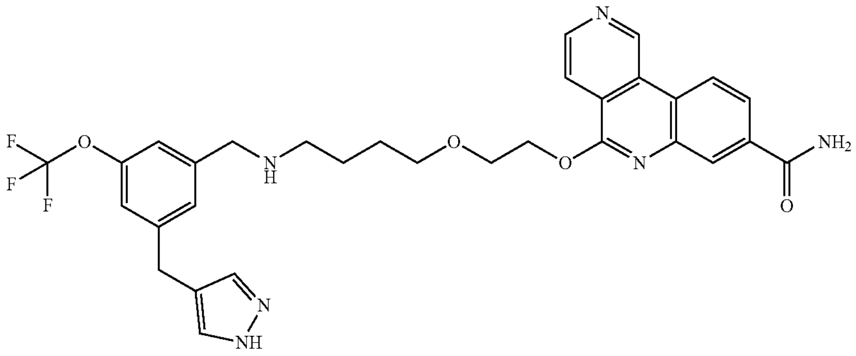 [SMILES: NC(=O)c1ccc2c(c1)nc(OCCOCCCCNCc1cc(Cc3cn[nH]c3)cc(OC(F)(F)F)c1)c1ccncc12]

To a solution of compound 1.829 (130 mg, 183.43 μmol) in MeOH (1.5 mL) was added $K_2CO_3$ (76.05 mg, 550.28 μmol) at 20° C. The reaction mixture was stirred at 20° C. for 1 h. The reaction mixture was filtered and the filtrate was concentrated in vacuo. The crude product was purified (PM166) to afford Example 177 (69.34 mg, 103.92 μmol, 56.7% yield, FA salt) as a white solid.

LCMS (AM3): rt=0.816 min, (609.3 $[M+H]^+$), 95.7% purity.

$^1$H NMR (400 MHz, MeOH-$d_4$) δ: 10.03 (s, 1H), 8.85 (d, J=5.6 Hz, 1H), 8.78 (d, J=8.4 Hz, 1H), 8.50 (s, 1H), 8.40 (d, J=1.6 Hz, 1H), 8.22 (d, J=5.6 Hz, 1H), 8.06 (dd, J=8.4, 2.0 Hz, 1H), 7.43 (s, 2H), 7.27 (s, 1H), 7.20 (s, 1H), 7.17 (s, 1H), 4.84-4.82 (m, 2H), 4.07 (s, 2H), 3.99 (t, J=4.8 Hz, 2H), 3.90 (s, 2H), 3.67 (t, J=6.0 Hz, 2H), 3.00 (t, J=7.6 Hz, 2H), 1.84-1.76 (m, 2H), 1.74-1.66 (m, 2H) ppm.

Example 179

(R)-5-((1-(4-((3,5-difluoro-4-(trifluoromethoxy)benzyl)amino)butoxy)propan-2-yl)oxy)benzo[c][2,6]naphthyridine-8-carboxylic acid

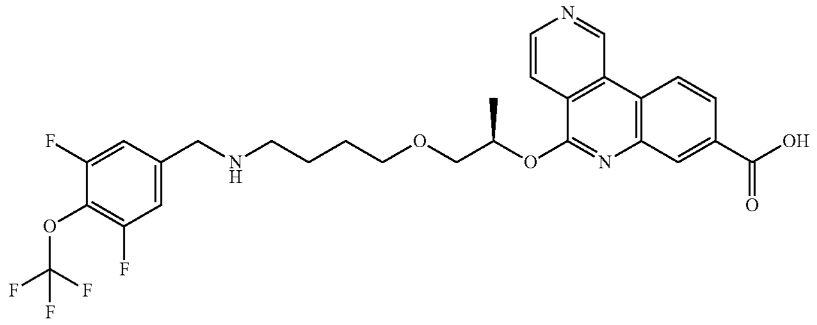 [SMILES: C[C@H](COCCCCNCc1cc(F)c(OC(F)(F)F)c(F)c1)Oc1nc2cc(C(=O)O)ccc2c2cnccc12]

A mixture of compound 1.507 (120 mg, 0.53 mmol), compound 1.832 (220 mg, 0.53 mmol, FA salt) and DIPEA (0.19 mL, 1.06 mmol) in MeOH (10 mL) was stirred at room temperature for 16 h, then sodium triacetoxyborohydride (450 mg, 2.12 mmol) was added. The reaction mixture was stirred at room temperature for 0.5 h. The reaction mixture was concentrated in vacuo and the residue was purified (PM173) to afford Example 179 (138.28 mg, 41.7% yield, FA salt) as a white solid.

LCMS (AM3): rt=0.861 min, (580.2 $[M+H]^+$), 100% purity.

$^1$H NMR (400 MHz, MeOH-$d_4$) δ: 9.91 (d, J=2.4 Hz, 1H), 8.77 (dd, J=5.6 Hz, 1.6 Hz, 1H), 8.59 (dd, J=8.4 Hz, 3.6 Hz, 1H), 8.45 (s, 1H), 8.37 (s, 1H), 8.12-8.07 (m, 2H), 7.31 (d, J=8.4 Hz, 2H), 5.89-5.81 (m, 1H), 4.07 (s, 2H), 3.85-3.81 (m, 1H), 3.74-3.68 (m, 2H), 3.62-3.56 (m, 1H), 2.96 (t, J=7.6 Hz, 2H), 1.82-1.73 (quin, 2H), 1.70-1.58 (m, 2H), 1.47 (d, J=6.4 Hz, 3H) ppm.

Example 180

(R)-5-((1-(4-((3-fluoro-4-(trifluoromethoxy)benzyl)amino)butoxy)propan-2-yl)oxy)benzo[c][2,6]naphthyridine-8-carboxylic acid

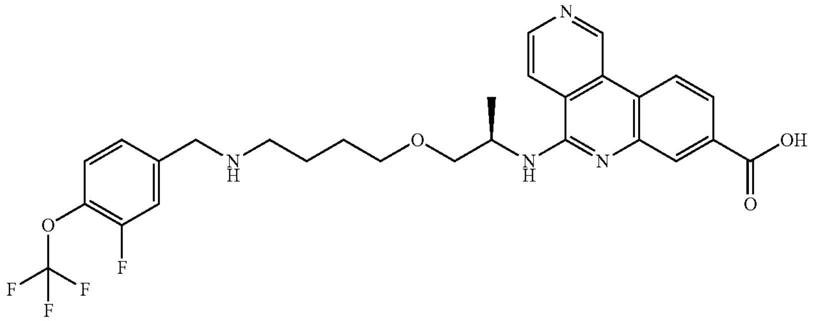 [SMILES: C[C@H](COCCCCNCc1ccc(OC(F)(F)F)c(F)c1)Nc1nc2cc(C(=O)O)ccc2c2cnccc12]

A mixture of 3-fluoro-4-(trifluoromethoxy)benzaldehyde (115 mg, 0.55 mmol), compound 1.832 (230 mg, 0.55 mmol, TFA salt) and DIPEA (0.19 mL, 1.11 mmol) in MeOH (10 mL) was stirred at room temperature for 16 h, then sodium triacetoxyborohydride (469 mg, 2.21 mmol) was added. The reaction mixture was stirred at room temperature for 0.5 h. The reaction mixture was concentrated in vacuo and the residue was purified (PM174) to afford Example 180 (150.91 mg, 44.9% yield, FA salt) as an off-white solid.

LCMS (AM3): rt=0.858 min, (562.2 $[M+H]^+$), 99.8% purity.

$^1H$ NMR (400 MHz, MeOH-$d_4$) δ: 9.89 (s, 1H), 8.76 (d, J=5.6 Hz, 1H), 8.56 (d, J=8.4 Hz, 1H), 8.47 (s, 1H), 8.35 (d, J=1.2 Hz, 1H), 8.09-8.06 (m, 2H), 7.48-7.43 (m, 2H), 7.33 (d, J=8.4 Hz, 1H), 5.87-5.80 (m, 1H), 4.10 (s, 2H), 3.84-3.80 (m, 1H), 3.74-3.66 (m, 2H), 3.61-3.55 (m, 1H), 3.00 (t, J=7.6 Hz, 2H), 1.83-1.76 (m, 2H), 1.70-1.56 (m, 2H), 1.46 (d, J=6.4 Hz, 3H) ppm.

Example 181

(R)-5-((1-(4-((3-fluoro-4-(trifluoromethoxy)benzyl)amino)butoxy)propan-2-yl)amino)benzo[c][2,6]naphthyridine-8-carboxylic acid

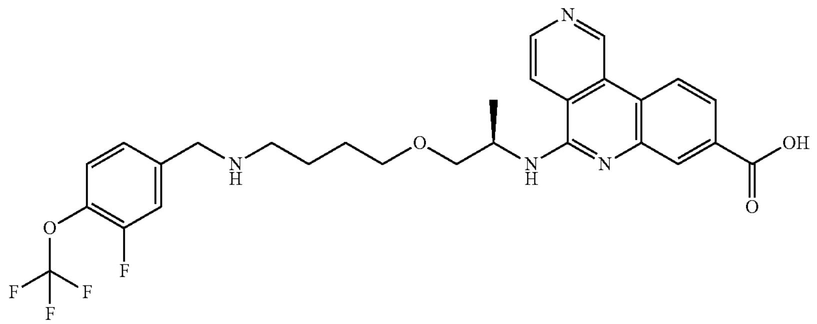 [SMILES: C[C@H](COCCCCNCc1ccc(OC(F)(F)F)c(F)c1)Nc1nc2cc(C(=O)O)ccc2c2cnccc12]

A mixture of compound 1.831 (130 mg, 0.21 mmol, FA salt) and lithium hydroxide monohydrate (53 mg, 1.26 mmol) in THF (4 mL) and $H_2O$ (1 mL) was stirred at room temperature for 16 h. The reaction mixture was concentrated in vacuo and the residue was purified (PM166) to afford Example 181 (89.54 mg, 70.5% yield, FA salt) as a yellow solid.

LCMS (AM3): rt=0.781 min, (561.5 $[M+H]^+$), 100% purity.

$^1H$ NMR (400 MHz, MeOH-$d_4$) δ: 9.90 (s, 1H), 8.74 (d, J=5.6 Hz, 1H), 8.53 (d, J=8.4 Hz, 1H), 8.43 (s, 1H), 8.26 (d, J=1.6 Hz, 1H), 8.18 (d, J=6.0 Hz, 1H), 7.92 (dd, J=8.4 Hz, 1.6 Hz, 1H), 7.48-7.42 (m, 2H), 7.32 (d, J=8.4 Hz, 1H), 4.86-4.85 (m, 1H), 4.08 (s, 2H), 3.78-3.71 (m, 2H), 3.63-3.56 (m, 1H), 3.53-3.47 (m, 1H), 3.01 (t, J=7.6 Hz, 2H), 1.85-1.76 (m, 2H), 1.70-1.61 (m, 2H), 1.37 (d, J=6.4 Hz, 3H) ppm.

Example 182

(R)-5-((1-(4-((3,5-difluoro-4-(trifluoromethoxy)benzyl)amino)butoxy)propan-2-yl)amino)benzo[c][2,6]naphthyridine-8-carboxylic acid

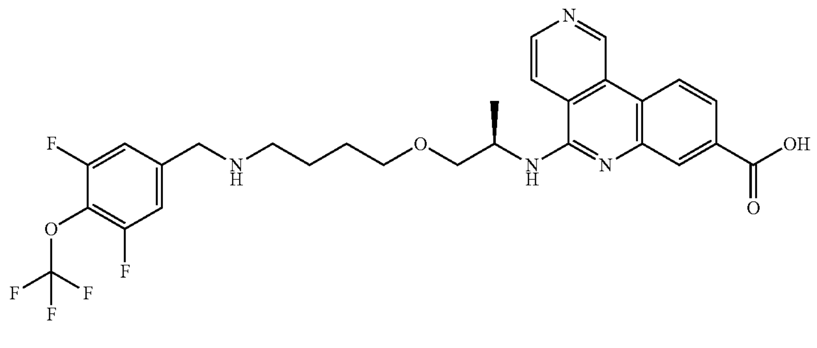 [SMILES: C[C@H](COCCCCNCc1cc(F)c(OC(F)(F)F)c(F)c1)Nc1nc2cc(C(=O)O)ccc2c2cnccc12]

To a solution of compound 1.830 (100 mg, 168.76 μmol) in THF (2 mL) and $H_2O$ (1.5 mL) was added $LiOH \cdot H_2O$ (35.41 mg, 843.80 μmol) at 20° C. The reaction mixture was stirred at 20° C. for 2 h. The reaction mixture was neutralized with formic acid to pH=6, then the mixture was concentrated in vacuo and the crude product was purified (PM172) to afford Example 182 (42.30 mg, 73.12 μmol, 43.3% yield) as a yellow solid.

LCMS (AM3): rt=0.792 min, (579.1 $[M+H]^+$), 100% purity.

$^1H$ NMR (400 MHz, DMSO-$d_6$): 10.03 (s, 1H), 8.85 (d, J=6.0 Hz, 1H), 8.66 (d, J=8.8 Hz, 1H), 8.35 (d, J=5.6 Hz, 1H), 8.12 (d, J=1.2 Hz, 1H), 7.82 (dd, J=8.4, 1.6 Hz, 1H), 7.52 (d, J=7.6 Hz, 1H), 7.30 (s, 1H), 7.28 (s, 1H), 4.74-4.67 (m, 1H), 3.66-3.62 (m, 3H), 3.47 (t, J=6.4 Hz, 2H), 3.44-3.39 (m, 1H), 2.42 (t, J=6.8 Hz, 2H), 1.56-1.49 (m, 2H), 1.49-1.41 (m, 2H), 1.30 (d, J=6.4 Hz, 3H) ppm.

Example 183

5-(2-(4-((3,5-Difluoro-4-(trifluoromethoxy)benzyl)amino)butoxy)ethoxy)benzo[c][2,6]naphthyridine-8-carboxamide

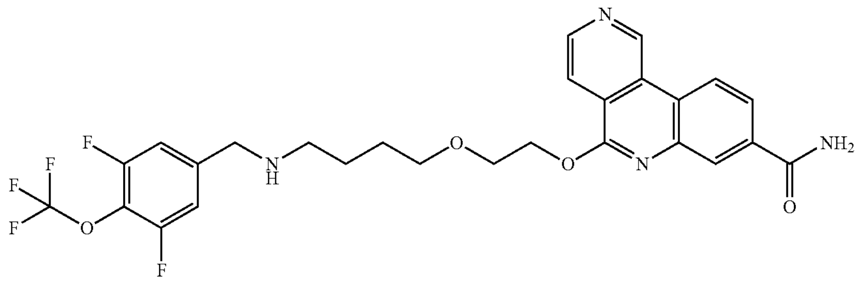 [SMILES: NC(=O)c1ccc2c(c1)nc(OCCOCCCCNCc1cc(F)c(OC(F)(F)F)c(F)c1)c1ccncc12]

To a solution of compound 1.840 (80.00 mg, 120.37 μmol) in DCM (1 mL) was added TFA (770.00 mg, 6.75 mmol) at 20° C. The resulting mixture was stirred at 20° C. for 2 h. The mixture was concentrated in vacuo to give a residue. The crude product was purified (PM158) to afford Example 183 (43.31 mg, 74.80 μmol, 62.2% yield) as white solid.

LCMS (AM3): rt=0.819 min, (565.2 $[M+H]^+$), 97.6% purity.

$^1H$ NMR (400 MHz, MeOH-$d_4$) δ: 10.04 (s, 1H), 8.87 (d, J=5.2 Hz, 1H), 8.79 (d, J=8.4 Hz, 1H), 8.40 (d, J=2.0 Hz, 1H), 8.23 (d, J=5.2 Hz, 1H), 8.08 (dd, J=8.4, 1.6 Hz, 1H), 7.33 (d, J=8.0 Hz, 2H), 4.87-4.85 (m, 2H), 4.17 (s, 2H), 4.02 (t, J=4.8 Hz, 2H), 3.71 (t, J=5.6 Hz, 2H), 3.09 (t, J=8.0 Hz, 2H), 1.88-1.81 (m, 2H), 1.77-1.71 (m, 2H) ppm.

BIOLOGICAL ASSAYS

Assay 1: Biochemical Assay for Inhibitors of CK2α Kinase Activity

The inhibitory activity of putative kinase inhibitors and the potency of selected compounds were determined using ADP-Glo™ assay. The kinase reaction was performed in the presence of excess peptide substrate and ATP at a concentration equivalent to $K_m$. Upon termination of the kinase reaction, remaining ATP was depleted leaving only ADP reaction product, which was converted back to ATP with a coupled luciferin/luciferase reaction. The luminescent output from the coupled reaction was quantified and correlated with the kinase activity.

CK2α (residues 2-329) was produced in *Escherichia coli* BL21 (DE3) for kinase activity screening. Single colonies of the cells were grown in 6×1 L of 2×TY with 100 μg/mL ampicillin at 37° C. Isopropyl thio-β-D-galactopyranoside (IPTG) was added to a final concentration of 0.4 mM to induce expression when the optical density at 600 nm reached 0.6. The cells were incubated overnight at 25° C. then harvested by centrifugation at 4,000 g for 20 minutes. The cell pellets were suspended in 20 mM Tris, 500 mM NaCl, pH 8.0 and lysed using a high pressure homogenizer. Protease inhibitor cocktail tablets (one tablet per 50 mL extract; Roche Diagnostics) and DNase I were then added. The crude cell extract was then centrifuged at 10,000 g for 45 minutes, the supernatant was filtered with a 0.22 μm filter. The soluble supernatant was applied on a Ni Sepharose Fast Flow6 column at pH 8.0, washed and eluted in 20 mM Tris pH 8.0, 500 mM NaCl, 200 mM imidazole. After overnight dialysis into 20 mM Tris, pH 8.0, 500 mM NaCl the N-terminal His6-tag was cleaved overnight by TEV protease and passed through a second metal affinity column to remove uncleaved protein and the protease. The cleaved protein was further purified on a Sepharose Q HP anion-exchange column and the main peak fraction from this column was further purified by gel filtration on a Superdex 75 16/60 HiPrep column equilibrated with Tris 20 mM, pH 8.0, 500 mM NaCl. Pure protein was concentrated to 15 mg/mL and flash frozen in liquid nitrogen.

Final assay conditions comprised 0.2 nM CK2α, 50 μM peptide substrate (RRRADDSDDDDD), 15 μM ATP in 1× reaction buffer (40 mM Tris pH7.5, 200 mM NaCl, 20 mM $MgCl_2$, 0.1 mg/mL BSA, 1% DMSO). The assay was conducted as follows:

1. Appropriate serial dilutions of test compound were prepared using Echo (Labcyte) and 50 nL of 100× compound in 100% DMSO transferred to the assay plate (white opaque OptiPlate-384, Perkin-Elmer).
2. Enzyme and peptide substrate were prepared in fresh reaction buffer and added to the assay plate in a total volume of 3 μl and incubated at room temperature for 15 minutes.
3. 2 μL of ATP solution freshly prepared in reaction buffer was added to start the reaction.
4. After 120 minutes, the reaction was stopped by addition of 5 μl ADP-Glo reagent (Promega V9102) and the plate incubated at room temperature for a further 60 minutes.
5. 10 μL of Kinase Detection reagent (Promega V9102) was added to assay plate and incubated for a further 30 minutes prior to reading luminescence on an Envision (Perkin-Elmer).

Data was analysed to calculate compound $IC_{50}$ and $K_i$ as follows:

1. All assay plates contained 32 wells designated as 0% inhibition control wells, which were treated with vehicle only (1% DMSO) and 32 wells designated as 100% inhibition control wells, which were treated with a high concentration of non-specific kinase inhibitor in 1% DMSO.
2. Percent inhibition in each test well was calculated using the formula ($MEAN_{0\%\ inhibition\ control\ wells}$−test well reading)/($MEAN_{0\%\ inhibition\ control\ wells}$−$MEAN_{100\%\ inhibition\ control\ wells}$)×100%.
3. $IC_{50}$ was determined using a standard 4-parameter fit method (Model 205, XL-fit).
4. Percent activity was calculated for each well using: (Test well reading—$MEAN_{100\%\ inhibition\ control\ wells}$)/($MEAN_{0\%\ inhlibiton\ control\ wells}$−$MEAN_{100\%\ inhlibiton\ control\ wells}$).
5. Morrison $K_i$ was determined using Morrison $K_i$ equation (XL-fit).

Assay 2: Biochemical Assay for Inhibitors of CLK2 Kinase Activity

The assay was conducted in the same way as described for CK2α, with final assay conditions comprising 20 nM CLK2 (Carna Biosciences-04-127), 50 μM peptide substrate (KRRRLASLR), 100 μM ATP in 1× reaction buffer (40 mM Tris pH7.5, 200 mM NaCl, 20 mM MgCl2, 0.1 mg/mL BSA, 1% DMSO).

Assay 3: Cell-Based NanoBRET™ Assay for Inhibitor Binding to Intracellular CK2α

This assay used the NanoBRET™ System (Promega), an energy transfer technique designed to measure molecular proximity in living cells. The assay measured the apparent affinity of test compounds by competitive displacement of a NanoBRET™ tracer reversibly bound to a NanoLucR luciferase CK2α fusion protein in cells. A fixed concentration of tracer was added to cells expressing the desired NanoLucR-CK2α fusion protein to generate a BRET reporter complex. Introduction of competing compounds resulted in a dose-dependent decrease in NanoBRET™ energy transfer, which allowed quantitation of the apparent intracellular affinity of the target protein for the test compound.

The assay was conducted as follows using HCT116 cell line (ATCC CCL-247™) transiently transfected with CSNK2A2-NanoLuc@ Fusion Vector (Promega NV1191):

1. Cells were resuspended to $2\times10^5$ cells/mL in Opti-MEM (Invitrogen 11058021).
2. DNA complex was prepared in a final volume of 1.4 ml Opti-MEM containing 15 μg DNA and 42 μl FuGENE HD Transfection reagent (Promega E2311).
3. 20 ml cell suspension was combined with 1 ml DNA complex, added to T75 flask and incubated overnight at 37° C. in 5% $CO_2$ incubator.
4. Appropriate serial dilutions of test compound were prepared and 5 μl/well transferred to the assay plate (white opaque CulturPlate-384, Perkin-Elmer) using Bravo (Agilent) with 5 μl NanoBRET Tracer K-5 (Promega N2501) diluted to the recommended concentration in assay buffer (Invitrogen 11058021) and 30 μl cell suspension. The plate was incubated for 2 hours at 37° C. in 5% $CO_2$ incubator.
5. 20 μl 3× complete substrate plus inhibitor solution (containing NanoBRET Nano-Glo substrate and extracellular NanoLuc inhibitor diluted to manufacturer's recommendations in assay medium) was added to each well.
6. Donor emission wavelength (450 nm) and acceptor emission wavelength (610 nm or 630 nm) were measured on the Envision (Perkin-Elmer) and BRET ratio calculated for data analysis: BRET Ratio=($Acceptor_{sample}$/$Donor_{sample}$)×1,000.
7. All assay plates contained 32 wells designated as 0% inhibition control wells, which were treated with vehicle only (1% DMSO) and 32 wells designated as 100% inhibition control wells, which were treated with a high concentration of non-specific kinase inhibitor in 1% DMSO. Percent inhibition in each test well was calculated using the formula ($MEAN_{0\%\ inhibition\ control\ wells}$−test well reading)/($MEAN_{0\%\ inhibition\ control\ wells}$−$MEAN_{100\%\ inhibition\ control\ wells}$)×100%.
8. $IC_{50}$ was determined using a standard 4-parameter fit method (Model 205, XL-fit).

Biological Data:

| Example No | Assay 1: CK2a Enzyme $IC_{50}$ (nM) | Assay 2: CLK2 Enzyme $IC_{50}$ (nM) | Assay 3: NanoBRET ™ $IC_{50}$ for binding to intracellular CK2α (nM) |
|---|---|---|---|
| 1 | 0.4249 | 1448 | 204 |
| 2 | 0.3062 | 943.3 | 35 |
| 3 | 0.2984 | 931.4 | 26 |
| 4 | 1.158 | 492.6 | 57 |
| 5 | 1.72 | 1785 | 136 |
| 6 | 0.378 | 725.8 | 70 |
| 7 | 0.5857 | 896.7 | 42 |
| 8 | 0.8619 | 565.6 | 72 |
| 9 | 0.5678 | 422.6 | 42 |
| 10 | 0.372 | 408.2 | 32 |
| 11 | 0.2438 | 748.6 | 37 |
| 12 | 0.4807 | 590.4 | 32 |
| 13 | 0.6347 | 476.3 | 183 |
| 14 | 9.929 | 1069 | 799 |
| 15 | 0.3817 | 451.2 | 32 |
| 16 | 0.8056 | 1356 | 215 |
| 17 | 2.939 | 792.5 | 139 |
| 18 | 1.007 | 743.7 | 83 |
| 19 | 6.25 | 1586 | 1490 |
| 20 | 0.2783 | 608.9 | 41 |
| 21 | 1.743 | 801.5 | 372 |
| 22 | 15.62 | 1241 | 5532 |
| 23 | 1.183 | 1319 | 229 |
| 24 | 10 | 1537 | 2174 |
| 25 | 0.3664 | 506.6 | 129 |
| 26 | 0.5535 | 687.5 | 19500 |
| 27 | 0.4588 | 562.3 | 5323 |
| 28 | 0.3459 | 366.1 | 47 |
| 29 | 7.203 | 1604 | 1155 |

-continued

| Example No | Assay 1: CK2a Enzyme $IC_{50}$ (nM) | Assay 2: CLK2 Enzyme $IC_{50}$ (nM) | Assay 3: NanoBRET ™ $IC_{50}$ for binding to intracellular CK2α (nM) |
|---|---|---|---|
| 30 | 0.5182 | 175.9 | 339 |
| 31 | 0.6764 | 356.7 | 6184 |
| 32 | 0.9202 | 776.1 | 38500 |
| 33 | 0.2208 | 364.7 | 101 |
| 34 | 0.2482 | 587.6 | 343 |
| 35 | 3.025 | 1983 | 399 |
| 36 | 0.8204 | 2898 | 712 |
| 37 | 0.436 | 358.3 | 26470 |
| 38 | 9.455 | 2094 | 995 |
| 39 | 0.197 | 311.6 | 255 |
| 40 | 0.4033 | 507.1 | 21 |
| 41 | 0.1446 | 408.7 | 489 |
| 42 | 0.2029 | 255.2 | 1093 |
| 43 | 5.706 | 305.3 | 1599 |
| 44 | 0.8334 | 451.1 | 34 |
| 45 | 0.76 | 383.4 | 80 |
| 46 | 0.4041 | 131.8 | 12 |
| 47 | 3.077 | 694.5 | 103 |
| 48 | 0.7044 | 796.1 | 53 |
| 49 | 7.873 | 622.2 | 174 |
| 50 | 1.309 | 1195 | 130 |
| 51 | 2.39 | 708.7 | 77 |
| 52 | 1.278 | 1392 | 264 |
| 53 | 1.164 | 637.7 | 136 |
| 54 | 0.6876 | 142.4 | 73 |
| 55 | 1.669 | 493.8 | 316 |
| 56 | 0.4267 | 826.6 | 25 |
| 57 | 0.665 | 748 | 51 |
| 58 | 0.6385 | 603.1 | 88 |
| 59 | 8.92 | 1554 | 654 |
| 60 | 2.543 | 503.5 | 180 |
| 61 | 0.8546 | 294.1 | 51 |
| 62 | 4.476 | 1072 | 795 |
| 63 | 4.835 | 1914 | 988 |
| 64 | 0.5868 | 2364 | 252 |
| 65 | 4.934 | 362 | 175 |
| 66 | 5.745 | 695.9 | 188 |
| 67 | 11.84 | 804.9 | 634 |
| 68 | 27.48 | 1953 | 3833 |
| 69 | 0.633 | 331.9 | 4881 |
| 70 | 0.517 | 211.5 | 1196 |
| 71 | 0.6912 | 227.8 | 1693 |
| 72 | 0.6553 | 260.7 | 862 |
| 73 | 0.713 | 482 | 2656 |
| 74 | 0.7866 | 119 | 1455 |
| 75 | 0.773 | 81.65 | 335 |
| 76 | 0.7778 | 58.47 | 99 |
| 77 | 0.67 | 125.3 | 140 |
| 78 | 0.7253 | 147.3 | 734 |
| 79 | 1.439 | 78.4 | 6092 |
| 80 | 1.666 | 536.3 | >10000 |
| 81 | 1.378 | 49.8 | 17690 |
| 82 | 2.106 | 61.32 | 1149 |
| 83 | 11.82 | 558.4 | 2789 |
| 84 | 0.6122 | 815.1 | 17 |
| 85 | 4.828 | 878.5 | 350 |
| 86 | 0.3606 | 153.1 | 18 |
| 87 | 2.499 | 1152 | 82 |
| 88 | 0.3593 | 324.8 | 31 |
| 89 | 0.4689 | 918.8 | 4 |
| 90 | 0.5731 | 46.88 | 682 |
| 91 | 2.066 | 1013 | 111 |
| 92 | 1.606 | 670.9 | 57 |
| 93 | 0.3539 | 161.4 | 14 |
| 94 | 7.051 | 743.7 | 711 |
| 95 | 0.4176 | 169.8 | 323 |
| 96 | 2.931 | 508.8 | 179 |
| 97 | 1.137 | 518 | 61 |
| 98 | 22.29 | 989.9 | 2500 |
| 99 | 14.71 | 311.3 | 4331 |
| 100 | 1.074 | 394 | 16170 |
| 101 | 0.2578 | 201.2 | 368 |
| 102 | 0.3244 | 69.55 | 4547 |

-continued

| Example No | Assay 1: CK2a Enzyme $IC_{50}$ (nM) | Assay 2: CLK2 Enzyme $IC_{50}$ (nM) | Assay 3: NanoBRET ™ $IC_{50}$ for binding to intracellular CK2α (nM) |
|---|---|---|---|
| 103 | 0.4534 | 232.5 | 3137 |
| 104 | 13.27 | 185.9 | 1115 |
| 105 | 0.4756 | 302.6 | 59 |
| 106 | 0.2626 | 340.3 | 26 |
| 107 | 0.4369 | 2653 | 6 |
| 108 | 0.3036 | 513.3 | 302 |
| 109 | 0.4756 | 718.3 | 373 |
| 110 | 6.214 | 1348 | >50000 |
| 111 | 0.3538 | 201.7 | 71 |
| 112 | 0.4107 | 171.8 | 8 |
| 113 | 0.4089 | 123.8 | 6 |
| 114 | 0.3419 | 82.35 | 9 |
| 115 | 0.2477 | 87.98 | 10 |
| 116 | 0.3181 | 326.6 | 6 |
| 117 | 0.3655 | 284.3 | 9 |
| 118 | 0.747 | 187.7 | 87 |
| 119 | 0.516 | 291.9 | 46 |
| 120 | 0.4926 | 28.58 | 40 |
| 121 | 0.505 | 71.42 | 58 |
| 122 | 1.262 | 3850 | 1245 |
| 123 | 71.65 | 1006 | 166 |
| 124 | 75.33 | 173.9 | 6068 |
| 125 | 189.4 | 273 | 8824 |
| 126 | 88.34 | 844.7 | 6727 |
| 127 | 43.01 | 345.9 | 5565 |
| 128 | 61.01 | 324.3 | 2919 |
| 129 | 0.3328 | 113.8 | 96 |
| 130 | 1.399 | 484.9 | 158 |
| 131 | 0.4319 | 288.4 | 15 |
| 132 | 0.3702 | 190.4 | 15 |
| 133 | 0.403 | 282.6 | 164 |
| 134 | 0.5324 | 85.98 | 8 |
| 135 | 0.9302 | 812.5 | 50 |
| 136 | 0.7361 | 1674 | 57 |
| 137 | 1.97 | 1105 | 673 |
| 138 | 0.6573 | 768 | 50 |
| 139 | 0.6001 | 629.7 | 33 |
| 140 | 0.3487 | 1356 | 18 |
| 141 | 3.443 | 809 | 274 |
| 142 | 0.4573 | 948.7 | 479 |
| 143 | 0.8568 | 49.01 | 50 |
| 144 | 0.7964 | 76.53 | 126 |
| 145 | 1.039 | 146 | 319 |
| 146 | 0.9338 | 102.4 | 3167 |
| 147 | 0.6963 | 24.14 | 77 |
| 148 | 0.559 | 550.5 | 39 |
| 149 | 0.4945 | 113.9 | 4 |
| 150 | 0.8103 | 1460 | 27 |
| 151 | 0.9836 | 1725 | 12 |
| 152 | 0.5555 | 400.4 | 55 |
| 153 | 4.204 | 629.8 | 418 |
| 154 | 0.7486 | 488.8 | 26 |
| 155 | 17.81 | 2890 | 2702 |
| 156 | 0.8404 | 1392 | 22 |
| 157 | 0.553 | 3848 | 18 |
| 158 | 0.5929 | 2454 | 15 |
| 159 | 0.2166 | 1881 | 9 |
| 160 | 1.034 | 720.6 | 66 |
| 161 | 0.6615 | 2978 | 14 |
| 162 | 0.6015 | 1999 | 22 |
| 163 | 0.5238 | 1618 | 54 |
| 164 | 1.055 | 1858 | 26 |
| 165 | 0.3902 | 1294 | 17 |
| 166 | 0.4852 | 124.4 | 12 |
| 167 | 0.8467 | 1534 | 131 |
| 168 | 0.4794 | 1175 | 42 |
| 169 | 1.13 | 1497 | 41 |
| 170 | 0.5495 | 1081 | 165 |
| 171 | 1.17 | 1818 | 108 |
| 172 | 0.265 | 1156 | 47 |
| 173 | 0.223 | 2054 | 19 |
| 174 | 0.5733 | 992.3 | 39 |
| 175 | 0.2014 | 850.3 | 16 |

-continued

| Example No | Assay 1: CK2a Enzyme $IC_{50}$ (nM) | Assay 2: CLK2 Enzyme $IC_{50}$ (nM) | Assay 3: NanoBRET ™ $IC_{50}$ for binding to intracellular CK2α (nM) |
|---|---|---|---|
| 176 | 0.4917 | 3591 | 116 |
| 177 | 0.5928 | 1731 | 51 |
| 178 | 0.2361 | 244.8 | 30 |
| 179 | 0.4939 | 558.3 | 31 |
| 180 | 0.1801 | 611.7 | 48 |
| 181 | 0.4278 | 383.6 | 78 |
| 182 | 0.5692 | 353.1 | 28 |
| 183 | 1.765 | 2613 | 133 |

REFERENCES

Battistutta & Lolli (2011). Structural and functional determinants of protein kinase CK2α: facts and open questions. Mol. Cell. Biochem., 2011, 356, 67-73.

Niefind et al (2001). Crystal structure of human protein kinase CK2: insights into basic properties of the CK2 holoenzyme. EMBO J. 2001, 20, 5320-5331.

Meggio & Pinna (2003). One-thousand-and-one substrates of protein kinas CK2. The FASEB Journal 17, 349-368.

Behan et al (2019). Prioritizaion of cancer therapeutic targets using CRISPR-Cas9 screens. Nature 568, 511-516.

Lin et al (2011). Overexpression of Nuclear Protein Kinase CK2α z Catalytic Subunit (CK2α) as a Poor Prognosticator in Human Colorectal Cancer. PLoS ONE 6, 17193-

Ortega et al (2014). Mining CK2 in cancer. PLoS ONE 9, 115609-

Di Maira et al. (2019). The protein kinase CK2 contributes to the malignant phenotype of cholangiocarcinoma cells. Oncogenesis 8, 61-Zhan et al (2017). Wnt signaling in cancer. Oncogene 36, 1461-1473.

Gao & Wang (2006). Casein Kinase 2 is activated and essential for Wnt/β-Catenin signaling. Journal of Biological Chemistry 281, 189394-18400.

Dowling et al (2016). Potent and selective CK2 Kinase Inhibitors with effects on Wnt pathway signaling in vivo. ACS Med. Chem. Lett. 7, 300-305.

Brear et al. (2016). Specific inhibition of CK2α from an anchor outside the active site. Chem. Sci. 7, 6839-6845.

Ruzzene & Pinna (2010). Addiction to protein kinase CK2: A common denominator of diverse cancer cells? Biochimica et Biophysica Acta 1804, 499-504.

Montenarh (2016). Protein Kinase CK2 in DNA Damage and repair. Transl. Cancer Res. 5, 49-63.

Gordon, D. E., Jang, G. M., Bouhaddou, M. et al. (2020). A SARS-CoV-2 protein interaction map reveals targets for drug repurposing. *Nature* 583, 459-468.

Zakharia et al. (2019). Pre-clinical in vitro and in vivo evidence of an antitumour effect of CX-4945, a casein kinase 11 inhibitor, in cholangiocarcinoma. Translational Oncology 12, 143-153.

The invention claimed is:

1. A compound of formula I, or a salt thereof:

I

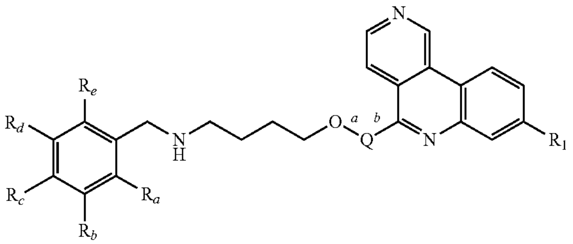

wherein:

$R_1$ is selected from —C(O)OH or —C(O)NH$_2$;

Q is selected from formula Ia or Ib:

Ia

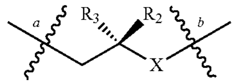

Ib

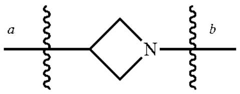

wherein:

bond a in formulae Ia and Ib corresponds with bond a in formula I and bond b in formulae Ia and Ib corresponds with bond b in formula I;

$R_2$ and $R_3$ are each independently selected from hydrogen or methyl; and

X is NH or O;

$R_a$ and $R_e$ are both independently selected from hydrogen, methyl or halo;

$R_b$ and $R_d$ are each independently selected from hydrogen, halo, cyano, (1-4C)alkyl, —$[CH_2]_{0-3}$-(1-4C)alkoxy,

—$[CH_2]_{0-3}$—C(O)NH$_2$,

—$[CH_2]_{0-3}$—C(O)NH(1-4C)alkyl,

—$[CH_2]_{0-3}$—C(O)N[(1-4C)alkyl]$_2$,

—$[CH_2]_{0-3}$—NH(1-4C)alkyl,

—$[CH_2]_{0-3}$—N[(1-4C)alkyl]$_2$,

—$[CH_2]_{0-3}$—S(O)$_q$-(1-4C)alkyl (wherein q is 0, 1 or 2),

—$[CH_2]_{0-3}$—C(O)(1-4C)alkyl,

—$[CH_2]_{0-3}$—C(O)O-(1-4C)alkyl,

—$[CH_2]_{0-3}$—N($R_f$)C(O)-(1-4C)alkyl (wherein $R_f$ is hydrogen or methyl),

—$[CH_2]_{0-3}$—S(O)$_2$NH(1-4C)alkyl,

—$[CH_2]_{0-3}$—S(O)$_2$N[(1-4C)alkyl]$_2$,

—$[CH_2]_{0-3}$—N($R_g$)SO$_2$-(1-4C)alkyl (wherein $R_g$ is hydrogen or methyl), a group of the formula:

$$—Y_1—[CH_2]_{0-3}—Z_1$$

wherein $Y_1$ is absent, —O—, —NH—, —NMe-, —S—, —S(O)— or —S(O)$_2$—; and $Z_1$ is (3-6C)cycloalkyl, phenyl, a 4- to 6-membered heterocyclyl or 5 or 6-membered heteroaryl;

and wherein:

any alkyl, alkoxy or any alkyl moiety within a $R_b$ and $R_d$ substituent group is optionally substituted by one or more substituents selected from halo, hydroxy, cyano, amino, —C(O)OH, —C(O)$NH_2$, (1-2C)alkoxy, or (3-4C)cycloalkoxy; and $Z_1$ is optionally substituted by one or more substituents selected from: halo, hydroxy, cyano, amino, —C(O)OH, —C(O)$NH_2$, (1-2C)alkoxy, (1-2C)alkyl, (3-4C)cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C)alkyl, —N($R_f$)C(O)-(1-2C)alkyl, —S(O)$_2$NH(1-2C)alkyl, —S(O)$_2$N[(1-2C)alkyl]$_2$, or —NHSO$_2$-(1-2C)alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl;

$R_c$ is selected from hydrogen, halo, cyano, —C(O)$NH_2$, (1-4C)alkyl,

—[$CH_2$]$_{0-3}$-(1-4C)alkoxy,
—[$CH_2$]$_{0-3}$-(3-6C)cycloalkoxy,
—[$CH_2$]$_{0-3}$—C(O)$NH_2$,
—[$CH_2$]$_{0-3}$—C(O)NH(1-4C)alkyl,
—[$CH_2$]$_{0-3}$—C(O)N[(1-4C)alkyl]$_2$,
—[$CH_2$]$_{0-3}$—NH(1-4C)alkyl,
—[$CH_2$]$_{0-3}$—N[(1-4C)alkyl]$_2$,
—[$CH_2$]$_{0-3}$—S(O)$_q$-(1-4C)alkyl (wherein q is 0, 1 or 2),
—[$CH_2$]$_{0-3}$—C(O)(1-4C)alkyl,
—[$CH_2$]$_{0-3}$—C(O)O-(1-4C)alkyl,
—[$CH_2$]$_{0-3}$—N($R_h$)C(O)-(1-4C)alkyl (wherein $R_h$ is hydrogen or methyl),
—[$CH_2$]$_{0-3}$—S(O)$_2$NH(1-4C)alkyl,
—[$CH_2$]$_{0-3}$—S(O)$_2$N[(1-4C)alkyl]$_2$,
—[$CH_2$]$_{0-3}$—N($R_i$)SO$_2$-(1-4C)alkyl (wherein $R_i$ is hydrogen or methyl), a group of the formula:

—$Y_2$—[$CH_2$]$_{0-3}$—$Z_2$ wherein $Y_2$ is absent, —O—, —NH—, —NMe-, —S—, —S(O)— or —S(O)$_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —C(O)$NH_2$, (1-2C)alkoxy, or (3-4C)cycloalkoxy; and $Z_2$ is optionally substituted by one or more substituents selected from: halo, hydroxy, cyano, amino, —C(O)OH, —C(O)$NH_2$, (1-2C)alkoxy, (1-2C)alkyl, (3-4C)cycloalkyl, (3-4C)cycloalkoxy, —C(O)NH(1-2C)alkyl, —C(O)N[(1-2C)alkyl]$_2$, —NH(1-2C)alkyl, —N[(1-2C)alkyl]$_2$, —S(O)$_q$-(1-2C)alkyl (wherein q is 0, 1 or 2), —C(O)(1-2C)alkyl, —C(O)O-(1-2C)alkyl, —N($R_f$)C(O)-(1-2C)alkyl, —S(O)$_2$NH(1-2C)alkyl, —S(O)$_2$N[(1-2C)alkyl]$_2$, or —NHSO$_2$-(1-2C)alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl.

2. A compound according to claim 1, or a salt thereof, wherein $R_1$ is —C(O)OH.

3. A compound according to claim 1, or a salt thereof, wherein $R_1$ is —C(O)$NH_2$.

4. A compound according to claim 1, or a salt thereof, wherein Q is selected from formula Ia or Ib:

Ia

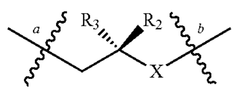

Ib

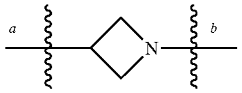

wherein:

bond a in formulae Ia and Ib corresponds with bond a in formula I and bond b in formulae Ia and Ib corresponds with bond b in formula I;

$R_2$ and $R_3$ are both hydrogen or one of $R_2$ and $R_3$ is hydrogen and the other is methyl;

X is O or NH.

5. A compound according to claim 1, or a salt thereof, wherein $R_a$ and $R_e$ are each independently selected from hydrogen, methyl, fluoro, chloro or bromo.

6. A compound according to claim 1, or a salt thereof, wherein one of $R_a$ and $R_e$ is hydrogen and the other is hydrogen or chloro.

7. A compound according to claim 1, or a salt thereof, wherein $R_b$ and $R_d$ are each independently selected from hydrogen, halo, cyano, (1-4C)alkyl, —[$CH_2$]$_{0-1}$-(1-4C)alkoxy,
—[$CH_2$]$_{0-1}$—C(O)$NH_2$,
—[$CH_2$]$_{0-1}$—C(O)NH(1-4C)alkyl,
—[$CH_2$]$_{0-1}$—C(O)N[(1-4C)alkyl]$_2$,
—[$CH_2$]$_{0-1}$—NH(1-4C)alkyl,
—[$CH_2$]$_{0-1}$—N[(1-4C)alkyl]$_2$,
—[$CH_2$]$_{0-1}$—S(O)$_q$-(1-4C)alkyl (wherein q is 0, 1 or 2),
—[$CH_2$]$_{0-1}$—C(O)(1-4C)alkyl,
—[$CH_2$]$_{0-1}$—C(O)O-(1-4C)alkyl,
—[$CH_2$]$_{0-1}$—NHC(O)-(1-4C)alkyl,
—[$CH_2$]$_{0-1}$—S(O)$_2$NH(1-4C)alkyl,
—[$CH_2$]$_{0-1}$—S(O)$_2$N[(1-4C)alkyl]2,
—[$CH_2$]$_{0-1}$—NHSO$_2$-(1-4C)alkyl, a group of the formula:

—$Y_1$—[$CH_2$]$_{0-1}$—$Z_1$ wherein $Y_1$ is absent, —O—, —NH—, —NMe-, —S—, —S(O)— or —S(O)$_2$—; and $Z_1$ is (3-6C)cycloalkyl, phenyl, a 4- to 6-membered heterocyclyl or 5 or 6-membered heteroaryl;

and wherein:

any alkyl, alkoxy or any alkyl moiety within a $R_b$ and $R_d$ substituent group is optionally substituted by one or more substituents selected from halo, hydroxy, cyano, amino, —C(O)OH, —C(O)$NH_2$, (1-2C)alkoxy, or (3-4C)cycloalkoxy; and $Z_1$ is optionally substituted by one or more substituents selected from: halo, hydroxy, cyano, amino, —C(O)OH, —C(O)$NH_2$, (1-2C)alkoxy, (1-2C)alkyl, (3-4C)cycloalkyl, (3-4C)cycloalkoxy, —C(O)NH(1-2C)alkyl, —$C(O)N[(1\text{-}2C)alkyl]_2$, —NH(1-2C)alkyl, —$N[(1\text{-}2C)alkyl]_2$, —$S(O)_q$-(1-2C)alkyl (wherein q is 0, 1 or 2), —C(O)(1-2C)alkyl, —C(O)O-(1-2C)alkyl, —$N(R_f)$C(O)-(1-2C)alkyl, —$S(O)_2NH$(1-2C)alkyl, —$S(O)_2N$[(1-2C)alkyl]2, or —$NHSO_2$-(1-2C)alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl, (1-2C)alkoxy or (1-2C)alkoxy-(1-2C)alkyl.

8. A compound according to claim 1, or a salt thereof, wherein $R_b$ and $R_d$ are each independently selected from hydrogen, halo, cyano, (1-4C)alkyl, halo(1-4C)alkyl, hydroxy(1-4C)alkyl, cyano(1-4C)alkyl, amino(1-4C)alkyl, (1-2C)alkoxy(1-4C)alkyl, (1-4C)alkoxy, halo(1-4C)alkoxy, hydroxy(1-4C)alkoxy, —$[CH_2]_{0\text{-}3}$—$C(O)NH_2$, or a group of the formula:

$$[CH_2]_{0\text{-}1}—Z_1$$

wherein $Z_1$ is (3-6C)cycloalkyl or a 5-membered heteroaryl;

and wherein $Z_1$ is optionally substituted by one or more cyano.

9. A compound according to claim 1, or a salt thereof, wherein $R_b$ and $R_d$ are each independently selected from hydrogen, fluoro, chloro, bromo, cyano, methyl, ethyl, methoxy, ethoxy, —$CH_2OH$, —$CH_2OCH_3$, —$CH_2NH_2$, —$CH_2CN$, —$CH_2CH_2OH$, —$CF_3$, —$OCF_3$, —O—$CH_2CH_2OH$, —O—$CH_2CF_3$, —$C(O)NH_2$, —$CH_2$—$C(O)NH_2$, —$CH(CH_3)CN$, —$C(CH_3)_2CN$, cyclopropyl, 1-cyanocyclopropyl, cyclopropylmethyl, furanylmethyl (e.g. furan-3-ylmethyl), imidazolylmethyl (e.g. imidazo-1-ylmethyl), pyrazolylmethyl (e.g. pyrazol-4-ylmethyl), oxazolylmethyl (e.g. oxazo-4-ylmethyl).

10. A compound according to claim 1, or a salt thereof, wherein one of $R_b$ and $R_d$ is hydrogen or halogen or —$OCF_3$ and the other is selected from hydrogen, fluoro, chloro, bromo, cyano, methyl, ethyl, methoxy, ethoxy, —$CH_2OH$, —$CH_2OCH_3$, —$CH_2NH_2$, —$CH_2CN$, —$CH_2CH_2OH$, —$CF_3$, —$OCF_3$, —O—$CH_2CH_2OH$, —O—$CH_2CF_3$, —$C(O)NH_2$, —$CH_2$—$C(O)NH_2$, —$CH(CH_3)CN$, —$C(CH_3)_2CN$, cyclopropyl, 1-cyanocyclopropyl, cyclopropylmethyl, furanylmethyl (e.g. furan-3-ylmethyl), imidazolylmethyl (e.g. imidazo-1-ylmethyl), pyrazolylmethyl (e.g. pyrazol-4-ylmethyl), oxazolylmethyl (e.g. oxazo-4-ylmethyl).

11. A compound according to claim 1, or a salt thereof, wherein one of $R_b$ and $R_d$ is hydrogen or halogen or —$OCF_3$ and the other is selected from hydrogen, fluoro, chloro, bromo, methyl, —$OCF_3$ or cyclopropyl.

12. A compound according to claim 1, or a salt thereof, wherein $R_c$ is selected from hydrogen, halo, cyano, —$C(O)NH_2$, (1-4C)alkyl, —$[CH_2]_{0\text{-}1}$-(1-4C)alkoxy,
—$[CH_2]_{0\text{-}1}$-(3-6C)cycloalkoxy,
—$[CH_2]_{0\text{-}1}$—$C(O)NH_2$,
—$[CH_2]_{0\text{-}1}$—C(O)NH(1-4C)alkyl,
—$[CH_2]_{0\text{-}1}$—$C(O)N[(1\text{-}4C)alkyl]_2$,
—$[CH_2]_{0\text{-}1}$—NH(1-4C)alkyl,
—$[CH_2]_{0\text{-}1}$—$N[(1\text{-}4C)alkyl]_2$,
—$[CH_2]_{0\text{-}1}$—$S(O)_q$-(1-4C)alkyl (wherein q is 0, 1 or 2),
—$[CH_2]_{0\text{-}1}$—C(O)(1-4C)alkyl,
—$[CH_2]_{0\text{-}1}$—C(O)O-(1-4C)alkyl,
—$[CH_2]_{0\text{-}1}$—N(H)C(O)-(1-4C)alkyl,
—$[CH_2]_{0\text{-}1}$—$S(O)_2NH$(1-4C)alkyl,
—$[CH_2]_{0\text{-}1}$—$S(O)_2N[(1\text{-}4C)alkyl]_2$,
—$[CH_2]_{0\text{-}1}$—$N(H)SO_2$-(1-4C)alkyl, a group of the formula:

$$—Y_2—[CH_2]_{0\text{-}1}—Z_2$$

wherein $Y_2$ is absent, —O—, —NH—, —NMe-, —S—, —S(O)— or —$S(O)_2$—; and $Z_2$ is (3-6C)cycloalkyl, phenyl, a 4- to 6-membered heterocyclyl or 5 or 6-membered heteroaryl;

and wherein:

any alkyl, alkoxy or any alkyl moiety within a $R_c$ substituent group is optionally substituted by one or more substituents selected from halo, hydroxy, cyano, amino, —C(O)OH, —$C(O)NH_2$, (1-2C)alkoxy, or (3-4C)cycloalkoxy; and $Z_2$ is optionally substituted by one or more substituents selected from: halo, hydroxy, cyano, amino, —C(O)OH, —$C(O)NH_2$, (1-2C)alkoxy, (1-2C)alkyl, (3-4C)cycloalkyl, (3-4C)cycloalkoxy, —C(O)NH(1-2C)alkyl, —$C(O)N[(1\text{-}2C)alkyl]_2$, —NH(1-2C)alkyl, —$N[(1\text{-}2C)alkyl]_2$, —$S(O)_q$-(1-2C)alkyl (wherein q is 0, 1 or 2), —C(O)(1-2C)alkyl, —C(O)O-(1-2C)alkyl, —$N(R_f)$C(O)-(1-2C)alkyl, —$S(O)_2NH$(1-2C)alkyl, —$S(O)_2N[(1\text{-}2C)alkyl]_2$, or —$NHSO_2$-(1-2C)alkyl, and wherein any (1-2C)alkoxy, (1-2C)alkyl, (3-4C)cycloalkyl or (3-4C)cycloalkoxy group is optionally substituted by one or more substituents selected from halo, cyano, hydroxy, (1-2C)alkyl or (1-2C)alkoxy.

13. A compound according to claim 1, or a salt thereof, wherein $R_c$ is selected from hydrogen, halo, cyano, (1-4C)alkyl, (1-4C)alkoxy, a group of the formula:

$$—Y_2—[CH_2]_{0\text{-}1}—Z_2$$

wherein $Y_2$ is absent or —O—; and $Z_2$ is (3-6C)cycloalkyl or phenyl;

and wherein:

any alkyl or alkoxy substituent group is optionally substituted by one or more substituents selected from halo or cyano; and $Z_2$ is optionally substituted by one or more (1-2C)alkyl substituents, and wherein a (1-2C)alkyl group is optionally substituted by one or more hydroxy substituents.

14. A compound according to claim 1, or a salt thereof, wherein $R_c$ is selected from hydrogen, fluoro, chloro, bromo, cyano, methyl, ethyl, methoxy, ethoxy, —O—$CH(CH_3)_2$, —$CH_2CN$, —$CF_3$, —$OCF_3$, —O—$CH_2CF_3$, cyclopropyl, cyclopropoxy, cyclobutoxy, cyclopentoxy, phenyl or 2-hydroxymethylphenyl.

15. A compound according to claim 1, or a salt, hydrate or solvate thereof, wherein $R_c$ is selected from hydrogen, chloro or —$OCF_3$.

16. A compound according to claim 1, or a salt thereof, wherein either:

(i) at least one of $R_a$, $R_b$, $R_c$, $R_d$ or $R_e$ is a non-hydrogen substituent;

(ii) one to four of $R_a$, $R_b$, $R_c$, $R_d$ or $R_e$ is/are a non-hydrogen substituent(s);

(iii) one to three of $R_a$, $R_b$, $R_c$, $R_d$ or $R_e$ is/are a non-hydrogen substituent(s); or (iv) two to four of $R_a$, $R_b$, $R_c$, $R_d$ or $R_e$ are hydrogen and the remainder are non-hydrogen substituents.

17. A compound according to claim 1, or a salt thereof, wherein if $R_c$ is a group of the formula —$Y_2$—$[CH_2]_{0\text{-}3}$—$Z_2$ then $R_b$ and $R_d$ cannot be a group of the formula —$Y_1$—$[CH_2]_{0\text{-}3}$—$Z_1$; and if one of $R_b$ and $R_d$ is a group of the formula —$Y_1$—$[CH_2]_{0\text{-}3}$—$Z_1$ as defined herein, then the other cannot be a group of the formula —$Y_1$—$[CH_2]_{0-3}$—$Z_1$ and $R_c$ cannot be a group of the formula —$Y_2$—$[CH_2]_{0-3}$—$Z_2$.

18. A compound according to claim 1, or a salt thereof, wherein the compound is selected from any one of the following:

5-((2-(4-(((2-chloro-[1,1'-biphenyl]-4-yl)methyl)amino)butoxy)ethyl)amino)benzo[c][2,6]naphthyridine-8-carboxamide;

5-((2-(4-((3-chloro-4-(trifluoromethoxy)benzyl)amino)butoxy)ethyl)amino)benzo[c][2,6]naphthyridine-8-carboxamide;

5-((2-(4-((3-chlorobenzyl)amino)butoxy)ethyl)amino)benzo[c][2,6]naphthyridine-8-carboxamide;

5-((2-(4-(((2-chloro-2'-(hydroxymethyl)-[1,1'-biphenyl]-4-yl)methyl)amino)butoxy)ethyl)amino)benzo[c][2,6]naphthyridine-8-carboxamide;

5-((2-(4-((3-fluoro-4-(trifluoromethoxy)benzyl)amino)butoxy)ethyl)amino)benzo[c][2,6]naphthyridine-8-carboxamide;

5-((2-(4-((3-chloro-4-(trifluoromethyl)benzyl)amino)butoxy)ethyl)amino)benzo[c][2,6]naphthyridine-8-carboxamide;

5-((2-(4-((3-chloro-4-cyclopropylbenzyl)amino)butoxy)ethyl)amino)benzo[c][2,6]naphthyridine-8-carboxamide;

5-((2-(4-((3-chloro-4-cyclobutoxybenzyl)amino)butoxy)ethyl)amino)benzo[c][2,6]naphthyridine-8-carboxamide;

5-((2-(4-((3-chloro-4-(cyclopentyloxy)benzyl)amino)butoxy)ethyl)amino)benzo[c][2,6]naphthyridine-8-carboxamide;

5-((2-(4-((3-chloro-4-cyclopropoxybenzyl)amino)butoxy)ethyl)amino)benzo[c][2,6]naphthyridine-8-carboxamide;

5-((2-(4-((3-(2-hydroxyethyl)benzyl)amino)butoxy)ethyl)amino)benzo[c][2,6]naphthyridine-8-carboxamide;

5-((2-(4-((3-chloro-4-(trifluoromethoxy)benzyl)amino)butoxy)ethyl)amino)benzo[c][2,6]naphthyridine-8-carboxylic acid;

5-(2-(4-((3-chloro-4-(trifluoromethoxy)benzyl)amino)butoxy)ethoxy)benzo[c][2,6]naphthyridine-8-carboxamide;

5-(2-(4-((3-chlorobenzyl)amino)butoxy)ethoxy)benzo[c][2,6]naphthyridine-8-carboxamide;

5-((2-(4-((3-(2-hydroxyethoxy)benzyl)amino)butoxy)ethyl)amino)benzo[c][2,6]naphthyridine-8-carboxamide;

5-((2-(4-((3-cyano-4-cyclopropylbenzyl)amino)butoxy)ethyl)amino)benzo[c][2,6]naphthyridine-8-carboxamide;

5-((2-(4-((3-chloro-5-(hydroxymethyl)benzyl)amino)butoxy)ethyl)amino)benzo[c][2,6]naphthyridine-8-carboxamide;

5-((2-(4-((3-cyano-4-(trifluoromethoxy)benzyl)amino)butoxy)ethyl)amino)benzo[c][2,6]naphthyridine-8-carboxamide;

5-((2-(4-((3-(hydroxymethyl)benzyl)amino)butoxy)ethyl)amino)benzo[c][2,6]naphthyridine-8-carboxamide;

5-((2-(4-((3-(cyanomethyl)benzyl)amino)butoxy)ethyl)amino)benzo[c][2,6]naphthyridine-8-carboxamide;

5-((2-(4-((3-cyano-4-cyclobutoxybenzyl)amino)butoxy)ethyl)amino)benzo[c][2,6]naphthyridine-8-carboxamide;

5-((2-(4-((3-(hydroxymethyl)-4-(trifluoromethoxy)benzyl)amino)butoxy)ethyl)amino)benzo[c][2,6]naphthyridine-8-carboxamide;

5-((2-(4-((4-cyclobutoxy-3-(hydroxymethyl)benzyl)amino)butoxy)ethyl)amino)benzo[c][2,6]naphthyridine-8-carboxamide;

5-((2-(4-((4-chloro-3-(2-hydroxyethoxy)benzyl)amino)butoxy)ethyl)amino)benzo[c][2,6]naphthyridine-8-carboxamide;

5-((2-(4-((3-chloro-4-cyclobutoxybenzyl)amino)butoxy)ethyl)amino)benzo[c][2,6]naphthyridine-8-carboxylic acid;

5-((2-(4-((3-(2-hydroxyethoxy)benzyl)amino)butoxy)ethyl)amino)benzo[c][2,6]naphthyridine-8-carboxylic acid;

5-((2-(4-((3-(cyanomethyl)benzyl)amino)butoxy)ethyl)amino)benzo[c][2,6]naphthyridine-8-carboxylic acid;

5-((2-(4-((3-fluoro-4-(trifluoromethoxy)benzyl)amino)butoxy)ethyl)amino)benzo[c][2,6]naphthyridine-8-carboxylic acid;

5-((2-(4-((4-cyclopropyl-3-(hydroxymethyl)benzyl)amino)butoxy)ethyl)amino)benzo[c][2,6]naphthyridine-8-carboxamide;

5-((2-(4-((3-chlorobenzyl)amino)butoxy)ethyl)amino)benzo[c][2,6]naphthyridine-8-carboxylic acid;

5-((2-(4-((3-chloro-5-(hydroxymethyl)benzyl)amino)butoxy)ethyl)amino)benzo[c][2,6]naphthyridine-8-carboxylic acid;

5-((2-(4-((3-(2-hydroxyethyl)benzyl)amino)butoxy)ethyl)amino)benzo[c][2,6]naphthyridine-8-carboxylic acid;

5-((2-(4-((3-chloro-4-cyclopropylbenzyl)amino)butoxy)ethyl)amino)benzo[c][2,6]naphthyridine-8-carboxylic acid;

5-((2-(4-((3-chloro-4-cyclopropoxybenzyl)amino)butoxy)ethyl)amino)benzo[c][2,6]naphthyridine-8-carboxylic acid;

5-((2-(4-((3-(2-hydroxyethoxy)-4-(trifluoromethoxy)benzyl)amino)butoxy)ethyl)amino)benzo[c][2,6]naphthyridine-8-carboxamide;

5-((2-(4-((4-cyclobutoxy-3-(2-hydroxyethoxy)benzyl)amino)butoxy)ethyl)amino)benzo[c][2,6]naphthyridine-8-carboxamide 5-((2-(4-((3-(hydroxymethyl)benzyl)amino)butoxy)ethyl)amino)benzo[c][2,6]naphthyridine-8-carboxylic acid;

5-((2-(4-((3-(2-hydroxyethoxy)-4-(trifluoromethyl)benzyl)amino)butoxy)ethyl)amino)benzo[c][2,6]naphthyridine-8-carboxamide;

5-((2-(4-((3-cyano-4-cyclopropylbenzyl)amino)butoxy)ethyl)amino)benzo[c][2,6]naphthyridine-8-carboxylic acid;

5-((2-(4-((3-chloro-5-(cyanomethyl)benzyl)amino)butoxy)ethyl)amino)benzo[c][2,6]naphthyridine-8-carboxamide;

5-((2-(4-((3-cyano-4-cyclobutoxybenzyl)amino)butoxy)ethyl)amino)benzo[c][2,6]naphthyridine-8-carboxylic acid;

5-((2-(4-((3-chloro-5-(cyanomethyl)benzyl)amino)butoxy)ethyl)amino)benzo[c][2,6]naphthyridine-8-carboxylic acid;

5-((2-(4-((3-(aminomethyl)-5-chlorobenzyl)amino)butoxy)ethyl)amino)benzo[c][2,6]naphthyridine-8-carboxamide;

5-(2-(4-((3-chloro-5-(cyanomethyl)benzyl)amino)butoxy)ethoxy)benzo[c][2,6]naphthyridine-8-carboxamide;

5-(2-(4-((3-chloro-4-cyclobutoxybenzyl)amino)butoxy)ethoxy)benzo[c][2,6]naphthyridine-8-carboxamide;

5-(2-(4-((3-chloro-4-(trifluoromethoxy)benzyl)amino)butoxy)ethoxy)benzo[c][2,6]naphthyridine-8-carboxylic acid;

5-((2-(4-((3-(hydroxymethyl)-5-methylbenzyl)amino)butoxy)ethyl)amino)benzo[c][2,6]naphthyridine-8-carboxamide;

5-((2-(4-((2-chloro-5-(hydroxymethyl)benzyl)amino)butoxy)ethyl)amino)benzo[c][2,6]naphthyridine-8-carboxamide;

5-((2-(4-((3-(hydroxymethyl)-5-(trifluoromethyl)benzyl)amino)butoxy)ethyl)amino)benzo[c][2,6]naphthyridine-8-carboxamide;

5-((2-(4-((4-chloro-3-(hydroxymethyl)benzyl)amino)butoxy)ethyl)amino)benzo[c][2,6]naphthyridine-8-carboxamide;

5-(2-(4-((3-fluoro-4-(trifluoromethoxy)benzyl)amino)butoxy)ethoxy)benzo[c][2,6]naphthyridine-8-carboxamide;

5-(2-(4-((3-cyano-4-cyclopropylbenzyl)amino)butoxy)ethoxy)benzo[c][2,6]naphthyridine-8-carboxamide;

5-(2-(4-((4-cyclobutoxy-3-(hydroxymethyl)benzyl)amino)butoxy)ethoxy)benzo[c][2,6]naphthyridine-8-carboxamide;

5-(2-(4-((3-chloro-5-(hydroxymethyl)benzyl)amino)butoxy)ethoxy)benzo[c][2,6]naphthyridine-8-carboxamide;

5-(3-(4-((3-chloro-4-(trifluoromethoxy)benzyl)amino)butoxy)azetidin-1-yl)benzo[c][2,6]naphthyridine-8-carboxylic acid;

5-((2-(4-((3-fluoro-5-(hydroxymethyl)benzyl)amino)butoxy)ethyl)amino)benzo[c][2,6]naphthyridine-8-carboxamide;

5-((2-(4-((3-(cyanomethyl)-5-(trifluoromethyl)benzyl)amino)butoxy)ethyl)amino)benzo[c][2,6]naphthyridine-8-carboxamide;

5-((2-(4-((3-(cyanomethyl)-5-fluorobenzyl)amino)butoxy)ethyl)amino)benzo[c][2,6]naphthyridine-8-carboxamide;

5-((2-(4-((3-(cyanomethyl)-5-methylbenzyl)amino)butoxy)ethyl)amino)benzo[c][2,6]naphthyridine-8-carboxamide;

5-((2-(4-((2-chloro-5-(cyanomethyl)benzyl)amino)butoxy)ethyl)amino)benzo[c][2,6]naphthyridine-8-carboxamide;

5-((2-(4-((4-cyano-3-cyclopropylbenzyl)amino)butoxy)ethyl)amino)benzo[c][2,6]naphthyridine-8-carboxamide;

5-((2-(4-((3-chloro-4-(cyanomethyl)benzyl)amino)butoxy)ethyl)amino)benzo[c][2,6]naphthyridine-8-carboxamide;

5-((2-(4-((3-(hydroxymethyl)-4-(2,2,2-trifluoroethoxy)benzyl)amino)butoxy)ethyl)amino)benzo[c][2,6]naphthyridine-8-carboxamide;

5-((2-(4-((3-(hydroxymethyl)-4-isopropoxybenzyl)amino)butoxy)ethyl)amino)benzo[c][2,6]naphthyridine-8-carboxamide;

5-((2-(4-((4-(cyclopentyloxy)-3-(hydroxymethyl)benzyl)amino)butoxy)ethyl)amino)benzo[c][2,6]naphthyridine-8-carboxamide;

5-((2-(4-((4-chloro-3-(cyanomethyl)benzyl)amino)butoxy)ethyl)amino)benzo[c][2,6]naphthyridine-8-carboxamide;

5-((2-(4-((2-chloro-3-(cyanomethyl)benzyl)amino)butoxy)ethyl)amino)benzo[c][2,6]naphthyridine-8-carboxamide;

5-((2-(4-((2-chloro-3-(hydroxymethyl)benzyl)amino)butoxy)ethyl)amino)benzo[c][2,6]naphthyridine-8-carboxamide;

5-((2-(4-((4-ethoxy-3-(hydroxymethyl)benzyl)amino)butoxy)ethyl)amino)benzo[c][2,6]naphthyridine-8-carboxamide;

5-((2-(4-((3-fluoro-5-(hydroxymethyl)benzyl)amino)butoxy)ethyl)amino)benzo[c][2,6]naphthyridine-8-carboxylic acid;

5-((2-(4-((3-(hydroxymethyl)-5-(trifluoromethyl)benzyl)amino)butoxy)ethyl)amino)benzo[c][2,6]naphthyridine-8-carboxylic acid;

5-((2-(4-((3-(cyanomethyl)-5-fluorobenzyl)amino)butoxy)ethyl)amino)benzo[c][2,6]naphthyridine-8-carboxylic acid;

5-((2-(4-((3-(cyanomethyl)-5-(trifluoromethyl)benzyl)amino)butoxy)ethyl)amino)benzo[c][2,6]naphthyridine-8-carboxylic acid;

5-((2-(4-((3-(cyanomethyl)-5-methylbenzyl)amino)butoxy)ethyl)amino)benzo[c][2,6]naphthyridine-8-carboxylic acid;

5-(2-(4-((3-fluoro-5-(hydroxymethyl)benzyl)amino)butoxy)ethoxy)benzo[c][2,6]naphthyridine-8-carboxylic acid;

5-(2-(4-((3-(hydroxymethyl)-5-(trifluoromethyl)benzyl)amino)butoxy)ethoxy)benzo[c][2,6]naphthyridine-8-carboxylic acid;

5-(2-(4-((3-chloro-5-(cyanomethyl)benzyl)amino)butoxy)ethoxy)benzo[c][2,6]naphthyridine-8-carboxylic acid;

5-(2-(4-((3-(cyanomethyl)-5-(trifluoromethyl)benzyl)amino)butoxy)ethoxy)benzo[c][2,6]naphthyridine-8-carboxylic acid;

5-(2-(4-((3-(cyanomethyl)-5-methylbenzyl)amino)butoxy)ethoxy)benzo[c][2,6]naphthyridine-8-carboxylic acid;

5-(3-(4-((3-(cyanomethyl)-5-fluorobenzyl)amino)butoxy)azetidin-1-yl)benzo[c][2,6]naphthyridine-8-carboxylic acid;

5-(3-(4-((3-(cyanomethyl)-5-methylbenzyl)amino)butoxy)azetidin-1-yl)benzo[c][2,6]naphthyridine-8-carboxylic acid;

5-(3-(4-((3-chloro-5-(hydroxymethyl)benzyl)amino)butoxy)azetidin-1-yl)benzo[c][2,6]naphthyridine-8-carboxylic acid;

5-(3-(4-((3-chloro-5-(hydroxymethyl)benzyl)amino)butoxy)azetidin-1-yl)benzo[c][2,6]naphthyridine-8-carboxamide;

5-(3-(4-((3-fluoro-5-(hydroxymethyl)benzyl)amino)butoxy)azetidin-1-yl)benzo[c][2,6]naphthyridine-8-carboxylic acid;

5-(3-(4-((3-fluoro-5-(hydroxymethyl)benzyl)amino)butoxy)azetidin-1-yl)benzo[c][2,6]naphthyridine-8-carboxamide;

5-(3-(4-((3-(hydroxymethyl)-5-(trifluoromethyl)benzyl)amino)butoxy)azetidin-1-yl)benzo[c][2,6]naphthyridine-8-carboxamide;

5-(3-(4-((3-fluoro-4-(trifluoromethoxy)benzyl)amino)butoxy)azetidin-1-yl)benzo[c][2,6]naphthyridine-8-carboxamide;

5-((2-(4-((3-(hydroxymethyl)-5-(trifluoromethoxy)benzyl)amino)butoxy)ethyl)amino)benzo[c][2,6]naphthyridine-8-carboxamide;

5-((2-(4-((3-(hydroxymethyl)-4-(trifluoromethyl)benzyl)amino)butoxy)ethyl)amino)benzo[c][2,6]naphthyridine-8-carboxamide;

(S)-5-((1-(4-((3-chloro-4-(trifluoromethoxy)benzyl)amino)butoxy)propan-2-yl)amino)benzo[c][2,6]naphthyridine-8-carboxylic acid;

5-((2-(4-((3-(cyanomethyl)-5-methoxybenzyl)amino)butoxy)ethyl)amino)benzo[c][2,6]naphthyridine-8-carboxamide;

(R)-5-((1-(4-((3-chloro-4-(trifluoromethoxy)benzyl)amino)butoxy)propan-2-yl)amino)benzo[c][2,6]naphthyridine-8-carboxylic acid;

5-((2-(4-((3-(cyanomethyl)-5-(trifluoromethoxy)benzyl)amino)butoxy)ethyl)amino)benzo[c][2,6]naphthyridine-8-carboxamide;

5-(2-(4-((3-chloro-5-(hydroxymethyl)benzyl)amino)butoxy)ethoxy)benzo[c][2,6]naphthyridine-8-carboxylic acid;

5-(2-(4-((3-(hydroxymethyl)-5-(trifluoromethyl)benzyl)amino)butoxy)ethoxy)benzo[c][2,6]naphthyridine-8-carboxamide;

5-(2-(4-((3-(cyanomethyl)-5-fluorobenzyl)amino)butoxy)ethoxy)benzo[c][2,6]naphthyridine-8-carboxamide;

5-(2-(4-((3-fluoro-4-(trifluoromethoxy)benzyl)amino)butoxy)ethoxy)benzo[c][2,6]naphthyridine-8-carboxylic acid;

5-(2-(4-((3-fluoro-5-(hydroxymethyl)benzyl)amino)butoxy)ethoxy)benzo[c][2,6]naphthyridine-8-carboxamide;

5-(2-(4-((3-(cyanomethyl)-5-fluorobenzyl)amino)butoxy)ethoxy)benzo[c][2,6]naphthyridine-8-carboxylic acid;

5-(2-(4-((3-(cyanomethyl)-5-methylbenzyl)amino)butoxy)ethoxy)benzo[c][2,6]naphthyridine-8-carboxamide;

5-(2-(4-((3-(cyanomethyl)-5-(trifluoromethyl)benzyl)amino)butoxy)ethoxy)benzo[c][2,6]naphthyridine-8-carboxamide;

5-(3-(4-((3-(cyanomethyl)-5-methylbenzyl)amino)butoxy)azetidin-1-yl)benzo[c][2,6]naphthyridine-8-carboxamide;

5-(3-(4-((3-(cyanomethyl)-5-fluorobenzyl)amino)butoxy)azetidin-1-yl)benzo[c][2,6]naphthyridine-8-carboxamide;

5-(3-(4-((3-(cyanomethyl)-5-(trifluoromethyl)benzyl)amino)butoxy)azetidin-1-yl)benzo[c][2,6]naphthyridine-8-carboxamide;

5-(3-(4-((3-chloro-4-(trifluoromethoxy)benzyl)amino)butoxy)azetidin-1-yl)benzo[c][2,6]naphthyridine-8-carboxamide;

5-(3-(4-((3-(hydroxymethyl)-5-(trifluoromethyl)benzyl)amino)butoxy)azetidin-1-yl)benzo[c][2,6]naphthyridine-8-carboxylic acid;

5-(3-(4-((3-fluoro-4-(trifluoromethoxy)benzyl)amino)butoxy)azetidin-1-yl)benzo[c][2,6]naphthyridine-8-carboxylic acid;

5-(3-(4-((3-chloro-5-(cyanomethyl)benzyl)amino)butoxy)azetidin-1-yl)benzo[c][2,6]naphthyridine-8-carboxylic acid;

5-(3-(4-((3-(cyanomethyl)-5-(trifluoromethyl)benzyl)amino)butoxy)azetidin-1-yl)benzo[c][2,6]naphthyridine-8-carboxylic acid;

5-(3-(4-((3-chloro-5-(cyanomethyl)benzyl)amino)butoxy)azetidin-1-yl)benzo[c][2,6]naphthyridine-8-carboxamide;

5-((2-(4-((3-chloro-5-(2-cyanopropan-2-yl)benzyl)amino)butoxy)ethyl)amino)benzo[c][2,6]naphthyridine-8-carboxamide;

5-((2-(4-((3-chloro-5-(1-cyanocyclopropyl)benzyl)amino)butoxy)ethyl)amino)benzo[c][2,6]naphthyridine-8-carboxamide;

5-(2-(4-((3-(cyanomethyl)-5-(trifluoromethoxy)benzyl)amino)butoxy)ethoxy)benzo[c][2,6]naphthyridine-8-carboxamide;

5-((2-(4-((3-(cyanomethyl)-5-(trifluoromethoxy)benzyl)amino)butoxy)ethyl)amino)benzo[c][2,6]naphthyridine-8-carboxylic acid;

5-(3-(4-((3-(cyanomethyl)-5-(trifluoromethoxy)benzyl)amino)butoxy)azetidin-1-yl)benzo[c][2,6]naphthyridine-8-carboxylic acid;

5-(3-(4-((3-(cyanomethyl)-5-(trifluoromethoxy)benzyl)amino)butoxy)azetidin-1-yl)benzo[c][2,6]naphthyridine-8-carboxamide;

5-(2-(4-((3-(cyanomethyl)-5-(trifluoromethoxy)benzyl)amino)butoxy)ethoxy)benzo[c][2,6]naphthyridine-8-carboxylic acid;

5-(2-(4-((3-bromo-4-(trifluoromethoxy)benzyl)amino)butoxy)ethoxy)benzo[c][2,6]naphthyridine-8-carboxylic acid;

5-(2-(4-((4-chloro-3-(trifluoromethoxy)benzyl)amino)butoxy)ethoxy)benzo[c][2,6]naphthyridine-8-carboxylic acid;

5-(2-(4-((3-chloro-5-(trifluoromethoxy)benzyl)amino)butoxy)ethoxy)benzo[c][2,6]naphthyridine-8-carboxylic acid;

5-(2-(4-((3-bromo-5-(trifluoromethoxy)benzyl)amino)butoxy)ethoxy)benzo[c][2,6]naphthyridine-8-carboxylic acid;

5-(2-(4-((3,5-difluoro-4-(trifluoromethoxy)benzyl)amino)butoxy)ethoxy)benzo[c][2,6]naphthyridine-8-carboxylic acid;

5-(2-(4-((3-cyclopropyl-5-(trifluoromethoxy)benzyl)amino)butoxy)ethoxy)benzo[c][2,6]naphthyridine-8-carboxylic acid;

5-(3-(4-((3-fluoro-5-(trifluoromethoxy)benzyl)amino)butoxy)azetidin-1-yl)benzo[c][2,6]naphthyridine-8-carboxylic acid;

5-(3-(4-((3,5-difluoro-4-(trifluoromethoxy)benzyl)amino)butoxy)azetidin-1-yl)benzo[c][2,6]naphthyridine-8-carboxylic acid;

5-(3-(4-((3-chloro-5-(trifluoromethoxy)benzyl)amino)butoxy)azetidin-1-yl)benzo[c][2,6]naphthyridine-8-carboxylic acid;

5-(3-(4-((3-bromo-4-(trifluoromethoxy)benzyl)amino)butoxy)azetidin-1-yl)benzo[c][2,6]naphthyridine-8-carboxylic acid;

5-(3-(4-((3-cyclopropyl-5-(trifluoromethoxy)benzyl)amino)butoxy)azetidin-1-yl)benzo[c][2,6]naphthyridine-8-carboxylic acid;

5-(2-(4-((3-chloro-5-(1-cyanocyclopropyl)benzyl)amino)butoxy)ethoxy)benzo[c][2,6]naphthyridine-8-carboxylic acid;

5-(2-(4-((3-chloro-5-(2-cyanopropan-2-yl)benzyl)amino)butoxy)ethoxy)benzo[c][2,6]naphthyridine-8-carboxylic acid;

5-(2-(4-((3-cyclopropyl-4-(trifluoromethoxy)benzyl)amino)butoxy)ethoxy)benzo[c][2,6]naphthyridine-8-carboxylic acid;

5-(2-(4-((3-methyl-4-(trifluoromethoxy)benzyl)amino)butoxy)ethoxy)benzo[c][2,6]naphthyridine-8-carboxylic acid;

5-(2-(4-((3-methoxy-4-(trifluoromethoxy)benzyl)amino)butoxy)ethoxy)benzo[c][2,6]naphthyridine-8-carboxylic acid;

5-(2-(4-((3,4-dichloro-5-(trifluoromethoxy)benzyl)amino)butoxy)ethoxy)benzo[c][2,6]naphthyridine-8-carboxylic acid;

5-((2-(4-((3-(cyanomethyl)-5-cyclopropylbenzyl)amino)butoxy)ethyl)amino)benzo[c][2,6]naphthyridine-8-carboxamide;

5-((2-(4-((3-(cyanomethyl)-5-ethoxybenzyl)amino)butoxy)ethyl)amino)benzo[c][2,6]naphthyridine-8-carboxamide;

5-((2-(4-((3-cyclopropyl-5-(hydroxymethyl)benzyl)amino)butoxy)ethyl)amino)benzo[c][2,6]naphthyridine-8-carboxamide;

(R)-5-((2-(4-((3-chloro-5-(1-cyanoethyl)benzyl)amino)butoxy)ethyl)amino)benzo[c][2,6]naphthyridine-8-carboxamide;

(S)-5-((2-(4-((3-chloro-5-(1-cyanoethyl)benzyl)amino)butoxy)ethyl)amino)benzo[c][2,6]naphthyridine-8-carboxamide;

5-((2-(4-((3-(cyanomethyl)-5-(2,2,2-trifluoroethoxy)benzyl)amino)butoxy)ethyl)amino)benzo[c][2,6]naphthyridine-8-carboxamide;

(R)-5-((1-(4-((3-chloro-4-(trifluoromethoxy)benzyl)amino)butoxy)propan-2-yl)amino)benzo[c][2,6]naphthyridine-8-carboxamide;

5-(3-(4-((3-cyclopropyl-4-(trifluoromethoxy)benzyl)amino)butoxy)azetidin-1-yl)benzo[c][2,6]naphthyridine-8-carboxylic acid;

5-(3-(4-((3-bromo-5-(trifluoromethoxy)benzyl)amino)butoxy)azetidin-1-yl)benzo[c][2,6]naphthyridine-8-carboxylic acid;

5-(3-(4-((4-chloro-3-(trifluoromethoxy)benzyl)amino)butoxy)azetidin-1-yl)benzo[c][2,6]naphthyridine-8-carboxylic acid;

5-(3-(4-((3-methyl-4-(trifluoromethoxy)benzyl)amino)butoxy)azetidin-1-yl)benzo[c][2,6]naphthyridine-8-carboxylic acid;

5-(3-(4-((3-methoxy-4-(trifluoromethoxy)benzyl)amino)butoxy)azetidin-1-yl)benzo[c][2,6]naphthyridine-8-carboxylic acid;

5-(3-(4-((3,4-dichloro-5-(trifluoromethoxy)benzyl)amino)butoxy)azetidin-1-yl)benzo[c][2,6]naphthyridine-8-carboxylic acid;

(S)-5-((1-(4-((3-chloro-4-(trifluoromethoxy)benzyl)amino)butoxy)propan-2-yl)amino)benzo[c][2,6]naphthyridine-8-carboxamide;

5-((1-(4-((3-chloro-4-(trifluoromethoxy)benzyl)amino)butoxy)-2-methylpropan-2-yl)amino)benzo[c][2,6]naphthyridine-8-carboxylic acid;

5-((2-(4-((3-(cyanomethyl)-5-ethylbenzyl)amino)butoxy)ethyl)amino)benzo[c][2,6]naphthyridine-8-carboxamide;

5-((2-(4-((3-(cyanomethyl)-5-(cyclopropylmethyl)benzyl)amino)butoxy)ethyl)amino)benzo[c][2,6]naphthyridine-8-carboxamide;

5-((1-(4-((3-chloro-4-(trifluoromethoxy)benzyl)amino)butoxy)-2-methylpropan-2-yl)amino)benzo[c][2,6]naphthyridine-8-carboxamide;

5-((2-(4-((3-(cyanomethyl)-5-(methoxymethyl)benzyl)amino)butoxy)ethyl)amino)benzo[c][2,6]naphthyridine-8-carboxamide;

(R)-5-((1-(4-((3-chloro-4-(trifluoromethoxy)benzyl)amino)butoxy)propan-2-yl)oxy)benzo[c][2,6]naphthyridine-8-carboxylic acid;

(R)-5-((1-(4-((3-chloro-4-(trifluoromethoxy)benzyl)amino)butoxy)propan-2-yl)oxy)benzo[c][2,6]naphthyridine-8-carboxamide;

5-((2-(4-((3-cyano-5-(trifluoromethoxy)benzyl)amino)butoxy)ethyl)amino)benzo[c][2,6]naphthyridine-8-carboxamide;

5-((2-(4-((3-(2-hydroxyethoxy)-5-(trifluoromethoxy)benzyl)amino)butoxy)ethyl)amino)benzo[c][2,6]naphthyridine-8-carboxamide;

5-((2-(4-((3-(oxazol-4-ylmethyl)-5-(trifluoromethoxy)benzyl)amino)butoxy)ethyl)amino)benzo[c][2,6]naphthyridine-8-carboxamide;

5-((2-(4-((3-(oxazol-5-ylmethyl)-5-(trifluoromethoxy)benzyl)amino)butoxy)ethyl)amino)benzo[c][2,6]naphthyridine-8-carboxamide;

5-(2-(4-((3-cyano-5-(trifluoromethoxy)benzyl)amino)butoxy)ethoxy)benzo[c][2,6]naphthyridine-8-carboxamide;

5-(2-(4-((3-(2-hydroxyethoxy)-5-(trifluoromethoxy)benzyl)amino)butoxy)ethoxy)benzo[c][2,6]naphthyridine-8-carboxamide;

5-(2-(4-((3-(oxazol-5-ylmethyl)-5-(trifluoromethoxy)benzyl)amino)butoxy)ethoxy)benzo[c][2,6]naphthyridine-8-carboxamide;

5-(2-(4-((3-(oxazol-4-ylmethyl)-5-(trifluoromethoxy)benzyl)amino)butoxy)ethoxy)benzo[c][2,6]naphthyridine-8-carboxamide;

5-(2-(4-((3-(2-hydroxyethyl)-5-(trifluoromethoxy)benzyl)amino)butoxy)ethoxy)benzo[c][2,6]naphthyridine-8-carboxamide;

5-((2-(4-((3-(2-hydroxyethyl)-5-(trifluoromethoxy)benzyl)amino)butoxy)ethyl)amino)benzo[c][2,6]naphthyridine-8-carboxamide;

(S)-5-((1-(4-((3-chloro-4-(trifluoromethoxy)benzyl)amino)butoxy)propan-2-yl)oxy)benzo[c][2,6]naphthyridine-8-carboxylic acid;

(S)-5-((1-(4-((3-chloro-4-(trifluoromethoxy)benzyl)amino)butoxy)propan-2-yl)oxy)benzo[c][2,6]naphthyridine-8-carboxamide;

5-((2-(4-((3-carbamoyl-5-(trifluoromethoxy)benzyl)amino)butoxy)ethyl)amino)benzo[c][2,6]naphthyridine-8-carboxamide;

5-(2-(4-((3-carbamoyl-5-(trifluoromethoxy)benzyl)amino)butoxy)ethoxy)benzo[c][2,6]naphthyridine-8-carboxamide;

5-((2-(4-((3-(2-amino-2-oxoethyl)-5-(trifluoromethoxy)benzyl)amino)butoxy)ethyl)amino)benzo[c][2,6]naphthyridine-8-carboxamide;

5-(2-(4-((3-(2-amino-2-oxoethyl)-5-(trifluoromethoxy)benzyl)amino)butoxy)ethoxy)benzo[c][2,6]naphthyridine-8-carboxamide;

5-((2-(4-((3-((1H-imidazol-1-yl)methyl)-5-(trifluoromethoxy)benzyl)amino)butoxy)ethyl)amino)benzo[c][2,6]naphthyridine-8-carboxamide;

5-((2-(4-((3-(furan-3-ylmethyl)-5-(trifluoromethoxy)benzyl)amino)butoxy)ethyl)amino)benzo[c][2,6]naphthyridine-8-carboxamide;

5-(2-(4-((3-((1H-imidazol-1-yl)methyl)-5-(trifluoromethoxy)benzyl)amino)butoxy)ethoxy)benzo[c][2,6]naphthyridine-8-carboxamide;

5-((2-(4-((3-((1H-pyrazol-4-yl)methyl)-5-(trifluoromethoxy)benzyl)amino)butoxy)ethyl)amino)benzo[c][2,6]naphthyridine-8-carboxamide;

5-(2-(4-((3-(furan-3-ylmethyl)-5-(trifluoromethoxy)benzyl)amino)butoxy)ethoxy)benzo[c][2,6]naphthyridine-8-carboxamide;

5-(2-(4-((3-((1H-pyrazol-4-yl)methyl)-5-(trifluoromethoxy)benzyl)amino)butoxy)ethoxy)benzo[c][2,6]naphthyridine-8-carboxamide;

5-((2-(4-((3,5-difluoro-4-(trifluoromethoxy)benzyl)amino)butoxy)ethyl)amino)benzo[c][2,6]naphthyridine-8-carboxylic acid;

(R)-5-((1-(4-((3,5-difluoro-4-(trifluoromethoxy)benzyl)amino)butoxy)propan-2-yl)oxy)benzo[c][2,6]naphthyridine-8-carboxylic acid;

(R)-5-((1-(4-((3-fluoro-4-(trifluoromethoxy)benzyl)amino)butoxy)propan-2-yl)oxy)benzo[c][2,6]naphthyridine-8-carboxylic acid;

(R)-5-((1-(4-((3-fluoro-4-(trifluoromethoxy)benzyl)amino)butoxy)propan-2-yl)amino)benzo[c][2,6]naphthyridine-8-carboxylic acid;

(R)-5-((1-(4-((3,5-difluoro-4-(trifluoromethoxy)benzyl)amino)butoxy)propan-2-yl)amino)benzo[c][2,6]naphthyridine-8-carboxylic acid; or 5-(2-(4-((3,5-Difluoro-4-(trifluoromethoxy)benzyl)amino)butoxy)ethoxy)benzo[c][2,6]naphthyridine-8-carboxamide.

19. A pharmaceutical composition comprising a compound according to claim 1, or a pharmaceutically acceptable salt thereof, and a pharmaceutically acceptable excipient.

20. A method of:

(i) treating a disease or condition in which CK2a activity is implicated;

(ii) treating a disease or condition associated with aberrant activity of CK2a;

(iii) treating a proliferative disorder;

(iv) benign neoplasms; and/or (v) treating cancer;

said method comprising administering to a subject in need thereof an effective amount of a compound according to claim 1, or a pharmaceutically acceptable salt thereof.

* * * * *